US012780811B2

(12) United States Patent
Li et al.

(10) Patent No.: US 12,780,811 B2
(45) Date of Patent: Nov. 3, 2026

(54) INHIBITOR OF ENHANCER OF ZESTE HOMOLOGUE 2, AND USE THEREOF

(71) Applicant: Xizang Haisco Pharmaceutical Co., Ltd., Lhoka (CN)

(72) Inventors: Yao Li, Chengdu (CN); Zongjun Shi, Chengdu (CN); Guobiao Zhang, Chengdu (CN); Wenjing Wang, Chengdu (CN); Lei Chen, Chengdu (CN); Yunpeng Pei, Chengdu (CN); Long Yang, Chengdu (CN); Changwei Song, Chengdu (CN); Pingming Tang, Chengdu (CN); Fei Ye, Chengdu (CN); Chen Zhang, Chengdu (CN); Jia Ni, Chengdu (CN); Pangke Yan, Chengdu (CN)

(73) Assignee: Xizang Haisco Pharmaceutical Co., Ltd., Lhoka (CN)

( * ) Notice: Subject to any disclaimer, the term of this patent is extended or adjusted under 35 U.S.C. 154(b) by 1054 days.

(21) Appl. No.: 18/029,571

(22) PCT Filed: Mar. 15, 2021

(86) PCT No.: PCT/CN2021/080732
§ 371 (c)(1),
(2) Date: Mar. 30, 2023

(87) PCT Pub. No.: WO2021/180235
PCT Pub. Date: Sep. 16, 2021

(65) Prior Publication Data

US 2023/0365541 A1 Nov. 16, 2023

(30) Foreign Application Priority Data

Mar. 13, 2020 (CN) ......................... 202010174741.7
Apr. 1, 2020 (CN) ......................... 202010242647.0
Jul. 20, 2020 (CN) ......................... 202010697086.3
Sep. 3, 2020 (CN) ......................... 202010915674.X
Nov. 17, 2020 (CN) ......................... 202011283498.9
Feb. 7, 2021 (CN) ......................... 202110167158.8

(51) Int. Cl.
*C07D 405/14* (2006.01)
*A61P 35/00* (2006.01)
*C07D 405/12* (2006.01)
*C07D 491/056* (2006.01)

(52) U.S. Cl.
CPC ............ *C07D 405/14* (2013.01); *A61P 35/00* (2018.01); *C07D 405/12* (2013.01); *C07D 491/056* (2013.01)

(58) Field of Classification Search
CPC ................ C07D 405/14; C07D 405/12; C07D 491/056; A61P 35/00
See application file for complete search history.

(56) References Cited

U.S. PATENT DOCUMENTS

2018/0282313 A1 10/2018 Kanno et al.
2019/0343816 A1 11/2019 Yamano et al.

FOREIGN PATENT DOCUMENTS

WO WO-2019204490 A1 * 10/2019 ........... C07D 405/14
WO WO-2021016409 A1 * 1/2021 ............. A61K 31/58

OTHER PUBLICATIONS

Kaur, Global Journal of Pharmacy and Pharmaceutical Science, vol. 1, Issue 4, Mar. 2017 (Year: 2017).*
Hernandes, Current Drug Targets, Mar. 2010, 11, 3, 303-314 (Year: 2010).*
English Translation of International Search Report for Application No. PCT/CN2021/080732, mailed Jun. 23, 2021, 4 pages.

* cited by examiner

*Primary Examiner* — John S Kenyon
*Assistant Examiner* — Phillip Matthew Rzeczycki
(74) *Attorney, Agent, or Firm* — Meunier Carlin & Curfman LLC

(57) ABSTRACT

Disclosed are a compound of formula (I), a stereoisomer, a pharmaceutically acceptable salt, a solvate, and a eutectic or deuterated compound thereof, or a pharmaceutical composition comprising same, and a use thereof as an EZH2 inhibitor in the preparation of a medication for treating related diseases. The definition of each group in formula (I) is consistent with that in the description.

(I)

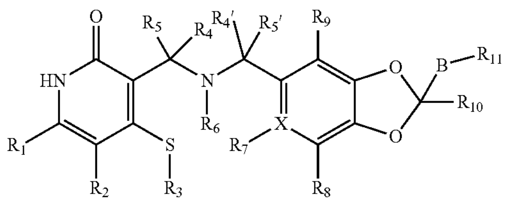

8 Claims, No Drawings

INHIBITOR OF ENHANCER OF ZESTE HOMOLOGUE 2, AND USE THEREOF

TECHNICAL FIELD

The present disclosure belongs to the field of medication, and in particular relates to a compound having an EZH2 inhibitory activity or a stereoisomer, a pharmaceutically acceptable salt, a solvate, and a eutectic or deuterated compound thereof, and the use thereof in the preparation of a medication for treating related diseases.

BACKGROUND ART

At present, the methods for treating cancers mainly comprise radiotherapy, surgery therapy and pharmaceutical therapy, and treatment with drugs targeting lesions has currently become the main means of clinical tumor treatment. However, due to the rapid development of drug resistance in tumor cells, people are basically at a loss for tumor metastasis and recurrence at the present stage.

Lysine methyltransferase can methylate histones and non-histones, and the aberrant expression of lysine methyltransferase is closely related to the occurrence of various tumors, which has become a hot spot in the field of epigenetics for a dozen of years. Targeting lysine methyltransferase to reverse aberrant methylation level of histones or non-histones is regarded as a new method for treating tumors. PRC2 (polycomb repressive complex 2) is a polysubunit protein complex consisting of EZH1 (enhancer of zeste homologue 1, KMT6B) or EZH2 (enhancer of zeste homologue 2, KMT6A), SUZ12 (suppressor of zeste 12), and EED (embryonic ectoderm development), and is used for catalyzing trimethylation of H3K27. The PCR2 complex methylates nucleosomal histone H3 at lysine 9 (H3K9) and lysine 27 (H3K27) by the SET domain of EZH2, and then triggers the PCR1 complex to aggregate at a specific gene locus, thereby silencing target genes (such as CDKN1C, CDH1 and RUNX3) and promoting cell proliferation. Researches have suggested that the overexpression of EZH2 and the mutation (Y641F, Y641N, A687V and A677G point mutations) in the SET domain both lead to abnormal elevation of H3K27me3 and promote the growth and development of various types of tumors, such as breast cancer, prostate cancer and leukemia.

SUMMARY OF THE DISCLOSURE

The compounds provided in the present disclosure and the stereoisomer, pharmaceutically acceptable salt, solvate and eutectic or deuterated compound thereof have an inhibitory effect on EZH2, can inhibit cell proliferation, possess good pharmacokinetic characteristics, high bioavailability, good safety and low toxicity and side effects, have no inhibition to CYP enzymes, can be administered orally, and have fast absorption and high clearance rate.

The present disclosure provides a compound having an EZH2 inhibitory activity, or a stereoisomer, a pharmaceutically acceptable salt, a solvate, and a eutectic or deuterated compound thereof, wherein the compound is as shown in formula (I), (I)

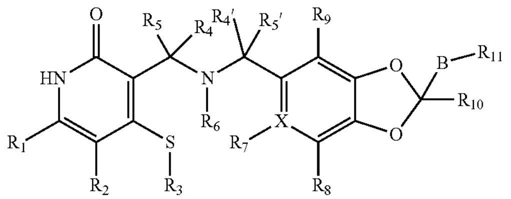

wherein $R_1$ is selected from H, D, cyano, $C_{1-4}$ alkyl, $C_{3-6}$ cycloalkyl or halo $C_{1-4}$ alkyl; in some embodiments, $R_1$ is selected from H, cyano, $C_{1-4}$ alkyl, $C_{3-6}$ cycloalkyl or halo $C_{1-4}$ alkyl; in some embodiments, $R_1$ is selected from $C_{1-4}$ alkyl or $C_{3-6}$ cycloalkyl; in some embodiments, $R_1$ is selected from $C_{1-4}$ alkyl; in some embodiments, $R_1$ is selected from methyl; in some embodiments, $R_1$ is selected from cyclopropyl; in some embodiments, $R_1$ is selected from H;

$R_2$ is selected from H, D or $C_{1-4}$ alkyl; in some embodiments, $R_2$ is selected from H or $C_{1-4}$ alkyl; in some embodiments, $R_2$ is selected from H; in some embodiments, $R_2$ is selected from methyl;

$R_3$ is selected from $C_{1-6}$ alkyl, halo $C_{1-6}$ alkyl, 3- to 6-membered heterocycloalkyl or $C_{3-6}$ cycloalkyl, wherein the alkyl, cycloalkyl or heterocycloalkyl is optionally substituted with 1-3 of the following groups: D, OH, CN, amino or halogen; in some embodiments, $R_3$ is selected from $C_{1-6}$ alkyl, halo $C_{1-6}$ alkyl, 3- to 6-membered heterocycloalkyl or $C_{3-6}$ cycloalkyl, wherein the alkyl, cycloalkyl or heterocycloalkyl is optionally substituted with 1-3 of the following groups: OH, cyano, amino or halogen; in some embodiments, $R_3$ is selected from $C_{1-6}$ alkyl, 3- to 6-membered heterocycloalkyl or $C_{3-6}$ cycloalkyl, wherein the alkyl, cycloalkyl or heterocycloalkyl is optionally substituted with 1-3 of the following groups: OH or halogen; in some embodiments, $R_3$ is selected from methyl, hydroxyethyl,

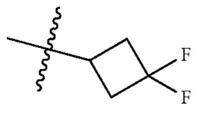 or 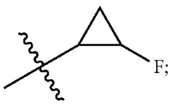

oxetanyl F or F; in some embodiments, $R_3$ is selected from methyl;

alternatively, $R_1$ and $R_2$ form 3- to 6-membered cycloalkyl, wherein the cycloalkyl is optionally substituted with 1-3 of halogen, D, CN, OH, amino or $C_{1-4}$ alkyl; in some embodiments, $R_1$ and $R_2$ form 3- to 6-membered cycloalkyl, wherein the cycloalkyl is optionally substituted with 1-3 halogen; in some embodiments, $R_1$ and $R_2$ form cyclopentyl; or alternatively, $R_2$ and $R_3$ form 3- to 6-membered heterocycloalkyl (R2 and R3 together with the atoms to which they are attached form 3- to 6-membered heterocycloalkyl), wherein the heterocycloalkyl is optionally substituted with 1-3 of halogen, D, OH, amino, $C_{1-4}$ alkyl or CN; in some embodiments, $R_2$ and $R_3$ form 3- to 6-membered heterocycloalkyl, wherein the heterocycloalkyl is optionally substituted with 1-3 of halogen, OH or amino; in some embodiments, $R_2$ and $R_3$ form thiacyclopentyl;

$R_4$ and $R_5$ are each independently selected from H, D, halogen or $C_{1-4}$ alkyl; in some embodiments, $R_4$ and $R_5$ are each independently selected from H, halogen or $C_{1-4}$ alkyl; in some embodiments, $R_4$ and $R_5$ are each independently selected from H;

$R_{4'}$ and $R_{5'}$ together with the carbon atom to which they are attached form $C_{3-6}$ carbocycle, or 3- to 7-membered heterocycloalkyl containing 1-3 heteroatoms selected from N, S or O; in some embodiments, $R_{4'}$ and $R_{5'}$ together with the carbon atom to which they are attached form oxetanyl; or $R_{4'}$ and $R_{5'}$ together form =O;

$R_6$ is selected from H, D or $C_{1-4}$ alkyl; in some embodiments, $R_6$ is selected from H;

$R_7$ is selected from H, D or halogen; in some embodiments, $R_7$ is selected from H, $C_1$ or F; in some embodiments, $R_7$ is selected from H; in some embodiments, $R_7$ is absent;

$R_8$ is selected from H, D, CN, $C_{1-6}$ alkyl, halo $C_{1-6}$ alkyl, halogen, —$NR^{8a}R^{8b}$—, —$NR^{8a}$—C(O)—$C_{1-4}$ alkyl, $C_{1-6}$ alkoxy, halo $C_{1-6}$ alkoxy, $C_{2-6}$ alkenyl, $C_{2-6}$ alkynyl, $C_{3-6}$ cycloalkyl, 3- to 6-membered heterocycloalkyl, 6- to 12-membered aryl, 5- to 10-membered heteroaryl or —Si($C_{1-4}$ alkyl)$_3$, wherein the alkyl, alkoxy, cycloalkyl, heterocycloalkyl, aryl or heteroaryl is optionally substituted with 1-3 of halogen, D, $C_{1-4}$ alkyl, OH, CN or amino; in some embodiments, $R_8$ is selected from H, halogen, $C_{3-6}$ cycloalkyl, 3- to 6-membered heterocycloalkyl, $C_{1-4}$ alkoxy or —Si($C_{1-4}$ alkyl)$_3$, wherein the alkoxy, cycloalkyl or heterocycloalkyl is optionally substituted with 1-3 halogen; in some embodiments, $R_8$ is selected from halogen; in some embodiments, $R_8$ is selected from Cl, cycloalkyl, oxetanyl, methoxy,

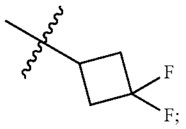 [SMILES: *C1CC(F)(F)C1]

;

in some embodiments, $R_8$ is selected from Cl; or $R_7$ and $R_8$ together with the atoms to which they are attached form $C_{3-6}$ cycloalkyl, 3- to 6-membered heterocycloalkyl, 6- to 12-membered aryl or 5- to 10-membered heteroaryl, wherein the cycloalkyl, heterocycloalkyl, aryl or heteroaryl is optionally substituted with 1-3 of halogen, D, $C_{1-4}$ alkyl, halo $C_{1-4}$ alkyl, $C_{1-4}$ alkoxy or halo $C_{1-4}$ alkoxy; in some embodiments, $R_7$ and $R_8$ together with the atoms to which they are attached form $C_{3-6}$ cycloalkyl, 3- to 6-membered heterocycloalkyl, 6- to 12-membered aryl or 5- to 10-membered heteroaryl, wherein the cycloalkyl, heterocycloalkyl, aryl or heteroaryl is optionally substituted with 1-3 of halogen, $C_{1-4}$ alkyl or halo $C_{1-4}$ alkyl; in some embodiments, $R_7$ and $R_8$ together with the atoms to which they are attached form 5-membered cycloalkyl, 5-membered heterocycloalkyl or 5-membered heterocycloaryl, wherein the cycloalkyl, heterocycloalkyl or heterocycloaryl is optionally substituted with 1-3 of $C_{1-4}$ alkyl or halo $C_{1-4}$ alkyl;

$R^{8a}$ and $R^{8b}$ are each independently selected from H, D, halogen, $C_{1-4}$ alkyl, OH or CN; in some embodiments, $R^{8a}$ and $R^{8b}$ are each independently selected from H or $C_{1-4}$ alkyl;

$R_9$ is selected from $C_{1-4}$ alkyl, $C_{2-6}$ alkynyl, $C_{2-6}$ alkynyl, $C_{3-6}$ cycloalkyl, $C_{1-4}$ alkoxy or —Si($C_{1-4}$ alkyl)$_3$, wherein the alkyl, cycloalkyl or alkoxy is optionally substituted with 1-3 of halogen, D, CN, OH or $C_{1-4}$ alkyl; in some embodiments, $R_9$ is selected from $C_{1-4}$ alkyl; in some embodiments, $R_9$ is selected from methyl, cyclopropyl, ethynyl, propynyl, methoxy or trifluoromethoxy; in some embodiments, $R_9$ is selected from methyl;

$R_{10}$ is selected from $C_{1-4}$ alkyl, wherein the alkyl is optionally substituted with 1-3 of halogen, D, CN, OH, —O—Si($C_{1-4}$ alkyl)$_3$ or —$(CH_2)_n$—Si($C_{1-4}$ alkyl)$_3$; in some embodiments, $R_{10}$ is selected from methyl, wherein the methyl is optionally substituted with 1-3 —Si($C_{1-4}$ alkyl)$_3$; in some embodiments, $R_{10}$ is selected from methyl or ethyl, wherein the methyl or ethyl is optionally substituted with trimethylsilyl; in some embodiments, $R_{10}$ is selected from methyl or ethyl; in some embodiments, $R_{10}$ is selected from methyl;

B is 3- to 12-membered carbocycle or heterocycle containing 0-3 heteroatoms selected from N, S, O or Si, wherein the carbocycle or heterocycle is optionally substituted with 1-3 groups selected from =O, $C_{1-4}$ alkyl, $C_{1-4}$ alkoxy, halo $C_{1-4}$ alkyl, amino, —C(O)$C_{1-4}$ alkyl, hydroxyl and halogen; in some embodiments, B is 4- to 10-membered carbocycle or heterocycle containing 0-3 heteroatoms selected from N, S or O, wherein the carbocycle or heterocycle is optionally substituted with 1-3 groups selected from =O or $C_{1-4}$ alkyl; in some embodiments, B is azacyclohexyl; in some embodiments, B is cyclohexyl; in some embodiments, B is azacyclohexyl; in some embodiments, B is

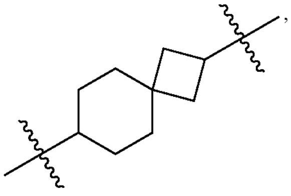

,

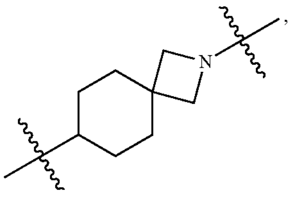

,

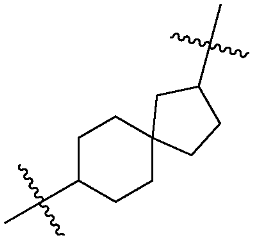

,

-continued

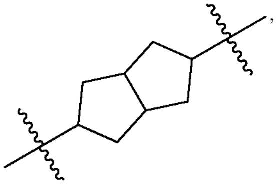

,

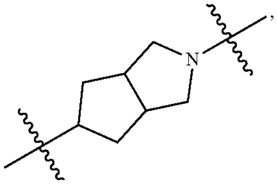

,

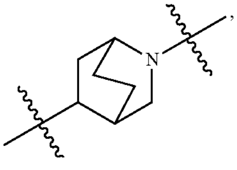

,

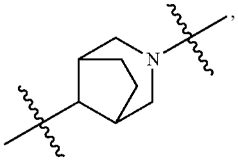

,

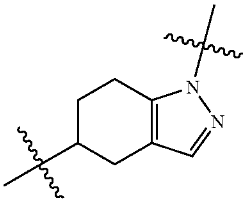

,

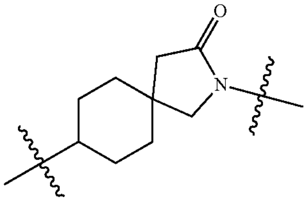

or

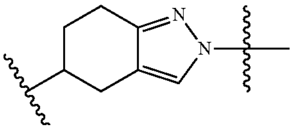

;

alternatively, two substituents on the same carbon atom on the carbocycle or heterocycle in B ring together with the carbon atom to which they are attached form $C_{3-6}$ carbocycle or 3- to 6-membered heterocycloalkyl;

$R_{11}$ is selected from halogen, =O, OH, CN, =N—$R^{11d}$, —$OR^b$, —C(O)$R^{11c}$, —$(CH_2)_n$—$NR^{11a}$—C(O)$R^{11c}$, $C_{1-4}$ alkyl, halo $C_{1-4}$ alkyl, —$C_{1-4}$ alkyl-$C_{1-4}$ alkoxy, $C_{1-4}$ alkoxy, $C_{2-6}$ alkenyl, $C_{2-6}$ alkynyl, —$(CH_2)_n$-(6- to 12-membered aryl), —$(CH_2)_n$-(5- to 10-membered heteroaryl), —$(CH_2)_n$—$C_{3-12}$ cycloalkyl, —$(CH_2)_n$-(3- to 12-membered heterocycloalkyl), —$(CH_2)_n$—Si($C_{1-4}$ alkyl)$_3$, —$S(O)_2NR^{11a}R^{11b}$, —$S(O)_2R^{11c}$—$(CH_2)_n$—C(O)$NR^{11a}R^{11b}$ or —$(CH_2)_n$—$NR^{11a}R^{11b}$, wherein the $CH_2$, alkyl, alkoxy, alkenyl, alkynyl, aryl, heteroaryl, cycloalkyl or heterocycloalkyl is optionally substituted with 1-3 groups selected from: halogen, D, $C_{1-4}$ alkyl, halo $C_{1-4}$ alkyl, $C_{1-4}$ alkoxy, —$C_{1-4}$ alkyl-$C_{1-4}$ alkoxy, =O, CN, OH, —$NR^{11a'}R^{11b'}$, —C(O)—$NR^{11a'}R^{11b'}$, —C(O)$C_{1-4}$ alkyl, —O—$(CH_2)_n$—Si($C_{1-4}$ alkyl)$_3$, —$(CH_2)_n$—Si($C_{1-4}$ alkyl)$_3$, $C_{3-6}$ cycloalkyl, 3- to 12-membered heterocycloalkyl or —O—$(CH_2)_n$—$C_{3-6}$ cycloalkyl, wherein the $CH_2$, alkyl, alkoxy, cycloalkyl or heterocycloalkyl is optionally substituted with 1-3 groups selected from $R^a$; in some embodiments, $R_{11}$ is selected from halogen, =O, OH, CN, =N—$R^{11d}$, —$OR^b$, —C(O)$R_{11c}$, —$(CH_2)_n$—$NR^{11a}$—C(O)$R^{11c}$, $C_{1-4}$ alkyl, halo $C_{1-4}$ alkyl, —$C_{1-4}$ alkyl-$C_{1-4}$ alkoxy, $C_{1-4}$ alkoxy, $C_{2-6}$-alkenyl, $C_{2-6}$ alkynyl, —$(CH_2)_n$-(6- to 12-membered aryl), —$(CH_2)_n$-(5- to 10-membered heteroaryl), —$(CH_2)_n$—$C_{3-12}$ cycloalkyl, —$(CH_2)_n$-(3- to 12-membered heterocycloalkyl), —$(CH_2)_n$—Si($C_{1-4}$ alkyl)$_3$, —$S(O)_2NR^{11a}R^{11b}$—$S(O)_2R^{11c}$, —$(CH_2)_n$—C(O)$NR^{11a}R^{11b}$ or —$(CH_2)_n$—$NR^{11a}R^{11b}$, wherein the $CH_2$, alkyl, alkoxy, alkenyl, alkynyl, aryl, heteroaryl, cycloalkyl or heterocycloalkyl is optionally substituted with 1-3 groups selected from: halogen, D, $C_{1-4}$ alkyl, halo $C_{1-4}$ alkyl, $C_{1-4}$ alkoxy, —$C_{1-4}$ alkyl-$C_{1-4}$ alkoxy, =O, CN, OH, —$NR^{11a'}R^{11b'}$, —C(O)—$NR^{11a'}R^{11b'}$, —C(O)$C_{1-4}$ alkyl, —O—$(CH_2)_n$—Si($C_{1-4}$ alkyl)$_3$, —$(CH_2)_n$—Si($C_{1-4}$ alkyl)$_3$, $C_{3-6}$ cycloalkyl, 3- to 12-membered heterocycloalkyl or —O—$(CH_2)_n$—$C_{3-6}$ cycloalkyl, wherein the $CH_2$, alkyl, alkoxy, cycloalkyl or heterocycloalkyl is optionally substituted with 1-3 groups selected from $R^a$; in some embodiments, $R_{11}$ is selected from —$NR^{11a}R^{11b}$, =N—$R^{11d}$, —$OR^b$, —C(O)$R^{11c}$, $C_{2-6}$ alkynyl, 6- to 12-membered aryl, 5- to 10-membered heteroaryl, $C_{3-6}$ cycloalkyl, 3- to 6-membered heterocycloalkyl or —$(CH_2)_n$—Si($C_{1-4}$ alkyl)$_3$, wherein the aryl, heteroaryl, cycloalkyl or heterocycloalkyl is optionally substituted with 1-3 of halogen, $C_{1-4}$ alkyl, —C(O)$C_{1-4}$ alkyl, —O—$(CH_2)_n$—Si($C_{1-4}$ alkyl)$_3$ or —$(CH_2)_n$—Si($C_{1-4}$ alkyl)$_3$; in some embodiments, $R_{11}$ is selected from —$NR^{11a}R^{11b}$, =N—$R^{11d}$—$OR^b$, —C(O)$R^{11c}$, $C_{2-6}$ alkynyl, 6- to 12-membered aryl or 5- to 10-membered heteroaryl, wherein the aryl or heteroaryl is optionally substituted with 1-3 of halogen, $C_{1-4}$ alkyl or —C(O)$C_{1-4}$ alkyl; in some embodiments, $R_{11}$ is selected from —$NR^{11a}R^{11b}$, —C(O)$R^{11c}$, 6- to 12-membered aryl or 5- to 10-membered heteroaryl, wherein the aryl or heteroaryl is optionally substituted with 1-3 of halogen, $C_{1-4}$ alkyl or —C(O)$C_{1-4}$ alkyl; in some embodiments, $R_{11}$ is selected from —$NR^{11a}R^{11b}$, —C(O)$R^{11c}$ or 5- to 10-membered heteroaryl, wherein the heteroaryl is optionally substituted with 1-3 of halogen, $C_{1-4}$ alkyl or —C(O)$C_{1-4}$ alkyl; in some embodiments, $R_{11}$ is selected from —$NR^{11a}R^{11b}$; in some embodiments, $R_{11}$ is selected from —C(O)$R^{11c}$; in some embodiments, $R_{11}$ is selected from 5- to 10-membered heteroaryl, wherein the heteroaryl is optionally substituted with 1-3 of $C_{1-4}$ alkyl or —C(O)$C_{1-4}$ alkyl;

$R^{11a}$ and $R^{11b}$ are each independently selected from H, D, $C_{1-4}$ alkyl, $C_{1-4}$ alkoxy, —C(O)$R^{11c}$, —C(O)—$(CH_2)_n$—$R^{11c}$, —$S(O)_2$—$NR^{11a'}R^{11b'}$, —$S(O)_2R^{11c}$—$(CH_2)_n$-(6- to 12-membered aryl), —$(CH_2)_n$-(5- to 12-membered heteroaryl), —$(CH_2)_n$—$C_{3-12}$ cycloalkyl, —$(CH_2)_n$-(3- to 12-membered heterocycloalkyl), —$S(O)_2C_{1-4}$ alkyl or —$(CH_2)_n$—Si($C_{1-4}$ alkyl)$_3$, wherein the alkyl, alkoxy, aryl, heteroaryl, cycloalkyl or heterocycloalkyl is optionally substituted with 1-3 $R^a$; in some embodiments, $R^{11a}$ and $R^{11b}$ are each independently selected from H, $C_{1-4}$ alkyl, $C_{1-4}$ alkoxy, —C(O)$R^{11c}$, 6- to 12-membered aryl, 5- to 12-membered heteroaryl, $C_{3-6}$ cycloalkyl, 3- to 6-membered heterocycloalkyl, —$S(O)_2C_{1-4}$ alkyl or —$(CH_2)_n$—Si($C_{1-4}$ alkyl)$_3$, wherein the alkyl, alkoxy, aryl, heteroaryl, cycloalkyl or heterocycloalkyl is optionally substituted with 1-3 $R^a$; in some embodiments, $R^{11a}$ and $R^{11b}$ are each independently selected from H, $C_{1-4}$ alkyl, —C(O)$R^{11c}$, 5- to 12-membered heteroaryl, $C_{3-6}$ cycloalkyl, 3- to 6-membered heterocycloalkyl or —$S(O)_2C_{1-4}$ alkyl, wherein the alkyl, alkoxy, heteroaryl, cycloalkyl or heterocycloalkyl is optionally substituted with 1-3 $R^a$; in some embodiments, $R^{11a}$ is selected from H or $C_{1-4}$ alkyl; in some embodiments, $R^{11b}$ is selected from —C(O)$R^{11c}$, 5- to 12-membered heteroaryl, $C_{3-6}$ cycloalkyl, 3- to 6-membered heterocycloalkyl or —$S(O)_2C_{1-4}$ alkyl, wherein the heteroaryl, cycloalkyl or heterocycloalkyl is optionally substituted with 1-3 $R^a$; in some embodiments, $R^{11b}$ is selected from —$C(O)R^{11c}$; in some embodiments, $R^{11b}$ is selected from 5- to 12-membered heteroaryl, wherein the heteroaryl is optionally substituted with 1-3 $R^a$; in some embodiments, $R^{11b}$ is selected from $C_{3-6}$ cycloalkyl, wherein the cycloalkyl is optionally substituted with 1-3 $R^a$; in some embodiments, $R^{11b}$ is selected from 3- to 6-membered heterocycloalkyl, wherein the heterocycloalkyl is optionally substituted with 1-3 $R^a$;

alternatively, $R^{11a}$ and $R^{11b}$ together with the nitrogen atom to which they are attached form 3- to 6-membered heterocycloalkyl, wherein the heterocycloalkyl is optionally substituted with 1-3 $R^c$; in some embodiments, $R^{11a}$ and $R^{11b}$ together with the nitrogen atom to which they are attached form 3- to 6-membered heterocycloalkyl, wherein the heterocycloalkyl is optionally substituted with 1-3 of halogen, cyano, $C_{1-4}$ alkoxy, halo $C_{1-4}$ alkoxy, —$NHC_{1-4}$ alkyl, —$N(C_{1-4}$ alkyl$)_2$, —NH(3- to 6-membered heterocycloalkyl), —$NHC_{3-6}$ cycloalkyl, —O—$C_{3-6}$ cycloalkyl, —O-(3- to 6-membered heterocycloalkyl), —O—$(CH_2)_n$—Si($C_{1-4}$ alkyl$)_3$ or —$(CH_2)_n$—Si($C_{1-4}$ alkyl$)_3$; in some embodiments, $R^{11a}$ and $R^{11b}$ together with the nitrogen atom to which they are attached form azacyclobutyl, which is optionally substituted with 1-3 of halogen, cyano, $C_{1-4}$ alkoxy, halo $C_{1-4}$ alkoxy, —$NHC_{1-4}$ alkyl, —$N(C_{1-4}$ alkyl$)_2$, —NH(3- to 6-membered heterocycloalkyl), —$NHC_{3-6}$ cycloalkyl, —O—$C_{3-6}$ cycloalkyl or —O-(3- to 6-membered heterocycloalkyl);

$R^{11c}$ is selected from $C_{1-4}$ alkyl, $C_{1-4}$ alkoxy, $C_{1-4}$ alkyl-$C_{1-4}$ alkoxy, amino, —$NHC_{1-4}$ alkyl, —$N(C_{1-4}$ alkyl$)_2$, —NH(3- to 6-membered heterocycloalkyl), —$NHC_{3-6}$ cycloalkyl, —$(CH_2)_n$—$C_{3-6}$ cycloalkyl, —$(CH_2)_n$-(3- to 6-membered heterocycloalkyl), —O—$C_{1-4}$ alkyl, —O—$C_3$-6 cycloalkyl, —O-(3- to 6-membered heterocycloalkyl), —$(CH_2)_n$-(6- to 12-membered aryl), —$(CH_2)_n$-(5- to 12-membered heteroaryl) or —$(CH_2)_n$—Si($C_{1-4}$ alkyl$)_3$, wherein the alkyl, alkoxy, heterocycloalkyl, cycloalkyl, aryl or heteroaryl is optionally substituted with 1-3 of halogen, cyano, $C_{1-4}$ alkyl, halo $C_{1-4}$ alkyl, $C_{1-4}$ alkoxy, halo $C_{1-4}$ alkoxy, —$NHC_{1-4}$ alkyl, —$N(C_{1-4}$ alkyl$)_2$, —NH(3- to 6-membered heterocycloalkyl), —$NHC_{3-6}$ cycloalkyl, —O—$C_{3-6}$ cycloalkyl, —O-(3- to 6-membered heterocycloalkyl) or —Si($C_{1-4}$ alkyl$)_3$; in some embodiments, $R^{11c}$ is selected from $C_{1-4}$ alkyl, $C_{1-4}$ alkoxy, amino, —$NHC_{1-4}$ alkyl, —$N(C_{1-4}$ alkyl$)_2$, —NH(3- to 6-membered heterocycloalkyl), —$NHC_{3-6}$ cycloalkyl, $C_{3-6}$ cycloalkyl, 3- to 6-membered heterocycloalkyl, —O—$C_{1-4}$ alkyl, —O—$C_{3-6}$ cycloalkyl, —O-(3- to 6-membered heterocycloalkyl) or —$(CH_2)_n$—Si($C_{1-4}$ alkyl$)_3$, wherein the alkyl, alkoxy, heterocycloalkyl or cycloalkyl is optionally substituted with 1-3 of halogen, cyano, $C_{1-4}$ alkoxy, halo $C_{1-4}$ alkoxy, —$NHC_{1-4}$ alkyl, —$N(C_{1-4}$ alkyl$)_2$, —NH(3- to 6-membered heterocycloalkyl), —$NHC_{3-6}$ cycloalkyl, —O—$C_{3-6}$-cycloalkyl, —O-(3- to 6-membered heterocycloalkyl) or —Si ($C_{1-4}$ alkyl$)_3$; in some embodiments, $R^{11c}$ is selected from $C_{1-4}$ alkyl, $C_{1-4}$ alkoxy, amino, —$NHC_{1-4}$ alkyl, —$N(C_{1-4}$ alkyl$)_2$, —NH(3- to 6-membered heterocycloalkyl), 3- to 6-membered heterocycloalkyl or —$(CH_2)_n$—Si($C_{1-4}$ alkyl$)_3$, wherein the heterocycloalkyl or cycloalkyl is optionally substituted with 1-3 of halogen, cyano, $C_{1-4}$ alkoxy, halo $C_{1-4}$ alkoxy, —$NHC_{1-4}$ alkyl, —$N(C_{1-4}$ alkyl$)_2$, —NH(3- to 6-membered heterocycloalkyl), —$NHC_{3-6}$ cycloalkyl, —O—$C_{3-6}$ cycloalkyl, —O-(3- to 6-membered heterocycloalkyl) or —Si($C_{1-4}$ alkyl$)_3$; in some embodiments, $R^{11c}$ is selected from $C_{1-4}$ alkyl, $C_{1-4}$ alkoxy, —$NHC_{1-4}$ alkyl, —NH(3- to 6-membered heterocycloalkyl) or 3- to 6-membered heterocycloalkyl, wherein the heterocycloalkyl or cycloalkyl is optionally substituted with 1-3 of halogen, cyano, $C_{1-4}$ alkoxy, halo $C_{1-4}$ alkoxy, —$NHC_{1-4}$ alkyl, —$N(C_{1-4}$-alkyl$)_2$, —NH(3- to 6-membered heterocycloalkyl), —$NHC_{3-6}$ cycloalkyl, —O—$C_{3-6}$ cycloalkyl or —O-(3- to 6-membered heterocycloalkyl); in some embodiments, $R^{11c}$ is selected from $C_{1-4}$ alkyl or $C_{1-4}$ alkoxy; in some embodiments, $R^{11c}$ is selected from —$NHC_{1-4}$ alkyl, —NH(3- to 6-membered heterocycloalkyl) or 3- to 6-membered heterocycloalkyl, wherein the heterocycloalkyl or alkyl is optionally substituted with 1-3 of halogen, cyano, $C_{1-4}$ alkoxy, halo $C_{1-4}$ alkoxy, —$NHC_{1-4}$ alkyl, —$N(C_{1-4}$ alkyl$)_2$, —NH(3- to 6-membered heterocycloalkyl), —$NHC_{3-6}$ cycloalkyl, —O—$C_{3-6}$ cycloalkyl or —O-(3- to 6-membered heterocycloalkyl); in some embodiments, $R^{11c}$ is selected from —$NHC_{1-4}$ alkyl, —NH(3- to 6-membered heterocycloalkyl) or 3- to 6-membered heterocycloalkyl;

$R^{11d}$ is selected from —O—$R^a$; in some embodiments, $R^{11d}$ is selected from —O-(3-6-membered heterocycloalkyl);

$R^a$ is selected from halogen, D, OH, cyano, $C_{1-4}$ alkyl, halo $C_{1-4}$ alkyl, $C_{1-4}$ alkoxy, halo $C_{1-4}$ alkoxy, $C_{2-6}$ alkenyl, $C_{2-6}$ alkynyl, —$S(O)_2C_{1-4}$ alkyl, —$C(O)C_{1-4}$ alkyl, —$(CH_2)_n$—Si($C_{1-4}$ alkyl$)_3$, $C_{3-6}$ cycloalkyl, 3- to 6-membered heterocycloalkyl, 6- to 12-membered aryl or 5- to 12-membered heteroaryl, wherein the alkyl, alkoxy, cycloalkyl, heterocycloalkyl, aryl or heteroaryl is optionally substituted with 1-3 of halogen, D, cyano, hydroxyl, $C_{1-4}$ alkyl or halo $C_{1-4}$ alkyl; in some embodiments, $R^a$ is selected from halogen, cyano, $C_{1-4}$ alkyl, halo $C_{1-4}$ alkyl, $C_{1-4}$ alkoxy, halo $C_{1-4}$ alkoxy, $C_{2-6}$ alkenyl, $C_{2-6}$ alkynyl, —$S(O)_2C_{1-4}$ alkyl, —C(O) $C_{1-4}$ alkyl or —$(CH_2)_n$—Si($C_{1-4}$ alkyl$)_3$, wherein the alkyl or alkoxy is optionally substituted with 1-3 of halogen, cyano or hydroxyl; in some embodiments, $R^a$ is selected from halogen, cyano, $C_{1-4}$ alkyl, $C_{1-4}$ alkoxy, halo $C_{1-4}$ alkoxy, $C_{2-6}$ alkynyl, —$S(O)_2C_{1-4}$ alkyl or —$C(O)C_{1-4}$ alkyl, wherein the alkyl or alkoxy is optionally substituted with 1-3 of halogen, cyano or hydroxyl;

$R^b$ is selected from —$(CH_2)_n$-(6- to 12-membered aryl), —$(CH_2)_n$-(5- to 12-membered heteroaryl), —$(CH_2)_n$-(3- to 6-membered heterocycloalkyl), —$(CH_2)_n$—$C_{3-6}$ cycloalkyl, $C_{1-4}$ alkyl, $C_{2-6}$ alkenyl, $C_{2-6}$ alkynyl or —$(CH_2)_n$—C(O)—$NR^{11a'}R^{11b'}$, wherein the aryl, heteroaryl, cycloalkyl, heterocycloalkyl, alkyl, alkenyl or alkynyl is optionally substituted with 1-3 of halogen, $C_{1-4}$ alkyl, halo $C_{1-4}$ alkyl, CN or —$(CH_2)_n$—Si($C_{1-4}$ alkyl$)_3$; in some embodiments, $R^b$ is selected from 6- to 12-membered aryl, 5- to 12-membered heteroaryl, $C_{3-6}$ cycloalkyl or 3- to 6-membered heterocycloalkyl, wherein the aryl, heteroaryl, cycloalkyl or heterocycloalkyl is optionally substituted with 1-3 halogen; in some embodiments, $R^b$ is selected from $C_{3-6}$ cycloalkyl, wherein the cycloalkyl is optionally substituted with 1-3 halogen;

$R^c$ is selected from halogen, =O, CN, OH, $C_{1-4}$ alkyl, halo $C_{1-4}$ alkyl, $C_{1-4}$ alkoxy, halo $C_{1-4}$ alkoxy, —$NHC_{1-4}$ alkyl, —$N(C_{1-4}$ alkyl$)_2$, —C(O)—$NR^{11a'}R^{11b'}$, 3- to 6-membered heterocycloalkyl, —$C_{3-6}$ cycloalkyl, —NH(3- to 6-membered heterocycloalkyl), —$NHC_{3-6}$ cycloalkyl, —O—$(CH_2)_n$—$C_{3-6}$ cycloalkyl, —O—$(CH_2)_n$-(3- to 6-membered heterocycloalkyl), —O—$(CH_2)_n$—$Si(C_{1-4}$ alkyl$)_3$ or —$(CH_2)_n$—$Si(C_{1-4}$ alkyl$)_3$, wherein the alkyl, alkoxy, cycloalkyl or heterocycloalkyl is optionally further substituted with 1-3 of halogen, D, CN, OH, amino, $C_{1-4}$ alkyl or $C_{1-4}$ alkoxy; in some embodiments, $R^c$ is selected from CN, OH, $C_{1-4}$ alkyl, $C_{1-4}$ alkoxy, —$NHC_{1-4}$ alkyl, —$N(C_{1-4}$ alkyl$)_2$, —C(O)—$NR^{11a'}R^{11b'}$, 3- to 6-membered heterocycloalkyl, —$C_{3-6}$ cycloalkyl, —NH(3- to 6-membered heterocycloalkyl), —$NHC_{3-6}$ cycloalkyl, —O—$(CH_2)_n$—$C_{3-6}$ cycloalkyl, —O—$(CH_2)_n$-(3- to 6-membered heterocycloalkyl), —O—$(CH_2)_n$—$Si(C_{1-4}$ alkyl$)_3$ or —$(CH_2)_n$—$Si(C_{1-4}$ alkyl$)_3$, wherein the alkyl, alkoxy, cycloalkyl or heterocycloalkyl is optionally further substituted with 1-3 of halogen or $C_{1-4}$ alkyl; in some embodiments, $R^c$ is selected from methoxy, ethoxy, cyano, —$N(CH_3)_2$, —$CH_2$-methoxy, hydroxyl, —O—$(CH_2)_2$—$C_{3-6}$ cycloalkyl, —$C(O)N(CH_3)_2$, 5- to 6-membered heterocycloalkyl, —$Si(CH_3)_3$ or —O-$CD_3$; in some embodiments, $R^c$ is selected from

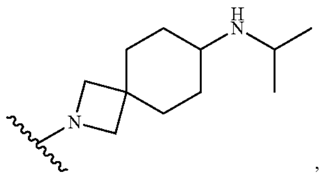

,

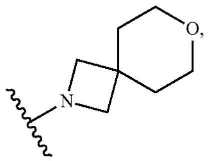

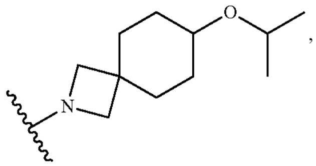

,

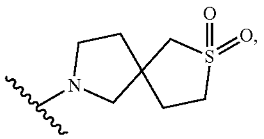

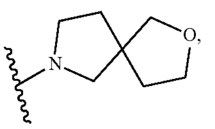

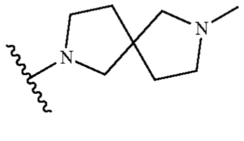

or

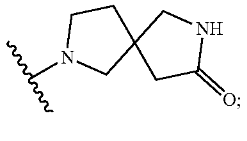

$R^{11a'}$ and $R^{11b'}$ are each independently selected from H, D, $C_{1-4}$ alkyl, halogen, CN or OH; in some embodiments, $R^{11a'}$ and $R^{11b'}$ are each independently selected from H;

alternatively, $R^{11a'}$ and $R^{11b'}$ together with the nitrogen atom to which they are attached form 3- to 6-membered heterocycloalkyl, wherein the heterocycloalkyl is optionally substituted with 1-3 of halogen, D, CN, OH, $C_{1-4}$ alkyl, halo $C_{1-4}$ alkyl, $C_{1-4}$ alkoxy or halo $C_{1-4}$ alkoxy; in some embodiments, $R^{11a'}$ and $R^{11b'}$ together with the nitrogen atom to which they are attached form 5- to 6-membered heterocycloalkyl, wherein the heterocycloalkyl is optionally substituted with 1-3 of halogen, $C_{1-4}$ alkyl, $C_{1-4}$ alkoxy or halo $C_{1-4}$ alkoxy;

X is selected from —C— or —N—; in some embodiments, X is selected from —C—; in some embodiments, X is N, provided that when X is N, $R_7$ is absent;

n is selected from 0, 1, 2, 3, 4 or 5; in some embodiments, n is selected from 0, 1, 2 or 3; in some embodiments, n is selected from 0 or 1;

provided that the compound of formula (I) is not selected from the following compounds: when $R_1$ is selected from methyl, $R_2$ is selected from H, $R_3$ is selected from methyl, $R_4$ and $R_5$ are selected from H, $R_{4'}$ and $R_{5'}$ together with the carbon atom to which they are attached form ═O, $R_6$ and $R_7$ are selected from H, X is selected from —C—, $R_8$ is selected from Cl, $R_9$ is selected from methyl, $R_{10}$ is selected from methyl, and Y is selected from —CH—:

(1) $R_{11}$ is selected from —$N(CH_3)_2$,

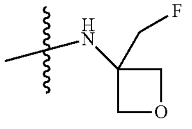

or

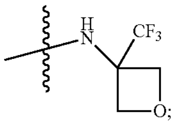

or (2) if $R^{11a}$ and $R^{11b}$ together with the nitrogen atom form azacyclobutyl, or $R_{11}$ is selected from azacyclobutyl, the azacyclobutyl is substituted with the following substituents: F, difluoromethoxy, cyclopropyloxy or methoxy.

Embodiment one of the present disclosure relates to a compound of formula (I), or a stereoisomer, a pharmaceutically acceptable salt, a solvate, and a eutectic or deuterated compound thereof, (I)

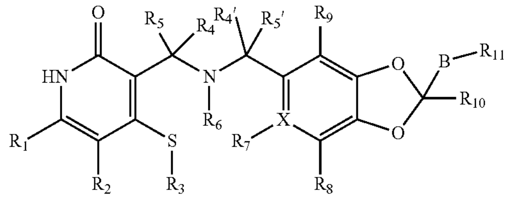

wherein $R_1$ is selected from H, D, cyano, $C_{1-4}$ alkyl, $C_{3-6}$ cycloalkyl or halo $C_{1-4}$ alkyl;

$R_2$ is selected from H, D or $C_{1-4}$ alkyl;

$R_3$ is selected from $C_{1-6}$ alkyl, halo $C_{1-6}$ alkyl, 3- to 6-membered heterocycloalkyl or $C_{3-6}$ cycloalkyl, wherein the alkyl, cycloalkyl or heterocycloalkyl is optionally substituted with 1-3 of the following groups: D, OH, CN, amino or halogen;

alternatively, $R_1$ and $R_2$ form 3- to 6-membered cycloalkyl, wherein the cycloalkyl is optionally substituted with 1-3 of halogen, D, CN, OH, amino or $C_{1-4}$ alkyl; or alternatively, $R_2$ and $R_3$ form 3- to 6-membered heterocycloalkyl, wherein the heterocycloalkyl is optionally substituted with 1-3 of halogen, D, OH, amino, $C_{1-4}$ alkyl or CN;

$R_4$ and $R_5$ are each independently selected from H, D, halogen or $C_{1-4}$ alkyl;

$R_{4'}$ and $R_{5'}$ together with the carbon atom to which they are attached form $C_{3-6}$ carbocycle, or 3- to 7-membered heterocycloalkyl containing 1-3 heteroatoms selected from N, S or O; or $R_{4'}$ and $R_{5'}$ together form ═O;

$R_6$ is selected from H, D or $C_{1-4}$ alkyl;

$R_7$ is selected from H, D or halogen;

$R_8$ is selected from H, D, CN, $C_{1-6}$ alkyl, halo $C_{1-6}$ alkyl, halogen, —$NR^{8a}R^{8b}$—, —$NR^{8a}$—C(O)—$C_{1-4}$ alkyl, $C_{1-6}$ alkoxy, halo $C_{1-6}$ alkoxy, $C_{2-6}$ alkenyl, $C_{2-6}$ alkynyl, $C_{3-6}$ cycloalkyl, 3- to 6-membered heterocycloalkyl, 6- to 12-membered aryl, 5- to 10-membered heteroaryl or —Si($C_{1-4}$ alkyl)$_3$, wherein the alkyl, alkoxy, cycloalkyl, heterocycloalkyl, aryl or heteroaryl is optionally substituted with 1-3 of halogen, D, $C_{1-4}$ alkyl, OH, CN or amino; or $R_7$ and $R_8$ together with the atoms to which they are attached form $C_{3-6}$ cycloalkyl, 3- to 6-membered heterocycloalkyl, 6- to 12-membered aryl or 5- to 10-membered heteroaryl, wherein the cycloalkyl, heterocycloalkyl, aryl or heteroaryl is optionally substituted with 1-3 of halogen, D, $C_{1-4}$ alkyl, halo $C_{1-4}$ alkyl, $C_{1-4}$ alkoxy or halo $C_{1-4}$ alkoxy;

$R^{8a}$ and $R^{8b}$ are each independently selected from H, D, halogen, $C_{1-4}$ alkyl, OH or CN;

$R_9$ is selected from $C_{1-4}$ alkyl, $C_{2-6}$ alkenyl, $C_{2-6}$ alkynyl, $C_{3-6}$ cycloalkyl, $C_{1-4}$ alkoxy or —Si($C_{1-4}$ alkyl)$_3$, wherein the alkyl, cycloalkyl or alkoxy is optionally substituted with 1-3 of halogen, D, CN, OH or $C_{1-4}$ alkyl;

$R_{10}$ is selected from $C_{1-4}$ alkyl, wherein the alkyl is optionally substituted with 1-3 of halogen, D, CN, OH, —O—Si($C_{1-4}$ alkyl)$_3$ or —$(CH_2)_n$—Si($C_{1-4}$ alkyl)$_3$;

B is 3- to 12-membered carbocycle or heterocycle containing 0-3 heteroatoms selected from N, S, O or Si, wherein the carbocycle or heterocycle is optionally substituted with 1-3 groups selected from =O, $C_{1-4}$ alkyl, $C_{1-4}$ alkoxy, halo $C_{1-4}$ alkyl, amino, —C(O)$C_{1-4}$ alkyl, hydroxyl and halogen; alternatively, two substituents on the same carbon atom on the carbocycle or heterocycle together with the carbon atom to which they are attached form $C_{3-6}$ carbocycle or 3- to 6-membered heterocycloalkyl;

$R_{11}$ is selected from halogen, =O, OH, CN, =N—$R^{11d}$, —$OR^b$, —C(O)$R^{11c}$, —$(CH_2)_n$—$NR^{11a}$—C(O)$R^{11c}$, $C_{1-4}$ alkyl, halo $C_{1-4}$ alkyl, —$C_{1-4}$ alkyl-$C_{1-4}$ alkoxy, $C_{1-4}$ alkoxy, $C_{2-6}$ alkenyl, $C_{2-6}$ alkynyl, —$(CH_2)_n$-(6- to 12-membered aryl), —$(CH_2)_n$-(5- to 10-membered heteroaryl), —$(CH_2)_n$—$C_{3-12}$ cycloalkyl, —$(CH_2)_n$-(3- to 12-membered heterocycloalkyl), —$(CH_2)_n$—Si($C_{1-4}$ alkyl)$_3$, —$S(O)_2NR^{11a}R^{11b}$, —$S(O)_2R^{11c}$, —$(CH_2)_n$—C(O)$NR^{11a}R^{11b}$ or —$(CH_2)_n$—$NR^{11a}R^{11b}$, wherein the $CH_2$, alkyl, alkoxy, alkenyl, alkynyl, aryl, heteroaryl, cycloalkyl or heterocycloalkyl is optionally substituted with 1-3 groups selected from: halogen, D, $C_{1-4}$ alkyl, halo $C_{1-4}$ alkyl, $C_{1-4}$ alkoxy, —$C_{1-4}$ alkyl-$C_{1-4}$ alkoxy, =O, CN, OH, —$NR^{11a'}R^{11b'}$, —C(O)—$NR^{11a'}R^{11b'}$, —C(O)$C_{1-4}$ alkyl, —O—$(CH_2)_n$—Si($C_{1-4}$ alkyl)$_3$, —$(CH_2)_n$—Si($C_{1-4}$ alkyl)$_3$, $C_{3-6}$ cycloalkyl, 3- to 12-membered heterocycloalkyl or —O—$(CH_2)_n$—$C_{3-6}$ cycloalkyl, wherein the $CH_2$, alkyl, alkoxy, cycloalkyl or heterocycloalkyl is optionally substituted with 1-3 groups selected from $R^a$;

$R^{11a}$ and $R^{11b}$ are each independently selected from H, D, $C_{1-4}$ alkyl, $C_{1-4}$ alkoxy, —C(O)$R^{11c}$—C(O)—$(CH_2)_n$—$R^{11c}$—$S(O)_2$—$NR^{11a'}R^{11b'}$, —$S(O)_2R^{11c}$, —$(CH_2)_n$-(6- to 12-membered aryl), —$(CH_2)_n$-(5- to 12-membered heteroaryl), —$(CH_2)_n$—$C_{3-12}$ cycloalkyl, —$(CH_2)_n$-(3- to 12-membered heterocycloalkyl), —$S(O)_2C_{1-4}$ alkyl or —$(CH_2)_n$—Si($C_{1-4}$ alkyl)$_3$, wherein the alkyl, alkoxy, aryl, heteroaryl, cycloalkyl or heterocycloalkyl is optionally substituted with 1-3 $R^a$;

alternatively, $R^{11a}$ and $R^{11b}$ together with the nitrogen atom to which they are attached form 3- to 12-membered heterocycloalkyl, wherein the heterocycloalkyl is optionally substituted with 1-3 $R^c$;

$R^{11c}$ is selected from $C_{1-4}$ alkyl, $C_{1-4}$ alkoxy, $C_{1-4}$ alkyl-$C_{1-4}$ alkoxy, amino, —$NHC_{1-4}$ alkyl, —N($C_{1-4}$ alkyl)$_2$, —NH(3- to 6-membered heterocycloalkyl), —$NHC_{3-6}$ cycloalkyl, —$(CH_2)_n$—$C_{3-6}$ cycloalkyl, —$(CH_2)_n$-(3- to 6-membered heterocycloalkyl), —O—$C_{1-4}$ alkyl, —O—$C_{3-6}$ cycloalkyl, —O-(3- to 6-membered heterocycloalkyl), —$(CH_2)_n$-(6- to 12-membered aryl), —$(CH_2)_n$-(5- to 12-membered heteroaryl) or —$(CH_2)_n$—Si($C_{1-4}$ alkyl)$_3$, wherein the alkyl, alkoxy, heterocycloalkyl, cycloalkyl, aryl or heteroaryl is optionally substituted with 1-3 of halogen, cyano, $C_{1-4}$ alkyl, halo $C_{1-4}$ alkyl, $C_{1-4}$ alkoxy, halo $C_{1-4}$ alkoxy, —$NHC_{1-4}$ alkyl, —N($C_{1-4}$ alkyl)$_2$, —NH(3- to 6-membered heterocycloalkyl), —$NHC_{3-6}$ cycloalkyl, —O—$C_{3-6}$ cycloalkyl, —O-(3- to 6-membered heterocycloalkyl) or —Si($C_{1-4}$ alkyl)$_3$;

$R^{11d}$ is selected from —O—$R^a$;

$R^a$ is selected from halogen, D, OH, cyano, $C_{1-4}$ alkyl, halo $C_{1-4}$ alkyl, $C_{1-4}$ alkoxy, halo $C_{1-4}$ alkoxy, $C_{2-6}$ alkenyl, $C_{2-6}$ alkynyl, —$S(O)_2C_{1-4}$ alkyl, —C(O)$C_{1-4}$ alkyl, —$(CH_2)_n$—Si($C_{1-4}$ alkyl)$_3$, $C_{3-6}$ cycloalkyl, 3- to 6-membered heterocycloalkyl, 6- to 12-membered aryl or 5- to 12-membered heteroaryl, wherein the alkyl, alkoxy, cycloalkyl, heterocycloalkyl, aryl or heteroaryl is optionally substituted with 1-3 of halogen, D, cyano, hydroxyl, $C_{1-4}$ alkyl or halo $C_{1-4}$ alkyl;

$R^b$ is selected from —$(CH_2)_n$-(6- to 12-membered aryl), —$(CH_2)_n$-(5- to 12-membered heteroaryl), —$(CH_2)_n$-(3- to 6-membered heterocycloalkyl), —$(CH_2)_n$—$C_{3-6}$ cycloalkyl, $C_{1-4}$ alkyl, $C_{2-6}$ alkenyl, $C_{2-6}$ alkynyl or —$(CH_2)_n$—C(O)—$NR^{11a'}R^{11b'}$, wherein the aryl, heteroaryl, cycloalkyl, heterocycloalkyl, alkyl, alkenyl or alkynyl is optionally substituted with 1-3 of halogen, $C_{1-4}$ alkyl, halo $C_{1-4}$ alkyl, CN or —$(CH_2)_n$—Si($C_{1-4}$ alkyl)$_3$;

$R^c$ is selected from halogen, =O, CN, OH, $C_{1-4}$ alkyl, halo $C_{1-4}$ alkyl, $C_{1-4}$ alkoxy, halo $C_{1-4}$ alkoxy, —$NHC_{1-4}$ alkyl, —N($C_{1-4}$ alkyl), —C(O)—$NR^{11a'}R^{11b'}$, 3- to 6-membered heterocycloalkyl, —$C_{3-6}$ cycloalkyl, —NH(3- to 6-membered heterocycloalkyl), —$NHC_{3-6}$ cycloalkyl, —O—$(CH_2)_n$—$C_{3-6}$ cycloalkyl, —O—$(CH_2)_n$-(3- to 6-membered heterocycloalkyl), —O—$(CH_2)_n$—Si($C_{1-4}$ alkyl)$_3$ or —$(CH_2)_n$—Si($C_{1-4}$ alkyl)$_3$, wherein the alkyl, alkoxy, cycloalkyl or heterocycloalkyl is optionally further substituted with 1-3 of halogen, D, CN, OH, amino, $C_{1-4}$ alkyl or $C_{1-4}$ alkoxy;

$R^{11a'}$ and $R^{11b'}$ are each independently selected from H, D, $C_{1-4}$ alkyl, halogen, CN or OH;

alternatively, $R^{11a'}$ and $R^{11b'}$ together with the nitrogen atom to which they are attached form 3- to 6-membered heterocycloalkyl, wherein the heterocycloalkyl is optionally substituted with 1-3 of halogen, D, CN, OH, $C_{1-4}$ alkyl, halo $C_{1-4}$ alkyl, $C_{1-4}$ alkoxy or halo $C_{1-4}$ alkoxy;

X is selected from —C— or —N—; provided that when X is selected from N, $R_7$ is absent;

n is selected from 0, 1, 2, 3, 4 or 5.

Embodiment two of the present disclosure relates to a compound of formula (I), or a stereoisomer, a pharmaceutically acceptable salt, a solvate, and a eutectic or deuterated compound thereof, wherein the compound has a structure of formula (I-a):

(I-a)

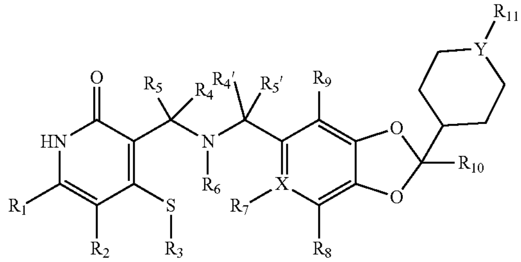

wherein $R_1$ is selected from H, cyano, $C_{1-4}$ alkyl, $C_{3-6}$ cycloalkyl or halo $C_{1-4}$ alkyl;

$R_2$ is selected from H or $C_{1-4}$ alkyl;

$R_3$ is selected from $C_{1-6}$ alkyl, halo $C_{1-6}$ alkyl, 3- to 6-membered heterocycloalkyl or $C_{3-6}$ cycloalkyl, wherein the alkyl, cycloalkyl or heterocycloalkyl is optionally substituted with 1-3 of the following groups: OH, cyano, amino or halogen;

alternatively, $R_1$ and $R_2$ form 3- to 6-membered cycloalkyl, wherein the cycloalkyl is optionally substituted with 1-3 halogen; or alternatively, $R_2$ and $R_3$ form 3- to 6-membered heterocycloalkyl, wherein the heterocycloalkyl is optionally substituted with 1-3 of halogen, OH or amino;

$R_4$ and $R_5$ are each independently selected from H, halogen or $C_{1-4}$ alkyl;

$R_{4'}$ and $R_{5'}$ together with the carbon atom to which they are attached form 3- to 5-membered heterocycloalkyl; or $R_{4'}$ and $R_{5'}$ together form =O;

$R_6$ is selected from H or $C_{1-4}$ alkyl;

$R_7$ is selected from H or halogen;

$R_8$ is selected from H, halogen, $C_{3-6}$ cycloalkyl, 3- to 6-membered heterocycloalkyl, $C_{1-4}$ alkoxy or —Si($C_{1-4}$ alkyl)$_3$, wherein the alkoxy, cycloalkyl or heterocycloalkyl is optionally substituted with 1-3 halogen; or $R_7$ and $R_8$ together with the atoms to which they are attached form $C_{3-6}$ cycloalkyl, 3- to 6-membered heterocycloalkyl, 6- to 12-membered aryl or 5- to 10-membered heteroaryl, wherein the cycloalkyl, heterocycloalkyl, aryl or heteroaryl is optionally substituted with 1-3 of halogen, $C_{1-4}$ alkyl or halo $C_{1-4}$ alkyl;

$R_9$ is selected from $C_{1-4}$ alkyl, $C_{2-6}$ alkynyl, $C_{3-6}$ cycloalkyl, $C_{1-4}$ alkoxy or —Si($C_{1-4}$ alkyl)$_3$, wherein the alkyl, cycloalkyl or alkoxy is optionally substituted with 1-3 halogen;

$R_{10}$ is selected from $C_{1-4}$ alkyl, wherein the alkyl is optionally substituted with 1-3 of halogen or —Si($C_{1-4}$ alkyl)$_3$;

$R_{11}$ is selected from —$NR^{11a}R^{11b}$, =N—$R^{11d}$—$OR^b$, —C(O)$R^{11c}$, $C_{2-6}$ alkynyl, 6- to 12-membered aryl, 5- to 10-membered heteroaryl, $C_{3-6}$ cycloalkyl, 3- to 6-membered heterocycloalkyl or —$(CH_2)_n$—Si($C_{1-4}$ alkyl)$_3$, wherein the aryl, heteroaryl, cycloalkyl or heterocycloalkyl is optionally substituted with 1-3 of halogen, $C_{1-4}$ alkyl, —C(O)$C_{1-4}$ alkyl, —O—$(CH_2)_n$—Si($C_{1-4}$ alkyl)$_3$ or —$(CH_2)_n$—Si($C_{1-4}$ alkyl)$_3$;

$R^{11a}$ and $R^{11b}$ are each independently selected from H, $C_{1-4}$ alkyl, $C_{1-4}$ alkoxy, —C(O)$R^{11c}$, 6- to 12-membered aryl, 5- to 12-membered heteroaryl, $C_{3-6}$ cycloalkyl, 3- to 6-membered heterocycloalkyl, —S(O)$_2C_{1-4}$ alkyl or —$(CH_2)_n$—Si($C_{1-4}$ alkyl)$_3$, wherein the alkyl, alkoxy, aryl, heteroaryl, cycloalkyl or heterocycloalkyl is optionally substituted with 1-3 $R^a$;

$R^{11a}$ and $R^{11b}$ together with the nitrogen atom to which they are attached form 3- to 6-membered heterocycloalkyl, wherein the heterocycloalkyl is optionally substituted with 1-3 of halogen, cyano, $C_{1-4}$ alkoxy, halo $C_{1-4}$ alkoxy, —NH$C_{1-4}$ alkyl, —N($C_{1-4}$ alkyl)$_2$, —NH(3- to 6-membered heterocycloalkyl), —NH$C_{3-6}$ cycloalkyl, —O—$C_{3-6}$ cycloalkyl, —O-(3- to 6-membered heterocycloalkyl), —O—$(CH_2)_n$—Si($C_{1-4}$ alkyl)$_3$ or —$(CH_2)_n$—Si($C_{1-4}$ alkyl)$_3$;

$R^{11c}$ is selected from $C_{1-4}$ alkyl, $C_{1-4}$ alkoxy, amino, —NH$C_{1-4}$ alkyl, —N($C_{1-4}$ alkyl)$_2$, —NH(3- to 6-membered heterocycloalkyl), —NH$C_{3-6}$ cycloalkyl, $C_{3-6}$ cycloalkyl, 3- to 6-membered heterocycloalkyl, —O—$C_{1-4}$ alkyl, —O—$C_{3-6}$ cycloalkyl, —O-(3- to 6-membered heterocycloalkyl) or —$(CH_2)_n$—Si($C_{1-4}$ alkyl)$_3$, wherein the alkyl, alkoxy, heterocycloalkyl or cycloalkyl is optionally substituted with 1-3 of halogen, cyano, $C_{1-4}$ alkoxy, halo $C_{1-4}$ alkoxy, —NH$C_{1-4}$ alkyl, —N($C_{1-4}$ alkyl)$_2$, —NH(3- to 6-membered heterocycloalkyl), —NH$C_{3-6}$ cycloalkyl, —O—$C_{3-6}$ cycloalkyl, —O-(3- to 6-membered heterocycloalkyl) or —Si($C_{1-4}$ alkyl)$_3$;

$R^{11d}$ is selected from —O-(3-6-membered heterocycloalkyl);

$R^a$ is selected from halogen, cyano, $C_{1-4}$ alkyl, halo $C_{1-4}$ alkyl, $C_{1-4}$ alkoxy, halo $C_{1-4}$ alkoxy, $C_{2-6}$ alkenyl, $C_{2-6}$ alkynyl, —S(O)$_2C_{1-4}$ alkyl, —C(O)$C_{1-4}$ alkyl or —$(CH_2)_n$—Si($C_{1-4}$ alkyl)$_3$, wherein the alkyl or alkoxy is optionally substituted with 1-3 of halogen, cyano or hydroxyl;

$R^b$ is selected from 6- to 12-membered aryl, 5- to 12-membered heteroaryl, $C_{3-6}$ cycloalkyl or 3- to 6-membered heterocycloalkyl, wherein the aryl, heteroaryl, cycloalkyl or heterocycloalkyl is optionally substituted with 1-3 of halogen or —$(CH_2)_n$—Si($C_{1-4}$ alkyl)$_3$;

X is selected from —C— or —N—;

Y is selected from —CH— or —N—;

n is selected from 0, 1, 2 or 3;

provided that the compound of formula (I) is not selected from the following compounds: when $R_1$ is selected from methyl, $R_2$ is selected from H, $R_3$ is selected from methyl, $R_4$ and $R_5$ are selected from H, $R_{4'}$ and $R_{5'}$ together with the carbon atom to which they are attached form =O, $R_6$ and $R_7$ are selected from H, X is selected from —C—, $R_8$ is selected from Cl, $R_9$ is selected from methyl, $R_{10}$ is selected from methyl, and Y is selected from C:

(1) $R_1$ is selected from —N($CH_3$)$_2$,

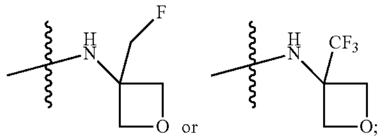 [SMILES: *NC1(CF)COC1 ; *NC1(C(F)(F)F)COC1]

or (2) if $R^{11a}$ and $R^{11b}$ together with the nitrogen atom form azacyclobutyl, or $R_{11}$ is selected from azacyclobutyl, the azacyclobutyl is substituted with the following substituents: F, difluoromethoxy, cyclopropyloxy or methoxy.

Embodiment three of the present disclosure relates to a compound of formula (I), or a stereoisomer, a pharmaceutically acceptable salt, a solvate, and a eutectic or deuterated compound thereof, wherein $R_4$ and $R_5$ are each independently selected from H or D;

$R_{4'}$ and $R_{5'}$ together form =O;

$R_6$ is selected from H;

other groups have the same definitions as those in embodiment one or two.

Embodiment four of the present disclosure relates to a compound of formula (I), or a stereoisomer, a pharmaceutically acceptable salt, a solvate, and a eutectic or deuterated compound thereof, wherein the compound has a structure of formula (I-1):

(I-1)

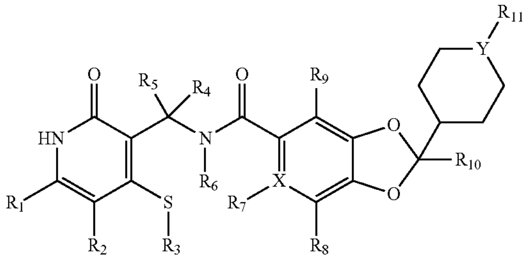

provided that when $R_1$ is selected from methyl, $R_2$ is selected from H, $R_3$ is selected from methyl, $R_4$ and $R_5$ are selected from H, $R_6$ and $R_7$ are selected from H, X is selected from —C—, $R_8$ is selected from Cl, $R_9$ is selected from methyl, $R_{10}$ is selected from methyl, and Y is selected from —CH—, $R_{11}$ is not selected from —N(CH$_3$)$_2$,

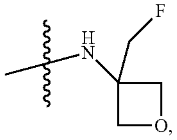

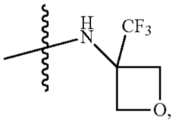

trifluoroethyl, or

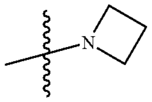 [SMILES: *N1CCC1]

substituted with the following groups: F, difluoromethoxy, cyclopropyloxy or methoxy;

Y is selected from —CH— or —N—;

other groups have the same definitions as those in embodiment one.

Embodiment five of the present disclosure relates to a compound of formula (I), or a stereoisomer, a pharmaceutically acceptable salt, a solvate, and a eutectic or deuterated compound thereof, wherein B is 4- to 5-membered carbocycle, a 6- to 12-membered spiro ring containing 0-3 heteroatoms selected from N, S, O or Si, a 5- to 10-membered bridged ring containing 0-3 heteroatoms selected from N, S, O or Si, a 5- to 10-membered fused ring containing 0-3 heteroatoms selected from N, S, O or Si, or 4- to 5-membered heterocycle, wherein the carbocycle, spiro ring, bridged ring, fused ring or heterocycle is optionally substituted with 1-3 groups selected from =O, $C_{1-4}$ alkyl, $C_{1-4}$ alkoxy, halo $C_{1-4}$ alkyl, amino, —C(O)$C_{1-4}$ alkyl, hydroxyl and halogen;

other groups have the same definitions as those in embodiment one.

Embodiment six of the present disclosure relates to a compound of formula (I), or a stereoisomer, a pharmaceutically acceptable salt, a solvate, and a eutectic or deuterated compound thereof, wherein B is 4- to 5-membered cycloalkyl, a 8- to 11-membered spiro ring containing 0-3 heteroatoms selected from N, S, O or Si, a 5- to 8-membered bridged ring containing 0-3 heteroatoms selected from N, S, O or Si, a 6- to 10-membered fused ring containing 0-3 heteroatoms selected from N, S, O or Si, or a 4- to 5-membered heterocycloalkyl, wherein the carbocycle, spiro ring, bridged ring, fused ring or heterocycle is optionally substituted with 1-3 groups selected from =O, $C_{1-4}$ alkyl, $C_{1-4}$ alkoxy, halo $C_{1-4}$ alkyl, —C(O)$C_{1-4}$ alkyl and halogen;

other groups have the same definitions as those in embodiment five.

Embodiment seven of the present disclosure relates to a compound of formula (I), or a stereoisomer, a pharmaceutically acceptable salt, a solvate, and a eutectic or deuterated compound thereof, wherein B is a 8- to 10-membered spiro ring containing 0-3 heteroatoms selected from N, S, O or Si, a 6- to 8-membered bridged ring containing 0-3 heteroatoms selected from N, S, O or Si or a 8- to 10-membered fused ring containing 0-3 heteroatoms selected from N, S, O or Si, wherein the spiro ring, bridged ring or fused ring is optionally substituted with 1-3 groups selected from =O, $C_{1-4}$ alkyl, $C_{1-4}$ alkoxy, halo $C_{1-4}$ alkyl, —C(O)$C_{1-4}$ alkyl and halogen; other groups have the same definitions as those in embodiment five or six.

Embodiment eight of the present disclosure relates to a compound of formula (I), or a stereoisomer, a pharmaceutically acceptable salt, a solvate, and a eutectic or deuterated compound thereof, wherein $R_1$ is selected from $C_{1-4}$ alkyl, $C_{3-6}$ cycloalkyl or halo $C_{1-4}$ alkyl;

$R_2$ is selected from H;

$R_3$ is selected from $C_{1-6}$ alkyl, 3- to 6-membered heterocycloalkyl or $C_{3-6}$ cycloalkyl, wherein the alkyl, cycloalkyl or heterocycloalkyl is optionally substituted with 1-3 of the following groups: OH or halogen;

alternatively, $R_1$ and $R_2$ form 3- to 6-membered cycloalkyl; or alternatively, $R_2$ and $R_3$ form 3- to 6-membered heterocycloalkyl;

other groups have the same definitions as those in any of embodiments one to seven.

Embodiment nine of the present disclosure relates to a compound of formula (I), or a stereoisomer, a pharmaceutically acceptable salt, a solvate, and a eutectic or deuterated compound thereof, wherein $R_7$ is selected from H;

$R_8$ is selected from halogen, $C_{3-6}$ cycloalkyl, 3- to 6-membered heterocycloalkyl, $C_{1-4}$ alkoxy or —Si($C_{1-4}$ alkyl)$_3$, wherein the alkoxy, cycloalkyl or heterocycloalkyl is optionally substituted with 1-3 halogen; or $R_7$ and $R_8$ together with the atoms to which they are attached form 5-membered cycloalkyl, 5-membered heterocycloalkyl or 5-membered heterocycloaryl, wherein the cycloalkyl, heterocycloalkyl or heterocycloaryl is optionally substituted with 1-3 of $C_{1-4}$ alkyl or halo $C_{1-4}$ alkyl;

$R_9$ is selected from $C_{1-4}$ alkyl, $C_{2-6}$ alkynyl, $C_{3-6}$ cycloalkyl, $C_{1-4}$ alkoxy or —Si($C_{1-4}$ alkyl)$_3$, wherein the alkyl, cycloalkyl or alkoxy is optionally substituted with 1-3 halogen;

$R_{10}$ is selected from methyl, wherein the methyl is optionally substituted with 1-3 —Si($C_{1-4}$ alkyl)$_3$;

other groups have the same definitions as those in any of embodiments one to eight.

Embodiment ten of the present disclosure relates to a compound of formula (I), or a stereoisomer, a pharmaceutically acceptable salt, a solvate, and a eutectic or deuterated compound thereof, wherein $R_1$ is selected from H, cyano, methyl or cyclopropyl;

$R_2$ is selected from H or methyl;

$R_3$ is selected from oxetanyl, fluorocyclopropyl, methyl or hydroxyethyl;

alternatively, $R_2$ and $R_1$ together form cyclopentyl; or alternatively, $R_2$ and $R_3$ together form thiacyclopentyl;

$R_4$ and $R_5$ are selected from H or D;

$R_{4'}$ and $R_{5'}$ together form ═O;

$R_6$ is selected from H;

$R_7$ is selected from H or halogen;

$R_8$ is selected from H, Cl, methoxy, cyclopropyl, oxetanyl, —Si($CH_3$)$_3$ or

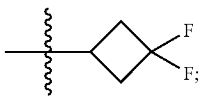 [SMILES: *C1CC(F)(F)C1]

$R_9$ is selected from methyl, methoxy, trifluoromethoxy, cyclopropyl, ethynyl, —Si($CH_3$)$_3$ or propynyl;

$R_{10}$ is selected from methyl or —$CH_2$—Si($CH_3$)$_3$;

other groups have the same definitions as those in any of embodiments one to seven.

Embodiment eleven of the present disclosure relates to a compound of formula (I), or a stereoisomer, a pharmaceutically acceptable salt, a solvate, and a eutectic or deuterated compound thereof, wherein the compound has a structure of formula (II):

(II)

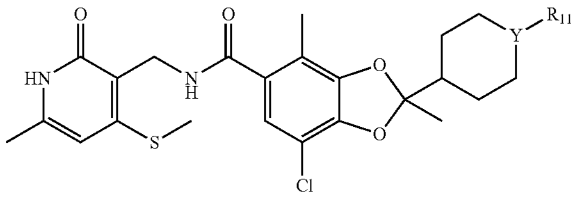

$R_{11}$ is selected from —$NR^{11a}R^{11b}$, ═N—$R^{11d}$, —$OR^b$, —C(O)$R^{11c}$, $C_{2-6}$ alkynyl, 6- to 12-membered aryl, 5- to 10-membered heteroaryl, $C_{3-6}$ cycloalkyl, 3- to 6-membered heterocycloalkyl or —$(CH_2)_n$—Si($C_{1-4}$ alkyl)$_3$, wherein the aryl, heteroaryl, cycloalkyl or heterocycloalkyl is optionally substituted with 1-3 of halogen, $C_{1-4}$ alkyl, —C(O)$C_{1-4}$ alkyl, —O—$(CH_2)_n$—Si($C_{1-4}$ alkyl)$_3$ or —$(CH_2)_n$—Si($C_{1-4}$ alkyl)$_3$;

$R^{11a}$ and $R^{11b}$ are each independently selected from H, $C_{1-4}$ alkyl, $C_{1-4}$ alkoxy, —C(O)$R^{11c}$, 6- to 12-membered aryl, 5- to 12-membered heteroaryl, $C_{3-6}$ cycloalkyl, 3- to 6-membered heterocycloalkyl, —S(O)$_2C_{1-4}$ alkyl or —$(CH_2)_n$—Si($C_{1-4}$ alkyl)$_3$, wherein the alkyl, alkoxy, aryl, heteroaryl, cycloalkyl or heterocycloalkyl is optionally substituted with 1-3 $R^a$;

alternatively, $R^{11a}$ and $R^{11b}$ together with the nitrogen atom to which they are attached form 3- to 6-membered heterocycloalkyl, wherein the heterocycloalkyl is optionally substituted with 1-3 of cyano, —N($C_{1-4}$ alkyl)$_2$, $C_{1-4}$ alkoxy, halo $C_{1-4}$ alkoxy, —O—$(CH_2)_n$—Si($C_{1-4}$ alkyl)$_3$ or —$(CH_2)_n$—Si($C_{1-4}$ alkyl)$_3$;

$R^{11c}$ is selected from $C_{1-4}$ alkyl, $C_{1-4}$ alkoxy, amino, —NH$C_{1-4}$ alkyl, —N($C_{1-4}$ alkyl)$_2$, —NH(3- to 6-membered heterocycloalkyl), —NH$C_{3-6}$ cycloalkyl, $C_{3-6}$ cycloalkyl, 3- to 6-membered heterocycloalkyl, —O—$C_{1-4}$ alkyl, —O—$C_{3-6}$ cycloalkyl, —O-(3- to 6-membered heterocycloalkyl) or —$(CH_2)_n$—Si($C_{1-4}$ alkyl)$_3$, wherein the alkyl, alkoxy, heterocycloalkyl or cycloalkyl is optionally substituted with 1-3 of halogen, cyano, $C_{1-4}$ alkoxy, halo $C_{1-4}$ alkoxy, —NH$C_{1-4}$ alkyl, —N($C_{1-4}$ alkyl)$_2$, —NH(3- to 6-membered heterocycloalkyl), —NH$C_{3-6}$ cycloalkyl, —O—$C_{3-6}$ cycloalkyl, —O-(3- to 6-membered heterocycloalkyl) or —Si($C_{1-4}$ alkyl)$_3$;

$R^{11d}$ is selected from —O-(3-6-membered heterocycloalkyl);

$R^a$ is selected from halogen, cyano, $C_{1-4}$ alkyl, halo $C_{1-4}$ alkyl, $C_{1-4}$ alkoxy, halo $C_{1-4}$ alkoxy, $C_{2-6}$ alkenyl, $C_{2-6}$ alkynyl, —S(O)$_2C_{1-4}$ alkyl, —C(O)$C_{1-4}$ alkyl or —$(CH_2)_n$—Si($C_{1-4}$ alkyl)$_3$, wherein the alkyl or alkoxy is optionally substituted with 1-3 of halogen, cyano or hydroxyl;

$R^b$ is selected from 6- to 12-membered aryl, 5- to 12-membered heteroaryl, $C_{3-6}$ cycloalkyl or 3- to 6-membered heterocycloalkyl, wherein the aryl, heteroaryl, cycloalkyl or heterocycloalkyl is optionally substituted with 1-3 of halogen or —$(CH_2)_n$—Si($C_{1-4}$ alkyl)$_3$;

Y is selected from —CH— or —N—;

n is selected from 0, 1 or 2;

provided that the compound of formula (I) is not selected from the following compounds: when Y is selected from C:

(1) $R_{11}$ is selected from —N($CH_3$)$_2$,

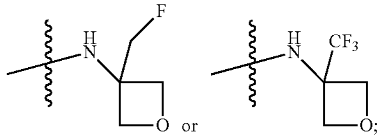 [SMILES: *NC1(CF)COC1 ; *NC1(C(F)(F)F)COC1]

or (2) if $R^{11a}$ and $R^{11b}$ together with the nitrogen atom form azacyclobutyl, or $R_{11}$ is selected from azacyclobutyl, the azacyclobutyl is substituted with the following substituents: F, difluoromethoxy, cyclopropyloxy or methoxy.

Embodiment twelve of the present disclosure relates to a compound of formula (II), or a stereoisomer, a pharmaceutically acceptable salt, a solvate, and a eutectic or deuterated compound thereof, wherein $R_{11}$ is selected from —$NR^{11a}R^{11b}$, —C(O)$R^{11c}$, $C_{2-6}$ alkynyl, 6- to 12-membered aryl or 5- to 10-membered heteroaryl, wherein the aryl or heteroaryl is optionally substituted with 1-3 of halogen, $C_{1-4}$ alkyl, —$C(O)C_{1-4}$ alkyl or —$(CH_2)_n$—$Si(C_{1-4}$ alkyl$)_3$;

$R^{11a}$ is selected from H or $C_{1-4}$ alkyl;

$R^{11b}$ is selected from —$C(O)R^{11c}$, 5- to 12-membered heteroaryl, $C_{3-6}$ cycloalkyl or 3- to 6-membered heterocycloalkyl, wherein the heteroaryl, cycloalkyl or heterocycloalkyl is optionally substituted with 1-3 $R^a$;

alternatively, $R^{11a}$ and $R^{11b}$ together with the nitrogen atom to which they are attached form 3- to 6-membered heterocycloalkyl, wherein the heterocycloalkyl is optionally substituted with 1-3 of cyano, —$N(C_{1-4}$ alkyl$)_2$, $C_{1-4}$ alkoxy, halo $C_{1-4}$ alkoxy, —O—$(CH_2)_n$—$Si(C_{1-4}$ alkyl$)_3$ or —$(CH_2)_n$—$Si(C_{1-4}$ alkyl$)_3$;

$R^{11c}$ is selected from $C_{1-4}$ alkyl, $C_{1-4}$ alkoxy, —$NHC_{1-4}$ alkyl, —NH(3- to 6-membered heterocycloalkyl), 3- to 6-membered heterocycloalkyl or —$(CH_2)_n$—$Si(C_{1-4}$ alkyl$)_3$;

$R^a$ is selected from halogen, cyano, $C_{1-4}$ alkyl, halo $C_{1-4}$ alkyl, $C_{1-4}$ alkoxy, halo $C_{1-4}$ alkoxy, $C_{2-6}$ alkenyl, $C_{2-6}$ alkynyl, —$S(O)_2C_{1-4}$ alkyl or —$C(O)C_{1-4}$ alkyl, wherein the alkyl or alkoxy is optionally substituted with 1-3 of halogen, cyano or hydroxyl;

other groups have the same definitions as those in embodiment eleven.

Embodiment thirteen of the present disclosure relates to a compound of formula (I), or a stereoisomer, a pharmaceutically acceptable salt, a solvate, and a eutectic or deuterated compound thereof, wherein $R_{11}$ is selected from —$NR^{11a}R^{11b}$;

$R^{11a}$ is selected from H or $C_{1-4}$ alkyl;

$R^{11b}$ is selected from —$C(O)R^{11c}$, 5- to 12-membered heteroaryl, $C_{3-6}$ cycloalkyl or 3- to 6-membered heterocycloalkyl, wherein the heteroaryl, cycloalkyl or heterocycloalkyl is optionally substituted with 1-3 $R^a$;

alternatively, $R^{11a}$ and $R^{11b}$ together with the nitrogen atom to which they are attached form 3- to 6-membered heterocycloalkyl, wherein the heterocycloalkyl is optionally substituted with 1-3 of cyano, —$N(C_{1-4}$ alkyl$)_2$, $C_{1-4}$ alkoxy or halo $C_{1-4}$ alkoxy;

$R^{11c}$ is selected from $C_{1-4}$ alkyl, $C_{1-4}$ alkoxy, —$NHC_{1-4}$ alkyl, —NH(3- to 6-membered heterocycloalkyl) or 3- to 6-membered heterocycloalkyl;

$R^a$ is selected from halogen, cyano, $C_{1-4}$ alkyl, halo $C_{1-4}$ alkyl, $C_{1-4}$ alkoxy, halo $C_{1-4}$ alkoxy, $C_{2-6}$ alkenyl, $C_{2-6}$ alkynyl, —$S(O)_2C_{1-4}$ alkyl or —$C(O)C_{1-4}$ alkyl, wherein the alkyl or alkoxy is optionally substituted with 1-3 of halogen, cyano or hydroxyl;

other groups have the same definitions as those in embodiment eleven or embodiment twelve.

Embodiment fourteen of the present disclosure relates to a compound of formula (I), or a stereoisomer, a pharmaceutically acceptable salt, a solvate, and a eutectic or deuterated compound thereof, wherein $R_{11}$ is selected from 6- to 12-membered aryl or 5- to 10-membered heteroaryl, wherein the aryl or heteroaryl is optionally substituted with 1-3 of halogen, $C_{1-4}$ alkyl or —$C(O)C_{1-4}$ alkyl;

other groups have the same definitions as those in embodiment eleven;

in some embodiments, other groups have the same definitions as those in embodiment twelve.

Embodiment fifteen of the present disclosure relates to a compound of formula (I), or a stereoisomer, a pharmaceutically acceptable salt, a solvate, and a eutectic or deuterated compound thereof, wherein the compound has a structure of formula (I-2), (I-3), (I-4) or (I-5), (I-2)

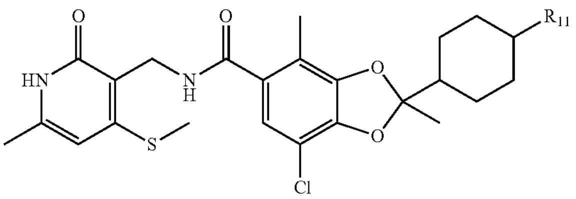

(I-3)

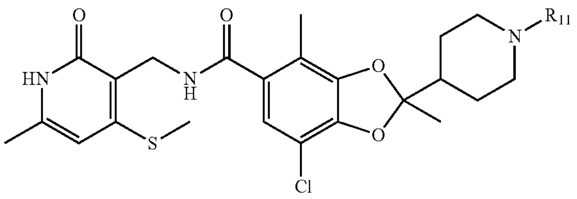

(I-4)

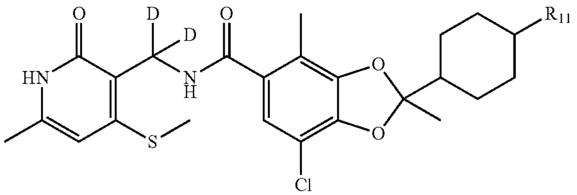

(I-5)

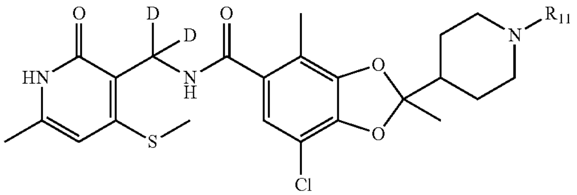

$R_{11}$ is selected from halogen, =O, OH, CN, =N—$R^{11d}$, —$OR^b$, —$C(O)R^{11c}$, —$(CH_2)_n$—$NR^{11a}$—$C(O)R^{11c}$, $C_{1-4}$ alkyl, halo $C_{1-4}$ alkyl, —$C_{1-4}$ alkyl-$C_{1-4}$ alkoxy, $C_{1-4}$ alkoxy, $C_{2-6}$ alkenyl, $C_{2-6}$ alkynyl, —$(CH_2)_n$-(6- to 12-membered aryl), —$(CH_2)_n$-(5- to 10-membered heteroaryl), —$(CH_2)_n$—$C_{3-12}$ cycloalkyl, —$(CH_2)_n$-(3- to 12-membered heterocycloalkyl), —$(CH_2)_n$—$Si(C_{1-4}$ alkyl$)_3$, —$S(O)_2NR^{11a}R^{11b}$, —$S(O)_2R^{11c}$—$(CH_2)_n$—C(O)$NR^{11a}R^{11b}$ or —$(CH_2)_n$—$NR^{11a}R^{11b}$, wherein the $CH_2$, alkyl, alkoxy, alkenyl, alkynyl, aryl, heteroaryl, cycloalkyl or heterocycloalkyl is optionally substituted with 1-3 groups selected from: halogen, D, $C_{1-4}$ alkyl, halo $C_{1-4}$ alkyl, $C_{1-4}$ alkoxy, —$C_{1-4}$ alkyl-$C_{1-4}$ alkoxy, =O, CN, OH, —$NR^{11a'}R^{11b'}$, —C(O)—$NR^{11a'}R^{11b'}$, —$C(O)C_{1-4}$ alkyl, —O—$(CH_2)_n$—$Si(C_{1-4}$ alkyl$)_3$, —$(CH_2)_n$—$Si(C_{1-4}$ alkyl$)_3$, $C_{3-6}$ cycloalkyl, 3- to 12-membered heterocycloalkyl or —O—$(CH_2)_n$—$C_{3-6}$ cycloalkyl, wherein the $CH_2$, alkyl, alkoxy, cycloalkyl or heterocycloalkyl is optionally substituted with 1-3 groups selected from $R^a$;

provided that $R_{11}$ is not selected from —$N(CH_3)_2$,

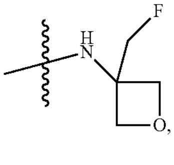

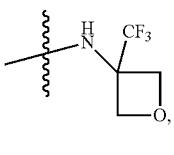

trifluoroethyl, or

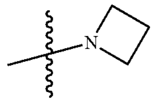 [SMILES: *N1CCC1]

substituted with the following groups: F, difluoromethoxy, cyclopropyloxy or methoxy;

other groups have the same definitions as those in embodiment one.

Embodiment sixteen of the present disclosure relates to a compound of formula (I), or a stereoisomer, a pharmaceutically acceptable salt, a solvate, and a eutectic or deuterated compound thereof, wherein the compound has a structure of formula (IV):

(IV)

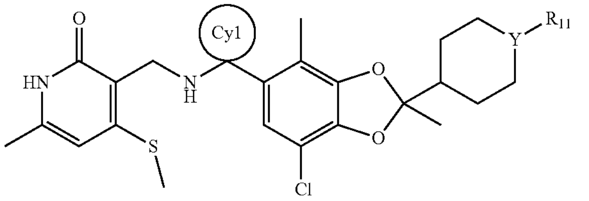

wherein Cyl is 3- to 5-membered heterocycloalkyl containing 1-3 heteroatoms selected from O, N or S;

Y is selected from —CH— or —N—;

other groups have the same definitions as those in embodiment one.

Embodiment seventeen of the present disclosure relates to a compound of formula (I), or a stereoisomer, a pharmaceutically acceptable salt, a solvate, and a eutectic or deuterated compound thereof, wherein

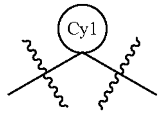 is 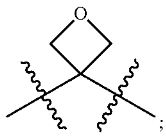;

other groups have the same definitions as those in embodiment sixteen.

Embodiment eighteen of the present disclosure relates to a compound of formula (I), or a stereoisomer, a pharmaceutically acceptable salt, a solvate, and a eutectic or deuterated compound thereof, wherein (1) $R_{11}$ is selected from $—NR^{11a}R^{11b}$ $R^{11a}$ is selected from H, D, $C_{1-4}$ alkyl or $C_{1-4}$ alkoxy;

$R^{11b}$ is selected from D, $—C(O)R^{11c}$, $—C(O)—(CH_2)_n—R^{11c}$, $—S(O)_2—NR^{11a'}R^{11b'}$, $—S(O)_2R^{11c}—(CH_2)_n$-(6- to 12-membered aryl), $—(CH_2)_n$-(5- to 12-membered heteroaryl), $—(CH_2)_n—C_{3-12}$ cycloalkyl, $—(CH_2)_n$-(3- to 12-membered heterocycloalkyl), $—S(O)_2C_{1-4}$ alkyl or $—(CH_2)_n—Si(C_{1-4}\ alkyl)_3$, wherein the heterocycloalkyl contains at least 1 Si atom as a heteroatom, and the aryl, heteroaryl, cycloalkyl or heterocycloalkyl is optionally substituted with 1-3 $R^a$;

$R^{11c}$ is selected from $C_{1-4}$ alkyl, $C_{1-4}$ alkoxy, $C_{1-4}$ alkyl-$C_{1-4}$ alkoxy, amino, $—NHC_{1-4}$ alkyl, $—N(C_{1-4}\ alkyl)_2$, —NH(3- to 6-membered heterocycloalkyl), $—NHC_{3-6}$ cycloalkyl, $—(CH_2)_n—C_{3-6}$ cycloalkyl, $—(CH_2)_n$-(3- to 6-membered heterocycloalkyl), $—O—C_{1-4}$ alkyl, $—O—C_3$-6 cycloalkyl, —O-(3- to 6-membered heterocycloalkyl), $—(CH_2)_n$-(6- to 12-membered aryl), $—(CH_2)_n$-(5- to 12-membered heteroaryl) or $—(CH_2)_n—Si(C_{1-4}\ alkyl)_3$, wherein the alkyl, alkoxy, heterocycloalkyl, cycloalkyl, aryl or heteroaryl is optionally substituted with 1-3 of halogen, cyano, $C_{1-4}$ alkyl, halo $C_{1-4}$ alkyl, $C_{1-4}$ alkoxy, halo $C_{1-4}$ alkoxy, $—NHC_{1-4}$ alkyl, $—N(C_{1-4}\ alkyl)_2$, —NH(3- to 6-membered heterocycloalkyl), $—NHC_{3-6}$ cycloalkyl, $—O—C_{3-6}$ cycloalkyl, —O-(3- to 6-membered heterocycloalkyl) or $—Si(C_{1-4}\ alkyl)_3$; or (2) $R_{11}$ is selected from $—NR^{11a}R^{11b}$;

$R^{11a}$ is selected from H, D, $C_{1-4}$ alkyl or halo $C_{1-4}$ alkyl;

$R^{11b}$ is selected from 3- to 12-membered heterocycloalkyl containing 1-3 heteroatoms selected from N, O or S, wherein the heterocycloalkyl is optionally substituted with D, OH, cyano-substituted alkyl, cyano, $C_{2-6}$ alkenyl, $C_{2-6}$ alkynyl, $—S(O)_2C_{1-4}$ alkyl, $—C(O)C_{1-4}$ alkyl, $—(CH_2)_n—Si(C_{1-4}\ alkyl)_3$, $C_{3-6}$ cycloalkyl, 3- to 6-membered heterocycloalkyl, 6- to 12-membered aryl or 5- to 12-membered heteroaryl, wherein the cycloalkyl, heterocycloalkyl, aryl or heteroaryl is optionally substituted with 1-3 of halogen, D, cyano, hydroxyl, $C_{1-4}$ alkyl or halo $C_{1-4}$ alkyl; or (3) $R_1$ is selected from $—(CH_2)_{1-3}—NR^{11a}R^{11b}$, $—(CH_2)_n—C(O)NR^{11a}R^{11b}$, $—C(O)R^{11c}—OR^b$ or $—(CH_2)_n—NR^{11a}—C(O)R^{11c}$;

$R^{11a}$ and $R^{11b}$ are each independently selected from H, D, $C_{1-4}$ alkyl, $C_{1-4}$ alkoxy, $—C(O)R^{11c}—C(O)—(CH_2)_n—R^{11c}$, $—S(O)_2—NR^{11a'}R^{11b'}$, $—S(O)_2R^{11c}$, $—(CH_2)_n$-(6- to 12-membered aryl), $—(CH_2)_n$-(5- to 12-membered heteroaryl), $—(CH_2)_n—C_{3-12}$ cycloalkyl, $—(CH_2)_n$-(3- to 12-membered heterocycloalkyl), $—S(O)_2C_{1-4}$ alkyl or $—(CH_2)_n—Si(C_{1-4}\ alkyl)_3$, wherein the alkyl, alkoxy, aryl, heteroaryl, cycloalkyl or heterocycloalkyl is optionally substituted with 1-3 $R^a$;

alternatively, $R^{11a}$ and $R^{11b}$ together with the nitrogen atom to which they are attached form 3- to 12-membered heterocycloalkyl, wherein the heterocycloalkyl is optionally substituted with 1-3 $R^c$;

$R^{11c}$ is selected from $C_{1-4}$ alkyl, $C_{1-4}$ alkoxy, $C_{1-4}$ alkyl-$C_{1-4}$ alkoxy, amino, $—NHC_{1-4}$ alkyl, $—N(C_{1-4}\ alkyl)_2$, —NH(3- to 6-membered heterocycloalkyl), $—NHC_{3-6}$ cycloalkyl, $—(CH_2)_n—C_{3-6}$ cycloalkyl, $—(CH_2)_n$-(3- to 6-membered heterocycloalkyl), $—O—C_{1-4}$ alkyl, $—O—C_3$-6 cycloalkyl, —O-(3- to 6-membered heterocycloalkyl), $—(CH_2)_n$-(6- to 12-membered aryl), $—(CH_2)_n$-(5- to 12-membered heteroaryl) or $—(CH_2)_n—Si(C_{1-4}\ alkyl)_3$, wherein the alkyl, alkoxy, heterocycloalkyl, cycloalkyl, aryl or heteroaryl is optionally substituted with 1-3 of halogen, cyano, $C_{1-4}$ alkyl, halo $C_{1-4}$ alkyl, $C_{1-4}$ alkoxy, halo $C_{1-4}$ alkoxy, $—NHC_{1-4}$ alkyl, $—N(C_{1-4}\ alkyl)_2$, —NH(3- to 6-membered heterocycloalkyl), $—NHC_{3-6}$ cycloalkyl, $—O—C_{3-6}$ cycloalkyl, —O-(3- to 6-membered heterocycloalkyl) or $—Si(C_{1-4}\ alkyl)_3$;

$R^b$ is selected from $—(CH_2)_n$-(6- to 12-membered aryl), $—(CH_2)_n$-(5- to 12-membered heteroaryl), $—(CH_2)_n$-(3- to 6-membered heterocycloalkyl), $—(CH_2)_n—C_{3-6}$ cycloalkyl, $C_{1-4}$ alkyl, $C_{2-6}$ alkenyl, $C_{2-6}$ alkynyl or $—(CH_2)_n—C(O)—NR^{11a'}R^{11b'}$, wherein the aryl, heteroaryl, cycloalkyl, heterocycloalkyl, alkyl, alkenyl or alkynyl is optionally substituted with 1-3 of halogen, $C_{1-4}$ alkyl, halo $C_{1-4}$ alkyl, CN or $-(CH_2)_n-Si(C_{1-4}$ alkyl$)_3$;

$R^c$ is selected from halogen, =O, CN, OH, $C_{1-4}$ alkyl, halo $C_{1-4}$ alkyl, $C_{1-4}$ alkoxy, halo $C_{1-4}$ alkoxy, $-NHC_{1-4}$ alkyl, $-N(C_{1-4}$ alkyl$)_2$, $-C(O)-NR^{11a'}R^{11b'}$, 3- to 6-membered heterocycloalkyl, $-C_{3-6}$ cycloalkyl, —NH(3- to 6-membered heterocycloalkyl), $-NHC_{3-6}$ cycloalkyl, $-O-(CH_2)_n-C_{3-6}$ cycloalkyl, $-O-(CH_2)_n$-(3- to 6-membered heterocycloalkyl), $-O-(CH_2)_n-Si(C_{1-4}$ alkyl$)_3$ or $-(CH_2)_n-Si(C_{1-4}$ alkyl$)_3$, wherein the alkyl, alkoxy, cycloalkyl or heterocycloalkyl is optionally further substituted with 1-3 of halogen, D, CN, OH, amino, $C_{1-4}$ alkyl or $C_{1-4}$ alkoxy; or (4) $R_{11}$ is selected from $-(CH_2)_n$-(6- to 12-membered aryl), $-(CH_2)_n$-(5- to 10-membered heteroaryl), $-(CH_2)_n-C_{3-12}$ cycloalkyl, $-(CH_2)_n$-(8- to 12-membered heterocycloalkyl) or $-(CH_2)_{1-3}$-(4- to 7-membered heterocycloalkyl), wherein the aryl, heteroaryl, cycloalkyl or heterocycloalkyl is optionally substituted with 1-3 groups selected from: halogen, D, $C_{1-4}$ alkoxy, $C_{1-4}$ alkyl, $-C_{1-4}$ alkyl-$C_{1-4}$ alkoxy, =O, CN, OH, $-NR^{11a'}R^{11b'}$, $-C(O)-NR^{11a'}R^{11b'}$, $-C(O)C_{1-4}$ alkyl, $-O-(CH_2)_n-Si(C_{1-4}$ alkyl$)_3$, $-(CH_2)_n-Si(C_{1-4}$ alkyl$)_3$, $C_{3-6}$ cycloalkyl, 3- to 12-membered heterocycloalkyl or $-O-(CH_2)_n-C_{3-6}$ cycloalkyl, wherein the alkyl, alkoxy, cycloalkyl or heterocycloalkyl is optionally substituted with 1-3 groups selected from $R^a$; or (5) $R_{11}$ is selected from 4- to 7-membered heterocycloalkyl, wherein $R_{11}$ is not selected from heterocycloalkyl in which the group linking site between $R_1$ and B is an N atom, and the heterocycloalkyl is optionally substituted with 1-3 groups selected from: halogen, D, $C_{1-4}$ alkyl, halo $C_{1-4}$ alkyl, $C_{1-4}$ alkoxy, $-C_{1-4}$ alkyl-$C_{1-4}$ alkoxy, =O, CN, OH, $-NR^{11a'}R^{11b'}$, $-C(O)-NR^{11a'}R^{11b'}$, $-C(O)C_{1-4}$ alkyl, $-O-(CH_2)_n-Si(C_{1-4}$ alkyl$)_3$, $-(CH_2)_n-Si(C_{1-4}$ alkyl$)_3$, $C_{3-6}$ cycloalkyl, 3- to 12-membered heterocycloalkyl or $-O-(CH_2)_n-C_{3-6}$ cycloalkyl, wherein the $CH_2$, alkyl, alkoxy, cycloalkyl or heterocycloalkyl is optionally substituted with 1-3 groups selected from $R^a$; or (6) $R_{11}$ is selected from $-NR^{11a}R^{11b}$;

$R^{11a}$ and $R^{11b}$ form

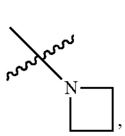, which is optionally substituted with CN, =O, OH, $-NHC_{1-4}$ alkyl, $-N(C_{1-4}$ alkyl$)_2$, $-C_{1-4}$ alkyl $C_{1-4}$ alkoxy, $-C(O)-NR^{11a'}R^{11b'}$, 3- to 6-membered heterocycloalkyl, $-C_{3-6}$ cycloalkyl, —NH(3- to 6-membered heterocycloalkyl), $-NHC_{3-6}$ cycloalkyl, $-O-(CH_2)_{1-3}-C_{3-6}$ cycloalkyl, $-O-(CH_2)_n$-(3- to 6-membered heterocycloalkyl), $-O-(CH_2)_n-Si(C_{1-4}$ alkyl$)_3$ or $-(CH_2)_n-Si(C_{1-4}$ alkyl$)_3$, wherein the alkyl, alkoxy, cycloalkyl or heterocycloalkyl is optionally further substituted with 1-3 of halogen, D, CN, OH, amino, $C_{1-4}$ alkyl or $C_{1-4}$ alkoxy; or (7) $R_{11}$ is selected from $=N-R^{11d}$, and $R^{11d}$ is selected from $-O-R^a$; or (8) $R_{11}$ is selected from $C_{2-6}$ alkenyl, $C_{2-6}$ alkynyl, $-S(O)_2R^{11c}$, OH, cyano-substituted alkyl or $-(CH_2)_n-Si(C_{1-4}$ alkyl$)_3$, wherein the alkyl, alkenyl or alkynyl is optionally substituted with 1-3 groups selected from: halogen, D, $C_{1-4}$ alkyl or CN;

$R^{11c}$ is selected from $C_{1-4}$ alkyl, $C_{1-4}$ alkoxy, $C_{1-4}$ alkyl-$C_{1-4}$ alkoxy, amino, $-NHC_{1-4}$ alkyl, $-N(C_{1-4}$ alkyl$)_2$, —NH(3- to 6-membered heterocycloalkyl), $-NHC_{3-6}$ cycloalkyl, $-(CH_2)_n-C_{3-6}$ cycloalkyl, $-(CH_2)_n$-(3- to 6-membered heterocycloalkyl), $-O-C_{1-4}$ alkyl, $-O-C_3$-6 cycloalkyl, —O-(3- to 6-membered heterocycloalkyl), $-(CH_2)_n$-(6- to 12-membered aryl), $-(CH_2)_n$-(5- to 12-membered heteroaryl) or $-(CH_2)_n-Si(C_{1-4}$ alkyl$)_3$, wherein the alkyl, alkoxy, heterocycloalkyl, cycloalkyl, aryl or heteroaryl is optionally substituted with 1-3 of halogen, cyano, $C_{1-4}$ alkyl, halo $C_{1-4}$ alkyl, $C_{1-4}$ alkoxy, halo $C_{1-4}$ alkoxy, $-NHC_{1-4}$ alkyl, $-N(C_{1-4}$ alkyl$)_2$, —NH(3- to 6-membered heterocycloalkyl), $-NHC_{3-6}$ cycloalkyl, $-O-C_{3-6}$ cycloalkyl, —O-(3- to 6-membered heterocycloalkyl) or $-Si(C_{1-4}$ alkyl$)_3$;

(9) $R_{11}$ is selected from $-NR^{11a}R^{11b}$;

$R^{11a}$ is selected from H, D, $C_{1-4}$ alkyl or halo $C_{1-4}$ alkyl;

$R^{11b}$ is selected from $-(CH_2)_{1-3}$-3- to 12-membered heterocycloalkyl containing 1-3 heteroatoms selected from N, O or S, wherein the heterocycloalkyl is optionally substituted with D, OH, $C_{1-4}$ alkyl, cyano-substituted alkyl, cyano, $C_{2-6}$ alkenyl, $C_{2-6}$ alkynyl, $-S(O)_2C_{1-4}$-alkyl, $-C(O)C_{1-4}$ alkyl, $-(CH_2)_n-Si(C_{1-4}$ alkyl$)_3$, $C_{3-6}$ cycloalkyl, 3- to 6-membered heterocycloalkyl, 6- to 12-membered aryl, 5- to 12-membered heteroaryl, wherein the cycloalkyl, heterocycloalkyl, aryl or heteroaryl is optionally substituted with 1-3 of halogen, D, cyano, hydroxyl, $C_{1-4}$ alkyl or halo $C_{1-4}$ alkyl;

each $R^a$ is selected from halogen, D, OH, cyano, $C_{1-4}$ alkyl, halo $C_{1-4}$ alkyl, $C_{1-4}$ alkoxy, halo $C_{1-4}$ alkoxy, $C_{2-6}$ alkenyl, $C_{2-6}$ alkynyl, $-S(O)_2C_{1-4}$ alkyl, $-C(O)C_{1-4}$ alkyl, $-(CH_2)_n-Si(C_{1-4}$ alkyl$)_3$, $C_{3-6}$ cycloalkyl, 3- to 6-membered heterocycloalkyl, 6- to 12-membered aryl or 5- to 12-membered heteroaryl, wherein the alkyl, alkoxy, cycloalkyl, heterocycloalkyl, aryl or heteroaryl is optionally substituted with 1-3 of halogen, D, cyano, hydroxyl, $C_{1-4}$ alkyl or halo $C_{1-4}$ alkyl;

$R^{11a'}$ and $R^{11b'}$ are each independently selected from H, D, $C_{1-4}$ alkyl, halogen, CN or OH;

alternatively, $R^{11a'}$ and $R^{11b'}$ together with the nitrogen atom to which they are attached form 3- to 6-membered heterocycloalkyl, wherein the heterocycloalkyl is optionally substituted with 1-3 of halogen, D, CN, OH, $C_{1-4}$ alkyl, halo $C_{1-4}$ alkyl, $C_{1-4}$ alkoxy or halo $C_{1-4}$ alkoxy;

each n is 0, 1, 2 or 3;

other groups have the same definitions as those in any of embodiments one to ten;

in some embodiments, other groups have the same definitions as those in any of embodiments fifteen to seventeen.

Embodiment nineteen of the present disclosure relates to a compound of formula (I), or a stereoisomer, a pharmaceutically acceptable salt, a solvate, and a eutectic or deuterated compound thereof, wherein (1) $R_{11}$ is selected from $-NR^{11a}R^{11b}$;

$R^{11a}$ is selected from H, D or $C_{1-4}$ alkyl;

$R^{11b}$ is selected from D, $-C(O)R^{11c}$, $-C(O)-(CH_2)_n-R^{11c}$, $-S(O)_2-NR^{11a'}R^{11b'}$, $-S(O)_2R^{11c}$, $-(CH_2)_n$-(5- to 12-membered heteroaryl), $-(CH_2)_n-C_{3-12}$ cycloalkyl or $-(CH_2)_n$-6- to 12-membered heterocycloalkyl, wherein the heterocycloalkyl contains at least 1 Si atom as a heteroatom, and the heteroaryl, cycloalkyl or heterocycloalkyl is optionally substituted with 1-3 $R^a$;

$R^{11c}$ is selected from $C_{1-4}$ alkyl, $C_{1-4}$ alkoxy, $C_{1-4}$ alkyl-$C_{1-4}$ alkoxy, —$NHC_{1-4}$ alkyl, —$N(C_{1-4}$ alkyl$)_2$, —$(CH_2)_n$—$C_{3-6}$ cycloalkyl, —$(CH_2)_n$-(3- to 6-membered heterocycloalkyl), —$(CH_2)_n$-(5- to 12-membered heteroaryl) or —$(CH_2)_n$—$Si(C_{1-4}$ alkyl$)_3$, wherein the alkyl, alkoxy, heterocycloalkyl, cycloalkyl or heteroaryl is optionally substituted with 1-3 of halogen, $C_{1-4}$ alkyl or halo $C_{1-4}$ alkyl;

$R^a$ is selected from halogen, D, OH, cyano, $C_{1-4}$ alkyl, $C_{1-4}$ alkoxy, halo $C_{1-4}$ alkoxy, $C_2$-6 alkenyl, $C_{2-6}$ alkynyl, —$S(O)_2C_{1-4}$ alkyl or —$C(O)C_{1-4}$ alkyl, wherein the alkyl or alkoxy is optionally substituted with 1-3 of halogen, D or cyano;

$R^{11a'}$ and $R^{11b'}$ are each independently selected from H, D or $C_{1-2}$ alkyl;

n is 0, 1, 2 or 3; or (2) $R_{11}$ is selected from —$NR^{11a}R^{11b}$;

$R^{11a}$ is selected from H;

$R^{11b}$ is selected from 4- to 7-membered monocyclic heterocycloalkyl containing 1-3 heteroatoms selected from N, O or S, a 5- to 8-membered bridged ring containing 1-3 heteroatoms selected from N, O or S, 5- to 6-membered heteroaryl containing 1-3 heteroatoms selected from N, O or S, a 8- to 10-membered spiro ring containing 1-3 heteroatoms selected from N, O or S or a 8- to 10-membered fused ring containing 1-3 heteroatoms selected from N, O or S, wherein the monocyclic heterocycloalkyl, bridged ring, heteroaryl, spiro ring or fused ring is optionally substituted with 1-3 of D, cyano-substituted alkyl, cyano, —$S(O)_2C_{1-4}$ alkyl or —$C(O)C_{1-4}$ alkyl; or (3) $R_{11}$ is selected from —$(CH_2)_{1-3}$—$NR^{11a}R^{11b}$, —$(CH_2)_n$—$C(O)NR^{11a}R^{11b}$, —$C(O)R^{11c}$—$OR^b$ or —$(CH_2)_n$—$NR^{11a}$—$C(O)R^{11c}$;

$R^{11a}$ and $R^{11b}$ are each independently selected from H, D, $C_{1-4}$ alkyl, —$(CH_2)_n$-(5- to 12-membered heteroaryl), —$(CH_2)_n$—$C_{3-12}$ cycloalkyl or —$(CH_2)_n$-(3- to 12-membered heterocycloalkyl), wherein the alkyl, heteroaryl, cycloalkyl or heterocycloalkyl is optionally substituted with 1-3 $R^a$;

$R^{11c}$ is selected from $C_{1-4}$ alkyl, $C_{1-4}$ alkoxy, —$(CH_2)_n$—$C_{3-6}$ cycloalkyl, —$(CH_2)_n$-(3- to 6-membered heterocycloalkyl), —$(CH_2)_n$-(5- to 12-membered heteroaryl) or —$(CH_2)_n$—$Si(C_{1-4}$ alkyl$)_3$, wherein the alkyl, alkoxy, heterocycloalkyl, cycloalkyl or heteroaryl is optionally substituted with 1-3 of halogen, cyano, $C_{1-4}$ alkyl, halo $C_{1-4}$ alkyl or $C_{1-4}$ alkoxy;

$R^a$ is selected from halogen, D, cyano, $C_{1-4}$ alkyl or halo $C_{1-4}$ alkyl, wherein the alkyl is optionally substituted with 1-3 of halogen, D or cyano;

$R^b$ is selected from —$(CH_2)_n$-(5- to 12-membered heteroaryl), —$(CH_2)_n$-(3- to 6-membered heterocycloalkyl), —$(CH_2)_n$—$C_{3-6}$ cycloalkyl, $C_{1-4}$ alkyl, $C_{2-6}$ alkenyl, $C_{2-6}$ alkynyl or —$(CH_2)_n$—$C(O)$—$NR^{11a'}R^{11b'}$, wherein the heteroaryl, cycloalkyl, heterocycloalkyl, alkyl, alkenyl or alkynyl is optionally substituted with 1-3 of halogen, $C_{1-4}$ alkyl, halo $C_{1-4}$ alkyl or CN;

$R^{11a'}$ and $R^{11b'}$ are each independently selected from H, D, $C_{1-2}$ alkyl or halogen;

alternatively, $R^{11a'}$ and $R^{11b'}$ together with the nitrogen atom to which they are attached form 3- to 6-membered heterocycloalkyl, wherein the heterocycloalkyl is optionally substituted with 1-3 of halogen, D or $C_{1-4}$ alkyl;

n is 0, 1, 2 or 3; or (4) $R_{11}$ is selected from —$(CH_2)_n$-(6- to 12-membered aryl), —$(CH_2)_n$-(5- to 10-membered heteroaryl), —$(CH_2)_n$—$C_{3-12}$ cycloalkyl, —$(CH_2)_n$-(8- to 12-membered heterocycloalkyl) or —$(CH_2)_{1-3}$-(4- to 7-membered heterocycloalkyl), wherein the aryl, heteroaryl, cycloalkyl or heterocycloalkyl is optionally substituted with 1-3 groups selected from: halogen, D, $C_{1-4}$ alkoxy, $C_{1-4}$ alkyl, =O or —O—$(CH_2)_n$—$C_{3-6}$ cycloalkyl, wherein the alkyl, alkoxy or cycloalkyl is optionally substituted with 1-3 groups selected from $R^a$;

$R^a$ is selected from halogen, D or $C_{1-4}$ alkyl;

n is 0, 1, 2 or 3; or (5) $R_{11}$ is selected from 4- to 6-membered heterocycloalkyl, wherein $R_{11}$ is not selected from heterocycloalkyl in which the group linking site between $R_1$ and B is an N atom, and the heterocycloalkyl is optionally substituted with 1-3 groups selected from: halogen, D, $C_{1-4}$ alkyl, halo $C_{1-4}$ alkyl, $C_{1-4}$ alkoxy, =O, CN, OH, —$C_{1-4}$ alkyl $C_{1-4}$ alkoxy, —$N(C_{1-4}$ alkyl$)_2$, —$C(O)$—$NR^{11a'}R^{11b'}$, 3- to 6-membered heterocycloalkyl, —O—$(CH_2)_n$—$C_{3-6}$ cycloalkyl, —O—$(CH_2)_n$—$Si(C_{1-4}$ alkyl$)_3$ or —$(CH_2)_n$—$Si(C_{1-4}$ alkyl$)_3$, wherein the alkyl, alkoxy, cycloalkyl or heterocycloalkyl is optionally further substituted with 1-3 of halogen, D or OH;

$R^{11a'}$ and $R^{11b'}$ are each independently selected from H, D or $C_{1-2}$ alkyl;

n is selected from 0, 1, 2 or 3; or (6) $R_{11}$ is selected from —$NR^{11a}R^{11b}$;

$R^{11a}$ and $R^{11b}$ form

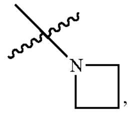 [SMILES: *N1CCC1]

, which is optionally substituted with CN, OH, —$C_{1-4}$ alkyl $C_{1-4}$ alkoxy, —$N(C_{1-4}$ alkyl$)_2$, —$C(O)$—$NR^{11a'}R^{11b'}$, 3- to 6-membered heterocycloalkyl, —O—$(CH_2)_{1-3}$—$C_{3-6}$ cycloalkyl, —O—$(CH_2)_n$—$Si(C_{1-4}$ alkyl$)_3$ or —$(CH_2)_n$—$Si(C_{1-4}$ alkyl$)_3$, wherein the alkyl, alkoxy, cycloalkyl or heterocycloalkyl is optionally further substituted with 1-3 of halogen, D or OH;

$R^{11a'}$ and $R^{11b'}$ are each independently selected from H, D or $C_{1-2}$ alkyl;

n is selected from 0, 1, 2 or 3; or (7) $R_{11}$ is selected from =N—$R^{11d}$, and $R^{11d}$ is selected from —O—$R^a$;

$R^a$ is selected from 3- to 6-membered heterocycloalkyl; or (8) $R_{11}$ is selected from $C_{2-6}$ alkenyl, $C_{2-6}$ alkynyl, —$S(O)_2R^{11c}$, OH, cyano-substituted alkyl or —$(CH_2)_n$—$Si(C_{1-4}$ alkyl$)_3$;

$R^{11c}$ is selected from $C_{1-4}$ alkyl, —$NHC_{1-4}$ alkyl or —$(CH_2)_n$—$C_{3-6}$ cycloalkyl, wherein the alkyl or cycloalkyl is optionally substituted with 1-3 of halogen or $C_{1-4}$ alkyl;

n is 0, 1, 2 or 3; or (9) $R_{11}$ is selected from —$NR^{11a}R^{11b}$;

$R^{11a}$ is selected from H;

$R^{11b}$ is selected from —$(CH_2)_{1-3}$ 4- to 7-membered monocyclic heterocycloalkyl containing 1-3 heteroatoms selected from N, O or S, wherein the monocyclic heterocycloalkyl is optionally substituted with 1-3 groups selected from D, $C_{1-4}$ alkyl, cyano-substituted alkyl, cyano, —$S(O)_2C_{1-4}$ alkyl or —$C(O)C_{1-4}$ alkyl;

other groups have the same definitions as those in embodiments one to ten;

in some embodiments, other groups have the same definitions as those in any of embodiments fifteen to seventeen.

For embodiment twenty of the present disclosure, in some embodiments, (1) $R_{11}$ is selected from —$NR^{11a}R^{11b}$;

$R^{11a}$ is selected from H, D or $C_{1-4}$ alkyl;

$R^{11b}$ is selected from D, —$C(O)R_{11c}$, —C(O)—$(CH_2)$—$R^{11c}$, —$S(O)_2$—$NR^{11a'}R^{11b'}$, —$S(O)_2R^{11c}$—$(CH_2)_n$-5-membered heteroaryl, —$(CH_2)_n$-6-membered heteroaryl, —$(CH_2)_n$-3-membered monocyclic cycloalkyl, —$(CH_2)_n$-4-membered monocyclic cycloalkyl, —$(CH_2)_n$-5-membered monocyclic cycloalkyl, —$(CH_2)_n$-6-membered monocyclic cycloalkyl, —$(CH_2)_n$-6-membered monocyclic heterocycloalkyl or —$(CH_2)_n$-10-membered bicyclic heterocycloalkyl, wherein the heterocycloalkyl contains at least 1 Si atom as a heteroatom, and the heteroaryl, cycloalkyl or heterocycloalkyl is optionally substituted with 1-3 $R^a$;

$R^{11c}$ is selected from $C_{1-2}$ alkyl, $C_{1-2}$ alkoxy, $C_{1-2}$ alkyl-$C_{1-2}$ alkoxy, —$NHC_{1-2}$ alkyl, —$N(C_{1-2}$ alkyl$)_2$, —$(CH_2)_n$-3-membered monocyclic cycloalkyl, —$(CH_2)_n$-4-membered monocyclic cycloalkyl, —$(CH_2)_n$-5-membered monocyclic cycloalkyl, —$(CH_2)_n$-6-membered monocyclic cycloalkyl, —$(CH_2)_n$-5-membered bicyclic cycloalkyl, —$(CH_2)_n$-6-membered bicyclic cycloalkyl, —$(CH_2)_n$-(4-membered heterocycloalkyl), —$(CH_2)_n$-(5-membered heterocycloalkyl), —$(CH_2)_n$-(6-membered heterocycloalkyl), —$(CH_2)_n$-(5-membered heteroaryl), —$(CH_2)_n$-(6-membered heteroaryl) or —$(CH_2)_n$—Si$(C_{1-2}$ alkyl$)_3$, wherein the alkyl, alkoxy, heterocycloalkyl, cycloalkyl or heteroaryl is optionally substituted with 1-3 of halogen, $C_{1-2}$ alkyl or halo $C_{1-2}$ alkyl;

$R^a$ is selected from halogen, D, OH, cyano, $C_{1-4}$ alkyl, $C_{1-2}$ alkoxy, halo $C_{1-4}$ alkoxy, $C_2$-4 alkynyl, —$S(O)_2C_{1-2}$ alkyl or —$C(O)C_{1-2}$ alkyl, wherein the alkyl or alkoxy is optionally substituted with 1-3 of halogen, D or cyano;

$R^{11a'}$ and $R^{11b'}$ are each independently selected from H, D or $C_{1-2}$ alkyl;

n is 0 or 1; or (2) $R_{11}$ is selected from —$NR^{11a}R^{11b}$;

$R^{11a}$ is selected from H;

$R^{11b}$ is selected from 4-membered monocyclic heterocycloalkyl containing 1-3 heteroatoms selected from N, O or S, 5-membered monocyclic heterocycloalkyl containing 1-3 heteroatoms selected from N, O or S, 6-membered monocyclic heterocycloalkyl containing 1-3 heteroatoms selected from N, O or S, a 5-membered bridged ring containing 1-3 heteroatoms selected from N, O or S, a 6-membered bridged ring containing 1-3 heteroatoms selected from N, O or S, a 7-membered bridged ring containing 1-3 heteroatoms selected from N, O or S or a 8-membered bridged ring containing 1-3 heteroatoms selected from N, O or S, wherein the monocyclic heterocycloalkyl or bridged ring is optionally substituted with 1-3 groups selected from D, cyano-substituted alkyl, cyano, —$S(O)_2C_{1-2}$ alkyl or —$C(O)C_{1-2}$ alkyl; or (3) $R_{11}$ is selected from —$(CH_2)$—$NR^{11a}R^{11b}$, —$(CH_2)_n$—$C(O)NR^{11a}R^{11b}$, —$C(O)R^{11c}$—$OR^b$ or —$(CH_2)_n$—$NR^{11a}$—$C(O)R^{11c}$;

each $R^{11a}$ is independently selected from H, D or $C_{1-2}$ alkyl;

each $R^{11b}$ is independently selected from $C_{1-2}$ alkyl, —$(CH_2)_n$-(5-membered heteroaryl), —$(CH_2)_n$-(6-membered heteroaryl), —$(CH_2)_n$-3-membered cycloalkyl, —$(CH_2)_n$-4-membered cycloalkyl, —$(CH_2)_n$-5-membered cycloalkyl, —$(CH_2)_n$-6-membered cycloalkyl, —$(CH_2)_n$-(4-membered heterocycloalkyl), —$(CH_2)_n$-(5-membered heterocycloalkyl) or —$(CH_2)_n$-(6-membered heterocycloalkyl), wherein the alkyl, heteroaryl, cycloalkyl or heterocycloalkyl is optionally substituted with 1-3 $R^a$;

$R^{11c}$ is selected from $C_{1-2}$ alkyl, $C_{1-2}$ alkoxy, —$(CH_2)_n$-3-membered cycloalkyl, —$(CH_2)_n$-4-membered cycloalkyl, —$(CH_2)_n$-5-membered cycloalkyl, —$(CH_2)_n$-6-membered cycloalkyl, —$(CH_2)_n$-(3-membered heterocycloalkyl), —$(CH_2)_n$-(4-membered heterocycloalkyl), —$(CH_2)_n$-(5-membered heterocycloalkyl), —$(CH_2)_n$-(6-membered heterocycloalkyl), —$(CH_2)_n$-(5-membered heteroaryl), —$(CH_2)_n$-(6-membered heteroaryl) or —$(CH_2)_n$—Si$(C_{1-2}$ alkyl$)_3$, wherein the alkyl, alkoxy, heterocycloalkyl, cycloalkyl or heteroaryl is optionally substituted with 1-3 of halogen, cyano, $C_{1-4}$ alkyl, halo $C_{1-2}$ alkyl or $C_{1-2}$ alkoxy;

$R^a$ is selected from halogen, D, cyano, $C_{1-2}$ alkyl or halo $C_{1-2}$ alkyl, wherein the alkyl is optionally substituted with 1-3 of halogen, D or cyano;

$R^b$ is selected from —$(CH_2)_n$-(5-membered heteroaryl), —$(CH_2)_n$-(6-membered heteroaryl), —$(CH_2)_n$-3-membered cycloalkyl, —$(CH_2)_n$-4-membered cycloalkyl, —$(CH_2)_n$-5-membered cycloalkyl, —$(CH_2)_n$-6-membered cycloalkyl, $C_{1-2}$ alkyl, $C_{2-4}$ alkenyl or —$(CH_2)_n$—C(O)—$NR^{11a'}R^{11b'}$, wherein the heteroaryl, cycloalkyl, alkyl or alkenyl is optionally substituted with 1-3 of halogen, $C_{1-2}$ alkyl, halo $C_{1-2}$ alkyl or CN;

$R^{11a'}$ and $R^{11b'}$ are each independently selected from H, D or $C_{1-2}$ alkyl;

alternatively, $R^{11a'}$ and $R^{11b'}$ together with the nitrogen atom to which they are attached form 3-membered heterocycloalkyl, 4-membered heterocycloalkyl, 5-membered heterocycloalkyl or 6-membered heterocycloalkyl, wherein the heterocycloalkyl is optionally substituted with 1-3 of halogen, D or $C_{1-2}$ alkyl;

n is 0 or 1; or (4) $R_{11}$ is selected from —$(CH_2)_n$-phenyl, —$(CH_2)_n$-5-membered heteroaryl, —$(CH_2)_n$-6-membered heteroaryl, —$(CH_2)_n$-8-membered heteroaryl, —$(CH_2)_n$-9-membered heteroaryl, —$(CH_2)_n$-10-membered heteroaryl, —$(CH_2)_n$-3-membered cycloalkyl, —$(CH_2)_n$-4-membered cycloalkyl, —$(CH_2)_n$-5-membered cycloalkyl, —$(CH_2)_n$-6-membered cycloalkyl, —$(CH_2)_n$-(8- to 12-membered bicyclic heterocycloalkyl), —$(CH_2)$-(4-membered heterocycloalkyl), —$(CH_2)$-(5-membered heterocycloalkyl) or —$(CH_2)$-(6-membered heterocycloalkyl), wherein the aryl, heteroaryl, cycloalkyl or heterocycloalkyl is optionally substituted with 1-3 groups selected from: halogen, D, $C_{1-2}$ alkoxy, $C_{1-2}$ alkyl, =O, —O—$(CH_2)_n$-3-membered cycloalkyl, —O—$(CH_2)_n$-4-membered cycloalkyl or —O—$(CH_2)_n$-5-membered cycloalkyl, wherein the alkyl, alkoxy or cycloalkyl is optionally substituted with 1-3 groups selected from $R^a$;

$R^a$ is selected from halogen, D or $C_{1-2}$ alkyl;

n is 0 or 1; or (5) $R_{11}$ is selected from 4-membered heterocycloalkyl, 5-membered heterocycloalkyl or 6-membered heterocycloalkyl, wherein $R_{11}$ is not selected from heterocycloalkyl in which the group linking site between $R_{11}$ and B is an N atom, and the heterocycloalkyl is optionally substituted with 1-3 groups selected from: halogen, D, $C_{1-2}$ alkyl, halo $C_{1-2}$ alkyl, $C_{1-2}$ alkoxy, CN or OH; or (6) $R_{11}$ is selected from —$NR^{11a}R^{11b}$;

$R^{11a}$ and $R^{11b}$ form

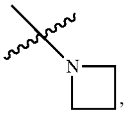, which is optionally substituted with CN, OH, —$C_{1-2}$ alkyl $C_{1-2}$ alkoxy, —$N(C_{1-2}$ alkyl$)_2$, —C(O)—$NR^{11a'}R^{11b'}$, 4-membered heterocycloalkyl, 5-membered heterocycloalkyl, 6-membered heterocycloalkyl, —O—$(CH_2)$-3-membered cycloalkyl, —O—$(CH_2)$-4-membered cycloalkyl, —O—$(CH_2)$-5-membered cycloalkyl or —$(CH_2)_n$—$Si(C_{1-2}$ alkyl$)_3$, wherein the alkyl, alkoxy, cycloalkyl or heterocycloalkyl is optionally further substituted with 1-3 of halogen, D or OH;

$R^{11a'}$ and $R^{11b'}$ are each independently selected from H, D or $C_{1-2}$ alkyl;

n is selected from 0 or 1; or (7) $R_{11}$ is selected from =N—$R^{11d}$, and $R^{11d}$ is selected from —O—$R^a$.

$R^a$ is selected from 4-membered heterocycloalkyl or 5-membered heterocycloalkyl; or (8) $R_{11}$ is selected from $C_{2-6}$ alkynyl, —$S(O)_2R^{11c}$, OH, cyano-substituted alkyl or —$(CH_2)_n$—$Si(C_{1-2}$ alkyl$)_3$;

$R^{11c}$ is selected from $C_{1-2}$ alkyl, —$NHC_{1-2}$ alkyl, —$(CH_2)_n$-3-membered cycloalkyl, —$(CH_2)_n$-4-membered cycloalkyl or —$(CH_2)_n$-5-membered cycloalkyl, wherein the alkyl or cycloalkyl is optionally substituted with 1-3 of halogen or $C_{1-2}$ alkyl;

n is 0 or 1; or (9) $R_{11}$ is selected from —$NR^{11a}R^{11b}$;

$R^{11a}$ is selected from H;

$R^{11b}$ is selected from —$(CH_2)$-4- to 7-membered monocyclic heterocycloalkyl containing 1-3 heteroatoms selected from N, O or S, wherein the monocyclic heterocycloalkyl is optionally substituted with 1-3 groups selected from D, $C_{1-2}$ alkyl, cyano-substituted alkyl, cyano, —$S(O)_2C_{1-2}$ alkyl or —$C(O)C_{1-2}$ alkyl;

other groups have the same definitions as those in embodiments one to ten;

in some embodiments, other groups have the same definitions as those in any of embodiments fifteen to seventeen.

For embodiment twenty-one of the present disclosure, in some embodiments, $R_{11}$ is selected from cyclopropyl, oxetanyl,

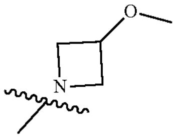
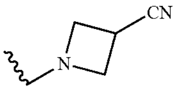
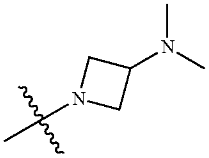
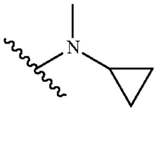

-continued

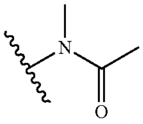
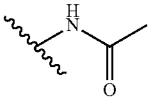
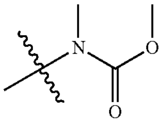
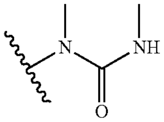
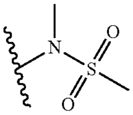
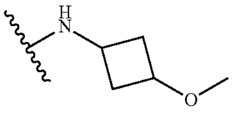
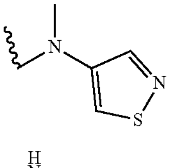
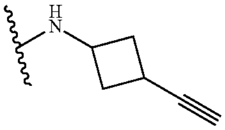
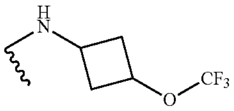
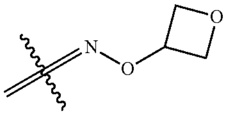
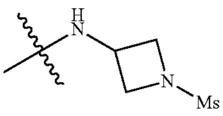
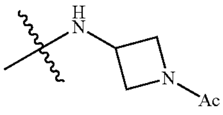
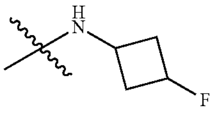
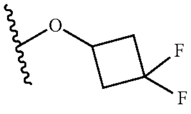
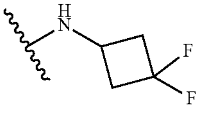
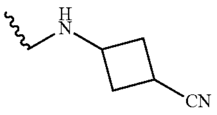
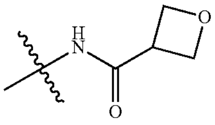
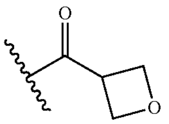
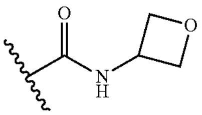
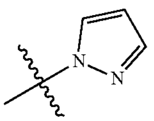
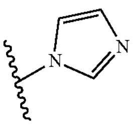
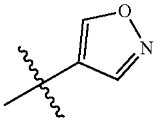
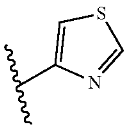
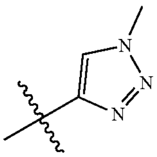
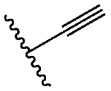
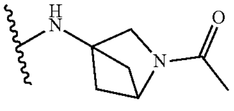
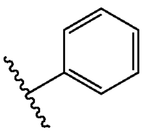
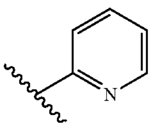
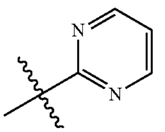

-continued
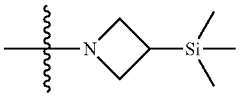
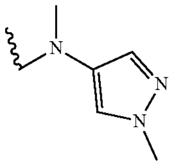
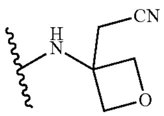
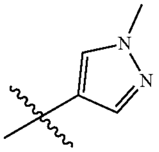
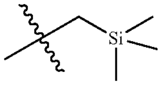
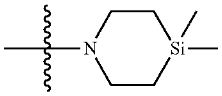
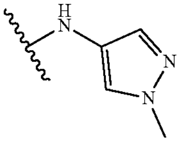
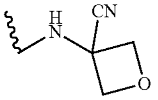
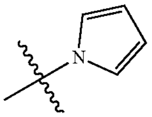
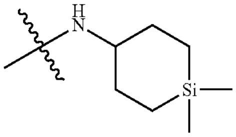
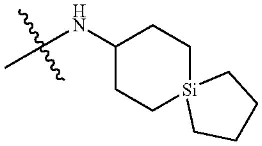
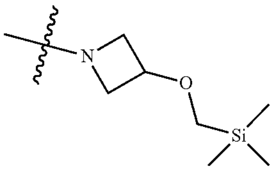
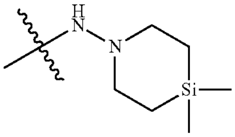
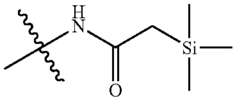
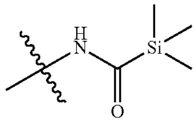
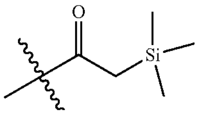
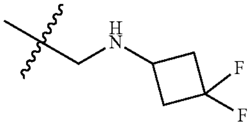
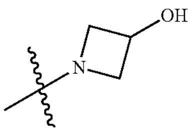
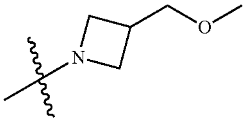
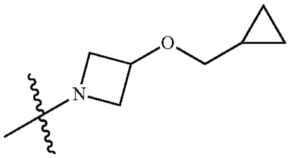
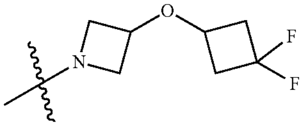
-continued
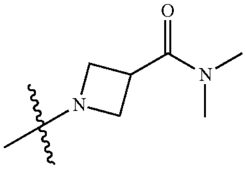
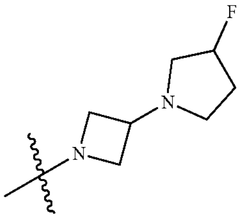
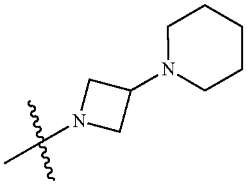
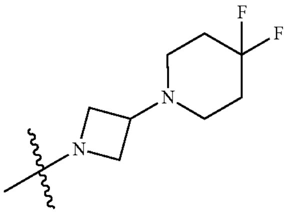
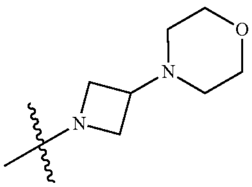
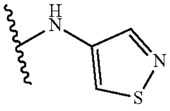
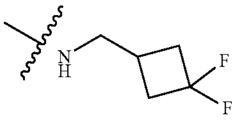
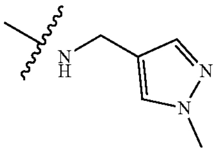
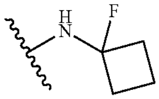
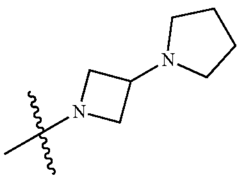
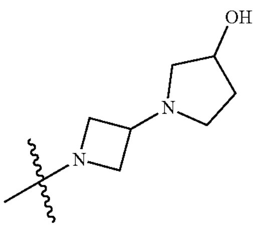
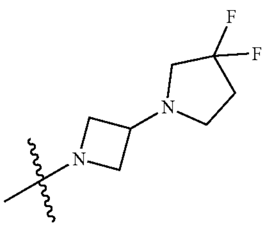
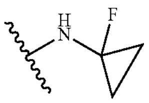

-continued
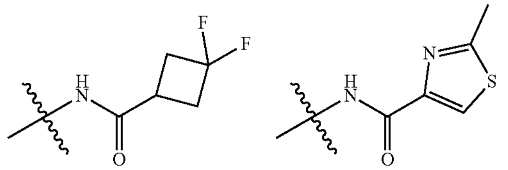
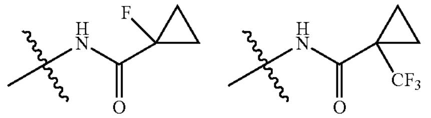
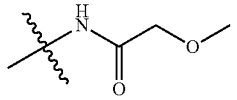
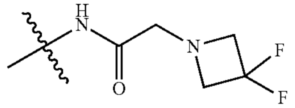
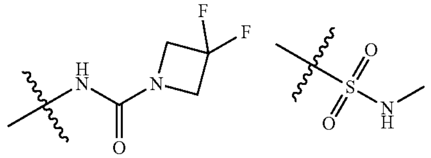
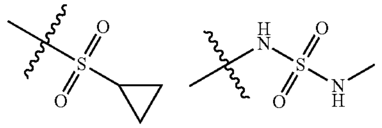
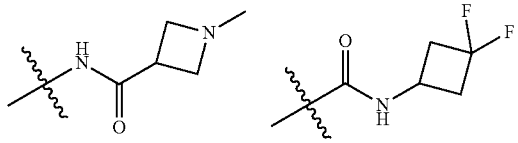
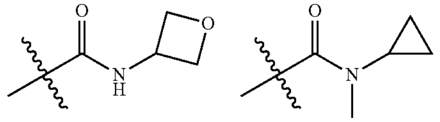
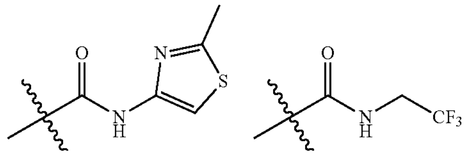
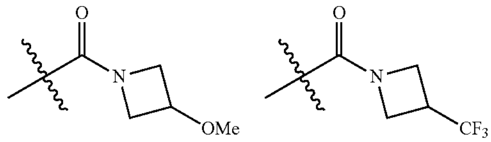
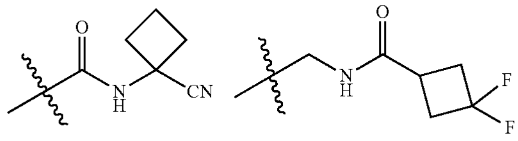
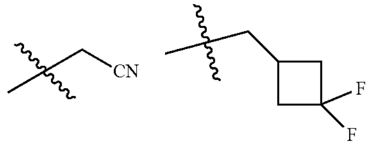
-continued
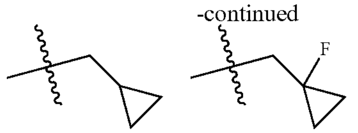
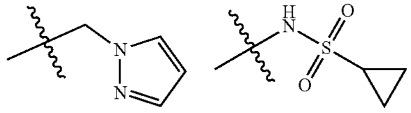
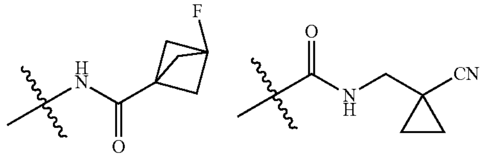
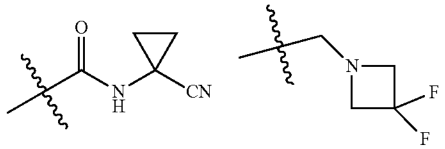
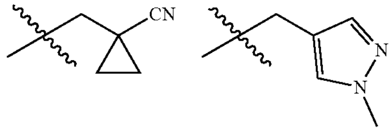
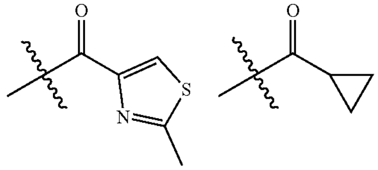
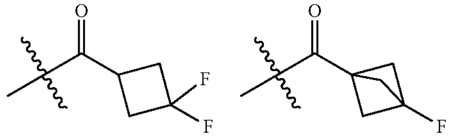
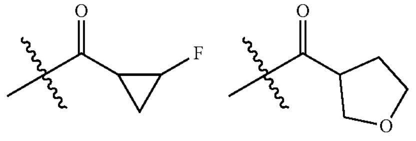
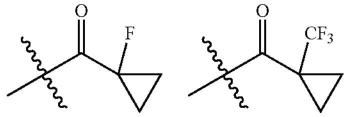
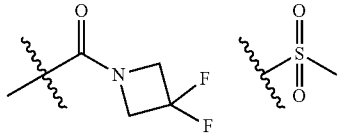
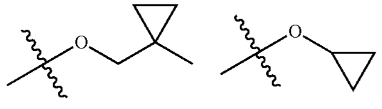
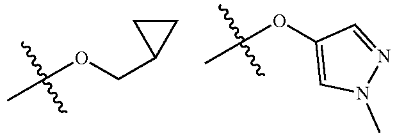
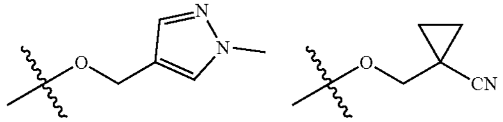

-continued

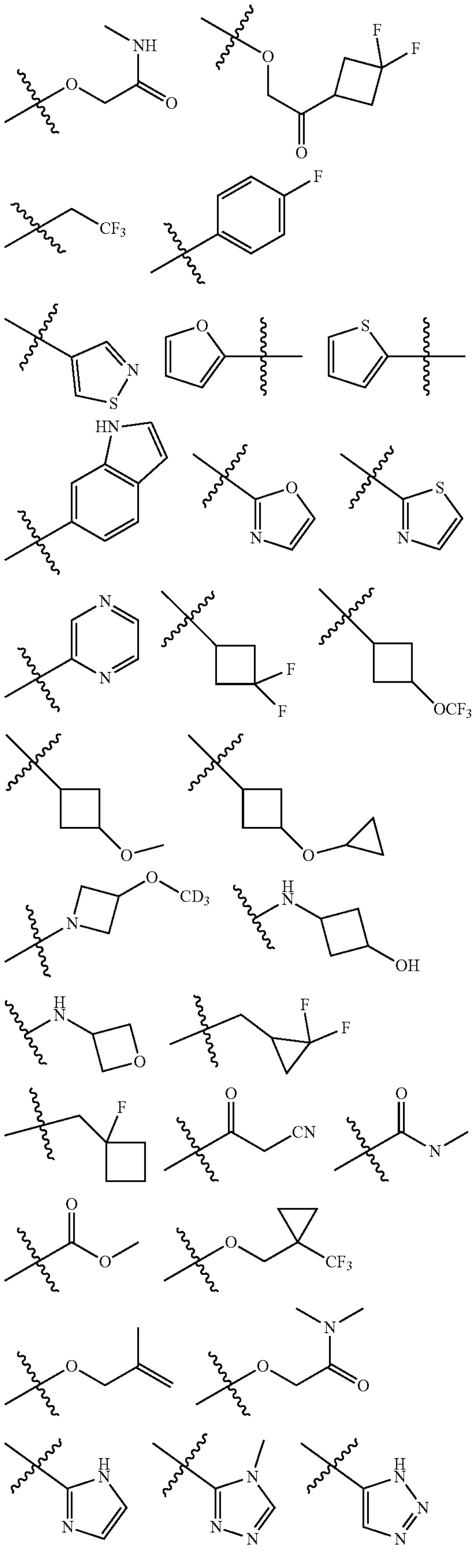

-continued

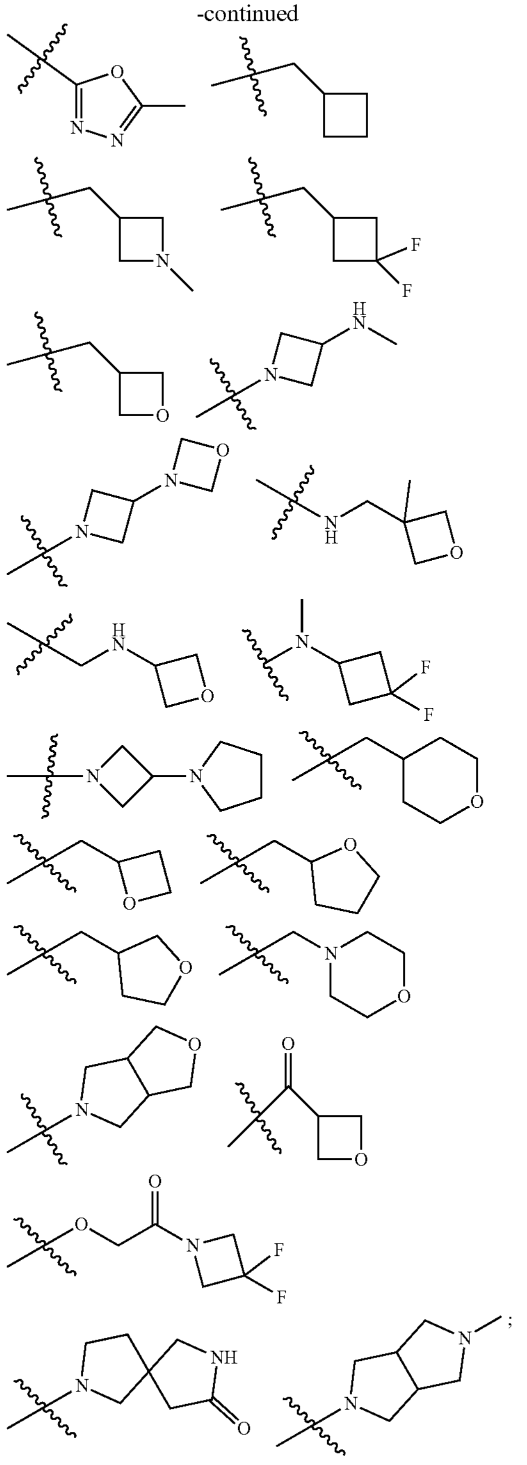

or $R_{11}$ is selected from methoxy or hydroxyl;

other groups have the same definitions as those in embodiments one to ten;

in some embodiments, other groups have the same definitions as those in any of embodiments fifteen to seventeen.

Embodiment twenty-two of the present disclosure relates to a compound of formula (I), or a stereoisomer, a pharmaceutically acceptable salt, a solvate, and a eutectic or deuterated compound thereof, wherein $R_{11}$ is selected from —$NR^{11a}R^{11b}$, 3- to 6-membered heterocycloalkyl or $C_{1-4}$ alkyl, wherein the heterocycloalkyl or alkyl is optionally substituted with 1-3 groups selected from: halogen, D, $C_{1-4}$ alkyl, halo $C_{1-4}$ alkyl, $C_{1-4}$ alkoxy, —$C_{1-4}$ alkyl-$C_{1-4}$ alkoxy, =O, CN, OH, —$NR^{11a'}R^{11b'}$, —C(O)—$NR^{11a'}R^{11b'}$, —C(O)$C_{1-4}$ alkyl, —O—$(CH_2)_n$—Si($C_{1-4}$ alkyl)$_3$, —$(CH_2)_n$—Si($C_{1-4}$ alkyl)$_3$, $C_{3-6}$ cycloalkyl, 3- to 12-membered heterocycloalkyl or —O—$(CH_2)_n$—$C_{3-6}$ cycloalkyl, wherein the $CH_2$, alkyl, alkoxy, cycloalkyl or heterocycloalkyl is optionally substituted with 1-3 groups selected from $R^a$;

$R^{11a}$ and $R^{11b}$ are each independently selected from H, D, $C_{1-4}$ alkyl, $C_{1-4}$ alkoxy, —C(O)$R_{11c}$, —C(O)—$(CH_2)_n$—$R^{11c}$, —$S(O)_2$—$NR^{11a'}R^{11b'}$, —$S(O)_2R^{11c}$, —$(CH_2)_n$-(6- to 12-membered aryl), —$(CH_2)_n$-(5- to 12-membered heteroaryl), —$(CH_2)_n$—$C_{3-12}$ cycloalkyl, —$(CH_2)_n$-(3- to 12-membered heterocycloalkyl), —$S(O)_2C_{1-4}$ alkyl or —$(CH_2)_n$—Si($C_{1-4}$ alkyl)$_3$, wherein the alkyl, alkoxy, aryl, heteroaryl, cycloalkyl or heterocycloalkyl is optionally substituted with 1-3 $R^a$;

alternatively, $R^{11a}$ and $R^{11b}$ together with the nitrogen atom to which they are attached form 3- to 12-membered heterocycloalkyl, wherein the heterocycloalkyl is optionally substituted with 1-3 $R^c$;

$R^{11c}$ is selected from $C_{1-4}$ alkyl, $C_{1-4}$ alkoxy, $C_{1-4}$ alkyl-$C_{1-4}$ alkoxy, amino, —$NHC_{1-4}$ alkyl, —N($C_{1-4}$ alkyl)$_2$, —NH(3- to 6-membered heterocycloalkyl), —$NHC_{3-6}$ cycloalkyl, —$(CH_2)_n$—$C_{3-6}$ cycloalkyl, —$(CH_2)_n$-(3- to 6-membered heterocycloalkyl), —O—$C_{1-4}$ alkyl, —O—$C_3$-6 cycloalkyl, —O-(3- to 6-membered heterocycloalkyl), —$(CH_2)_n$-(6- to 12-membered aryl), —$(CH_2)_n$-(5- to 12-membered heteroaryl) or —$(CH_2)_n$—Si($C_{1-4}$ alkyl)$_3$, wherein the alkyl, alkoxy, heterocycloalkyl, cycloalkyl, aryl or heteroaryl is optionally substituted with 1-3 of halogen, cyano, $C_{1-4}$ alkyl, halo $C_{1-4}$ alkyl, $C_{1-4}$ alkoxy, halo $C_{1-4}$ alkoxy, —$NHC_{1-4}$ alkyl, —N($C_{1-4}$ alkyl)$_2$, —NH(3- to 6-membered heterocycloalkyl), —$NHC_{3-6}$ cycloalkyl, —O—$C_{3-6}$ cycloalkyl, —O-(3- to 6-membered heterocycloalkyl) or —Si($C_{1-4}$ alkyl)$_3$;

$R^a$ is selected from halogen, D, OH, cyano, $C_{1-4}$ alkyl, halo $C_{1-4}$ alkyl, $C_{1-4}$ alkoxy, halo $C_{1-4}$ alkoxy, $C_{2-6}$ alkenyl, $C_{2-6}$ alkynyl, —$S(O)_2C_{1-4}$ alkyl, —C(O)$C_{1-4}$ alkyl, —$(CH_2)_n$—Si($C_{1-4}$ alkyl)$_3$, $C_{3-6}$ cycloalkyl, 3- to 6-membered heterocycloalkyl, 6- to 12-membered aryl or 5- to 12-membered heteroaryl, wherein the alkyl, alkoxy, cycloalkyl, heterocycloalkyl, aryl or heteroaryl is optionally substituted with 1-3 of halogen, D, cyano, hydroxyl, $C_{1-4}$ alkyl or halo $C_{1-4}$ alkyl;

$R^{11a'}$ and $R^{11b'}$ are each independently selected from H, D, $C_{1-4}$ alkyl, halogen, CN or OH;

alternatively, $R^{11a'}$ and $R^{11b'}$ together with the nitrogen atom to which they are attached form 3- to 6-membered heterocycloalkyl, wherein the heterocycloalkyl is optionally substituted with 1-3 of halogen, D, CN, OH, $C_{1-4}$ alkyl, halo $C_{1-4}$ alkyl, $C_{1-4}$ alkoxy or halo $C_{1-4}$ alkoxy;

n is 0, 1, 2 or 3;

other groups have the same definitions as those in embodiments five to seven;

Embodiment twenty-three of the present disclosure relates to a compound of formula (I), or a stereoisomer, a pharmaceutically acceptable salt, a solvate, and a eutectic or deuterated compound thereof, wherein $R_1$ is selected from H, cyano, methyl or cyclopropyl;

$R_2$ is selected from H or methyl;

$R_3$ is selected from oxetanyl, fluorocyclopropyl, methyl or hydroxyethyl;

alternatively, $R_2$ and $R_1$ together form cyclopentyl; or alternatively, $R_2$ and $R_3$ together form thiacyclopentyl;

$R_4$ and $R_5$ are selected from H;

$R_{4'}$ and $R_{5'}$ together form =O;

$R_6$ is selected from H;

$R_7$ is selected from H or halogen;

$R_8$ is selected from H, Cl, methoxy, cyclopropyl, oxetanyl, —Si$(CH_3)_3$ or

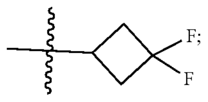 [SMILES: *C1CC(F)(F)C1]

$R_9$ is selected from methyl, methoxy, trifluoromethoxy, cyclopropyl, ethynyl, —Si$(CH_3)_3$ or propynyl;

$R_{10}$ is selected from methyl or —$CH_2$—Si$(CH_3)_3$;

other groups have the same definitions as those in embodiment twenty.

Embodiment twenty-four of the present disclosure relates to a compound of formula (I), or a stereoisomer, a pharmaceutically acceptable salt, a solvate, and a eutectic or deuterated compound thereof, wherein the compound has a structure of formula (III):

(III)

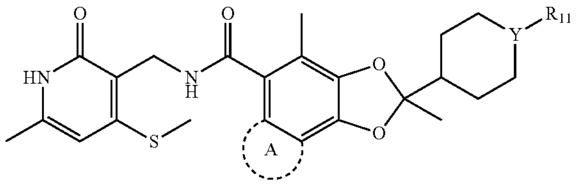

ring A is 5-membered cycloalkyl, 5-membered heterocycloalkyl or 5-membered heterocycloaryl, wherein the cycloalkyl, heterocycloalkyl or heterocycloaryl is optionally substituted with 1-3 of $C_{1-4}$ alkyl or halo $C_{1-4}$ alkyl;

Y is selected from —CH— or —N—;

other groups have the same definitions as those in embodiment one.

Embodiment twenty-five of the present disclosure relates to a compound of formula (I), or a stereoisomer, a pharmaceutically acceptable salt, a solvate, and a eutectic or deuterated compound thereof, wherein

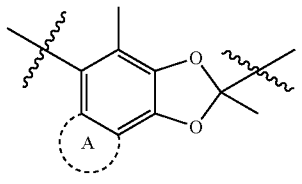

has a structure as follows:

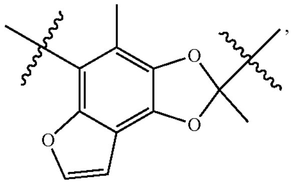

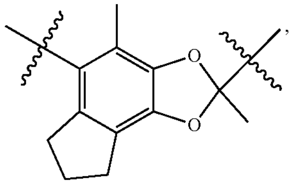

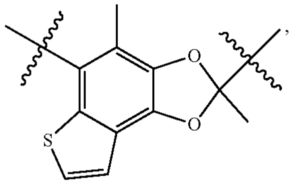

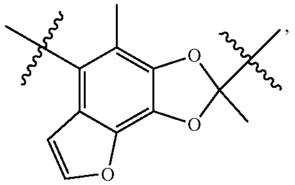

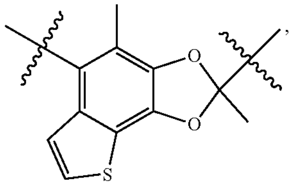

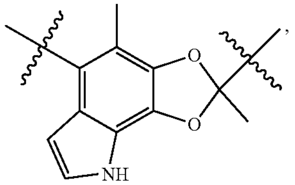

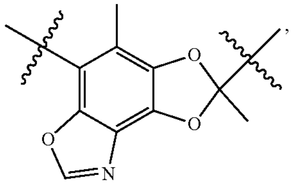

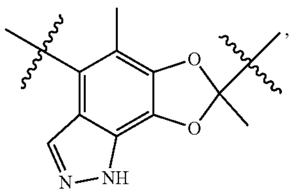

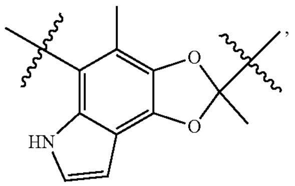

-continued

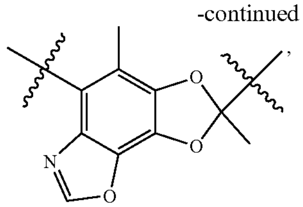

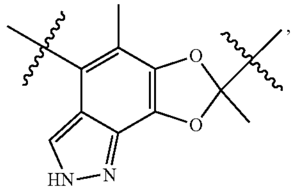

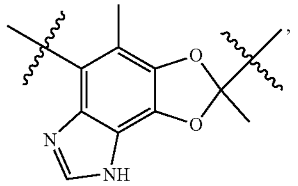

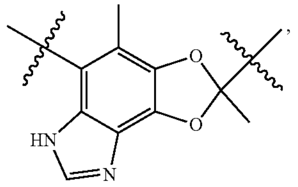

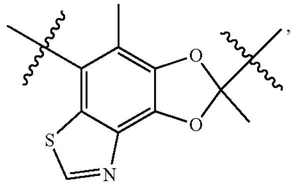

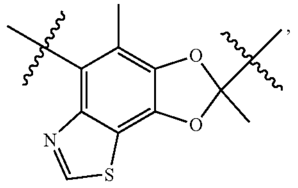

wherein the ring A may be optionally substituted with 1-3 of $C_{1-4}$ alkyl or halo $C_{1-4}$ alkyl;

other groups have the same definitions as those in embodiment twenty-four.

Embodiment twenty-six of the present disclosure relates to a compound of formula (I), or a stereoisomer, a pharmaceutically acceptable salt, a solvate, and a eutectic or deuterated compound thereof, wherein $R_{11}$ is selected from —$NR^{11a}R^{11b}$;

$R^{11a}$ is selected from H or $C_{1-4}$ alkyl;

$R^{11b}$ is selected from —C(O)$R_{11c}$, 5- to 12-membered heteroaryl, $C_{3-6}$ cycloalkyl or 3- to 6-membered heterocycloalkyl, wherein the heteroaryl, cycloalkyl or heterocycloalkyl is optionally substituted with 1-3 $R^a$;

alternatively, $R^{11a}$ and $R^{11b}$ together with the nitrogen atom to which they are attached form 3- to 6-membered heterocycloalkyl, wherein the heterocycloalkyl is optionally substituted with 1-3 of cyano, —N($C_{1-4}$ alkyl)$_2$, $C_{1-4}$ alkoxy or halo $C_{1-4}$ alkoxy;

$R^{11c}$ is selected from $C_{1-4}$ alkyl, $C_{1-4}$ alkoxy, —$NHC_{1-4}$ alkyl, —NH(3- to 6-membered heterocycloalkyl) or 3- to 6-membered heterocycloalkyl;

$R^a$ is selected from halogen, cyano, $C_{1-4}$ alkyl, halo $C_{1-4}$ alkyl, $C_{1-4}$ alkoxy, halo $C_{1-4}$ alkoxy, $C_{2-6}$ alkenyl, $C_{2-6}$ alkynyl, $—S(O)_2C_{1-4}$ alkyl or $—C(O)C_{1-4}$ alkyl, wherein the alkyl or alkoxy is optionally substituted with 1-3 of halogen, cyano or hydroxyl;

other groups have the same definitions as those in embodiment twenty-four or embodiment twenty-five.

Embodiment twenty-seven of the present disclosure relates to a compound of formula (I), or a stereoisomer, a pharmaceutically acceptable salt, a solvate, and a eutectic or deuterated compound thereof, wherein $R_{11}$ is selected from $—NR^{11a}R^{11b}$;

$R^{11a}$ and $R^{11b}$ together with the nitrogen atom to which they are attached form azacyclobutyl, wherein the azacyclobutyl is optionally substituted with 1-3 $C_{1-4}$ alkoxy;

other groups have the same definitions as those in embodiment twenty-four or embodiment twenty-five.

Embodiment twenty-eight of the present disclosure relates to a compound of formula (I), or a stereoisomer, a pharmaceutically acceptable salt, a solvate, and a eutectic or deuterated compound thereof, wherein the compound has a structure of formula (V):

(V)

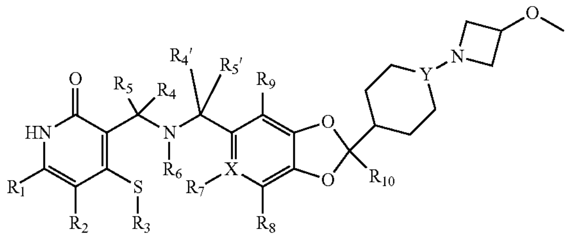

$R_8$ is selected from CN, $—NR^{8a}R^{8b}—$, $—NR^{8a}—C(O)—C_{1-4}$ alkyl, $C_{1-6}$ alkoxy, halo $C_{1-6}$ alkoxy, $C_{2-6}$ alkenyl, $C_{2-6}$ alkynyl, 3- to 6-membered heterocycloalkyl or 5- to 10-membered heteroaryl, wherein the alkyl, alkoxy, heterocycloalkyl or heteroaryl is optionally substituted with 1-3 of halogen, $C_{1-4}$ alkyl or OH;

$R^{8a}$ and $R^{8b}$ are each independently selected from H or $C_{1-4}$ alkyl;

Y is selected from —CH— or —N—;

other groups have the same definitions as those in embodiment one.

Embodiment twenty-nine of the present disclosure relates to a compound of formula (I), or a stereoisomer, a pharmaceutically acceptable salt, a solvate, and a eutectic or deuterated compound thereof, wherein $R_1$ is selected from $C_{1-4}$ alkyl, CN or $C_{3-6}$ cycloalkyl;

$R_2$ is selected from H or $C_{1-4}$ alkyl;

$R_3$ is selected from $C_{1-4}$ alkyl, halo $C_{1-4}$ alkyl, 3- to 6-membered heterocycloalkyl or $C_{3-6}$ cycloalkyl, wherein the alkyl, cycloalkyl or heterocycloalkyl is optionally substituted with 1-3 of the following groups: D, OH or halogen;

alternatively, $R_1$ and $R_2$ form 3- to 6-membered cycloalkyl, wherein the cycloalkyl is optionally substituted with 1-3 of halogen, D or $C_{1-4}$ alkyl; or alternatively, $R_2$ and $R_3$ form 3- to 6-membered heterocycloalkyl, wherein the heterocycloalkyl is optionally substituted with 1-3 of halogen, D or $C_{1-4}$ alkyl;

$R_4$ and $R_5$ are each independently selected from H or D;

$R_{4'}$ and $R_{5'}$ together with the carbon atom to which they are attached form 4- to 5-membered heterocycloalkyl; or $R_{4'}$ and $R_{5'}$ together form =O;

$R_6$ is selected from H;

$R_7$ is selected from H or halogen;

$R_9$ is selected from $C_{1-4}$ alkyl, $C_{2-6}$ alkynyl, $C_{3-6}$ cycloalkyl, $C_{1-4}$ alkoxy or $—Si(C_{1-4}\ alkyl)_3$, wherein the alkyl, cycloalkyl or alkoxy is optionally substituted with 1-3 of halogen, D or $C_{1-4}$ alkyl;

$R_{10}$ is selected from $C_{1-4}$ alkyl, wherein the alkyl is optionally substituted with 1-3$—(CH_2)_n—Si(C_{1-4}\ alkyl)_3$;

other groups have the same definitions as those in embodiment twenty-eight.

In some embodiments of the present disclosure, $R_1$ is selected from H, cyano, $C_{1-4}$ alkyl or $C_{3-6}$ cycloalkyl; in some embodiments of the present disclosure, $R_1$ is selected from $C_{1-4}$ alkyl; in some embodiments of the present disclosure, $R_1$ is selected from cyano or $C_{3-6}$ cycloalkyl; in some embodiments of the present disclosure, $R_1$ is selected from $C_{3-6}$ cycloalkyl; in some embodiments of the present disclosure, $R_1$ is selected from H, cyano, cyclopropyl or methyl; in some embodiments of the present disclosure, $R_1$ is selected from methyl.

In some embodiments of the present disclosure, $R_2$ is selected from H or $C_{1-4}$ alkyl; in some embodiments of the present disclosure, $R_2$ is selected from H or methyl; in some embodiments of the present disclosure, $R_2$ is selected from H.

In some embodiments of the present disclosure, $R_3$ is selected from $C_{1-6}$ alkyl, 3- to 6-membered heterocycloalkyl or $C_{3-6}$ cycloalkyl, wherein the alkyl or heterocycloalkyl is optionally substituted with 1-3 of the following groups: OH or halogen; in some embodiments of the present disclosure, $R_3$ is selected from methyl, oxetanyl, hydroxyethyl or

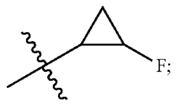 [SMILES: *C1CC1F]

in some embodiments of the present disclosure, $R_3$ is selected from $C_{1-6}$ alkyl; in some embodiments of the present disclosure, $R_3$ is selected from methyl.

In some embodiments of the present disclosure, $R_1$ and $R_2$ form 3- to 6-membered cycloalkyl, wherein the cycloalkyl is optionally substituted with 1-3 halogen; in some embodiments of the present disclosure, $R_1$ and $R_2$ form cyclopentyl.

In some embodiments of the present disclosure, $R_2$ and $R_3$ form 3- to 6-membered heterocycloalkyl, wherein the heterocycloalkyl is optionally substituted with 1-3 of halogen, OH or amino; in some embodiments of the present disclosure, $R_2$ and $R_3$ together with the sulfur atom attached form thiacyclopentyl.

In some embodiments of the present disclosure, $R_4$ and $R_5$ are each independently selected from H or $C_{1-4}$ alkyl; in some embodiments of the present disclosure, $R_4$ and $R_5$ are each independently selected from H.

In some embodiments of the present disclosure, $R_{4'}$ and $R_{5'}$ together with the carbon atom to which they are attached form oxetanyl; in some embodiments, $R_{4'}$ and $R_{5'}$ together form =O.

In some embodiments of the present disclosure, $R_6$ is selected from H; in some embodiments of the present disclosure, $R_6$ is selected from methyl.

In some embodiments of the present disclosure, $R_7$ is selected from H, F or Cl; in some embodiments of the present disclosure, $R_7$ is selected from H.

In some embodiments of the present disclosure, $R_8$ is selected from H, halogen, $C_{3-6}$ cycloalkyl, 3- to 6-membered heterocycloalkyl or $C_{1-4}$ alkoxy, wherein the alkoxy, cycloalkyl or heterocycloalkyl is optionally substituted with 1-3 of F or Cl; in some embodiments of the present disclosure, $R_8$ is selected from H, methoxy, cyclopropyl, Cl, oxetanyl or

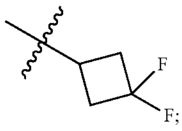 [SMILES: *C1CC(F)(F)C1];

in some embodiments of the present disclosure, $R_8$ is selected from $C_1$.

In some embodiments of the present disclosure, $R_7$ and $R_8$ together with the atoms to which they are attached form $C_{3-6}$ cycloalkyl, 3- to 6-membered heterocycloalkyl, 6- to 12-membered aryl or 5- to 10-membered heteroaryl, wherein the cycloalkyl, heterocycloalkyl, aryl or heteroaryl is optionally substituted with 1-3 of halogen, $C_{1-4}$ alkyl or halo $C_{1-4}$ alkyl; in some embodiments of the present disclosure, $R_7$ and $R_8$ together with the atoms to which they are attached form 5-membered cycloalkyl, 5-membered heterocycloalkyl or 5-membered heterocycloaryl, wherein the cycloalkyl, heterocycloalkyl or heterocycloaryl is optionally substituted with 1-3 of $C_{1-4}$ alkyl or halo $C_{1-4}$ alkyl.

In some embodiments of the present disclosure, $R_9$ is selected from $C_{1-4}$ alkyl, $C_{2-6}$ alkynyl, $C_{3-6}$ cycloalkyl, $C_{1-4}$ alkoxy or —Si($C_{1-4}$ alkyl)$_3$, wherein the alkyl, cycloalkyl or alkoxy is optionally substituted with 1-3 of F or Cl; in some embodiments of the present disclosure, $R_9$ is selected from $C_{1-4}$ alkyl; in some embodiments of the present disclosure, $R_9$ is selected from methyl, trifluoromethoxy, methoxy, cyclopropyl, ethynyl or propynyl; in some embodiments of the present disclosure, $R_9$ is selected from methyl.

In some embodiments of the present disclosure, $R_{10}$ is selected from methyl or ethyl; in some embodiments of the present disclosure, $R_{10}$ is selected from methyl; in some embodiments of the present disclosure, $R_{10}$ is selected from methyl, wherein the methyl is optionally substituted with —Si($CH_3$)$_3$.

In some embodiments of the present disclosure, $R_1$ is selected from —$NR^{11a}R^{11b}$. =N—$R^{11d}$, —$OR^b$, —C(O)$R^{11c}$, $C_{2-6}$ alkynyl, 6- to 12-membered aryl, 5- to 10-membered heteroaryl, $C_{3-6}$ cycloalkyl, 3- to 6-membered heterocycloalkyl or —($CH_2$)$_n$—Si($C_{1-4}$ alkyl)$_3$, wherein the alkynyl, aryl, heteroaryl, cycloalkyl or heterocycloalkyl is optionally substituted with 1-3 of halogen, $C_{1-4}$ alkyl, —C(O)$C_{1-4}$ alkyl, —O—($CH_2$)$_n$—Si($C_{1-4}$ alkyl)$_3$ or —($CH_2$)$_n$—Si($C_{1-4}$ alkyl)$_3$; in some embodiments of the present disclosure, $R_{11}$ is selected from —$NR^{11a}R^{11b}$, —$OR^b$, —C(O)$R^{11c}$, $C_{2-6}$ alkynyl, 6- to 12-membered aryl, 5- to 10-membered heteroaryl, $C_{3-6}$ cycloalkyl or 3- to 6-membered heterocycloalkyl, wherein the alkynyl, aryl, heteroaryl, cycloalkyl or heterocycloalkyl is optionally substituted with 1-3 of halogen, $C_{1-4}$ alkyl or —C(O)$C_{1-4}$ alkyl; in some embodiments of the present disclosure, $R_{11}$ is selected from —$NR^{11a}R^{11b}$, 6- to 12-membered aryl or 5- to 10-membered heteroaryl, wherein the aryl or heteroaryl is optionally substituted with 1-3 of halogen, $C_{1-4}$ alkyl or —C(O)$C_{1-4}$ alkyl; in some embodiments of the present disclosure, $R_{11}$ is selected from —$NR^{11a}R^{11b}$; in some embodiments of the present disclosure, $R_1$ is selected from 6- to 12-membered aryl or 5- to 10-membered heteroaryl, wherein the aryl or heteroaryl is optionally substituted with 1-3 of halogen, $C_{1-4}$ alkyl or —C(O)$C_{1-4}$ alkyl; in some embodiments of the present disclosure, $R_{11}$ is selected from 5- to 10-membered heteroaryl, wherein the heteroaryl is optionally substituted with 1-3 of halogen, $C_{1-4}$ alkyl or —C(O)$C_{1-4}$ alkyl; in some embodiments of the present disclosure, $R_{11}$ is selected from cyclopropyl, oxetanyl,

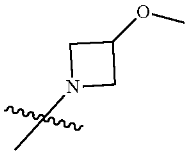
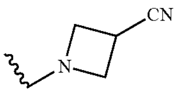
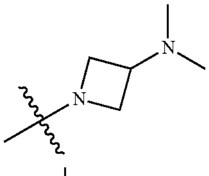
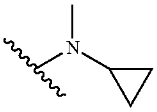
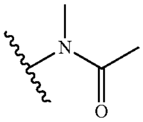
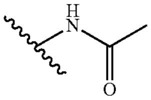
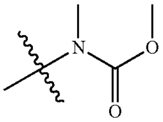
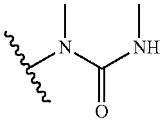
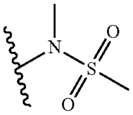
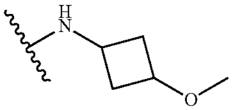
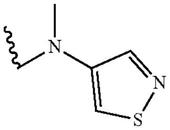
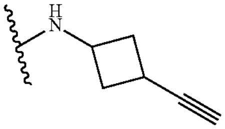
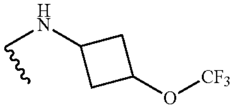
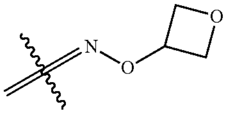
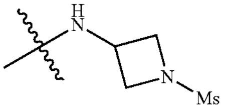
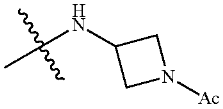
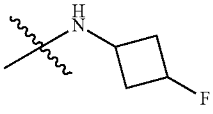
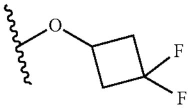
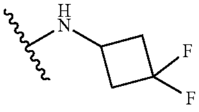
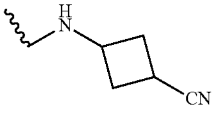
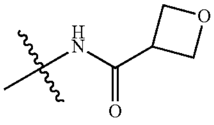

-continued
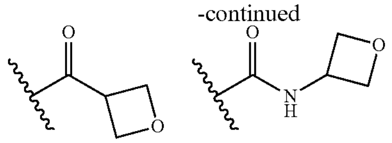
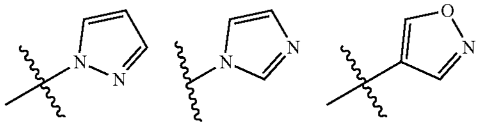
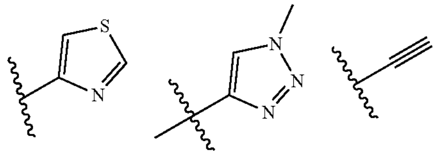
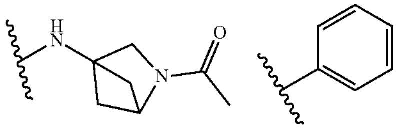
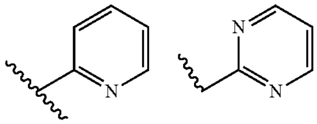
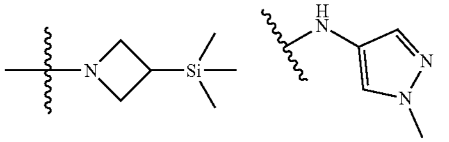
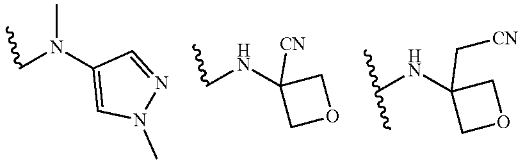
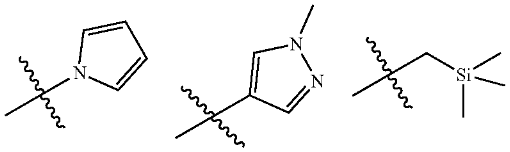
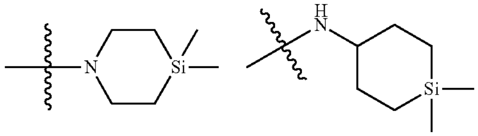
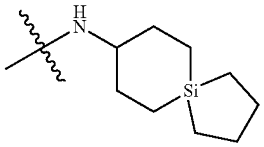
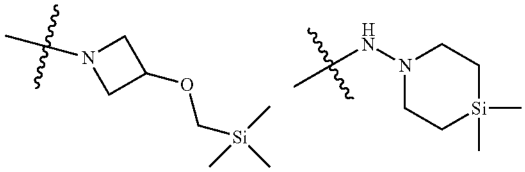
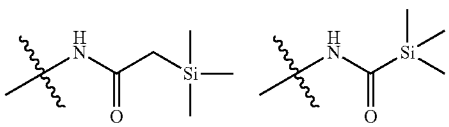
-continued
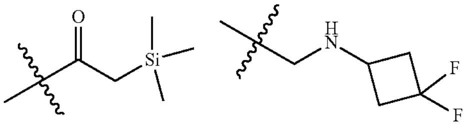
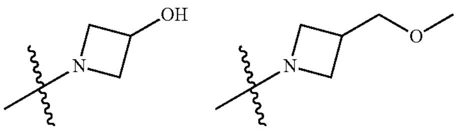
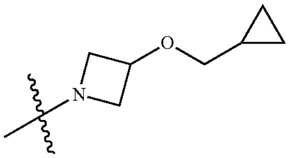
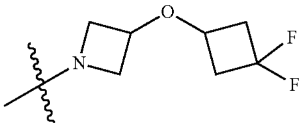
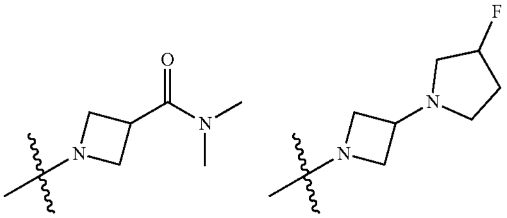
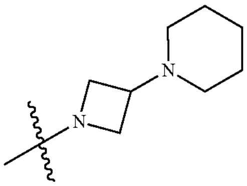
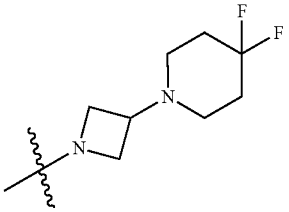
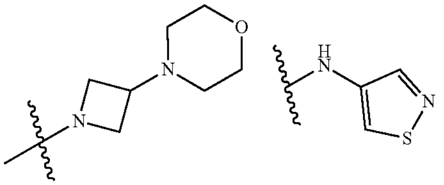
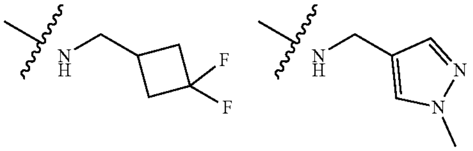
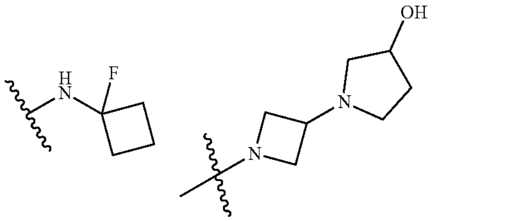

-continued
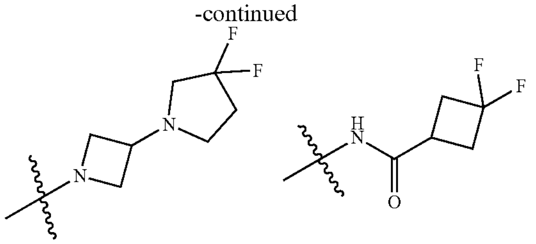
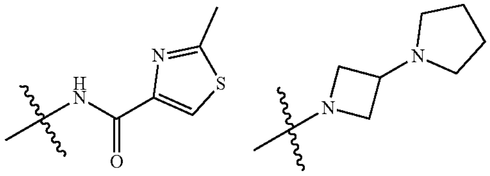
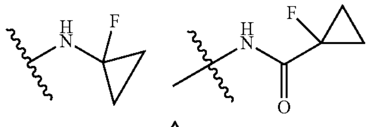
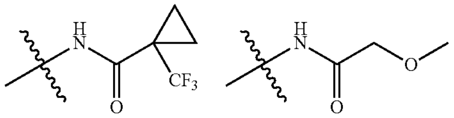
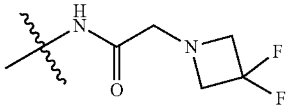
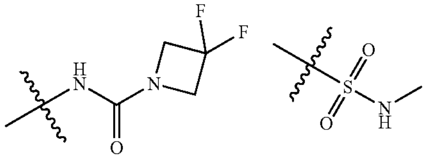
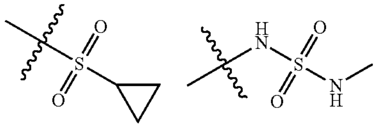
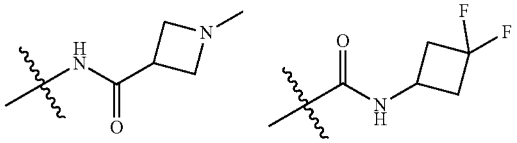
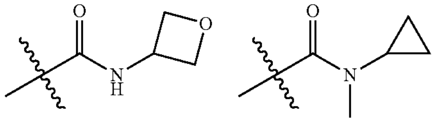
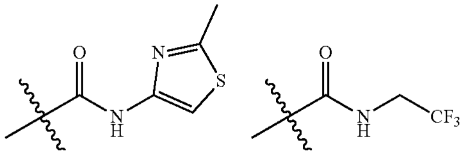
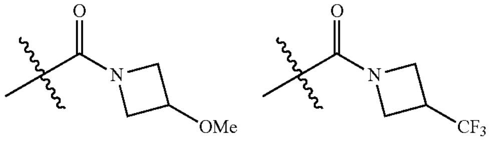
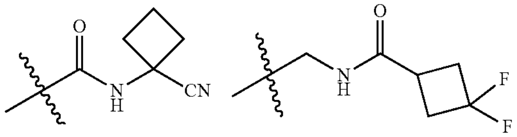
-continued
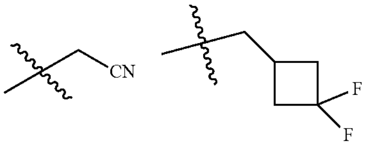
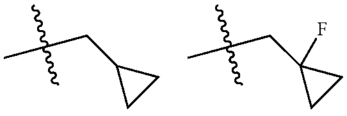
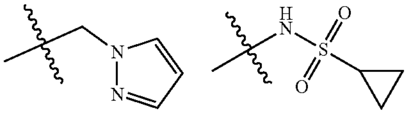
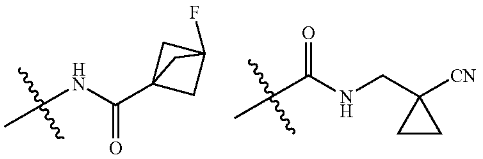
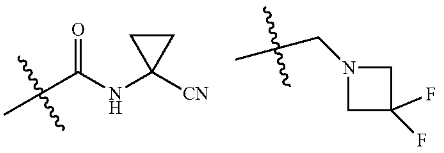
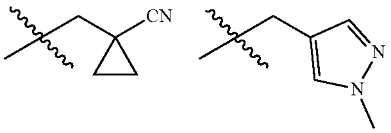
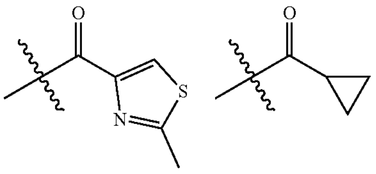
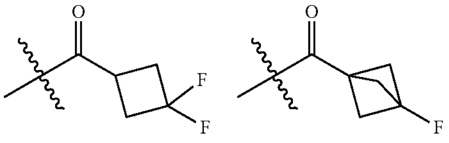
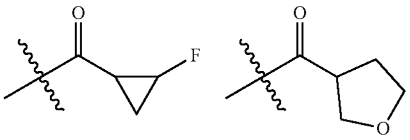
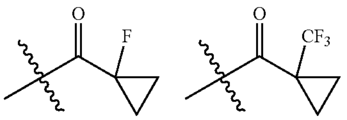
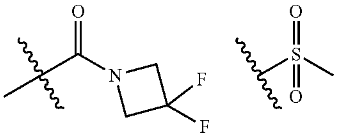
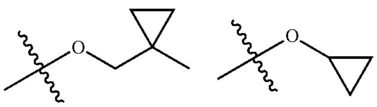

-continued
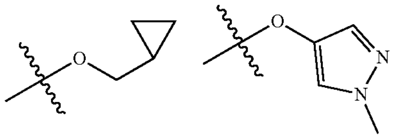
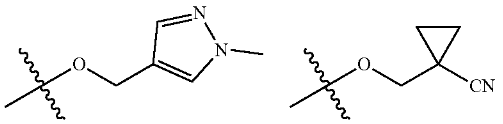
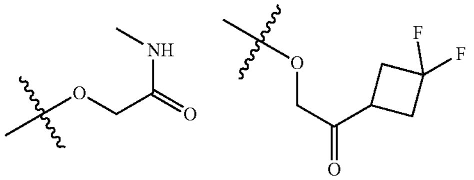
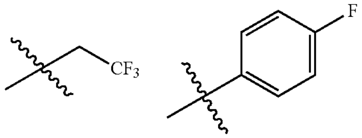
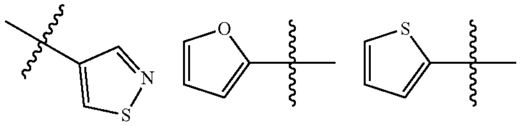
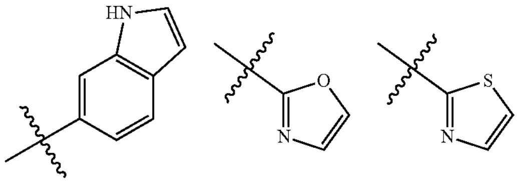
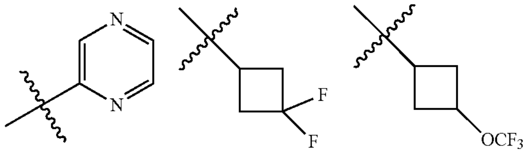
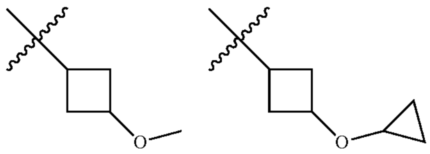
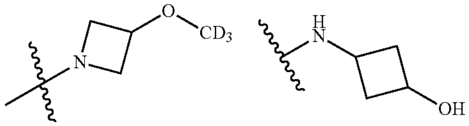
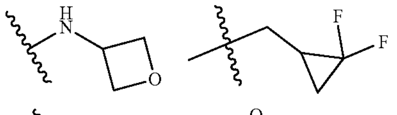
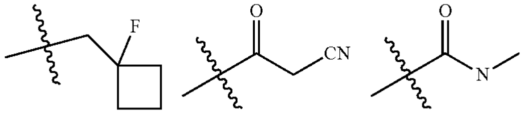
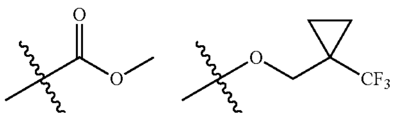
-continued
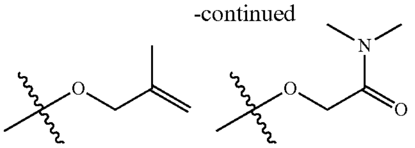
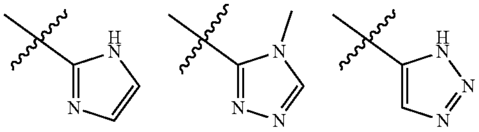
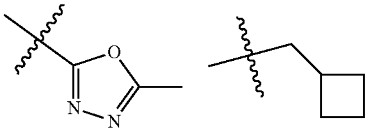
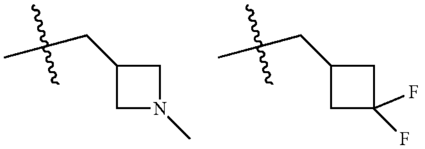
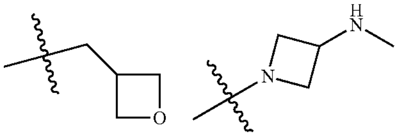
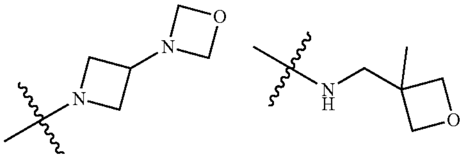
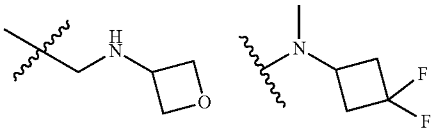
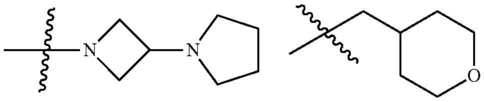
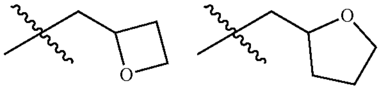
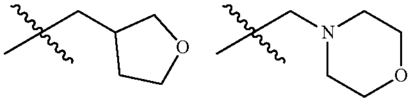
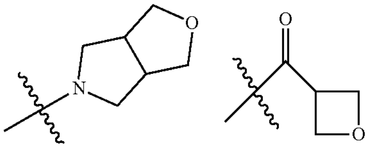
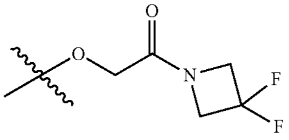
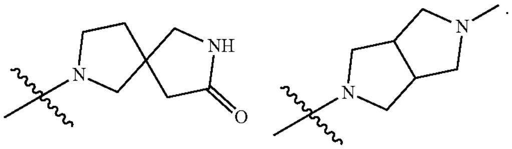

In some embodiments of the present disclosure, $R_{11}$ is selected from —$NR^{11a}R^{11b}$; $R^{11a}$ is selected from H, D or $C_{1-4}$ alkyl; $R^{11b}$ is selected from —$(CH_2)_n$—$C_{3-12}$ cycloalkyl, wherein the cycloalkyl is optionally substituted with 1-3 $R^a$; $R^a$ is selected from halogen, D, OH, cyano, $C_{1-4}$ alkyl, $C_{1-4}$ alkoxy, halo $C_{1-4}$ alkoxy, $C_{2-6}$ alkenyl, $C_{2-6}$ alkynyl, —$S(O)_2C_{1-4}$ alkyl or —$C(O)C_{1-4}$ alkyl, wherein the alkyl or alkoxy is optionally substituted with 1-3 of halogen, D or cyano; n is 0, 1, 2 or 3; in some embodiments, $R_{11}$ is selected from —$NR^{11a}R^{11b}$; $R^{11a}$ is selected from H, D or $C_{1-2}$ alkyl; $R^{11b}$ is selected from —$(CH_2)_n$-3-membered monocyclic cycloalkyl, —$(CH_2)_n$-4-membered monocyclic cycloalkyl or —$(CH_2)_n$-5-membered monocyclic cycloalkyl, wherein the cycloalkyl is optionally substituted with 1-3 $R^a$; $R^a$ is selected from F, Cl, D, OH, cyano, $C_{1-2}$ alkyl, $C_{1-2}$ alkoxy or halo $C_{1-2}$ alkoxy, wherein the alkyl or alkoxy is optionally substituted with 1-3 F, Cl, D or cyano; n is 0 or 1.

In some embodiments of the present disclosure, $R_{11}$ is selected from —$NR^{11a}R^{11b}$; $R^{11a}$ is selected from H; $R^{11b}$ is selected from 4- to 7-membered monocyclic heterocycloalkyl containing 1-3 heteroatoms selected from N, O or S, wherein the monocyclic heterocycloalkyl is optionally substituted with 1-3 of D, cyano-substituted alkyl, cyano, —$S(O)_2C_{1-4}$ alkyl or —$C(O)C_{1-4}$ alkyl; in some embodiments, $R_{11}$ is selected from —$NR^{11a}R^{11b}$; $R^{11a}$ is selected from H or D; $R^{11b}$ is selected from 4-membered monocyclic heterocycloalkyl containing 1-3 heteroatoms selected from N, O or S, 5-membered monocyclic heterocycloalkyl containing 1-3 heteroatoms selected from N, O or S, or 6-membered monocyclic heterocycloalkyl containing 1-3 heteroatoms selected from N, O or S, wherein the monocyclic heterocycloalkyl is optionally substituted with 1-3 groups selected from D, cyano-substituted alkyl or cyano.

In some embodiments of the present disclosure, $R_1$ is selected from —$(CH_2)_n$—$C_{3-12}$ cycloalkyl, wherein the cycloalkyl is optionally substituted with 1-3 groups selected from: halogen, D, $C_{1-4}$ alkoxy, $C_{1-4}$ alkyl, =O or —O—$(CH_2)_n$—$C_{3-6}$ cycloalkyl, wherein the alkyl, alkoxy or cycloalkyl is optionally substituted with 1-3 groups selected from $R^a$; $R^a$ is selected from halogen, D or $C_{1-4}$ alkyl.

In some embodiments of the present disclosure, n is 0 or 1; in some embodiments of the present disclosure, n is 0; in some embodiments of the present disclosure, n is 1.

In some embodiments of the present disclosure, $R^{11a}$ and $R^{11b}$ are each independently selected from H, $C_{1-4}$ alkyl, $C_{1-4}$ alkoxy, —$C(O)R_{11c}$, 6- to 12-membered aryl, 5- to 12-membered heteroaryl, $C_{3-6}$ cycloalkyl, 3- to 6-membered heterocycloalkyl, —$S(O)_2C_{1-4}$ alkyl or —$(CH_2)_n$—$Si(C_{1-4}$ alkyl$)_3$, wherein the alkyl, alkoxy, aryl, heteroaryl, cycloalkyl or heterocycloalkyl is optionally substituted with 1-3 $R^a$; in some embodiments, $R^{11a}$ is selected from H or $C_{1-4}$ alkyl; in some embodiments, $R^{11b}$ is selected from —$C(O)R^{11c}$, 6- to 12-membered aryl, 5- to 12-membered heteroaryl, $C_{3-6}$ cycloalkyl, 3- to 6-membered heterocycloalkyl or —$S(O)_2C_{1-4}$ alkyl, wherein the aryl, heteroaryl, cycloalkyl or heterocycloalkyl is optionally substituted with 1-3 $R^a$; in some embodiments, $R^{11b}$ is selected from —$C(O)R^{11c}$, 5- to 12-membered heteroaryl, $C_{3-6}$ cycloalkyl, 3- to 6-membered heterocycloalkyl or —$S(O)_2C_{1-4}$ alkyl, wherein the heteroaryl, cycloalkyl or heterocycloalkyl is optionally substituted with 1-3 $R^a$; in some embodiments, $R^{11b}$ is selected from —$C(O)R^{11c}$; in some embodiments, $R^{11b}$ is selected from 5- to 12-membered heteroaryl, $C_{3-6}$ cycloalkyl or 3- to 6-membered heterocycloalkyl, wherein the heteroaryl, cycloalkyl or heterocycloalkyl is optionally substituted with 1-3 $R^a$; in some embodiments, $R^{11a}$ and $R^{11b}$ together with the nitrogen atom to which they are attached form 3- to 6-membered heterocycloalkyl, wherein the heterocycloalkyl is optionally substituted with 1-3 of halogen, cyano, $C_{1-4}$ alkoxy, halo $C_{1-4}$ alkoxy, —$NHC_{1-4}$ alkyl, —$N(C_{1-4}$ alkyl$)_2$, —NH(3- to 6-membered heterocycloalkyl), —$NHC_{3-6}$ cycloalkyl, —O—$C_{3-6}$ cycloalkyl, —O-(3- to 6-membered heterocycloalkyl), —O—$(CH_2)_n$—$Si(C_{1-4}$ alkyl$)_3$ or —$(CH_2)_n$—$Si(C_{1-4}$ alkyl$)_3$; in some embodiments, $R^{11a}$ and $R^{11b}$ together with the nitrogen atom to which they are attached form azacyclobutyl, azacyclopentyl or azacyclohexyl, which is optionally substituted with 1-3 of halogen, cyano, $C_{1-4}$ alkoxy, halo $C_{1-4}$ alkoxy, —$NHC_{1-4}$ alkyl, —$N(C_{1-4}$ alkyl$)_2$, —NH(3- to 6-membered heterocycloalkyl), —$NHC_{3-6}$ cycloalkyl, —O—$C_{3-6}$ cycloalkyl, —O-(3- to 6-membered heterocycloalkyl), —O—$(CH_2)_n$—$Si(C_{1-4}$ alkyl$)_3$ or —$(CH_2)_n$—$Si(C_{1-4}$ alkyl$)_3$;

in some embodiments of the present disclosure, $R^{11c}$ is selected from $C_{1-4}$ alkyl, $C_{1-4}$ alkoxy, amino, —$NHC_{1-4}$ alkyl, —$N(C_{1-4}$ alkyl$)_2$, —NH(3- to 6-membered heterocycloalkyl), —$NHC_{3-6}$ cycloalkyl, $C_{3-6}$ cycloalkyl, 3- to 6-membered heterocycloalkyl, —O—$C_{1-4}$ alkyl, —O—$C_{3-6}$ cycloalkyl, —O-(3- to 6-membered heterocycloalkyl) or —$(CH_2)_n$—$Si(C_{1-4}$ alkyl$)_3$, wherein the alkyl, alkoxy, heterocycloalkyl or cycloalkyl is optionally substituted with 1-3 of halogen, cyano, $C_{1-4}$ alkoxy, halo $C_{1-4}$ alkoxy, —$NHC_{1-4}$ alkyl, —$N(C_{1-4}$ alkyl$)_2$, —NH(3- to 6-membered heterocycloalkyl), —$NHC_{3-6}$ cycloalkyl, —O—$C_{3-6}$ cycloalkyl, —O-(3- to 6-membered heterocycloalkyl) or —$Si(C_{1-4}$ alkyl$)_3$; in some embodiments, $R^{11c}$ is selected from $C_{1-4}$ alkyl, $C_{1-4}$ alkoxy, —$NHC_{1-4}$ alkyl, —$N(C_{1-4}$ alkyl$)_2$, —NH(3- to 6-membered heterocycloalkyl) or 3- to 6-membered heterocycloalkyl, wherein the alkyl, alkoxy, heterocycloalkyl or cycloalkyl is optionally substituted with 1-3 of halogen, cyano, $C_{1-4}$ alkoxy, halo $C_{1-4}$ alkoxy, —$NHC_{1-4}$ alkyl, —$N(C_{1-4}$ alkyl$)_2$, —NH(3- to 6-membered heterocycloalkyl), —$NHC_{3-6}$ cycloalkyl, —O—$C_3$-6 cycloalkyl or —O-(3- to 6-membered heterocycloalkyl); in some embodiments, $R^{11c}$ is selected from $C_{1-4}$ alkyl, $C_{1-4}$ alkoxy, —$NHC_{1-4}$ alkyl, —$N(C_{1-4}$ alkyl$)_2$, —NH(3- to 6-membered heterocycloalkyl) or 3- to 6-membered heterocycloalkyl; in some embodiments, $R^{11c}$ is selected from methyl, methoxy or methylamino.

In some embodiments of the present disclosure, $R^a$ is selected from halogen, cyano, $C_{1-4}$ alkyl, halo $C_{1-4}$ alkyl, $C_{1-4}$ alkoxy, halo $C_{1-4}$ alkoxy, $C_{2-6}$ alkenyl, $C_{2-6}$ alkynyl, —$S(O)_2C_{1-4}$ alkyl, —$C(O)C_{1-4}$ alkyl or —$(CH_2)_n$—$Si(C_{1-4}$ alkyl$)_3$, wherein the alkyl or alkoxy is optionally substituted with 1-3 of halogen, cyano or hydroxyl; In some embodiments, $R^a$ is selected from $C_{1-4}$ alkyl, halo $C_{1-4}$ alkyl, $C_{1-4}$ alkoxy, halo $C_{1-4}$ alkoxy, $C_{2-6}$ alkenyl or $C_{2-6}$ alkynyl, wherein the alkyl or alkoxy is optionally substituted with 1-3 of halogen, cyano or hydroxyl.

In some embodiments of the present disclosure, $R^b$ is selected from 6- to 12-membered aryl, 5- to 12-membered heteroaryl, $C_{3-6}$ cycloalkyl or 3- to 6-membered heterocycloalkyl, wherein the aryl, heteroaryl, cycloalkyl or heterocycloalkyl is optionally substituted with 1-3 of halogen or —$(CH_2)_n$—$Si(C_{1-4}$ alkyl$)_3$; in some embodiments, $R^b$ is selected from 6- to 12-membered aryl, 5- to 12-membered heteroaryl, $C_{3-6}$ cycloalkyl or 3- to 6-membered heterocycloalkyl, wherein the aryl, heteroaryl, cycloalkyl or heterocycloalkyl is optionally substituted with 1-3 halogen.

In some embodiments of the present disclosure, $R^{11d}$ is selected from —O— oxetanyl.

In some embodiments of the present disclosure, X is selected from —C— or —N—; in some embodiments, X is selected from —C—.

The present disclosure relates to a compound of formula (I-1), (I-a), (I-2), (I-3), (I-4), (I-5), (II), (III), (IV) or (V), or a stereoisomer, a pharmaceutically acceptable salt, a solvate, and a eutectic or deuterated compound thereof. In some embodiments, Y is selected from —CH— or —N—; in some embodiments, Y is selected from —CH—; in some embodiments, Y is selected from —N—.

Embodiment thirty of the present disclosure relates to a compound of formula (I), (I-a), (I-1), (I-2), (I-3), (I-4), (I-5), (II), (III), (IV) or (V), or a stereoisomer, a pharmaceutically acceptable salt, a solvate, and a eutectic or deuterated compound thereof, wherein the compound has a structure selected from one of

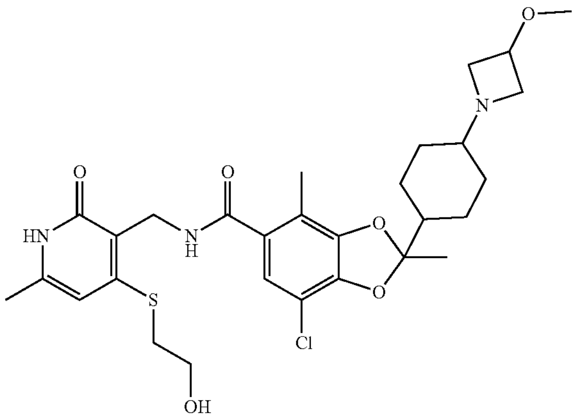

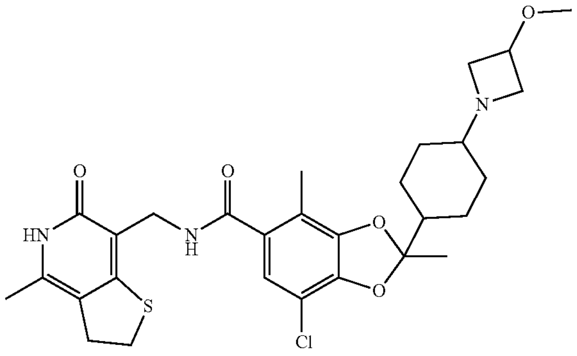

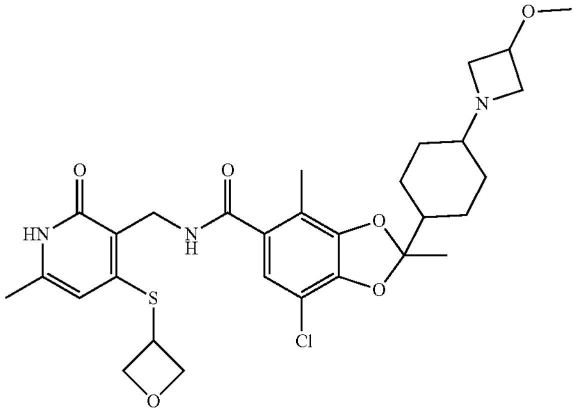

-continued

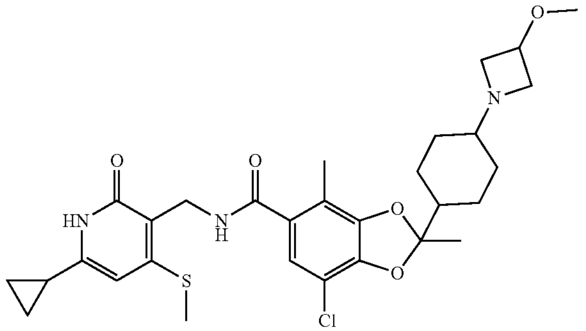

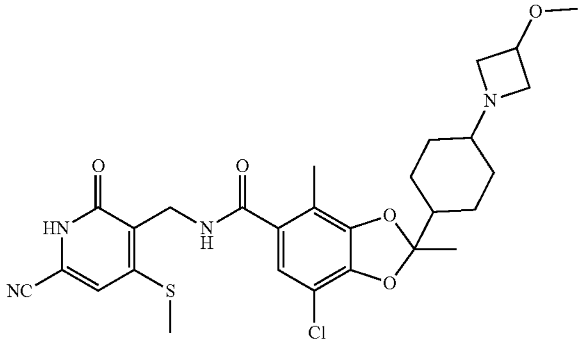

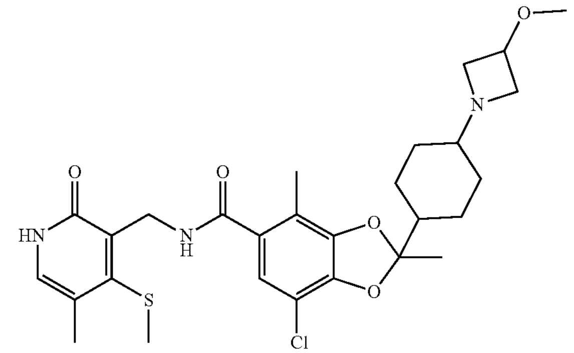

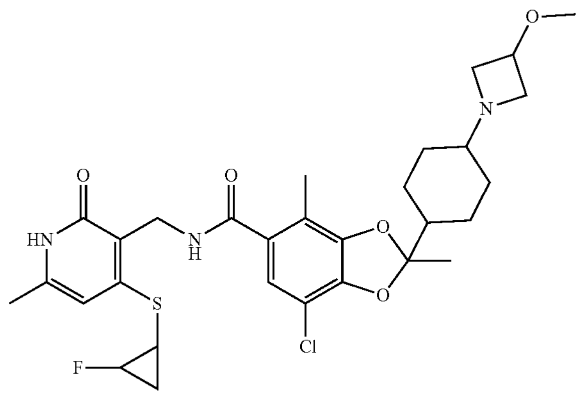

-continued
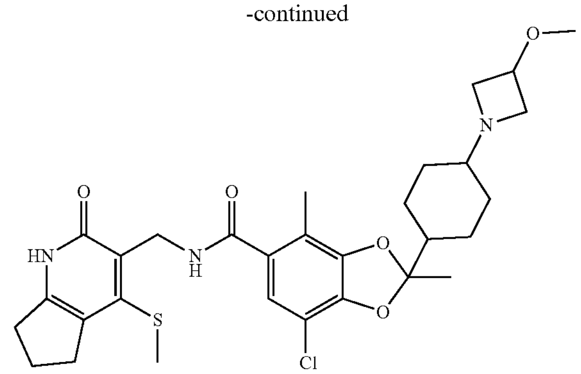
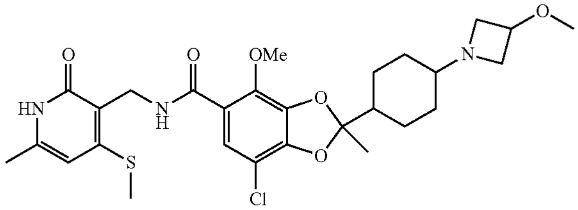
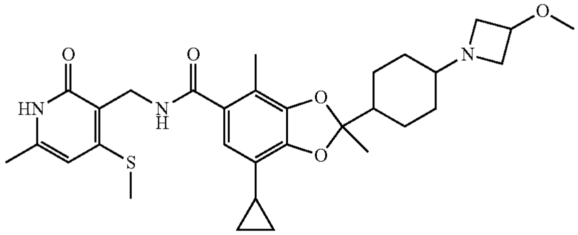
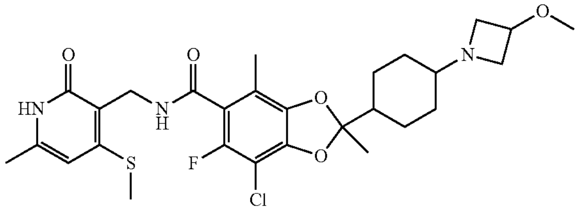
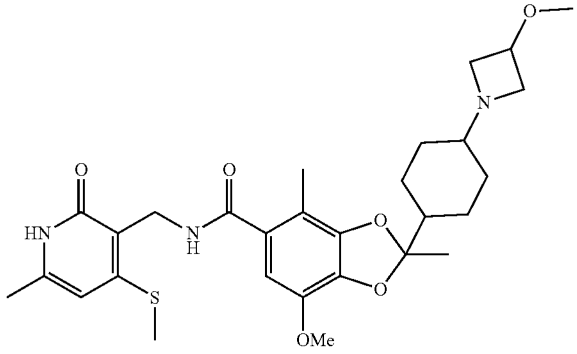
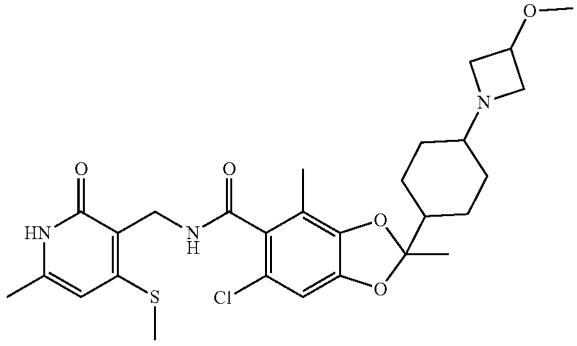
-continued
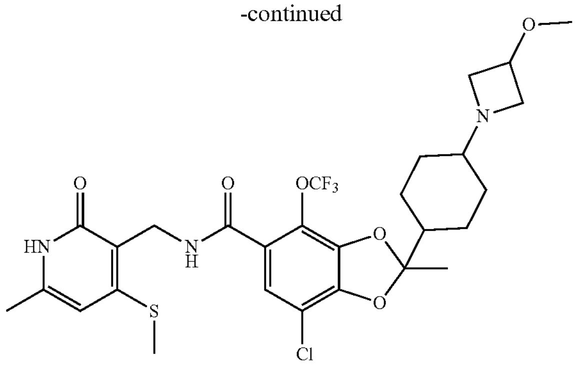
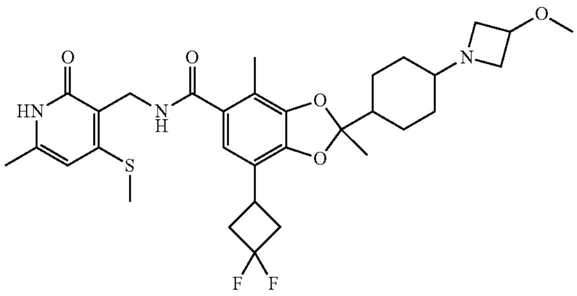
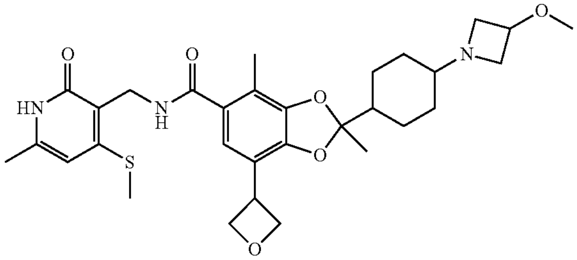
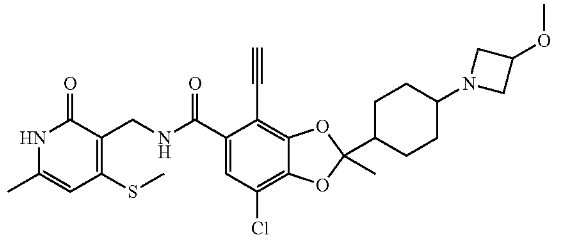
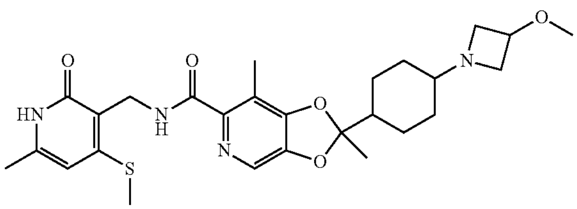
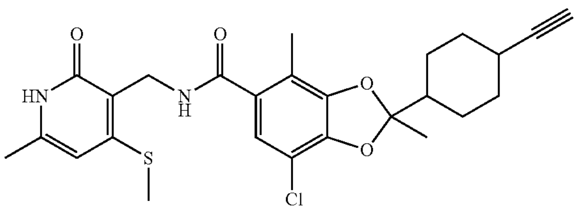

-continued
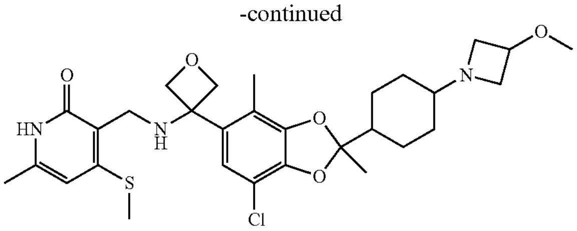
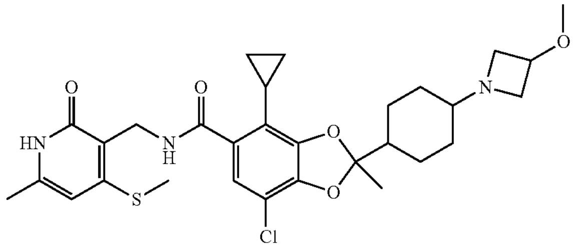
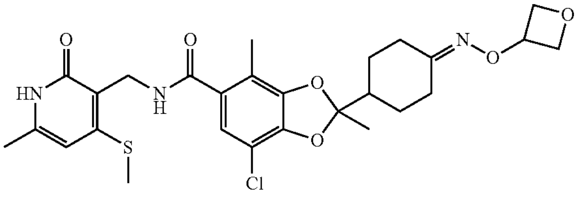
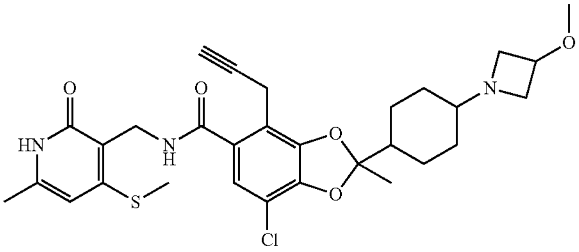
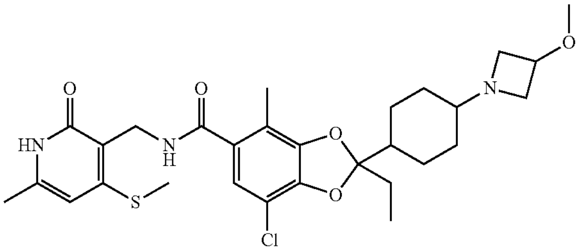
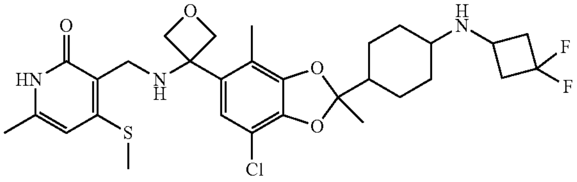
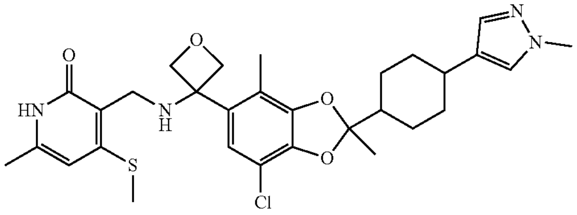
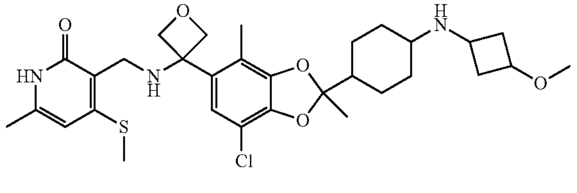
-continued
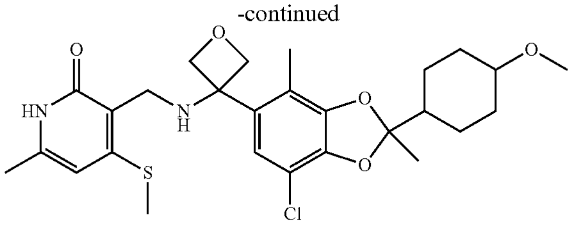
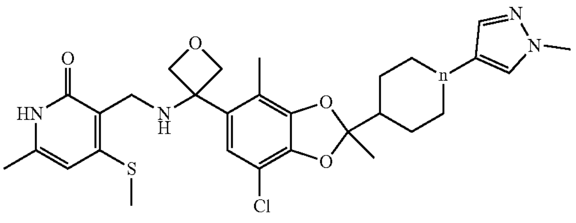
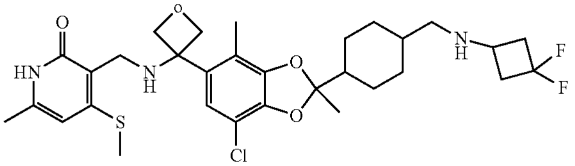
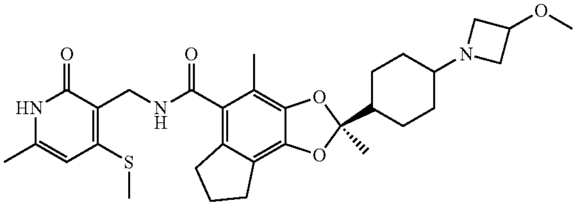
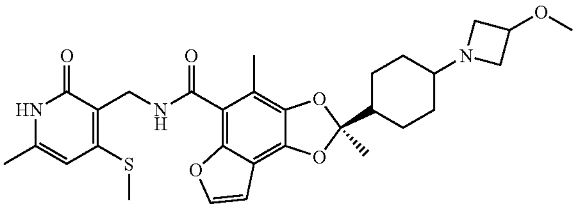
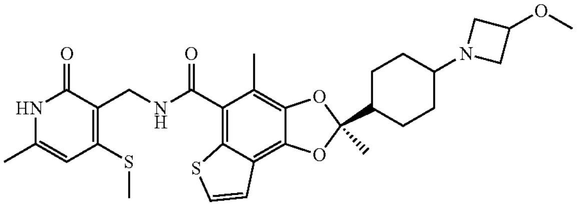
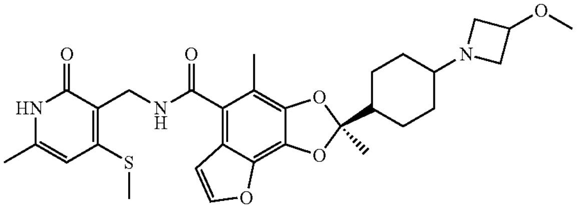
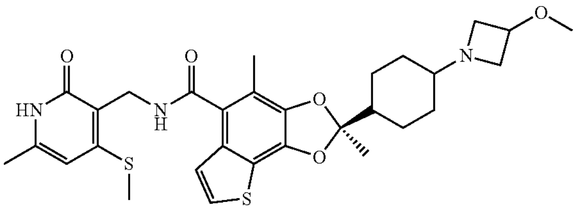

-continued
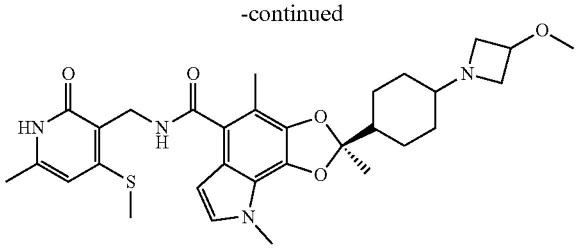
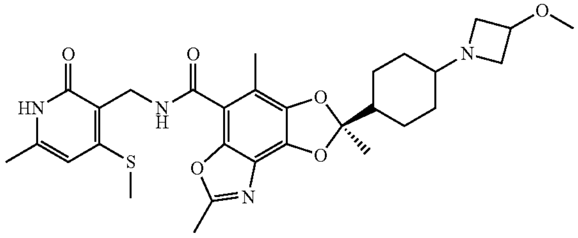
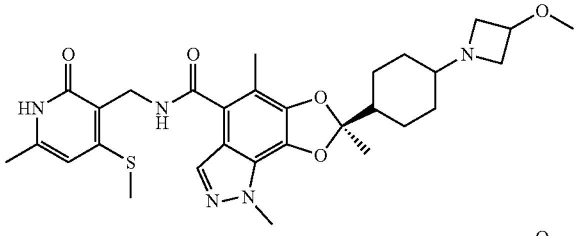
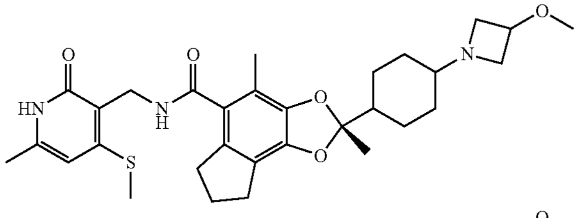
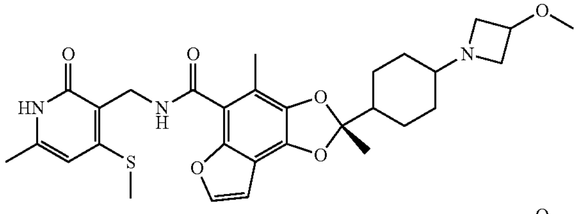
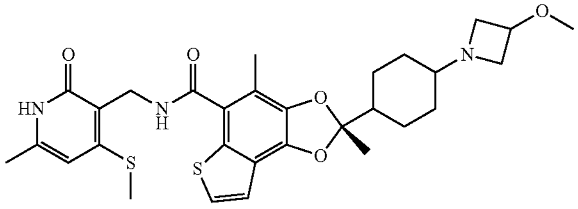
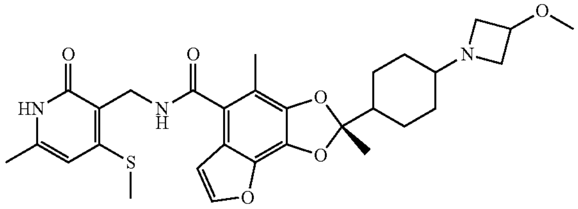
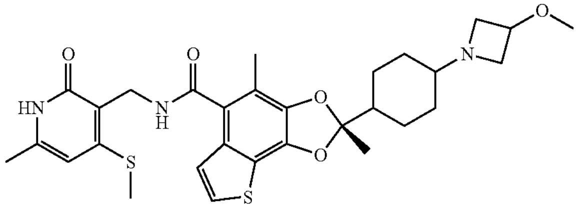
-continued
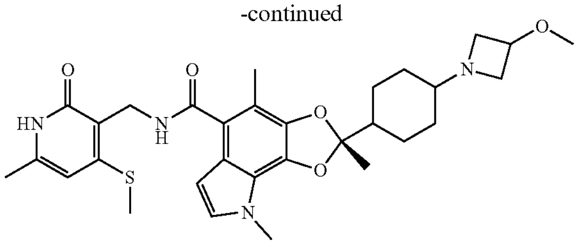
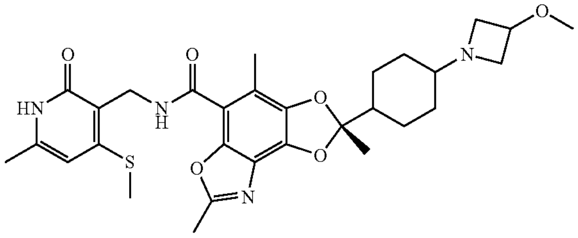
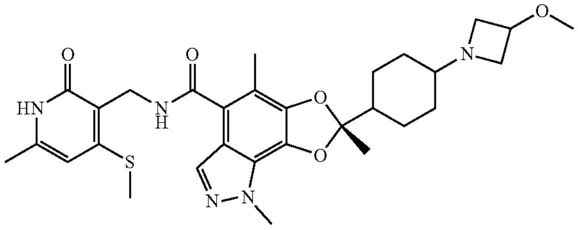
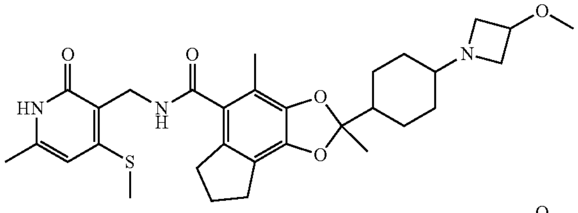
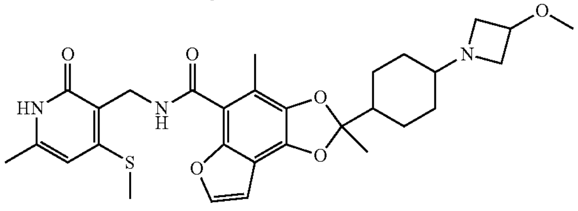
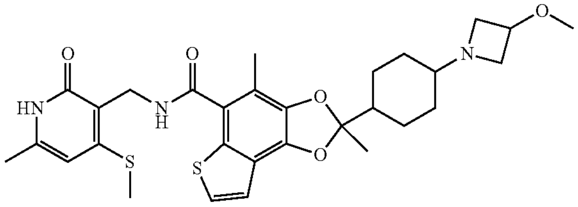
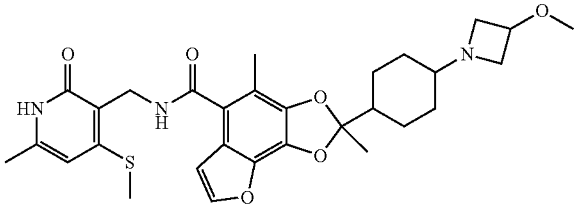
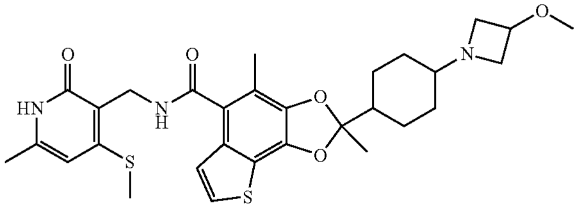

-continued
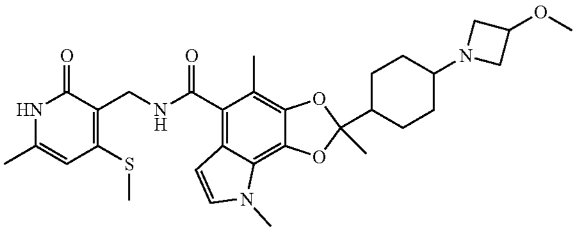
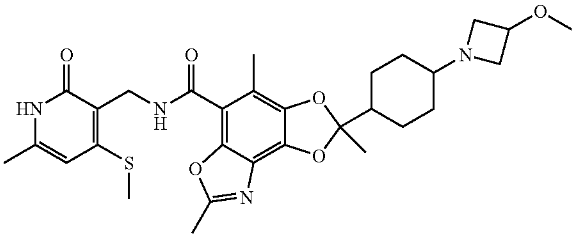
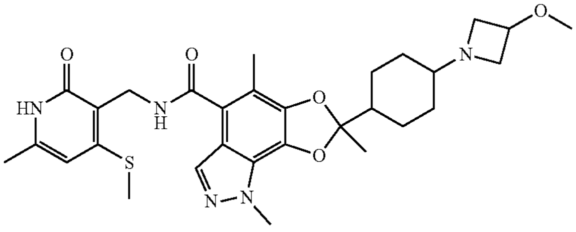
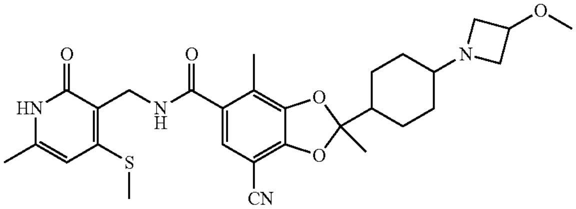
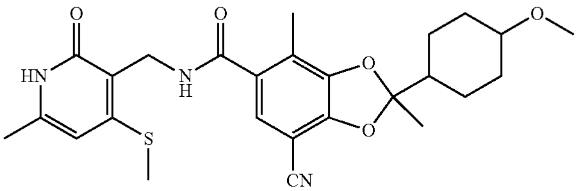
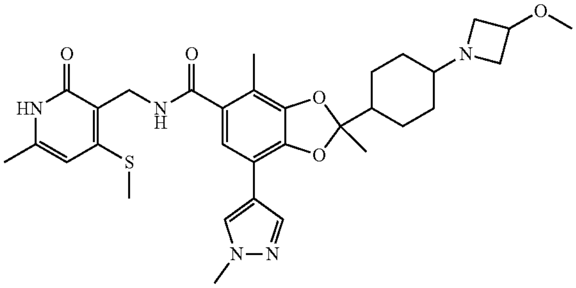
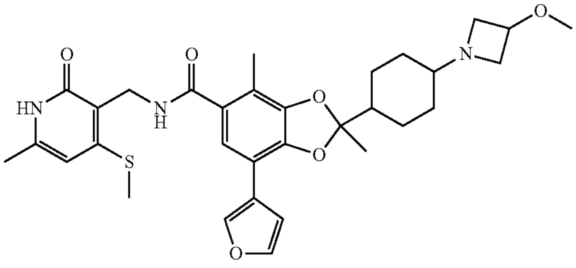
-continued
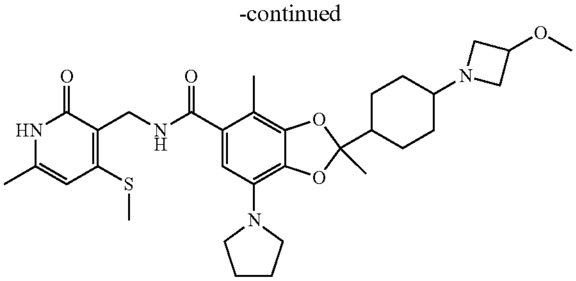
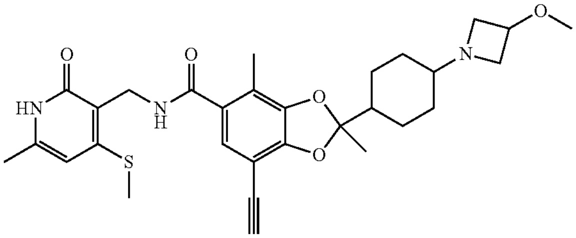
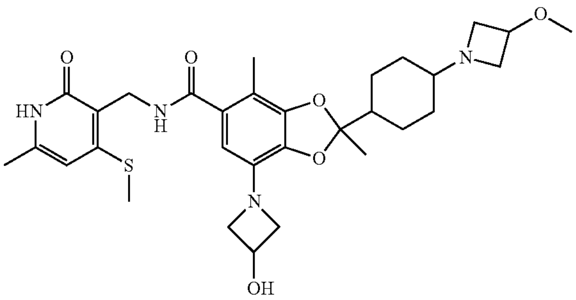
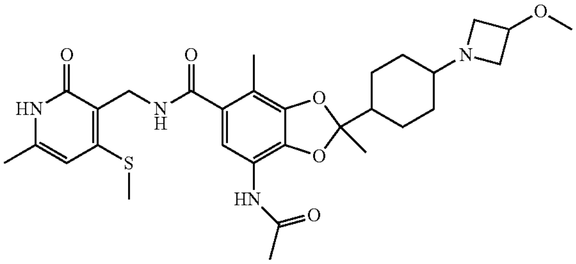
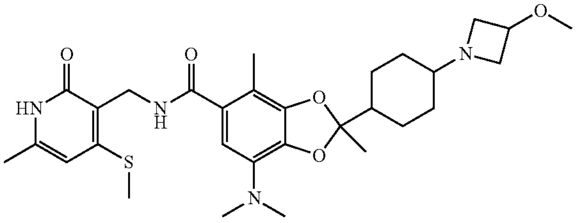
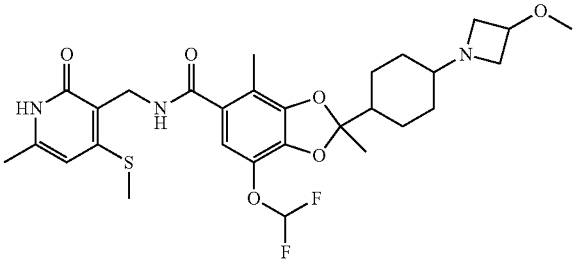

-continued
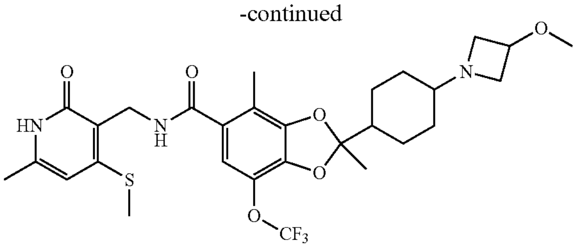
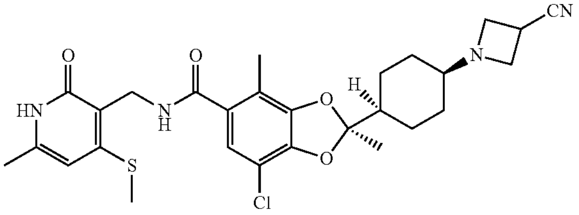
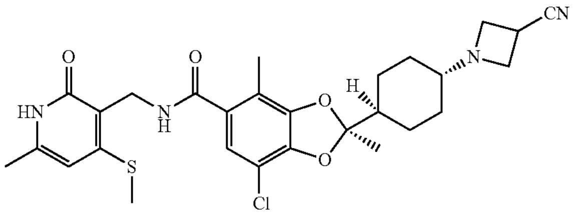
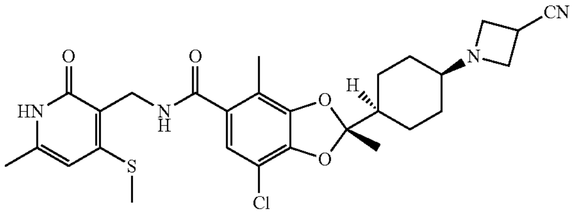
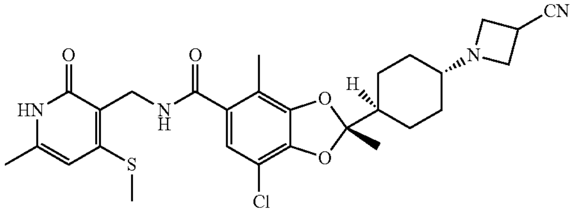
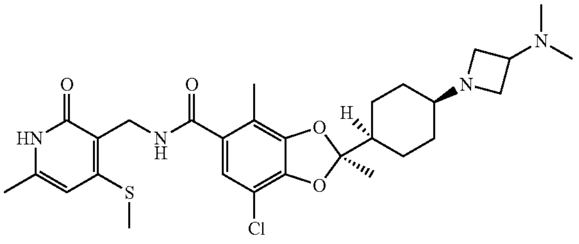
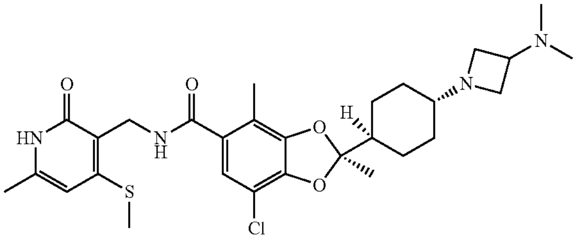
-continued
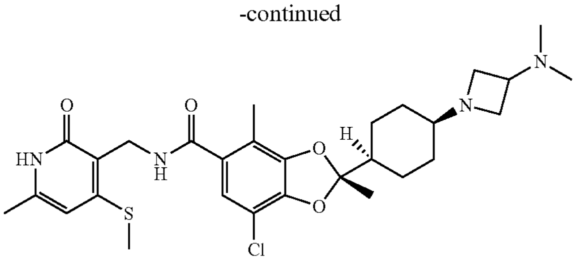
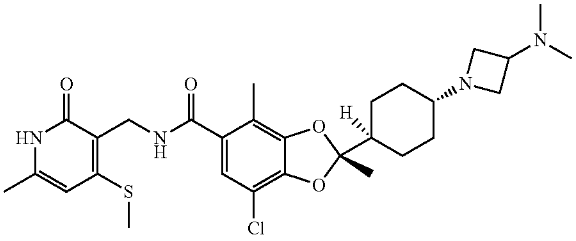
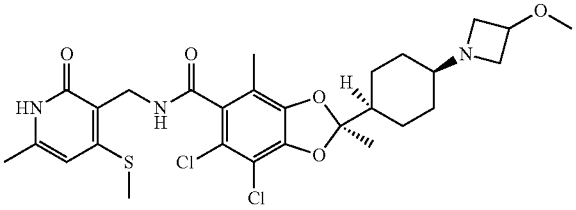
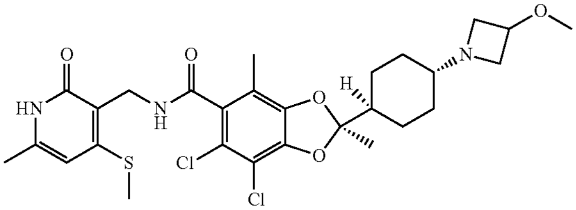
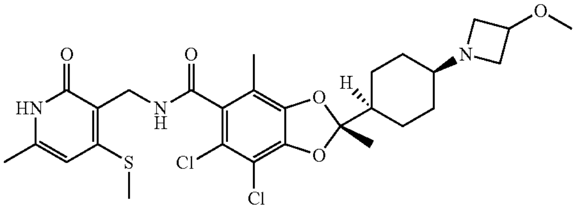
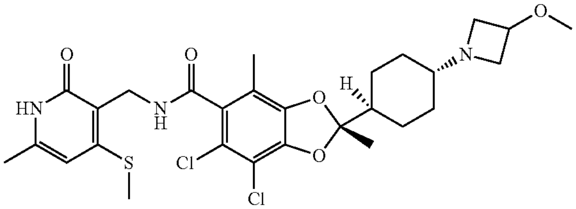
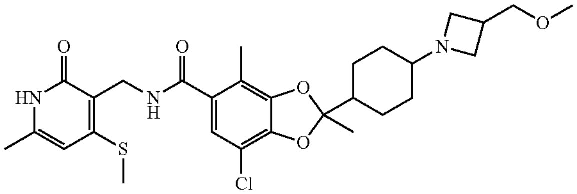
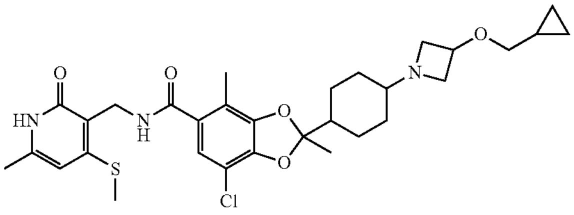

-continued
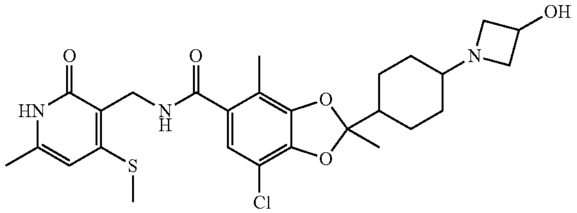
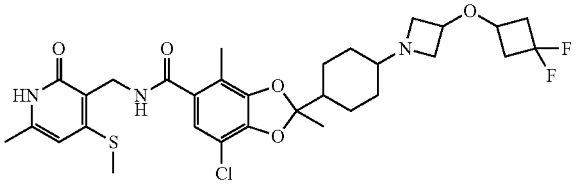
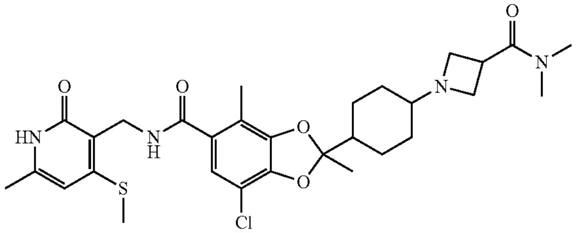
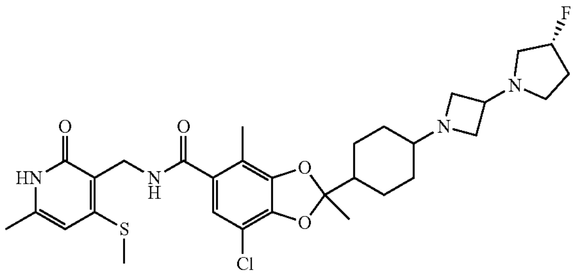
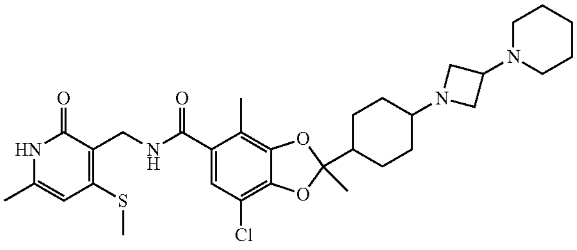
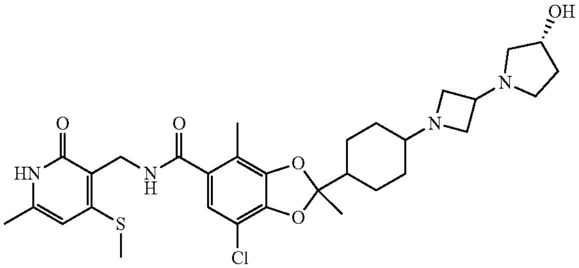
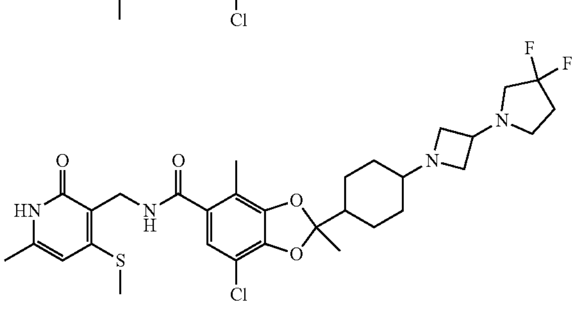
-continued
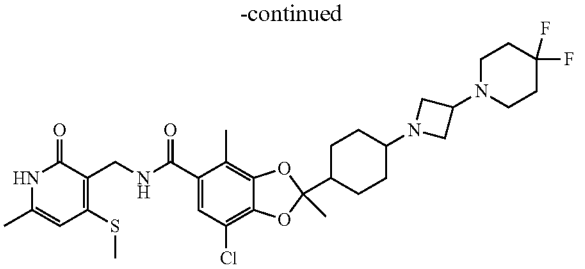
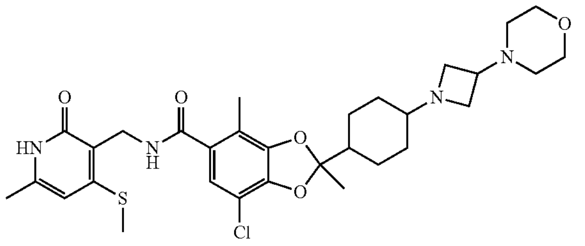
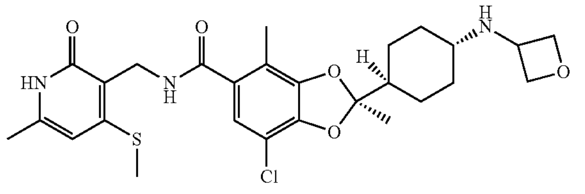
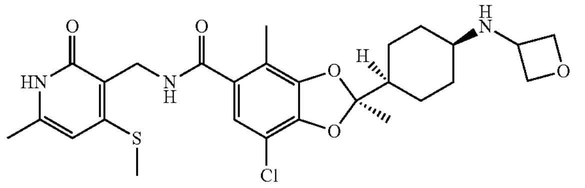
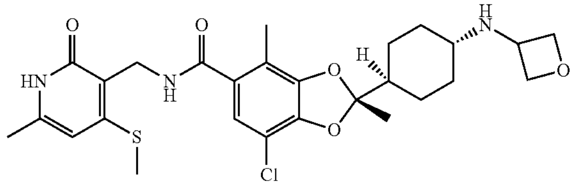
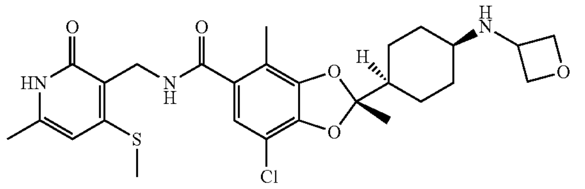
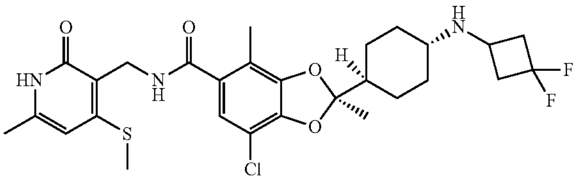
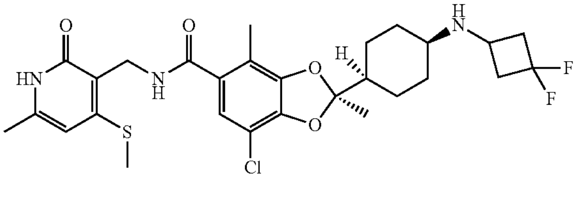

-continued
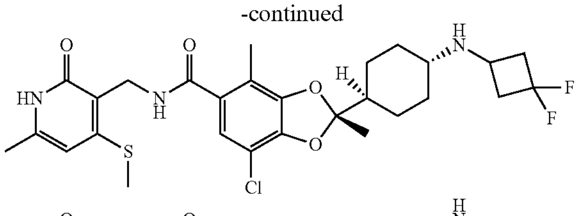
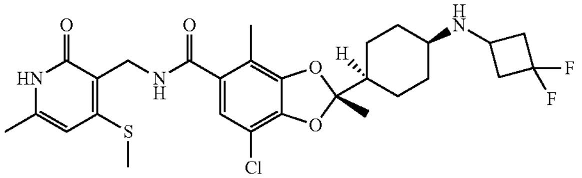
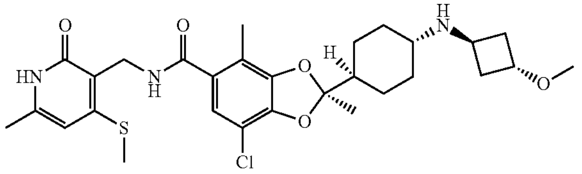
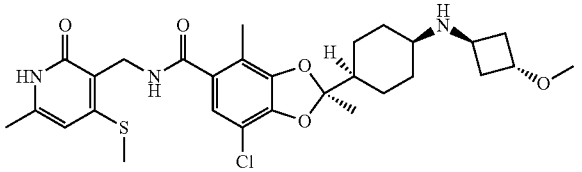
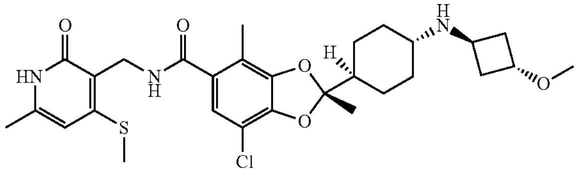
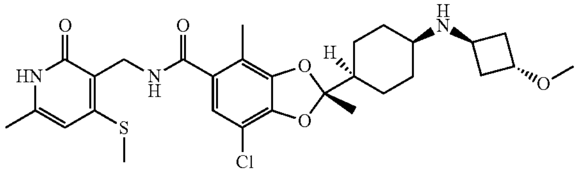
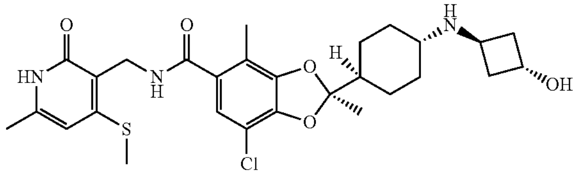
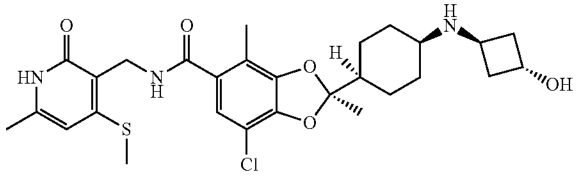
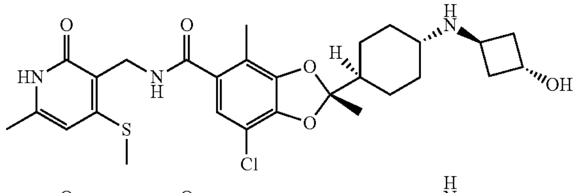
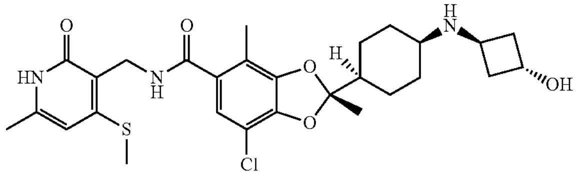
-continued
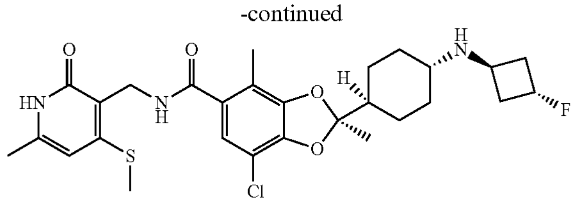
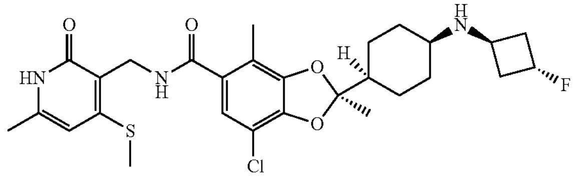
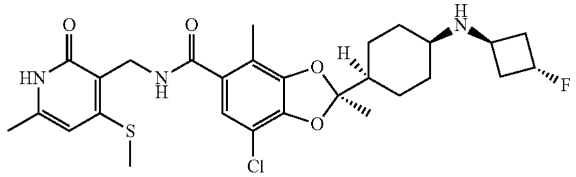
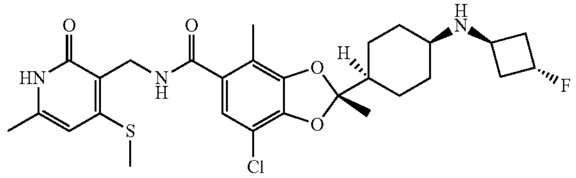
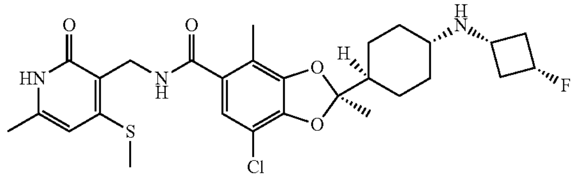
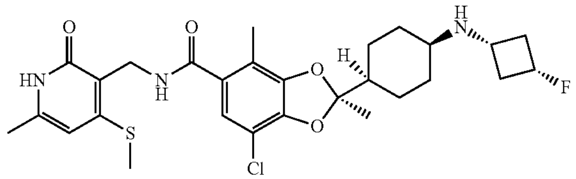
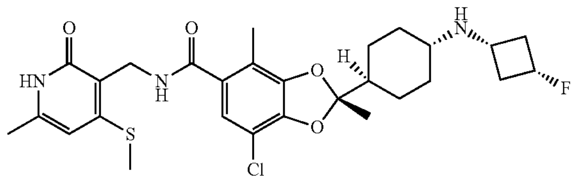
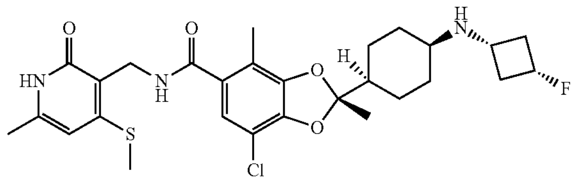
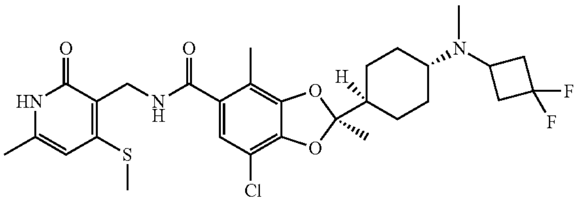

-continued
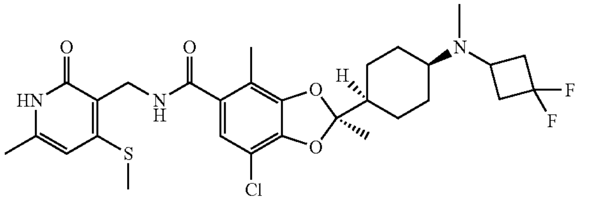
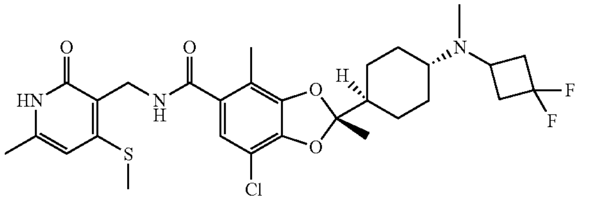
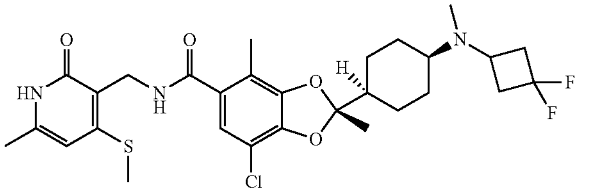
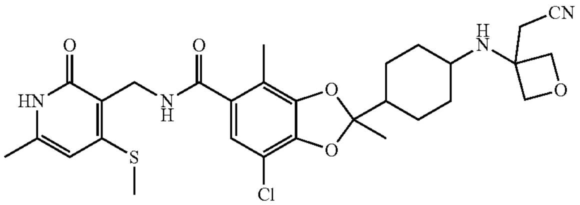
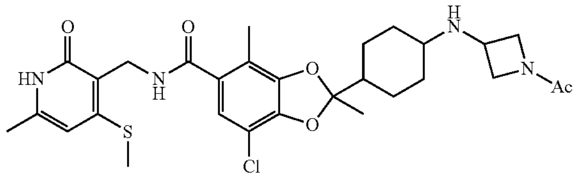
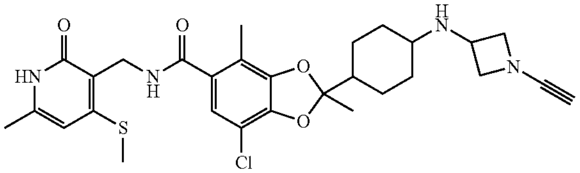
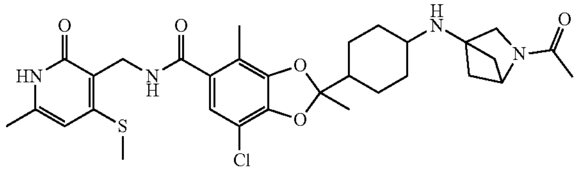
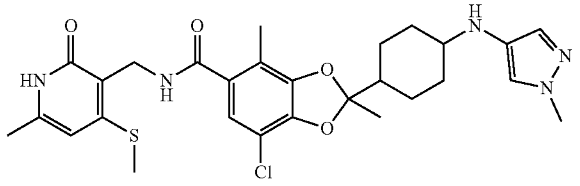
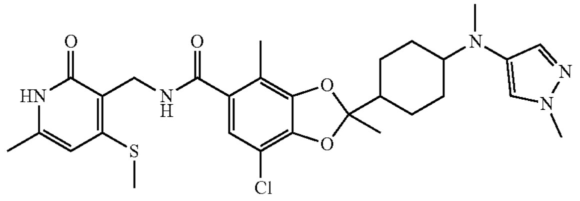
-continued
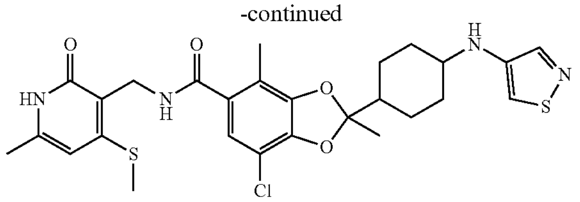
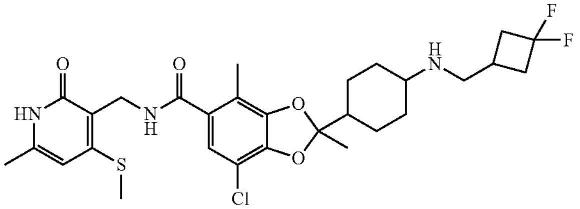
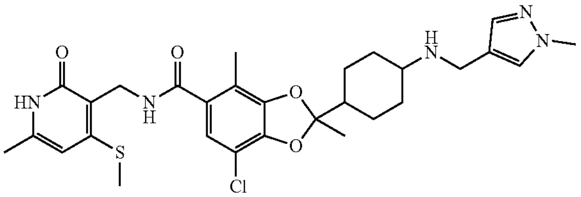
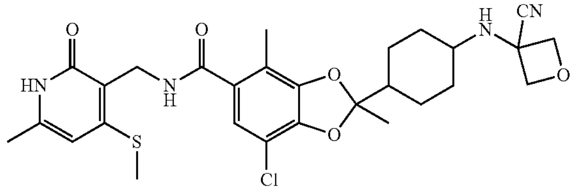
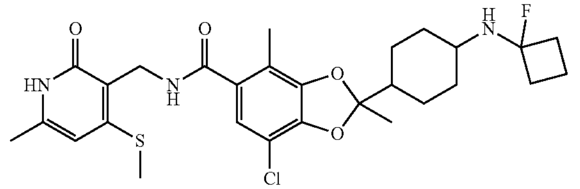
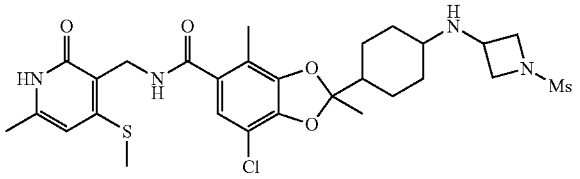
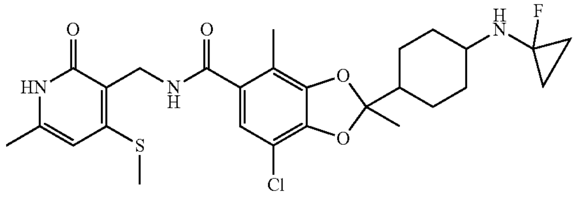
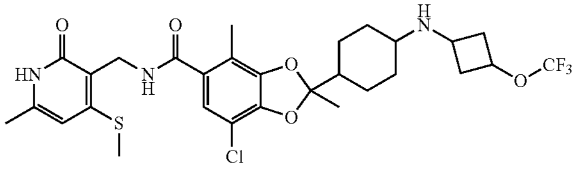
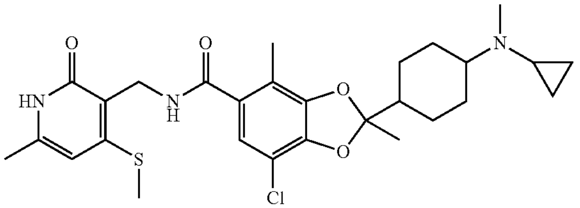

-continued
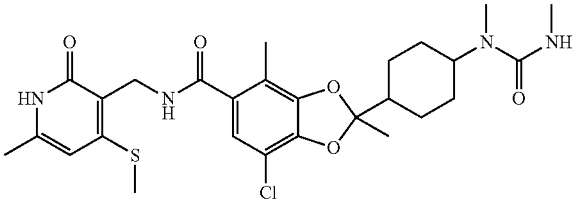
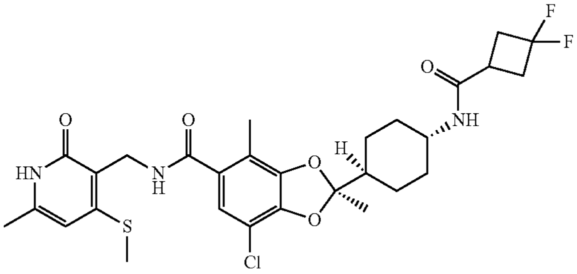
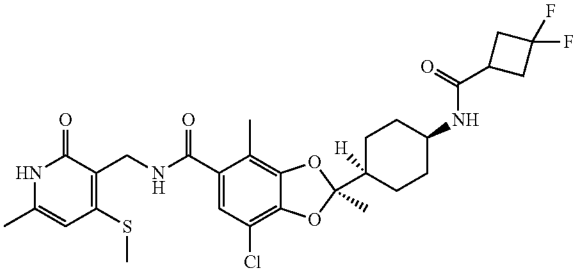
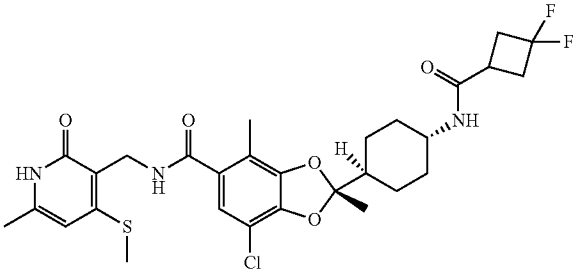
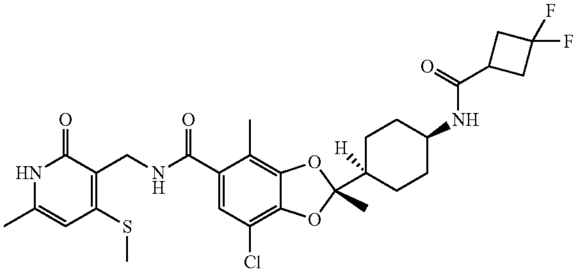
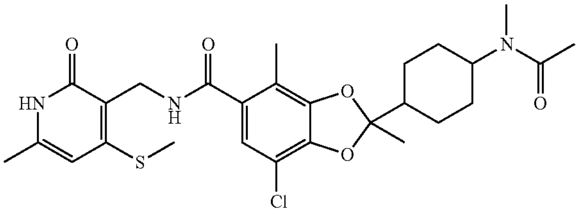
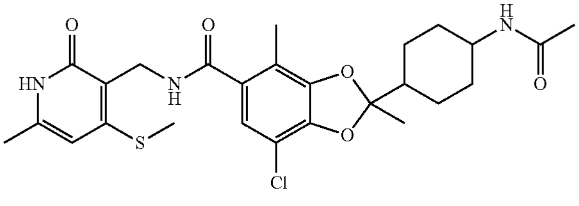
-continued
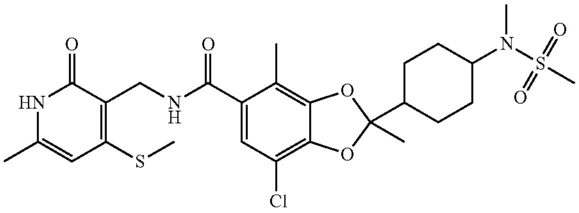
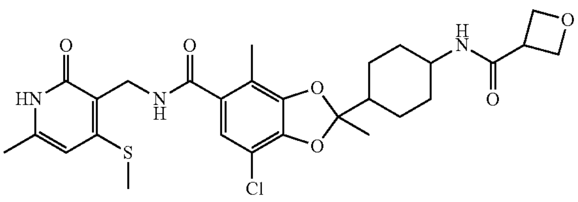
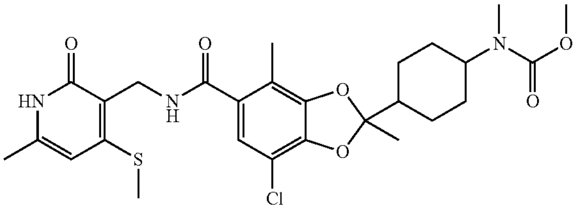
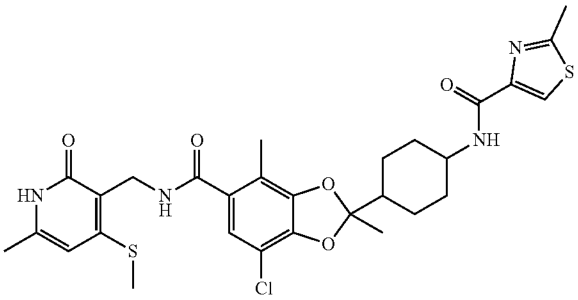
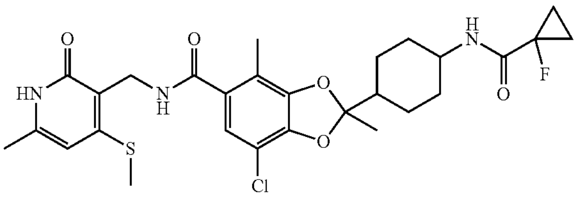
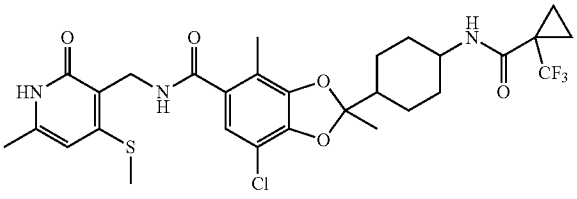
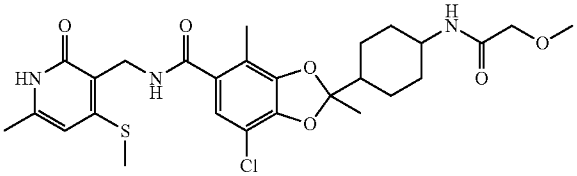
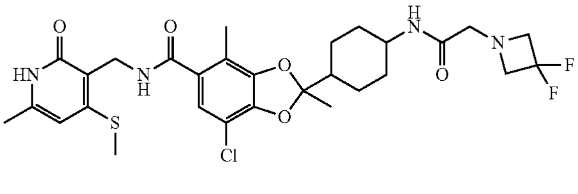

-continued
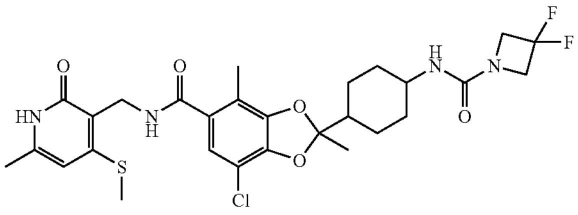
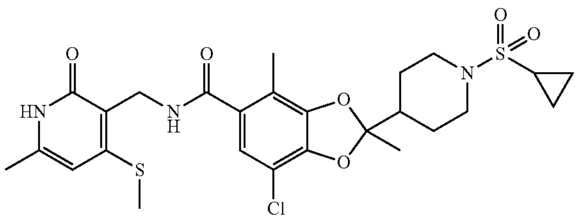
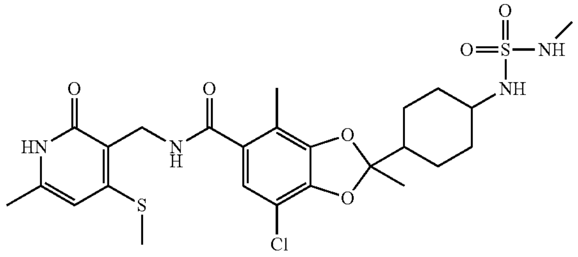
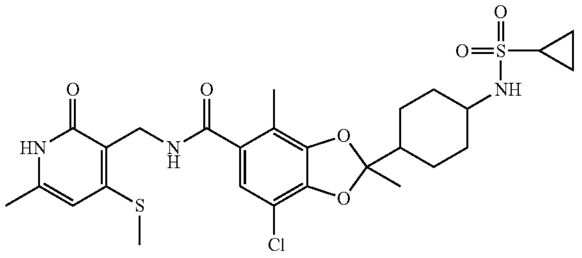
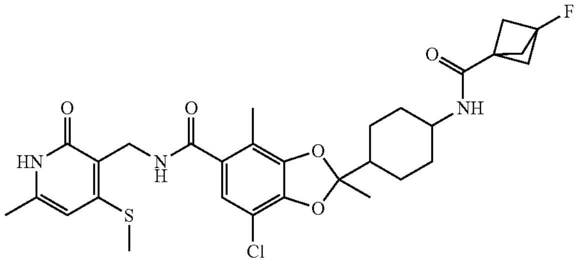
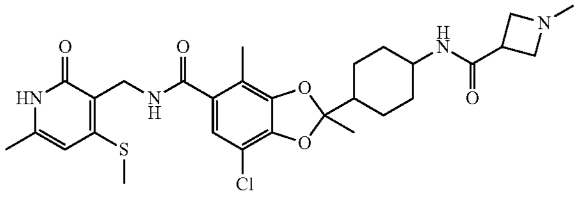
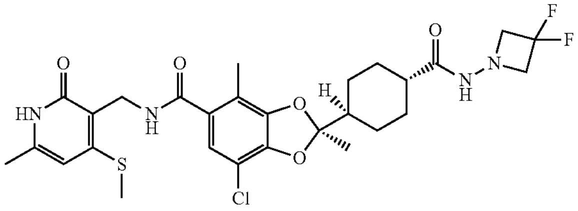
-continued
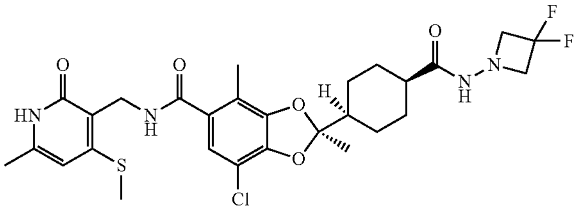
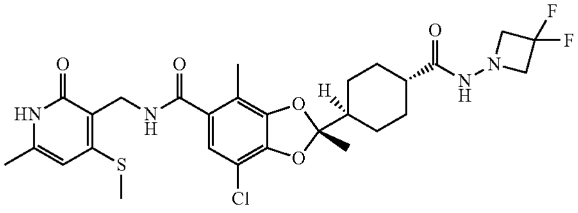
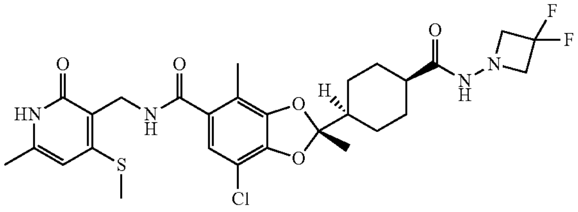
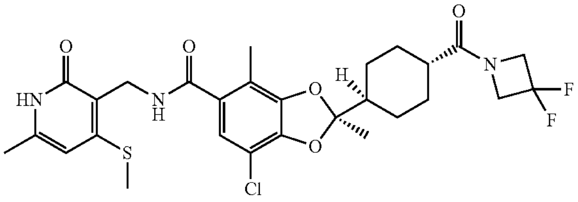
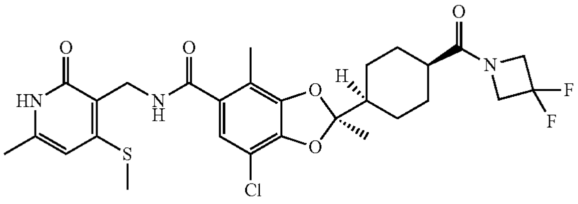
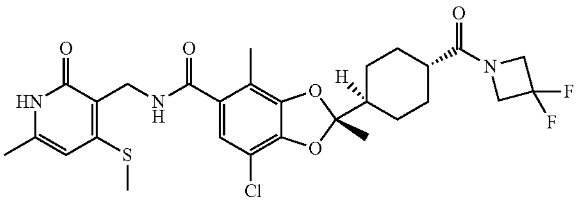
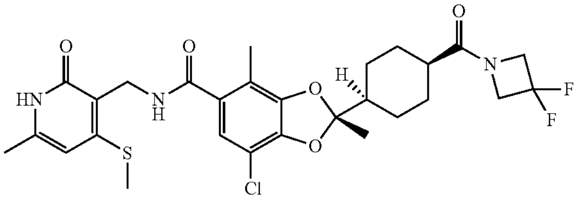
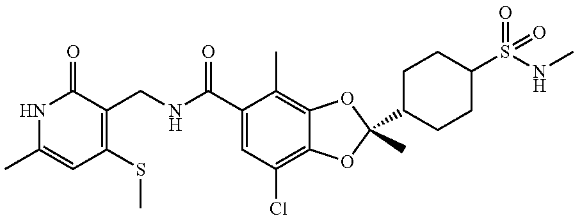

-continued
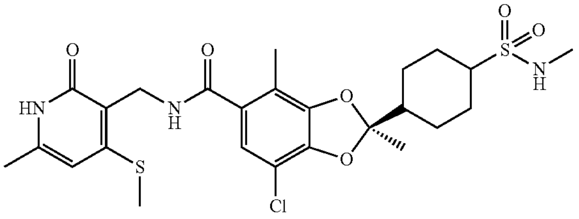
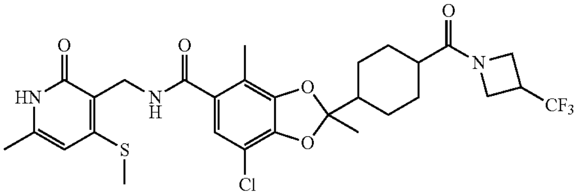
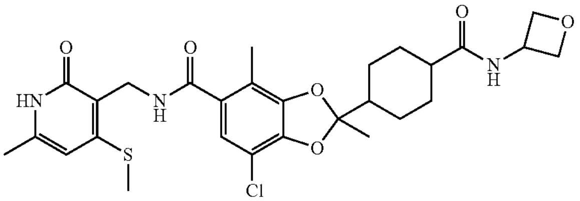
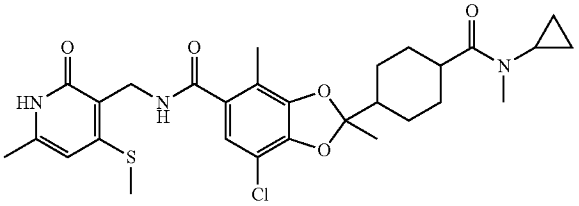
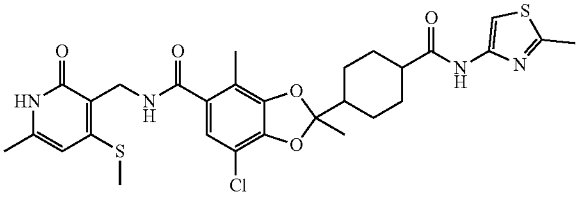
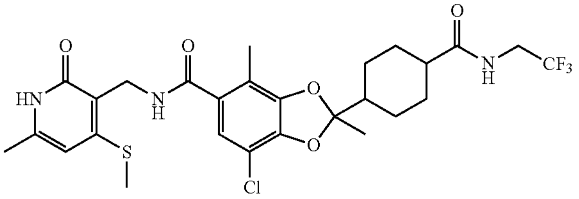
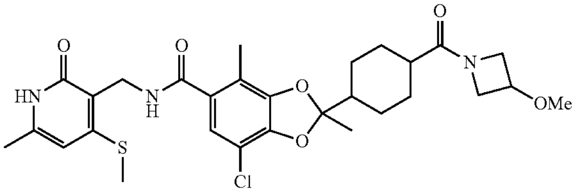
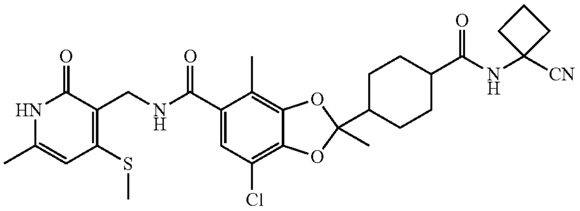
-continued
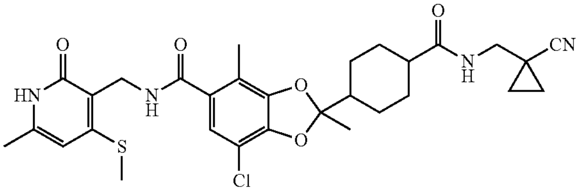
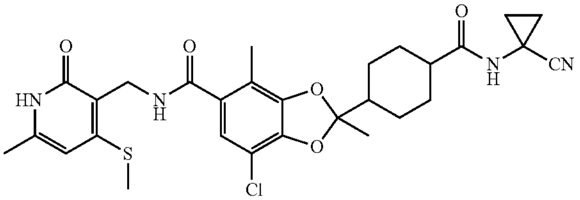
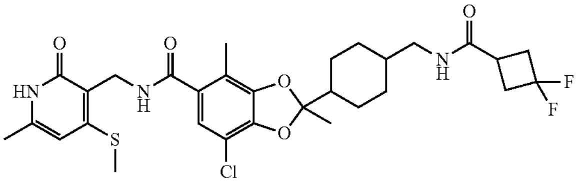
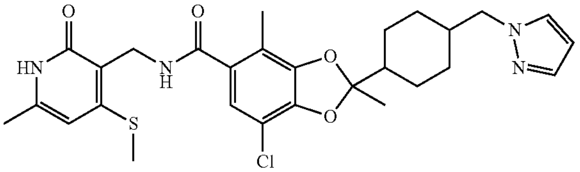
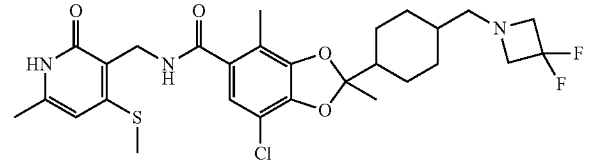
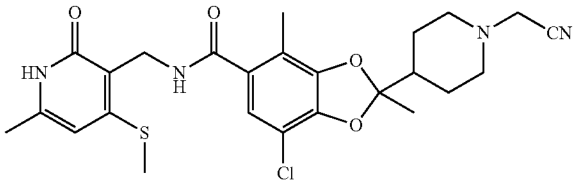
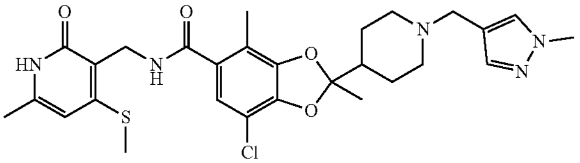
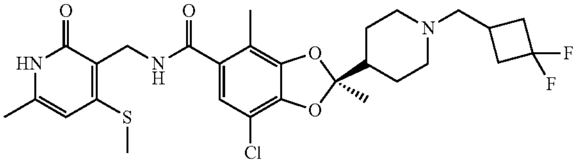
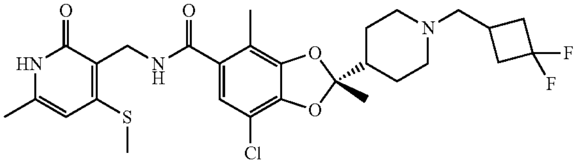

-continued
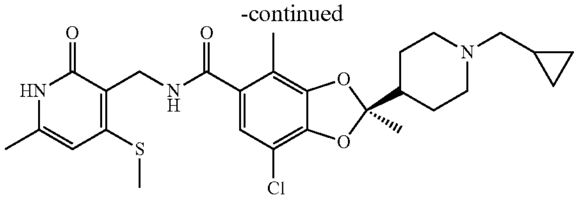
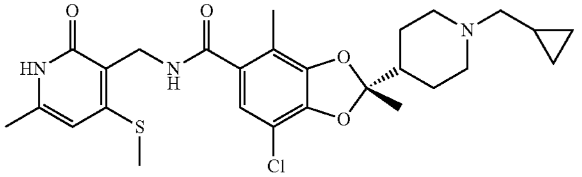
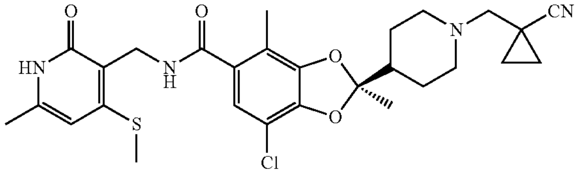
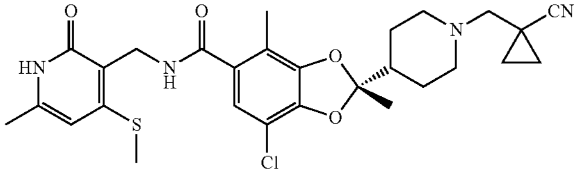
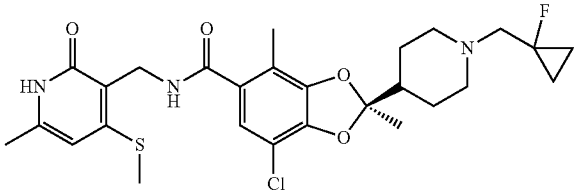
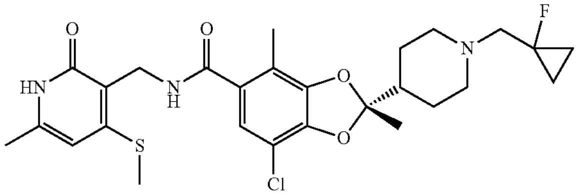
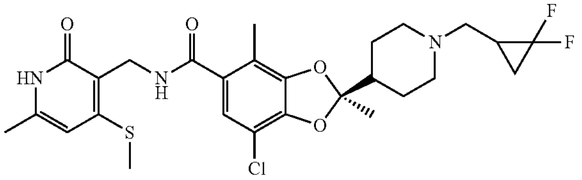
-continued
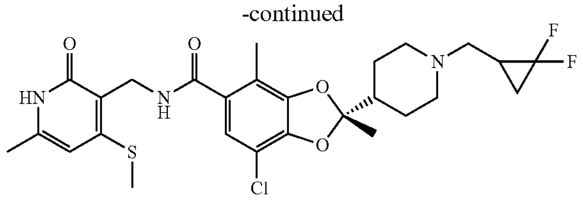
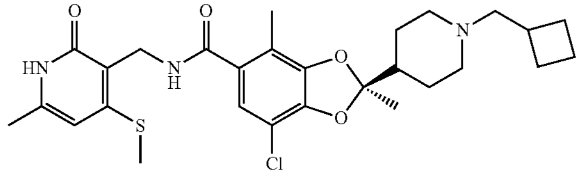
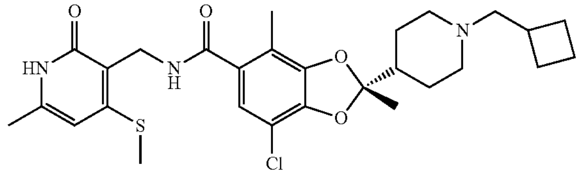
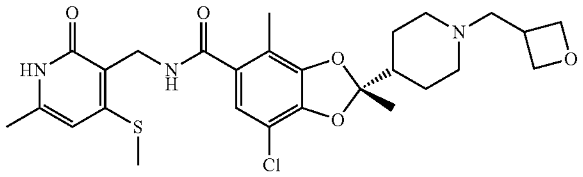
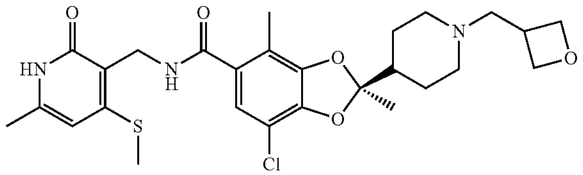
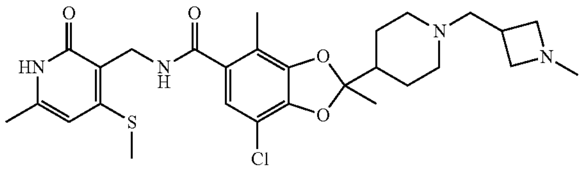
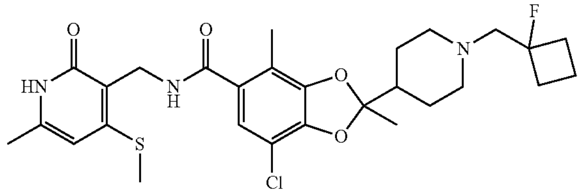
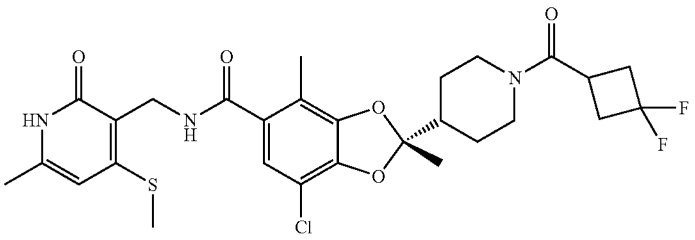

-continued
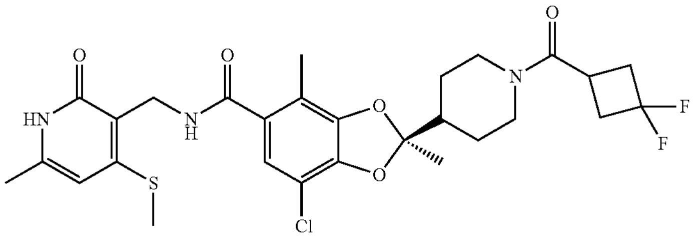
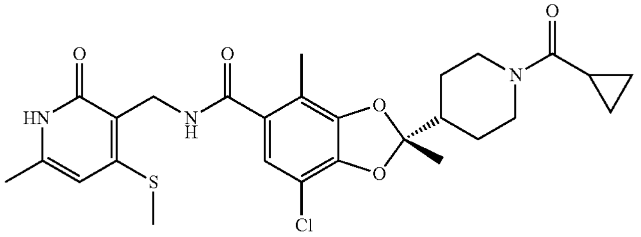
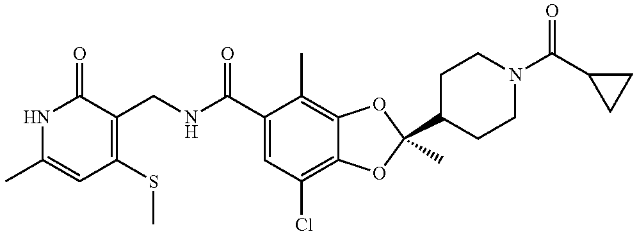
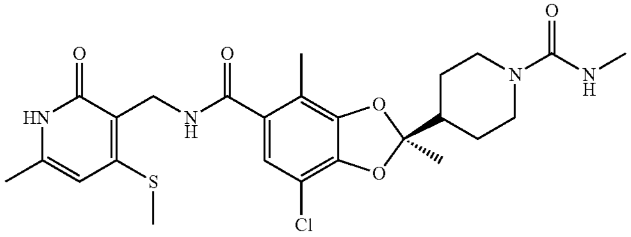
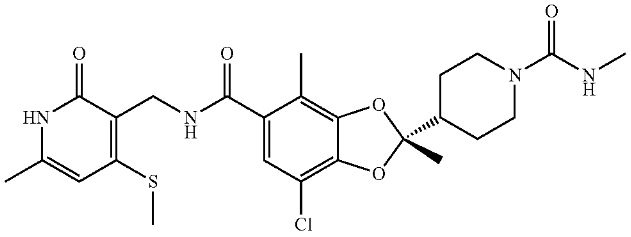
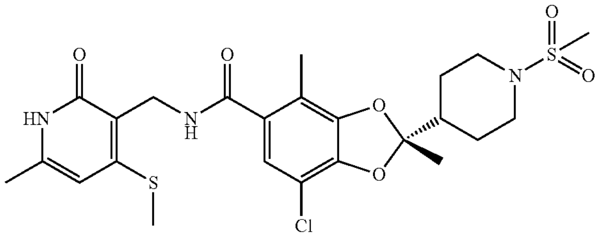
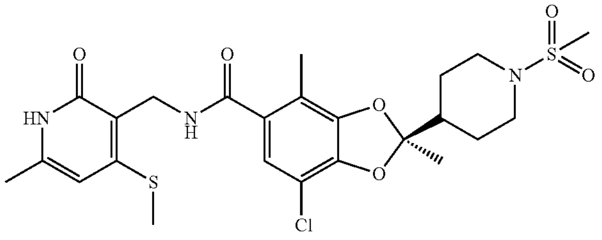

-continued
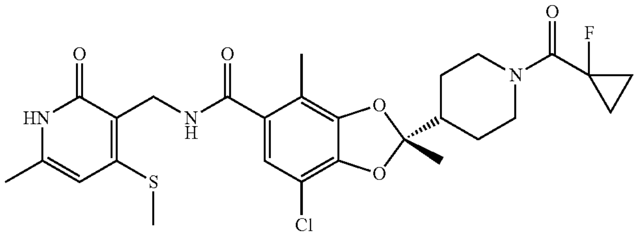
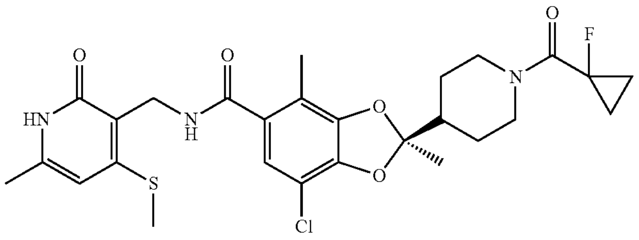
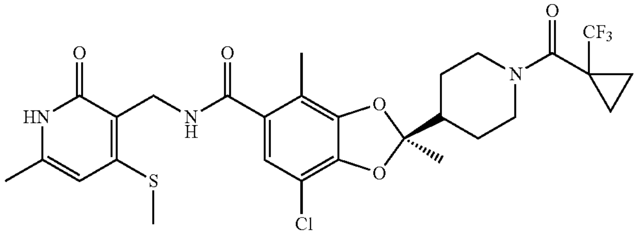
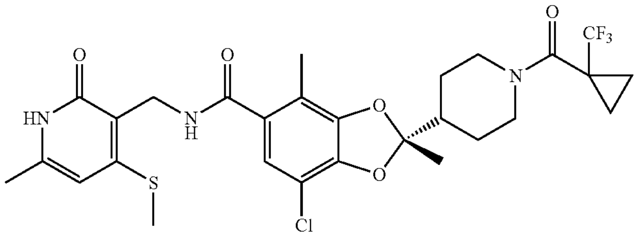
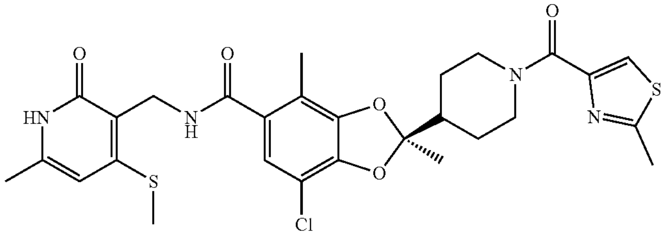
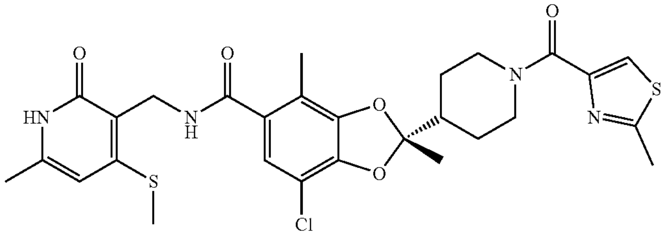
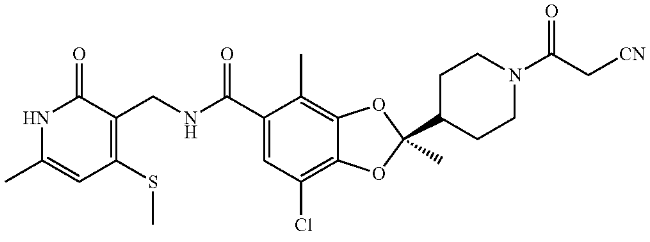

-continued
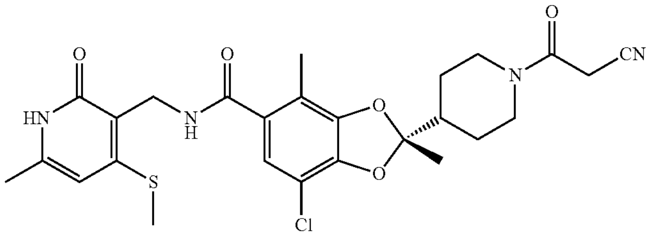
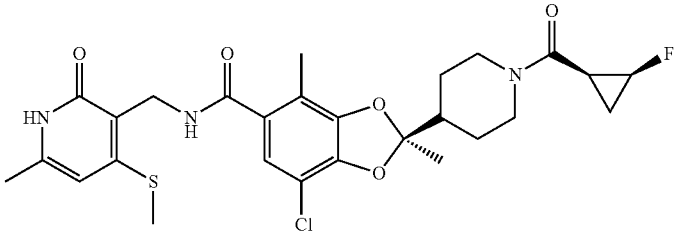
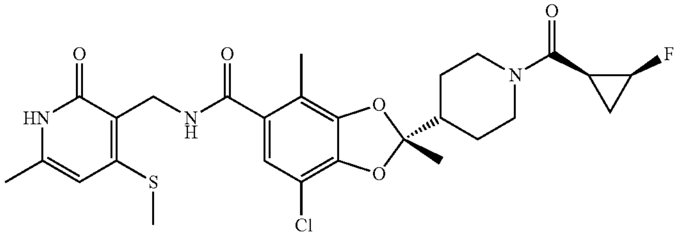
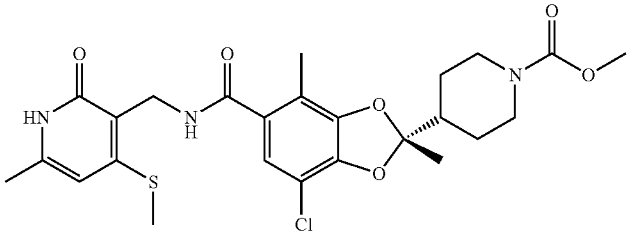
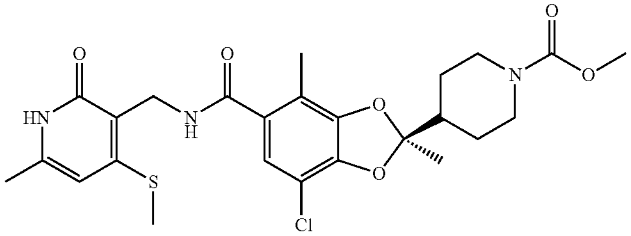
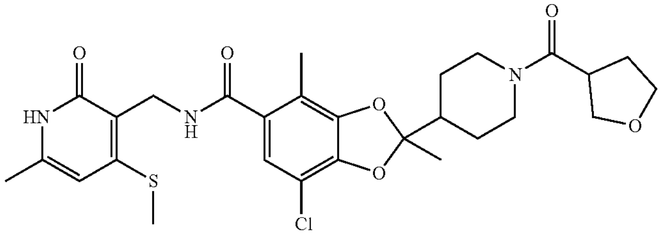
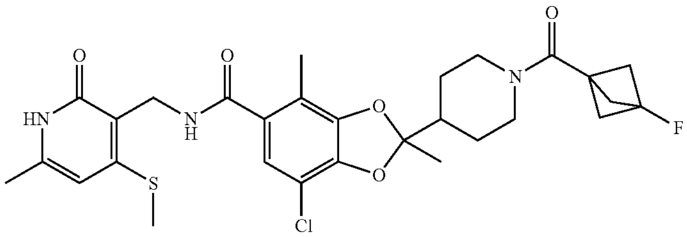

-continued
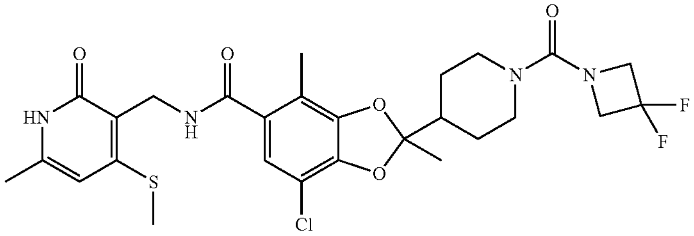
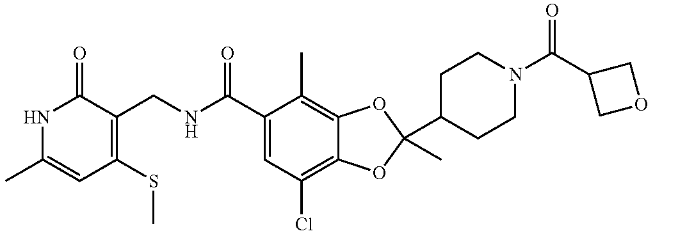
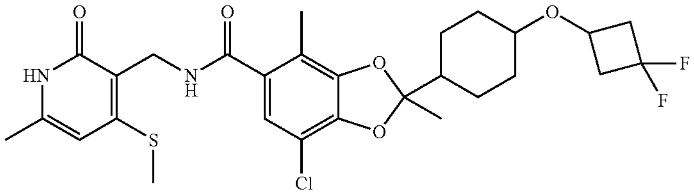
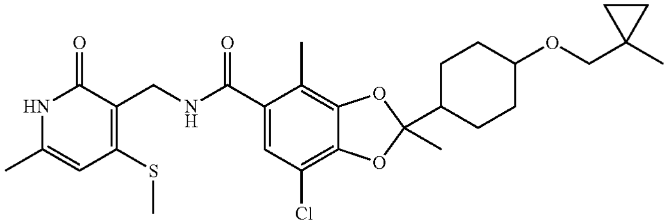
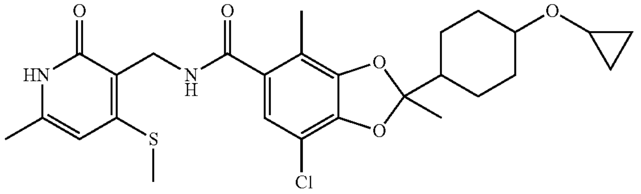
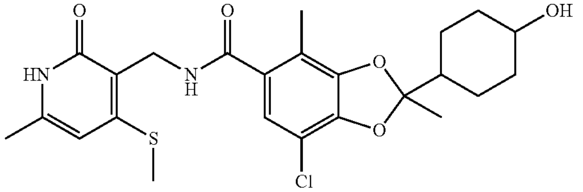
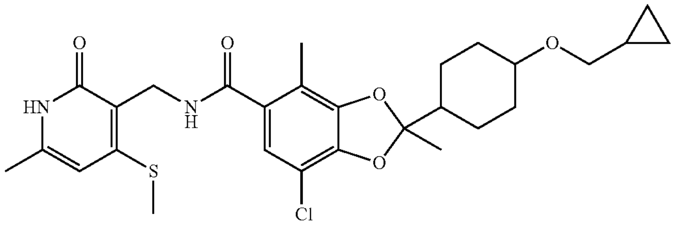
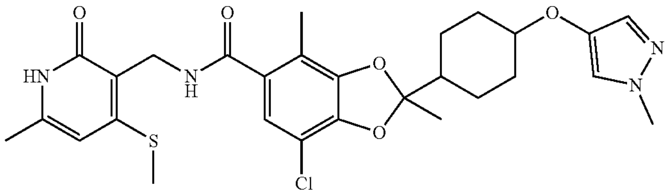

-continued
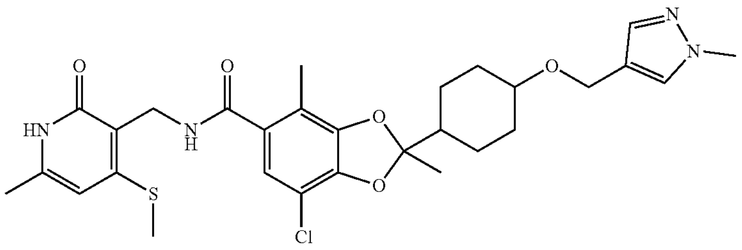
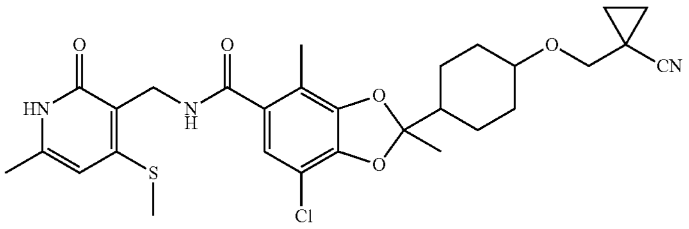
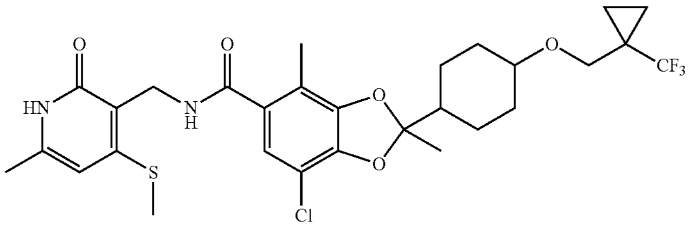
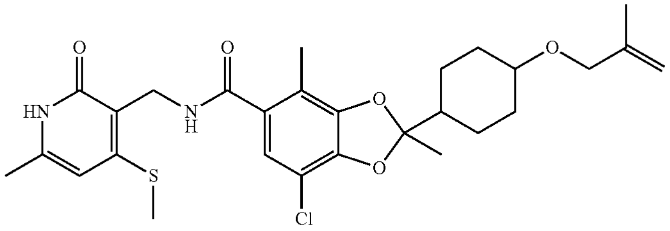
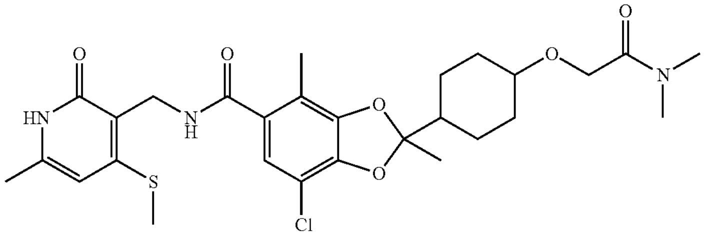
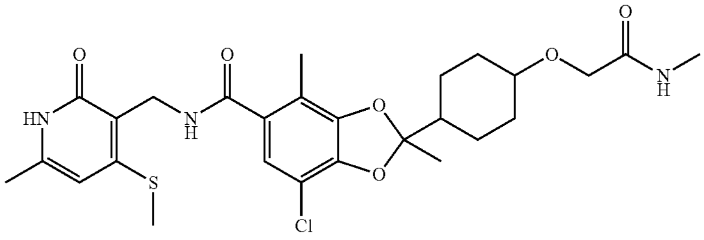
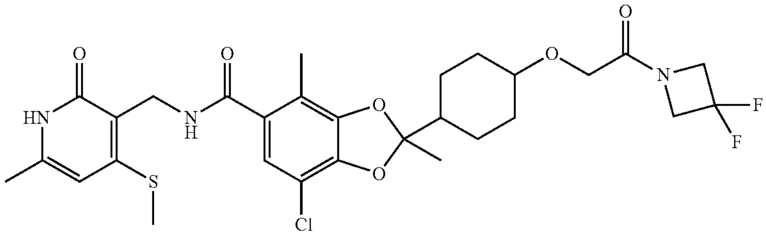

-continued
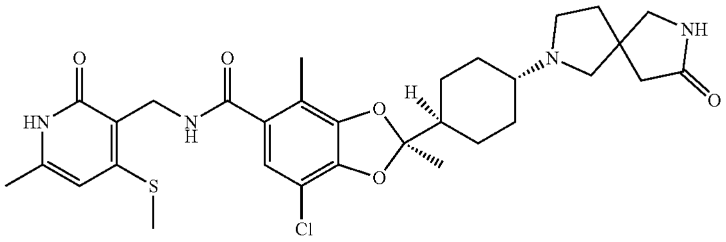
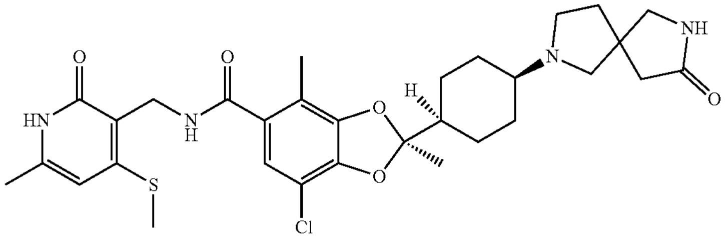
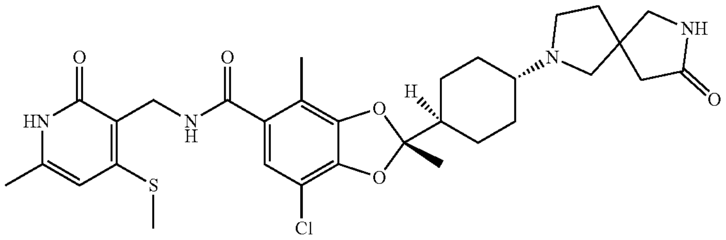
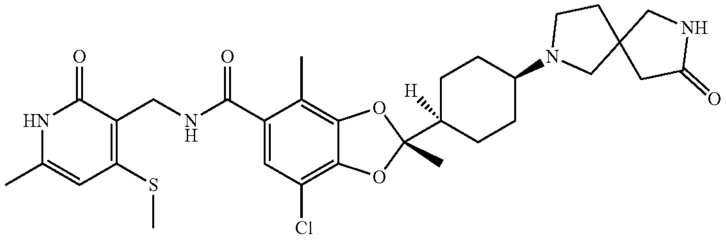
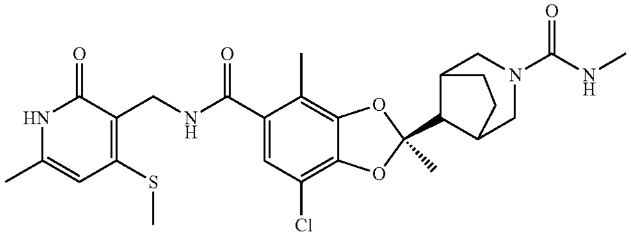
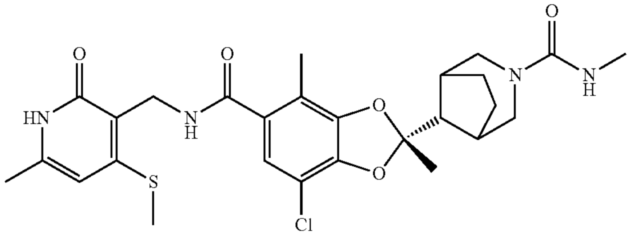
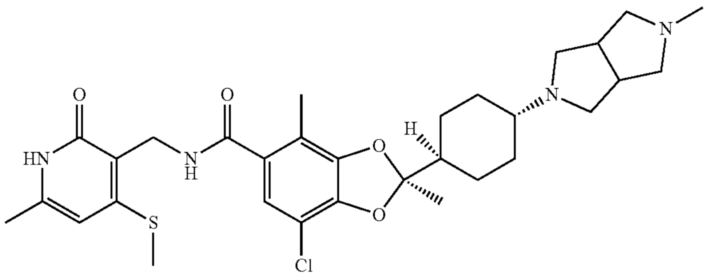

-continued
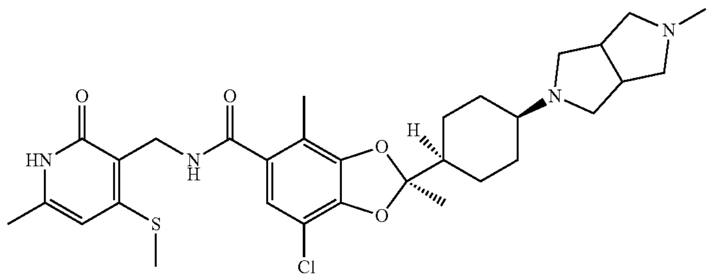
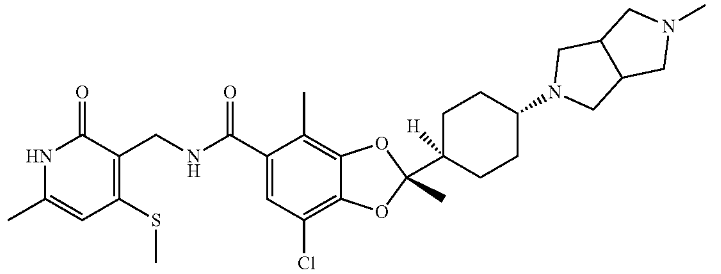
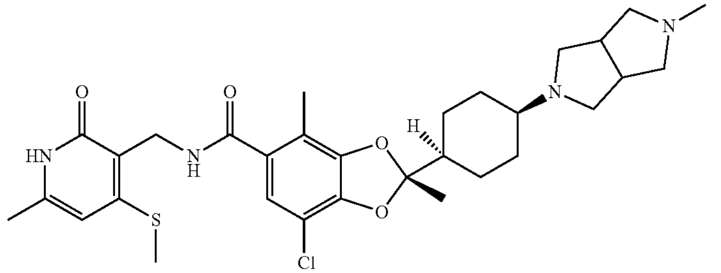
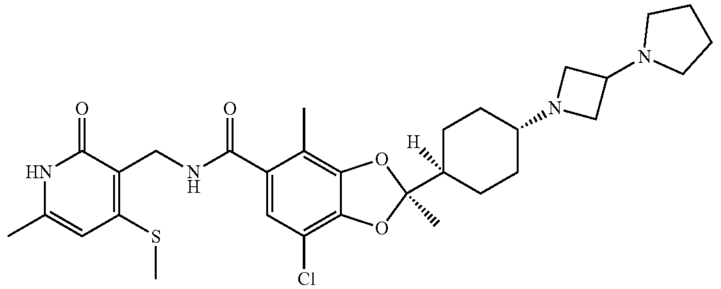
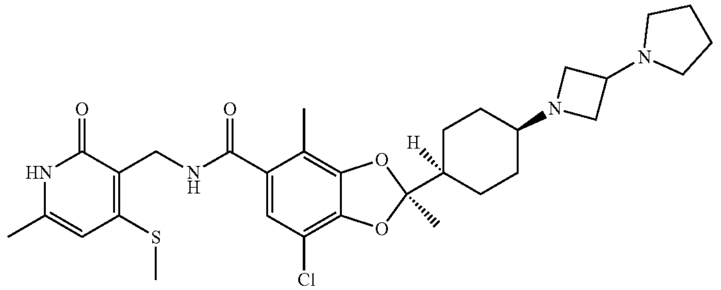
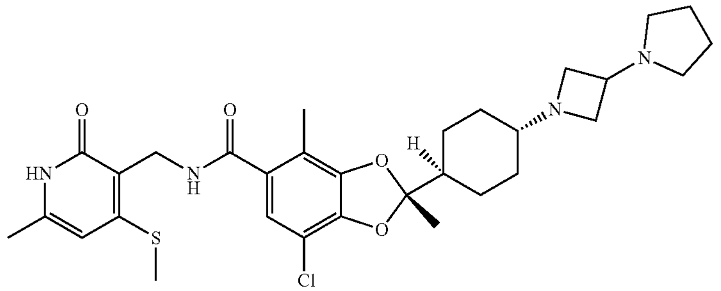

-continued
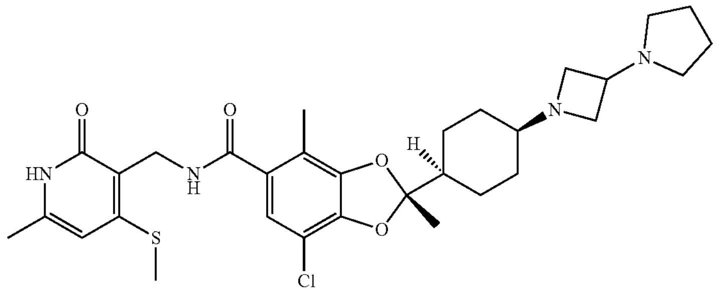
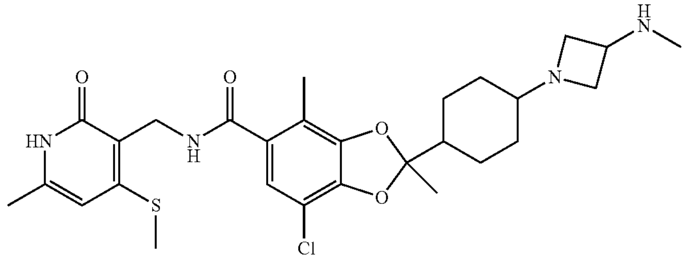
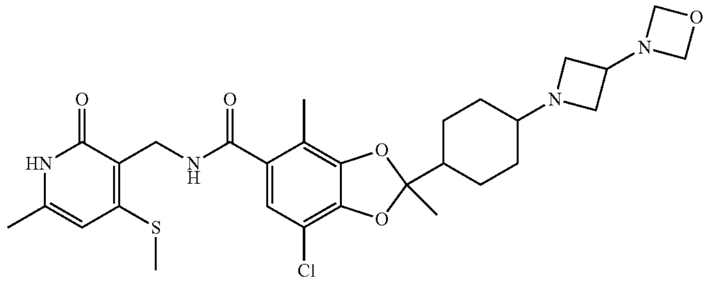
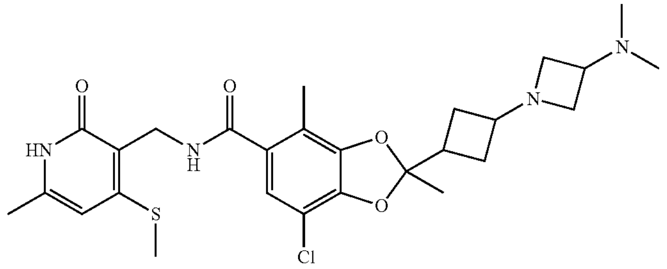
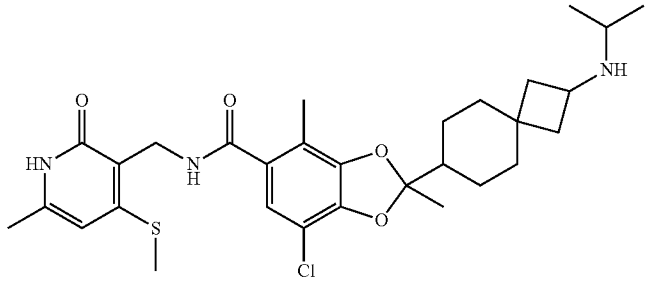
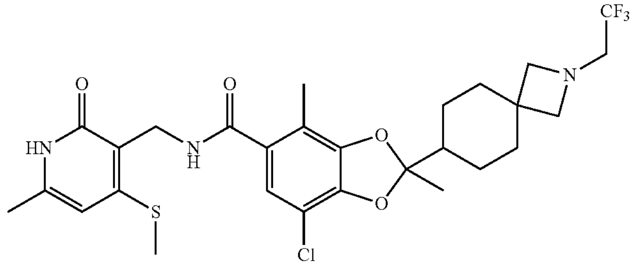

-continued
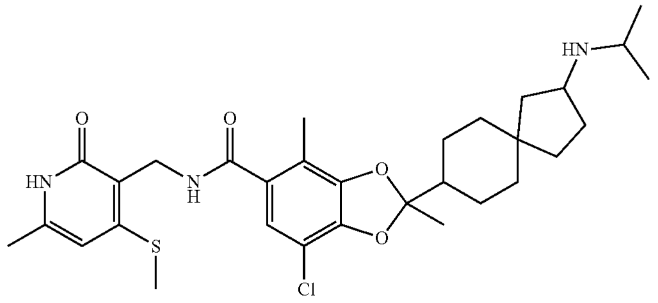
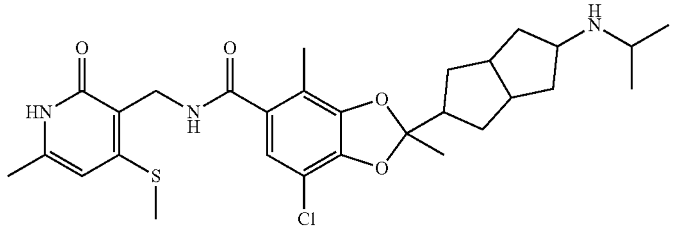
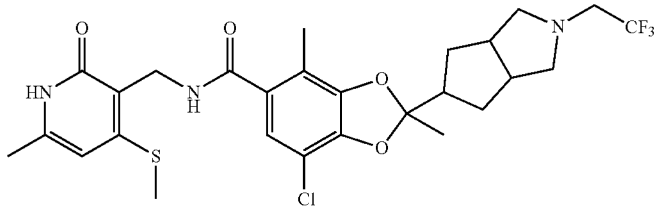
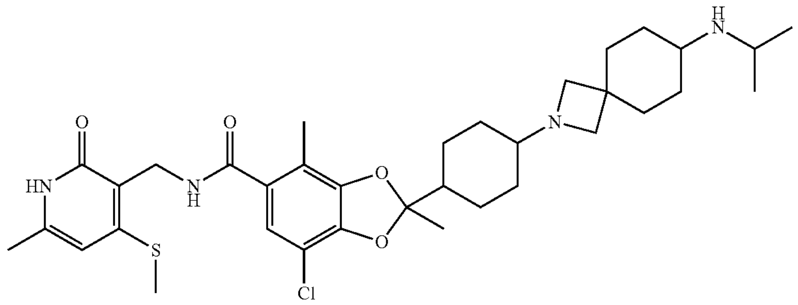
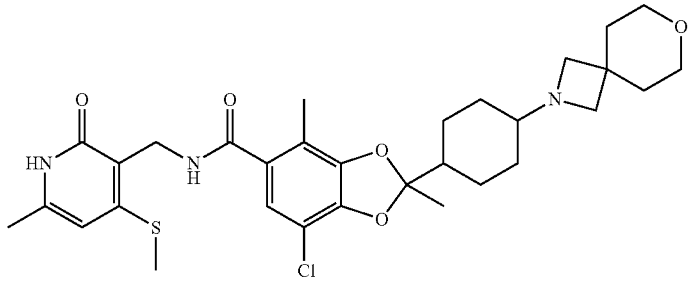
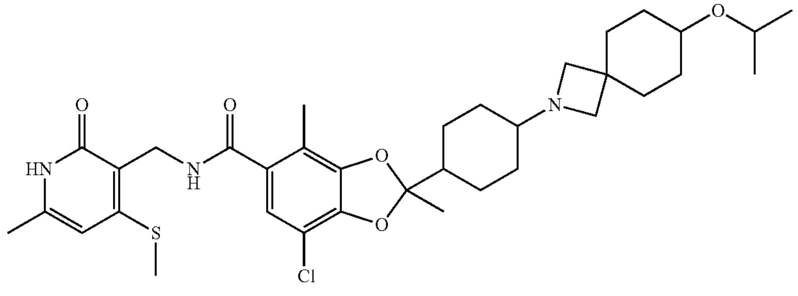

-continued
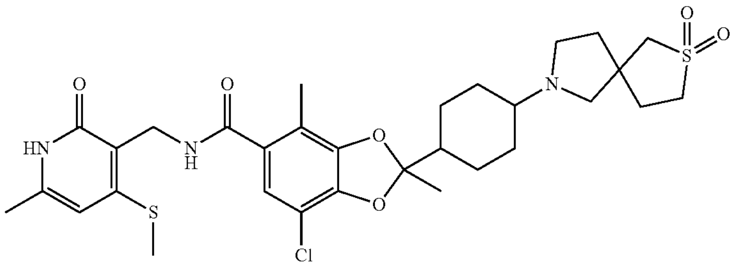
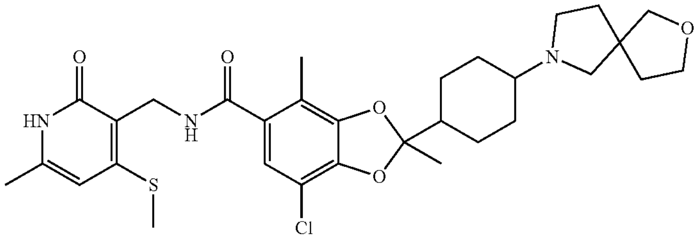
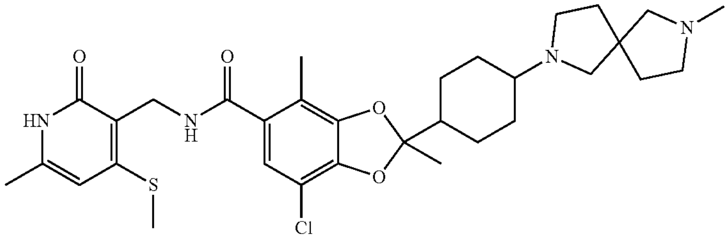
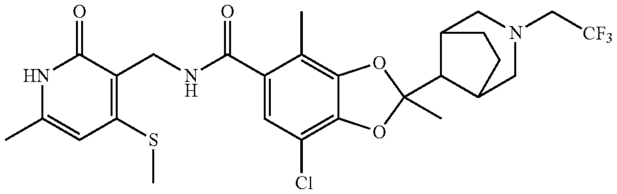
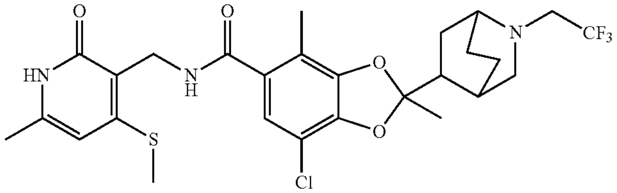
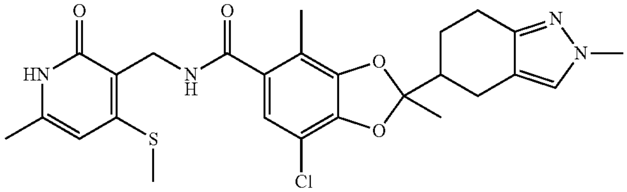
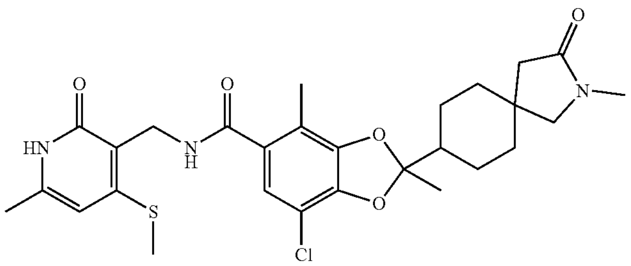

-continued
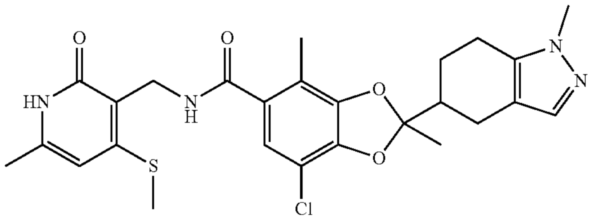
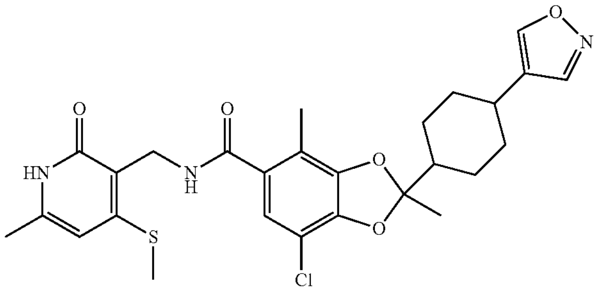
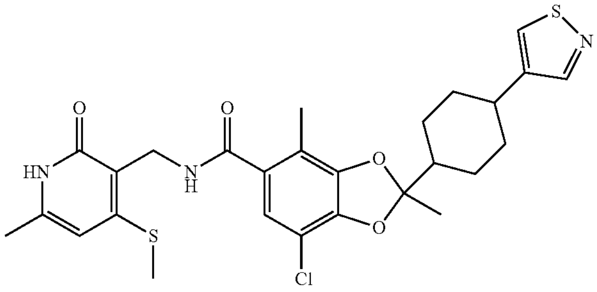
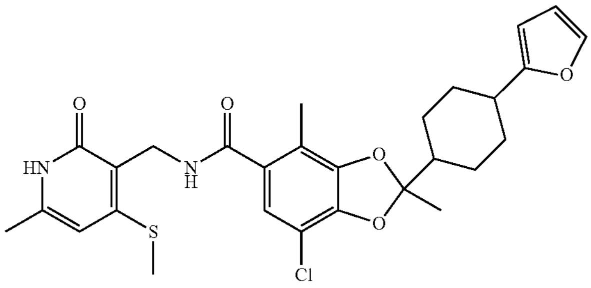
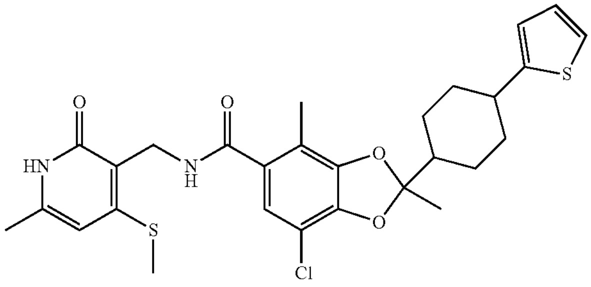
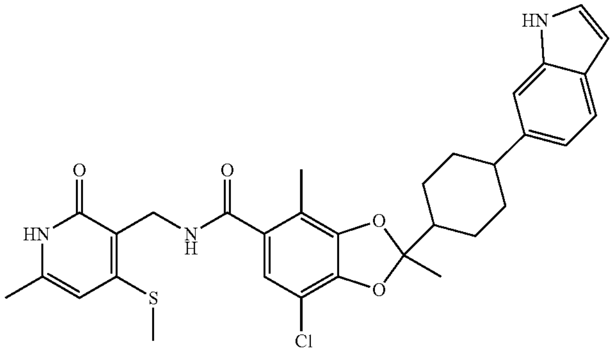

-continued
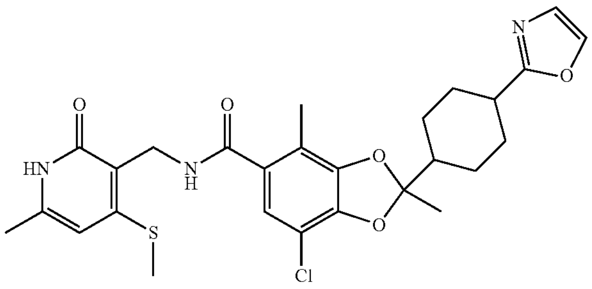
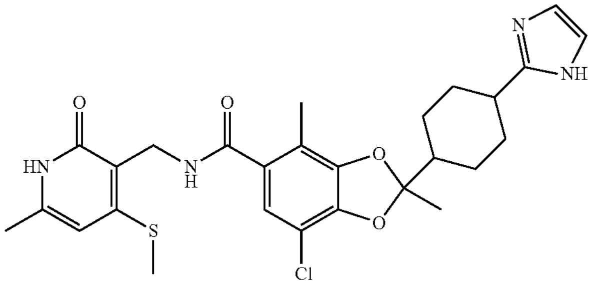
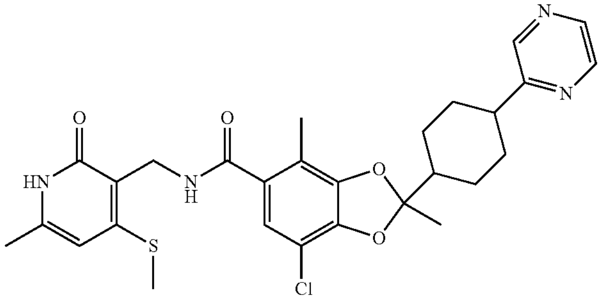
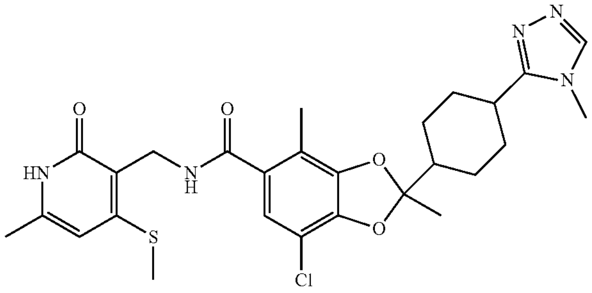
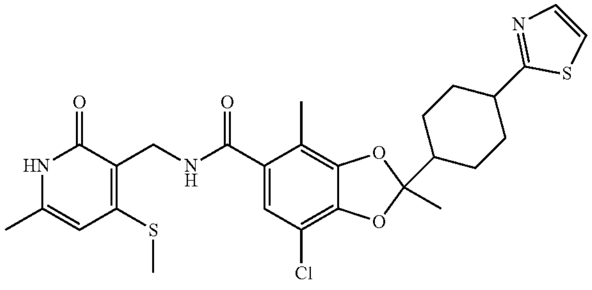
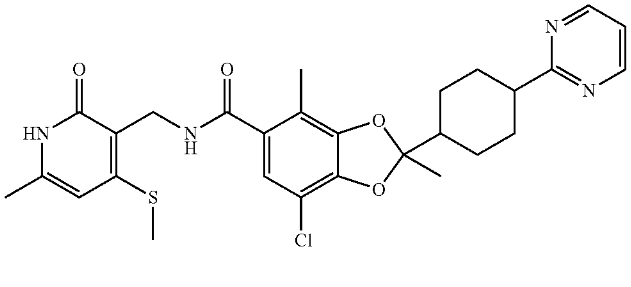

-continued
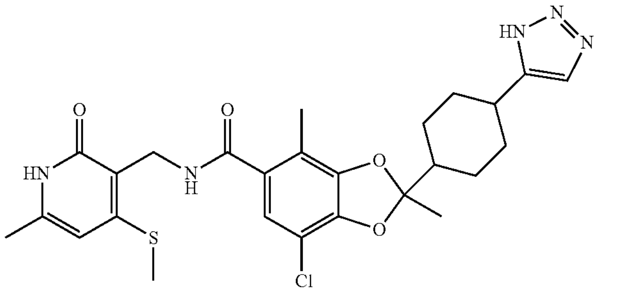
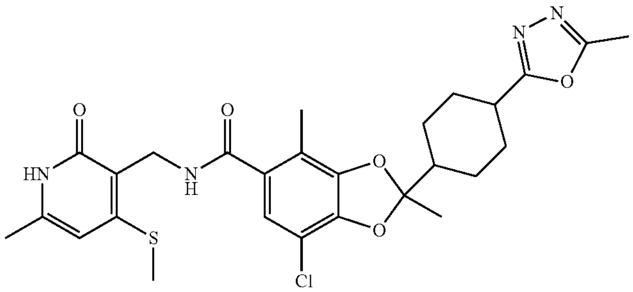
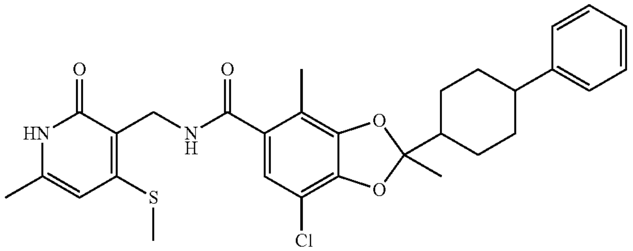
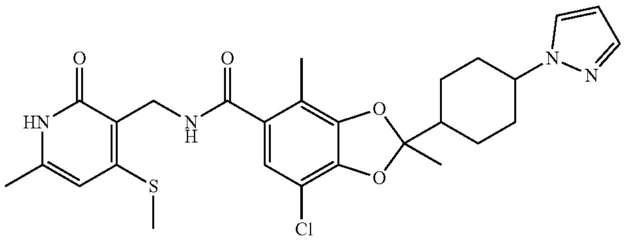
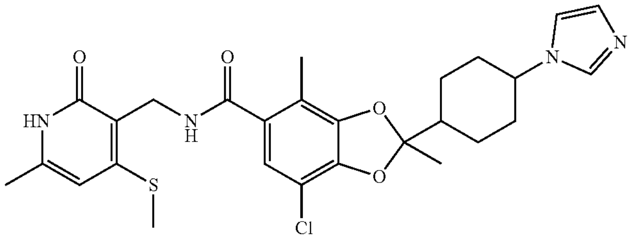
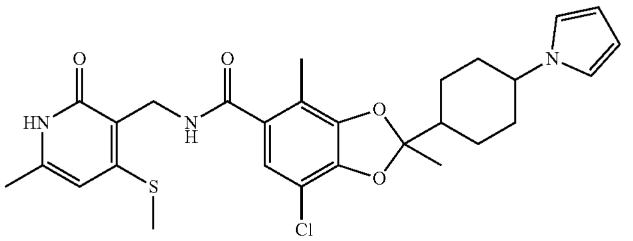

-continued
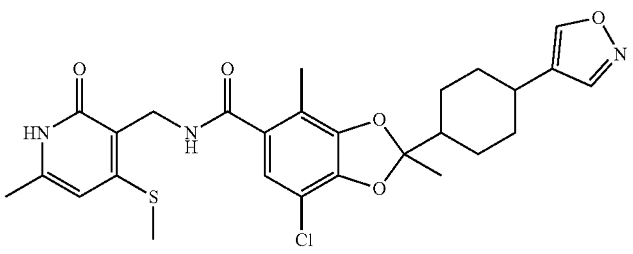
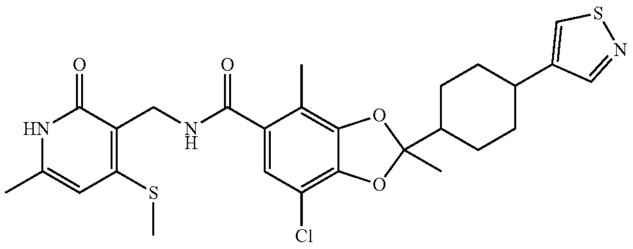
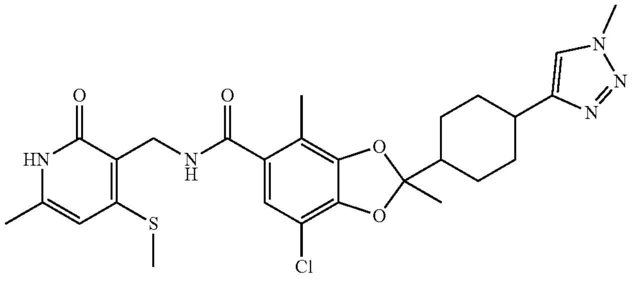
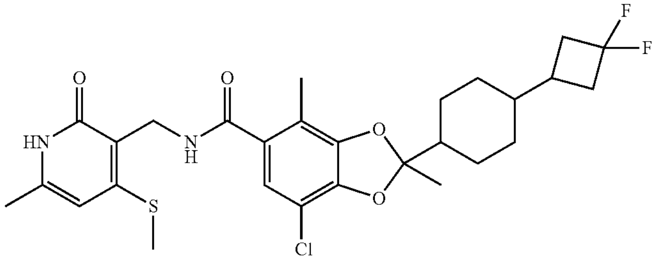
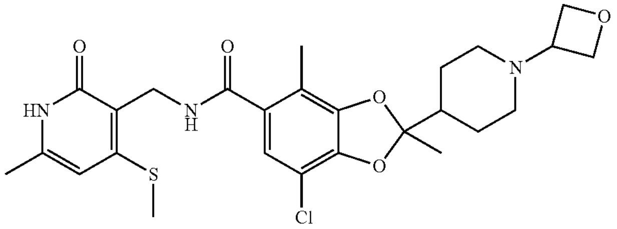
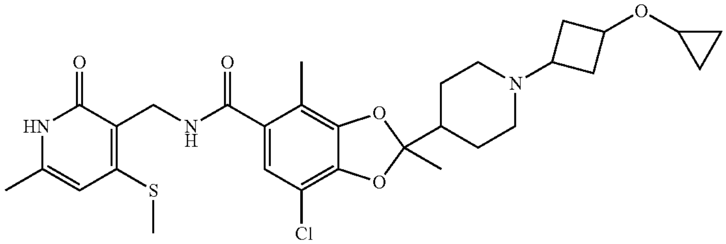

-continued
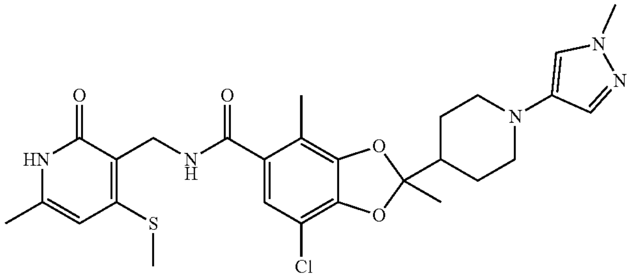
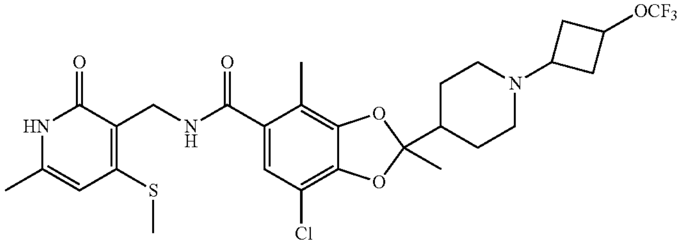
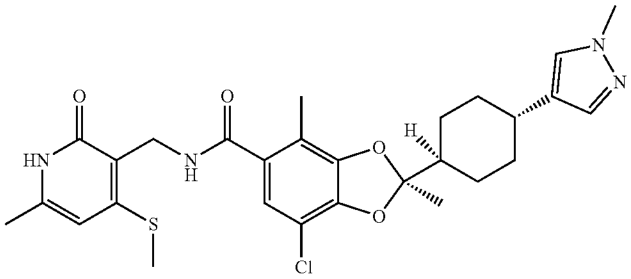
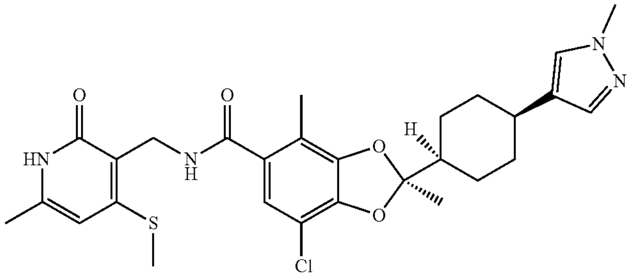
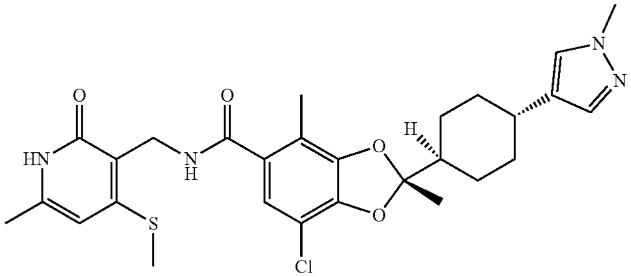
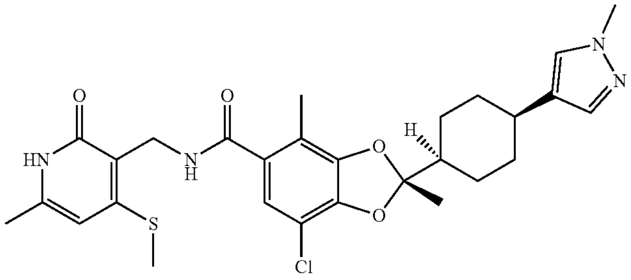

-continued
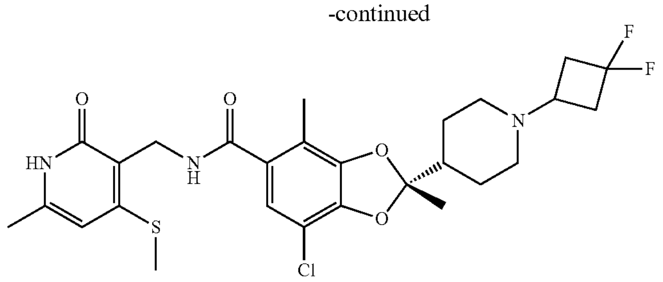
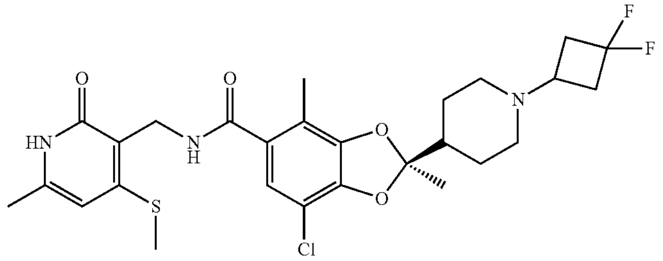
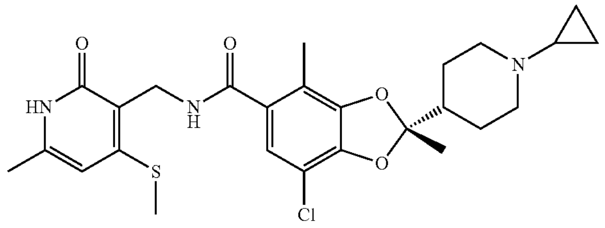
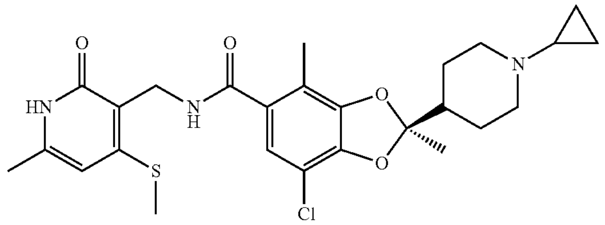
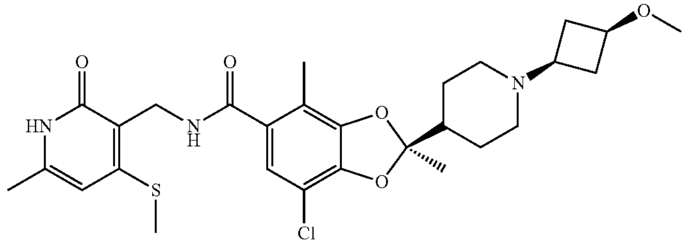
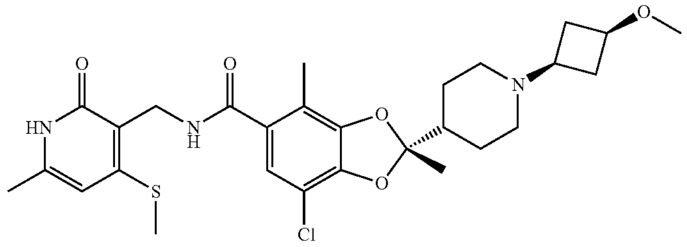
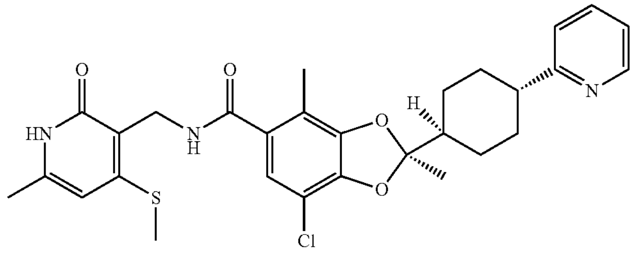

-continued
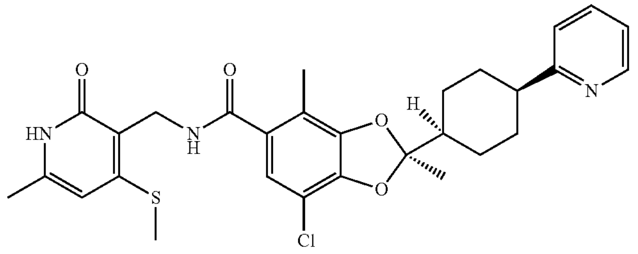
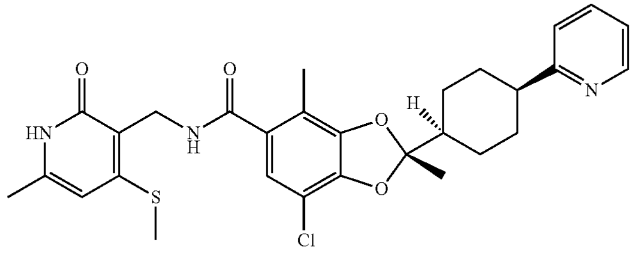
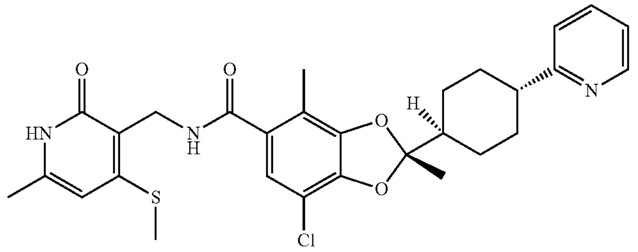
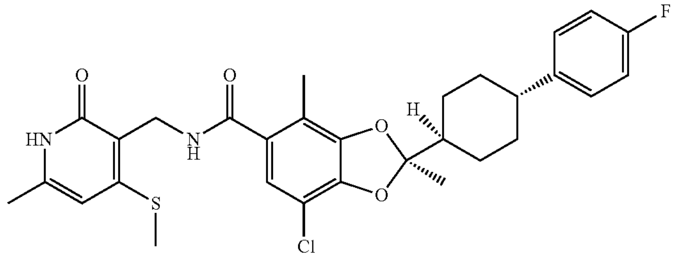
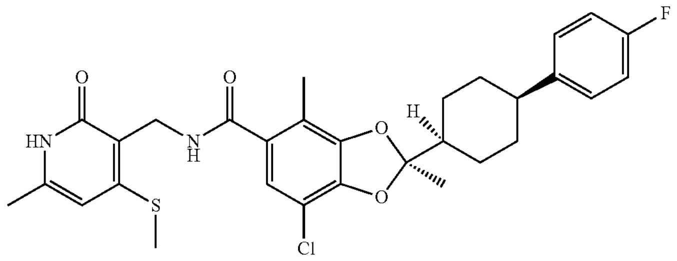
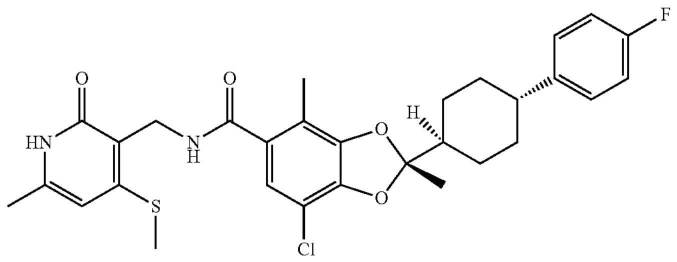

-continued
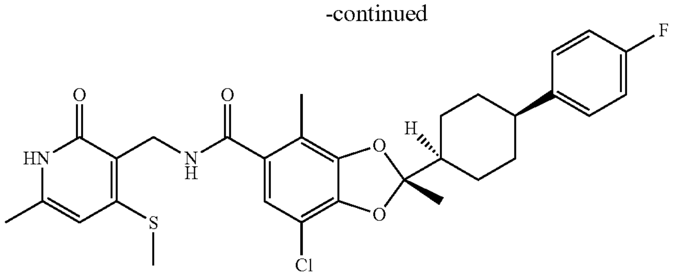
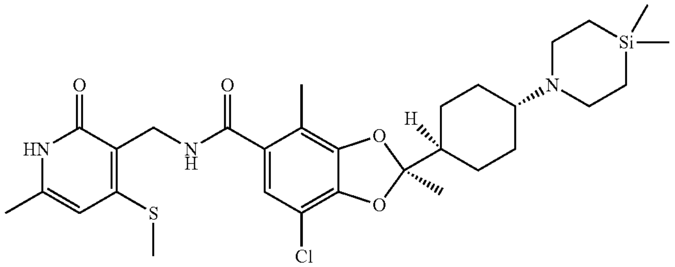
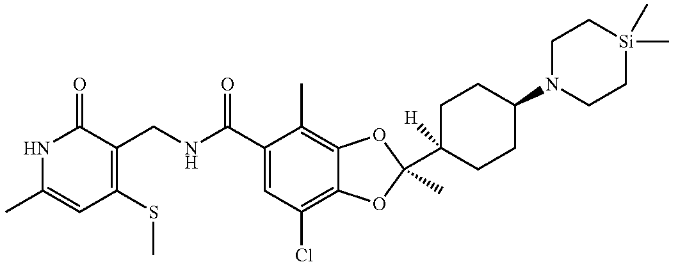
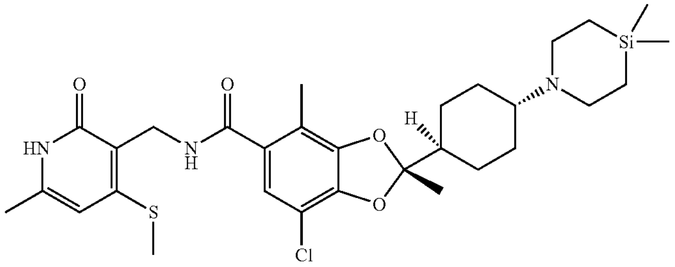
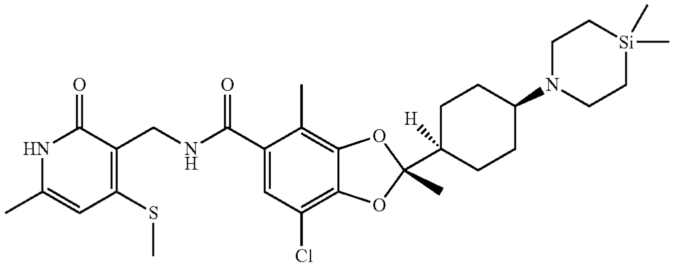
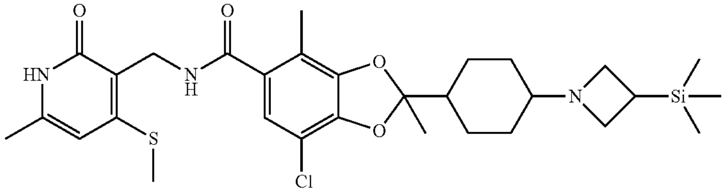
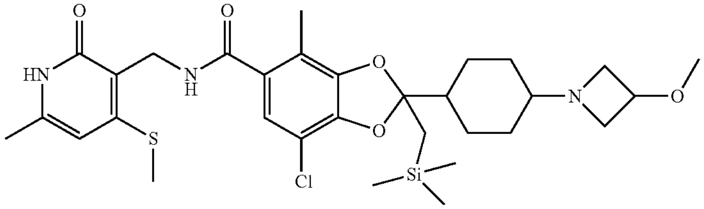

-continued
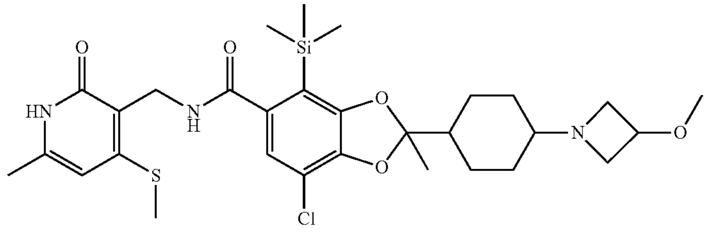
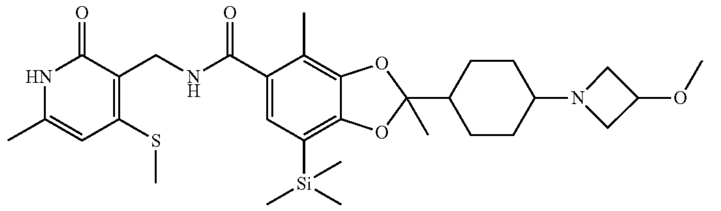
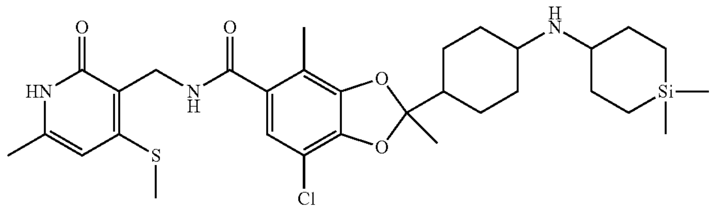
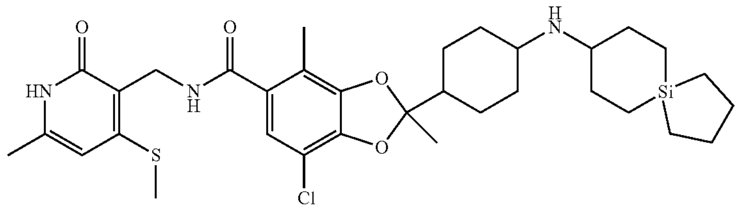
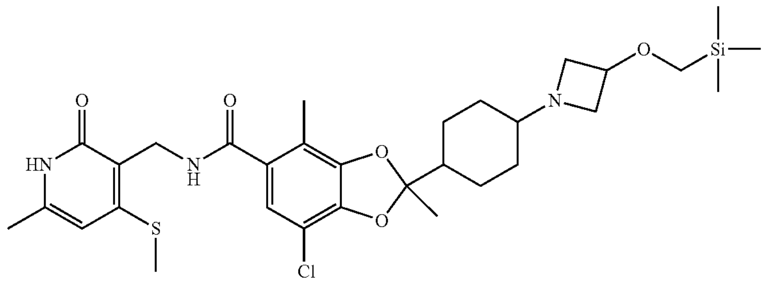
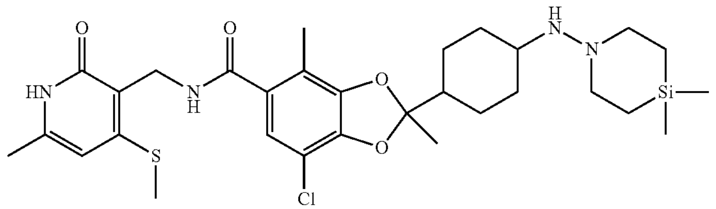
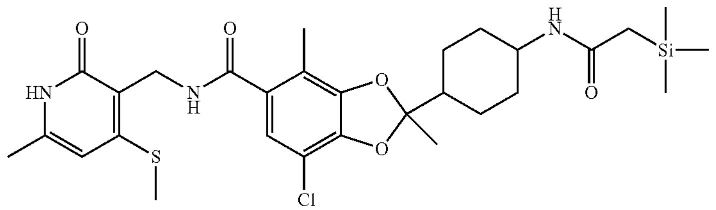

-continued
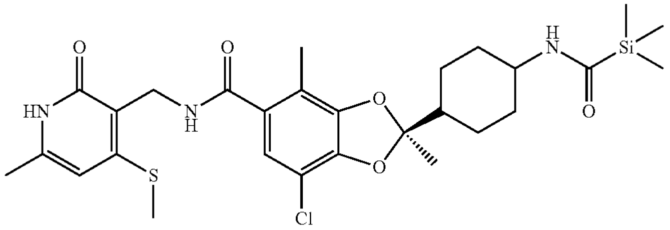
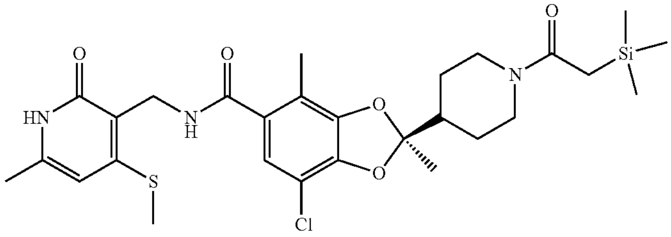
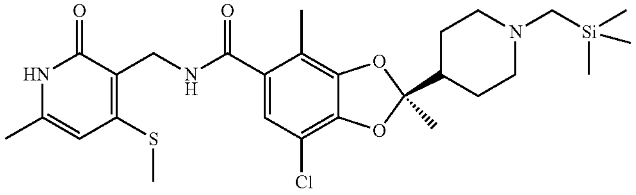
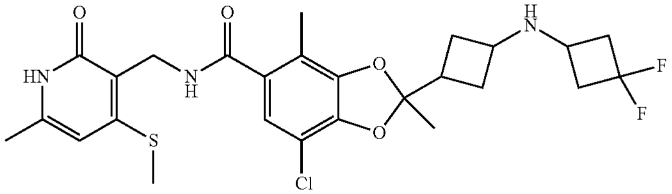
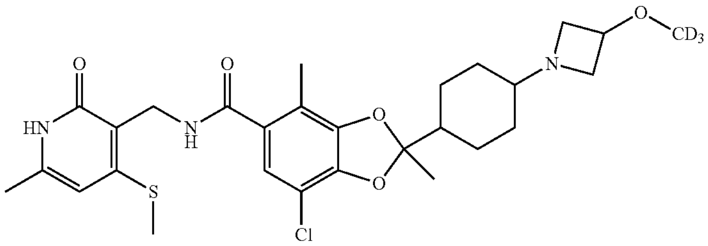
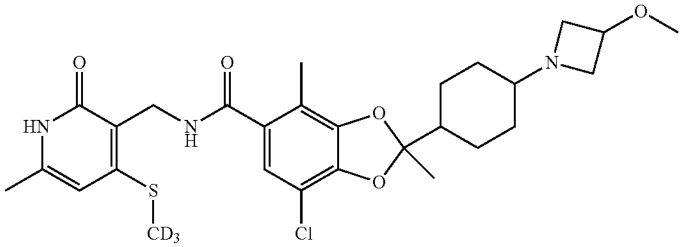
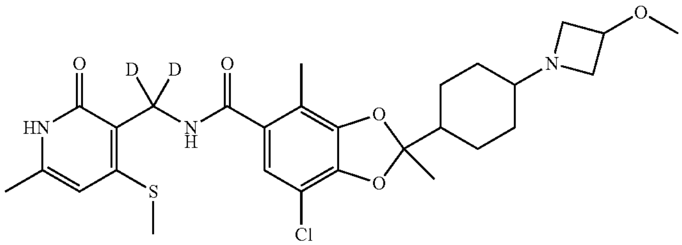

-continued
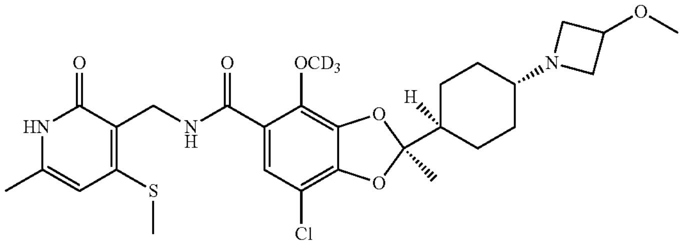
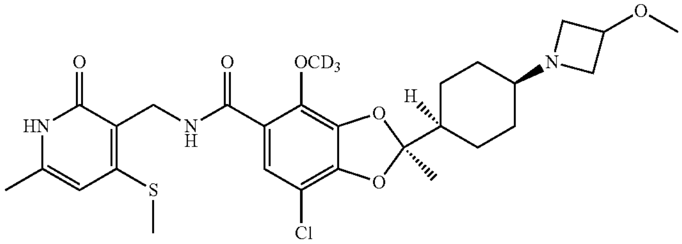
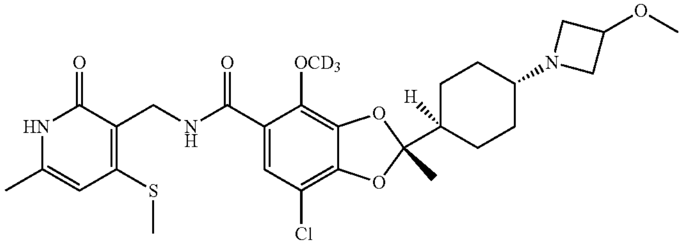
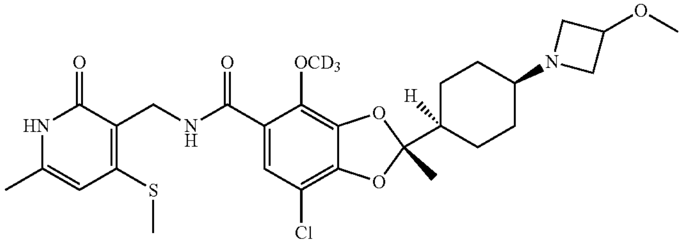
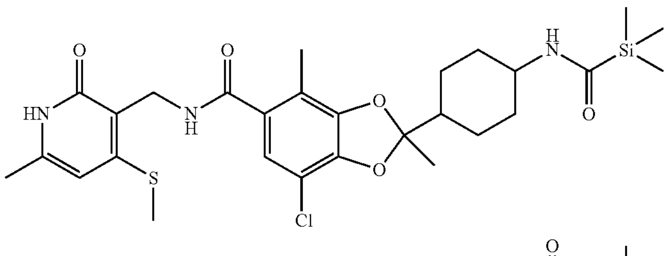
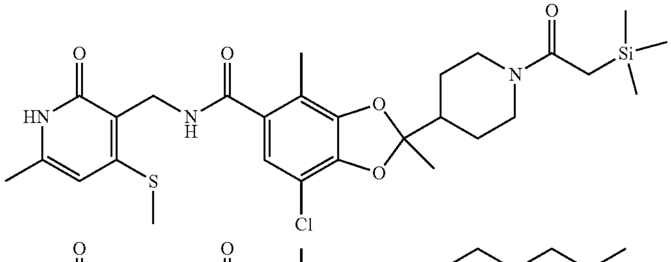
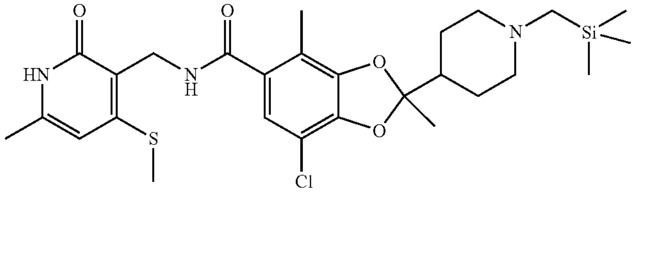

-continued
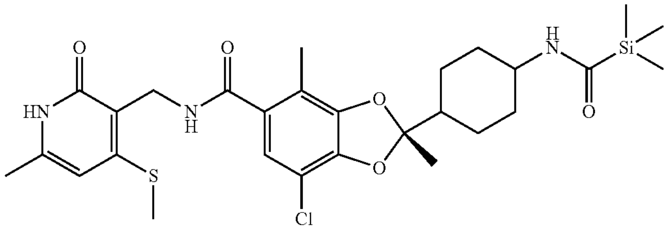
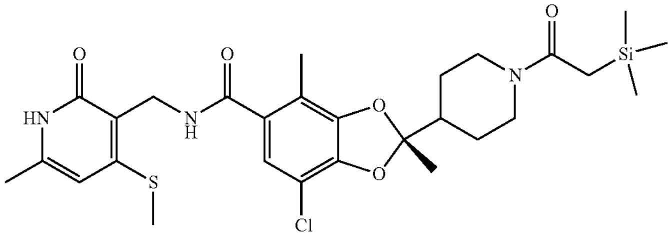
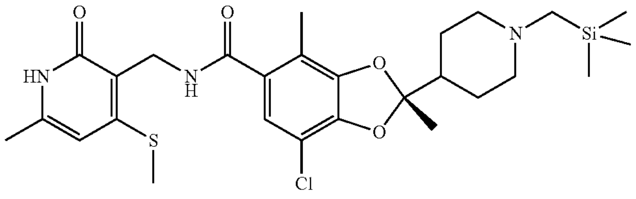
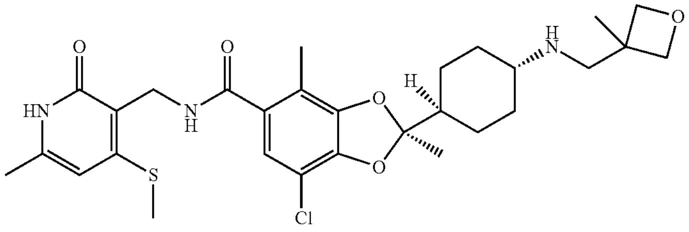
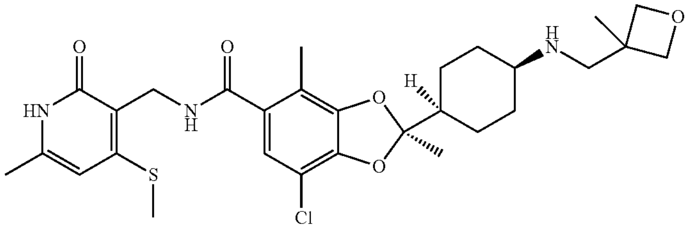
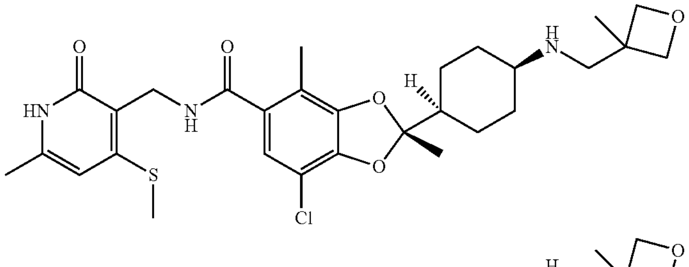
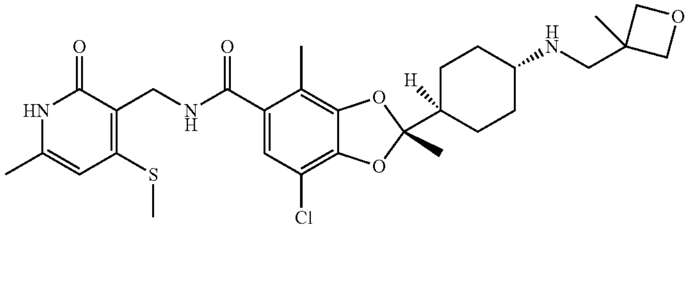

-continued
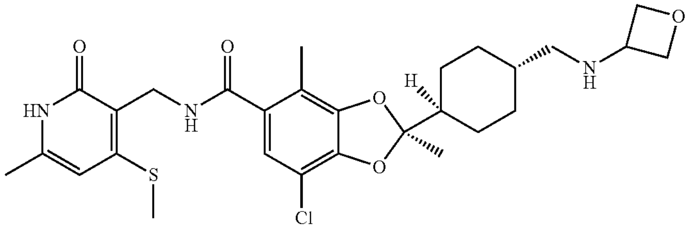
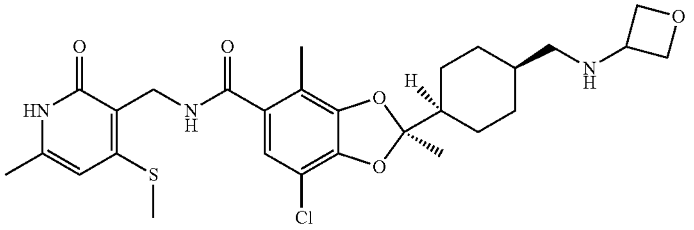
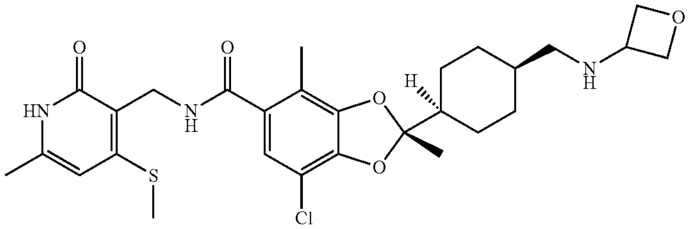
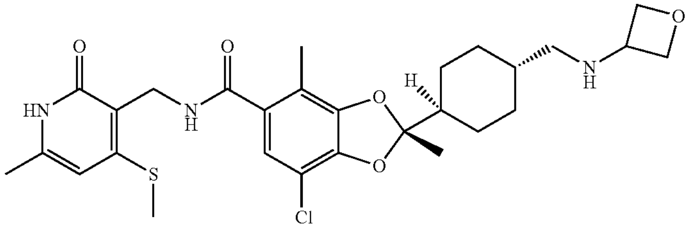
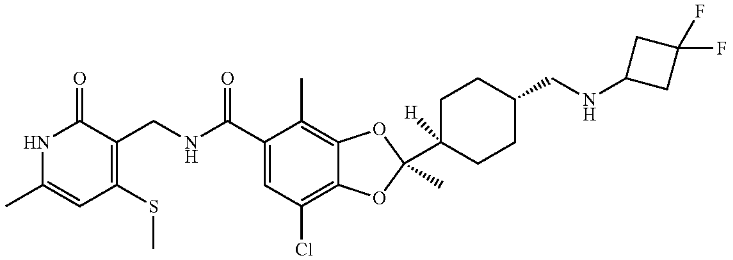
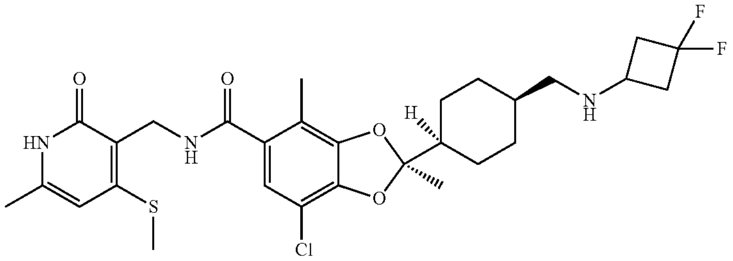
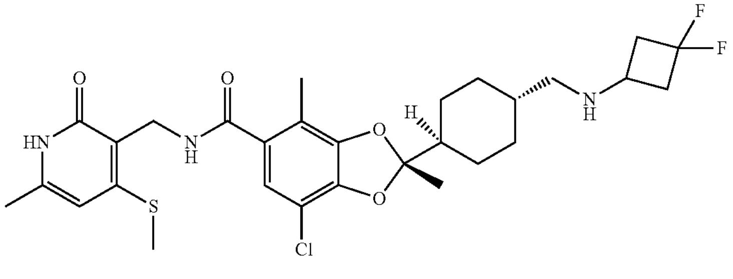

-continued
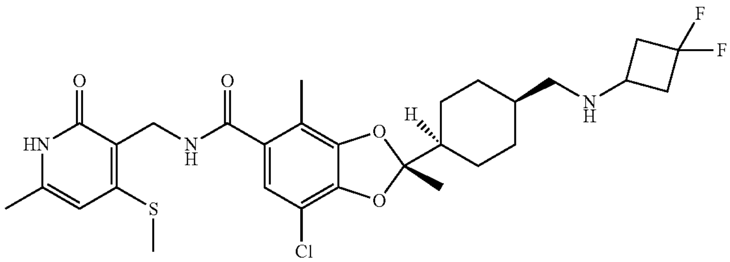
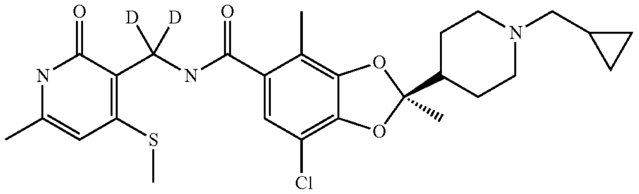
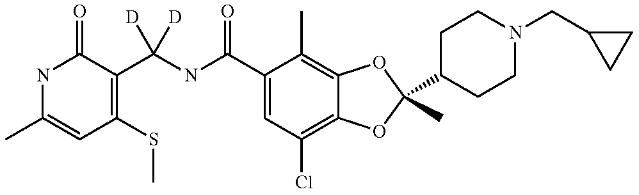
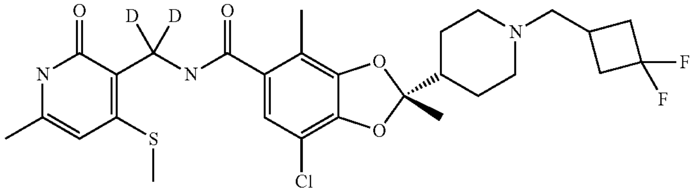
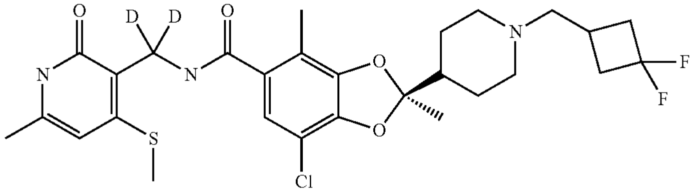
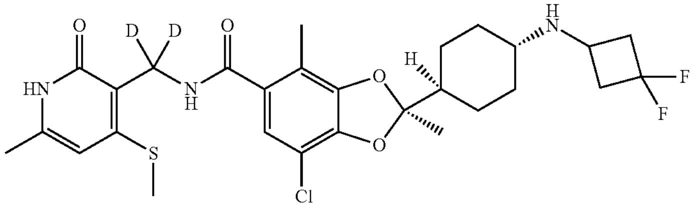
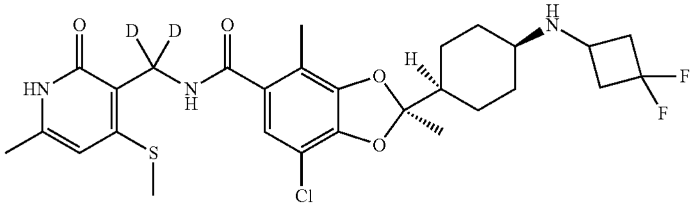
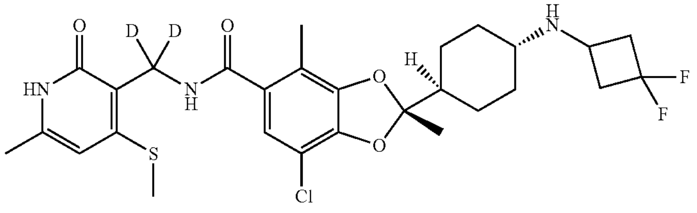

-continued
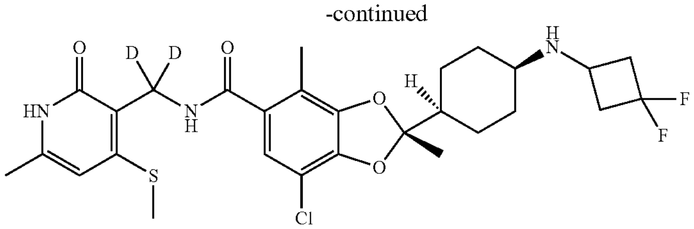
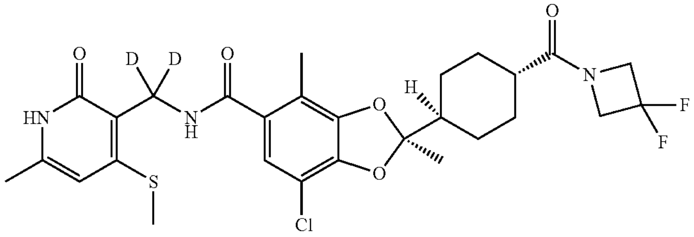
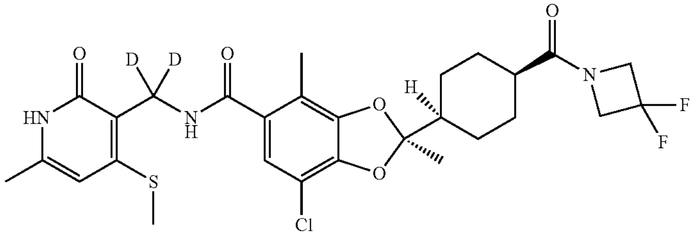
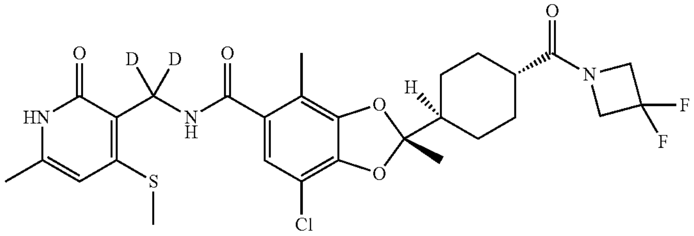
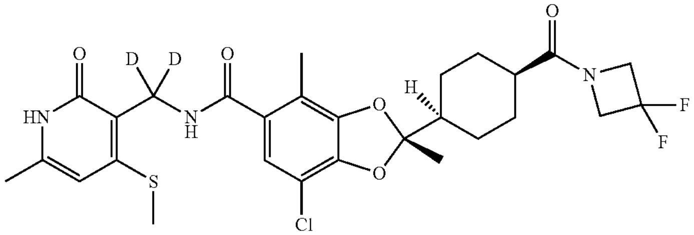
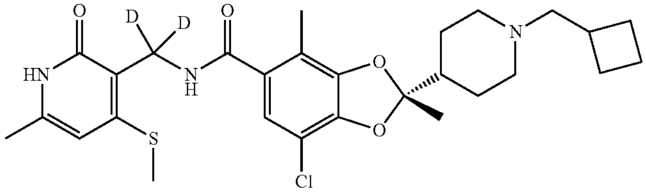
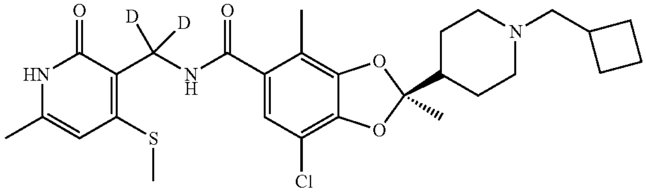
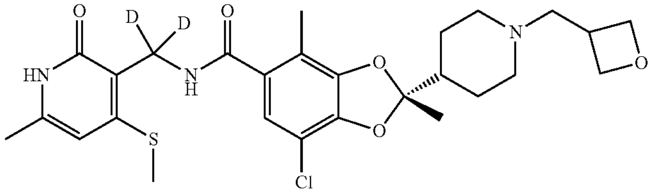

-continued
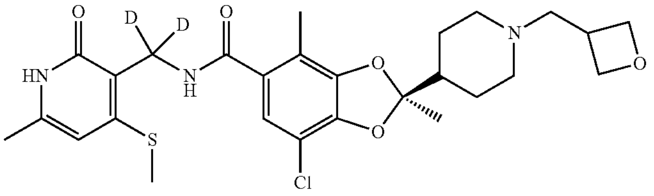
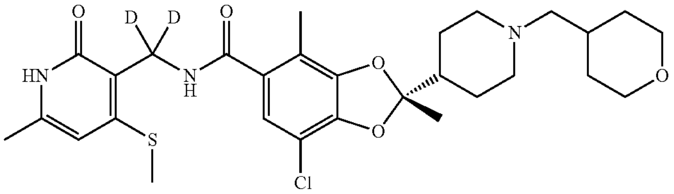
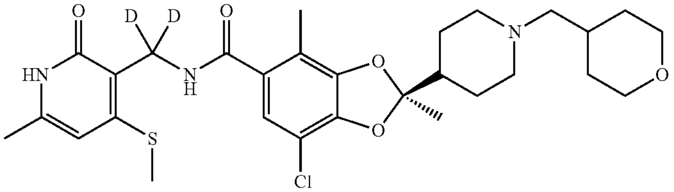
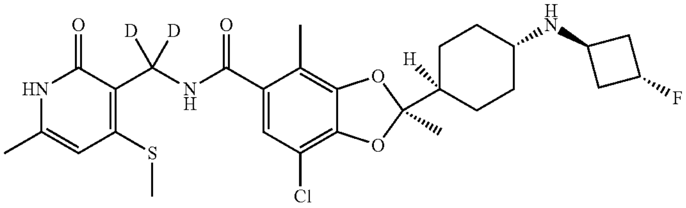
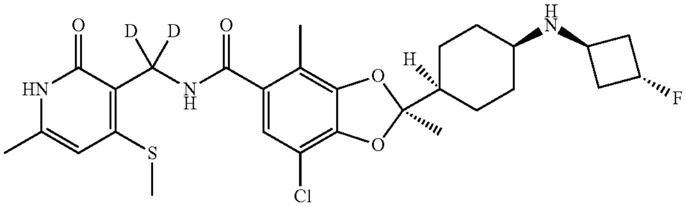
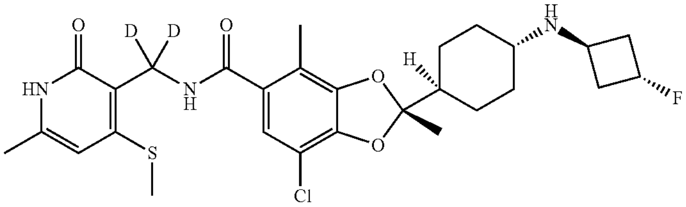
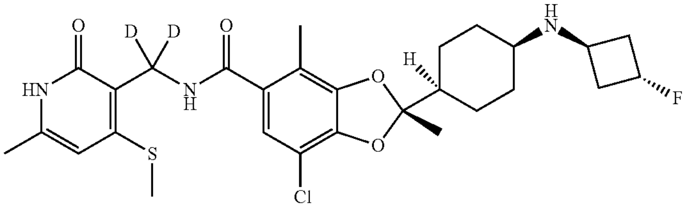
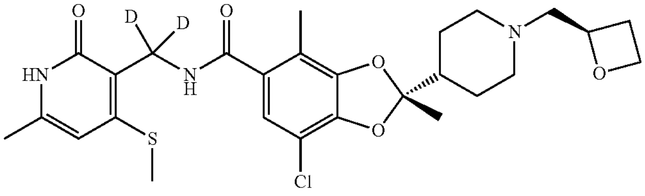

-continued
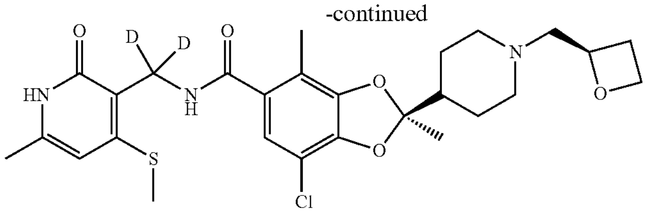
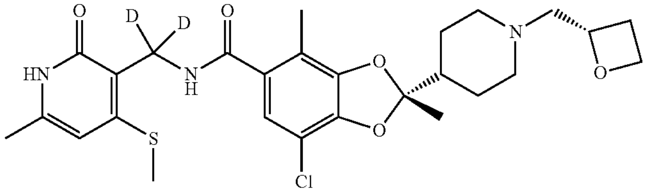
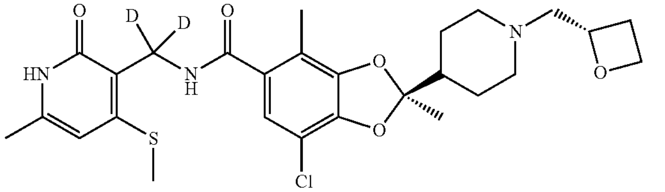
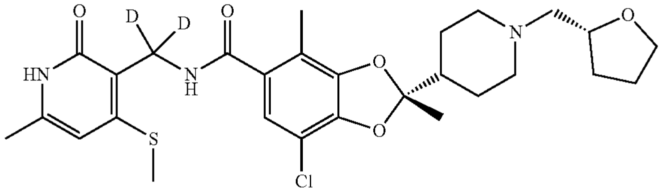
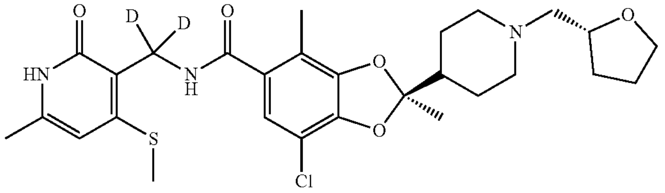
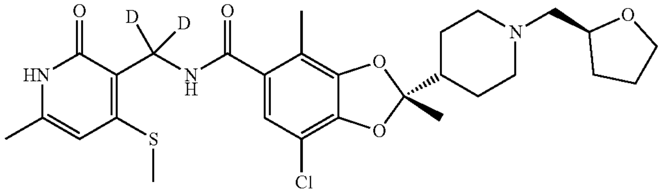
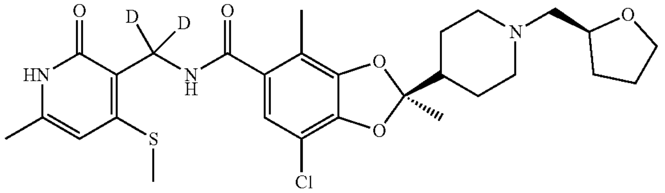
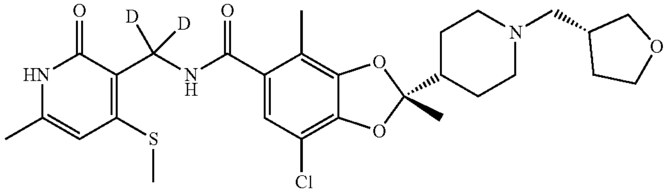
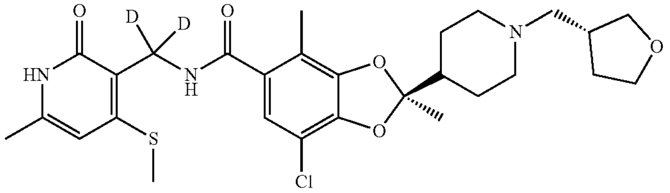

-continued
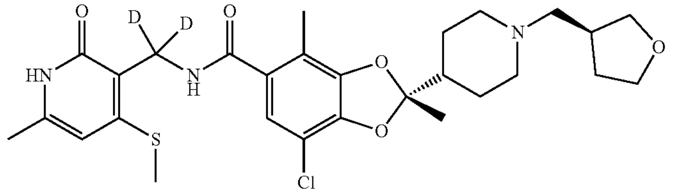
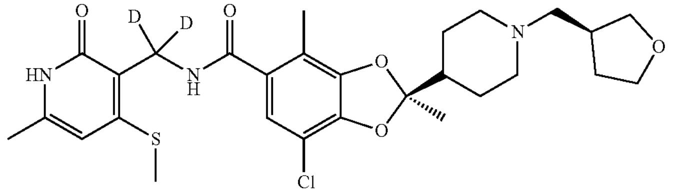
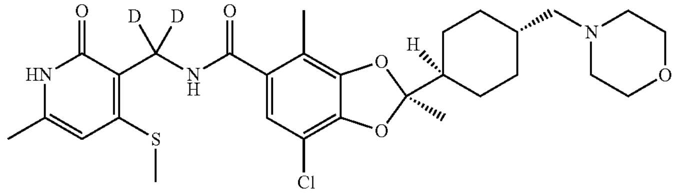
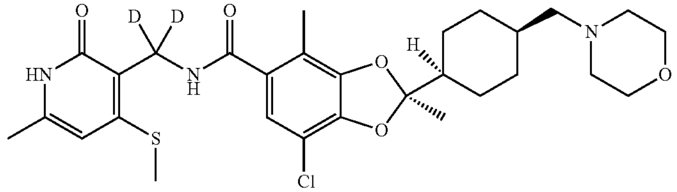
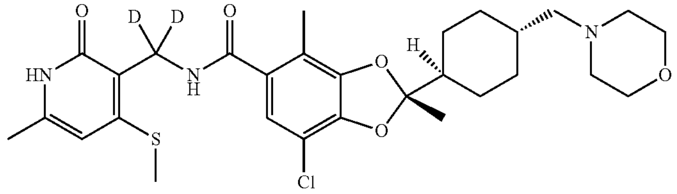
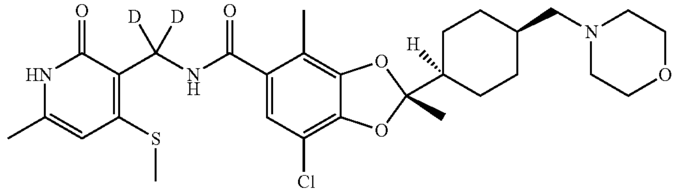
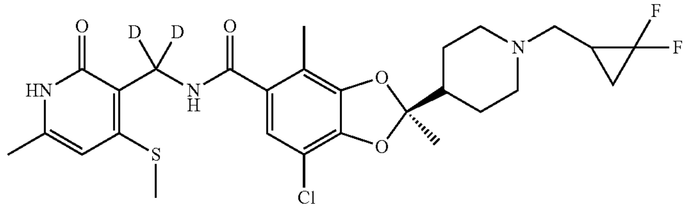
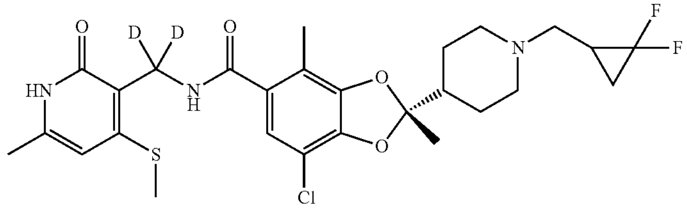

-continued
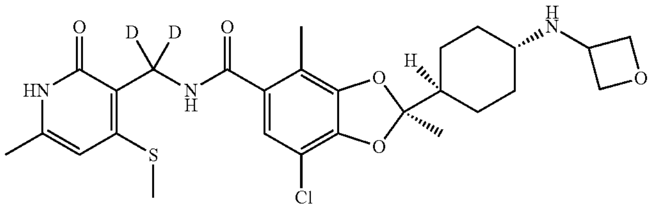
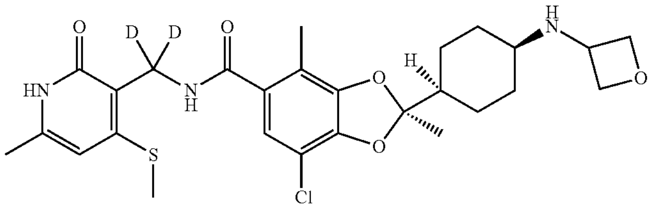
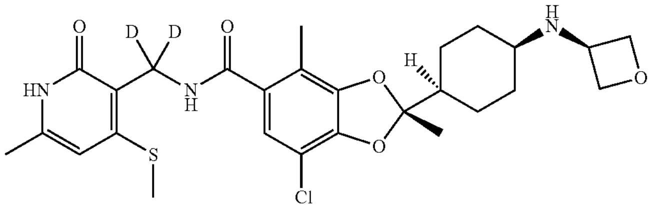
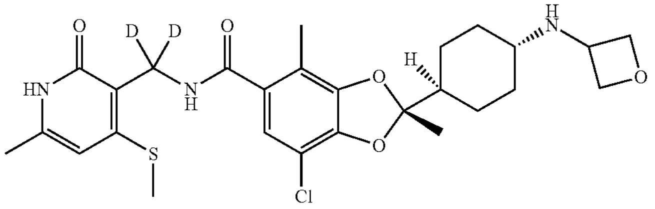
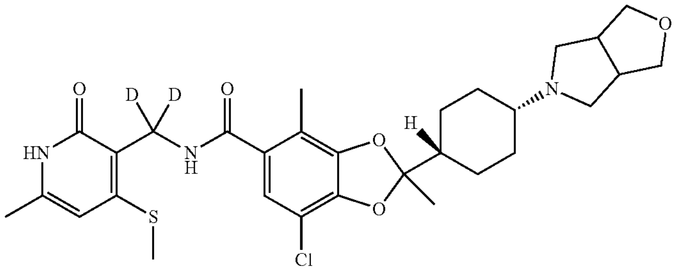
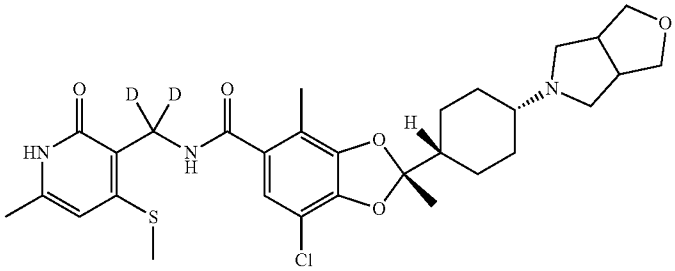
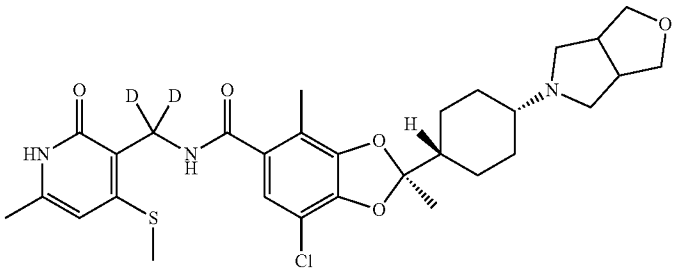

-continued
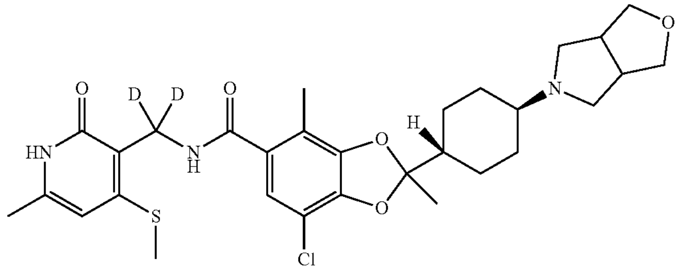
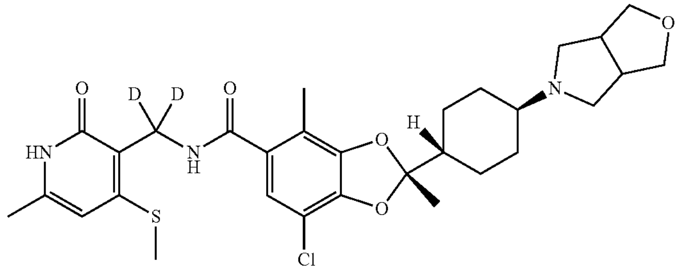
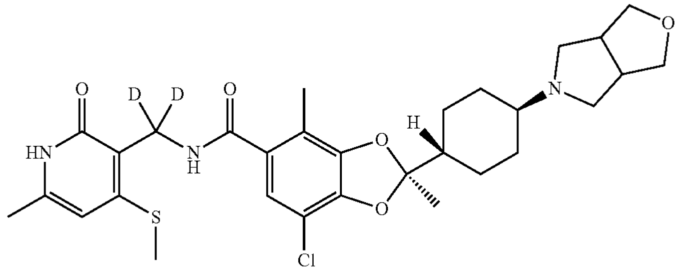
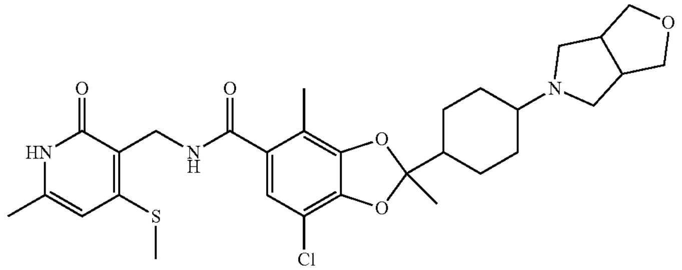
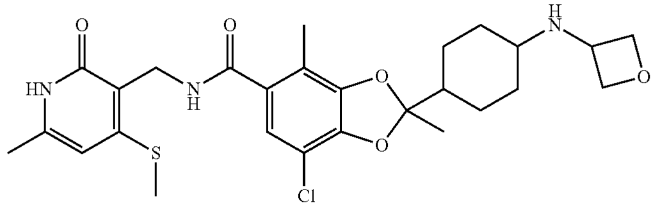
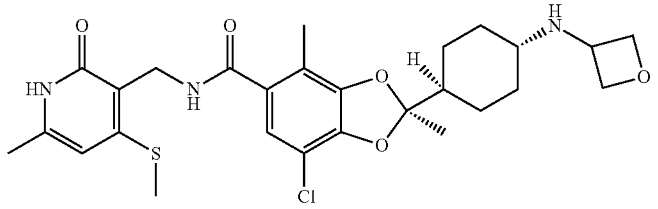
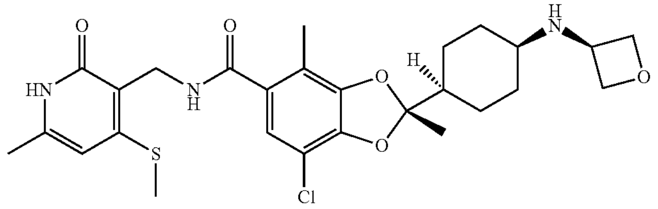

-continued

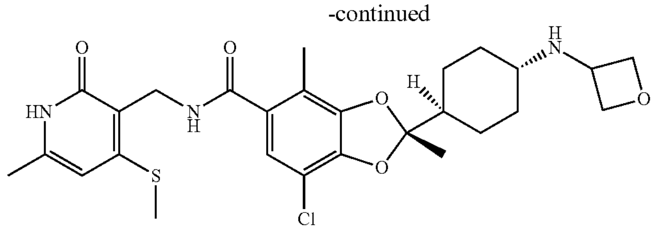

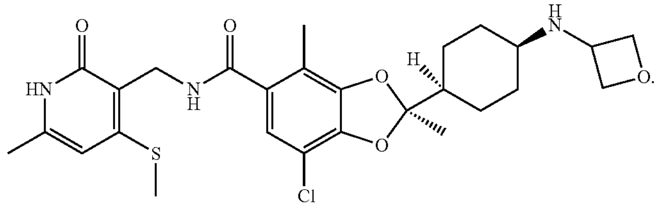

The present disclosure further relates to a pharmaceutical composition comprising the compound, or the stereoisomer, pharmaceutically acceptable salt, solvate, and eutectic or deuterated compound thereof of the present disclosure, and a pharmaceutically acceptable adjuvant and/or carrier.

The present disclosure further relates to the use of the compound, or the stereoisomer, pharmaceutically acceptable salt, solvate, and eutectic or deuterated compound thereof, or the pharmaceutical composition of the present disclosure in the preparation of a medication for treating an EZH2-mediated disease, wherein the EZH2-mediated disease is a tumor or an autoimmune disease.

The present disclosure further relates to a method for treating an EZH2-mediated disease, which comprises administering the compound, or the stereoisomer, pharmaceutically acceptable salt, solvate, and eutectic or deuterated compound thereof, or the pharmaceutical composition of the present disclosure, wherein the EZH2-mediated disease is a tumor or an autoimmune disease.

Synthetic Route

Patent document WO 2019204490 A1 introduces a method for preparing a class of EZH2 inhibitors, and those skilled in the art would have been able to prepare the compounds of the present disclosure by means of combining the document and known organic synthesis techniques, wherein the starting materials used therein are commercially available chemicals and (or) compounds described in chemical documents. "Commercially available chemicals" are obtained from regular commercial sources, and suppliers include: Titan Technology Co., Ltd., Energy Chemical Co., Ltd., Shanghai Demo Co., Ltd., Chengdu Kelong Chemical Co., Ltd., Accela ChemBio Co., Ltd., PharmaBlock Sciences (Nanjing), Inc., WuXi Apptec Co., Ltd., J&K Scientific and the like.

References and monographs in the art introduce in detail the synthesis of reactants that can be used to prepare the compounds described herein, or provide articles describing the preparation method for reference. The references and monographs include: "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992; Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and similar reactants can be selectively identified by the indexes of known chemicals prepared by the Chemical Abstracts Service of the American Chemical Society, wherein the indexes are available in most public libraries or university libraries and online. Chemicals that are known but not commercially available in the catalog are optionally prepared by custom chemical synthesis plants, wherein many of standard chemical supply plants (for example, those listed above) provide custom synthesis services. Reference document for the preparation and selection of the pharmaceutically acceptable salts of the compounds described herein is P. H. Stahl & C. G. Wermuth "Handbook of Pharmaceutical Salts", Verlag Helvetica Chimica Acta, Zurich, 2002.

Term

Unless otherwise specified, the terms of the present disclosure have the following meanings.

The term "halogen" herein refers to F, Cl, Br, I, or isotopes thereof.

The term "halo" or "substituted with halogen" refers to being substituted with one or more groups selected from F, Cl, Br, I, or isotopes thereof, wherein the upper limit of the number of halogen substituents is equal to the sum of the number of hydrogens that can be substituted in the group to be substituted. Without particular limitation, the number of halogen substituents is any integer between 1 and the upper limit, and when the number of halogen substituents is greater than 1, the group to be substituted can be substituted with the same or different halogen.

The term "alkyl" refers to a monovalent straight or branched saturated aliphatic hydrocarbon group, and non-limiting examples of alkyl include methyl, ethyl, n-propyl, isopropyl, n-butyl, sec-butyl, neobutyl, tert-butyl, n-pentyl, isopentyl, neopentyl, n-hexyl and various branched isomers thereof. The alkyl can be further substituted with any substituent.

The term "deuterated" refers to the case where a hydrogen atom on alkyl, cycloalkyl, alkylene, aryl, heteroaryl, alkenyl, alkynyl and other groups is substituted with at least one isotope deuterium, wherein the upper limit of the number of deuterium substituents is equal to the sum of the number of hydrogens that can be substituted in the group to be substituted. Without particular limitation, the number of deuterium substituents is any integer between 1 and the upper limit, preferably 1-20 deuterium atoms, more preferably 1-10 deuterium atoms, more preferably 1-6 deuterium atoms, further preferably 1-3 deuterium atoms.

The term "cycloalkyl" refers to a monovalent saturated or unsaturated non-aromatic carbocyclic hydrocarbon group and can be a monocyclic ring, a bicyclic ring, a spiro ring, a bridged ring or a fused ring, and non-limiting examples of cycloalkyl include cyclopropyl, cyclobutyl, cyclopentyl, cyclohexyl, cycloheptyl, cyclopentenyl,

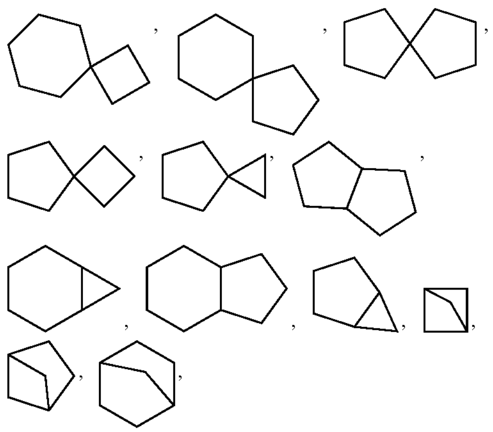

etc. The cycloalkyl can be optionally further substituted with any substituent.

The bicyclic ring of the present disclosure includes a spiro ring, a bridged ring or a fused ring.

The term "heterocycloalkyl" refers to a substituted or unsubstituted, saturated or unsaturated non-aromatic ring. Unless otherwise specified, the heterocycloalkyl contains 1 to 3 heteroatoms selected from N, O, P, Si or S, and may be a monocyclic ring, a bicyclic ring, a bridged ring, a fused ring or a spiro ring. Unless otherwise specified, the heterocycloalkyl is 3- to 12-membered heterocycle, more preferably 4- to 12-membered heterocycle, and more preferably 4- to 10-membered heterocycle. The optionally substituted N, S and P in the ring of heterocyclyl may be oxidized to various oxidation states. Non-limiting examples include heterocyclopropyl, oxecyclopropyl, thiacyclopropyl, azacyclobutyl, azacyclopentyl, piperidine, oxetanyl, oxacyclopentyl, oxacyclohexyl, thiacyclobutyl, pyrrolidinyl, pyrazolidinyl, tetrahydrofuryl, tetrahydrothienyl, azaadamantyl, oxaspiro[3,3]heptanyl,

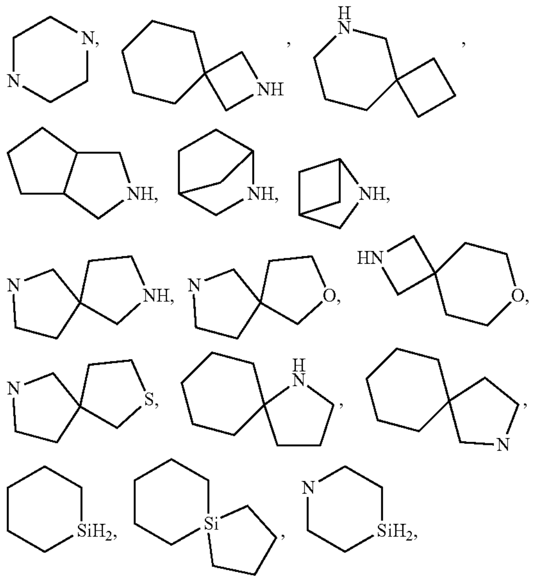

etc. The heterocycloalkyl can be optionally further substituted with any substituent.

The term "aryl" refers to a substituted or unsubstituted aromatic 5- to 15-membered carbocycle, including monocyclic aryl and fused aryl, preferably a 5- to 10-membered aromatic ring, further preferably a 5- to 8-membered aromatic ring; and non-limiting examples of aryl include phenyl, naphthyl, anthryl, phenanthryl, etc. The aryl ring can be fused to a heteroaryl, heterocycloalkyl or cycloalkyl ring, wherein the ring connected to the parent structure is an aryl ring, and non-limiting examples include

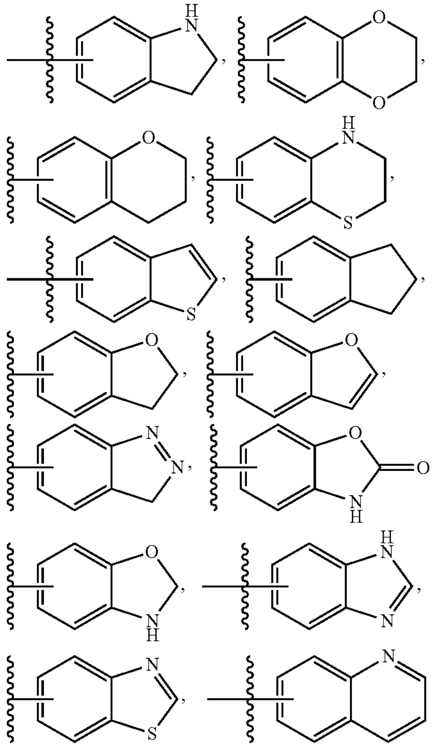

and

-continued

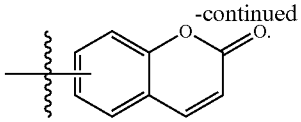

The aryl can be optionally further substituted with any substituent.

The term “heteroaryl” refers to a substituted or unsubstituted 5- to 15-membered aromatic ring containing 1 to 5 heteroatoms selected from N, O, P, Si or S and various oxidized forms of the heteroatoms, preferably a 5- to 10-membered heteroaromatic ring, further preferably a 5- to 8-membered heteroaromatic ring. Non-limiting examples of heteroaryl include, but are not limited to, furyl, oxazolyl, furyl, thienyl, N-alkylpyrrolyl, pyrazinyl, pyridazinyl, piperidyl, morpholine, thiomorpholine, 1,3-dithiane, benzimidazole, piperidyl,

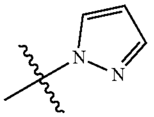 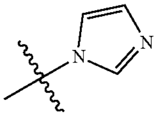 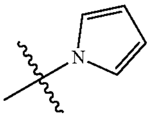

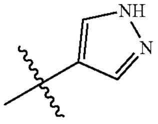 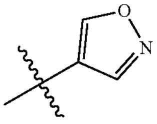 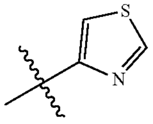

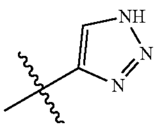 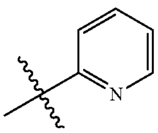 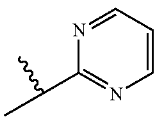.

The heteroaryl ring can be fused to an aryl, heterocycloalkyl or cycloalkyl ring, wherein the ring connected to the parent structure is a heteroaryl ring, and non-limiting examples include

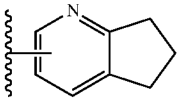, 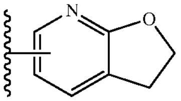,

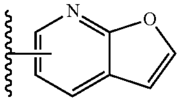, 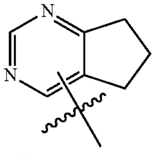,

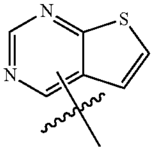, 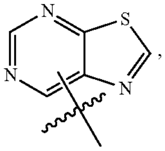,

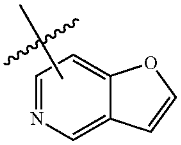 and 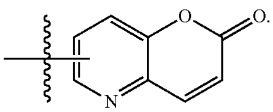

The heteroaryl can be optionally further substituted with any substituent.

The term “alkynyl” refers to a linear or branched monovalent unsaturated hydrocarbon group containing one or more carbon-carbon triple bonds. Unless otherwise specified, the alkynyl contains 2-6 carbon atoms, preferably contains 2-4 carbon atoms, and non-limiting examples of the alkynyl are ethynyl, propynyl, propargyl, etc.

The term “alkenyl” refers to a linear or branched monovalent unsaturated hydrocarbon group containing one or more carbon-carbon double bonds. Unless otherwise specified, the alkenyl contains 2-6 carbon atoms, preferably contains 2-4 carbon atoms, and non-limiting examples of the alkenyl are ethenyl, propenyl, allyl, 2-butenyl, 1-butenyl etc.

The term “alkoxy” or “alkyloxy” refers to —O-alkyl. Non-limiting examples of the alkoxy or alkyloxy include methoxy, ethoxy, n-propoxy, isopropoxy, n-butoxy, secbutoxy, tert-butoxy, n-pentoxy, n-hexyloxy, cyclopropoxy, cyclobutoxy, etc.

The term “haloalkoxy” refers to —O-haloalkyl. Non-limiting examples of haloalkoxy include monofluoromethoxy, difluoromethoxy, trifluoromethoxy, difluoroethyloxy, etc.

The term “alkylamino” or “alkamino” refers to amino substituted with one or two alkyl, and is also written as —N-$(alkyl)_2$ or —NH-alkyl, wherein the latter is also known as monoalkylamino. Non-limiting examples of alkylamino or alkamino include dimethylamino, monomethylamino, diethylamino, monoethylamino, etc.

The term “optional” or “optionally” refers to that the event or circumstance subsequently described may but not necessarily occur, and the description includes the occasions where the events or circumstances occur or do not occur. For example, “alkyl optionally substituted with F” means that an alkyl may but not necessarily be substituted by F, and the description includes the case where the alkyl is substituted with F and the case where the alkyl is not substituted with F.

The term “pharmaceutically acceptable salt” refers to a salt of the compound of the present disclosure, which salt maintains the biological effectiveness and characteristics of a free acid or a free base and is obtained by reacting the free acid with a non-toxic inorganic base or organic base, or reacting the free base with a non-toxic inorganic acid or organic acid.

The term “pharmaceutical composition” represents a mixture of one or more compounds described herein or the stereoisomers, solvates, pharmaceutically acceptable salts or eutectic compounds thereof and other components comprising physiologically/pharmaceutically acceptable carriers and/or excipients.

The term “carrier” refers to: a system that does not cause significant irritation to the organism and does not eliminate the biological activity and characteristics of the administered compound, and can change the way the drug enters the human body and the distribution of the drug in the body, control the release rate of the drug and delivery the drug to targeted organs. Non-limiting examples of the carrier include microcapsule, microsphere, nanoparticle, liposome, etc.

The term “excipient” refers to: a substance that is not a therapeutic agent per se, but used as a diluent, adjuvant, adhesive and/or vehicle for addition to a pharmaceutical composition, thereby improving the disposal or storage properties thereof, or allowing to or promoting the formation of a compound or a pharmaceutical composition into a unit dosage form for administration. As is known to those skilled in the art, a pharmaceutically acceptable excipient can provide various functions and can be described as a wetting agent, a buffer, a suspending agent, a lubricant, an emulsifier, a disintegrating agent, an absorbent, a preservative, a surfactant, a colorant, a flavoring agent and a sweetening agent. Examples of pharmaceutically acceptable excipients include, but are not limited to: (1) sugars, such as lactose, glucose and sucrose; (2) starch, such as corn starch and potato starch; (3) cellulose and derivatives thereof, such as sodium carboxymethyl cellulose, ethyl cellulose, cellulose acetate, hydroxypropyl methylcellulose, hydroxypropyl cellulose, microcrystalline cellulose and croscarmellose (such as croscarmellose sodium); (4) tragacanth powder; (5) malt; (6) gelatin; (7) talc; (8) excipients, such as cocoa butter or suppository wax; (9) oils, such as peanut oil, cottonseed oil, safflower oil, sesame oil, olive oil, corn oil and soybean oil; (10) diols, such as propylene glycol; (11) polyols, such as glycerol, sorbitol, mannitol and polyethylene glycol; (12) esters, such as ethyl oleate and ethyl laurate; (13) agar; (14) buffers, such as magnesium hydroxide and aluminum hydroxide; (15) alginic acid; (16) pyrogen-free water; (17) isotonic saline; (18) Ringer's solution; (19) ethanol; (20) pH buffered solution; (21) polyester, polycarbonate and/or polyanhydride; and (22) other non-toxic compatible substances used in a pharmaceutical preparation.

The term "stereoisomer" refers to an isomer produced as a result of different spatial arrangement of atoms in molecules, including cis-trans isomers, enantiomers and conformational isomers.

The term "solvate" refers to a substance formed by the compound of the present disclosure or the salt thereof and a stoichiometric or non-stoichiometric solvent bound by intermolecular non-covalent forces. When the solvent is water, the solvate is a hydrate.

The term "eutectic compound" refers to a crystal formed by the combination of active pharmaceutical ingredient (API) and co-crystal former (CCF) under the action of hydrogen bonds or other non-covalent bonds. The pure state of API and CCF are both solid at room temperature, and there is a fixed stoichiometric ratio between various components. The eutectic compound is a multi-component crystal, which includes both a binary eutectic compound formed between two neutral solids and a multi-element eutectic compound formed between a neutral solid and a salt or solvate.

DETAILED DESCRIPTION OF EMBODIMENTS

The content of the present disclosure is described in detail with the following examples. If a specific condition is not indicated in the examples, a conventional condition is used in an experimental method. The listed examples are intended to better illustrate the content of the present disclosure, but should not be construed as limiting the content of the present disclosure. According to the above-mentioned content of the disclosure, those skilled in the art can make unsubstantial modifications and adjustments to the embodiments, which still fall within the scope of protection of the present disclosure.

Test Method

The structures of the compounds are determined by nuclear magnetic resonance (NMR) or (and) mass spectrometry (MS). The NMR shift (δ) is given in the unit of 10-6 (ppm). NMR is determined with Bruker Avance III 400 and Bruker Avance 300; the solvent for determination is deuterated dimethyl sulfoxide (DMSO-d6), deuterated chloroform ($CDCl_3$) and deuterated methanol ($CD_3OD$); and the internal standard is tetramethylsilane (TMS).

MS is measured with (Agilent 6120B(ESI) and Agilent 6120B(APCI));

HPLC is measured with Agilent 1260DAD high pressure liquid chromatography (Zorbax SB-C18 100×4.6 mm, 3.5 μM);

Yantai Huanghai HSGF254 or Qingdao GF254 silica gel plate is used as a thin layer chromatography silica plate, and the silica gel plate for the thin layer chromatography (TLC) is of the specification of 0.15 mm-0.20 mm, and the specification when separating and purifying a product by thin layer chromatography is 0.4 mm-0.5 mm.

For the column chromatography, Yantai Huanghai silica gel of 200-300 mesh silica gel is generally used as a carrier.

Intermediate 1 and Intermediate 2 methyl 7-chloro-2,4-dimethyl-2-(4-oxocyclohexyl) benzo[d][1,3]dioxole-5-carboxylate

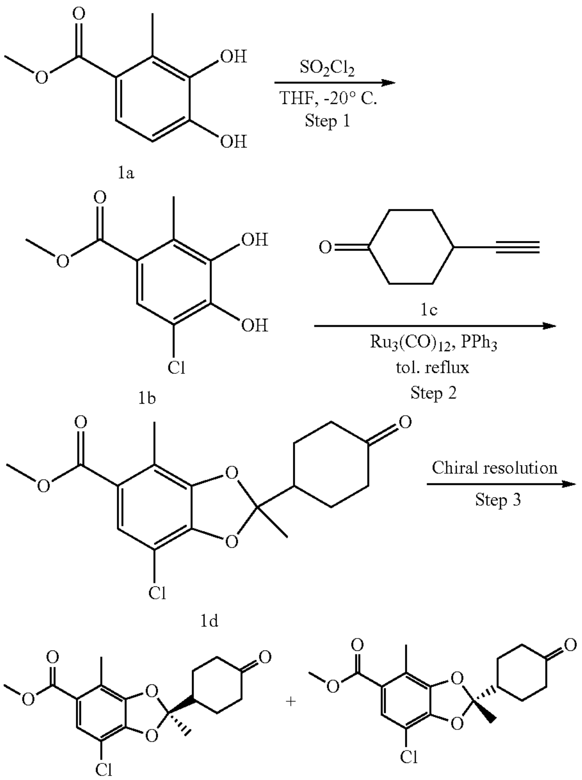

1a
1b
1c
1d
+

Intermediate 1 and intermediate 2

Step 1:

Methyl 3,4-dihydroxy-2-methylbenzoate (5.11 g, 27.9 mmol) was dissolved in tetrahydrofuran (200 mL). At −20° C., sulfonyl chloride (2.45 mL, 30.6 mmol) was slowly added dropwise, and after the dropwise addition was completed, the mixture was stirred at −20° C. for another 3 h. After TLC showed that the reaction was completed, the reaction was quenched with a saturated ammonium chloride solution (50 mL), and the residue was extracted with ethyl acetate (25 mL×3). The organic phase was back-flushed with saturated brine (25 mL), dried over anhydrous sodium sulfate and concentrated under reduced pressure, and then the residue was separated by column chromatography to obtain compound 1b (4.12 g, 68%).

LC-MS (ESI): m/z=217.1 $[M+H]^+$.

Step 2:

Methyl 5-chloro-3,4-dihydroxy-2-methylbenzoate (1.2 g, 5.53 mmol), triruthenium dodecacarbonyl (176 mg, 0.28 mmol) and triphenylphosphine (145 mg, 0.55 mmol) were successively dissolved in toluene (8.1 mL). Under nitrogen protection, the reaction was heated to reflux for half an hour. 4-ethynylcyclohexyl-1-one (1.34 g, 11 mmol) was dissolved in toluene (17 mL) and added to the reaction system, and the mixture was refluxed and stirred for 23 h. After the reaction was completed, the reaction system was cooled to room temperature and concentrated under reduced pressure, and then the residue was separated by column chromatography to obtain compound 1d (1.33 g, 70%).

LC-MS (ESI): m/z=361.1 $[M+H]^+$.

Step 3:

Compound 1d was separated by chiral preparative HPLC to obtain intermediate 1 and intermediate 2. Chiral preparative separation conditions: preparation instrument: Waters UPCC with PDA Detector, preparative column: Chiralpak AY-3 150×4.6 mm I.D., 3 um, mobile phase system: A: $CO_2$; B: isopropanol (0.05% DEA), retention time: intermediate 1:2.871 min, and intermediate 2:2.904 min.

LC-MS (ESI): m/z=361.1 $[M+H]^+$.

Intermediate 3 and Intermediate 4 methyl 7-chloro-2,4-dimethyl-2-(piperidin-4-yl) benzo[d][1,3]dioxole-5-carboxylate hydrochloride

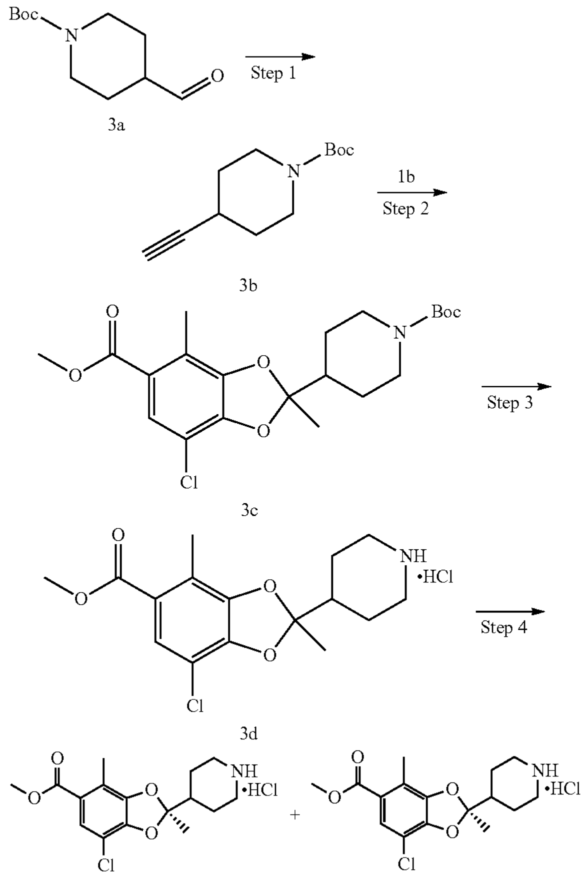

3a

3b

3c

3d

Intermediate 3 and intermediate 4

Step 1:

Compound 3a (50.0 g, 234.4 mmol) was dissolved in methanol (400 mL). At 0° C., a solution of dimethyl(1-diazo-2-oxopropyl)phosphonate (45.0 g) in methanol (400 mL) was added dropwise. After the addition was completed, the mixture was stirred at room temperature overnight. The reaction liquid was filtered, and the filtrate was concentrated under reduced pressure, dissolved with ethyl acetate (2.0 L) and stirred for 10 minutes. After filtration, the filter cake was washed twice with ethyl acetate, the filtrate was combined and concentrated under reduced pressure, and then the residue was separated by column chromatography to obtain compound 3b (47 g, 95.8%).

Step 2:

3b (82 g, 378.5 mmol) was dissolved in toluene (1.5 L), 1b (158.4 g, 757.0 mmol) was added, the mixture was subjected to nitrogen replacement 3 times, and $PPh_3$ (9.9 g, 37.9 mmol) and triruthenium dodecacarbonyl (12.1 g, 18.9 mmol) were added. After the addition was completed, the resulting mixture was subjected to nitrogen replacement again 3 times, warmed to 90° C. and stirred overnight. After the reaction was cooled to room temperature, the reaction liquid was concentrated under reduced pressure, and then the residue was separated and purified by column chromatography to obtain compound 3c (33.2 g, 20.6%).

$^1H$ NMR (400 MHz, DMSO-d6) δ 7.45 (s, 1H), 3.79 (s, 3H), 7.74-7.65 (m, 2H), 2.32 (s, 3H), 2.16-2.10 (m, 1H), 1.75 (d, 2H), 1.65 (s, 3H), 1.38 (s, 9H), 1.25-1.16 (m, 4H).

Step 3:

Compound 3c (33.2 g, 78.0 mmol) was placed in a 1 L single-necked flask, hydrochloric acid-1,4-dioxane (4M, 400 mL) was added, and the mixture was stirred at room temperature for 3 hours. The reaction liquid was concentrated under reduced pressure, and the residue was slurried and purified with EA/EtOH=10/1 to obtain the compound racemate 3d (24.8 g, 87.8%).

$^1H$ NMR (400 MHz, DMSO-d6) δ 7.45 (s, 1H), 3.79 (s, 3H), 3.11 (d, 2H), 2.60 (t, 2H), 2.32 (s, 3H), 2.14-2.08 (m, 1H), 1.77-1.74 (m, 2H), 1.66 (s, 3H), 1.42-1.33 (m, 2H).

LC-MS (ESI): m/z=326.2$[M+H]^+$.

Step 4:

Compound 3d was separated by chiral preparative HPLC to obtain intermediate 3 and intermediate 4. Chiral preparative separation conditions: preparation instrument: Waters UPC2 analytical SFC (SFC-H), preparative column: Chiral-Cel OX, 100×4.6 mm I.D., 3 μm, mobile phase system: A: $CO_2$, B: ethanol (0.05% DEA), retention time: intermediate 3:3.882 min, intermediate 4:4.229 min.

Intermediate 5

3-(aminomethyl)-6-methyl-4-(methylthio)pyridin-2 (1H)-one hydrochloride

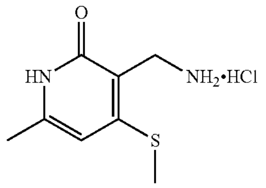

Intermediate 5 was prepared with reference to the method in patent WO 2019094552.

Intermediate 6

3-(aminomethyl-d2)-6-methyl-4-(methylthio)pyridin-2(1H)-one hydrochloride (intermediate 6)

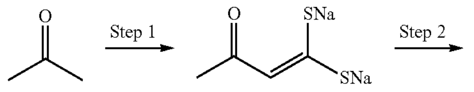

6a 6b

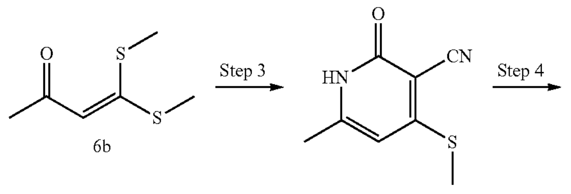

6b 6d

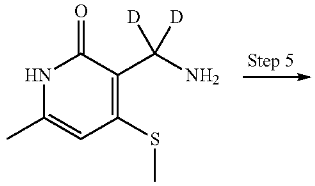

6e

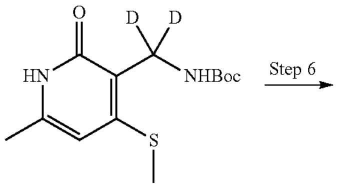

6f

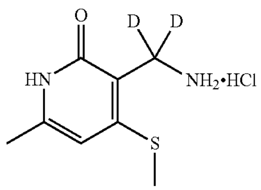

Intermediate 6

Step 1:

To sodium tert-butoxide (16.6 g, 172 mmol) was added 30 mL of toluene, and the mixture was subjected to nitrogen replacement three times. At 0° C., acetone (5.00 g, 86 mmol) was added dropwise. After the dropwise addition was completed, the temperature was controlled at 0-5° C., and carbon disulfide (6.6 g, 86 mmol) was slowly added dropwise. After the dropwise addition was completed, the temperature was controlled at 0° C., and the mixture was reacted for 4 hours. After the reaction was completed, the reaction liquid was filtered, and the filter cake was dried to obtain compound 6b (12.8 g, crude), which was directly used in the next step without further purification.

Step 2:

Compound 6b (12.8 g, 72 mmol) was dissolved in 100 ml of methanol. Iodomethane (20.5 g, 142 mmol) was added dropwise slowly. After the dropwise addition was completed, the mixture was warmed to 70° C. and reacted for 2 hours. The reaction was cooled to room temperature and then concentrated under reduced pressure to remove methanol. To the residue was added 200 mL of water, and the mixture was extracted with ethyl acetate (100 mL×2). The combined organic phase was dried over anhydrous sodium sulfate, filtered and concentrated under reduced pressure. The resulting solution was crystallized with petroleum ether to obtain compound 6c (5.3 g, 45%).

LC-MS (ESI): m/z=163.1[M+H]$^+$.

Step 3:

Compound 6c (5.3 g, 32.7 mmol) and cyanoacetamide (2.75 g, 32.7 mmol) were dissolved in 50 mL of tert-butanol. Then potassium tert-butoxide (4.03 g, 36.0 mmol) was added. After the addition, the mixture was warmed to 80° C. and stirred for 12 hours. After the reaction was completed, 20 mL of water was added. The reaction liquid was adjusted to pH=5-6 with 1N hydrochloric acid, stirred for 30 minutes and filtered. The filter cake was dried to obtain compound 6d (4.6 g, 78%).

LC-MS (ESI): m/z=181.1[M+H]$^+$.

Step 4:

Compound 6d (1.0 g, 5.5 mmol) was dissolved in tetrahydrofuran (10 mL). Under nitrogen protection, the mixture was cooled to 0° C. Lithium aluminum tetradeuterium (236.0 mg, 5.6 mmol) was added. Upon completion of the addition, the mixture was stirred for 30 minutes. The reaction was quenched by slowly adding a 10% aqueous sodium hydroxide solution (1 mL) dropwise. The reaction liquid was filtered, and the filtrate was concentrated to obtain compound 6e (0.9 g).

LC-MS (ESI): m/z=187.1[M+H]$^+$.

Step 5:

Compound 6e (0.9 g, 4.8 mmol) was dissolved in tetrahydrofuran (10 mL). Triethylamine (0.97 g, 9.6 mmol) and $(Boc)_2O$ (1.26 g, 5.8 mmol) were successively added. Upon completion of the addition, the mixture was reacted at room temperature for 15 hours. After the reaction was completed, 10 mL of water was added. The residue was extracted with ethyl acetate (50 mL×2). The organic phase was dried over anhydrous sodium sulfate, filtered and concentrated under reduced pressure. The residue was separated to obtain compound 6f (0.9 g, 65%).

LC-MS (ESI): m/z=287.1[M+H]$^+$.

Step 6:

Compound 6f (0.9 g, 3.1 mmol) was dissolved in dichloromethane (5 mL). A solution of hydrogen chloride in dioxane (5 mL) was added. Upon completion of the addition, the mixture was stirred at room temperature for 5 hours. After the reaction was completed, the mixture was filtered, and the filter cake was dried to obtain intermediate 6 (310 mg, 45%).

LC-MS (ESI): m/z=187.1[M+H]$^+$.

$^1$H NMR (400 MHz, $D_2O$) δ 6.49 (s, 1H), 2.63 (s, 3H), 2.40 (s, 3H).

Embodiment 1

7-chloro-2-(4-(3-(dimethylamino)azetidin-1-yl)cyclohexyl)-2,4-dimethyl-N-((6-methyl-4-(methylthio)-2-oxo-1,2-dihydropyridin-3-yl)methyl)benzo[d][1,3]dioxole-5-carboxamide (compound 1)

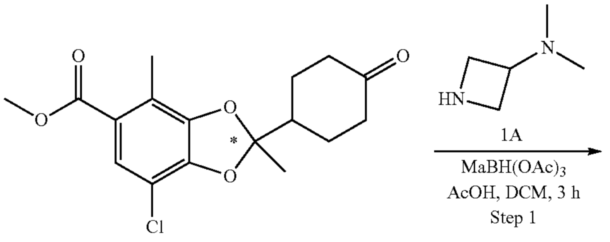

Intermediate 2

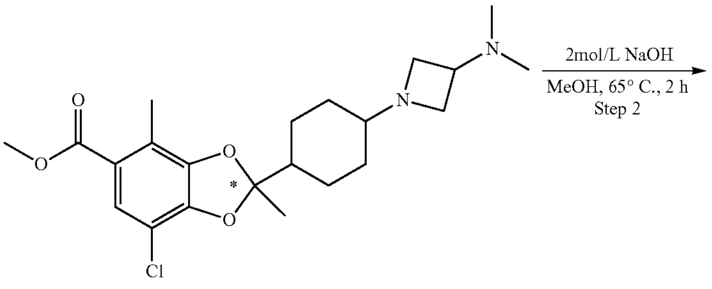

1B

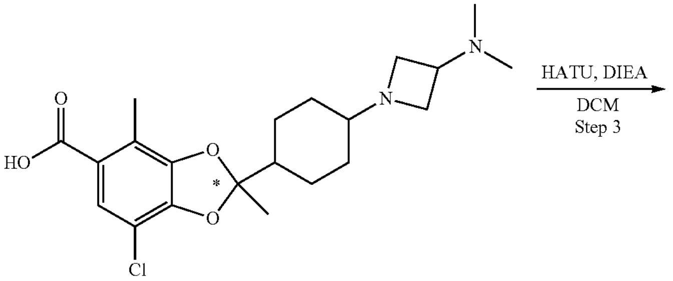

1C

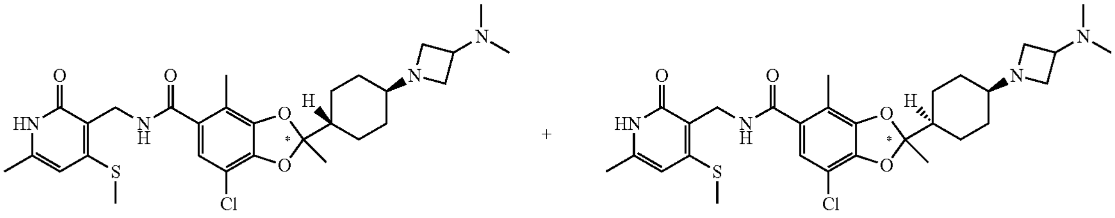

Compound 1

Step 1:

At room temperature, to intermediate 2 (0.2 g, 0.59 mmol) were successively added dichloromethane (4 mL), N,N-dimethylazetidinamine (0.14 g, 0.77 mmol) and two drops of glacial acetic acid, and the mixture was stirred for 1 h. Sodium triacetylborohydride (0.25 g, 1.2 mmol) was added, and the mixture was stirred at room temperature for 2 h and extracted with water and dichloromethane. The organic phase was washed with saturated brine (20 mL), dried over anhydrous sodium sulfate and concentrated under reduced pressure, and then the residue was separated by column chromatography to obtain 1B (0.22 g, 88%).

LC-MS (ESI): m/z=423.3 $[M+H]^+$.

Step 2:

At room temperature, to 1B (0.22 g, 0.52 mmol) were successively added methanol (10 mL) and 2 mol/L sodium hydroxide (2.5 mL), and the mixture was stirred at 65° C. for 2 h. The reaction was cooled to room temperature, adjusted to pH 5-6 with 3N hydrochloric acid and extracted with ethyl acetate. The organic phase was dried over anhydrous sodium sulfate and concentrated under reduced pressure to obtain crude product 1C (0.2 g, 94%).

LC-MS (ESI): m/z=409.3 $[M+H]^+$.

Step 3:

At room temperature, to 1C (0.2 g, 0.49 mmol) were successively added intermediate 5 (0.11 g, 0.49 mmol), DCM (4 mL), HATU (2-(7-azabenzotriazol)-N,N,N',N'-tetramethyluronium hexafluorophosphate, 0.19 g, 0.49 mmol) and N,N-diisopropylethylamin (0.2 g, 1.59 mmol), and the mixture was stirred at room temperature for 2 hours, diluted by adding water and extracted with ethyl acetate. The organic phase was washed with saturated brine (20 mL), dried over anhydrous sodium sulfate and concentrated under reduced pressure, and then the residue was separated and purified by preparative HPLC to obtain isomer 1 (0.04 g, 14%) of compound 1 and isomer 2 (0.04 g, 14%) of compound 1.

Preparative HPLC separation methods: 1. Instrument: waters 2767 (preparative liquid phase chromatographic instrument); chromatographic column: SunFire@ Prep C18 (19 mm×250 mm). 2. The sample was dissolved in DMF and filtered with a 0.45 μm filter to prepare a sample solution. 3. Preparative chromatography conditions: a. composition of mobile phases A and B: mobile phase A: acetonitrile; mobile phase B: water (containing 1% TFA); b. gradient elution, mobile phase A: 5% to 50%; c. flow rate: 12 ml/min; d. elution time: 20 min;

retention time for isomer 1:14.8 min;

$^1$H NMR (400 MHz, $CDCl_3$) δ12.32 (s, 1H), 7.16-7.13 (t, 1H), 6.90 (s, 1H), 6.02 (s, 1H), 4.60-4.59 (d, 2H), 3.56 (s, 2H), 2.88-2.86 (m, 2H), 2.48 (s, 3H), 2.30 (s, 3H), 2.26 (s, 3H), 2.10 (s, 6H), 1.93-1.86 (m, 5H), 1.81-1.78 (m, 1H), 1.59 (s, 3H), 1.26-1.16 (m, 3H), 1.09-0.99 (m, 2H).

LC-MS (ESI): m/z=575.3 $[M+H]^+$.

retention time for isomer 2:15.2 min;

$^1$H NMR (400 MHz, $CDCl_3$) δ12.36 (s, 1H), 7.16-7.13 (t, 1H), 6.89 (s, 1H), 6.02 (s, 1H), 4.60-4.59 (d, 2H), 3.44 (s, 2H), 2.78-2.76 (m, 2H), 2.48 (s, 3H), 2.30 (s, 3H), 2.27 (s, 3H), 2.13 (s, 6H), 1.81-1.71 (m, 5H), 1.59 (s, 3H), 1.58-1.53 (m, 3H), 1.30-0.26 (m, 3H).

LC-MS (ESI): m/z=575.3 $[M+H]^+$.

Embodiment 2

7-chloro-2-(4-(3-cyanoazetidin-1-yl)cyclohexyl)-2,4-dimethyl-N-((6-methyl-4-(methylthio)-2-oxo-1,2-dihydropyridin-3-yl)methyl)benzo[d][1,3]dioxole-5-carboxamide (compound 2)

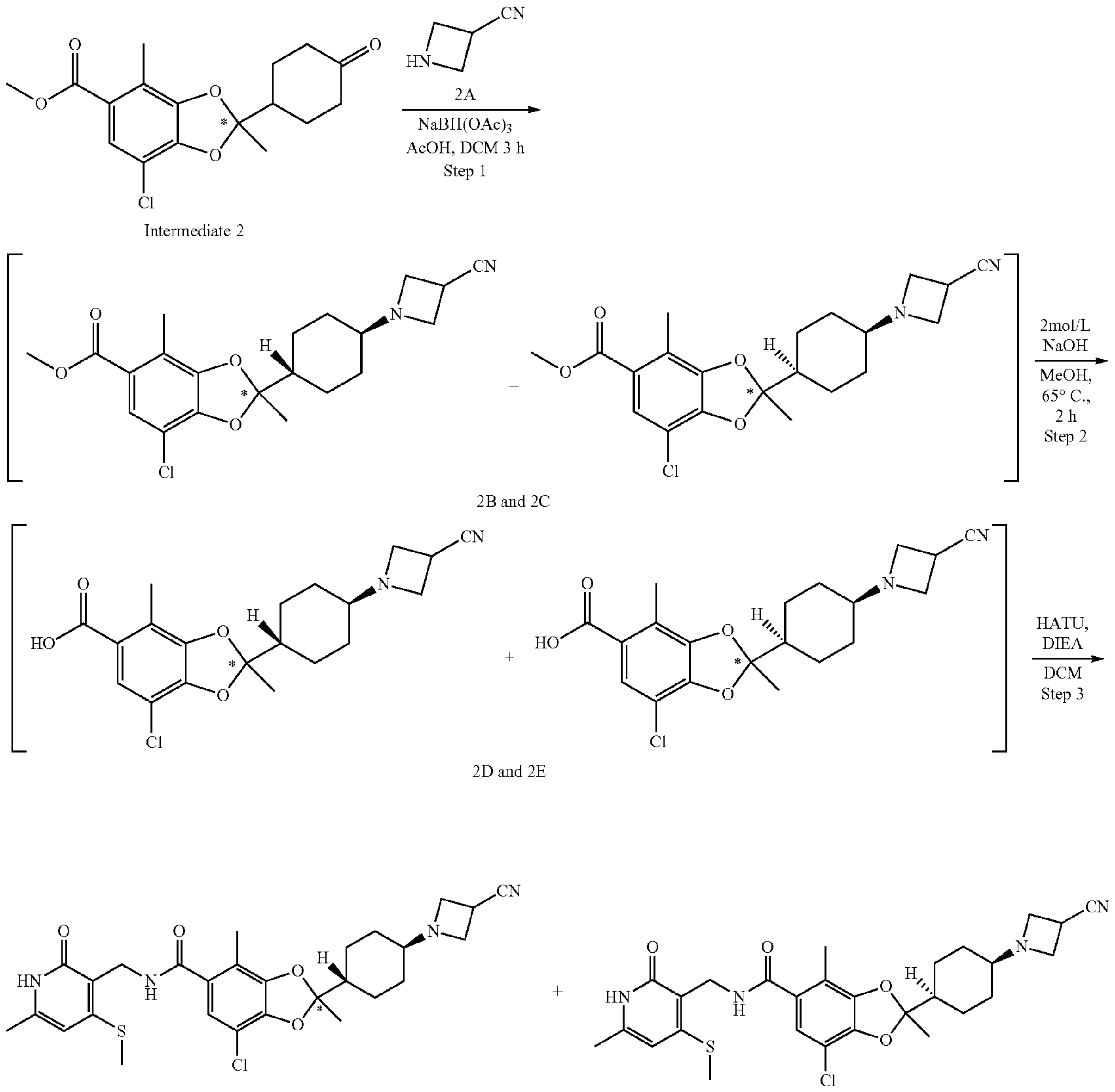

Intermediate 2

2B and 2C 2D and 2E

Compound 2

Step 1:

At room temperature, to intermediate 2 (0.22 g, 0.65 mmol) were successively added dichloromethane (4 mL), 3-cyanoazetidinamine (0.1 g, 0.84 mmol) and two drops of glacial acetic acid, and the mixture was stirred for 1 h. Sodium triacetylborohydride (0.28 g, 1.3 mmol) was added, and the mixture was stirred at room temperature for 2 h and extracted with water and dichloromethane. The organic phase was washed with saturated brine (20 mL), dried over anhydrous sodium sulfate and concentrated under reduced pressure, and then the residue was purified by column chromatography to obtain 2B (83 mg, 31.7%) and 2C (90 mg, 34.3%) (eluent: ethyl acetate/petroleum ether=0%-60% to obtain 2B, and ethyl acetate/petroleum ether=80% to obtain 2C).

LC-MS (ESI): m/z=405.2 $[M+H]^+$.

Step 2:

At room temperature, to 2B (0.083 g, 0.2 mmol) were successively added methanol (5 mL) and 2 mol/L sodium hydroxide (1.2 mL), and the mixture was stirred at 65° C. for 2 h. The reaction was adjusted to pH 5-6 with 3N hydrochloric acid and extracted with ethyl acetate. The organic phase was dried over anhydrous sodium sulfate and concentrated under reduced pressure to obtain crude product 2D (0.08 g, 100%).

LC-MS (ESI): m/z=391.2 $[M+H]^+$.

At room temperature, to 2C (0.09 g, 0.2 mmol) were successively added methanol (5 mL) and 2 mol/L sodium hydroxide (1.2 mL), and the mixture was stirred at 65° C. for 2 h. The reaction was adjusted to pH 5-6 with 3N hydrochloric acid, extracted with ethyl acetate, dried over anhydrous sodium sulfate and concentrated under reduced pressure to obtain 2E (0.085 g, 98%).

LC-MS (ESI): m/z=391.2 $[M+H]^+$.

Step 3:

At room temperature, to 2D (0.08 g, 0.2 mmol) were successively added intermediate 5 (0.05 g, 0.22 mmol), DCM (4 mL), HATU (0.086 g, 0.22 mmol) and N,N-diisopropylethylamin (0.08 g, 0.66 mmol). The mixture was stirred at room temperature for 2 hours, diluted by adding water and extracted with ethyl acetate. The organic phase was washed with saturated brine (20 mL), dried over anhydrous sodium sulfate and concentrated under reduced pressure, and then the residue was separated and purified by column chromatography to obtain isomer 1 (0.04 g, 35%) of compound 2.

$^1H$ NMR (400 MHz, $CDCl_3$) δ 12.26 (s, 1H), 7.08-7.06 (t, 1H), 6.89 (s, 1H), 6.03 (s, 1H), 4.59-4.58 (d, 2H), 3.51 (s, 2H), 3.19-3.17 (m, 2H), 2.48 (s, 3H), 2.32 (s, 3H), 2.26 (s, 3H), 1.82-1.78 (m, 1H), 1.66-1.63 (m, 3H), 1.59 (s, 3H), 1.57-1.49 (m, 4H), 1.34-1.27 (m, 3H).

LC-MS (ESI): m/z=557.2 $[M+H]^+$.

At room temperature, to 2E (0.085 g, 0.218 mmol) were successively added intermediate 5 (0.056 g, 0.24 mmol), DCM (4 mL), HATU (0.09 g, 0.24 mmol) and N,N-diisopropylethylamin (0.09 g, 0.72 mmol). The mixture was stirred at room temperature for 2 hours, diluted by adding water and extracted with ethyl acetate. The organic phase was washed with saturated brine (20 mL), dried over anhydrous sodium sulfate and concentrated under reduced pressure, and then the residue was separated and purified by column chromatography to obtain isomer 2 (0.04 g, 30%) of compound 2.

$^1H$ NMR (400 MHz, $CDCl_3$) δ 12.09 (s, 1H), 7.06-7.04 (t, 1H), 6.90 (s, 1H), 6.04 (s, 1H), 4.59-4.57 (d, 2H), 3.61-3.60 (m, 2H), 3.30-3.27 (m, 2H), 2.48 (s, 3H), 2.32 (s, 3H), 2.26 (s, 3H), 2.03-2.00 (m, 1H), 1.93-1.90 (m, 2H), 1.81-1.78 (m, 3H), 1.60 (s, 3H), 1.26-1.17 (m, 3H), 1.02-0.93 (m, 2H).

LC-MS (ESI): m/z=557.2 $[M+H]^+$.

Embodiment 3

7-chloro-2,4-dimethyl-N-((6-methyl-4-(methylthio)-2-oxo-1,2-dihydropyridin-3-yl)methyl)-2-(4-(((3-methyloxetan-3-yl)methyl)amino)cyclohexyl)benzo[d][1,3]dioxole-5-carboxamide trifluoroacetate (compound 3)

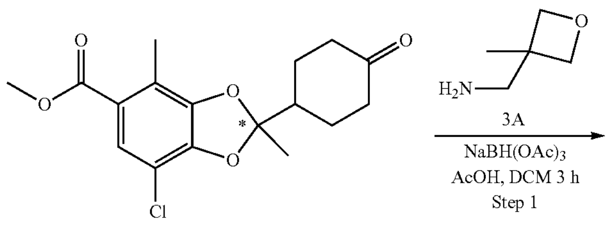

Intermediate 2

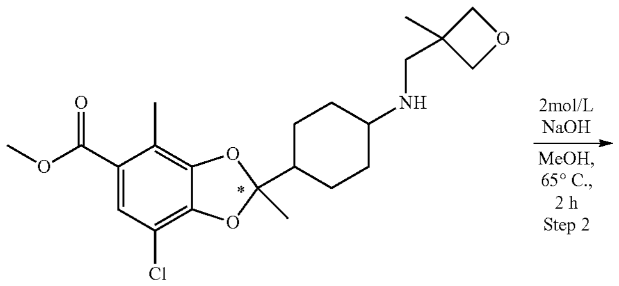

3B

-continued

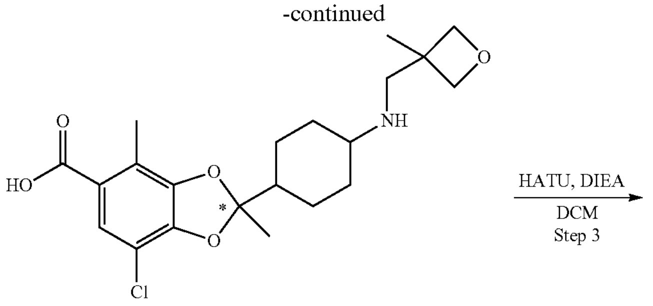

3C

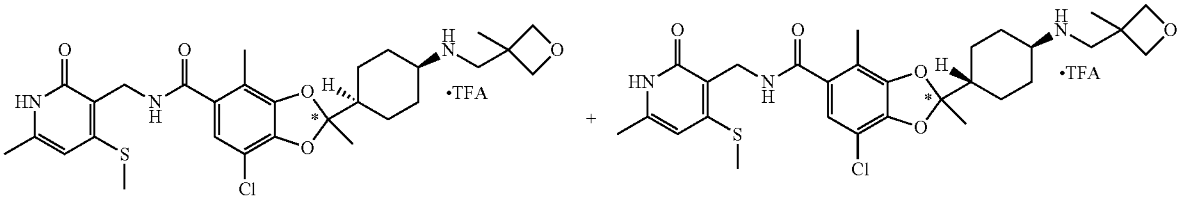

Compound 3

Step 1:

At room temperature, to intermediate 2 (0.2 g, 0.59 mmol) were successively added dichloromethane (4 mL), (3-methyloxetan-3-yl)methanamine (0.078 g, 0.77 mmol) and two drops of glacial acetic acid, and the mixture was stirred for 1 h. Sodium triacetylborohydride (0.25 g, 1.2 mmol) was added, and the mixture was stirred at room temperature for 2 h and extracted with water and dichloromethane. The organic phase was washed with saturated brine (20 mL), dried over anhydrous sodium sulfate and concentrated under reduced pressure, and then the residue was separated by column chromatography to obtain 3B (0.22 g, 88%).

LC-MS (ESI): m/z=424.2 $[M+H]^+$.

Step 2:

At room temperature, to 3B (0.22 g, 0.52 mmol) were successively added methanol (10 mL) and 2 mol/L sodium hydroxide (2.5 mL), and the mixture was stirred at 65° C. for 2 h. The reaction was adjusted to pH 5-6 with 3N hydrochloric acid and extracted with ethyl acetate. The organic phase was dried over anhydrous sodium sulfate and concentrated under reduced pressure to obtain 3C (0.2 g, 94%).

LC-MS (ESI): m/z=410.2 $[M+H]^+$.

Step 3:

At room temperature, to 3C (0.2 g, 0.49 mmol) were successively added intermediate 5 (0.11 g, 0.49 mmol), DCM (4 mL), HATU (0.19 g, 0.49 mmol) and N,N-diisopropylethylamin (0.2 g, 1.59 mmol). The mixture was stirred at room temperature for 2 hours, diluted by adding water, and extracted with ethyl acetate. The organic phase was washed with saturated brine (20 mL), dried over anhydrous sodium sulfate and concentrated under reduced pressure to obtain a crude product, which was separated and purified by preparative HPLC to obtain isomer 1 (0.04 g, 12%) of compound 3 and isomer 2 (0.015 g, 5%) of compound 3. Preparative HPLC separation methods: 1. Instrument: waters 2767 (preparative liquid phase chromatographic instrument); chromatographic column: SunFire@Prep C18 (19 mm×250 mm). 2. The sample was dissolved in DMF and filtered with a 0.45 m filter to prepare a sample solution. 3. Preparative chromatography conditions: a. composition of mobile phases A and B: mobile phase A: acetonitrile; mobile phase B: water (containing 0.1% TFA); b. gradient elution, mobile phase A: 5% to 50%; c. flow rate: 12 ml/min; d. elution time: 20 min;

retention time for isomer 1 of compound 3:14.2 min;

$^1H$ NMR (400 MHz, DMSO) δ 11.51 (s, 1H), 8.31 (s, 2H), 8.01 (t, 1H), 6.88 (s, 1H), 6.08 (s, 1H), 4.38 (d, 2H), 4.27 (d, 2H), 4.24 (d, 2H), 3.26-3.24 (m, 2H), 3.13-3.15 (m, 1H), 2.45 (s, 3H), 2.17 (s, 3H), 2.15 (s, 3H), 2.15-2.11 (m, 2H), 1.96-1.94 (m, 3H), 1.62 (s, 3H), 1.47-1.34 (m, 2H), 1.33 (s, 3H), 1.31-1.18 (m, 2H).

LC-MS (ESI): m/z=576.2 $[M+H]^+$.

retention time for isomer 2 of compound 3:14.6 min;

$^1H$ NMR (400 MHz, DMSO) δ 11.51 (s, 1H), 8.30 (s, 2H), 8.01 (t, 1H), 6.89 (s, 1H), 6.08 (s, 1H), 4.38 (d, 2H), 4.28-4.25 (m, 4H), 3.31-3.29 (m, 3H), 2.45 (s, 3H), 2.17 (s, 6H), 2.03-2.00 (m, 3H), 1.72-1.68 (m, 6H), 1.62 (s, 3H), 1.38 (s, 3H).

LC-MS (ESI): m/z=576.2 $[M+H]^+$.

Embodiment 4

7-chloro-2-(4-((3,3-difluorocyclobutyl)amino)cyclohexyl)-2,4-dimethyl-N-((6-methyl-4-(methylthio)-2-oxo-1,2-dihydropyridin-3-yl)methyl)benzo[d][1,3]dioxole-5-carboxamide (compound 4)

acid, diluted by adding water (50 mL) and extracted with ethyl acetate (70 mL×2). The combined organic phase was washed with saturated brine, dried over anhydrous sodium sulfate and concentrated under reduced pressure to obtain compound 4C (400 mg) as a yellow solid.

LC-MS (ESI): m/z=416.1 $[M+H]^+$.

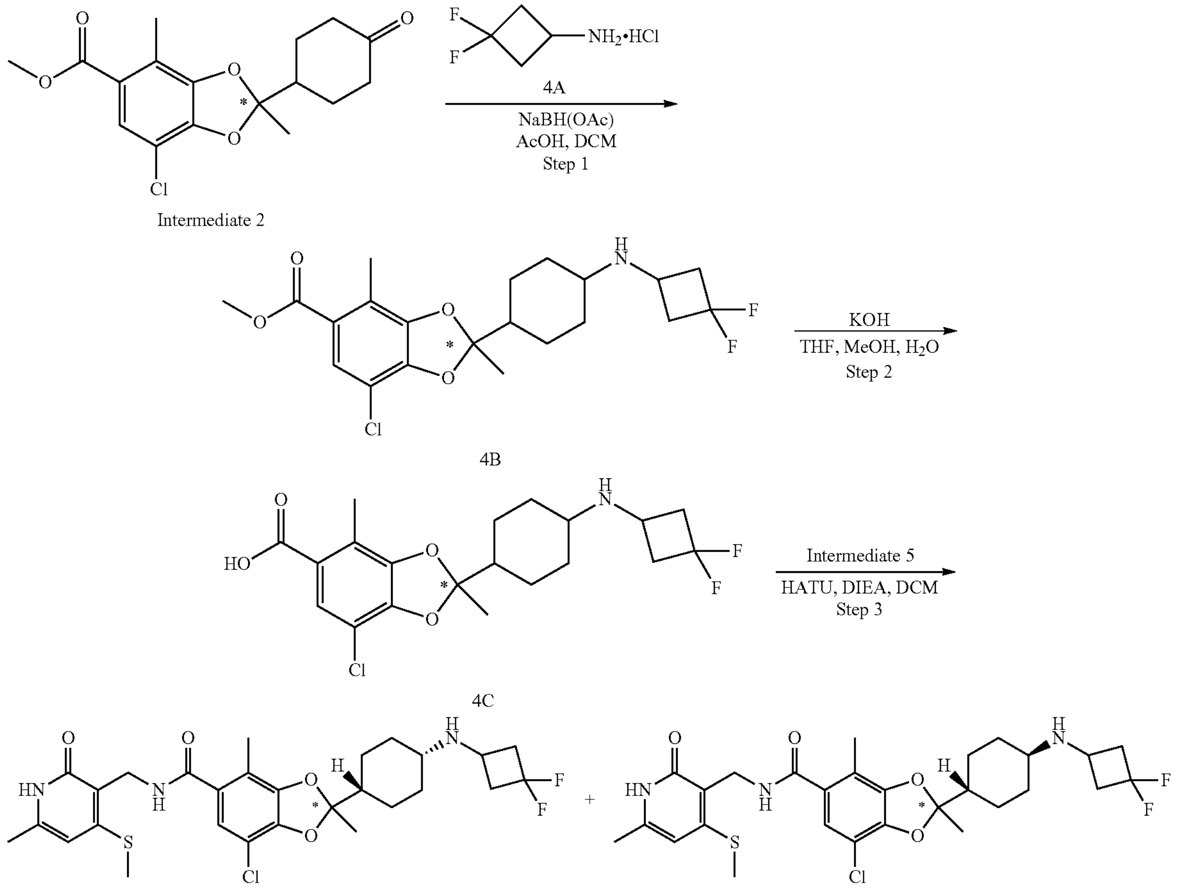

Compound 4

Step 1:

Intermediate 2 (400 mg, 1.18 mmol) was dissolved in DCM (10 mL), and 3,3-difluorocyclobutylamine hydrochloride (4A, 186 mg, 1.30 mmol) and one drop of glacial acetic acid were successively added. The mixture was stirred at room temperature for 2 h, and then sodium triacetylborohydride (751 mg, 3.54 mmol) was added. The resulting mixture was reacted at room temperature for 3 h. Water (30 mL) was added to the reaction liquid, and the mixture was extracted with ethyl acetate (50 mL×2). The combined organic phase was washed with saturated brine, dried over anhydrous sodium sulfate and concentrated under reduced pressure to obtain compound 4B (400 mg) as a yellow solid.

LC-MS (ESI): m/z=430.1 $[M+H]^+$.

Step 2:

Compound 4B (500 mg, 1.16 mmol) was dissolved in a mixed solvent (6 mL) of THF/MeOH/$H_2O$=1/1/1, and potassium hydroxide (979 mg, 17.45 mmol) was added. The reaction was refluxed overnight, cooled to room temperature, adjusted to about pH=4 by adding dilute hydrochloric Step 3:

Compound 4C (400 mg, 0.96 mmol) was dissolved in DCM (16 mL), and intermediate 5 (354 mg, 1.92 mmol), HATU (548 mg, 1.44 mmol) and DIEA (N,N-diisopropylethylamin, 372 mg, 2.89 mmol) were successively added. The mixture was reacted at room temperature for 4 h. Water (30 mL) was added, and the reaction liquid was extracted with ethyl acetate (50 mL×2), washed with saturated brine, dried over anhydrous sodium sulfate and concentrated under reduced pressure to obtain the crude compound 4 (400 mg) as a yellow solid. The crude compound 4 (400 mg) was separated by preparative HPLC, with separation conditions as follows: instrument: waters 2767 (preparative liquid phase chromatographic instrument); chromatographic column: XSelect@ CSH Prep (19 mm×150 mm). The sample was dissolved in water and filtered with a 0.45 μm filter to prepare a sample solution. Preparative chromatography conditions: a. composition of mobile phases A and B: mobile phase A: acetonitrile; mobile phase B: water (containing 0.3% ammonia water); gradient elution, mobile phase A: 30%-75%; flow rate: 12 mL/min; elution time: 20 min. After separation, isomer 1 (retention time: 15.30 min, 100 mg, 18%) of compound 4 and isomer 2 (retention time: 15.8 min, 50 mg, 9%) of compound 4 were obtained.

Isomer 1 of compound 4:

LC-MS (ESI): m/z=582.1 $[M+H]^+$.

$^1$H NMR (400 MHz, $CD_3OD$) δ 6.88 (s, 1H), 6.27 (s, 1H), 4.49 (s, 2H), 3.28-3.25 (m, 1H), 2.81-2.71 (m, 2H), 2.52 (s, 3H), 2.46-2.27 (m, 6H), 2.18 (s, 3H), 1.98-1.83 (m, 5H), 1.60 (s, 3H), 1.33-1.23 (m, 2H), 1.16-1.07 (m, 2H).

Isomer 2 of compound 4:

LC-MS (ESI): m/z=582.1 $[M+H]^+$.

$^1$H NMR (400 MHz, $CDCl_3$) δ 6.88 (s, 1H), 6.27 (s, 1H), 4.49 (s, 2H), 3.23-3.20 (m, 1H), 2.87-2.74 (m, 3H), 2.52 (s, 3H), 2.42-2.29 (m, 5H), 2.20 (s, 3H), 1.93-1.87 (m, 1H), 1.81-1.79 (m, 2H), 1.69-1.48 (m, 9H).

Embodiment 5

7-chloro-2-(1-(3,3-difluorocyclobutane-1-carbonyl) piperidin-4-yl)-2,4-dimethyl-N-((6-methyl-4-(methylthio)-2-oxo-1,2-dihydropyridin-3-yl)methyl)benzo [d][1,3]dioxole-5-carboxamide (compound 5)

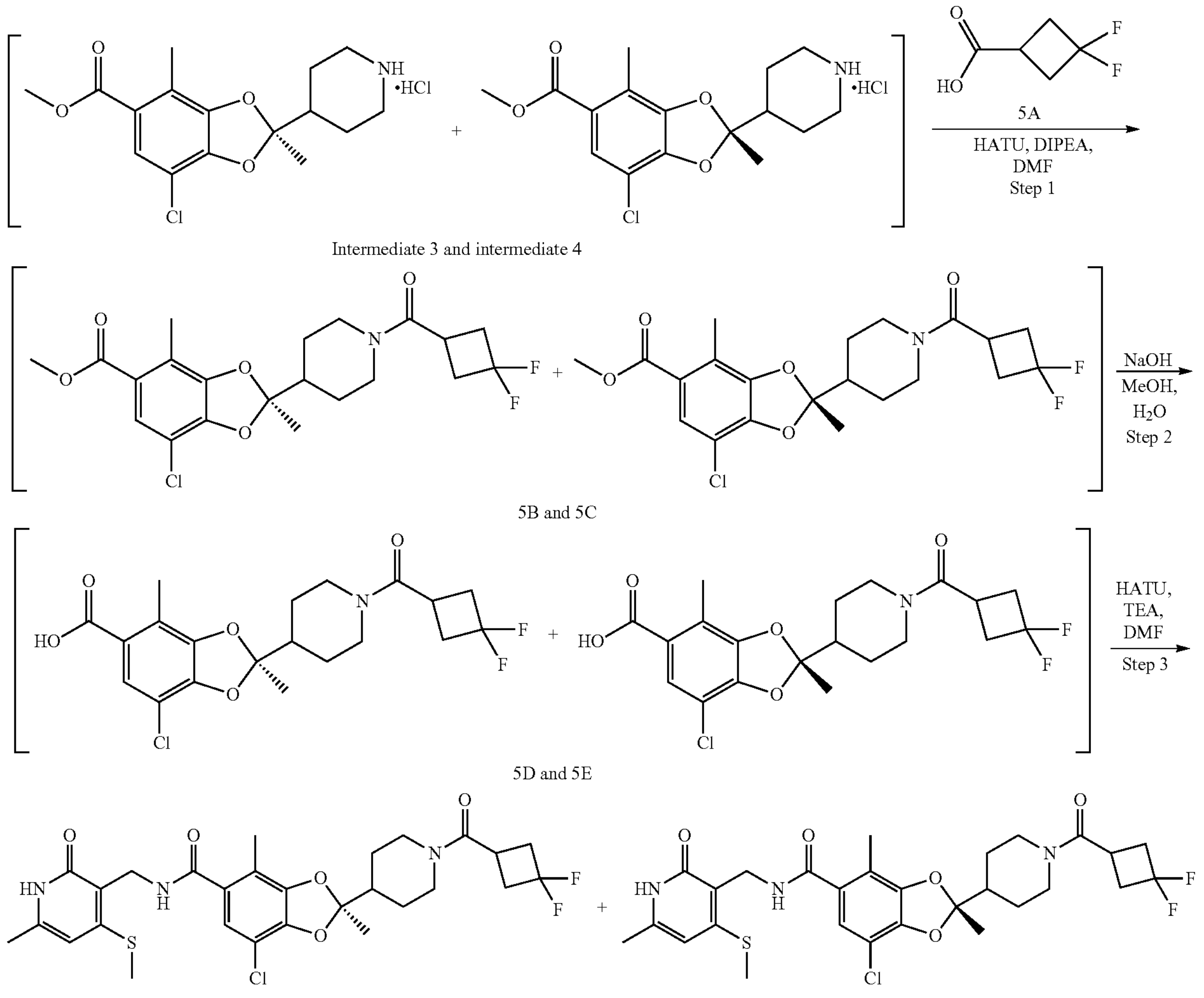

Intermediate 3 and intermediate 4

5B and 5C 5D and 5E

Compound 5

Step 1:

In a 50 mL single-necked flask, intermediate 3 (230 mg, 0.64 mmol) was added and dissolved in DMF (6 mL), and then triethylamine (193 mg, 1.91 mmol) and HATU (365 mg, 0.96 mmol) were added. The mixture was stirred at room temperature for 0.5 h, and 3,3-difluorocyclobutane-1-carboxylic acid (131 mg, 0.96 mmol) was then added. The resulting mixture was stirred at room temperature for 1 h. Water (10 mL) was added, and the reaction liquid was extracted three times with EA (20 mL). The combined organic phase was dried over anhydrous sodium sulfate, filtered and concentrated, and the residue was separated by column chromatography (PE:EA=1:1) to obtain 5B (230 mg, 81% yield) as a yellow solid.

LC-MS (ESI): m/z=444.1 $[M+H]^+$.

In a 50 mL single-necked flask, intermediate 4 (230 mg, 0.64 mmol) was added and dissolved in DMF (6 mL), and then triethylamine (193 mg, 1.91 mmol) and HATU (365 mg, 0.96 mmol) were added. The mixture was stirred at room temperature for 0.5 h, and 3,3-difluorocyclobutane-1-carboxylic acid (131 mg, 0.96 mmol) was then added. The resulting mixture was stirred at room temperature for 1 h. Water (10 mL) was added, and the reaction liquid was extracted three times with EA (20 mL). The combined organic phase was dried over anhydrous sodium sulfate and concentrated, and the residue was separated by column chromatography (PE:EA=1:1) to obtain 5C (230 mg, 81% yield) as a yellow solid.

LC-MS (ESI): m/z=444.1 $[M+H]^+$.

Step 2:

In a 50 mL single-necked flask, 5B (230 mg, 0.52 mmol) was added and dissolved in methanol (8 mL), and an aqueous NaOH solution (104 mg, 2.60 mmol, 2 mL) was then added. The reaction was stirred at 25° C. TLC showed that the reaction of the raw materials was completed. The reaction liquid was adjusted to pH=3-4 by dropwise adding 2N hydrochloric acid and concentrated under reduced pressure to obtain a crude. The crude was soaked with a mixed solvent (DCM:MeOH=10:1, 20 mL) and then filtered, and the filtrate was concentrated to obtain 5D (180 mg, 81%).

LC-MS (ESI): m/z=430.1 $[M+H]^+$.

In a 50 mL single-necked flask, 5C (230 mg, 0.52 mmol) was added and dissolved in methanol (8 mL), and an aqueous NaOH solution (104 mg, 2.60 mmol, 2 mL) was then added. The reaction was stirred at 25° C. TLC showed that the reaction of the raw materials was completed. The reaction liquid was adjusted to pH=3-4 by dropwise adding 2N hydrochloric acid and concentrated under reduced pressure to obtain a crude. The crude was soaked with a mixed solvent (DCM:MeOH=10:1, 20 mL) and then filtered, and the filtrate was concentrated to obtain 5E (180 mg, 81% yield).

LC-MS (ESI): m/z=430.1 $[M+H]^+$.

Step 3:

In a 50 mL single-necked flask, 5D (180 mg, 0.42 mmol) was added and dissolved in DMF (6 mL), and then triethylamine (127 mg, 1.26 mmol) and HATU (239 mg, 0.63 mmol) were added. The mixture was stirred at room temperature for 0.5 h, intermediate 5 (186 mg, 0.84 mmol) was added, and the resulting mixture was stirred at room temperature for 5 h. Water (10 mL) was added to the reaction liquid, and the mixture was extracted with EA (20 mL×3). The combined organic phase was dried over anhydrous sodium sulfate and concentrated, and the residue was separated by column chromatography to obtain isomer 1 (100 mg, yield: 40%) of compound 5.

LC-MS (ESI): m/z=596.2 $[M+H]^+$.

$^1$H NMR (400 MHz, DMSO-$d_6$) δ 11.49 (s, 1H), 8.00 (t, 1H), 6.87 (s, 1H), 6.07 (s, 1H), 4.45-4.48 (m, 1H), 4.27 (d, 2H), 3.80-3.83 (m, 1H), 321-3.25 (m, 1H), 2.92-2.98 (m, 1H), 2.67-2.78 (m, 4H), 2.53-2.57 (m, 2H), 2.44 (s, 3H), 2.17 (s, 3H), 2.14 (s, 3H), 1.77-1.79 (m, 2H), 1.61 (s, 3H), 1.17-1.29 (m, 2H).

In a 50 mL single-necked flask, 5E (180 mg, 0.42 mmol) was added and dissolved in DMF (6 mL), and then triethylamine (127 mg, 1.26 mmol) and HATU (239 mg, 0.63 mmol) were added. The mixture was stirred at room temperature for 0.5 h, intermediate 5 (186 mg, 0.84 mmol) was added, and the resulting mixture was stirred at room temperature for 5 h. Water (10 mL) was added to the reaction liquid, and the mixture was extracted with EA (20 mL×3). The combined organic phase was dried over anhydrous sodium sulfate and concentrated, and the residue was separated by column chromatography to obtain isomer 2 (60 mg, yield: 24%) of compound 5.

LC-MS (ESI): m/z=596.2 $[M+H]^+$.

$^1$H NMR (400 MHz, DMSO-$d_6$) δ 11.51 (s, 1H), 8.00 (t, 1H), 6.87 (s, 1H), 6.08 (s, 1H), 4.45-4.48 (m, 1H), 4.27 (d, 2H), 3.80-3.83 (m, 1H), 321-3.25 (m, 1H), 2.92-2.98 (m, 1H), 2.67-2.78 (m, 4H), 2.53-2.57 (m, 2H), 2.45 (s, 3H), 2.17 (s, 3H), 2.14 (s, 3H), 1.77-1.79 (m, 2H), 1.61 (s, 3H), 1.17-1.29 (m, 2H).

Embodiment 6

7-chloro-2-(4-(3,3-difluorocyclobutane-1-carboxamido)cyclohexyl)-2,4-dimethyl-N-((6-methyl-4-(methylthio)-2-oxo-1,2-dihydropyridin-3-yl)methyl)benzo[d][1,3]dioxole-5-carboxamide (compound 6)

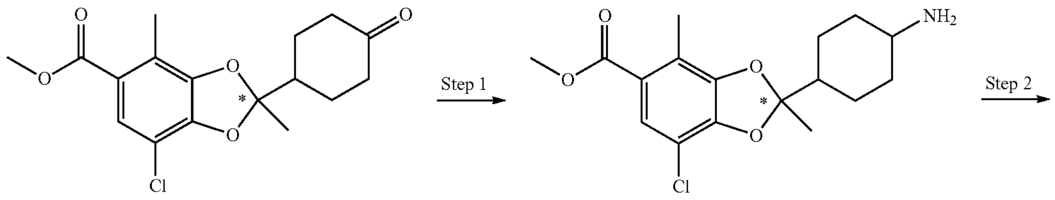

Intermediate 2

6A

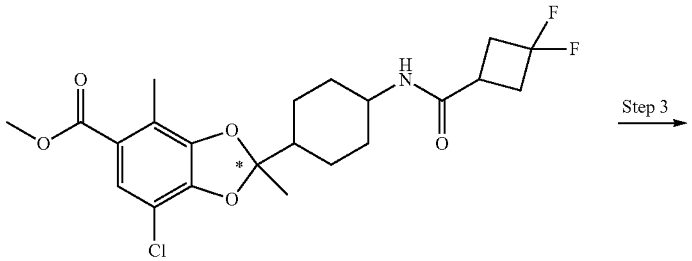

6B

-continued

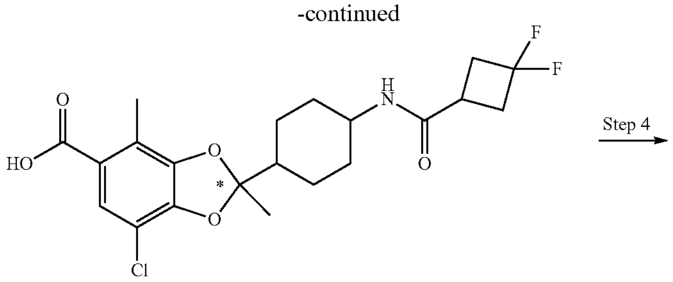

6C

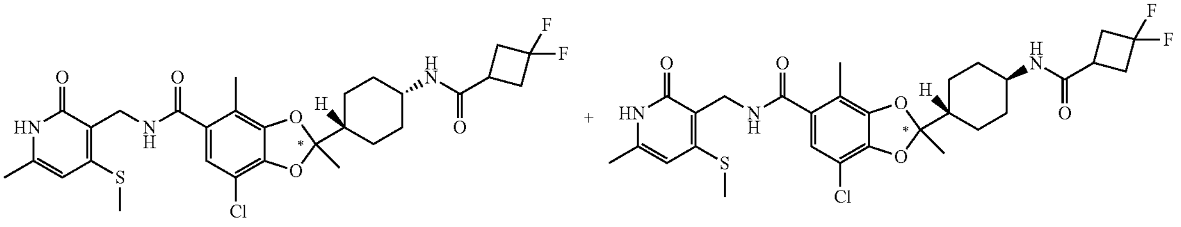

Compound 6

Step 1:

At room temperature, to intermediate 2 (1.0 g, 2.96 mmol) were successively added anhydrous ethanol (30 mL), ammonium acetate (1 g) and sodium triacetoxyborohydride (1.9 g, 8.88 mmol), and the reaction was stirred at room temperature for 2 hours. The reaction liquid was poured into water (50 mL), adjusted to pH 7-8 with potassium carbonate and extracted with ethyl acetate (50 mL×3). The combined organic phase was washed with water (30 mL×2), dried over anhydrous sodium sulfate and concentrated under reduced pressure, and then the residue was separated and purified by column chromatography to obtain compound 6A (0.6 g, 60%).

LC-MS (ESI): m/z=340 $[M+H]^+$.

Step 2:

At room temperature, DMF (10 mL), 3,3-difluorocyclobutane-1-carboxylic acid (150 mg, 1.11 mmol), HATU (421 mg, 1.11 mmol) and DIPEA (N,N-diisopropylethylamin, 286 mg, 2.22 mmol) were successively added to compound 6A (250 mg, 0.74 mmol), and the mixture was stirred at room temperature for 1 hour. The reaction was quenched by adding water (30 mL) and extracted with ethyl acetate (50 mL×2). The combined organic phase was washed with water (30 mL×2), dried over anhydrous sodium sulfate and concentrated under reduced pressure, and then the residue was separated and purified by column chromatography to obtain compound 6B (250 mg, 73%).

LC-MS (ESI): m/z=458 $[M+H]^+$.

Step 3:

At room temperature, methanol (10 mL), water (10 mL) and sodium hydroxide (250 mg) were successively added to compound 6B (250 mg, 0.54 mmol). The reaction was heated to reflux for 3 hours, cooled to room temperature and then concentrated under reduced pressure to remove most of methanol. Water (30 mL) was added to the residue, and the reaction liquid was extracted with ethyl acetate (50 mL×1). The aqueous phase was adjusted to pH 5-6 with 3N hydrochloric acid and extracted with ethyl acetate (50 mL×3). The combined organic phase was dried over anhydrous sodium sulfate and concentrated under reduced pressure to obtain compound 6C (200 mg, 84%).

LC-MS (ESI): m/z=444 $[M+H]^+$.

Step 4:

At room temperature, THE (20 mL), HOBt (1-hydroxybenzotriazole, 92 mg, 0.68 mmol), EDCI (1-ethyl-3(3-dimethylpropylamine)carbodiimide, 130 mg, 0.68 mmol), intermediate 5 (180 mg, 0.82 mmol) and triethylamine (212 mg, 2.1 mmol) were successively added to compound 6C (200 mg, 0.45 mmol), and the mixture was stirred at room temperature for 4 hours. The reaction liquid was poured into water (30 mL) and extracted with ethyl acetate (30 mL×3). The combined organic phase was washed with saturated brine (30 mL×1), dried over anhydrous sodium sulfate and concentrated under reduced pressure to obtain a crude product, which was separated by chiral preparative HPLC. Separation conditions: instrument: GilsonGX-281 (preparative liquid phase chromatographic instrument); chromatographic column: CHIRALPAK@AD_H (19 mm× 250 mm). The sample was dissolved in ethanol and filtered with a 0.45 μm filter to prepare a sample solution. Preparative chromatography conditions: mobile phase A: n-hexane, mobile phase B: isopropanol; isocratic elution, mobile phase A: 30%; flow rate: 9 mL/min; elution time: 20 min.

Isomer 1 (35 mg, yield: 12%) of compound 6 was obtained, with retention time of about 17 min.

LC-MS (ESI): m/z=610$[M+H]^+$.

$^1$H NMR (400 MHz, DMSO-$d_6$) δ 11.49 (s, 1H), 8.03-7.97 (m, 1H), 7.90 (d, 1H), 6.86 (s, 1H), 6.07 (s, 1H), 4.27 (d, 2H), 3.46 (s, 1H), 2.86-2.73 (m, 1H), 2.70-2.58 (m, 4H), 2.45 (s, 3H), 2.17 (s, 3H), 2.14 (s, 3H), 1.89-1.80 (m, 5H), 1.60 (s, 3H), 1.25-1.13 (m, 4H).

Isomer 2 (25 mg, yield: 9%) of compound 6 was obtained, with retention time of about 18 min.

LC-MS (ESI): m/z=610.3$[M+H]^+$.

$^1$H NMR (400 MHz, DMSO-$d_6$) δ 11.50 (s, 1H), 8.02-7.95 (m, 1H), 7.89 (d, J=6.5 Hz, 1H), 6.86 (s, 1H), 6.08 (s, 1H), 4.27 (d, J=4.4 Hz, 2H), 3.82 (s, 1H), 3.04-2.84 (m, 1H), 2.75-2.57 (m, 4H), 2.45 (s, 3H), 2.17 (s, 3H), 2.15 (s, 3H), 1.92-1.69 (m, 3H), 1.61 (s, 5H), 1.51-1.36 (m, 4H).

Embodiment 7

7-chloro-2-(1-(cyclopropanecarbonyl)piperidin-4-yl)-2,4-dimethyl-N-((6-methyl-4-(methylthio)-2-oxo-1,2-dihydropyridin-3-yl)methyl)benzo[d][1,3]dioxole-5-carboxamide (compound 7)

was completed, the reaction liquid was adjusted to pH 4-5 by adding dilute hydrochloric acid and extracted with ethyl acetate. The organic phase was dried over anhydrous sodium sulfate and concentrated under reduced pressure to obtain a crude of compound 7D (320 mg).

LC-MS (ESI): m/z=380.1[M+H]+.

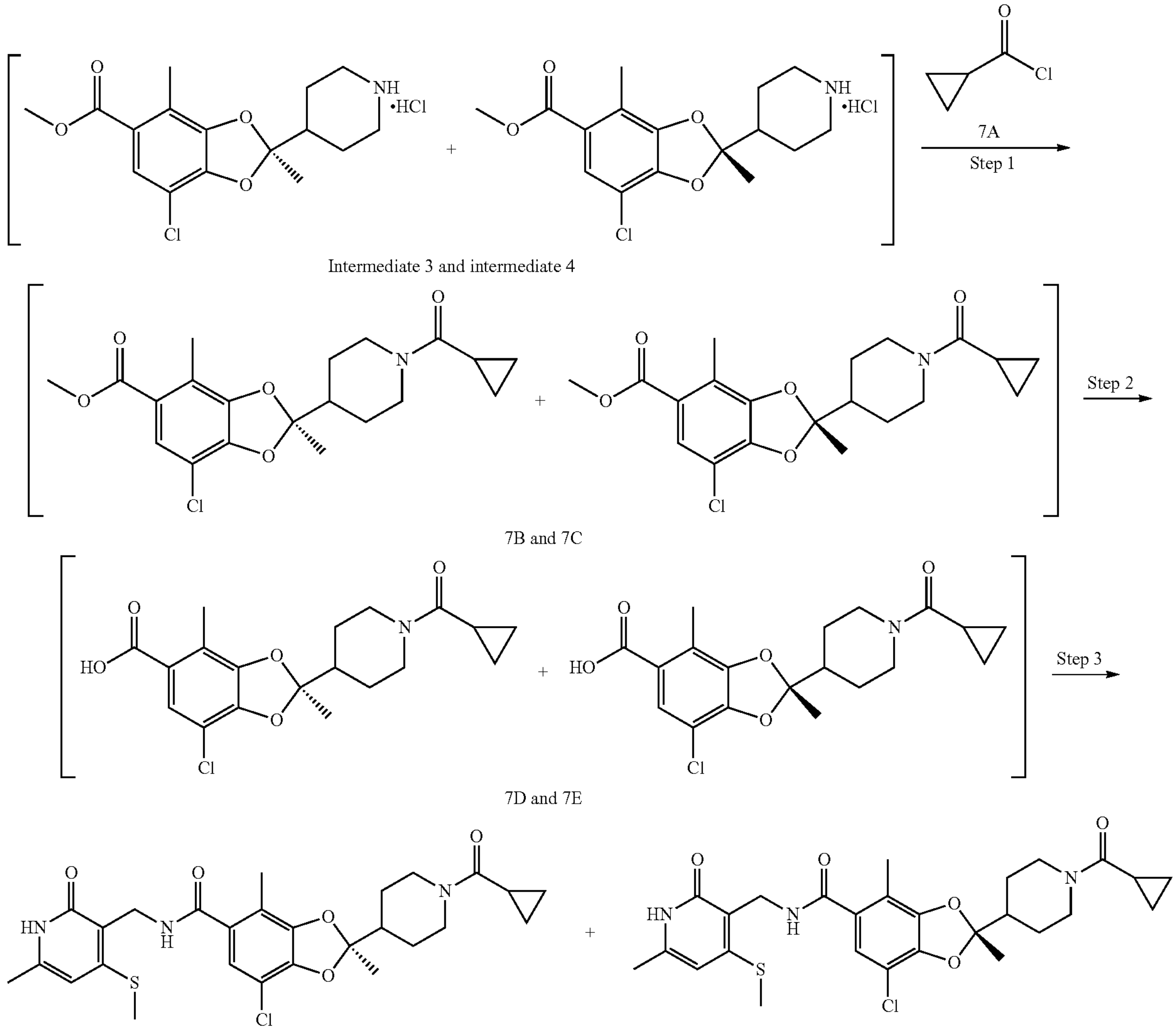

Compound 7

Step 1:

The compound intermediate 3 (250 mg, 0.69 mmol) was dissolved in dichloromethane (5 mL). Cyclopropanecarbonyl chloride (108 mg, 1.04 mmol) and potassium carbonate (144 mg, 1.04 mmol) were successively added. The reaction was stirred at room temperature overnight and filtered, the filtrate was concentrated, and then the residue was separated by column chromatography to obtain compound 7B (257 mg, 94%).

LC-MS (ESI): m/z=394.1[M+H]+.

Step 2:

Compound 7B (257 mg, 0.65 mmol) was dissolved in methanol (5 mL). An aqueous solution (0.5 mL) of sodium hydroxide (130 mg, 3.25 mmol) was added, and the reaction was stirred at room temperature overnight. After the reaction Step 3:

The crude of compound 7D (320 mg) was dissolved in DMF (5 mL). DIPEA (277 mg, 2.15 mmol), HATU (371 mg, 0.98 mmol) and intermediate 5 (186 mg, 0.85 mmol) were successively added, and the reaction was stirred at room temperature overnight. After the reaction was completed, the reaction liquid was diluted by adding water and extracted with ethyl acetate. The organic phase was dried over anhydrous sodium sulfate and concentrated under reduced pressure to obtain a crude product, which was further separated and purified by preparative HPLC to obtain isomer 1 (80 mg, two-step (steps 2 and 3) yield: 22%) of compound 7. Preparative HPLC separation conditions: preparation instrument: Waters 2767, preparative column: SunFire C18; mobile phase system: acetonitrile: 1% trifluoroacetic acid aqueous solution; retention time: 11.73 min.

LC-MS (ESI): m/z=546.2[M+H]+.

$^1$H NMR (400 MHz, Chloroform-d) δ 12.26 (s, 1H), 7.14 (s, 1H), 6.92 (s, 1H), 6.04 (s, 1H), 4.72 (s, 1H), 4.59 (d, 2H), 4.31 (s, 1H), 3.05 (s, 1H), 2.53 (s, 1H), 2.48 (s, 3H), 2.31 (s, 3H), 2.26 (s, 3H), 2.11 (t, 1H), 1.89 (s, 2H), 1.73 (t, 1H), 1.43 (d, 2H), 1.28 (d, 2H), 0.97 (s, 2H), 0.91-0.81 (m, 1H), 0.74 (dd, 2H).

With reference to synthesis of isomer 1 of compound 7, intermediate 4 was used as a raw material to obtain isomer 2 of compound 7. Preparative HPLC separation conditions: preparation instrument: Waters 2767, preparative column: SunFire C18; mobile phase system: acetonitrile: 1% trifluoroacetic acid aqueous solution; retention time: 12.68 min.

LC-MS (ESI): m/z=546.2[M+H]$^+$.

$^1$H NMR (400 MHz, Chloroform-d) δ 12.26 (s, 1H), 7.14 (s, 1H), 6.92 (s, 1H), 6.04 (s, 1H), 4.72 (s, 1H), 4.59 (d, 2H), 4.31 (s, 1H), 3.05 (s, 1H), 2.53 (s, 1H), 2.48 (s, 3H), 2.31 (s, 3H), 2.26 (s, 3H), 2.11 (tt, 1H), 1.89 (s, 2H), 1.73 (tt, 1H), 1.43 (d, 2H), 1.28 (d, 2H), 0.97 (s, 2H), 0.91-0.81 (m, 1H), 0.74 (dd, 2H).

Embodiment 8

7-chloro-2,4-dimethyl-2-(4-(1-methyl-1H-pyrazol-4-yl)cyclohexyl)-N-((6-methyl-4-(methylthio)-2-oxo-1,2-dihydropyridin-3-yl)methyl)benzo[d][1,3]dioxole-5-carboxamide (compound 8)

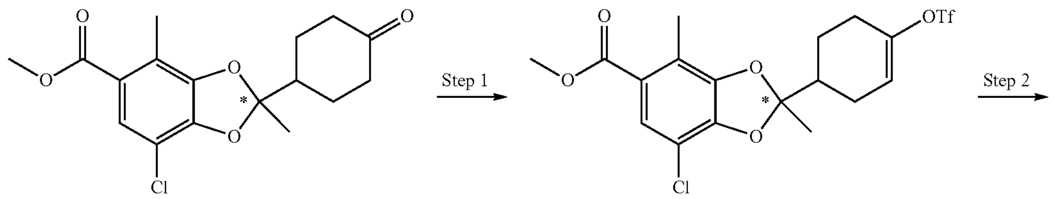

Intermediate 2 8A

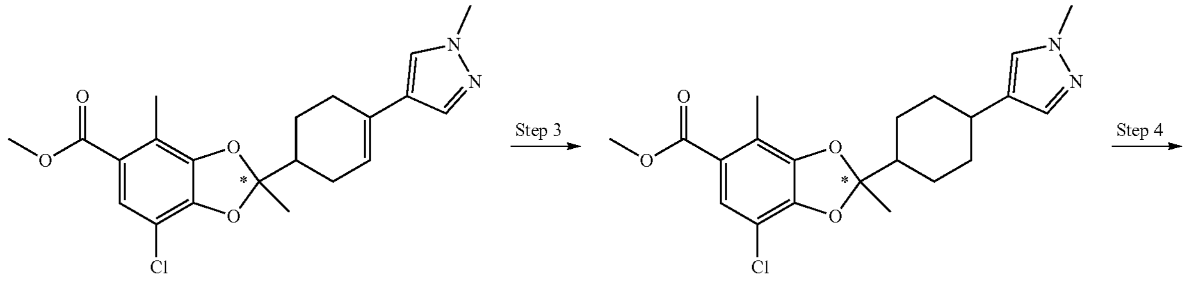

8B 8C

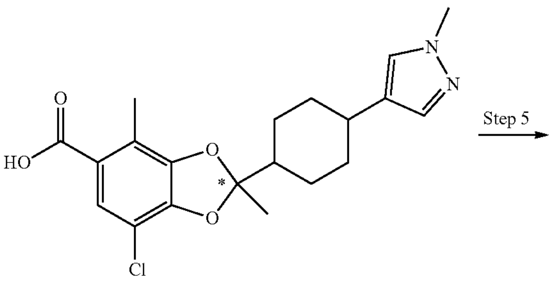

8D

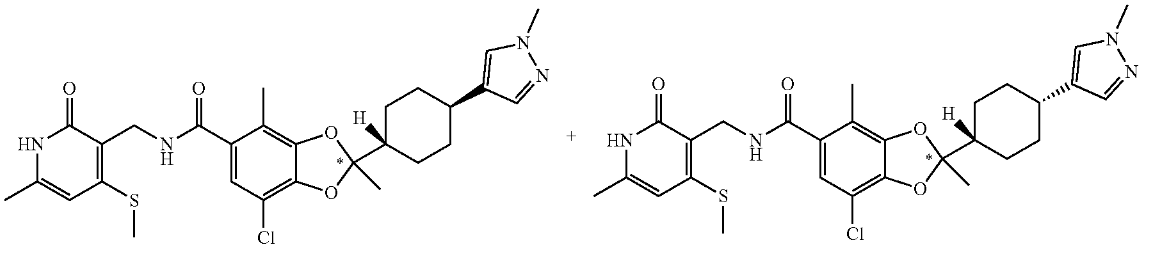

Compound 8

Step 1:

Intermediate 2 (0.40 g, 1.18 mmol) and THE (10 mL) were added to a 100 mL three-necked flask. At −78° C., LDA (lithium diisopropylamide, 1.77 mL, 1.77 mmol, 1M in THF) was added dropwise and reacted for 1 h, and then a solution of 1,1,1-trifluoro-N-phenyl-N-((trifluoromethyl)sulfonyl)methanesulfonamide (0.50 g, 1.42 mmol) in tetrahydrofuran was added. After the addition, the mixture was naturally warmed to room temperature and stirred for 16 h. The reaction was quenched with a saturated aqueous ammonium chloride solution (30 mL) and extracted with ethyl acetate (50 mL×3). The organic phases were combined, dried over anhydrous sodium sulfate and concentrated under reduced pressure, and the residue was separated by column chromatography (PE:EA=10:1) to obtain 8A (0.25 g, 45% yield) as a colorless transparent liquid.

$^1$H NMR (400 MHz, $CDCl_3$) δ 7.56 (s, 1H), 5.80-5.74 (m, 1H), 3.86 (s, 3H), 2.49-2.33 (m, 6H), 2.30-2.18 (m, 2H), 2.11 (d, 1H), 1.68 (s, 3H), 1.26 (d, 1H).

Step 2:

In a 50 mL single-necked flask, 8A (200 mg, 0.425 mmol), 1-methyl-4-(4,4,5,5-tetramethyl-1,3,2-dioxaborolan-2-yl)-1H-pyrazole (133 mg, 0.437 mmol), potassium carbonate (117 mg, 0.850 mmol), water (1.5 mL) and ethylene glycol dimethyl ether (6 mL) were successively added. Under nitrogen protection, the reaction was warmed to 80° C. and stirred for 4 hours. After TLC showed that the reaction of the raw materials was completed, the reaction liquid was cooled to room temperature and concentrated. 10 mL of water was added, and the resulting solution was extracted with ethyl acetate (20 mL×3). The combined organic phase was dried over anhydrous sodium sulfate and concentrated under reduced pressure, and then the residue was separated by column chromatography (PE:EA=5:1) to obtain 8B (0.16 g, 93% yield) as a white solid.

LC-MS (ESI): m/z=403.1 $[M+H]^+$.

Step 3:

In a 50 mL single-necked flask, substrate 8B (0.16 g, 0.40 mmol) was added and dissolved in methanol (10 mL). Palladium on carbon (0.1 g) and hydrochloric acid in dioxane (1 mL, 4 mol/L) were added. Under hydrogen atmosphere, the mixture was stirred at room temperature for 1.0 h, filtered and concentrated to obtain crude 8C (160 mg), which was directly used in the next reaction.

LC-MS (ESI): m/z=405.1 $[M+H]^+$.

Step 4:

In a 50 mL single-necked flask, 8C (160 mg, 0.40 mmol), MeOH (10 mL) and an aqueous NaOH solution (2N, 5 mL) were successively added, and the mixture was stirred at room temperature for 16 h, adjusted to pH 3-4 by dropwise adding HCl (2 M) and extracted with ethyl acetate (50 mL×2). The combined organic phase was dried over anhydrous sodium sulfate and concentrated under reduced pressure to obtain 8D (110 mg) as a colorless oil, which was directly used in the next reaction.

LC-MS (ESI): m/z=391.1 $[M+H]^+$.

Step 5:

In a 50 mL single-necked flask, 8D (110 mg, 0.28 mmol) was added and dissolved in DCM (10 mL). Triethylamine (84 mg, 0.85 mmol) and HATU (128 mg, 0.338 mmol) were added. The mixture was stirred at room temperature for 0.5 h, and intermediate 5 (93 mg, 0.50 mmol) was added. The resulting mixture was stirred at room temperature for 5 h. Water (10 mL) was added to the reaction liquid, and the mixture was extracted with DCM (10 mL×3). The combined organic phase was dried over anhydrous sodium sulfate and concentrated under reduced pressure to obtain a crude product, which was separated by preparative HPLC to obtain isomer 1 (28 mg, yield: 18%) of compound 8 and isomer 2 (2.0 mg, yield: 1%) of compound 8.

LC-MS (ESI): m/z=557.2 $[M+H]^+$.

1. Preparative HPLC separation conditions: instrument: GilsonGX-281 (preparative liquid phase chromatographic instrument); chromatographic column: CHIRALPAK@AD_H (19 mm×250 mm). 2. The sample was dissolved in ethanol and filtered with a 0.45 μm filter to prepare a sample solution. 3. Preparative chromatography conditions: a. composition of mobile phases A and B: mobile phase A: n-hexane; mobile phase B: isopropanol; b. isocratic elution, mobile phase A: 30%; c. flow rate: 9 mL/min; d. elution time: 60 min; retention time: isomer 1 (35 min) and isomer 2 (55 min).

Isomer 1: $^1$H NMR (400 MHz, $CDCl_3$) δ 7.37 (s, 1H), 7.21 (s, 1H), 7.15 (s, 1H), 6.92 (s, 1H), 6.07 (s, 1H), 4.61 (s, 2H), 3.90 (s, 3H), 3.00 (s, 1H), 2.50 (s, 3H), 2.33 (s, 3H), 2.25 (s, 3H), 1.99 (d, 3H), 1.72 (d, 4H), 1.60 (d, 3H), 1.55-1.41 (m, 3H).

Isomer 2: $^1$H NMR (400 MHz, $CDCl_3$) δ 7.49 (s, 1H), 7.24 (s, 1H), 6.88 (s, 1H), 6.47 (s, 1H), 6.41 (s, 1H), 4.63 (d, 2H), 4.01 (s, 3H), 2.56 (s, 3H), 2.51 (d, 3H), 2.27-2.21 (m, 3H), 2.03 (dd, 5H), 1.90 (s, 1H), 1.65 (s, 3H), 1.44-1.22 (m, 5H).

Embodiment 9

7-chloro-2-(4-((trans-3-methoxycyclobutyl)amino)cyclohexyl)-2,4-dimethyl-N-((6-methyl-4-(methylthio)-2-oxo-1,2-dihydropyridin-3-yl)methyl)benzo[d][1,3]dioxole-5-carboxamide (compound 9)

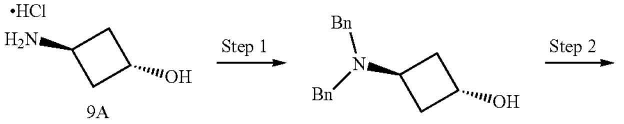

9A
9B

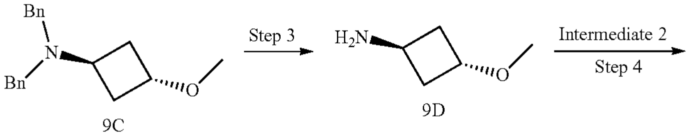

9C
9D

-continued

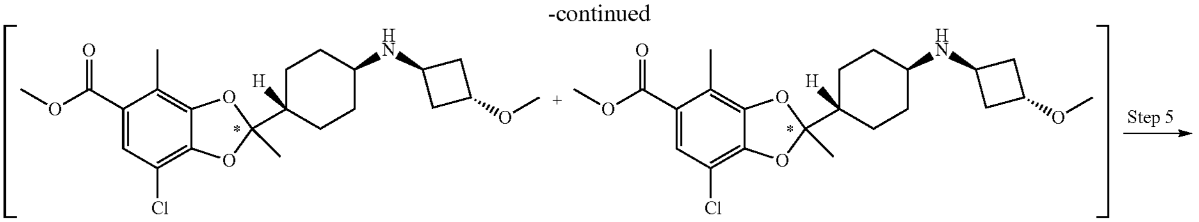

9E & 9F

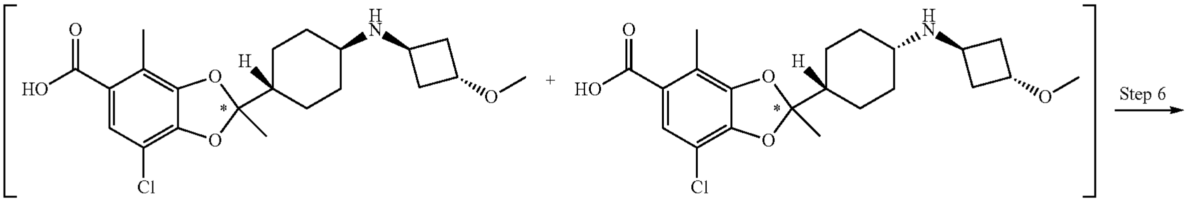

9G & 9H

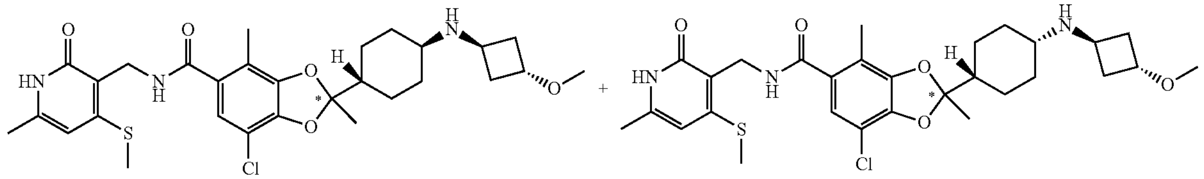

Compound 9

Step 1:

Compound 9A (1.0 g, 8.09 mmol) was dissolved in acetonitrile (30 mL), potassium carbonate (5.59 g, 40.5 mmol) and benzyl bromide (2.91 g, 16.99 mmol) were added, and the mixture was stirred at room temperature overnight. The reaction was quenched with water (20 mL) and concentrated under reduced pressure to remove most of acetonitrile, and the residue was extracted with ethyl acetate (50 mL×2). The combined organic phase was dried over anhydrous sodium sulfate and concentrated under reduced pressure, and the residue was separated by column chromatography (PE:EA=3:1) to obtain 9B (2.0 g, 93% yield) as a white solid.

LC-MS (ESI): m/z=268.3 $[M+H]^+$.

Step 2:

Compound 9B (0.60 g, 2.24 mmol) was dissolved in 100 mL of THF, NaH (0.294 g, 6.73 mmol) was slowly added at room temperature, and the mixture was stirred for 0.5 hours. Iodomethane (1.59 g, 11.2 mmol) was added, and the resulting mixture was stirred at room temperature for another 2 hours. After the reaction was completed, the reaction was quenched by adding a saturated aqueous ammonium chloride solution (10 mL) and extracted with ethyl acetate (30 mL×2). The organic phases were combined, dried over anhydrous sodium sulfate and concentrated under reduced pressure to obtain crude compound 9C (0.6 g), which was directly used in the next reaction.

LC-MS (ESI): m/z=282.3$[M+H]^+$.

Step 3:

Compound 9C (0.60 g) was dissolved in 20 mL of methanol, palladium on carbon (300 mg) was added, and under hydrogen atmosphere, the mixture was stirred at room temperature overnight. After the reaction was completed, the mixture was filtered, and the filter cake was washed with methanol. To the filtrate was added 4N hydrochloric acid in dioxane (1 mL), and the mixture was concentrated under reduced pressure to obtain crude compound 9D (0.20 g), which was directly used in the next reaction.

LC-MS (ESI): m/z=102.3 $[M+H]^+$.

Step 4:

The crude compound 9D (0.2 g) was dissolved in 1,2-dichloroethan (20 mL), and intermediate 2 (0.44 g, 1.29 mmol) and acetic acid (100 mg, 1.61 mmol) were added. The mixture was stirred at room temperature for 1.0 h, and $NaBH(OAc)_3$ (1.38 g, 6.5 mmol) was added. The reaction was stirred at room temperature for 2 h, quenched by adding water, adjusted to pH 8-9 by adding a saturated aqueous sodium bicarbonate solution and extracted with DCM (2×100 mL). The combined organic phase was dried over anhydrous sodium sulfate and concentrated under reduced pressure, and then the residue was separated by column chromatography (DCM:MeOH=20:1) to obtain cis-trans isomer 9E (100 mg, yield: 19%) and intermediate 9F (250 mg, yield: 47%).

LC-MS (ESI): m/z=424.1 $[M+H]^+$.

Step 5:

Intermediate 9E (0.10 g, 0.236 mmol) was dissolved in MeOH (6 mL) and an aqueous NaOH solution (2N, 3 mL), and the mixture was stirred at room temperature for 16 h, adjusted to pH 6-7 with dilute hydrochloric acid (2 M) and extracted with ethyl acetate (50 mL×2). The combined organic phase was dried over anhydrous sodium sulfate and concentrated under reduced pressure to obtain 9G (90 mg) as a colorless oil, which was directly used in the next reaction.

LC-MS (ESI): m/z=410.2 $[M+H]^+$.

Step 6:

In a 50 mL single-necked flask, 9G (90 mg, 0.22 mmol) was added and dissolved in DCM (10 mL), and triethylamine (74 mg, 0.73 mmol) and HATU (111 mg, 0.29 mmol) were added. The mixture was stirred at room temperature for 0.5 h, intermediate 5 (93 mg, 0.50 mmol) was added, and the resulting mixture was stirred at room temperature for 5 h. Water (10 mL) was added to the reaction liquid, and the mixture was extracted three times with DCM (10 mL×2). The combined organic phase was dried over anhydrous sodium sulfate and concentrated under reduced pressure to obtain a crude product, which was separated by preparative HPLC to obtain isomer 1 (35 mg, yield: 28%) of compound 9.

Preparative HPLC separation conditions: instrument: waters 2767 (preparative liquid phase chromatographic instrument); chromatographic column: SunFire@ Prep C18 (19 mm×250 mm); The sample was dissolved in DMF and filtered with a 0.45 μm filter to prepare a sample solution. Preparative chromatography conditions: a. composition of mobile phases A and B: mobile phase A: acetonitrile; mobile phase B: water (containing 1% TFA); b. gradient elution, mobile phase A: 20% to 60%; c. flow rate: 12 ml/min; d. elution time: 20 min; retention time: 16 min.

$^1$H NMR (400 MHz, $CDCl_3$) δ 6.97 (s, 1H), 6.90 (s, 1H), 6.02 (s, 1H), 4.58 (d, 3H), 4.02 (s, 1H), 3.68 (s, 1H), 3.22 (s, 4H), 2.57 (s, 1H), 2.48 (s, 3H), 2.32 (d, 3H), 2.26 (d, 6H), 2.11-1.80 (m, 8H), 1.58 (s, 5H).

Embodiment 10

7-chloro-2-(1-((3,3-difluorocyclobutyl)methyl)piperidin-4-yl)-2,4-dimethyl-N-((6-methyl-4-(methylthio)-2-oxo-1,2-dihydropyridin-3-yl)methyl)benzo[d][1,3]dioxole-5-carboxamide (compound 10)

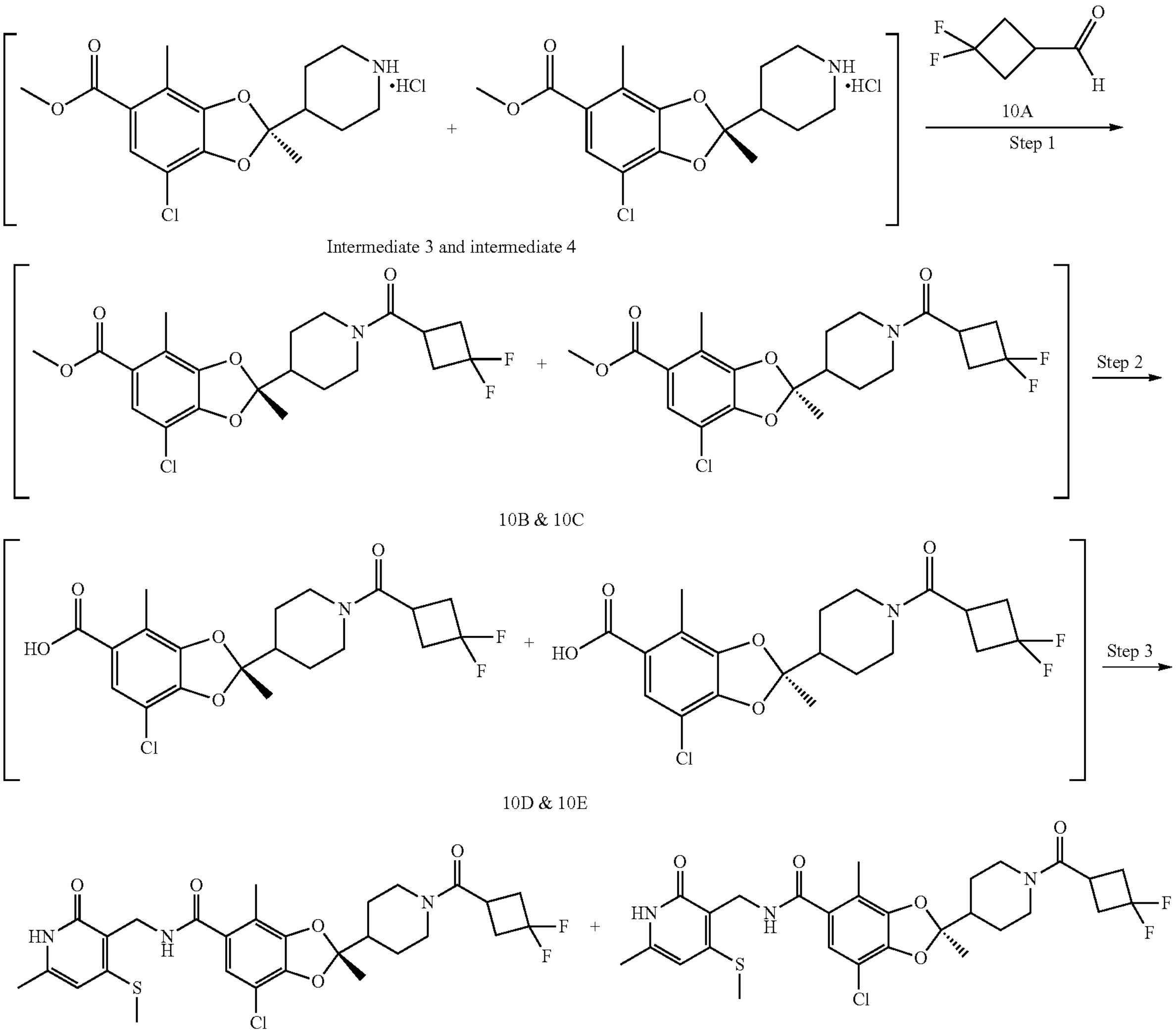

Intermediate 3 and intermediate 4

10B & 10C

10D & 10E

Compound 10

LC-MS (ESI): m/z=576.2 $[M+H]^+$.

$^1$H NMR (400 MHz, $CDCl_3$) δ 6.94 (t, 1H), 6.88 (s, 1H), 6.05 (s, 1H), 4.57 (d, 2H), 4.07-3.96 (m, 1H), 3.66-3.59 (m, 1H), 3.22 (s, 3H), 2.97 (s, 2H), 2.48 (s, 3H), 2.33 (s, 3H), 2.24 (s, 7H), 1.96-1.80 (m, 3H), 1.77-1.62 (m, 3H), 1.62-1.46 (m, 7H).

With reference to the synthetic method of isomer 1 of compound 9, 9F (250 mg) was used as a raw material to obtain isomer 2 (60 mg, yield: 21%) of compound 9.

Step 1:

In a 50 mL single-necked flask, intermediate 3 (0.3 g, 0.9 mmol) was added and dissolved in dichloromethane (10 mL), and 3,3-difluorocyclobutylcarbaldehyde (0.3 g, 3.0 mmol) and acetic acid (60 mg, 0.9 mmol) were added. The mixture was stirred at room temperature for 1 h, sodium triacetylborohydride (0.4 g, 2.0 mmol) was added, and the resulting mixture was stirred at room temperature for 3 h. The reaction was quenched with a saturated sodium bicarbonate solution (20 mL) and extracted with dichloromethane (30 mL×2). The organic phases were combined, dried over anhydrous sodium sulfate and concentrated under reduced pressure, and the residue was subjected to column chromatography (petroleum ether:ethyl acetate=4:1) to obtain 10B (0.34 g, 90% yield) as a colorless oil.

LC-MS (ESI): m/z=430.1 $[M+H]^+$.

Step 2:

In a 50 mL single-necked flask, 10B (0.34 g, 0.79 mmol), MeOH (2 mL), THE (2 mL) and water (2 mL) were added and dissolved, and NaOH (0.16 g, 4.0 mmol) was added. The mixture was stirred at room temperature for 16 h, adjusted to pH 3-4 with dilute hydrochloric acid (2 M) and extracted with ethyl acetate (20 mL×2). The organic phases were combined, dried over anhydrous sodium sulfate and concentrated under reduced pressure to obtain 10D (0.3 g, 91% yield) as a white solid.

LC-MS (ESI): m/z=416.1 $[M+H]^+$.

Step 3:

In a 50 mL single-necked flask, 10D (0.12 g, 0.29 mmol) was added and dissolved in DMF (5 mL), triethylamine (88 mg, 0.87 mmol) and HATU (0.13 g, 0.35 mmol) were added, and the mixture was stirred at room temperature for 0.5 h. Intermediate 5 (80 mg, 0.43 mmol) was added, and the mixture was stirred at room temperature for 16 h. Water (10 mL) was added to the reaction liquid, and the mixture was extracted twice with EA (10 mL×2). The organic phase was dried over anhydrous sodium sulfate and concentrated under reduced pressure, and then the residue was separated by column chromatography to obtain isomer 1 (0.040 g, 24% yield) of compound 10.

LC-MS (ESI): m/z=582.2$[M+H]^+$.

$^1$H NMR (400 MHz, $CDCl_3$) δ 12.01 (s, 1H), 7.12 (t, 1H), 6.90 (s, 1H), 6.02 (s, 1H), 4.59 (d, 2H), 3.05-2.85 (m, 2H), 2.68-2.66 (m, 2H), 2.48 (s, 5H), 2.33-2.29 (m, 3H), 2.25 (s, 5H), 1.98 (s, 2H), 1.82 (d, 4H), 1.61 (s, 3H).

With reference to the synthetic method of isomer 1 of compound 10, intermediate 4 was used as a raw material to obtain isomer 2 of compound 10.

LC-MS (ESI): m/z=582.2$[M+H]^+$.

Embodiment 11

7-chloro-2-(1-(3,3-difluorocyclobutane-1-carbonyl)piperidin-4-yl)-2,4-dimethyl-N-((6-methyl-4-(methylthio)-2-oxo-1,2-dihydropyridin-3-yl)methyl)benzo[d][1,3]dioxole-5-carboxamide (compound 11)

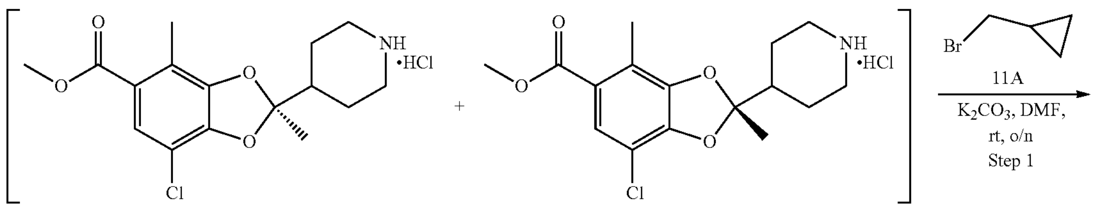

Intermediate 3 and intermediate 4

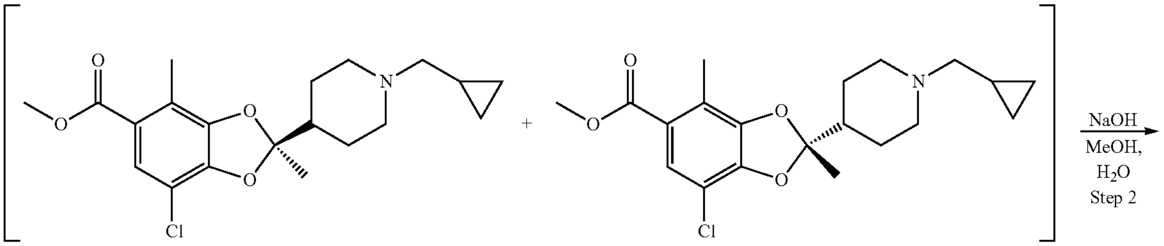

11B & 11C

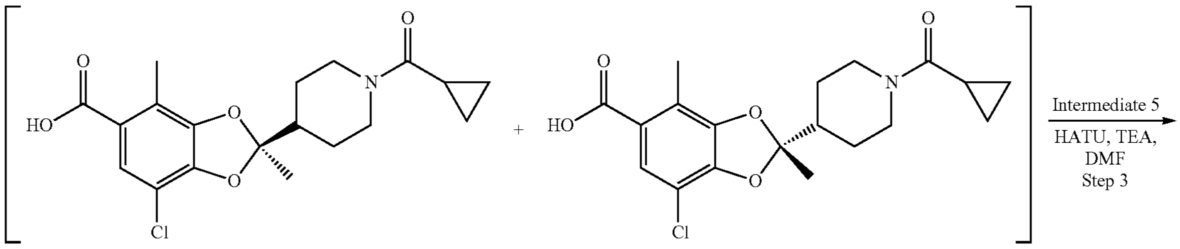

11D & 11E

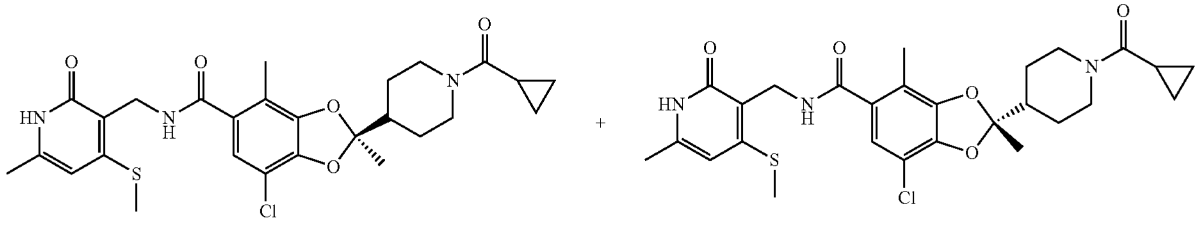

Compound 11

Step 1:

Intermediate 3 (200 mg, 0.55 mmol) was dissolved in DMF (6 mL), potassium carbonate (152 mg, 1.10 mmol) and bromomethylcyclopropane (149 mg, 1.10 mmol) were added, and the mixture was stirred at room temperature overnight. Water (20 mL) was added to the reaction liquid, and the mixture was extracted three times with EA (20 mL). The combined organic phase was dried over anhydrous sodium sulfate, filtered and concentrated, and the residue was separated by column chromatography (PE:EA=1:1) to obtain 11B (190 mg, 91% yield) as a yellow solid.

LC-MS (ESI): m/z=380.2 $[M+H]^+$.

Intermediate 4 (200 mg, 0.55 mmol) was dissolved in DMF (6 mL), potassium carbonate (152 mg, 1.10 mmol) and bromomethylcyclopropane (149 mg, 1.10 mmol) were added, and the mixture was stirred at room temperature overnight. Water (20 mL) was added to the reaction liquid, and the mixture was extracted three times with EA (20 mL). The combined organic phase was dried over anhydrous sodium sulfate, filtered and concentrated, and the residue was separated by column chromatography (PE:EA=1:1) to obtain 11C (190 mg, 91% yield) as a yellow solid.

LC-MS (ESI): m/z=380.2 $[M+H]^+$.

Step 2:

5B (190 mg, 0.50 mmol) was dissolved in methanol (8 mL). An aqueous NaOH solution (201 mg, 5.00 mmol, 2 mL) was added, and the reaction was stirred at 25° C. TLC showed that the reaction of the raw materials was completed. The reaction liquid was adjusted to pH=3-4 by dropwise adding 2N hydrochloric acid and concentrated under reduced pressure to obtain a crude. The crude was soaked with a mixed solvent (DCM:MeOH=10:1, 20 mL) and then filtered, and the filtrate was concentrated to obtain 11D (180 mg, 95%).

LC-MS (ESI): m/z=380.2 $[M+H]^+$.

11C (190 mg, 0.50 mmol) was dissolved in methanol (8 mL). An aqueous NaOH solution (201 mg, 5.00 mmol, 2 mL) was added, and the reaction was stirred at 25° C. TLC showed that the reaction of the raw materials was completed. The reaction liquid was adjusted to pH=3-4 by dropwise adding 2N hydrochloric acid and concentrated under reduced pressure to obtain a crude. The crude was soaked with a mixed solvent (DCM:MeOH=10:1, 20 mL) and then filtered, and the filtrate was concentrated to obtain 11E (180 mg, 95%).

LC-MS (ESI): m/z=380.2 $[M+H]^+$.

Step 3:

In a 50 mL single-necked flask, 11D (180 mg, 0.47 mmol) was added and dissolved in DMF (6 mL), and then triethylamine (127 mg, 1.26 mmol) and HATU (239 mg, 0.63 mmol) were added. The mixture was stirred at room temperature for 0.5 h, intermediate 5 (186 mg, 0.84 mmol) was added, and the resulting mixture was stirred at room temperature for 5 h. Water (10 mL) was added to the reaction liquid, and the mixture was extracted with EA (20 mL×3). The combined organic phase was dried over anhydrous sodium sulfate and concentrated, and the residue was separated by column chromatography (DCM:MeOH=20:1) to obtain isomer 1 (110 mg, yield: 44%) of compound 11.

LC-MS (ESI): m/z=532.2 $[M+H]^+$.

$^1$H NMR (400 MHz, DMSO-$d_6$) δ 11.50 (s, 1H), 8.00 (t, 1H), 6.86 (s, 1H), 6.08 (s, 1H), 4.28 (d, 2H), 3.04 (d, 2H), 2.45 (s, 3H), 2.17 (s, 3H), 2.15 (s, 3H), 2.12-2.16 (m, 2H), 1.87-1.91 (m, 3H), 1.69-1.72 (m, 2H), 1.62 (s, 3H), 1.34-1.41 (m, 2H), 0.80-0.83 (m, 1H), 0.43-0.46 (m, 2H), 0.01-0.06 (m, 2H).

In a 50 mL single-necked flask, 11E (180 mg, 0.47 mmol) was added and dissolved in DMF (6 mL), and then triethylamine (127 mg, 1.26 mmol) and HATU (239 mg, 0.63 mmol) were added. The mixture was stirred at room temperature for 0.5 h, intermediate 5 (186 mg, 0.84 mmol) was added, and the resulting mixture was stirred at room temperature for 5 h. Water (10 mL) was added to the reaction liquid, and the mixture was extracted with EA (20 mL×3). The combined organic phase was dried over anhydrous sodium sulfate and concentrated, and the residue was separated by column chromatography (DCM:MeOH=20:1) to obtain isomer 2 (60 mg, yield: 24%) of compound 11.

LC-MS (ESI): m/z=532.2 $[M+H]^+$.

$^1$H NMR (400 MHz, DMSO-$d_6$) δ 11.49 (s, 1H), 8.00 (t, 1H), 6.86 (s, 1H), 6.07 (s, 1H), 4.27 (d, 2H), 3.01 (d, 2H), 2.45 (s, 3H), 2.17 (s, 3H), 2.14 (s, 3H), 2.12-2.16 (m, 2H), 1.82-1.87 (m, 3H), 1.69-1.72 (m, 2H), 1.62 (s, 3H), 1.33-1.42 (m, 2H), 0.78-0.81 (m, 1H), 0.41-0.44 (m, 2H), 0.00-0.05 (m, 2H).

Embodiment 12

7-chloro-2-(1-(3,3-difluorocyclobutyl)piperidin-4-yl)-2,4-dimethyl-N-((6-methyl-4-(methylthio)-2-oxo-1,2-dihydropyridin-3-yl)methyl)benzo[d][1,3]dioxole-5-carboxamide (compound 12)

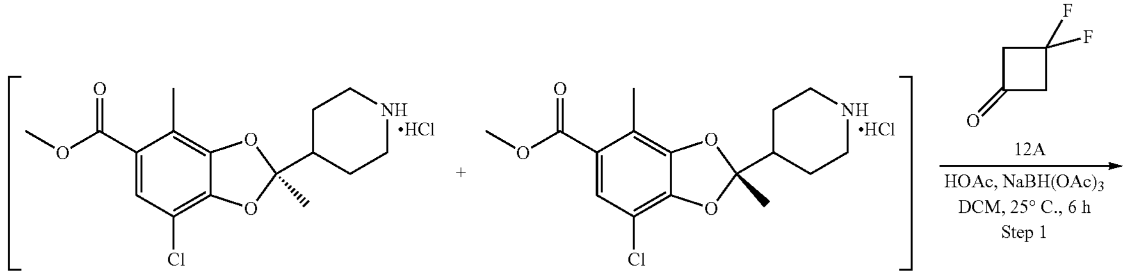

Intermediate 3 and intermediate 4

-continued

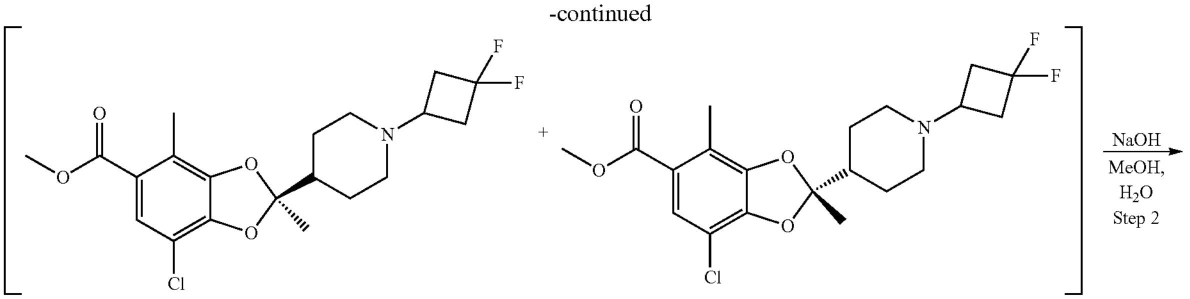

12B & 12C

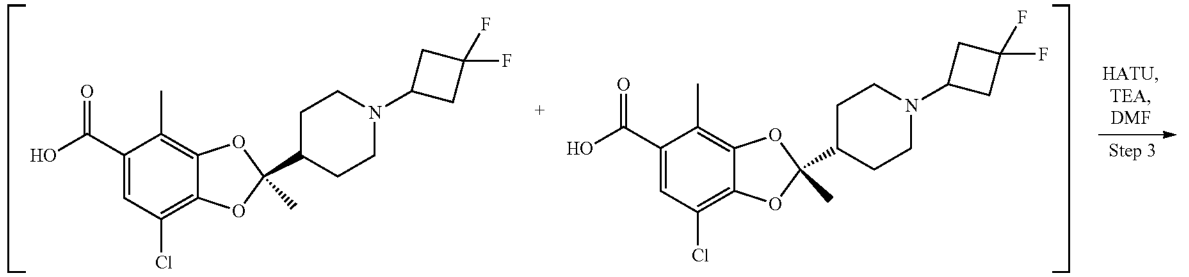

12D & 12E

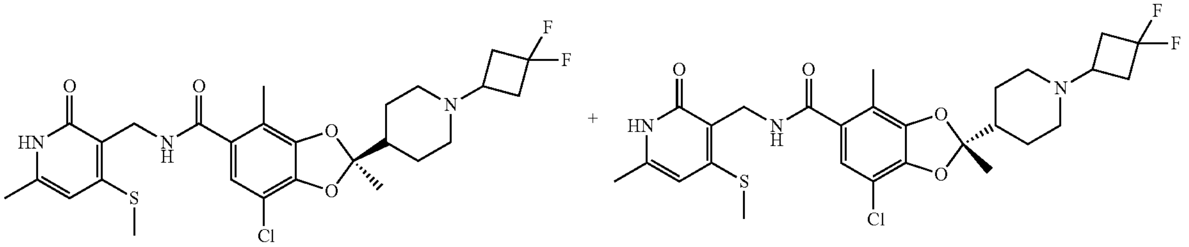

Compound 12

Step 1:

To a 50 mL single-necked flask were successively added compound 12A (682 mg, 4.63 mmol), dichloromethane (20 mL), intermediate 3 (400 mg, 1.10 mmol) and glacial acetic acid (66 mg, 1.10 mmol), and the mixture was stirred at room temperature for 5 h. $NaBH(OAc)_3$ (700 mg, 3.30 mmol) was added, and the mixture was stirred at room temperature for 1 h. The reaction was quenched with water, adjusted to pH 8-9 with saturated sodium bicarbonate and extracted with DCM (3×50 mL). The organic phases were combined, dried over anhydrous sodium sulfate and concentrated, and the residue was separated by column chromatography (DCM:MeOH=20:1) to obtain 12B (120 mg, yield: 26%) as a yellow viscous liquid.

LC-MS (ESI): m/z=416.1 $[M+H]^+$.

To a 50 mL single-necked flask were successively added compound 12A (682 mg, 4.63 mmol), dichloromethane (20 mL), intermediate 4 (400 mg, 1.10 mmol) and glacial acetic acid (66 mg, 1.10 mmol), and the mixture was stirred at room temperature for 5 h. $NaBH(OAc)_3$ (700 mg, 3.30 mmol) was added, and the mixture was stirred at room temperature for 1 h. The reaction was quenched with water, adjusted to pH 8-9 with saturated sodium bicarbonate and extracted with DCM (3×50 mL). The organic phases were combined, dried over anhydrous sodium sulfate and concentrated, and the residue was separated by column chromatography (DCM:MeOH=20:1) to obtain 12C (80 mg, yield: 18%) as a yellow viscous liquid.

LC-MS (ESI): m/z=416.1 $[M+H]^+$.

Step 2:

In a 50 mL single-necked flask, 12B (120 mg, 0.29 mmol) was added and dissolved in methanol (8 mL), and an aqueous NaOH solution (116 mg, 2.9 mmol, 2 mL) was then added. The reaction was stirred at 25° C. TLC showed that the reaction of the raw materials was completed. The reaction liquid was adjusted to pH=3-4 by dropwise adding 2N hydrochloric acid and concentrated under reduced pressure to obtain crude 12D (220 mg, 100%), which was directly used in the next reaction.

LC-MS (ESI): m/z=402.1 $[M+H]^+$.

In a 50 mL single-necked flask, 12C (80 mg, 0.19 mmol) was added and dissolved in methanol (8 mL), and an aqueous NaOH solution (76 mg, 1.9 mmol, 2 mL) was then added. The reaction was stirred at 25° C. TLC showed that the reaction of the raw materials was completed. The reaction liquid was adjusted to pH=3-4 by dropwise adding 2N hydrochloric acid and concentrated under reduced pressure to obtain crude 12E (130 mg, 100%), which was directly used in the next reaction.

LC-MS (ESI): m/z=402.1 $[M+H]^+$.

Step 4:

In a 50 mL single-necked flask, a crude containing 12D (116 mg, 0.29 mmol), DMF (6 mL), triethylamine (88 mg, 0.87 mmol) and HATU (165 mg, 0.44 mmol) were successively added, and the mixture was stirred at room temperature for 0.5 h. Intermediate 5 (128 mg, 0.58 mmol) was added, and the mixture was stirred at room temperature for 5 h. Water (10 mL) was added to the reaction liquid, and the mixture was extracted with EA (20 mL×3). The combined organic phase was dried over anhydrous sodium sulfate and concentrated, and the residue was separated by column chromatography (DCM:MeOH=20:1) to obtain isomer 1 (30 mg, yield: 44%) of compound 12.

LC-MS (ESI): m/z=568.2 $[M+H]^+$.

$^1$H NMR (400 MHz, DMSO-$d_6$) δ 11.49 (s, 1H), 8.02 (t, 1H), 6.86 (s, 1H), 6.07 (s, 1H), 4.27 (d, 2H), 2.84-2.86 (m, 2H), 2.57-2.67 (m, 3H), 2.44 (s, 3H), 2.29-2.41 (m, 2H), 2.16 (s, 3H), 2.14 (s, 3H), 1.86-1.92 (m, 1H), 1.71-1.76 (m, 4H), 1.62 (s, 3H), 1.30-1.40 (m, 2H).

In a 50 mL single-necked flask, a crude containing 12E (76 mg, 0.19 mmol), DMF (6 mL), triethylamine (58 mg, 0.57 mmol) and HATU (108 mg, 0.29 mmol) were successively added, and the mixture was stirred at room temperature for 0.5 h. Intermediate 5 (84 mg, 0.38 mmol) was added, and the mixture was stirred at room temperature for 5 h. Water (10 mL) was added to the reaction liquid, and the mixture was extracted with EA (20 mL×3). The combined organic phase was dried over anhydrous sodium sulfate and concentrated, and the residue was separated by column chromatography (DCM:MeOH=20:1) to obtain isomer 2 (25 mg, yield: 23%) of compound 12.

LC-MS (ESI): m/z=568.2 $[M+H]^+$.

$^1$H NMR (400 MHz, DMSO-$d_6$) δ 8.00 (t, 1H), 6.86 (s, 1H), 6.07 (s, 1H), 4.27 (d, 2H), 2.84-2.86 (m, 2H), 2.57-2.67 (m, 3H), 2.45 (s, 3H), 2.30-2.42 (m, 2H), 2.17 (s, 3H), 2.14 (s, 3H), 1.86-1.92 (m, 1H), 1.71-1.76 (m, 4H), 1.62 (s, 3H), 1.30-1.40 (m, 2H).

Embodiment 13

4-(7-chloro-2,4-dimethyl-5-(((6-methyl-4-(methylthio)-2-oxo-1,2-dihydropyridin-3-yl)methyl)carbamoyl)benzo[d][1,3]dioxol-2-yl)-N-methylpiperidine-1-carboxamide (compound 13)

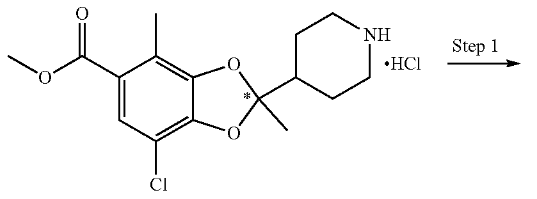

Intermediate 3

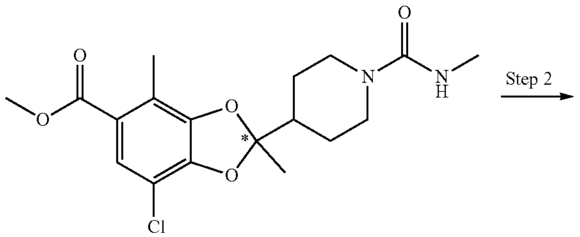

13A

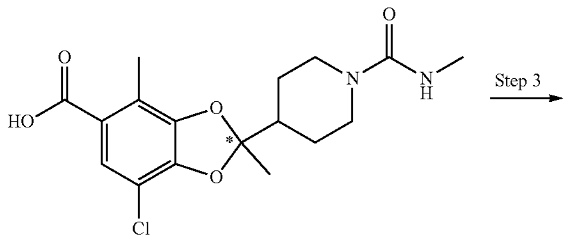

13B

-continued

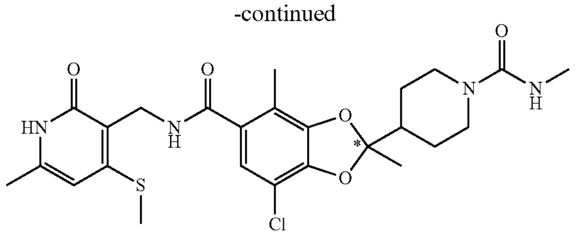

Compound 13

Step 1: methyl-7-chloro-2,4-dimethyl-2-(1-(methylcarbamoyl)piperidin-4-yl)benzo[d][1,3]dioxole-5-carboxylate (13A)

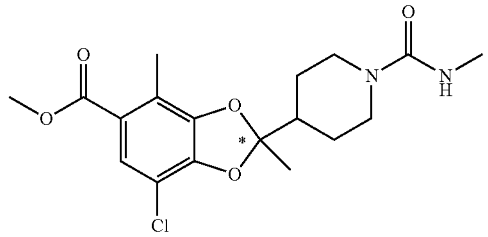

Intermediate 3 (0.4 g, 1.23 mmol) was dissolved in dichloromethane (10 mL), DMAP (0.075 g, 0.61 mmol), DIEA (1.58 g, 12.28 mmol) and triphosgene (0.73 g, 2.46 mmol) were added, and the mixture was reacted in an ice bath for 2 hours. Methanamine hydrochloride (0.38 g, 12.28 mmol) was added, and the mixture was reacted at room temperature for 12 hours. Toluene (10 mL) was added, and the mixture was reacted at 80° C. for 6 hours and cooled to room temperature. Water (30 mL) was added to the reaction liquid. Liquid separation was performed. The aqueous phase was extracted with dichloromethane (30 mL×3). The organic phases were combined, washed with water (50 mL×2), dried over anhydrous sodium sulfate and concentrated to obtain the title compound methyl-7-chloro-2,4-dimethyl-2-(1-(methylcarbamoyl)piperidin-4-yl)benzo[d][1,3]dioxole-5-carboxylate (13A) as a yellow solid (0.4 g, yield: 85%).

LCMS (ESI): m/z=383.1 $[M+1]^+$.

Step 2: 7-chloro-2,4-dimethyl-2-(1-(methylcarbamoyl)piperidin-4-yl)benzo[d][1,3]dioxole-5-carboxylic acid (13B)

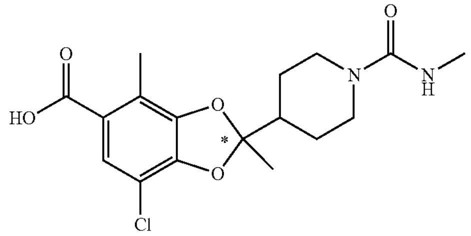 [SMILES: CNC(=O)N1CCC(C2(C)Oc3c(Cl)cc(C(=O)O)c(C)c3O2)CC1]

Methyl-7-chloro-2,4-dimethyl-2-(1-(methylcarbamoyl)piperidin-4-yl)benzo[d][1,3]dioxole-5-carboxylate (13A) (0.3 g, 0.78 mmol) was dissolved in a mixed solvent (12 mL)

of tetrahydrofuran/methanol/water (v/v/v=1/1/1), sodium hydroxide (0.31 g, 7.84 mmol) was added, and the mixture was reacted at room temperature for 4 hours. The reaction liquid was adjusted to about pH=2 by adding a hydrochloric acid solution (6 mol/L) and extracted with ethyl acetate (50 mL×3). The organic phases were combined, washed with water (50 mL), dried over anhydrous sodium sulfate and concentrated to obtain the title compound 7-chloro-2,4-dimethyl-2-(1-(methylcarbamoyl)piperidin-4-yl)benzo[d][1,3]dioxole-5-carboxylic acid(13B) as a pale yellow liquid (0.28 g, yield: 97%).

LCMS (ESI): m/z=369.1 $[M+1]^+$.

Step 3: 4-(7-chloro-2,4-dimethyl-5-(((6-methyl-4-(methylthio)-2-oxo-1,2-dihydropyridin-3-yl)methyl)carbamoyl)benzo[d][1,3]dioxol-2-yl)-N-methylpiperidine-1-carboxamide (compound 13)

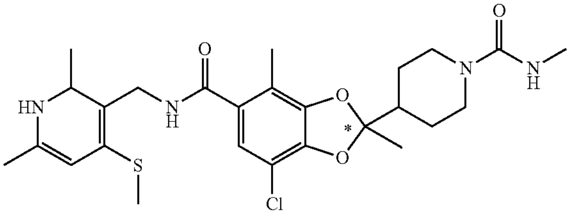

7-chloro-2,4-dimethyl-2-(1-(methylcarbamoyl)piperidin-4-yl)benzo[d][1,3]dioxole-5-carboxylic acid (13B) (0.28 g, 0.76 mmol), intermediate 5 (0.14 g, 0.76 mmol), HATU (0.43 g, 1.14 mmol) and DIEA (0.29 g, 2.28 mmol) were dissolved in dichloromethane (12 mL), and the mixture was reacted at room temperature for 12 hours. The reaction liquid was diluted by adding water. Liquid separation was performed. The aqueous phase was extracted with ethyl acetate (50 mL×3). The organic phases were combined, washed with water (50 mL), dried over anhydrous sodium sulfate and concentrated. The residue was separated and purified by silica gel column chromatography (dichloromethane:methanol (v/v)=1:0-9:1) to obtain the title compound 4-(7-chloro-2,4-dimethyl-5-(((6-methyl-4-(methylthio)-2-oxo-1,2-dihydropyridin-3-yl)methyl) carbamoyl)benzo[d][1,3]dioxol-2-yl)-N-methylpiperidine-1-carboxamide (compound 13) (51 mg, yield: 13%).

$^1$H NMR (400 MHz, DMSO-$d_6$) δ 11.51 (s, 1H), 8.00 (t, 1H), 6.86 (s, 1H), 6.34 (s, 1H), 6.08 (s, 1H), 4.27 (d, 2H), 4.00 (d, 2H), 2.59 (m, 5H), 2.45 (s, 3H), 2.17 (s, 3H), 2.14 (s, 3H), 2.07 (m, 1H), 1.70 (m, 2H), 1.61 (s, 3H), 1.18 (m, 2H).

LCMS (ESI): m/z=535.2 $[M+1]^+$.

Embodiment 14

7-chloro-2,4-dimethyl-N-((6-methyl-4-(methylthio)-2-oxo-1,2-dihydropyridin-3-yl)methyl)-2-(1-(methylsulfonyl)piperidin-4-yl)benzo[d][1,3]dioxole-5-carboxamide (compound 14)

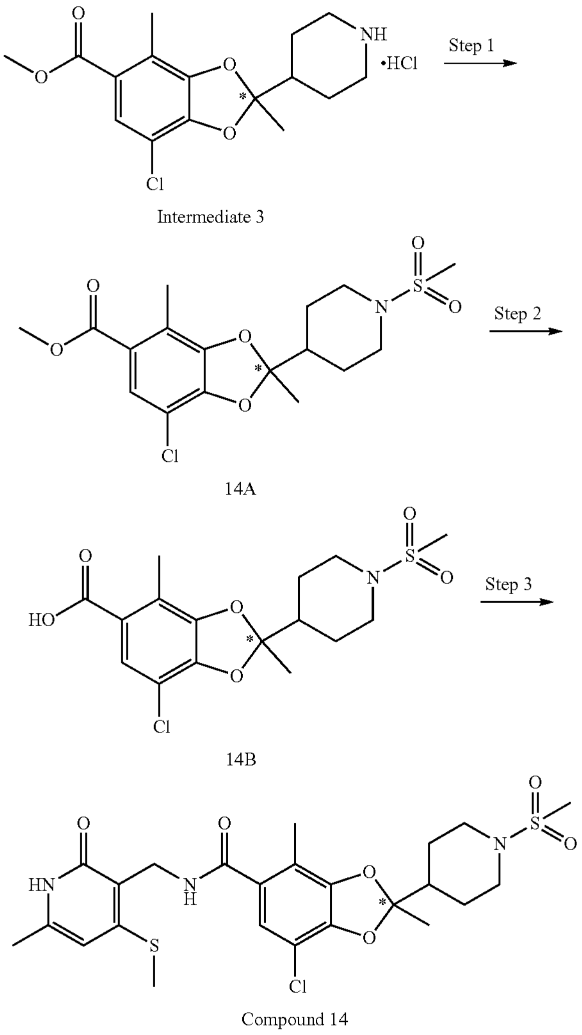

Step 1: methyl-7-chloro-2,4-dimethyl-2-(1-(methylsulfonyl)piperidin-4-yl)benzo[d][1,3]dioxole-5-carboxylate (14A)

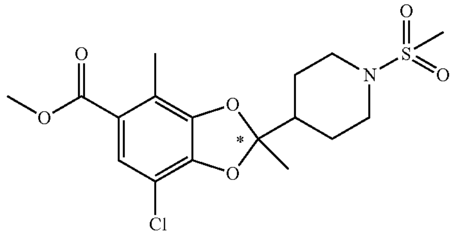

Intermediate 3 (0.4 g, 1.23 mmol) was dissolved in dichloromethane (10 mL). Methyl sulfonyl chloride (0.19 g, 1.47 mmol) and DIEA (0.48 g, 3.68 mmol) were added, and the mixture was reacted at room temperature for 4 hours. Water (30 mL) was added to the reaction liquid. Liquid separation was performed. The aqueous phase was extracted with dichloromethane (30 mL×3). The organic phases were combined, washed with water (50 mL×2), dried over anhydrous sodium sulfate and concentrated to obtain the title compound methyl-7-chloro-2,4-dimethyl-2-(1-(methylsulfonyl)piperidin-4-yl)benzo[d][1,3]dioxole-5-carboxylate (14A) as a yellow solid (0.42 g, yield: 85%).

LCMS (ESI): m/z=404.1 $[M+1]^+$.

Step 2: 7-chloro-2,4-dimethyl-2-(1-(methylsulfonyl) piperidin-4-yl)benzo[d][1,3]dioxole-5-carboxylic acid (14B)

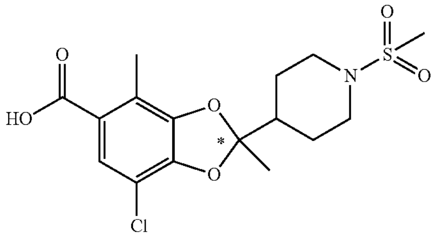 [SMILES: Cc1c(C(=O)O)cc(Cl)c2c1OC(C)(C1CCN(S(C)(=O)=O)CC1)O2]

With reference to the synthetic method (step 2) of compound 13, compound methyl-7-chloro-2,4-dimethyl-2-(1-(methylsulfonyl)piperidin-4-yl)benzo[d][1,3]dioxole-5-carboxylate(14A) (0.42 g, 1.04 mmol) was used as a raw material to obtain the title compound 7-chloro-2,4-dimethyl-2-(1-(methylsulfonyl)piperidin-4-yl)benzo[d][1,3]dioxole-5-carboxylic acid (14B) as a pale yellow liquid (0.40 g, yield: 99%).

LCMS (ESI): m/z=390.1 $[M+1]^+$.

Step 3: 7-chloro-2,4-dimethyl-N-((6-methyl-4-(methylthio)-2-oxo-1,2-dihydropyridin-3-yl)methyl)-2-(1-(methylsulfonyl)piperidin-4-yl)benzo[d][1,3] dioxole-5-carboxamide (compound 14)

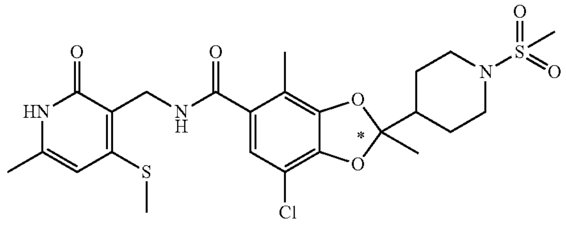

With reference to the synthetic method (step 3) of compound 14, compound 7-chloro-2,4-dimethyl-2-(1-(methylsulfonyl)piperidin-4-yl)benzo[d][1,3]dioxole-5-carboxylic acid (14B) (0.3 g, 0.77 mmol) was used as a raw material to obtain the title compound 7-chloro-2,4-dimethyl-N-((6-methyl-4-(methylthio)-2-oxo-1,2-dihydropyridin-3-yl) methyl)-2-(1-(methylsulfonyl)piperidin-4-yl)benzo[d][1,3] dioxole-5-carboxamide (compound 14) (0.14 g, yield: 33%).

1H NMR (400 MHz, DMSO-$d_6$) δ11.51 (s, 1H), 8.00 (t, 1H), 6.88 (s, 1H), 6.08 (s, 1H), 4.27 (d, 2H), 3.63 (d, 2H), 2.84 (s, 3H), 2.68 (m, 2H), 2.45 (s, 3H), 2.17 (s, 3H), 2.15 (s, 3H), 2.05 (m, 1H), 1.87 (m, 2H), 1.64 (s, 3H), 1.41 (m, 2H).

LCMS (ESI): m/z=556.1 $[M+1]^+$.

Embodiment 15

7-chloro-2,4-dimethyl-N-((6-methyl-4-(methylthio)-2-oxo-1,2-dihydropyridin-3-yl)methyl)-2-(4-((oxetan-3-ylamino)methyl)cyclohexyl)benzo[d][1,3]dioxole-5-carboxamide (compound 15)

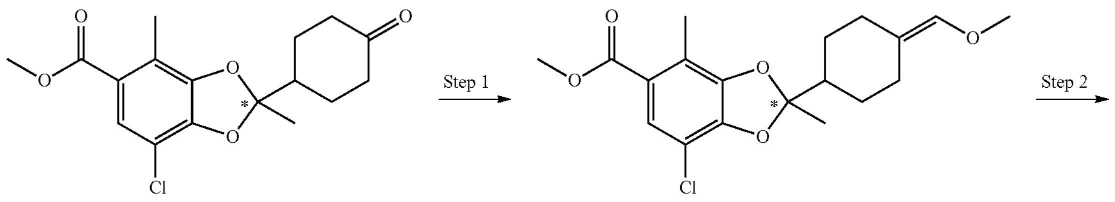

Intermediate 3 15A

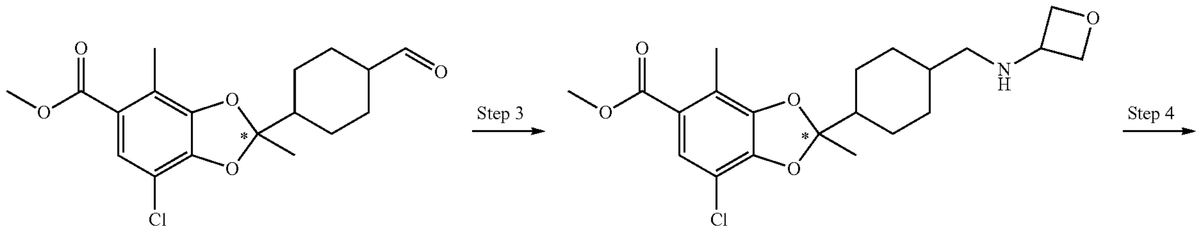

15B 15C

-continued

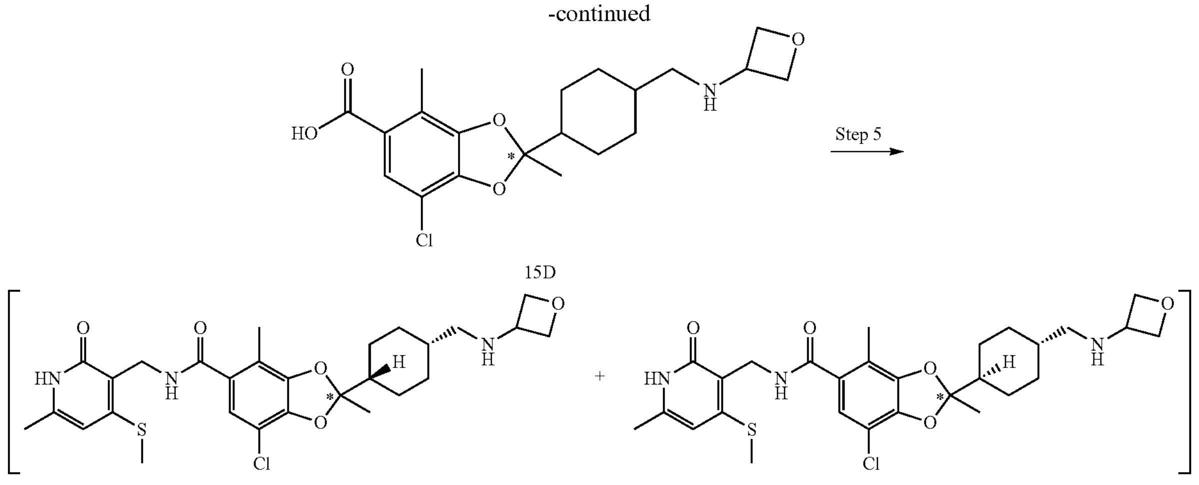

15D

Compound 15

Step 1: methyl-7-chloro-2-(4-(methoxymethylene)cyclohexyl)-2,4-dimethylbenzo[d][1,3]dioxole-5-carboxylate (15A)

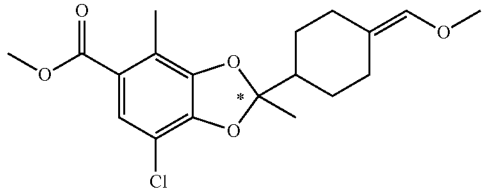

Chloro-(methoxy methyl)-triphenylphosphine (0.91 g, 2.66 mol) was dissolved in tetrahydrofuran (10 mL). Potassium tert-butoxide (0.30 g, 2.66 mmol) was added, and the mixture was reacted at 0° C. for 30 minutes. Methyl 7-chloro-2,4-dimethyl-2-(4-oxocyclohexyl)-1,3-benzodioxole-5-carboxylate (intermediate 3) (0.3 g, 0.89 mmol) was added. The mixture was reacted at 0° C. for 1 hour and at room temperature for 2 hours. A saturated aqueous ammonium chloride solution (30 mL) was added to the reaction liquid, and the mixture was extracted with ethyl acetate (50 mL). Liquid separation was performed. The aqueous phase was extracted with ethyl acetate (50 mL×3). The organic phases were combined, washed with water (50 mL×2), dried over anhydrous sodium sulfate and concentrated to obtain the title compound methyl-7-chloro-2-(4-(methoxymethylene)cyclohexyl)-2,4-dimethylbenzo[d][1,3]dioxole-5-carboxylate (15A) as a colorless oil (0.25 g, yield: 80%).

LCMS (ESI): m/z=367.1 $[M+1]^+$.

Step 2: methyl-7-chloro-2-(4-formylcyclohexyl)-2,4-dimethylbenzo[d][1,3]dioxole-5-carboxylate (15B)

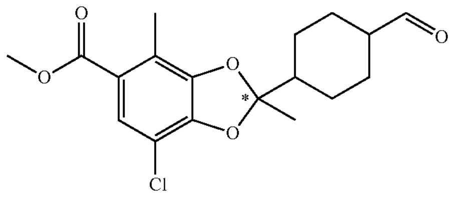 [SMILES: COC(=O)c1cc(Cl)c2c(c1C)OC(C)(C1CCC(C=O)CC1)O2]

Methyl-7-chloro-2-(4-(methoxymethylene)cyclohexyl)-2,4-dimethylbenzo[d][1,3]dioxole-5-carboxylate (15A) (0.25 g, 0.68 mol) was dissolved in a mixed solvent (10 mL) of DCM/HCOOH (v/v=1/1), and the mixture was reacted at room temperature for 1 hour. The reaction liquid was concentrated to obtain the title compound methyl-7-chloro-2-(4-formylcyclohexyl)-2,4-dimethylbenzo[d][1,3]dioxole-5-carboxylate (15B) as a yellow oil (0.23 g, yield: 96%).

LCMS (ESI): m/z=353.1 $[M+1]^+$.

Step 3: methyl-7-chloro-2,4-dimethyl-2-(4-((oxetan-3-ylamino)methyl)cyclohexyl)benzo[d][1,3]dioxole-5-carboxylate (15C)

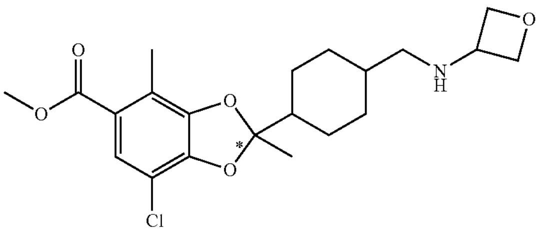 [SMILES: COC(=O)c1cc(Cl)c2c(c1C)OC(C)(C1CCC(CNC3COC3)CC1)O2]

Methyl-7-chloro-2-(4-formylcyclohexyl)-2,4-dimethylbenzo[d][1,3]dioxole-5-carboxylate (15B) (0.35 g, 0.99 mmol) was dissolved in DCM (10 mL). Oxetane-3-amine (0.15 g, 2.05 mmol) and one drop of glacial acetic acid were successively added, and the mixture was stirred at room temperature for 2 hours. Sodium triacetylborohydride (0.42 g, 1.98 mmol) was added, and the mixture was reacted at room temperature for 3 hours. Water (30 mL) was added to the reaction liquid, and the mixture was extracted with ethyl acetate (50 mL×2). The combined organic phase was washed with saturated brine (50 mL), dried over anhydrous sodium sulfate and concentrated under reduced pressure to obtain the title compound methyl-7-chloro-2,4-dimethyl-2-(4-((oxetan-3-ylamino)methyl)cyclohexyl)benzo[d][1,3]dioxole-5-carboxylate (15C) as a yellow solid (0.3 g, yield: 74%).

LCMS (ESI): m/z=410.2 $[M+1]^+$.

Step 4: 7-chloro-2,4-dimethyl-2-(4-((oxetan-3-ylamino)methyl)cyclohexyl)benzo[d][1,3]dioxole-5-carboxylic acid (15D)

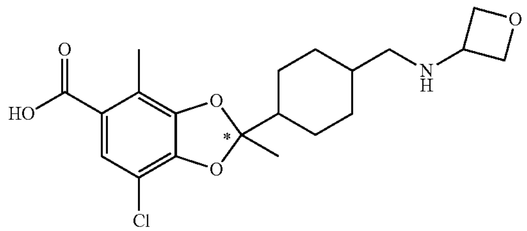 [SMILES: Cc1c(C(=O)O)cc(Cl)c2c1OC(C)(C1CCC(CNC3COC3)CC1)O2]

With reference to the synthetic method (step 2) of compound 13, compound methyl-7-chloro-2,4-dimethyl-2-(4-((oxetan-3-ylamino)methyl)cyclohexyl)benzo[d][1,3]dioxole-5-carboxylate (15C) (0.3 g, 0.73 mmol) was used as a raw material to obtain the title compound 7-chloro-2,4-dimethyl-2-(4-((oxetan-3-ylamino)methyl)cyclohexyl)benzo[d][1,3]dioxole-5-carboxylic acid (15D) as a pale yellow solid (0.27 g, yield: 93%). LCMS (ESI): m/z=396.2 $[M+1]^+$.

Step 5: 7-chloro-2,4-dimethyl-N-((6-methyl-4-(methylthio)-2-oxo-1,2-dihydropyridin-3-yl)methyl)-2-(4-((oxetan-3-ylamino)methyl)cyclohexyl)benzo[d][1,3]dioxole-5-carboxamide (compound 15)

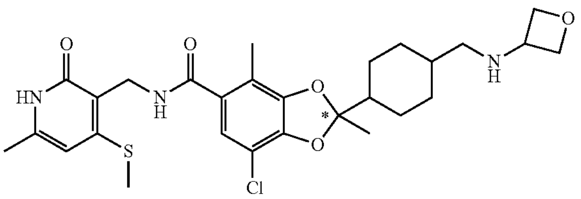 [SMILES: CSc1cc(C)[nH]c(=O)c1CNC(=O)c1cc(Cl)c2c(c1C)OC(C)(C1CCC(CNC3COC3)CC1)O2]

With reference to the synthetic method (step 3) of compound 13, compound 7-chloro-2,4-dimethyl-2-(4-((oxetan-3-ylamino)methyl)cyclohexyl)benzo[d][1,3]dioxole-5-carboxylic acid (15D) (0.3 g, 0.76 mmol) was used as a raw material to obtain the title compound 7-chloro-2,4-dimethyl-N-((6-methyl-4-(methylthio)-2-oxo-1,2-dihydropyridin-3-yl)methyl)-2-(4-((oxetan-3-ylamino)methyl)cyclohexyl)benzo[d][1,3]dioxole-5-carboxamide (compound 15) (0.2 g, yield: 47%). Compound 15 was separated by preparative HPLC to obtain isomer 1 (retention time: 12.27 s, 1.5 mg) of compound 15 and isomer 2 (retention time: 13.25 s, 1.6 mg) of compound 15.

Preparative HPLC separation conditions: instrument: waters 2767 (preparative liquid phase chromatographic instrument); chromatographic column: XSelect@ CSH Prep (19 mm×150 mm); mobile phase A: acetonitrile; mobile phase B: water (containing 5 nM ammonium bicarbonate); gradient elution, mobile phase A: 30%-75%; flow rate: 12 mL/min; elution time: 20 min.

Isomer 1 of compound 15: $^1$H NMR (400 MHz, $CD_3OD$) δ6.90 (s, 1H), 6.27 (s, 1H), 4.90 (t, 2H), 4.66 (m, 2H), 4.49 (s, 2H), 4.39 (m, 1H), 2.82 (d, 2H), 2.52 (s, 3H), 2.29 (s, 3H), 2.19 (s, 3H), 1.97 (m, 5H), 1.62 (m, 3H), 1.29 (m, 3H), 1.11 (m, 2H).

LCMS (ESI): m/z=562.2 $[M+1]^+$.

Isomer 2 of compound 15: $^1$H NMR (400 MHz, $CD_3OD$) δ6.90 (s, 1H), 6.27 (s, 1H), 4.90 (t, 2H), 4.67 (m, 2H), 4.49 (s, 2H), 4.37 (m, 1H), 2.81 (d, 2H), 2.52 (s, 3H), 2.29 (s, 3H), 2.19 (s, 3H), 1.99 (m, 5H), 1.62 (m, 3H), 1.29 (m, 3H), 1.10 (m, 2H).

LCMS (ESI): m/z=562.2 $[M+1]^+$.

Embodiment 16

7-chloro-2-(4-((3,3-difluorocyclobutyl)carbamoyl)cyclohexyl)-2,4-dimethyl-N-((6-methyl-4-(methylthio)-2-oxo-1,2-dihydropyridin-3-yl)methyl)benzo[d][1,3]dioxole-5-carboxamide (compound 16)

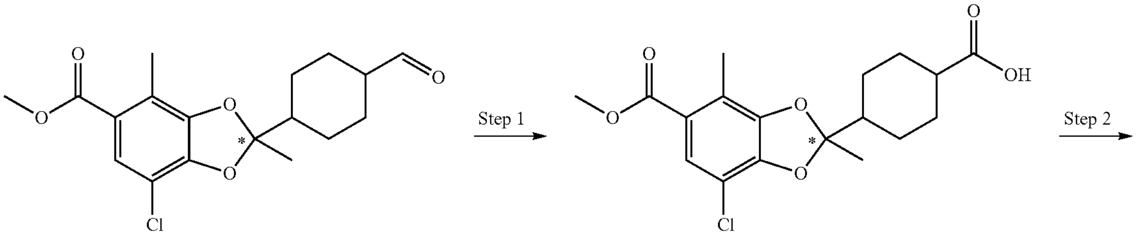

15B

16A

-continued

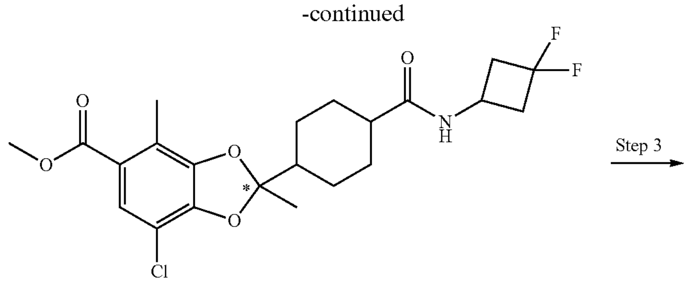

16B

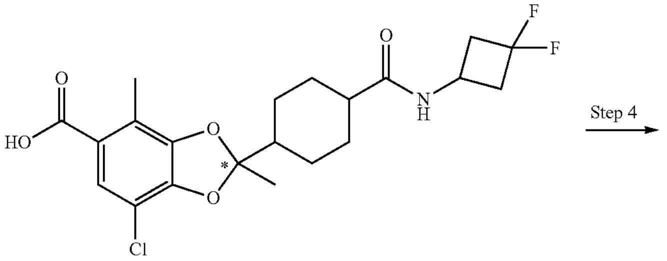

16C

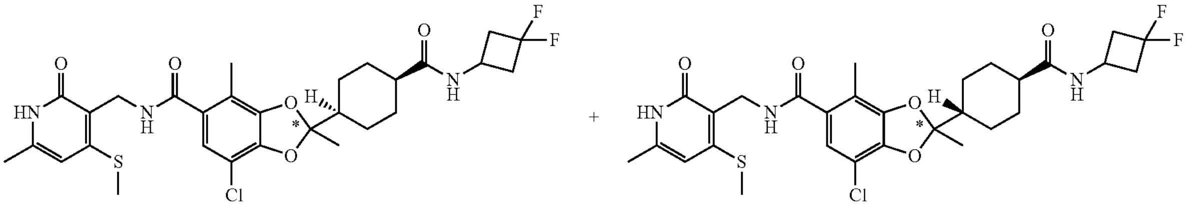

Compound 16

Step 1:

Methyl-7-chloro-2-(4-formylcyclohexyl)-2,4-dimethyl-benzo[d][1,3]dioxole-5-carboxylate (15B) (1 g, 2.84 mmol) and 2-methylbuta-2-en (2.58 g, 36.93 mmol) were dissolved in tert-butanol (15 mL), and then sodium chlorite (0.945 g, 10.5 mmol) and sodium dihydrogen phosphate dihydrate (2.2 g, 14.2 mmol) were dissolved in water (5 mL) and added dropwise to the reaction system. The mixture was reacted at room temperature for 1 h. An aqueous ammonium chloride solution was added, and the resulting mixture was extracted with EA (20 mL×3). The organic phases were combined, washed with a saturated sodium chloride solution, dried over anhydrous sodium sulfate and filtered, and the filtrate was concentrated to obtain the crude compound 4-(7-chloro-5-(methoxycarbonyl)-2,4-dimethyl benzo[d][1,3]dioxol-2-yl)cyclohexanecarboxylic acid (16A) (1.28 g).

LC-MS (ESI): m/z=369.1 $[M+H]^+$.

Step 2:

At room temperature, 4-(7-chloro-5-(methoxycarbonyl)-2,4-dimethyl benzo[d][1,3]dioxol-2-yl)cyclohexanecarboxylic acid (16A) (680 mg, 1.85 mmol), 3,3-difluorocyclobutylamine hydrochloride (396 mg, 2.77 mmol), HATU (1.05 g, 2.77 mmol) and DIPEA (716 mg, 5.55 mmol) were added to DCM (10 mL), and the mixture was reacted at room temperature for 1 h. 15 mL of water was added. Liquid separation was performed. The aqueous phase was extracted with DCM. The organic phases were combined, washed with a saturated sodium chloride solution, dried over anhydrous sodium sulfate and filtered, and the filtrate was concentrated. The residue was separated and purified by silica gel column chromatography (petroleum ether:ethyl acetate (v/v)=0:1-1:3) to obtain the compound methyl 7-chloro-2-(4-(((3,3-difluorocyclobutyl)carbamoyl)cyclohexyl)-2,4-dimethyl benzo[d][1,3]dioxole-5-carboxylate (16B) (600 mg, yield: 71%).

LC-MS (ESI): m/z=458.1 $[M+H]^+$.

Step 3:

To methyl 7-chloro-2-(4-(((3,3-difluorocyclobutyl)carbamoyl)cyclohexyl)-2,4-dimethyl benzo[d][1,3]dioxole-5-carboxylate (16B) (600 mg, 1.32 mmol) were successively added MeOH (10 mL) and an aqueous sodium hydroxide solution (2 mol/L, 3 mL). The mixture was warmed to 65° C. and reacted for 6 h. The reaction liquid was cooled to room temperature and adjusted to pH=5-6 with an aqueous hydrochloric acid solution. Water (20 mL) was added, and the reaction liquid was extracted with DCM. The organic phases were combined, washed with a saturated sodium chloride solution, dried over anhydrous sodium sulfate and filtered, and the filtrate was concentrated to obtain the crude compound 7-chloro-2-(4-(((3,3-difluorocyclobutyl)carbamoyl)cyclohexyl)-2,4-dimethyl benzo[d][1,3]dioxole-5-carboxylic acid (16C) (576 mg).

LC-MS (ESI): m/z=444.1 $[M+H]^+$.

Step 4:

At room temperature, to 7-chloro-2-(4-(((3,3-difluorocyclobutyl)carbamoyl)cyclohexyl)-2,4-dimethyl benzo[d][1,3]dioxole-5-carboxylic acid (16C) (576 mg, 1.3 mmol) were successively added intermediate 5 (572 mg, 2.6 mmol), DCM (10 mL), HATU (988 mg, 2.6 mmol) and N,N-diisopropylethylamin (671 mg, 5.2 mmol), and the mixture was stirred at room temperature for 2 hours, diluted by adding water and extracted with DCM. The organic phase was washed with saturated brine (20 mL), dried over anhydrous sodium sulfate and concentrated under reduced pressure to obtain a crude product, which was separated and purified by preparative HPLC to obtain isomer 1 (110 mg, 14%) of compound 16 and isomer 2 (106 mg, 13%) of compound 16.

Preparative HPLC separation methods: 1. Instrument: waters 2767 (preparative liquid phase chromatographic instrument); chromatographic column: SunFire@ Prep C18 (19 mm×250 mm). 2. The sample was dissolved in DMF and filtered with a 0.45 μm filter to prepare a sample solution. 3. Preparative chromatography conditions: a. composition of mobile phases A and B: mobile phase A: acetonitrile; mobile phase B: water (containing 0.1% TFA); b. gradient elution, mobile phase A: 5% to 50%; c. flow rate: 12 mL/min; d. elution time: 20 min;

retention time for isomer 1 of compound 16: 13.8 min;

$^1$H NMR (400 MHz, DMSO-d6) δ 11.51 (s, 1H), 8.14 (d, 1H), 8.00 (t, 1H), 6.86 (s, 1H), 6.08 (s, 1H), 4.27 (d, 2H), 4.01-3.96 (m, 2H), 2.93-2.86 (m, 2H), 2.49-2.45 (m, 1H), 2.45 (s, 3H), 2.17 (s, 3H), 2.14 (s, 3H), 2.04-1.98 (m, 1H), 1.87-1.85 (m, 3H), 1.80-1.77 (m, 2H), 1.60 (s, 3H), 1.36-1.30 (m, 2H), 1.20-1.07 (m, 2H).

LC-MS (ESI): m/z=610.2 [M+H]$^+$.

retention time for isomer 2 of compound 16: 14.1 min;

$^1$H NMR (400 MHz, DMSO-d6) δ 11.51 (s, 1H), 8.04 (d, 1H), 7.99 (t, 1H), 6.85 (s, 1H), 6.08 (s, 1H), 4.27 (d, 2H), 4.08-4.00 (m, 2H), 2.91-2.80 (m, 2H), 2.59-2.53 (m, 1H), 2.44 (s, 3H), 2.39-2.37 (m, 1H), 2.17 (s, 3H), 2.13 (s, 3H), 2.02-1.98 (m, 2H), 1.90-1.86 (m, 1H), 1.60-1.56 (m, 2H), 1.57 (s, 3H), 1.46-1.42 (m, 4H).

LC-MS (ESI): m/z=610.2 [M+H]$^+$.

Embodiment 17

7-chloro-2-(4-(3,3-difluoroazetidine-1-carbonyl)cyclohexyl)-2,4-dimethyl-N-((6-methyl-4-(methylthio)-2-oxo-1,2-dihydropyridin-3-yl)methyl)benzo[d][1,3]dioxole-5-carboxamide (compound 17)

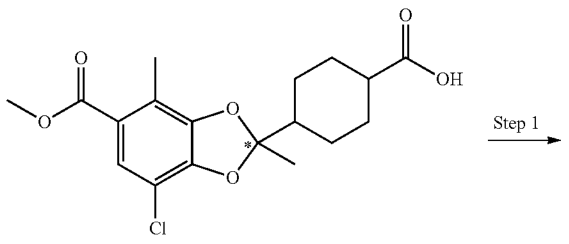

16A

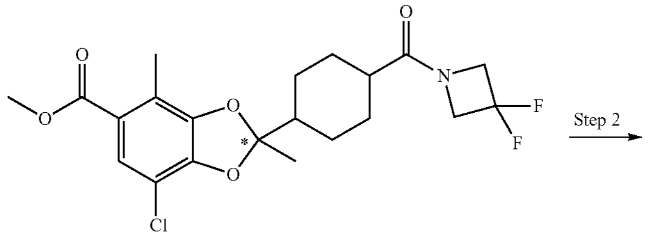

17A

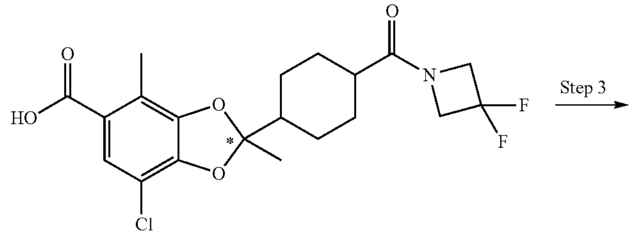

17B

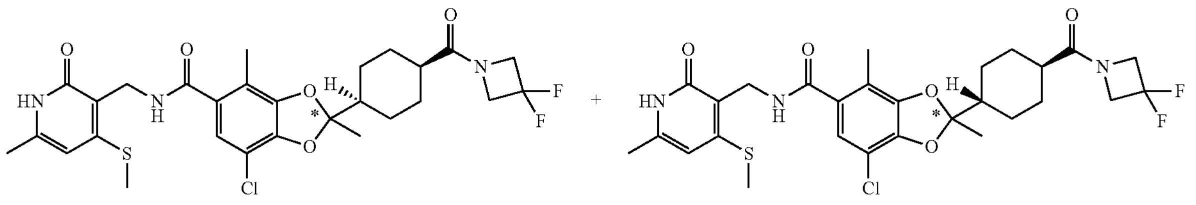

Compound 17

At room temperature, 4-(7-chloro-5-(methoxycarbonyl)-2,4-dimethyl benzo[d][1,3]dioxol-2-yl)cyclohexanecarboxylic acid (16A) (600 mg, 1.63 mmol), 3,3-difluoroazetidine hydrochloride (317 mg, 2.45 mmol), HATU (931 mg, 2.45 mmol) and DIPEA (630 mg, 4.89 mmol) were added to DCM (10 mL), and the mixture was reacted at room temperature for 1 h. 15 mL of water was added. Liquid separation was performed. The aqueous phase was extracted with DCM. The organic phases were combined, washed with a saturated sodium chloride solution, dried over anhydrous sodium sulfate and filtered, and the filtrate was concentrated. The residue was separated and purified by silica gel column chromatography (petroleum ether:ethyl acetate (v/v)=0:1-1:3) to obtain the compound methyl 7-chloro-2-(4-(4-(3,3-difluoroazetidine-1-carbonyl)cyclohexyl)-2,4-dimethyl benzo[d][1,3]dioxole-5-carboxylate (17A) (580 mg, yield: 80%).

LC-MS (ESI): m/z=444.1 $[M+H]^+$.

Step 2:

To methyl 7-chloro-2-(4-(4-(3,3-difluoroazetidine-1-carbonyl)cyclohexyl)-2,4-dimethyl benzo[d][1,3]dioxole-5-carboxylate (17A) (580 mg, 1.31 mmol) were added MeOH (10 mL) and then an aqueous sodium hydroxide solution (2 mol/L, 3 mL). The mixture was warmed to 65° C. and reacted for 6 h. The reaction liquid was cooled to room temperature and adjusted to pH=5-6 with an aqueous hydrochloric acid solution. Water (20 mL) was added, and the reaction liquid was extracted with DCM. The organic phases were combined, washed with a saturated sodium chloride solution, dried over anhydrous sodium sulfate and filtered, and the filtrate was concentrated to obtain the crude compound 7-chloro-2-(4-(3,3-difluoroazetidine-1-carbonyl)cyclohexyl)-2,4-dimethyl benzo[d][1,3]dioxole-5-carboxylic acid (17B) (560 mg).

LC-MS (ESI): m/z=430.1 $[M+H]^+$.

Step 3:

At room temperature, to 7-chloro-2-(4-(3,3-difluoroazetidine-1-carbonyl)cyclohexyl)-2,4-dimethyl benzo[d][1,3]dioxole-5-carboxylic acid (17B) (560 mg, 1.3 mmol) were successively added intermediate 5 (572 mg, 2.6 mmol), DCM (10 mL), HATU (988 mg, 2.6 mmol) and N,N-diisopropylethylamin (671 mg, 5.2 mmol). The mixture was stirred at room temperature for 2 hours, diluted by adding water and extracted with DCM. The organic phase was washed with saturated brine (20 mL), dried over anhydrous sodium sulfate and concentrated under reduced pressure to obtain a crude product, which was separated and purified by preparative HPLC to obtain isomer 1 (90 mg, 12%) of compound 17 and isomer 2 (60 mg, 8%) of compound 17. Preparative HPLC separation methods: 1. Instrument: waters 2767 (preparative liquid phase chromatographic instrument); chromatographic column: SunFire@ Prep C18 (19 mm×250 mm). 2. The sample was dissolved in DMF and filtered with a 0.45 μm filter to prepare a sample solution. 3. Preparative chromatography conditions: a. composition of mobile phases A and B: mobile phase A: acetonitrile; mobile phase B: water (containing 0.1% TFA); b. gradient elution, mobile phase A: 5% to 50%; c. flow rate: 12 mL/min; d. elution time: 20 min; retention time for isomer 1 of compound 17: 14.2 min;

$^1$H NMR (400 MHz, $CDCl_3$) δ 7.01-6.99 (m, 1H), 6.89 (s, 1H), 6.08 (s, 1H), 4.59 (d, 2H), 4.43-4.30 (m, 4H), 2.56-2.51 (m, 1H), 2.49 (s, 3H), 2.32 (s, 3H), 2.25 (s, 3H), 2.01-1.95 (m, 3H), 1.89-1.82 (m, 1H), 1.81-1.70 (m, 4H), 1.59 (s, 3H), 1.55-1.49 (m, 2H).

retention time for isomer 2 of compound 17: 14.5 min;

$^1$H NMR (400 MHz, $CDCl_3$) δ 7.01-6.99 (m, 1H), 6.90 (s, 1H), 6.11 (s, 1H), 4.59 (s, 2H), 4.47-4.41 (m, 2H), 4.33-4.27 (m, 2H), 2.50 (s, 3H), 2.35 (s, 3H), 2.26 (s, 3H), 2.15-2.10 (m, 1H), 2.01-1.98 (m, 2H), 1.93-1.90 (m, 1H), 1.86-1.82 (m, 3H), 1.61 (s, 3H), 1.57-1.54 (m, 2H), 1.29-1.23 (m, 2H).

LC-MS (ESI): m/z=596.2 $[M+H]^+$.

Embodiment 18

7-chloro-2,4-dimethyl-N-((6-methyl-4-(methylthio)-2-oxo-1,2-dihydropyridin-3-yl)methyl)-2-(4-(8-oxo-2,7-diazaspiro[4.4]nonan-2-yl)cyclohexyl)benzo[d][1,3]dioxole-5-carboxamide (compound 18)

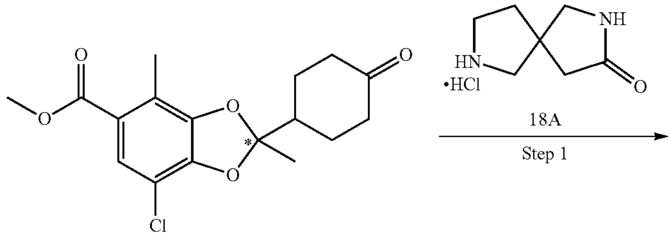

Intermediate 3

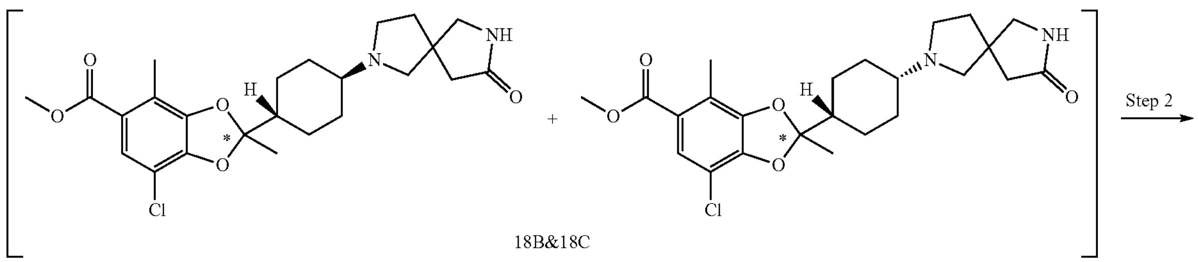

18B&18C

-continued

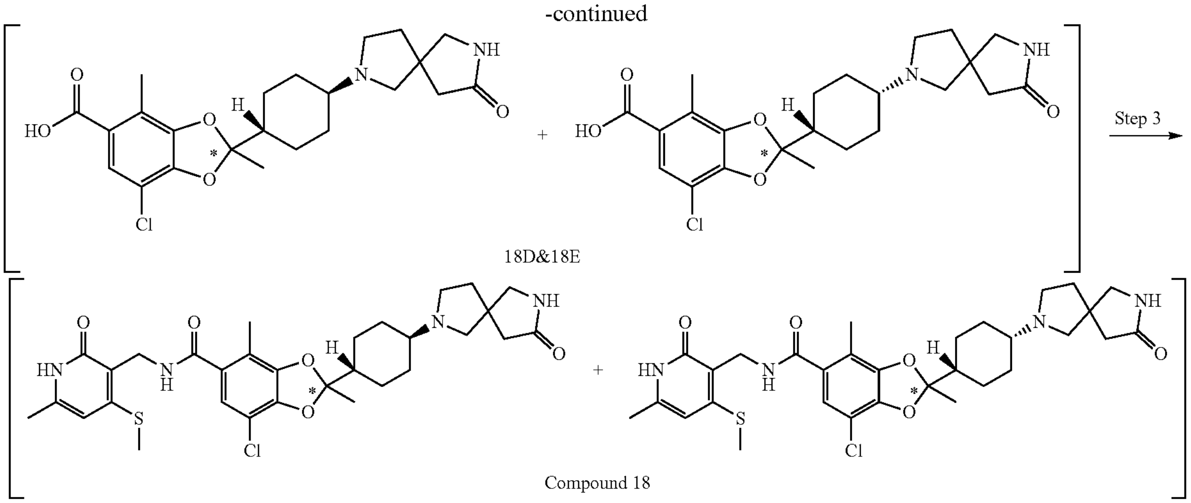

18D&18E

Compound 18

Step 1: methyl-7-chloro-2,4-dimethyl-2-(4-(8-oxo-2,7-diazaspiro[4.4]nonan-2-yl)cyclohexyl)benzo[d][1,3]dioxole-5-carboxylate (18B&18C)

2,7-diazaspiro[4.4]nonan-3-one hydrochloride (18A) (370 mg, 2.1 mmol) and intermediate 3 (580 mg, 1.71 mmol) were dissolved in 1,2-dichloroethan (10 mL). Acetic acid (129 mg, 2.1 mmol) was added dropwise, and the mixture was reacted at room temperature for 1 hour. Sodium triacetoxyborohydride (907 mg, 4.28 mmol) was slowly added, and the mixture was reacted at room temperature for 4 hours. The reaction was quenched by slowly adding water (100 mL) to the reaction liquid. Liquid separation was performed. The aqueous phase was extracted with ethyl acetate (100 mL×3). The organic phases were combined, washed with water (100 mL×2), dried over anhydrous sodium sulfate and concentrated. The residue was separated and purified by silica gel column chromatography (petroleum ether:ethyl acetate (v/v)=0:1-1:1) to obtain the title compound methyl-7-chloro-2,4-dimethyl-2-(4-(8-oxo-2,7-diazaspiro[4.4]nonan-2-yl)cyclohexyl)benzo[d][1,3]dioxole-5-carboxylate (18B&18C), wherein 18B has an Rf value of about 0.50 (petroleum ether:ethyl acetate (v/v)=2:1) as a white powder solid (320 mg, yield: 340%); and 18C has an Rf value of about 0.38 (petroleum ether:ethyl acetate (v/v)=2:1) as a white powder solid (210 mg, yield: 24%).

LC-MS (ESI): m/z=463.1 $[M+H]^+$.

Step 2: 7-chloro-2,4-dimethyl-2-(4-(8-oxo-2,7-diazaspiro[4.4]nonan-2-yl)cyclohexyl)benzo[d][1.3]dioxole-5-carboxylic acid (18D&18E 18B (320 mg, 0.69 mmol) was dissolved in methanol (15 mL). An aqueous sodium hydroxide solution (2M, 5 mL) was added dropwise, and the mixture was reacted at room temperature for 16 hours. The reaction liquid was adjusted to about pH=3 by slowly dropwise adding dilute hydrochloric acid. Water (50 mL) was added. The aqueous phase was extracted with ethyl acetate (50 mL×5). The organic phases were combined, washed with water (50 mL), dried over anhydrous sodium sulfate and concentrated to obtain the title compound 7-chloro-2,4-dimethyl-2-(4-(8-oxo-2,7-diazaspiro[4.4]nonan-2-yl)cyclohexyl)benzo[d][1,3]dioxole-5-carboxylic acid (18D) as a white powder solid (280 mg, yield: 90%).

LC-MS (ESI): m/z=449.3 $[M+H]^+$.

18C (210 mg, 0.45 mmol) was dissolved in methanol (15 mL). An aqueous sodium hydroxide solution (2M, 5 mL) was added dropwise, and the mixture was reacted at room temperature for 16 hours. The reaction liquid was adjusted to about pH=3 by slowly dropwise adding dilute hydrochloric acid. Water (50 ml) was added. The aqueous phase was extracted with ethyl acetate (50 mL×5). The organic phases were combined, washed with water (50 mL), dried over anhydrous sodium sulfate and concentrated to obtain the title compound 7-chloro-2,4-dimethyl-2-(4-(8-oxo-2,7-diazaspiro[4.4]nonan-2-yl)cyclohexyl)benzo[d][1,3]dioxole-5-carboxylic acid (18E) as a white powder solid (180 mg, yield: 86%).

LC-MS (ESI): m/z=449.3 $[M+H]^+$.

Step 3: 7-chloro-2,4-dimethyl-N-((6-methyl-4-(methylthio)-2-oxo-1,2-dihydropyridin-3-yl)methyl)-2-(4-(8-oxo-2,7-diazaspiro[4.4]nonan-2-yl)cyclohexyl)benzo[d][1,3]dioxole-5-carboxamide (compound 18)

7-chloro-2,4-dimethyl-2-(4-(8-oxo-2,7-diazaspiro[4.4]nonan-2-yl)cyclohexyl)benzo[d][1,3]dioxole-5-carboxylic acid (18D) (280 mg, 0.62 mmol), 3-(aminomethyl)-6-methyl-4-(methylthio)pyridine-2(1H)-one hydrochloride (intermediate 5) (207 mg, 0.94 mmol) and HATU (285 mg, 0.75 mmol) were dissolved in DMF (15 mL). DIPEA (316 mg, 3.1 mmol) was added dropwise. The mixture was reacted at room temperature for 8 hours. Water (50 mL) was added. The aqueous phase was extracted with ethyl acetate (50 mL×5). The organic phases were combined, washed with water (50 mL), dried over anhydrous sodium sulfate and concentrated. The residue was separated and purified by silica gel column chromatography (dichloromethane:methanol (v/v)=0:1-10:1) to obtain the title compound 7-chloro-2,4-dimethyl-N-((6-methyl-4-(methylthio)-2-oxo-1,2-dihydropyridin-3-yl)methyl)-2-(4-(8-oxo-2,7-diazaspiro[4.4]nonan-2-yl)cyclohexyl)benzo[d][1,3]dioxole-5-carboxamide (isomer 1 of compound 18) (65 mg, yield: 22%).

$^1$H NMR (400 MHz, DMSO-$d_6$) δ 7.99 (t, 1H), 7.52 (s, 1H), 6.86 (s, 1H), 6.08 (s, 1H), 4.27 (d, 2H), 3.13 (dd, 2H), 2.72 (dd, 4H), 2.45 (s, 3H), 2.16 (dd, 7H), 1.98 (s, 2H), 1.89 (d, 3H), 1.85 (d, 2H), 1.78 (dd, 2H), 1.60 (s, 3H), 1.24-1.10 (m, 4H).

LC-MS (ESI): m/z=615.3 [M+H]$^+$.

7-chloro-2,4-dimethyl-2-(4-(8-oxo-2,7-diazaspiro[4.4]nonan-2-yl)cyclohexyl)benzo[d][1,3]dioxole-5-carboxylic acid (18E) (180 mg, 0.40 mmol), 3-(aminomethyl)-6-methyl-4-(methylthio)pyridine-2(1H)-one hydrochloride (intermediate 5) (133 mg, 0.60 mmol) and HATU (183 mg, 0.48 mmol) were dissolved in DMF (15 mL). DIPEA (203 mg, 2.1 mmol) was added dropwise. The mixture was reacted at room temperature for 8 hours. Water (50 mL) was added. The aqueous phase was extracted with ethyl acetate (50 mL×5). The organic phases were combined, washed with water (50 mL), dried over anhydrous sodium sulfate and concentrated. The residue was separated and purified by silica gel column chromatography (dichloromethane:methanol (v/v)=0:1-10:1) to obtain the title compound 7-chloro-2,4-dimethyl-N-((6-methyl-4-(methylthio)-2-oxo-1,2-dihydropyridin-3-yl)methyl)-2-(4-(8-oxo-2,7-diazaspiro[4.4]nonan-2-yl)cyclohexyl)benzo[d][1,3]dioxole-5-carboxamide (isomer 2 of compound 18) (68 mg, yield: 28%).

$^1H$ NMR (400 MHz, DMSO-$d_6$) δ 8.01 (t, 1H), 7.68 (s, 1H), 6.89 (s, 1H), 6.08 (s, 1H), 4.28 (d, 2H), 3.73-3.61 (m, 2H), 3.28 (ddd, 5H), 2.45 (d, 3H), 2.42-2.22 (m, 2H), 2.17 (s, 6H), 2.13-1.88 (m, 5H), 1.69 (dd, 6H), 1.61 (s, 3H).

LC-MS (ESI): m/z=615.3 [M+H]$^+$.

Embodiment 19

7-chloro-2-(1-(1-fluorocyclopropane-1-carbonyl)piperidin-4-yl)-2,4-dimethyl-N-((6-methyl-4-(methylthio)-2-oxo-1,2-dihydropyridin-3-yl)methyl)benzo[d][1,3]dioxole-5-carboxamide (compound 19)

Compound 19

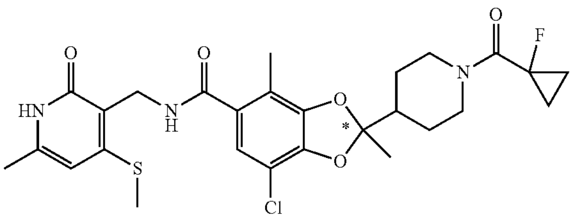

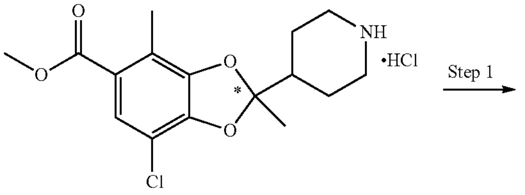

Intermediate 3

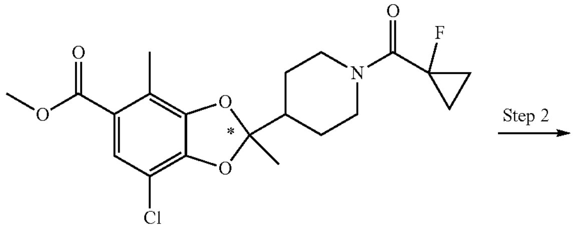

19A

-continued

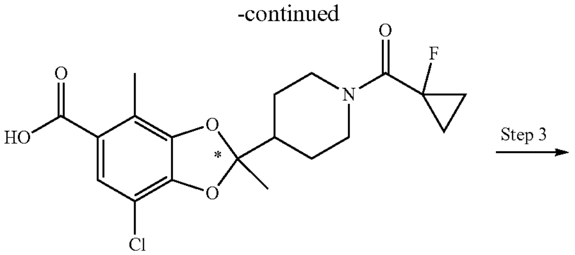

19B

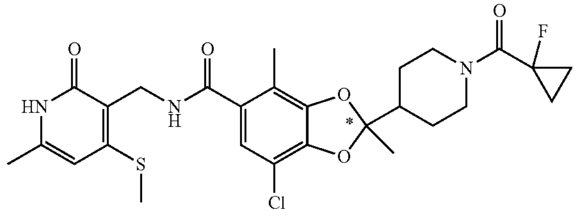

Compound 19

Step 1: methyl 7-chloro-2-(1-(1-fluorocyclopropane-1-carbonyl)piperidin-4-yl)-2,4-dimethylbenzo[d][1,3]dioxole-5-carboxylate (19A)

In a 50 mL single-necked flask, 1-fluorocyclopropane-1-carboxylic acid (96 mg, 0.92 mmol) was added and dissolved in dichloromethane (5 mL). Triethylamine (230 mg, 2.30 mmol) and HATU (350 mg, 0.92 mmol) were added, and the mixture was stirred at room temperature for 0.5 h. Intermediate 3 (250 mg, 0.77 mmol) was added, and the mixture was stirred at room temperature for 16 h. Water (10 mL) was added, and the reaction liquid was extracted twice with DCM (10 mL×2). The organic phases were combined, dried over anhydrous sodium sulfate and concentrated. The residue was separated and purified by silica gel column chromatography (petroleum ether:ethyl acetate (v/v)=4: 1-2: 1) to obtain the title compound methyl 7-chloro-2-(1-(1-fluorocyclopropane-1-carbonyl)piperidin-4-yl)-2,4-dimethylbenzo[d][1,3]dioxole-5-carboxylate (19A) as a yellow oil (200 mg, yield: 63%).

LCMS m/z=412.2 [M+1]$^+$.

Step 2: 7-chloro-2-(1-(1-fluorocyclopropane-1-carbonyl)piperidin-4-yl)-2,4-dimethylbenzo[d][1,3]dioxole-5-carboxylic acid (19B)

In a 50 mL single-necked flask, 19A (200 mg, 0.49 mmol) was added and dissolved in methanol (2 mL), tetrahydrofuran (2 mL) and water (2 mL). Lithium hydroxide (58 mg, 4.0 mmol) was added. The mixture was stirred at room temperature for 5 h, adjusted to pH 3-4 with hydrochloric acid (2 M) and extracted with dichloromethane (20 mL×2). The organic phases were combined, dried over anhydrous sodium sulfate and concentrated under reduced pressure to obtain the title compound 7-chloro-2-(1-(1-fluorocyclopropane-1-carbonyl)piperidin-4-yl)-2,4-dimethylbenzo[d][1,3]dioxole-5-carboxylic acid (19B) as a white solid (150 mg, 78% yield).

LCMS m/z=398.1 [M+1]$^+$.

Step 3: 7-chloro-2-(1-(1-fluorocyclopropane-1-carbonyl)piperidin-4-yl)-2,4-dimethyl-N-((6-methyl-4-(methylthio)-2-oxo-1,2-dihydropyridin-3-yl)methyl) benzo[d][1,3]dioxole-5-carboxamide (compound 19)

In a 50 mL single-necked flask, 19B (150 mg, 0.38 mmol) was added and dissolved in DMF (5 mL). Triethylamine (110 mg, 1.10 mmol) and HATU (170 mg, 0.45 mmol) were added. The mixture was stirred at room temperature for 0.5 h. Intermediate 5 (100 mg, 0.57 mmol) was added, and the mixture was stirred at room temperature for 16 h. Water (10 mL) was added, and the reaction liquid was extracted twice with EA (10 mL×2). The organic phase was dried over anhydrous sodium sulfate and concentrated. The residue was separated and purified by a liquid phase preparative column (liquid phase preparative conditions: C18 reverse-phase preparative column, mobile phase: deionized water containing 0.1% trifluoroacetic acid (A) and acetonitrile containing 0.1% trifluoroacetic acid (B), gradient elution, mobile phase B: 20%-70%, elution time: 20 min, flow rate: 15 mL/min, and retention time: 13.4 min, column temperature: 30° C.) to obtain the title compound 19 (20 mg, 9.4% yield).

$^1$H NMR (400 MHz, $CDCl_3$) δ 7.06 (s, 1H), 6.92 (s, 1H), 6.10 (s, 1H), 4.60 (s, 2H), 3.14-2.57 (m, 2H), 2.50 (s, 3H), 2.35 (s, 3H), 2.26 (s, 3H), 2.14 (tt, 1H), 2.01-1.85 (m, 6H), 1.62 (s, 3H), 1.55-1.39 (m, 2H), 1.21 (dd, 2H).

LCMS m/z=564.1 $[M+1]^+$.

Embodiment 20

7-chloro-2,4-dimethyl-N-((6-methyl-4-(methylthio)-2-oxo-1,2-dihydropyridin-3-yl)methyl)-2-(1-(1-(trifluoromethyl)cyclopropane-1-carbonyl)piperidin-4-yl)benzo[d][1,3]dioxole-5-carboxamide (compound 20)

Compound 20

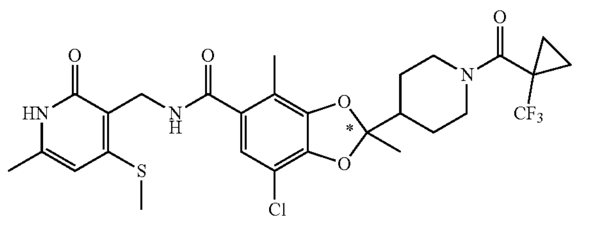

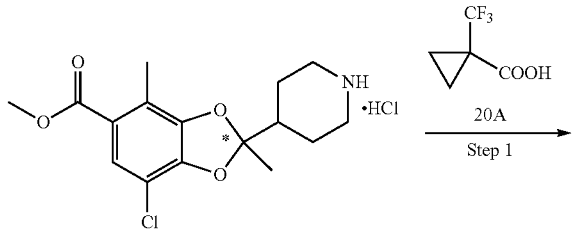

Intermediate 3

-continued

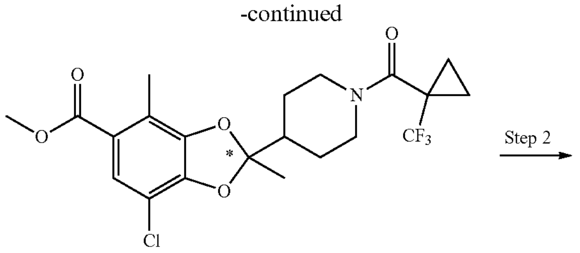

20B

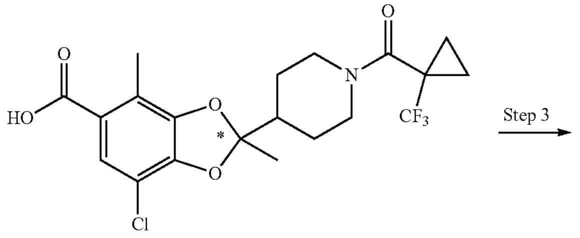

20C

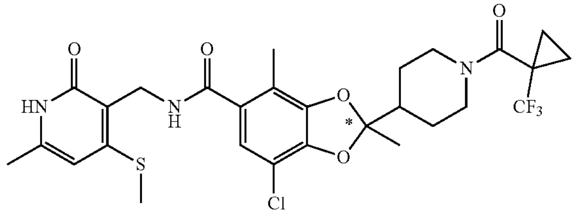

Compound 20

Step 1: methyl 7-chloro-2,4-dimethyl-2-(1-(1-(trifluoromethyl)cyclopropane-1-carbonyl)-piperidin-4-yl)benzo[d][1,3]dioxole-5-carboxylate (20B)

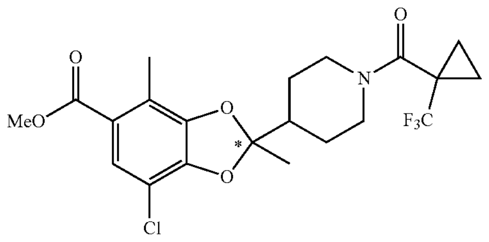 [SMILES: COC(=O)c1cc(Cl)c2c(c1C)OC(C)(C1CCN(C(=O)C3(C(F)(F)F)CC3)CC1)O2]

Intermediate 3 (0.25 g, 0.69 mmol) and 1-trifluoromethylcyclopropane-1-carboxylic acid (20A) (159 mg, 1.04 mmol) were dissolved in DCM (5 mL). EDCI (0.26 g, 1.38 mmol), HOBt (0.19 g, 1.38 mmol) and DIPEA (0.6 mL) were added. The mixture was reacted at room temperature for 3 hours. To the reaction liquid were added DCM and water. Liquid separation was performed. The aqueous phase was extracted with DCM (10 mL×3). The organic phases were combined, washed with saturated brine (10 mL), dried over anhydrous sodium sulfate and concentrated. The residue was separated and purified by silica gel column chromatography (petroleum ether:ethyl acetate (v/v)=10:1-5:1) to obtain the title compound methyl 7-chloro-2,4-dimethyl-2-(1-(1-(trifluoromethyl)cyclopropane-1-carbonyl)-piperidin-4-yl)benzo[d][1,3]dioxole-5-carboxylate (20B) as a light yellow solid (228 mg, yield: 72%).

LCMS m/z=462.1 $[M+1]^+$.

Step 2: 7-chloro-2,4-dimethyl-2-(1-(1-(trifluoromethyl)cyclopropane-1-carbonyl)piperidin-4-yl)benzo[d][1,3]dioxole-5-carboxylic acid (20C)

Methyl 7-chloro-2,4-dimethyl-2-(1-(1-(trifluoromethyl)cyclopropane-1-carbonyl)-piperidin-4-yl)benzo[d][1,3]dioxole-5-carboxylate (20B) (228 mg, 0.49 mmol) was dissolved in methanol (3 mL) and water (3 mL). KOH (56 mg, 1 mmol) was added, and the mixture was reacted at room temperature overnight. The reaction liquid was distilled under reduced pressure to remove methanol, adjusted to pH 7 with a 1N HCl solution and extracted with DCM (10 mL×3). The organic phases were combined, washed with saturated brine (10 mL), dried over anhydrous sodium sulfate and concentrated to obtain the title compound 7-chloro-2,4-dimethyl-2-(1-(1-(trifluoromethyl)cyclopropane-1-carbonyl)piperidin-4-yl)benzo[d][1,3]dioxole-5-carboxylic acid (20C) as a crude (200 mg), which was directly used in the next step.

LCMS m/z=448.1 $[M+1]^+$.

Step 3: 7-chloro-2,4-dimethyl-N-((6-methyl-4-(methylthio)-2-oxo-1,2-dihydropyridin-3-yl)methyl)-2-(1-(1-(trifluoromethyl)cyclopropane-1-carbonyl)piperidin-4-yl)benzo[d][1,3]dioxole-5-carboxamide (compound 20)

7-chloro-2,4-dimethyl-2-(1-(1-(trifluoromethyl)cyclopropane-1-carbonyl) piperidin-4-yl)benzo[d][1,3]dioxole-5-carboxylic acid (20C) as a crude (200 mg, 0.45 mmol) was dissolved in DCM (8 mL). HATU (254 mg, 0.68 mmol) and DIPEA (1.2 mL) were added. The mixture was reacted at room temperature for 15 minutes. 3-(aminomethyl)-6-methyl-4-(methylthio)pyridine-2(1H)-one hydrochloride (intermediate 5) (137 mg, 0.63 mmol) was then added, and the resulting mixture was reacted at room temperature for another 2 hours. The reaction was quenched with water and extracted with DCM (10 mL×3). The organic phases were combined, washed with saturated brine (10 mL), dried over anhydrous sodium sulfate and concentrated. The residue was separated and purified by silica gel column chromatography (DCM:MeOH (v/v)=50: 1-5:1) to obtain the title compound 7-chloro-2,4-dimethyl-N-((6-methyl-4-(methylthio)-2-oxo-1,2-dihydropyridin-3-yl)methyl)-2-(1-(1-(trifluoromethyl)cyclopropane-1-carbonyl)piperidin-4-yl)benzo[d][1,3]dioxole-5-carboxamide (compound 20) (120 mg, yield: 43%).

$^1$H NMR (400 MHz, $CDCl_3$) δ 6.90 (s, 1H), 6.51 (s, 1H), 6.48 (s, 1H), 4.63 (m, 2H), 4.06 (m, 2H), 2.57 (s, 3H), 2.50 (s, 3H), 2.23 (s, 3H), 2.17-2.06 (m, 1H), 1.94 (m, 2H), 1.63 (s, 3H), 1.41 (m, 2H), 1.33 (t, 2H), 1.15 (t, 2H).

LCMS m/z=614.1 $[M+1]^+$.

Embodiment 21

7-chloro-2,4-dimethyl-N-((6-methyl-4-(methylthio)-2-oxo-1,2-dihydropyridin-3-yl)methyl)-2-(1-(2-methylthiazole-4-carbonyl)piperidin-4-yl)benzo[d][1,3]dioxole-5-carboxamide (compound 21)

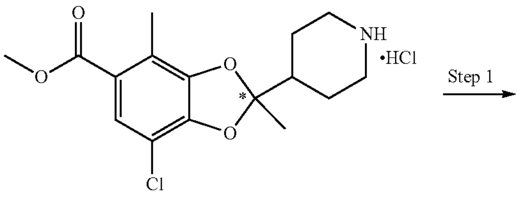

Intermediate 3

-continued

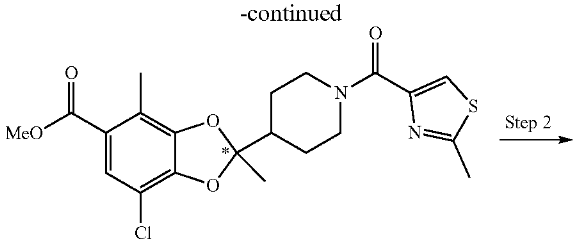

21A

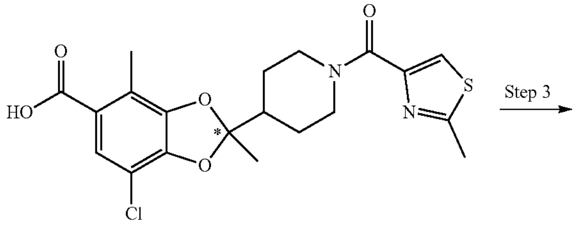

21B

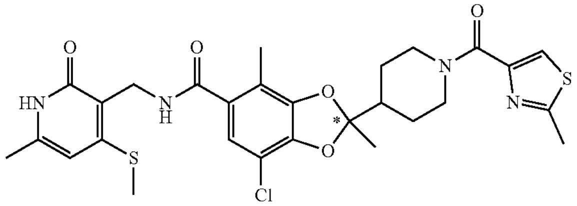

Compound 21

Step 1: methyl 7-chloro-2,4-dimethyl-2-(1-(2-methylthiazole-4-carbonyl)piperidin-4-yl)benzo[d][1,3]dioxole-5-carboxylate (21A)

Intermediate 3 (0.25 g, 0.77 mmol) was dissolved in dichloromethane (10 mL). N,N-diisopropylethylamin (0.30 g, 2.30 mmol), HATU (0.35 g, 0.92 mmol) and 2-methyl-1,3-thiazole-4-carboxylic acid (0.13 g, 0.92 mmol) were added. After the addition, the mixture was reacted at room temperature overnight. The reaction was quenched by dropwise adding a saturated aqueous ammonium chloride solution. A saturated aqueous sodium chloride solution (30 mL) was added, and the reaction liquid was extracted with ethyl acetate (25 mL×3). The combined organic phase was dried over anhydrous sodium sulfate, filtered and concentrated. The residue was separated and purified by silica gel column chromatography (petroleum ether:ethyl acetate (v/v)=3:1) to obtain the title compound 21A as a white solid (0.34 g, 98.2%).

LC-MS (ESI): m/z=451.1 $[M+H]^+$.

Step 2: 7-chloro-2,4-dimethyl-2-(1-(2-methylthiazole-4-carbonyl)piperidin-4-yl)benzo[d][1,3]dioxole-5-carboxylic acid (21B)

21A (0.34 g, 0.75 mmol) was dissolved in methanol (10 mL). Water (2 mL) and sodium hydroxide (0.30 g, 7.50 mmol) were added. After the addition, the mixture was reacted at room temperature overnight, adjusted to pH=2-3 by dropwise adding a dilute aqueous solution of hydrochloric acid (2M) and extracted with ethyl acetate (25 mL×3). The combined organic phase was dried over anhydrous sodium sulfate, filtered and concentrated to obtain the title compound 21B as a white solid (0.33 g, 99.7%).

LC-MS (ESI): m/z=437.1 $[M+H]^+$.

Step 3: 7-chloro-2,4-dimethyl-N-((6-methyl-4-(methylthio)-2-oxo-1,2-dihydropyridin-3-yl)methyl)-2-(1-(2-methylthiazole-4-carbonyl)piperidin-4-yl) benzo[d][1,3]dioxole-5-carboxamide (compound 21)

21B (0.33 g, 0.76 mmol) was dissolved in DMF (10 mL). N,N-diisopropylethylamin (0.29 g, 2.27 mmol), HATU (0.34 g, 0.91 mmol) and intermediate 5 (0.17 g, 0.91 mmol) were added. After the addition, the mixture was reacted at room temperature overnight. The reaction was quenched by dropwise adding a saturated aqueous ammonium chloride solution. A saturated aqueous sodium chloride solution (30 mL) was added. The reaction liquid was extracted with ethyl acetate (25 mL). The organic phase was washed with a saturated aqueous sodium chloride solution (25 mL×3), dried over anhydrous sodium sulfate, filtered and concentrated. The residue was separated and purified by silica gel column chromatography (dichloromethane:methanol (v/v) =40:1, 30:1, 10:1) to obtain the product, compound 21 (40 mg, 8.9%).

$^1$H NMR (400 MHz, $CDCl_3$) δ 7.69 (s, 1H), 6.91 (s, 1H), 6.04 (s, 1H), 4.59 (d, 2H), 3.15-2.82 (m, 2H), 2.72 (s, 3H), 2.48 (s, 3H), 2.31 (s, 3H), 2.26 (s, 3H), 2.14 (m, 1H), 1.85 (m, 4H), 1.63 (s, 3H), 1.53 (m, 2H).

LC-MS (ESI): m/z=603.1 [M+H]$^+$.

Embodiment 22

7-chloro-2-(1-(2-cyanoacetyl)piperidin-4-yl)-2,4-dimethyl-N-((6-methyl-4-(methylthio)-2-oxo-1,2-dihydropyridin-3-yl)methyl)benzo[d][1,3]dioxole-5-carboxamide (compound 22)

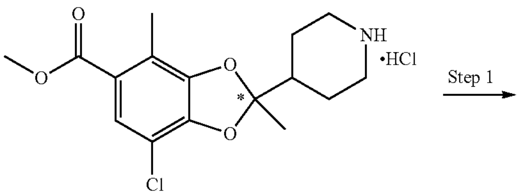

Intermediate 3

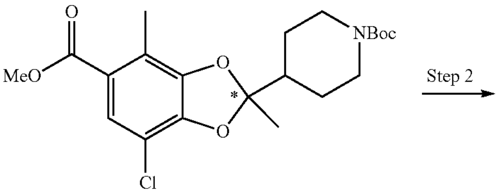

22A

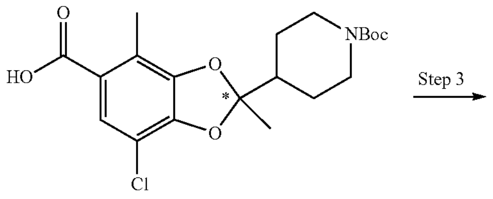

22B

-continued

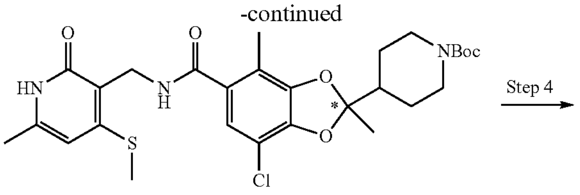

22C

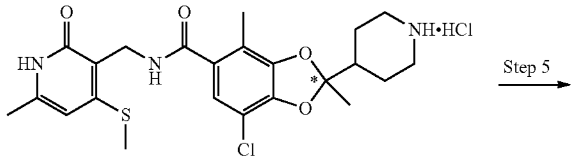

22D

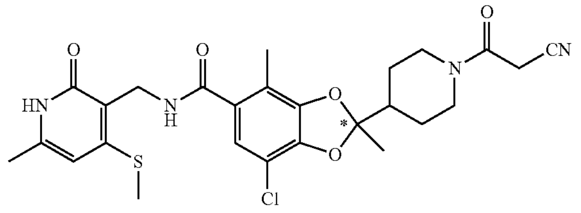

Compound 22

Step 1: tert-butyl 4-(7-chloro-5-(methoxycarbonyl)-2,4-dimethylbenzo[d][1,3]dioxol-2-yl)piperidine-1-carboxylate (22A)

Intermediate 3 (0.25 g, 0.76 mmol) was dissolved in DCM (10 mL). Triethylamine (0.23 g, 2.30 mmol), $(Boc)_2O$ (0.20 g, 0.92 mmol) and DMAP (9 mg, 0.07 mmol) were added. After the addition, the mixture was reacted at room temperature overnight. The reaction was quenched by dropwise adding a saturated aqueous ammonium chloride solution. A saturated aqueous sodium chloride solution (30 mL) was added, and the reaction liquid was extracted with dichloromethane (25 mL×3). The combined organic phase was dried over anhydrous sodium sulfate, filtered and concentrated. The residue was separated and purified by silica gel column chromatography (petroleum ether:ethyl acetate (v/v) =10:1) to obtain the title compound 22A as a white solid (0.33 g, 99%). LC-MS (ESI): m/z=426.2 [M+H]$^+$.

Step 2: 2-(1-(tert-butoxycarbonyl)piperidin-4-yl)-7-chloro-2,4-dimethylbenzo[d][1,3]dioxole-5-carboxylic acid (22B)

22A (0.33 g, 0.80 mmol) was dissolved in methanol (10 mL). Water (2 mL) and sodium hydroxide (0.30 g, 8.0 mmol) were added. After the addition, the mixture was reacted at room temperature overnight, adjusted to pH=2-3 by dropwise adding a dilute hydrochloric acid aqueous solution (2M) and extracted with ethyl acetate (25 mL×3). The combined organic phase was dried over anhydrous sodium sulfate, filtered and concentrated to obtain the title compound 22B as a white solid (0.33 g, 99.7%).

LC-MS (ESI): m/z=412.1 [M+H]$^+$.

Step 3: tert-butyl 4-(7-chloro-2,4-dimethyl-5-(((6-methyl-4-(methylthio)-2-oxo-1,2-dihydropyridin-3-yl)methyl)carbamoyl)benzo[d][1,3]dioxol-2-yl)piperidine-1-carboxylate (22C)

22B (0.33 g, 0.80 mmol) was dissolved in DMF (10 mL). N,N-diisopropylethylamin (0.31 g, 2.40 mmol), HATU (0.36 g, 0.96 mmol) and intermediate 5 (0.17 g, 0.96 mmol) were added. After the addition, the mixture was reacted at room temperature overnight. The reaction was quenched by dropwise adding a saturated aqueous ammonium chloride solution. A saturated aqueous sodium chloride solution (30 mL) was added, and the reaction liquid was extracted with ethyl acetate (25 mL×3). The combined organic phase was washed with a saturated aqueous sodium chloride solution (25 mL×3), dried over anhydrous sodium sulfate, filtered and concentrated. The residue was separated and purified by silica gel column chromatography (petroleum ether:ethyl acetate (v/v)=1:1) to obtain the title compound 22C as a white solid (0.30 g, 64.8%).

LC-MS (ESI): m/z=578.2 $[M+H]^+$.

Step 4: 7-chloro-2,4-dimethyl-N-((6-methyl-4-(methylthio)-2-oxo-1,2-dihydropyridin-3-yl)methyl)-2-(piperidin-4-yl)benzo[d][1,3]dioxole-5-carboxamide hydrochloride (22D)

22C (0.30 g, 0.52 mmol) was dissolved in a solution of hydrogen chloride in 1,4-dioxane (10 mL, 4M). After the addition, the mixture was reacted at room temperature overnight and concentrated to obtain the title compound 22D as a white solid (0.24 g, 96.8%).

LC-MS (ESI): m/z=478.2 $[M+H]^+$.

Step 5: 7-chloro-2-(1-(2-cyanoacetyl)piperidin-4-yl)-2,4-dimethyl-N-((6-methyl-4-(methylthio)-2-oxo-1,2-dihydropyridin-3-yl)methyl)benzo[d][1,3]dioxole-5-carboxamide (compound 22)

22D (0.33 g, 0.50 mmol) was dissolved in DCM (10 mL). N,N-diisopropylethylamin (0.19 g, 1.50 mmol), HATU (0.23 g, 0.60 mmol) and cyanoacetic acid (0.05 g, 0.60 mmol) were added. After the addition, the mixture was reacted at room temperature overnight. The reaction was quenched by dropwise adding a saturated aqueous ammonium chloride solution. A saturated aqueous sodium chloride solution (30 mL) was added. The reaction liquid was extracted with dichloromethane (25 mL×3). The organic phase was dried over anhydrous sodium sulfate, filtered and concentrated. The residue was separated and purified by silica gel column chromatography (dichloromethane:methanol (v/v)=50:1, 25:1, 10:1) to obtain the title compound 22 (75 mg, 27.0%).

$^1H$ NMR (400 MHz, $CDCl_3$) δ 6.89 (s, 1H), 6.44 (s, 1H), 4.65 (m, 3H), 3.78 (d, 1H), 3.48 (s, 2H), 3.16 (t, 1H), 2.68-2.51 (m, 4H), 2.49 (s, 3H), 2.23 (s, 3H), 2.13 (t, 1H), 2.04-1.88 (m, 2H), 1.64 (s, 3H), 1.46 (dd, 2H).

LC-MS (ESI): m/z=545.2 $[M+H]^+$.

Embodiment 23

7-chloro-2-(1-((1S,2S)-2-fluorocyclopropanecarbonyl)piperidin-4-yl)-2,4-dimethyl-N-((6-methyl-4-(methylthio)-2-oxo-1,2-dihydropyridin-3-yl)methyl)benzo[d][1,3]dioxole-5-carboxamide (compound 23)

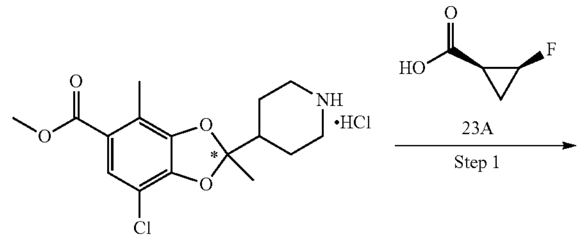

Intermediate 3

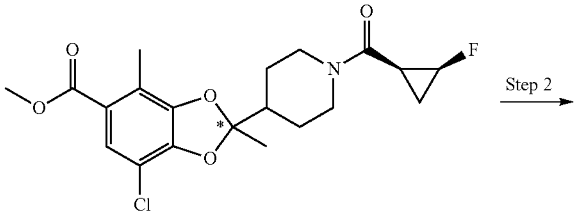

23B

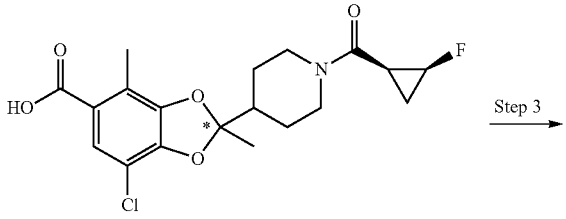

23C

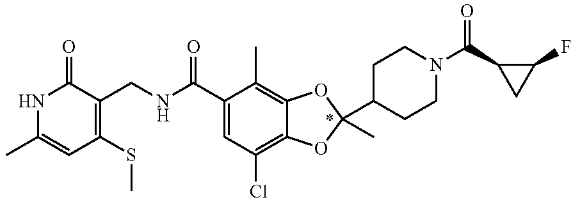

Compound 23

Step 1:

Intermediate 3 (250 mg, 0.69 mmol) was dissolved in dichloromethane (5 mL). Compound 23A (70 mg, 0.7 mmol), HATU (380 mg, 1.04 mmol) and triethylamine (210 mg, 2.1 mmol) were successively added, and the reaction was stirred at room temperature overnight. The reaction liquid was concentrated. The residue was separated by silica gel column chromatography to obtain the title compound 23B (270 mg, 95%)

LC-MS (ESI): m/z=412.8$[M+H]^+$.

Step 2:

Compound 23B (270 mg, 0.8 mmol) was dissolved in methanol (5 mL). A solution of sodium hydroxide (160 mg, 4 mmol) in water (0.5 mL) was added, and the reaction was stirred at room temperature overnight, adjusted to pH 4-5 by adding dilute hydrochloric acid and extracted with ethyl acetate. The organic phase was concentrated under reduced pressure to obtain the title compound 23C as a crude (300 mg).

LC-MS (ESI): m/z=398.1[M+H]$^+$.

Step 3:

The crude of compound 23C (300 mg) was dissolved in DMF (5 mL). DIPEA (277 mg, 2.15 mmol), HATU (371 mg, 0.98 mmol) and intermediate 5 (186 mg, 0.85 mmol) were successively added, and the reaction was stirred at room temperature overnight, diluted by adding water and extracted with ethyl acetate. The organic phase was concentrated under reduced pressure to obtain a crude product, which was further separated and purified by preparative HPLC to obtain compound 23 (100 mg, two-step yield: 27%). Preparative HPLC separation conditions: preparation instrument: Waters 2767, preparative column: SunFire C18; mobile phase system: acetonitrile: 1% trifluoroacetic acid aqueous solution; retention time 9.83 min.

LC-MS (ESI): m/z=565.0[M+H]$^+$.

$^1$H NMR (400 MHz, Chloroform-d) δ 7.04 (s, 1H), 6.92 (s, 1H), 6.14 (s, 1H), 4.62 (s, 1H), 4.69 (d, 2H), 4.21 (s, 1H), 3.06 (s, 1H), 2.61 (s, 1H), 2.50 (s, 3H), 2.31 (s, 3H), 2.26 (s, 3H), 2.11 (t, 1H), 1.84 (s, 2H), 1.43 (d, 2H), 1.28 (d, 2H), 0.97 (s, 2H), 0.91-0.81 (m, 2H), 0.74 (dd, 2H).

Embodiment 24

7-chloro-2-(1-cyclopropylpiperidin-4-yl)-2,4-dimethyl-N-((6-methyl-4-(methylthio)-2-oxo-1,2-dihydropyridin-3-yl)methyl)benzo[d][1,3]dioxole-5-carboxamide (compound 24)

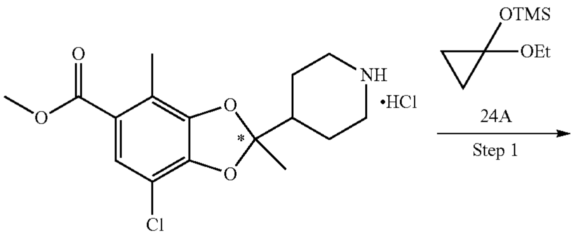

Intermediate 3

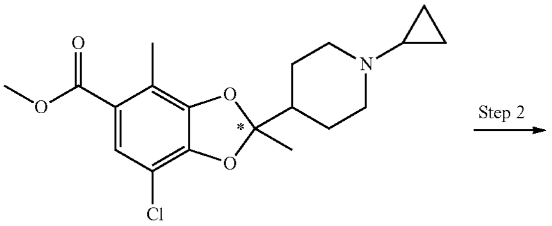

24B

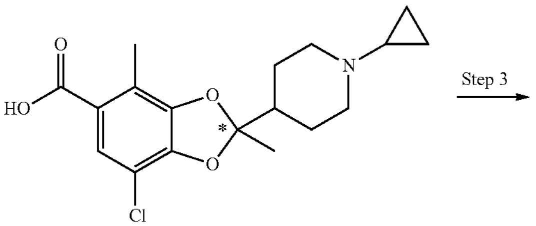

24C

-continued

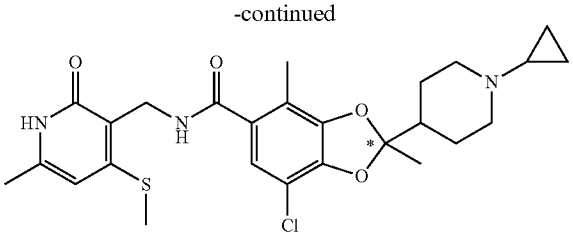

Compound 24

Step 1:

Intermediate 3 (250 mg, 0.69 mmol) was dissolved in methanol (10 mL). Compound 24A (181 mg, 1.04 mmol) and acetic acid (1 mL) were successively added. The reaction was stirred at room temperature for half an hour and then warmed to reflux overnight. After the reaction was cooled to room temperature, the mixture was concentrated under reduced pressure to remove the reaction liquid. The obtained residue was separated by column chromatography (eluent: PE:EA=20%-50%) to obtain compound 24B (196 mg, 78%).

LC-MS (ESI): m/z=366.7[M+H]$^+$.

Step 2:

Compound 24B (196 mg, 0.54 mmol) was dissolved in methanol (5 mL). A solution of sodium hydroxide (108 mg, 2.7 mmol) in water (0.5 mL) was added, and the reaction was stirred at room temperature overnight, adjusted to pH 4-5 by adding dilute hydrochloric acid and extracted with ethyl acetate. The organic phase was concentrated under reduced pressure to obtain compound 24C as a crude (320 mg).

LC-MS (ESI): m/z=352.7[M+H]$^+$.

Step 3:

The crude of compound 24C (320 mg) was dissolved in DMF (5 mL). DIPEA (209 mg, 1.62 mmol), HATU (267 mg, 0.70 mmol) and intermediate 5 (130 mg, 0.59 mmol) were successively added, and the reaction was stirred at room temperature overnight, diluted by adding water and extracted with ethyl acetate. The organic phase was concentrated under reduced pressure to obtain a crude product, which was separated by preparative HPLC to obtain compound 24 (180 mg, two-step yield: 64%).

Preparative HPLC separation methods: instrument: waters 2767 (preparative liquid phase chromatographic instrument); chromatographic column: SunFire@ Prep C18 (19 mm×250 mm); Preparative chromatography conditions: composition of mobile phases A and B: mobile phase A: acetonitrile; mobile phase B: water; gradient elution, mobile phase A: 20%-75%; flow rate: 12 mL/min; elution time: 20 min; retention time: 14.15 min.

$^1$H NMR (400 MHz, Chloroform-d) δ 12.15 (s, 1H), 7.13 (t, 1H), 6.90 (s, 1H), 6.02 (s, 1H), 4.59 (d, 2H), 3.10 (d, 2H), 2.48 (s, 3H), 2.32-2.27 (m, 3H), 2.25 (s, 3H), 2.18-2.05 (m, 3H), 1.91-1.76 (m, 4H), 1.60-1.41 (m, 4H), 0.49-0.35 (m, 4H).

LC-MS (ESI): m/z=546.2[M+H]$^+$.

Embodiment 25
7-chloro-4-(methoxy-d3)-2-(4-(3-methoxyazetidin-1-yl)cyclohexyl)-2-methyl-N-((6-methyl-4-(methylthio)-2-oxo-1,2-dihydropyridin-3-yl)methyl)benzo[d][1,3]dioxole-5-carboxamide (compound 25)
Compound 25
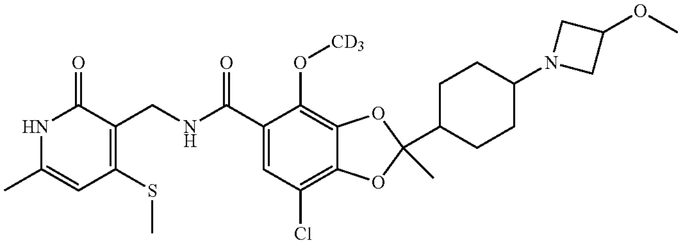
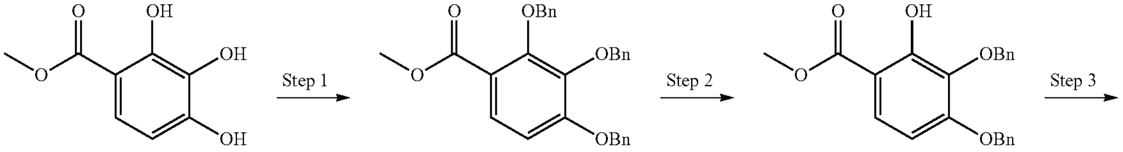
1b 25A 25B
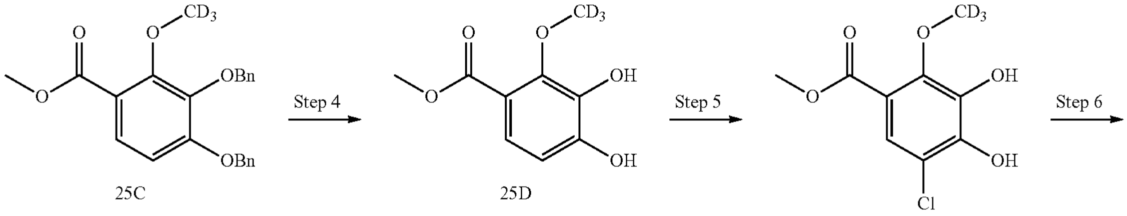
25C 25D 25E
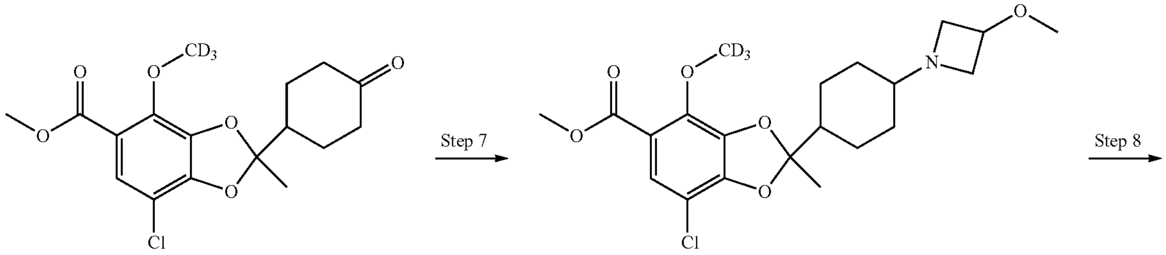
25F 25G
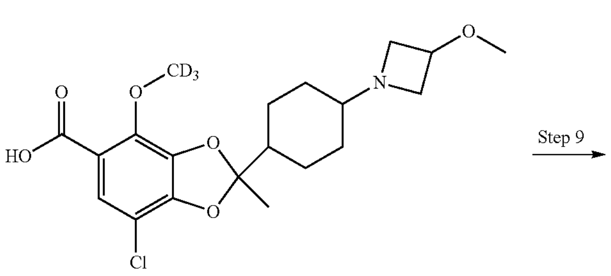
25H -continued

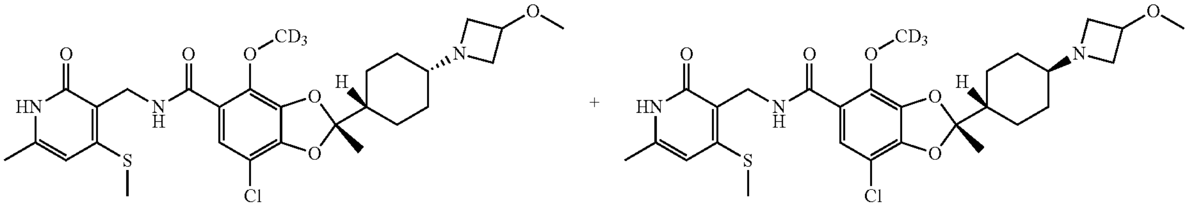

Compound 25, 4 isomers

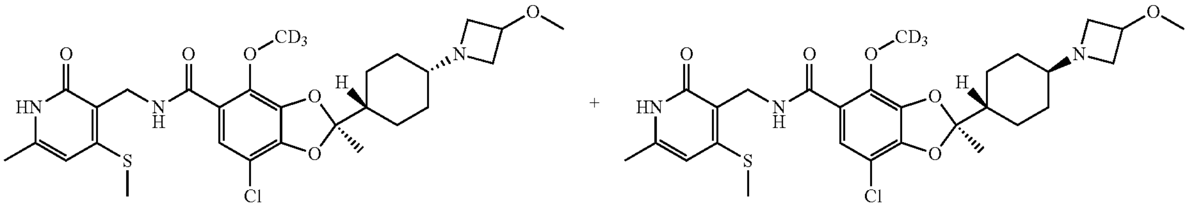

Step 1: methyl 2,3,4-tris(benzyloxy)benzoate (25A)

Methyl 2,3,4-trihydroxylbenzoate (1b) (9.5 g, 51.6 mmol) and benzyl bromide (26.5 g, 155 mmol) were dissolved in DMF (76 mL). Potassium carbonate (22 g, 155 mmol) was added, and the mixture was reacted at room temperature for 20 hours. The reaction liquid was poured into water (500 mL) and extracted with ethyl acetate (500 mL×2). The organic phases were combined, dried over anhydrous sodium sulfate and concentrated. The residue was separated and purified by silica gel column chromatography (petroleum ether:ethyl acetate (v/v)=10:1-4:1) to obtain the title compound methyl 2,3,4-tris(benzyloxy)benzoate (25A) as a white solid (16.0 g, yield: 69%).

LCMS m/z=455.2 $[M+1]^+$.

Step 2: methyl 3,4-bis(benzyloxy)-2-hydroxybenzoate (25B)

Methyl 2,3,4-tris(benzyloxy)benzoate (25A) (16 g, 35.2 mmol) was added to acetic acid (95 mL), and then concentrated hydrochloric acid (9.5 mL) was added. The mixture was warmed to 40° C. and reacted for 2 hours. The reaction liquid was poured into water (500 mL) and extracted with ethyl acetate (500 mL×2). The organic phases were combined, dried over anhydrous sodium sulfate and concentrated. The residue was separated and purified by silica gel column chromatography (petroleum ether:ethyl acetate (v/v)=10: 1-1:1) to obtain the title compound methyl 3,4-bis(benzyloxy)-2-hydroxybenzoate (25B) as a white solid (8.0 g, yield: 62.5%).

LCMS m/z=365.2 $[M+1]^+$.

Step 3: methyl 3,4-bis(benzyloxy)-2-(methoxy-d3)benzoate (25C)

Methyl 3,4-bis(benzyloxy)-2-hydroxybenzoate (25B) (7.5 g, 19.7 mmol) was added to acetone (80 mL), and then deuterated iodomethane (6.0 g, 39.4 mmol) and potassium carbonate (14.3 g, 98.4 mmol) were added. The mixture was reacted at room temperature for 16 hours. The reaction liquid was poured into water (100 mL) and extracted with ethyl acetate (100 mL×2). The organic phases were combined, dried over anhydrous sodium sulfate and concentrated. The residue was separated and purified by silica gel column chromatography (petroleum ether:ethyl acetate (v/v)=10:1-3:1) to obtain the title compound methyl 3,4-bis(benzyloxy)-2-(methoxy-d3)benzoate (25C) as a white solid (6.0 g, yield: 72.3%).

LCMS m/z=382.2 $[M+1]^+$.

Step 4: methyl 3,4-dihydroxy-2-(methoxy-d3)benzoate (25D)

Methyl 3,4-bis(benzyloxy)-2-(methoxy-d3)benzoate (25C) (5.5 g, 14.4 mmol) was added to methanol (55 mL). 10% palladium on carbon (500 mg) was then added, and the mixture was subjected to hydrogen replacement three times and reacted at room temperature under hydrogen atmosphere for 16 hours. The reaction liquid was filtered and concentrated to dryness. The residue was separated and purified by silica gel column chromatography (petroleum ether:ethyl acetate (v/v)=5: 1-1:2) to obtain the title compound methyl 3,4-dihydroxy-2-(methoxy-d3)benzoate (25D) as a colorless oil (2.4 g, yield: 82.7%).

LCMS m/z=202.1 $[M+1]^+$.

Step 5: methyl 5-chloro-3,4-dihydroxy-2-(methoxy-d3)benzoate (25E)

Methyl 3,4-dihydroxy-2-(methoxy-d3)benzoate (25D) (2.4 g, 12.0 mmol) was added to tetrahydrofuran (24 mL). Under nitrogen protection, the mixture was cooled to −20° C., and then thionyl chloride (1.78 g, 13.14 mmol) was added dropwise. After completion of the dropwise addition, the mixture was reacted at −20° C. for 3 hours. The reaction liquid was slowly poured into ice water and extracted with ethyl acetate (100 mL×2). The organic phases were combined, dried over anhydrous sodium sulfate and concentrated to dryness. The residue was separated and purified by a liquid phase preparative column (liquid phase preparative conditions: C18 reverse-phase preparative column, mobile phase: acetonitrile (A) and deionized water containing 5 mM ammonium acetate (B), gradient elution, mobile phase A: 20%-70%, elution time: 18 min, flow rate: 15 mL/min, and column temperature: 30° C.) to obtain the title compound methyl 5-chloro-3,4-dihydroxy-2-(methoxy-d3)benzoate (25E) as a colorless oil (2.2 g, yield: 78.6%).

LCMS m/z=236.1 $[M+1]^+$.

Step 6: methyl-7-chloro-4-(methoxy-d3)-2-methyl-2-(4-oxocyclohexyl)benzo[d][1,3]dioxole-5-carboxylate (25F)

Methyl 5-chloro-3,4-dihydroxy-2-(methoxy-d3)benzoate (25E) (2.2 g, 9.36 mmol) was added to toluene (44 mL), and then $Ru(CO)_{12}$ (300 mg, 0.468 mmol) and triphenylphosphine (260 mg, 0.94 mmol) were added. Under nitrogen protection, the reaction was warmed to 110° C. and stirred for 1 hour, and then 4-ethynylcyclohexane-1-one (4.52 g, 28.1 mmol) was added. After the addition was completed, the mixture was reacted at 110° C. for 16 hours. The reaction liquid was poured into ice water and extracted with ethyl acetate (100 mL×2). The organic phases were combined, dried over anhydrous sodium sulfate and concentrated to dryness. The residue was separated and purified by silica gel column chromatography (petroleum ether:ethyl acetate (v/v)=8: 1-2:1) to obtain the title compound methyl-7-chloro-4-(methoxy-d3)-2-methyl-2-(4-oxocyclohexyl) benzo[d][1,3]dioxole-5-carboxylate (25F) as a white solid (3.0 g, yield: 89.8%).

LCMS m/z=358.2 $[M+1]^+$.

Step 7: methyl-7-chloro-4-(methoxy-d3)-2-(4-(3-methoxyazetidin-1-yl)cyclohexyl)-2-methylbenzo[d][1,3]dioxole-5-carboxylate (25G)

Methyl-7-chloro-4-(methoxy-d3)-2-methyl-2-(4-oxocyclohexyl)benzo[d][1,3]dioxole-5-carboxylate (25F) (1.5 g, 4.2 mmol) was added to dichloromethane (30 mL), and then 3-methoxyazetidine hydrochloride (700 mg, 5.5 mmol) and acetic acid (252 mg, 4.2 mmol) were added. The reaction was stirred at room temperature for 1 hour, and then sodium triacetylborohydride (1.8 g, 8.4 mmol) was added. After the addition was completed, the mixture was reacted at room temperature for 16 hours. The reaction liquid was poured into water (100 mL) and extracted with dichloromethane (100 mL×2). The organic phases were combined, dried over anhydrous sodium sulfate and concentrated to dryness. The residue was separated and purified by silica gel column chromatography (petroleum ether:ethyl acetate (v/v)=8: 1-1: 1) to obtain the title compound methyl-7-chloro-4-(methoxy-d3)-2-(4-(3-methoxyazetidin-1-yl)cyclohexyl)-2-methylbenzo[d][1,3]dioxole-5-carboxylate (25G) as a white solid (1.5 g, yield: 83.8%).

LCMS m/z=429.2 $[M+1]^+$.

Step 8: 7-chloro-4-(methoxy-d3)-2-(4-(3-methoxyazetidin-1-yl)cyclohexyl)-2-methylbenzo[d][1,3]dioxole-5-carboxylic acid (25H)

Methyl-7-chloro-4-(methoxy-d3)-2-(4-(3-methoxyazetidin-1-yl)cyclohexyl)-2-methylbenzo[d][1,3]dioxole-5-carboxylate (25G) (1.0 g, 2.34 mmol) was added to methanol (16 mL), and then a sodium hydroxide solution (2 mol/L, 4 mL) was added. The reaction was stirred at room temperature for 2 hours. The reaction liquid was adjusted to pH 5-6 with 1N hydrochloric acid and extracted with ethyl acetate (50 mL×2). The organic phases were combined, dried over anhydrous sodium sulfate and concentrated to dryness to obtain the title compound 7-chloro-4-(methoxy-d3)-2-(4-(3-methoxyazetidin-1-yl)cyclohexyl)-2-methylbenzo[d][1,3] dioxole-5-carboxylic acid (25H) as a white solid (0.9 g, yield: 92.8%).

LCMS m/z=415.2 $[M+1]^+$.

Step 9: 7-chloro-4-(methoxy-d3)-2-(4-(3-methoxyazetidin-1-yl)cyclohexyl)-2-methyl-N-((6-methyl-4-(methylthio)-2-oxo-1,2-dihydropyridin-3-yl)methyl)benzo[d][1,3]dioxole-5-carboxamide (compound 25)

7-chloro-4-(methoxy-d3)-2-(4-(3-methoxyazetidin-1-yl) cyclohexyl)-2-methylbenzo[d][1,3]dioxole-5-carboxylic acid (25H) (450 mg, 1.08 mmol) was added to DMF (10 mL), and then intermediate 5 (266 mg, 1.2 mmol), HATU (456 mg, 1.2 mmol) and N,N-diisopropylethylamin (418 mg, 3.24 mmol) were added. The reaction was stirred at room temperature for 2 hours. The reaction liquid was poured into water (50 mL) and extracted with ethyl acetate (50 mL×2). The organic phases were combined, dried over anhydrous sodium sulfate and concentrated to dryness. The residue was separated and purified by a liquid phase preparative column (liquid phase preparative conditions: C18 reverse-phase preparative column, mobile phase: acetonitrile (A) and deionized water containing 5 mM ammonium acetate (B), gradient elution, mobile phase A: 20%-50%, elution time: 18 min, flow rate: 15 mL/min, and column temperature: 30° C.) to obtain cis-trans isomer 1 (retention time: 15.20 min, 300 mg, yield: 47.5%) and cis-trans isomer 2 (retention time: 17.22 min, 160 mg, yield: 25.4%) of the title compound 7-chloro-4-(methoxy-d3)-2-(4-(3-methoxyazetidin-1-yl)cyclohexyl)-2-methyl-N-((6-methyl-4-(methylthio)-2-oxo-1,2-dihydropyridin-3-yl)methyl) benzo[d][1,3]dioxole-5-carboxamide (compound 25), which were subjected to chiral resolution (chiral resolution preparative conditions: analytical instrument: Waters UPC2 analytical SFC (SFC-H); chromatographic column: ChiralPak IG, 150×4.6 mm (inner diameter), 3 μm mobile phase: A: $CO_2$, B: methanol (0.05% DEA); gradient: B 50%; flow rate: 2.5 ml/min; back pressure: 100 bar; column temperature: 35° C.; wavelength: 220 nm; instrument for preparative separation: MGII preparative SFC (SFC-14) chromatographic column: ChiralPak IG, 250×30 mm (inner diameter), 10 μm mobile phase: A: $CO_2$, B: methanol (0.1% $NH_3H_2O$); gradient: B 50%; flow rate: 80 ml/min), wherein cis-trans isomer 1 was subjected to chiral HPLC separation to obtain isomer 1-1 (retention time: 4.696 min, 60 mg, yield: 9.5%) of compound 25 and isomer 1-2 (retention time: 5.739 min, 60 mg, yield: 9.5%) of compound 25, and cis-trans isomer 2 was subjected to chiral HPLC separation to obtain isomer 2-1 (retention time: 4.894 min, 30 mg, yield: 4.7%) of compound 25 and isomer 2-2 (5.991 min, 30 mg, yield: 4.7%) of compound 25.

Isomer 1-1 LCMS m/z=581.2 $[M+1]^+$.

Isomer 1-2 LCMS m/z=581.2 $[M+1]^+$.

Isomer 2-1 LCMS m/z=581.2 $[M+1]^+$.

Isomer 2-2 LCMS m/z=581.2 $[M+1]^+$.

Isomer 1-1 $^1H$ NMR (400 MHz, $CDCl_3$) δ 11.90 (s, 1H), 8.58-8.56 (t, 1H), 7.74 (s, 1H), 5.98 (s, 1H), 4.64-4.63 (d, 2H), 3.98 (s, 1H), 3.55-3.53 (m, 2H), 3.25 (s, 3H), 2.75 (s, 1H), 2.46 (s, 3H), 2.33 (s, 3H), 1.87-1.85 (m, 1H), 1.68-1.56 (m, 11H), 1.32-1.26 (m, 2H).

Isomer 1-2 $^1H$ NMR (400 MHz, $CDCl_3$) δ 12.00 (s, 1H), 8.58-8.56 (t, 1H), 7.72 (s, 1H), 6.03 (s, 1H), 4.70-4.61 (d, 2H), 4.38-4.36 (m, 1H), 3.59 (s, 2H), 3.30 (s, 3H), 3.25-3.23 (m, 1H), 2.47 (s, 3H), 2.34 (s, 3H), 1.99-1.96 (m, 5H), 1.86-1.71 (m, 6H), 1.64 (s, 3H).

Isomer 2-1 $^1H$ NMR (400 MHz, $CDCl_3$) δ 11.57 (s, 1H), 8.60-8.57 (t, 1H), 7.74 (s, 1H), 5.98 (s, 1H), 4.64-4.62 (d, 2H), 3.97 (s, 1H), 3.55-3.51 (m, 2H), 3.26 (s, 3H), 2.74 (m, 1H), 2.46 (s, 3H), 2.32 (s, 3H), 1.87-1.85 (m, 1H), 1.73-1.55 (m, 11H), 1.30-1.26 (m, 2H)

Isomer 2-2 $^1$H NMR (400 MHz, $CDCl_3$) δ 11.74 (s, 1H), 8.56-8.54 (t, 1H), 7.71 (s, 1H), 6.00 (s, 1H), 4.63-4.62 (d, 2H), 4.16-3.98 (m, 3H), 3.27 (s, 3H), 3.15-3.12 (m, 1H), 2.75-2.70 (m, 1H), 2.47 (s, 3H), 2.33 (s, 3H), 1.89-1.81 (m, 5H), 1.70-1.66 (m, 3H), 1.63 (s, 3H), 1.47-1.40 (s, 2H).

Embodiment 26

7-chloro-2,4-dimethyl-N-((6-methyl-4-(methylthio)-2-oxo-1,2-dihydropyridin-3-yl)methyl)-2-(1-(N-methylsulfamoyl)piperidin-4-yl)benzo[d][1,3]dioxole-5-carboxamide (compound 26)

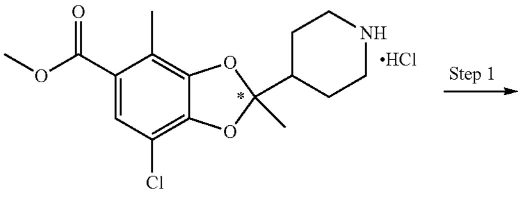

Intermediate 3

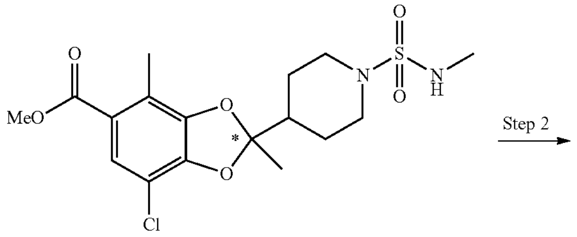

26A

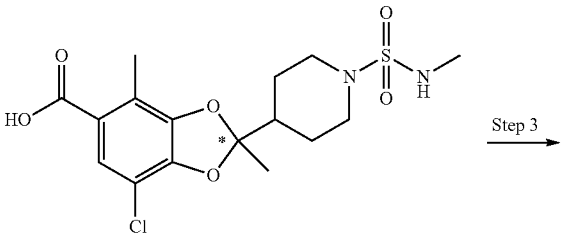

26B

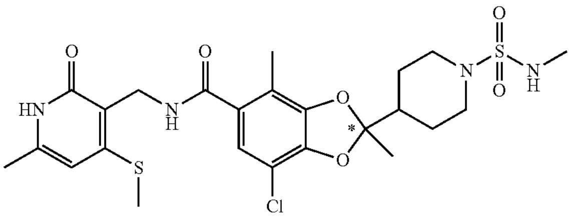

Compound 26

Step 1: methyl 7-chloro-2,4-dimethyl-2-(1-(N-methyl sulfamoyl)piperidin-4-yl)benzo[d][1,3]dioxole-5-carboxylate (26A)

Intermediate 3 (0.20 g, 0.61 mmol) was dissolved in dichloromethane (10 mL). Triethylamine (0.19 g, 1.80 mmol) and N-methylaminosulfonyl chloride (0.10 g, 0.74 mmol) were added. After the addition, the mixture was reacted at room temperature overnight. The reaction was quenched by dropwise adding a saturated aqueous ammonium chloride solution. A saturated aqueous sodium chloride solution (30 mL) was added, and the reaction liquid was extracted with dichloromethane (25 mL×3). The combined organic phase was dried over anhydrous sodium sulfate, filtered and concentrated. The residue was separated and purified by silica gel column chromatography (petroleum ether:ethyl acetate (v/v)=4:1) to obtain the title compound 26A as a white solid (0.25 g, 97.0%).

LC-MS (ESI): m/z=419.1 [M+H]$^+$.

Step 2: 7-chloro-2,4-dimethyl-2-(1-(N-methylsulfamoyl)piperidin-4-yl)benzo[d][1,3]dioxole-5-carboxylic acid (26B)

26A (0.25 g, 0.59 mmol) was dissolved in methanol (10 mL). Water (2 mL) and sodium hydroxide (0.24 g, 5.9 mmol) were added. After the addition, the mixture was reacted at room temperature overnight, adjusted to pH=2-3 by dropwise adding a dilute aqueous solution of hydrochloric acid (2M) and extracted with ethyl acetate (25 mL×3). The combined organic phase was dried over anhydrous sodium sulfate, filtered and concentrated to obtain the title compound 26B as a white solid (0.21 g, 86.9%).

LC-MS (ESI): m/z=405.1 [M+H]$^+$.

Step 3: 7-chloro-2,4-dimethyl-N-((6-methyl-4-(methylthio)-2-oxo-1,2-dihydropyridin-3-yl)methyl)-2-(1-(N-methylsulfamoyl)piperidin-4-yl)benzo[d][1,3]dioxole-5-carboxamide (compound 26)

26B (0.21 g, 0.52 mmol) was dissolved in DMF (10 mL). N,N-diisopropylethylamin(0.20 g, 1.56 mmol), HATU (0.26 g, 0.67 mmol) and intermediate 5 (0.11 g, 0.62 mmol) were added. After the addition, the mixture was reacted at room temperature overnight. The reaction was quenched by dropwise adding a saturated aqueous ammonium chloride solution. A saturated aqueous sodium chloride solution (30 mL) was added. The reaction liquid was extracted with ethyl acetate (25 mL). The organic phase was washed with a saturated aqueous sodium chloride solution (25 mL×3), dried over anhydrous sodium sulfate, filtered and concentrated. The residue was separated and purified by HPLC to obtain the product compound 26 (70 mg, 23.6%). Preparative HPLC separation conditions: instrument: waters 2767 (preparative liquid phase chromatographic instrument); chromatographic column: SunFire@ Prep C18 (19 mm×250 mm). The sample was dissolved in DMF and filtered with a 0.45 μm filter to prepare a sample solution. Preparative chromatography conditions: composition of mobile phases A and B: mobile phase A: acetonitrile; mobile phase B: water (containing 5 mM ammonium acetate); gradient elution, mobile phase A: 40%-70%; flow rate: 15 mL/min; elution time: 18 min; retention time: 11.46 min.

$^1$H NMR (400 MHz, $CDCl_3$) δ 6.89 (s, 1H), 6.38 (s, 1H), 4.61 (d, 2H), 3.84-3.71 (m, 2H), 2.81-2.66 (m, 5H), 2.54 (s, 3H), 2.45 (s, 3H), 2.23 (s, 3H), 2.01-1.86 (m, 3H), 1.70-1.43 (m, 5H).

LC-MS (ESI): m/z=571.2 [M+H]$^+$.

Embodiment 27

7-chloro-2-(1-(cyclopropylmethyl)piperidin-4-yl)-2,4-dimethyl-N-((6-methyl-4-(methylthio)-2-oxo-1,2-dihydropyridin-3-yl)methyl-d2)benzo[d][1,3]dioxole-5-carboxamide (compound 27)

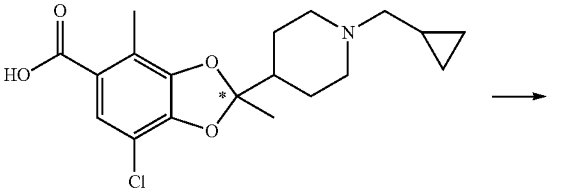

11D

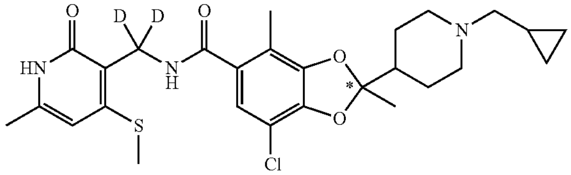

Compound 27

In a 50 mL single-necked flask, 11D (180 mg, 0.47 mmol) was added and dissolved in DMF (6 mL), and then triethylamine (127 mg, 1.26 mmol) and HATU (239 mg, 0.63 mmol) were added. The mixture was stirred at room temperature for 0.5 h. 3-(aminomethyl-d2)-6-methyl-4-(methylthio)pyridine-2(1H)-one hydrochloride (intermediate 6) (186 mg, 0.84 mmol) was added, and the resulting mixture was stirred at room temperature for 5 h. Water (10 mL) was added to the reaction liquid, and the mixture was extracted with EA (20 mL×3). The combined organic phase was dried over anhydrous sodium sulfate and concentrated, and the residue was separated by column chromatography (DCM:MeOH=20:1) to obtain compound 27 (50 mg, yield: 20%).

LC-MS (ESI): m/z=534.2 $[M+H]^+$.

$^1H$ NMR (400 MHz, DMSO-$d_6$) δ 11.49 (s, 1H), 7.98 (t, 1H), 6.86 (s, 1H), 6.07 (s, 1H), 3.01 (d, 2H), 2.45 (s, 3H), 2.17 (s, 3H), 2.14 (s, 3H), 2.12-2.16 (m, 2H), 1.82-1.87 (m, 3H), 1.69-1.72 (m, 2H), 1.62 (s, 3H), 1.33-1.42 (m, 2H), 0.78-0.81 (m, 1H), 0.41-0.44 (m, 2H), 0.00-0.05 (m, 2H).

Embodiment 28

7-chloro-2-(1-((3,3-difluorocyclobutyl)methyl)piperidin-4-yl)-2,4-dimethyl-N-((6-methyl-4-(methylthio)-2-oxo-1,2-dihydropyridin-3-yl)methyl-d2)benzo[d][1,3]dioxole-5-carboxamide (compound 28)

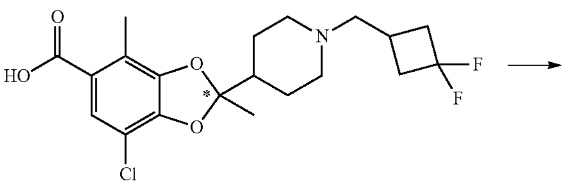

10D

-continued

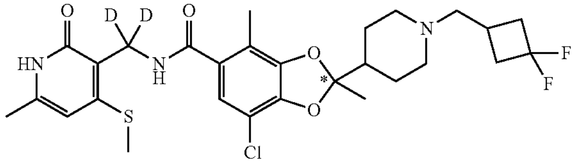

Compound 28

In a 50 mL single-necked flask, 10D (195 mg, 0.47 mmol) was added and dissolved in DMF (6 mL), and then triethylamine (127 mg, 1.26 mmol) and HATU (239 mg, 0.63 mmol) were added. The mixture was stirred at room temperature for 0.5 h. 3-(aminomethyl-d2)-6-methyl-4-(methylthio)pyridine-2(1H)-one hydrochloride (intermediate 6) (186 mg, 0.84 mmol) was added, and the resulting mixture was stirred at room temperature for 5 h. Water (10 mL) was added to the reaction liquid, and the mixture was extracted with EA (20 mL×3). The combined organic phase was dried over anhydrous sodium sulfate and concentrated, and the residue was separated by column chromatography (DCM:MeOH=20:1) to obtain compound 28 (50 mg, yield: 18%).

LC-MS (ESI): m/z=584.2 $[M+H]^+$.

$^1H$ NMR (400 MHz, DMSO-$d_6$) δ 11.50 (s, 1H), 7.97 (s, 1H), 6.86 (s, 1H), 6.07 (s, 1H), 2.85-2.88 (m, 2H), 2.58-2.64 (m, 2H), 2.44 (s, 3H), 2.36-2.38 (m, 2H), 2.23-2.33 (m, 1H), 2.20-2.22 (m, 1H), 2.17 (s, 3H), 2.14 (s, 3H), 1.81-1.91 (m, 4H), 1.67-1.70 (m, 2H), 1.61 (s, 3H), 1.30-1.39 (m, 2H).

Embodiment 29 methyl-4-(7-chloro-2,4-dimethyl-5-(((6-methyl-4-(methylthio)-2-oxo-1,2-dihydropyridin-3-yl)methyl)carbamoyl)benzo[d][1,3]dioxol-2-yl)piperidine-1-carboxylate (compound 29)

Compound 29

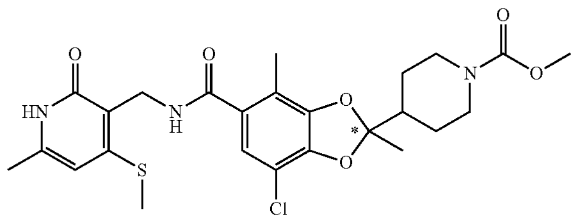

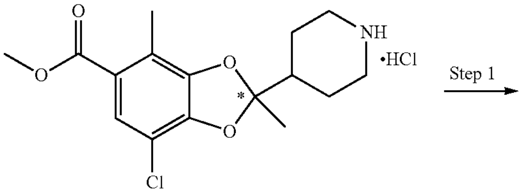

Intermediate 3

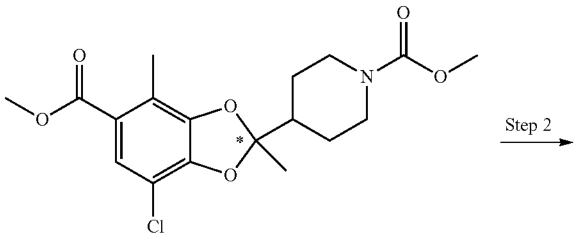

29A

-continued

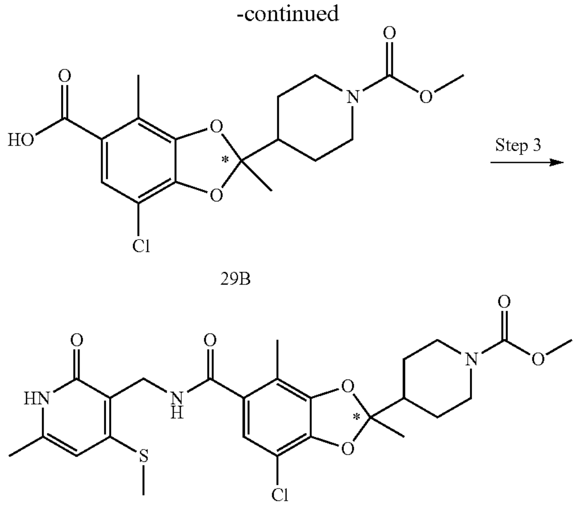

29B

Compound 29

Step 1: methyl-4-(7-chloro-5-(methoxycarbonyl)-2,4-dimethylbenzo[d][1,3]dioxol-2-yl)piperidine-1-carboxylate (29A)

Intermediate 3 (0.4 g, 1.23 mmol) was dissolved in dichloromethane (10 mL). DMAP (0.075 g, 0.61 mmol), DIEA (1.58 g, 12.28 mmol) and triphosgene (0.73 g, 2.46 mmol) were successively added, and the mixture was reacted in an ice bath for 2 hours. Anhydrous methanol (5 mL) was added, and the mixture was reacted at room temperature for 12 hours. Water (30 mL) was added to the reaction liquid. Liquid separation was performed. The aqueous phase was extracted with dichloromethane (30 mL×3). The organic phases were combined, washed with water (50 mL×2), dried over anhydrous sodium sulfate and concentrated to obtain the title compound methyl-4-(7-chloro-5-(methoxycarbonyl)-2,4-dimethylbenzo[d][1,3]dioxol-2-yl) piperidine-1-carboxylate (29A) as a yellow solid (0.2 g, yield: 42%).

LCMS m/z=384.1 $[M+1]^+$.

Step 2: 7-chloro-2-(1-(methoxycarbonyl)piperidin-4-yl)-2,4-dimethylbenzo[d][1,3]dioxole-5-carboxylic acid (29B)

Methyl-4-(7-chloro-5-(methoxycarbonyl)-2,4-dimethylbenzo[d][1,3]dioxol-2-yl)piperidine-1-carboxylate (29A) (0.2 g, 0.52 mmol) was dissolved in a mixed solvent (12 mL) of tetrahydrofuran/methanol/water (v/v/v=1/1/1). Sodium hydroxide (0.21 g, 5.21 mmol) was added, and the mixture was reacted at room temperature for 4 hours. The reaction liquid was adjusted to about pH=2 by adding a hydrochloric acid solution (6 mol/L) and extracted with ethyl acetate (50 mL×3). The organic phases were combined, washed with water (50 mL), dried over anhydrous sodium sulfate and concentrated to obtain the title compound 7-chloro-2-(1-(methoxycarbonyl)piperidin-4-yl)-2,4-dimethylbenzo[d][1,3]dioxole-5-carboxylic acid (29B) as a pale yellow liquid (0.18 g, yield: 93%).

LCMS m/z=370.1 $[M+1]^+$.

Step 3: methyl-4-(7-chloro-2,4-dimethyl-5-(((6-methyl-4-(methylthio)-2-oxo-1,2-dihydropyridin-3-yl)methyl)carbamoyl)benzo[d][1,3]dioxol-2-yl)piperidine-1-carboxylate (compound 29)

The compound 7-chloro-2-(1-(methoxycarbonyl)piperidin-4-yl)-2,4-dimethylbenzo[d][1,3]dioxole-5-carboxylic acid (29B) (0.17 g, 0.45 mmol), intermediate 5 (0.10 g, 0.55 mmol), HATU (0.26 g, 0.68 mmol) and DIEA (0.18 g, 1.36 mmol) were dissolved in dichloromethane (12 mL), and the mixture was reacted at room temperature for 12 hours. The reaction liquid was diluted by adding water. Liquid separation was performed. The aqueous phase was extracted with ethyl acetate (50 mL×3). The organic phases were combined, washed with water (50 mL), dried over anhydrous sodium sulfate and concentrated. The residue was separated and purified by silica gel column chromatography (dichloromethane:methanol (v/v)=1:0-9:1) to obtain the title compound methyl-4-(7-chloro-2,4-dimethyl-5-(((6-methyl-4-(methylthio)-2-oxo-1,2-dihydropyridin-3-yl)methyl) carbamoyl)benzo[d][1,3]dioxol-2-yl)piperidine-1-carboxylate (compound 29) (93 mg, yield: 38%).

$^1H$ NMR (400 MHz, $CD_3OD$) δ 6.90 (s, 1H), 6.27 (s, 1H), 4.49 (s, 2H), 4.18 (d, 2H), 3.67 (s, 3H), 2.79 (m, 2H), 2.52 (s, 3H), 2.29 (s, 3H), 2.19 (s, 3H), 2.13 (m, 1H), 1.83 (m, 2H), 1.62 (s, 3H), 1.33 (m, 2H).

LCMS m/z=536.2$[M+1]^+$.

Embodiment 30

7-chloro-2-(1-((1-cyanocyclopropyl)methyl)piperidin-4-yl)-2,4-dimethyl-N-((6-methyl-4-(methylthio)-2-oxo-1,2-dihydropyridin-3-yl)methyl)benzo[d][1,3]dioxole-5-carboxamide (compound 30)

Compound 30

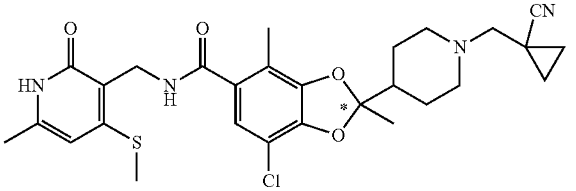

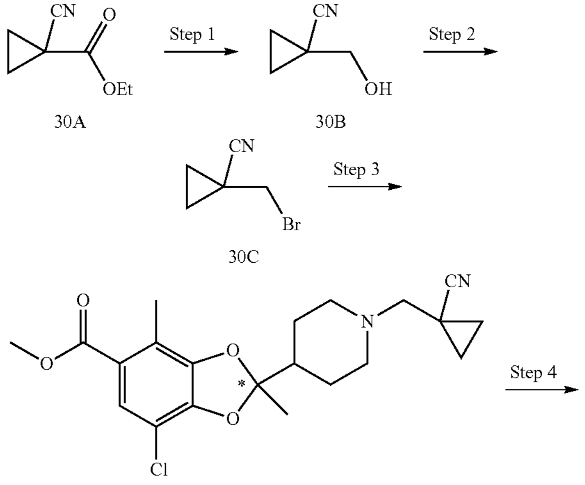

30A

30B

30C

30D

-continued

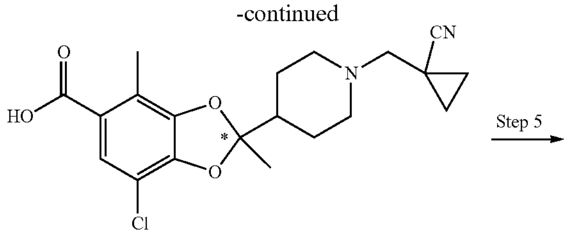

30E

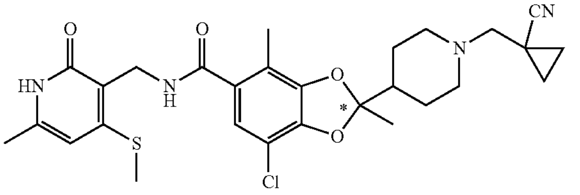

Compound 30

Step 1: 1-(hydroxymethyl)cyclopropane-1-carbonitrile (30B)

Ethyl 1-cyanocyclopropanecarboxylate (2 g, 14.37 mol) was dissolved in tetrahydrofuran (20 mL). Lithium borohydride (0.31 g, 14.37 mmol) was added. The reaction was refluxed for 1 hour. The reaction liquid was cooled to room temperature, adjusted to about pH=3 by adding 1 mol/L dilute hydrochloric acid and extracted with diethyl ether (50 mL×3). The organic phase was collected, dried over anhydrous sodium sulfate and concentrated to obtain a crude. The crude was dissolved in methanol (30 mL) and concentrated to obtain the title compound 1-(hydroxymethyl)cyclopropane-1-carbonitrile (30B) as a colorless oil (1.4 g, yield: 100%).

LCMS m/z=98.1 $[M+1]^+$.

Step 2: 1-(bromomethyl)cyclopropane-1-carbonitrile (30C)

1-(hydroxymethyl)cyclopropane-1-carbonitrile (30B) (1.4 g, 14.4 mol) and carbon tetrabromide (7.17 g, 21.6 mmol) were dissolved in diethyl ether (15 mL). A solution of triphenylphosphine (4.54 g, 17.3 mmol) in diethyl ether (8 mL) was added dropwise. The mixture was reacted at room temperature for 30 minutes and filtered by suction. The filtrate was collected, dried over anhydrous sodium sulfate and concentrated to obtain the title compound 1-(bromomethyl)cyclopropane-1-carbonitrile (30C) as a purple substance (1.8 g, yield: 78%).

Step 3: methyl-7-chloro-2-(1-((1-cyanocyclopropyl)methyl)piperidin-4-yl)-2,4-dimethylbenzo[d][1,3]dioxole-5-carboxylate (30D)

Intermediate 3 (3.7 g, 11 mmol), 1-(bromomethyl)cyclopropane-1-carbonitrile (30C) (1.8 g, 11 mmol), potassium carbonate (4.7 g, 34 mmol) and acetonitrile (20 mL) were evenly mixed, refluxed and stirred overnight. After the reaction was cooled to room temperature, water (30 mL) was added to the reaction liquid, and the mixture was extracted with ethyl acetate (50 mL×3). The combined organic phase was washed with saturated brine (50 mL), dried over anhydrous sodium sulfate and concentrated under reduced pressure, and then the residue was separated by column chromatography (PE/EA=2/1) to obtain the title compound methyl-7-chloro-2-(1-((1-cyanocyclopropyl)methyl)piperidin-4-yl)-2,4-dimethylbenzo[d][1,3]dioxole-5-carboxylate (30D) as a yellow solid (0.4 g, yield: 9%).

LCMS m/z=405.2 $[M+1]^+$.

Step 4: 7-chloro-2-(1-((1-cyanocyclopropyl)methyl)piperidin-4-yl)-2,4-dimethylbenzo[d][1,3]dioxole-5-carboxylic acid (30E)

The compound methyl-7-chloro-2-(1-((1-cyanocyclopropyl)methyl)piperidin-4-yl)-2,4-dimethylbenzo[d][1,3]dioxole-5-carboxylate (30D) (0.33 g, 0.82 mmol) was dissolved in a mixed solvent (12 mL) of THF/MeOH/$H_2O$ (1/1/1). Sodium hydroxide (0.33 g, 8.15 mmol) was added, and the mixture was reacted at room temperature for 5 hours. The reaction liquid was adjusted to about pH=2 by adding a hydrochloric acid solution (6 mol/L) and extracted with ethyl acetate (50 mL×3). The organic phases were combined, washed with water (50 mL), dried over anhydrous sodium sulfate and concentrated to obtain the title compound 7-chloro-2-(1-((1-cyanocyclopropyl)methyl)piperidin-4-yl)-2,4-dimethylbenzo[d][1,3]dioxole-5-carboxylic acid (30E) as a pale yellow solid (0.30 g, yield: 90%).

LCMS m/z=391.1 $[M+1]^+$.

Step 5: 7-chloro-2-(1-((1-cyanocyclopropyl)methyl)piperidin-4-yl)-2,4-dimethyl-N-((6-methyl-4-(methylthio)-2-oxo-1,2-dihydropyridin-3-yl)methyl)benzo[d][1,3]dioxole-5-carboxamide (compound 30)

The compound 7-chloro-2-(1-((1-cyanocyclopropyl)methyl)piperidin-4-yl)-2,4-dimethylbenzo[d][1,3]dioxole-5-carboxylic acid (30E) (0.3 g, 0.77 mmol), intermediate 5 (0.21 g, 1.15 mmol), HATU (0.44 g, 1.15 mmol) and DIEA (0.30 g, 2.30 mmol) were dissolved in dichloromethane (12 mL), and the mixture was reacted at room temperature for 12 hours. The reaction liquid was diluted by adding water. Liquid separation was performed. The aqueous phase was extracted with ethyl acetate (50 mL×3). The organic phases were combined, washed with water (50 mL), dried over anhydrous sodium sulfate and concentrated. The residue was separated and purified by silica gel column chromatography (dichloromethane:methanol (v/v)=1:0-9:1) to obtain the title compound 7-chloro-2-(1-((1-cyanocyclopropyl)methyl)piperidin-4-yl)-2,4-dimethyl-N-((6-methyl-4-(methylthio)-2-oxo-1,2-dihydropyridin-3-yl)methyl)benzo[d][1,3]dioxole-5-carboxamide (compound 30) (157 mg, yield: 37%).

$^1H$ NMR (400 MHz, $CD_3OD$) δ 6.90 (s, 1H), 6.27 (s, 1H), 4.49 (s, 2H), 3.14 (m, 2H), 2.52 (s, 3H), 2.45 (s, 2H), 2.29 (s, 3H), 2.20 (s, 3H), 1.96 (m, 7H), 1.63 (s, 3H), 1.58 (m, 2H), 1.26 (m, 2H), 0.96 (m, 2H).

MS M/Z (ESI): 557.2 $[M+1]^+$.

Embodiment 31

7-chloro-2-(1-((2,2-difluorocyclopropyl)methyl) piperidin-4-yl)-2,4-dimethyl-N-((6-methyl-4-(methylthio)-2-oxo-1,2-dihydropyridin-3-yl)methyl)benzo [d][1,3]dioxole-5-carboxamide (compound 31)

Compound 31

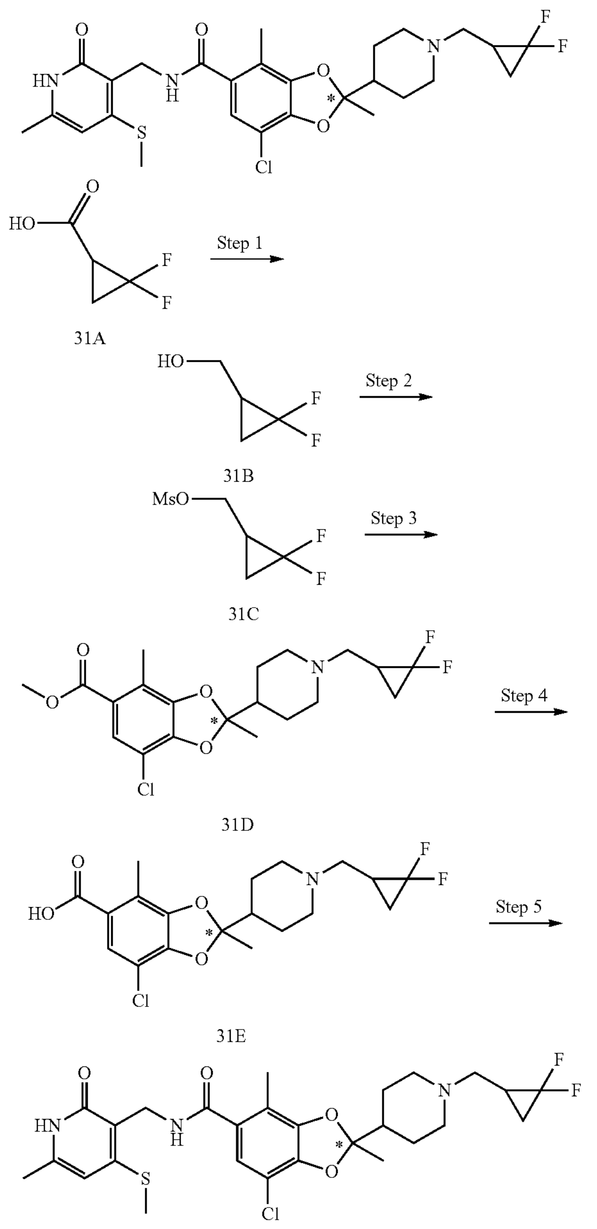

Compound 31

Step 1: (2,2-difluorocyclopropyl)methanol (31B)

2,2-difluorocyclopropanecarboxylic acid (31A) (0.5 g, 4.10 mmol) was dissolved in anhydrous THE (10 mL) and cooled to 0° C. in an ice bath. $LiAlH_4$ (234 mg, 6.15 mmol) was added in portions. After the addition was completed, the mixture was slowly returned to room temperature and stirred for 2 hours. The reaction liquid was cooled to 0° C. The reaction was quenched with water. $Mg_2SO_4$ (5 g) was then added, and the mixture was stirred for 10 minutes and filtered. The filter cake was washed twice with THF, and the filtrate was concentrated under reduced pressure to obtain the title compound (31B) as a colorless oil (0.4 g, yield: 90.9%).

Step 2: (2,2-difluorocyclopropyl)methyl methanesulfonate (31C)

(2,2-difluorocyclopropyl)methanol (31B) (0.4 g, 3.70 mmol) was dissolved in DCM (15 mL). $Et_3N$ (1121 mg, 11.1 mmol) and DMAP (45 mg, 0.37 mmol) were successively added. The reaction liquid was cooled to 0° C., and MsCl (509 mg, 4.44 mol) was added dropwise. After the addition was completed, the mixture was slowly returned to room temperature and stirred overnight. 30 mL of water was added to the reaction liquid, and the mixture was extracted 3 times with DCM. The organic phases were combined, washed twice with a saturated aqueous NaCl solution, dried over anhydrous sodium sulfate and filtered, and the filtrate was concentrated under reduced pressure to obtain the title compound (31C) as a colorless oil (0.4 g, yield: 58.1%).

Step 3: methyl 7-chloro-2-(1-((2,2-difluorocyclopropyl)methyl)piperidin-4-yl)-2,4-dimethylbenzo[d][1,3]dioxole-5-carboxylate (31D)

Intermediate 3 (380 mg, 1.05 mmol) was placed in a 50 mL single-necked flask. Acetonitrile (20 mL), DIPEA (568 mg, 4.20 mmol), KI (183 mg, 1.05 mmol) and compound 31C (391 mg, 2.10 mmol) were successively added. After the addition was completed, the mixture was warmed to 60° C. and stirred for 2 hours. The reaction was cooled to room temperature and then concentrated under reduced pressure to remove most of the reaction solvent. 30 mL of water was added to the residue, and the reaction liquid was extracted 3 times with EA. The organic phases were combined, dried over anhydrous sodium sulfate and filtered, and the filtrate was concentrated under reduced pressure. The residue was then separated and purified by column chromatography (PE/EA=4/1) to obtain the title compound (31D) as a colorless oil (0.33 g, yield: 75.7%).

Step 4: 7-chloro-2-(1-((2,2-difluorocyclopropyl) methyl)piperidin-4-yl)-2,4-dimethylbenzo[d][1,3] dioxole-5-carboxylic acid (31E)

Compound 31D (0.33 g, 0.79 mmol) was dissolved in 15 mL of $THF/H_2O$ (v/v=2/1). $LiOH{\cdot}H_2O$ (166 mg, 3.95 mmol) was added. The reaction was warmed to 60° C. and stirred for 5 hours. After the reaction was cooled to room temperature, the mixture was concentrated under reduced pressure to remove most of the organic solvent. After 15 mL of water was added to the residue, the reaction liquid was adjusted to pH=5 with 2N dilute hydrochloric acid and extracted 3 times with EA. The organic phases were combined, dried over anhydrous sodium sulfate and filtered, and the filtrate was concentrated under reduced pressure to obtain the title compound (31E) as a white solid (0.30 g, yield: 94.0%).

Step 5: 7-chloro-2-(1-((2,2-difluorocyclopropyl) methyl)piperidin-4-yl)-2,4-dimethyl-N-((6-methyl-4-(methylthio)-2-oxo-1,2-dihydropyridin-3-yl)methyl) benzo[d][1,3]dioxole-5-carboxamide (compound 31)

Compound 31E (0.20 g, 0.50 mmol) was dissolved in DMF (10 mL). HATU (285 mg, 0.75 mmol) was added, and the mixture was stirred at room temperature for 15 minutes. DIPEA (193 mg, 1.50 mmol) and intermediate 5 (132 mg, 0.6 mmol) were successively added. After the addition was completed, the mixture was stirred at room temperature overnight. 20 mL of water was added to the reaction liquid, and the mixture was extracted 4 times with EA. The organic phases were combined, washed twice with a saturated aqueous NaCl solution, dried over anhydrous sodium sulfate and filtered, and the filtrate was concentrated under reduced pressure. The residue was purified by preparative HPLC to obtain the title compound 31 (66 mg, yield: 23.3%).

Preparative HPLC separation methods: instrument: waters 2767 (preparative liquid phase chromatographic instrument); chromatographic column: SunFire@ Prep C18 (19 mm×250 mm). The sample was dissolved in DMF and filtered with a 0.45 μm filter to prepare a sample solution. Preparative chromatography conditions: a. composition of mobile phases A and B: mobile phase A: acetonitrile; mobile phase B: water (containing 0.05% ammonia water); b. gradient elution, mobile phase A: 25%-70%; c. flow rate: 12 mL/min; d. elution time: 20 min; retention time: 13.82 min.

$^1$H NMR (400 MHz, $CDCl_3$) δ 11.50 (s, 1H), 8.00 (t, 1H), 6.85 (s, 1H), 6.08 (s, 1H), 4.27 (d, 2H), 2.93 (t, 2H), 2.56-2.53 (m, 1H), 2.45 (s, 3H), 2.31-2.26 (m, 1H), 2.17 (s, 3H), 2.14 (s, 3H), 1.99-1.84 (m, 3H), 1.81-1.67 (m, 3H), 1.62 (s, 3H), 1.58-1.50 (m, 1H), 1.44-1.33 (m, 2H), 1.16-1.08 (m, 1H).

LCMS m/z=568.1 $[M+1]^+$.

Embodiment 32

7-chloro-2-(1-((1-fluorocyclopropyl)methyl)piperidin-4-yl)-2,4-dimethyl-N-((6-methyl-4-(methylthio)-2-oxo-1,2-dihydropyridin-3-yl)methyl)benzo[d][1,3]dioxole-5-carboxamide (compound 32)

Compound 32

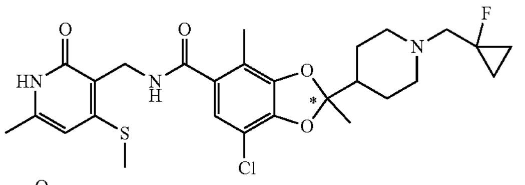

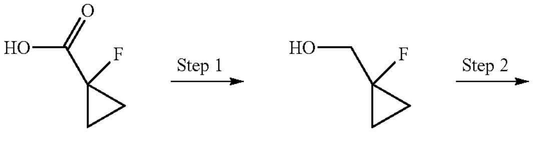

32A 32B

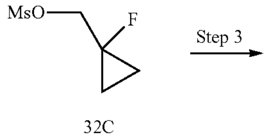

32C

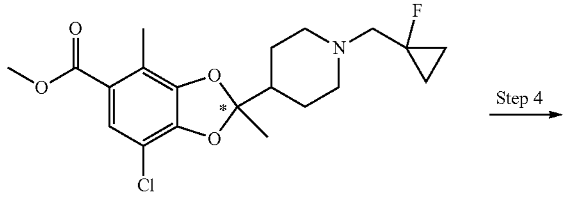

32D

-continued

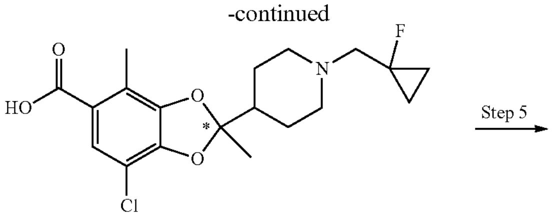

32E

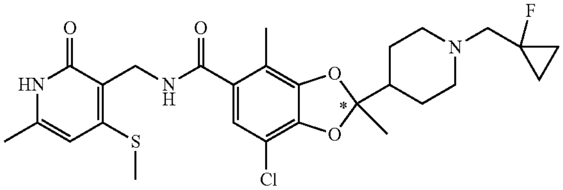

Compound 32

Step 1: (1-fluorocyclopropyl)methanol (32B)

1-fluorocyclopropane carboxylic acid (32A) (0.5 g, 4.8 mmol) was dissolved in anhydrous THE (10 mL) and cooled to 0° C. in an ice bath. $LiAlH_4$ (274 mg, 7.2 mmol) was added in portions. After the addition was completed, the mixture was slowly returned to room temperature and stirred for 2 hours. The reaction liquid was cooled to 0° C. The reaction was quenched by dropwise adding water. $Mg_2SO_4$ (5 g) was then added, and the mixture was stirred for 10 minutes and filtered. The filter cake was washed twice with THF, and the filtrate was concentrated under reduced pressure to obtain the title compound (32B) as a colorless oil (0.26 g, yield: 60.5%).

Step 2: (1-fluorocyclopropyl)methyl methanesulfonate (32C)

(1-fluorocyclopropyl)methanol (32B) (0.26 g, 2.9 mmol) was dissolved in DCM (10 mL). $Et_3N$ (586 mg, 2.8 mmol) and DMAP (35 mg, 0.29 mmol) were successively added. At 0° C., MsCl (401 mg, 3.5 mol) was added dropwise. After the addition was completed, the mixture was slowly returned to room temperature and stirred overnight. 20 mL of water was added to the reaction liquid, and the mixture was extracted 3 times with DCM. The organic phases were combined, washed twice with a saturated aqueous NaCl solution, dried over anhydrous sodium sulfate and filtered, and the filtrate was concentrated under reduced pressure to obtain the title compound (32C) as a colorless oil (0.37 g, yield: 75.8%).

Step 3: methyl 7-chloro-2-(1-((1-fluorocyclopropyl)methyl)piperidin-4-yl)-2,4-dimethylbenzo[d][1,3]dioxole-5-carboxylate (32D)

Intermediate 3 (400 mg, 1.10 mmol) was placed in a 50 mL single-necked flask. Acetonitrile (20 mL), DIPEA (568 mg, 4.40 mmol), KI (183 mg, 1.10 mmol) and compound 32C (370 mg, 2.20 mmol) were successively added. After the addition was completed, the mixture was warmed to 60° C. and stirred for 2 hours. The reaction was cooled to room temperature and then concentrated under reduced pressure to remove most of the reaction solvent. 30 mL of water was added to the residue, and the reaction liquid was extracted 3 times with EA. The organic phases were combined, dried over anhydrous sodium sulfate and filtered, and the filtrate was concentrated under reduced pressure. The residue was then separated and purified by column chromatography (PE/EA=4/1) to obtain the title compound (32D) as a colorless oil (330 mg, yield: 75.3%).

Step 4: 7-chloro-2-(1-((1-fluorocyclopropyl)methyl) piperidin-4-yl)-2,4-dimethylbenzo[d][1,3]dioxole-5-carboxylic acid (32E)

Compound 32D (330 mg, 0.83 mmol) was dissolved in 15 mL of $THF/H_2O$ (v/v=2/1). $LiOH \cdot H_2O$ (174 mg, 4.15 mmol) was added. After the addition was completed, the mixture was stirred at room temperature overnight and concentrated under reduced pressure to remove most of THF. 15 mL of water was added to the residue, and the reaction liquid was adjusted to pH=5 by dropwise adding 2N dilute hydrochloric acid and extracted 3 times with EA. The organic phases were combined, dried over anhydrous sodium sulfate and filtered, and the filtrate was concentrated under reduced pressure to obtain the title compound (32E) as a white solid (300 mg, yield: 94.0%).

Step 5: 7-chloro-2-(1-((1-fluorocyclopropyl)methyl) piperidin-4-yl)-2,4-dimethyl-N-((6-methyl-4-(methylthio)-2-oxo-1,2-dihydropyridin-3-yl)methyl)benzo [d][1,3]dioxole-5-carboxamide (compound 32)

Compound 32E (200 mg, 0.52 mmol) was dissolved in DMF (10 mL). HATU (296 mg, 0.78 mmol) was added, and the mixture was stirred at room temperature for 15 minutes. DIPEA (335 mg, 2.60 mmol) and intermediate 5 (137 mg, 0.62 mmol) were then successively added. After the addition was completed, the mixture was stirred at room temperature overnight. 20 mL of water was added to the reaction liquid, and the mixture was extracted 4 times with EA. The organic phases were combined, washed twice with a saturated aqueous NaCl solution, dried over anhydrous sodium sulfate and filtered, and the filtrate was concentrated under reduced pressure. The residue was purified by preparative HPLC to obtain the title compound 32 (72 mg, yield: 25.1%).

Preparative HPLC separation methods: instrument: waters 2767 (preparative liquid phase chromatographic instrument); chromatographic column: SunFire@Prep C18 (19 mm×250 mm). The sample was dissolved in DMF and filtered with a 0.45 μm filter to prepare a sample solution. Preparative chromatography conditions: a. composition of mobile phases A and B: mobile phase A: acetonitrile; mobile phase B: water (containing 0.05% ammonia water); b. gradient elution, mobile phase A: 25%-70%; c. flow rate: 12 mL/min; d. elution time: 20 min; retention time: 14.17 min.

$^1H$ NMR (400 MHz, $CDCl_3$) δ 11.50 (s, 1H), 8.00 (t, 1H), 6.86 (s, 1H), 6.07 (s, 1H), 4.27 (d, 2H), 3.02 (d, 2H), 2.69 (s, 1H), 2.63 (s, 1H), 2.45 (s, 3H), 2.17 (s, 3H), 2.15 (s, 3H), 2.03 (t, 2H), 1.90-1.82 (m, 1H), 1.73-1.70 (m, 2H), 1.60 (s, 3H), 1.44-1.33 (m, 2H), 0.98 (t, 1H), 0.93 (t, 1H), 0.65-0.59 (m, 2H).

LCMS m/z=550.2 $[M+1]^+$.

Embodiment 33

7-chloro-2-(1-(3-methoxycyclobutyl)piperidin-4-yl)-2,4-dimethyl-N-((6-methyl-4-(methylthio)-2-oxo-1,2-dihydropyridin-3-yl)methyl)benzo[d][1,3]dioxole-5-carboxamide (compound 33)

Compound 33

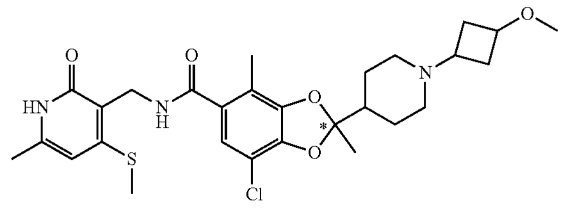

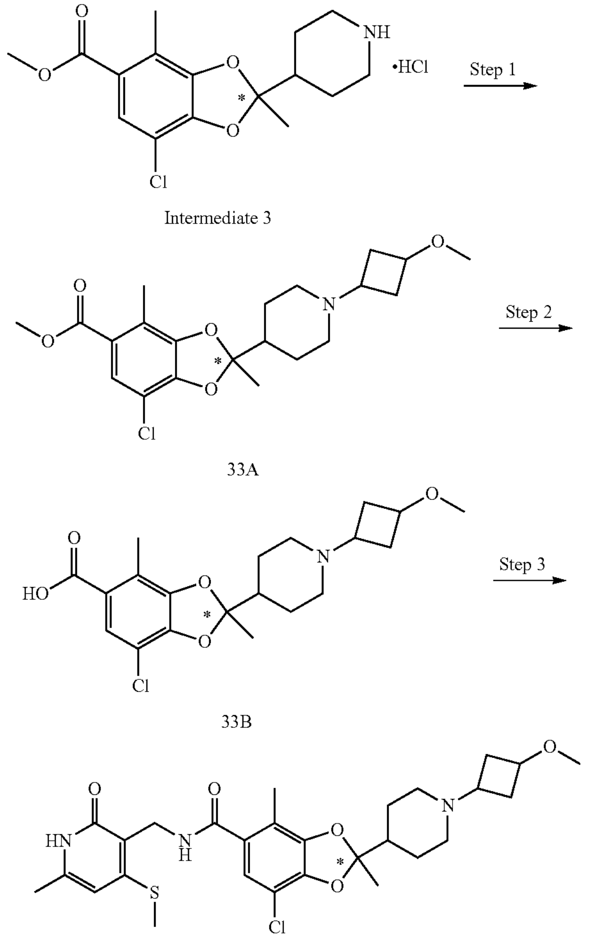

Intermediate 3

33A

33B

Compound 33

Step 1: methyl 7-chloro-2-(1-(3-methoxycyclobutyl) piperidin-4-yl)-2,4-dimethylbenzo[d][1,3]dioxole-5-carboxylate (33A)

In a 50 mL single-necked flask, intermediate 3 (250 mg, 0.77 mmol) was added and dissolved in dichloromethane (10 mL). 3-methoxycyclobutanone (120 mg, 1.20 mmol) and acetic acid (46 mg, 0.77 mmol) were added, and the mixture was stirred at room temperature for 1 h. Sodium triacetylborohydride (330 mg, 1.50 mmol) was added, and the mixture was stirred at room temperature for 16 h. The reaction liquid was washed with a saturated sodium bicarbonate solution (20 mL), dried over anhydrous sodium sulfate and concentrated to obtain the title compound methyl 7-chloro-2-(1-(3-methoxycyclobutyl)piperidin-4-yl)-2,4-dimethylbenzo[d][1,3]dioxole-5-carboxylate (33A) as a yellow oil (280 mg, yield: 89%).

LCMS m/z=410.2 $[M+1]^+$.

Step 2: 7-chloro-2-(1-(3-methoxycyclobutyl)piperidin-4-yl)-2,4-dimethylbenzo[d][1,3]dioxole-5-carboxylic acid (33B)

In a 50 mL single-necked flask, 33A (280 mg, 0.68 mmol) was added and dissolved in methanol (2 mL), tetrahydrofuran (2 mL) and water (2 mL). Sodium hydroxide (140 mg, 3.40 mmol) was added, and the mixture was stirred at room temperature for 16 h, adjusted to pH 3-4 with hydrochloric acid (2 M) and extracted with dichloromethane (20 mL×2). The organic phases were combined, dried over anhydrous sodium sulfate and concentrated under reduced pressure to obtain the title compound 7-chloro-2-(1-(3-methoxycyclobutyl)piperidin-4-yl)-2,4-dimethylbenzo[d][1,3]dioxole-5-carboxylic acid (33B) as a white solid (230 mg, 85% yield).

LCMS m/z=396.1 $[M+1]^+$.

Step 3: 7-chloro-2-(1-(3-methoxycyclobutyl)piperidin-4-yl)-2,4-dimethyl-N-((6-methyl-4-(methylthio)-2-oxo-1,2-dihydropyridin-3-yl)methyl)benzo[d][1,3]dioxole-5-carboxamide (compound 33)

In a 50 mL single-necked flask, 33B (150 mg, 0.38 mmol) was added and dissolved in DMF (5 mL). Triethylamine (120 mg, 1.10 mmol) and HATU (170 mg, 0.45 mmol) were added, and the mixture was stirred at room temperature for 0.5 h. Intermediate 5 (100 mg, 0.57 mmol) was added, and the mixture was stirred at room temperature for 16 h. Water (10 mL) was added, and the reaction liquid was extracted with EA (10 mL×2). The organic phase was dried over anhydrous sodium sulfate and concentrated. The residue was separated and purified by a liquid phase preparative column (liquid phase preparative conditions: C18 reverse-phase preparative column, mobile phase: acetonitrile (A) and water (with 0.05% ammonia water) (B), gradient elution, mobile phase A: 20%-70%, elution time: 20 min, flow rate: 15 mL/min, and retention time: 13.0 min; column temperature: 30° C.) to obtain the title compound 33 (20 mg, 10% yield).

$^1H$ NMR (400 MHz, $CDCl_3$) δ 12.47 (s, 1H), 7.16 (1H), 6.90 (s, 1H), 6.07-6.01 (m, 1H), 4.59 (d, 2H), 3.60 (t, 1H), 3.22 (s, 3H), 3.00 (d, 2H), 2.48 (s, 3H), 2.43 (ddt, 2H), 2.38-2.29 (m, 4H), 2.25 (s, 3H), 1.93-1.69 (m, 7H), 1.61 (brs, 5H)

LCMS m/z=562.2 $[M+1]^+$.

Embodiment 34

7-chloro-2-(4-((trans-3-fluorocyclobutyl)amino)cyclohexyl)-2,4-dimethyl-N-((6-methyl-4-(methylthio)-2-oxo-1,2-dihydropyridin-3-yl)methyl)benzo[d][1,3]dioxole-5-carboxamide (compound 34, isomer 1 and isomer 2)

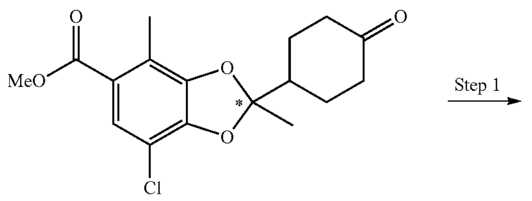

Intermediate 2

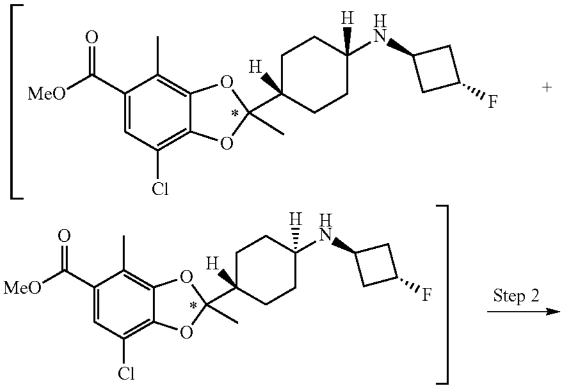

34A&34B

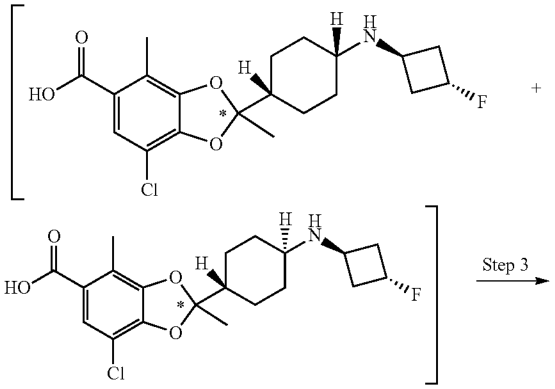

34C&34D

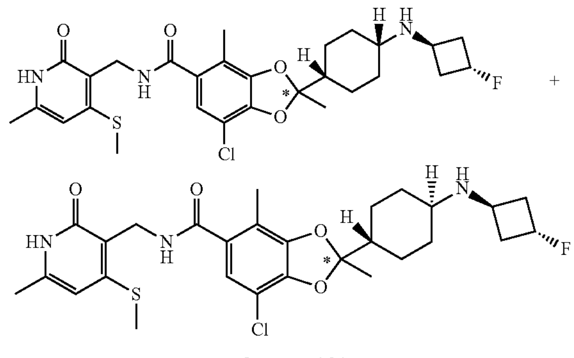

Compound 34

Step 1: methyl 7-chloro-2-(4-((trans-3-fluorocyclobutyl)amino)cyclohexyl)-2,4-dimethylbenzo[d][1,3]dioxole-5-carboxylate (34A&34B)

Intermediate 2 (0.50 g, 1.48 mmol) was dissolved in 1,2-dichloroethan (5 mL). Trans 3-fluorocyclobutylamine hydrochloride (0.46 g, 3.69 mmol) and acetic acid (0.09 g, 1.48 mmol) were added. After the addition, the mixture was reacted at room temperature for 3 h. Sodium triacetoxyborohydride (1.25 g, 5.90 mmol) was added. After the addition, the mixture was reacted at room temperature overnight and adjusted to pH=7-8 by dropwise adding a saturated aqueous sodium bicarbonate solution. A saturated aqueous sodium chloride solution (30 mL) was added, and the reaction liquid was extracted with dichloromethane (25 mL×3). The combined organic phase was dried over anhydrous sodium sulfate, filtered and concentrated. The residue was separated and purified by silica gel column chromatography (petroleum ether:ethyl acetate (v/v)=5:1) to obtain isomer 34A as a white solid (0.30 g, 49.1%) (petroleum ether:ethyl acetate (v/v)=2:1, Rf=0.45) and to obtain isomer 34B as a white solid (0.30 g, 49.1%) (petroleum ether:ethyl acetate (v/v)=2:1, Rf=0.40).

LC-MS (ESI): m/z=412.9 $[M+H]^+$.

Step 2: 7-chloro-2-(4-((trans-3-fluorocyclobutyl)amino)cyclohexyl)-2,4-dimethylbenzo[d][1,3]dioxole-5-carboxylic acid (34C&34D)

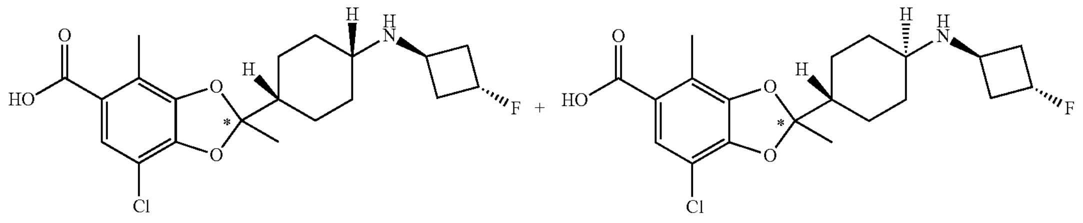

34C & 34D 34A (0.30 g, 0.73 mmol) was dissolved in methanol (10 mL). Water (2 mL) and sodium hydroxide (0.29 g, 7.3 mmol) were added. After the addition, the mixture was reacted at room temperature overnight, adjusted to pH=2-3 by dropwise adding a dilute hydrochloric acid aqueous solution (2M) and extracted with ethyl acetate (25 mL×3). The combined organic phase was dried over anhydrous sodium sulfate, filtered and concentrated to obtain the title compound, isomer 34C as a white solid (0.30 g, 100%).

LC-MS (ESI): m/z=398.9 $[M+H]^+$.

34B (0.30 g, 0.73 mmol) was dissolved in methanol (10 mL). Water (2 mL) and sodium hydroxide (0.29 g, 7.3 mmol) were added. After the addition, the mixture was reacted at room temperature overnight, adjusted to pH=2-3 by dropwise adding a dilute hydrochloric acid aqueous solution (2M) and extracted with ethyl acetate (25 mL×3). The combined organic phase was dried over anhydrous sodium sulfate, filtered and concentrated to obtain the title compound, isomer 34D as a white solid (0.28 g, 96.6%).

LC-MS (ESI): m/z=398.9 $[M+H]^+$.

Step 3: 7-chloro-2-(4-((trans-3-fluorocyclobutyl)amino)cyclohexyl)-2,4-dimethyl-N-((6-methyl-4-(methylthio)-2-oxo-1,2-dihydropyridin-3-yl)methyl)benzo[d][1,3]dioxole-5-carboxamide (compound 34, isomer 1 and isomer 2)

34C (0.30 g, 0.75 mmol) was dissolved in DMF (10 mL). N,N-diisopropylethylamin (0.29 g, 2.26 mmol), HATU (0.37 g, 0.98 mmol) and intermediate 5 (0.17 g, 0.90 mmol) were added. After the addition, the mixture was reacted at room temperature overnight. The reaction was quenched by dropwise adding a saturated aqueous ammonium chloride solution. A saturated aqueous sodium chloride solution (30 mL) was added. The reaction liquid was extracted with ethyl acetate (25 mL). The organic phase was washed with a saturated aqueous sodium chloride solution (25 mL×3), dried over anhydrous sodium sulfate, filtered and concentrated. The residue was separated and purified by preparative HPLC to obtain the product compound 34, isomer 1 (80 mg, 18.8%). Preparative HPLC separation conditions: instrument: waters 2767 (preparative liquid phase chromatographic instrument); chromatographic column: SunFire@ Prep C18 (19 mm×250 mm). The sample was dissolved in DMF and filtered with a 0.45 μm filter to prepare a sample solution. Preparative chromatography conditions: composition of mobile phases A and B: mobile phase A: acetonitrile; mobile phase B: water (containing 5 mM ammonium acetate); gradient elution, mobile phase A: 40%-70%; flow rate: 15 mL/min; elution time: 18 min; retention time: 11.97 min.

LC-MS (ESI): m/z=564.2 $[M+H]^+$.

$^1$H NMR (400 MHz, $CDCl_3$) δ 6.86 (s, 1H), 6.30 (s, 1H), 5.28-5.07 (m, 1H), 4.57 (t, 2H), 4.00 (d, 1H), 3.24 (s, 1H), 2.87-2.68 (m, 2H), 2.62-2.47 (m, 5H), 2.44 (d, 3H), 2.20 (d, 3H), 2.12-1.97 (m, 2H), 1.97-1.59 (m, 7H), 1.57 (d, 3H).

LC-MS (ESI): m/z=564.2 $[M+H]^+$.

34D (0.28 g, 0.70 mmol) was dissolved in DMF (10 mL). N,N-diisopropylethylamin (0.27 g, 2.11 mmol), HATU (0.35 g, 0.98 mmol) and intermediate 5 (0.15 g, 0.84 mmol) were added. After the addition, the mixture was reacted at room temperature overnight. The reaction was quenched by dropwise adding a saturated aqueous ammonium chloride solution. A saturated aqueous sodium chloride solution (30 mL) was added. The reaction liquid was extracted with ethyl acetate (25 mL). The organic phase was washed with a saturated aqueous sodium chloride solution (25 mL×3), dried over anhydrous sodium sulfate, filtered and concentrated. The residue was separated and purified by preparative HPLC to obtain the product compound 34, isomer 2 (280 mg, 70.5%). Preparative HPLC separation conditions: instrument: waters 2767 (preparative liquid phase chromatographic instrument); chromatographic column: SunFire@ Prep C18 (19 mm×250 mm). The sample was dissolved in DMF and filtered with a 0.45 μm filter to prepare a sample solution. Preparative chromatography conditions: composition of mobile phases A and B: mobile phase A: acetonitrile; mobile phase B: water (containing 5 mM ammonium acetate); gradient elution, mobile phase A: 40%-70%; flow rate: 15 mL/min; elution time: 18 min; retention time: 12.50 min.

$^1$H NMR (400 MHz, $CDCl_3$) δ 6.87 (s, 1H), 6.29 (s, 1H), 5.36-5.03 (m, 1H), 4.59 (s, 2H), 4.01 (s, 1H), 2.89 (s, 1H), 2.83-2.63 (m, 2H), 2.62-2.47 (m, 5H), 2.43 (s, 3H), 2.22 (s, 3H), 2.12 (d, 2H), 2.01 (d, 2H), 1.88 (t, 1H), 1.58 (s, 3H), 1.49 (dd, 2H), 1.28 (q, 2H).

LC-MS (ESI): m/z=564.2 $[M+H]^+$.

Embodiment 35

7-chloro-2-(4-((3,3-difluorocyclobutyl)(methyl)amino)cyclohexyl)-2,4-dimethyl-N-((6-methyl-4-(methylthio)-2-oxo-1,2-dihydropyridin-3-yl)methyl)benzo[d][1,3]dioxole-5-carboxamide (compound 35)

Compound 35

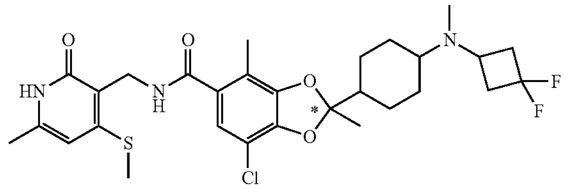

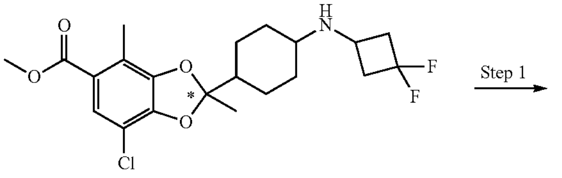

4B

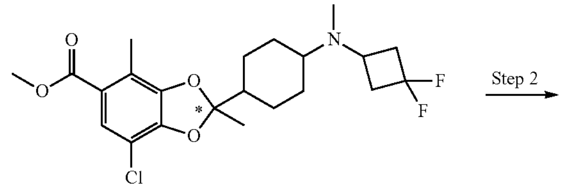

35A

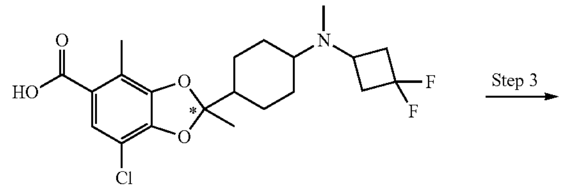

35B

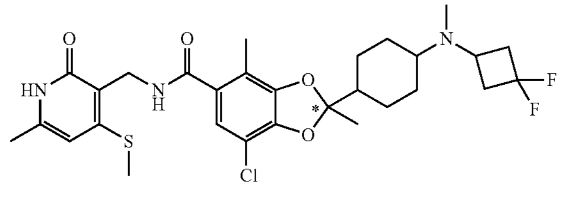

Compound 35

Step 1: methyl 7-chloro-2-(4-((3,3-difluorocyclobutyl)(methyl)amino)cyclohexyl)-2,4-dimethylbenzo[d][1,3]dioxole-5-carboxylate (35A)

Methyl 7-chloro-2-(4-((3,3-difluorocyclobutyl)amino)cyclohexyl)-2,4-dimethyl benzo[d][1,3]dioxole-5-carboxylate (4B) (500 mg, 1.16 mmol) and paraformaldehyde (157 mg, 1.74 mmol) were dissolved in 1,2-dichloroethan (10 mL); acetic acid (70 mg, 1.16 mmol) was added; and the mixture was reacted at room temperature for 1 hour. Sodium triacetoxyborohydride (493 mg, 2.33 mmol) was slowly added, and the mixture was reacted at room temperature for 4 hours. The reaction was quenched by slowly adding water (100 mL) to the reaction liquid. Liquid separation was performed. The aqueous phase was extracted with ethyl acetate (100 mL×3). The organic phases were combined, washed with water (100 mL×2), dried over anhydrous sodium sulfate and concentrated. The residue was separated and purified by silica gel column chromatography (petroleum ether:ethyl acetate (v/v)=0:1-1:1) to obtain the title compound methyl 7-chloro-2-(4-((3,3-difluorocyclobutyl)(methyl)amino)cyclohexyl)-2,4-dimethylbenzo[d][1,3]dioxole-5-carboxylate (35A) as a white powder solid (460 mg, yield: 89%).

LCMS m/z=444.1 $[M+1]^+$.

Step 2: 7-chloro-2-(4-((3,3-difluorocyclobutyl)(methyl)amino)cyclohexyl)-2,4-dimethylbenzo[d][1,3]dioxole-5-carboxylic acid (35B)

Methyl 7-chloro-2-(4-((3,3-difluorocyclobutyl)(methyl)amino)cyclohexyl)-2,4-dimethylbenzo[d][1,3]dioxole-5-carboxylate (35A) (450 mg, 1.01 mmol) was dissolved in methanol (15 mL). An aqueous sodium hydroxide solution (2M, 5 mL) was added dropwise, and the mixture was reacted at room temperature for 16 hours. The reaction liquid was adjusted to about pH=3 by slowly dropwise adding dilute hydrochloric acid. Water (50 mL) was added, and the reaction liquid was extracted with ethyl acetate (50 mL×5). The organic phases were combined, washed with water (50 mL×2), dried over anhydrous sodium sulfate and concentrated to obtain the title compound 7-chloro-2-(4-((3,3-difluorocyclobutyl)(methyl)amino)cyclohexyl)-2,4-dimethylbenzo[d][1,3]dioxole-5-carboxylic acid (35B) as a white powder solid (420 mg, yield: 96%).

LCMS m/z=430.2 $[M+1]^+$.

Step 3: 7-chloro-2-(4-((3,3-difluorocyclobutyl)(methyl)amino)cyclohexyl)-2,4-dimethyl-N-((6-methyl-4-(methylthio)-2-oxo-1,2-dihydropyridin-3-yl)methyl)benzo[d][1,3]dioxole-5-carboxamide (compound 35)

7-chloro-2-(4-((3,3-difluorocyclobutyl)(methyl)amino)cyclohexyl)-2,4-dimethylbenzo[d][1,3]dioxole-5-carboxylic acid (35B) (420 mg, 1.047 mmol), 3-(aminomethyl)-6-methyl-4-(methylthio)pyridine-2(1H)-one hydrochloride (intermediate 2) (277 mg, 1.26 mmol) and HATU (478 mg, 1.26 mmol) were dissolved in DMF (15 mL). DIPEA (530 mg, 5.23 mmol) was added dropwise, and the mixture was reacted at room temperature for 8 hours. Water (50 mL) was added. The aqueous phase was extracted with ethyl acetate (50 mL×5). The organic phases were combined, washed with water (50 mL×2), dried over anhydrous sodium sulfate and concentrated. The residue was separated and purified by silica gel column chromatography (dichloromethane:methanol (v/v)=0:1-10:1) to obtain the title compound 7-chloro-2-(4-((3,3-difluorocyclobutyl)(methyl)amino)cyclohexyl)-

2,4-dimethyl-N-((6-methyl-4-(methylthio)-2-oxo-1,2-dihydropyridin-3-yl)methyl)benzo[d][1,3]dioxole-5-carboxamide (compound 35) (387 mg, yield: 62%).

$^1$H NMR (400 MHz, DMSO) δ 11.49 (s, 1H), 8.01 (t, 1H), 6.86 (s, 1H), 6.07 (s, 1H), 4.27 (d, 2H), 3.15-3.04 (m, 1H), 2.65-2.54 (m, 2H), 2.48-2.35 (m, 6H), 2.16 (d, 6H), 2.06 (s, 3H), 2.03 (d, 1H), 1.72 (dd, 4H), 1.63 (s, 3H), 1.52 (dd, 2H), 1.41-1.31 (m, 2H).

LCMS m/z=596.2 [M+1]$^+$.

Embodiment 36

8-(7-chloro-2,4-dimethyl-5-(((6-methyl-4-(methylthio)-2-oxo-1,2-dihydropyridin-3-yl)methyl)carbamoyl)benzo[d][1,3]dioxol-2-yl)-N-methyl-3-azabicyclo[3.2.1]octane-3-carboxamide (compound 36)

Compound 36

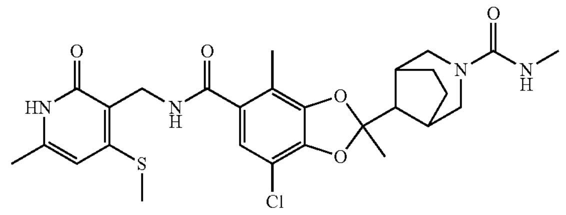

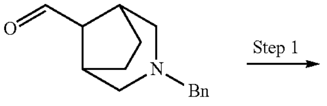

36A

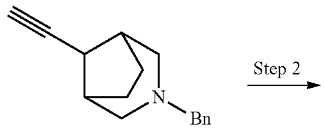

36B

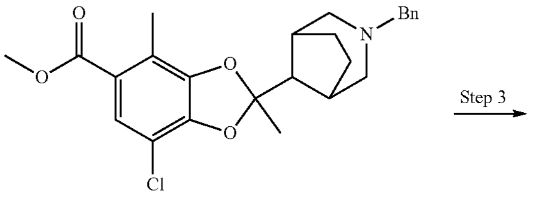

36C

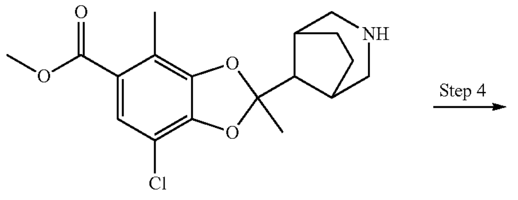

36D

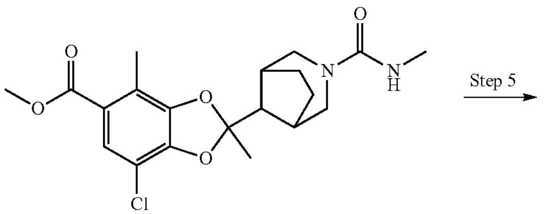

36E

-continued

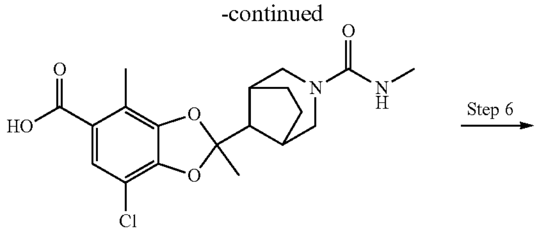

36F

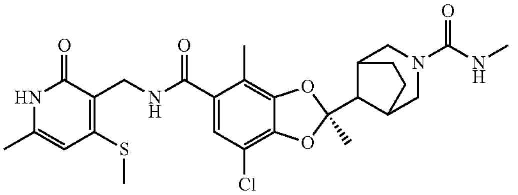

+

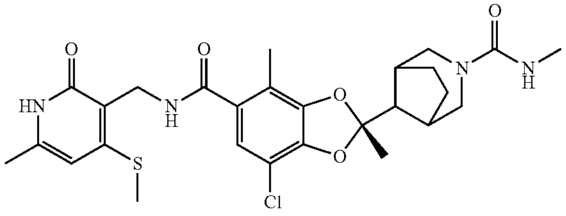

Compound 36

Step 1: 3-benzyl-8-ethynyl-3-azabicyclo[3.2.1]octane (36B)

3-benzyl-3-azabicyclo[3.2.1]octane-8-acetaldehyde (36A, obtained with reference to the method in WO 2007007282 and using cyclopentanone as a raw material) (3.4 g, 15 mmol) was dissolved in methanol (75 mL). Potassium carbonate (6.1 g, 44 mmol) was added. Under nitrogen protection, at 0° C., dimethyl(1-diazo-2-oxopropyl) phosphonate (7.1 g, 37 mmol) was slowly added. After the addition was completed, the mixture was reacted at room temperature for 3 hours. The reaction was quenched by slowly adding an ammonium chloride solution (10 mL). The aqueous phase was extracted with ethyl acetate (150 mL×3). The organic phases were combined, washed with water (150 mL×2), dried over anhydrous sodium sulfate and concentrated to obtain the title compound 3-benzyl-8-ethynyl-3-azabicyclo[3.2.1]octane (36B), as a colorless oily liquid (2.3 g, yield: 69%).

LCMS m/z=226.3 [M+1]$^+$.

Step 2: methyl 2-(3-benzyl-3-azabicyclo[3.2.1]octan-8-yl)-7-chloro-2,4-dimethylbenzo[d][1,3]dioxole-5-carboxylate (36C)

5-chloro-methyl 3,4-dihydroxy-2-methylbenzoate (1b) (800 mg, 3.69 mmol) was dissolved in toluene (10 mL). Triphenylphosphine (97 mg, 0.37 mmol) and rhodium dodecacarbonyl (5 mg, 0.04 mmol) were added. Under nitrogen protection, the mixture was reacted at 120° C. for 2 hours. A solution of 3-benzyl-8-ethynyl-3-azabicyclo[3.2.1]octane (1.25 g, 5.54 mmol) in toluene (5 mL) was added dropwise. The mixture was reacted at 120° C. for 2 hours and cooled to room temperature. Water was slowly added to the reaction liquid. The aqueous phase was extracted with ethyl acetate (150 mL×3). The organic phases were combined, washed with water (150 mL×2), dried over anhydrous sodium sulfate and concentrated. The residue was separated and purified by silica gel column chromatography (petroleum ether: ethyl acetate (v/v)=0:1-5:1) to obtain the title compound methyl 2-(3-benzyl-3-azabicyclo[3.2.1]octan-8-yl)-7-chloro-2,4-dimethylbenzo[d][1,3]dioxole-5-carboxylate (36C) as a white powder solid (520 mg, yield: 34%).

LCMS m/z=442.21 $[M+1]^+$.

Step 3: methyl 2-(3-benzyl-3-azabicyclo[3.2.1]octan-8-yl)-7-chloro-2,4-dimethylbenzo[d][1,3]dioxole-5-carboxylate (36D)

Methyl 2-(3-benzyl-3-azabicyclo[3.2.1]octan-8-yl)-7-chloro-2,4-dimethylbenzo[d][1,3]dioxole-5-carboxylate (36C) (440 mg, 0.996 mmol) was dissolved in methanol (9 mL) and hydrochloric acid in dioxane (3 mL). Palladium on carbon (62 mg, mass %=0.4) was added. The mixture was subjected to hydrogen replacement and reacted at 120° C. for 4 hours. The reaction liquid was filtered with Celite, and the filter cake was washed three times with methanol. The filtrate was concentrated to obtain the residue, which was the crude title compound methyl 2-(3-benzyl-3-azabicyclo[3.2.1]octan-8-yl)-7-chloro-2,4-dimethylbenzo[d][1,3]dioxole-5-carboxylate (36D) as a white powder solid (380 mg, yield: 98%).

LCMS m/z=352.1 $[M+1]^+$.

Step 4: methyl 7-chloro-2,4-dimethyl-2-(3-(methylcarbamoyl)-3-azabicyclo[3.2.1]octan-8-yl)benzo[d][1,3]dioxole-5-carboxylate (36E)

Methyl 2-(3-benzyl-3-azabicyclo[3.2.1]octan-8-yl)-7-chloro-2,4-dimethylbenzo[d][1,3]dioxole-5-carboxylate (36D) (100 mg, 0.284 mmol) was dissolved in dichloromethane (15 mL). Under nitrogen protection, at 0° C., triphosgene (30 mg, 0.1 mmol) was slowly added, and triethylamine (144 mg, 1.42 mmol) was added dropwise. After the addition was completed, the mixture was reacted at low temperature for 0.5 hours. At 0° C., a solution of methanamine hydrochloride (23 mg, 0.34 mmol) in dichloromethane was slowly added dropwise, and the mixture was reacted at room temperature for 1 hour. The reaction was quenched by slowly adding an ammonium chloride solution (10 mL) to the reaction liquid. Liquid separation was performed. The aqueous phase was extracted with ethyl acetate (150 mL×3). The organic phases were combined, washed with water (150 mL×2), dried over anhydrous sodium sulfate and concentrated. The residue was separated and purified by silica gel column chromatography (petroleum ether: ethyl acetate (v/v)=0:1-5:1) to obtain the title compound methyl 7-chloro-2,4-dimethyl-2-(3-(methylcarbamoyl)-3-azabicyclo[3.2.1]octan-8-yl)benzo[d][1,3]dioxole-5-carboxylate (36E) as a white powder solid (47 mg, yield: 34%).

LCMS m/z=410.1 $[M+1]^+$.

Step 5: 7-chloro-2,4-dimethyl-2-(3-(methylcarbamoyl)-3-azabicyclo[3.2.1]octan-8-yl)benzo[d][1,3]dioxole-5-carboxylic acid (36F)

Methyl 7-chloro-2,4-dimethyl-2-(3-(methylcarbamoyl)-3-azabicyclo[3.2.1]octan-8-yl)benzo[d][1,3]dioxole-5-carboxylate (36E) (180 mg, 0.44 mmol) was dissolved in methanol (15 mL). An aqueous sodium hydroxide solution (2M, 5 mL) was added dropwise, and the mixture was reacted at room temperature for 16 hours. The reaction liquid was adjusted to about pH=3 by slowly dropwise adding dilute hydrochloric acid. Water (50 mL) was added. The aqueous phase was extracted with ethyl acetate (50 mL×5). The combined organic phase was washed with water (50 mL), dried over anhydrous sodium sulfate and concentrated to obtain the title compound 7-chloro-2,4-dimethyl-2-(3-(methylcarbamoyl)-3-azabicyclo[3.2.1]octan-8-yl)benzo[d][1,3]dioxole-5-carboxylic acid (36F) as a white powder solid (160 mg, yield: 92%).

LCMS m/z=395.1 $[M+1]^+$.

Step 6: 8-(7-chloro-2,4-dimethyl-5-(((6-methyl-4-(methylthio)-2-oxo-1,2-dihydropyridin-3-yl)methyl)carbamoyl)benzo[d][1,3]dioxol-2-yl)-N-methyl-3-azabicyclo[3.2.1]octane-3-carboxamide (compound 36)

7-chloro-2,4-dimethyl-2-(3-(methylcarbamoyl)-3-azabicyclo[3.2.1]octan-8-yl)benzo[d][1,3]dioxole-5-carboxylic acid (36F) (160 mg, 0.63 mmol), 3-(aminomethyl)-6-methyl-4-(methylthio)pyridine-2(1H)-one hydrochloride (intermediate 2) (168 mg, 0.76 mmol) and HATU (289 mg, 0.76 mmol) were dissolved in DMF (15 mL). DIPEA (320 mg, 3.2 mmol) was added dropwise, and the mixture was reacted at room temperature for 8 hours. Water (50 mL) was added. The aqueous phase was extracted with ethyl acetate (50 mL×5). The organic phases were combined, washed with water (50 mL×2), dried over anhydrous sodium sulfate and concentrated. The residue was separated and purified by silica gel column chromatography (dichloromethane:methanol (v/v)=0:1-10:1) to obtain the title compound 8-(7-chloro-2,4-dimethyl-5-(((6-methyl-4-(methylthio)-2-oxo-1,2-dihydropyridin-3-yl)methyl)carbamoyl)benzo[d][1,3]dioxol-2-yl)-N-methyl-3-azabicyclo[3.2.1]octane-3-carboxamide (compound 36) (220 mg, yield: 95%).

LCMS m/z=561.3 $[M+1]^+$.

Resolution of Compound 36

8-(7-chloro-2,4-dimethyl-5-(((6-methyl-4-(methylthio)-2-oxo-1,2-dihydropyridin-3-yl)methyl)carbamoyl)benzo[d][1,3]dioxol-2-yl)-N-methyl-3-azabicyclo[3.2.1]octane-3-carboxamide (compound 36) (220 mg) was resolved and separated to obtain isomer 1 (retention time: 6.922 s, 96 mg) of compound 36 and isomer 2 (retention time: 9.746 s, 60 mg) of compound 36.

Resolution conditions: instrument: MG II preparative SFC (SFC-14); column: ChiralPak AD, 250×30 mm I.D., 5 μm; mobile phase: A for $CO_2$ and B for ethanol; gradient: B 50%; flow rate: 70 mL/min; back pressure: 100 bar; column temperature: 38° C.; wavelength: 220 nm; cycle: about 8.2 min; sample preparation: compound was dissolved in 15 ml of methanol/DCM; injection: 1 ml/injection.

Isomer 1 of Compound 36

$^1$H NMR (400 MHz, DMSO) δ 11.50 (s, 1H), 8.01 (t, 1H), 6.86 (s, 1H), 6.21 (s, 1H), 6.08 (s, 1H), 4.27 (d, 2H), 3.65 (d, 2H), 2.79 (d, 2H), 2.55-2.52 (m, 3H), 2.45 (s, 3H), 2.27 (d, 2H), 2.20-2.10 (m, 7H), 1.68 (s, 5H), 1.36 (d, 2H).

LCMS m/z=561.3 $[M+1]^+$.

Isomer 2 of Compound 36

$^1$H NMR (400 MHz, DMSO) δ 11.50 (s, 1H), 8.00 (t, 1H), 6.86 (s, 1H), 6.21 (d, 1H), 6.07 (s, 1H), 4.27 (d, 2H), 3.65 (d, J=11.6 Hz, 2H), 2.79 (d, 2H), 2.54 (d, 3H), 2.45 (s, 3H), 2.27 (d, 2H), 2.17 (d, 4H), 2.13 (s, 3H), 1.68 (s, 3H), 1.36 (d, 2H), 1.24 (s, 2H).

LCMS m/z=561.3 $[M+1]^+$.

Embodiment 37

7-chloro-2-(1-(cyclobutylmethyl)piperidin-4-yl)-2,4-dimethyl-N-((6-methyl-4-(methylthio)-2-oxo-1,2-dihydropyridin-3-yl)methyl)benzo[d][1,3]dioxole-5-carboxamide (compound 37)

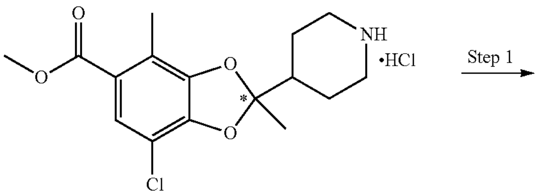

Intermediate 3

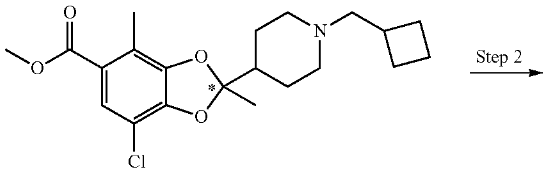

37A

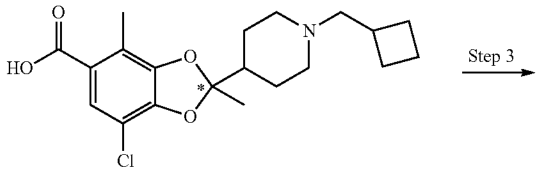

37B

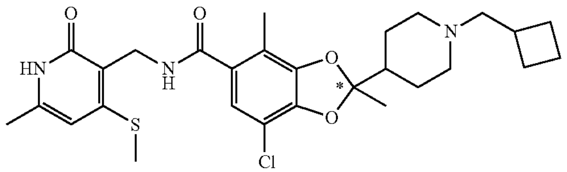

Compound 37

Step 1:

Intermediate 3 (200 mg, 0.55 mmol) was dissolved in DMF (6 mL). Potassium carbonate (152 mg, 1.10 mmol) and bromomethylcyclobutane (164 mg, 1.10 mmol) were added, and the mixture was stirred at room temperature overnight. Water (20 mL) was added to the reaction liquid, and the mixture was extracted three times with EA (20 mL). The combined organic phase was dried over anhydrous sodium sulfate, filtered and concentrated, and the residue was separated by column chromatography (PE:EA=1:1) to obtain 37A (190 mg, 88% yield) as a yellow solid.

LC-MS (ESI): m/z=394.2 $[M+H]^+$.

Step 2:

37A (190 mg, 0.48 mmol) was dissolved in methanol (8 mL). An aqueous NaOH solution (201 mg, 5.00 mmol, 2 mL) was added, and the reaction was stirred at 25° C. TLC showed that the reaction of the raw materials was completed. The reaction liquid was adjusted to pH=3-4 by dropwise adding 2N hydrochloric acid and concentrated under reduced pressure to obtain a crude. The crude was soaked with a mixed solvent (DCM:MeOH=10:1, 20 mL) and then filtered, and the filtrate was concentrated to obtain 37B (180 mg, 95%).

LC-MS (ESI): m/z=380.2 $[M+H]^+$.

Step 3:

In a 50 mL single-necked flask, 37B (90 mg, 0.24 mmol) was added and dissolved in DMF (6 mL). Triethylamine (64 mg, 0.63 mmol) and HATU (120 mg, 0.32 mmol) were added, and the mixture was stirred at room temperature for 0.5 h. Intermediate 5 (186 mg, 0.84 mmol) was added, and the mixture was stirred at room temperature for 5 h. Water (10 mL) was added to the reaction liquid, and the mixture was extracted with EA (20 mL×3). The combined organic phase was dried over anhydrous sodium sulfate and concentrated, and the residue was separated by column chromatography (DCM:MeOH=20:1) to obtain compound 37 (30 mg, yield: 23%).

LC-MS (ESI): m/z=546.2 $[M+H]^+$.

$^1$H NMR (400 MHz, DMSO-$d_6$) δ 11.50 (s, 1H), 7.99 (t, 1H), 6.85 (s, 1H), 6.07 (s, 1H), 4.27 (d, 2H), 2.84 (d, 2H), 2.45-2.48 (m, 1H), 2.44 (s, 3H), 2.28-2.30 (m, 2H), 2.17 (s, 3H), 2.14 (s, 3H), 1.95-2.01 (m, 3H), 1.75-1.85 (m, 5H), 1.64-1.69 (m, 2H), 1.61-1.63 (m, 1H), 1.60 (s, 3H), 1.32-1.40 (m, 2H).

Embodiment 38

7-chloro-2,4-dimethyl-N-((6-methyl-4-(methylthio)-2-oxo-1,2-dihydropyridin-3-yl)methyl)-2-(1-(oxetan-3-ylmethyl)piperidin-4-yl)benzo[d][1,3]dioxole-5-carboxamide (compound 38)

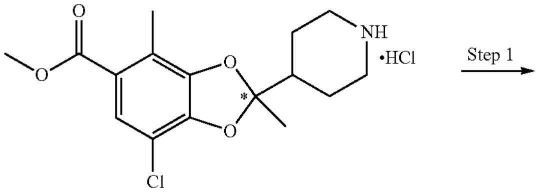

Intermediate 3

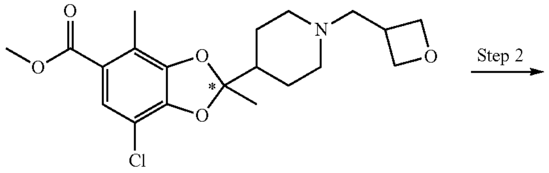

38A

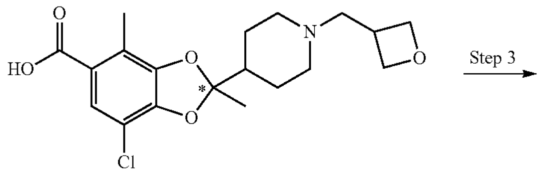

38B

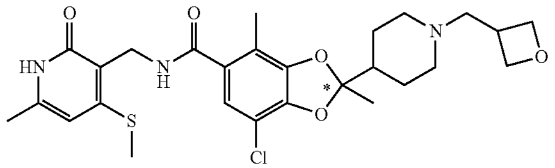

Compound 38

Step 1:

Intermediate 2 (200 mg, 0.55 mmol) was dissolved in DMF (6 mL). Potassium carbonate (152 mg, 1.10 mmol) and 3-(bromomethyl)oxetane (166 mg, 1.10 mmol) were added, and the mixture was stirred at room temperature overnight. Water (20 mL) was added to the reaction liquid, and the mixture was extracted three times with EA (20 mL). The combined organic phase was dried over anhydrous sodium sulfate, filtered and concentrated, and the residue was separated by column chromatography (PE:EA=1:1) to obtain 38A (190 mg, 88% yield) as a yellow solid.

LC-MS (ESI): m/z=396.1 $[M+H]^+$.

Step 2:

38A (190 mg, 0.48 mmol) was dissolved in methanol (8 mL). An aqueous NaOH solution (201 mg, 5.00 mmol, 2 mL) was added, and the reaction was stirred at 25° C. TLC showed that the reaction of the raw materials was completed. The reaction liquid was adjusted to pH=3-4 by dropwise adding 2N hydrochloric acid and concentrated under reduced pressure to obtain a crude. The crude was soaked with a mixed solvent (DCM:MeOH=10:1, 20 mL) and then filtered, and the filtrate was concentrated to obtain 38B (180 mg, 95%).

LC-MS (ESI): m/z=382.1 $[M+H]^+$.

Step 3:

In a 50 mL single-necked flask, 38B (90 mg, 0.24 mmol) was added and dissolved in DMF (6 mL). Triethylamine (64 mg, 0.63 mmol) and HATU (120 mg, 0.32 mmol) were added, and the mixture was stirred at room temperature for 0.5 h. Intermediate 5 (186 mg, 0.84 mmol) was added, and the mixture was stirred at room temperature for 5 h. Water (10 mL) was added to the reaction liquid, and the mixture was extracted with EA (20 mL×3). The combined organic phase was dried over anhydrous sodium sulfate and concentrated, and the residue was separated by column chromatography (DCM:MeOH=20:1) to obtain compound 38 (30 mg, yield: 23%).

LC-MS (ESI): m/z=548.2 $[M+H]^+$.

$^1H$ NMR (400 MHz, DMSO-$d_6$) δ 8.00 (t, 1H), 6.85 (s, 1H), 6.08 (s, 1H), 4.59-4.62 (m, 2H), 4.27 (d, 2H), 4.22 (t, 2H), 3.10-3.17 (m, 1H), 2.78 (d, 2H), 2.56 (d, 2H), 2.45 (s, 3H), 2.17 (s, 3H), 2.13 (s, 3H), 1.82-1.87 (m, 3H), 1.66-1.69 (m, 2H), 1.56 (s, 3H), 1.24-1.37 (m, 2H).

Embodiment 39

7-chloro-2,4-dimethyl-N-((6-methyl-4-(methylthio)-2-oxo-1,2-dihydropyridin-3-yl)methyl)-2-(4-(pyridin-2-yl)cyclohexyl)benzo[d][1,3]dioxole-5-carboxamide (compound 39)

Compound 39

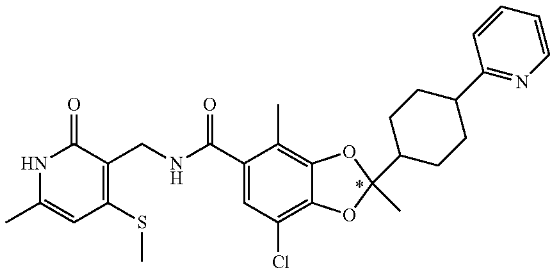

-continued

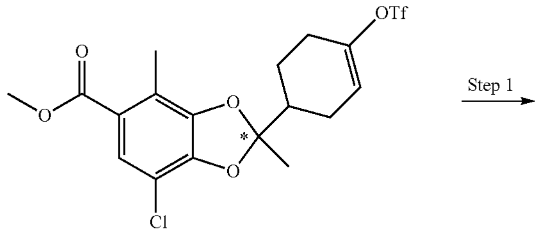

8A

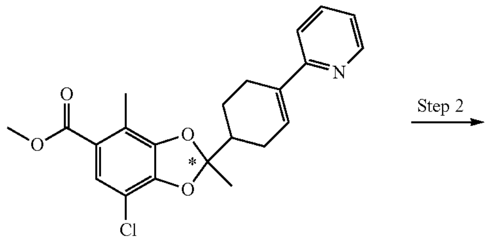

39A

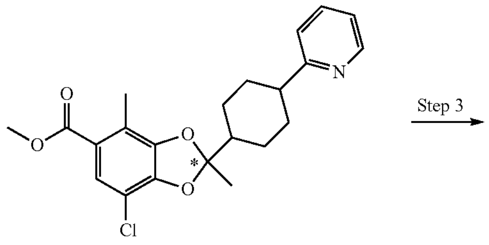

39B

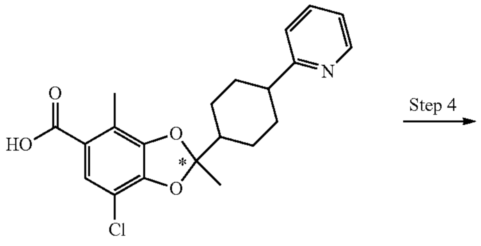

39c

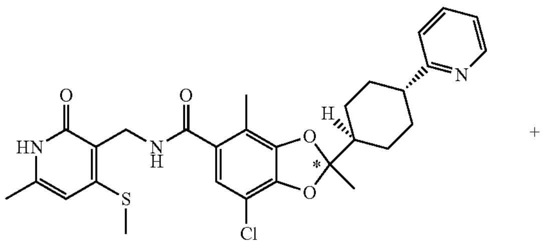

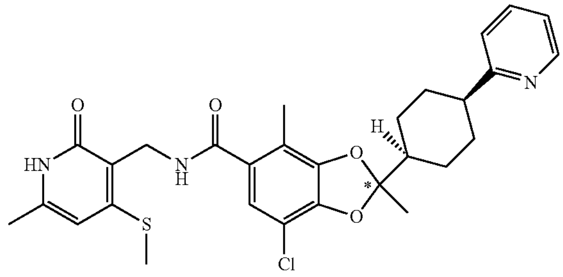

Compound 39, isomer 1 and isomer 2

Step 1: methyl 7-chloro-2,4-dimethyl-2-(4-(pyridin-2-yl)cyclohex-3-en-1-yl)benzo[d][1,3]dioxole-5-carboxylate (39A)

Compound 8A (300 mg, 0.64 mmol) and 2-pyridineboronic acid (118 mg, 0.96 mmol) were dissolved in ethylene glycol dimethyl ether (15 mL). [1,1'-bis(diphenylphosphino)ferrocene]palladium dichloride (47 mg, 0.064 mmol) and potassium carbonate (220 mg, 1.6 mmol) were added. Under nitrogen protection, the mixture was reacted at 80° C. for 3 hours. The reaction was quenched by slowly adding ice water (50 mL) to the reaction liquid. Liquid separation was performed. The aqueous phase was extracted with ethyl acetate (50 mL×3). The organic phases were combined, washed with water (50 mL×2), dried over anhydrous sodium sulfate and concentrated. The residue was separated and purified by silica gel column chromatography (petroleum ether:ethyl acetate (v/v)=0: 1-1:1) to obtain the title compound methyl 7-chloro-2,4-dimethyl-2-(4-(pyridin-2-yl)cyclohex-3-en-1-yl)benzo[d][1,3]dioxole-5-carboxylate (39A) as a white powder solid (155 mg, yield: 61%).

LCMS m/z=400.1 $[M+1]^+$.

Step 2: methyl 7-chloro-2,4-dimethyl-2-(4-(pyridin-2-yl)cyclohexyl)benzo[d][1,3]dioxole-5-carboxylate (39B)

Methyl 7-chloro-2,4-dimethyl-2-(4-(pyridin-2-yl)cyclohex-3-en-1-yl)benzo[d][1,3]dioxole-5-carboxylate (39A) (155 mg, 0.39 mmol) was dissolved in methanol (10 mL). Palladium on carbon (62 mg, mass %=0.4) was added. The mixture was subjected to hydrogen replacement and reacted for 16 hours. The reaction liquid was filtered with Celite, and the filter cake was washed three times with methanol. The filtrate was concentrated to obtain the residue, which was the crude title compound methyl 7-chloro-2,4-dimethyl-2-(4-(pyridin-2-yl)cyclohexyl)benzo[d][1,3]dioxole-5-carboxylate (39B) as a white powder solid (130 mg, yield: 84%).

LCMS m/z=402.1 $[M+1]^+$.

Step 3: 7-chloro-2,4-dimethyl-2-(4-(pyridin-2-yl)cyclohexyl)benzo[d][1,3]dioxole-5-carboxylic acid (39C)

Methyl 7-chloro-2,4-dimethyl-2-(4-(pyridin-2-yl)cyclohexyl)benzo[d][1,3]dioxole-5-carboxylate (39B) (130 mg, 0.32 mmol) was dissolved in methanol (15 mL). An aqueous sodium hydroxide solution (2M, 5 mL) was added dropwise, and the mixture was reacted at room temperature for 16 hours. The reaction liquid was adjusted to about pH=3 by slowly dropwise adding dilute hydrochloric acid. Water (50 mL) was added. The aqueous phase was extracted with ethyl acetate (50 mL×5). The organic phases were combined, washed with water (50 mL×2), dried over anhydrous sodium sulfate and concentrated to obtain the title compound 7-chloro-2,4-dimethyl-2-(4-(pyridin-2-yl)cyclohexyl)benzo[d][1,3]dioxole-5-carboxylic acid (39C) as a white powder solid (110 mg, yield: 88%).

LCMS m/z=388.1 $[M+1]^+$.

Step 4: 7-chloro-2,4-dimethyl-N-((6-methyl-4-(methylthio)-2-oxo-1,2-dihydropyridin-3-yl)methyl)-2-(4-(pyridin-2-yl)cyclohexyl)benzo[d][1,3]dioxole-5-carboxamide (compound 39)

7-chloro-2,4-dimethyl-2-(4-(pyridin-2-yl)cyclohexyl)benzo[d][1,3]dioxole-5-carboxylic acid (39C) (100 mg, 0.26 mmol), 3-(aminomethyl)-6-methyl-4-(methylthio)pyridine-2(1H)-one hydrochloride (intermediate 2) (68 mg, 0.31 mmol) and HATU (118 mg, 0.31 mmol) were dissolved in DMF (5 mL). DIPEA (130 mg, 1.3 mmol) was added dropwise, and the mixture was reacted at room temperature for 8 hours. Water (50 mL) was added. The aqueous phase was extracted with ethyl acetate (50 mL×5). The organic phases were combined, washed with water (50 mL×2), dried over anhydrous sodium sulfate and concentrated. The residue was separated and purified by silica gel column chromatography (dichloromethane:methanol (v/v)=0:1-10:1) to obtain the title compound 7-chloro-2,4-dimethyl-N-((6-methyl-4-(methylthio)-2-oxo-1,2-dihydropyridin-3-yl)methyl)-2-(4-(pyridin-2-yl)cyclohexyl)benzo[d][1,3]dioxole-5-carboxamide (compound 39) (125 mg, yield: 87%).

LCMS m/z=554.2 $[M+1]^+$.

Resolution of Compound 39

7-chloro-2,4-dimethyl-N-((6-methyl-4-(methylthio)-2-oxo-1,2-dihydropyridin-3-yl)methyl)-2-(4-(pyridin-2-yl)cyclohexyl)benzo[d][1,3]dioxole-5-carboxamide (compound 39) (125 mg) was resolved and separated to obtain isomer 1 (retention time: 1.867 s, 28 mg) of compound 39 and isomer 2 (retention time: 2.386 s, 26 mg) of compound 39.

Resolution conditions: instrument: MG II preparative SFC (SFC-14); column: ChiralPak AD, 250×30 mm I.D., 5 μm; mobile phase: A for $CO_2$ and B for ethanol (0.1% $NH_3H_2O$); gradient: B 50%; flow rate: 80 mL/min; back pressure: 100 bar; column temperature: 38° C.; wavelength: 220 nm; cycle: about 3.5 min; sample preparation: compound was dissolved in 20 ml of methanol/DCM; injection: 2 mL/injection.

Isomer 1 of Compound 39:

$^1H$ NMR (400 MHz, DMSO-$d_6$) δ 11.49 (s, 1H), 8.49 (d, 1H), 7.98 (t, 1H), 7.73-7.66 (m, 1H), 7.33 (d, 1H), 7.20-7.13 (m, 1H), 6.82 (s, 1H), 6.07 (s, 1H), 4.26 (d, 2H), 3.01 (s, 1H), 2.44 (s, 3H), 2.26 (d, 2H), 2.16 (s, 3H), 2.09 (s, 3H), 2.03 (s, 1H), 1.70 (s, 4H), 1.58 (s, 3H), 1.48 (d, 2H).

LCMS m/z=554.2 $[M+1]^+$.

Isomer 2 of Compound 39:

$^1H$ NMR (400 MHz, DMSO-$d_6$) δ 11.50 (s, 1H), 8.47 (d, 1H), 8.00 (t, 1H), 7.69 (td, 1H), 7.25 (d, 1H), 7.18 (dd, 1H), 6.87 (s, 1H), 6.08 (s, 1H), 4.27 (d, 2H), 2.65 (dd, 1H), 2.45 (s, 3H), 2.16 (d, 6H), 1.96 (dd, 5H), 1.65 (s, 3H), 1.59-1.50 (m, 2H), 1.37-1.32 (m, 2H).

LCMS m/z=554.2 $[M+1]^+$.

Embodiment 40
7-chloro-2-(4-(((3,3-difluorocyclobutyl)amino)methyl)cyclohexyl)-2,4-dimethyl-N-((6-methyl-4-(methylthio)-2-oxo-1,2-dihydropyridin-3-yl)methyl)benzo[d][1,3]dioxole-5-carboxamide (compound 40)
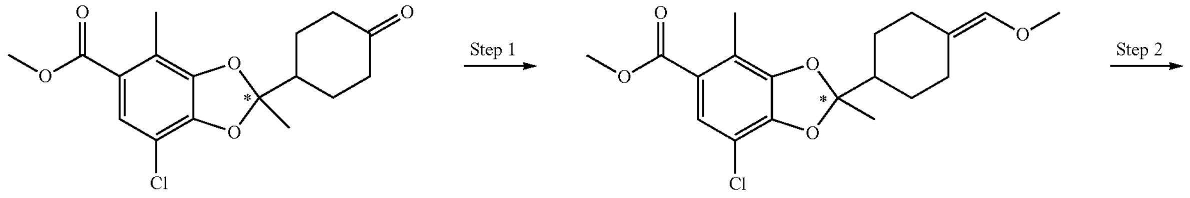
Intermediate 2 40A
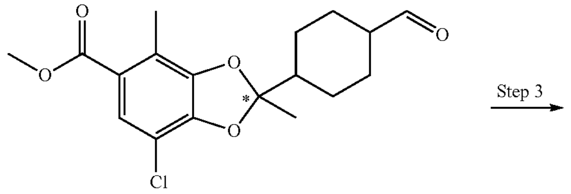
40B
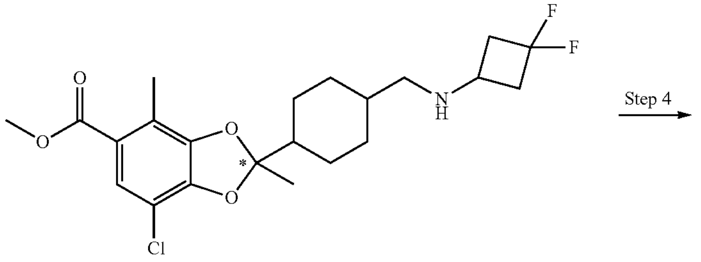
40C
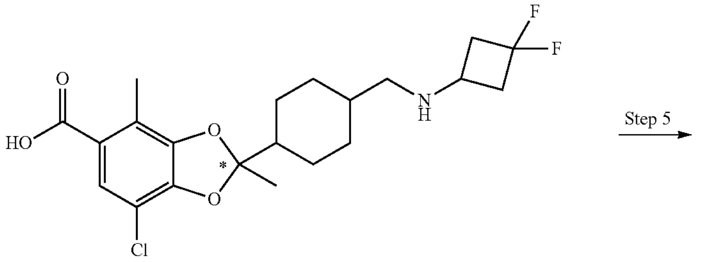
40D
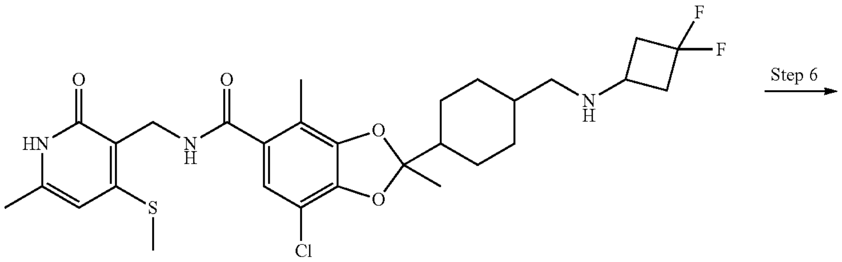
Compound 40

-continued

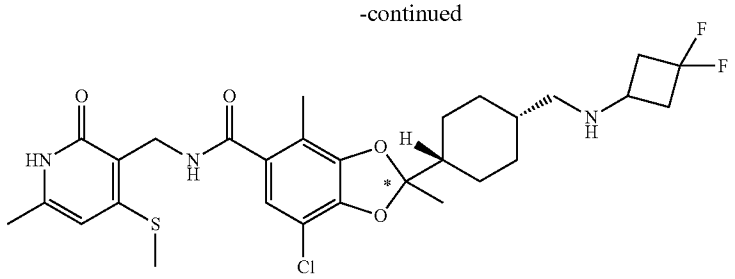

+

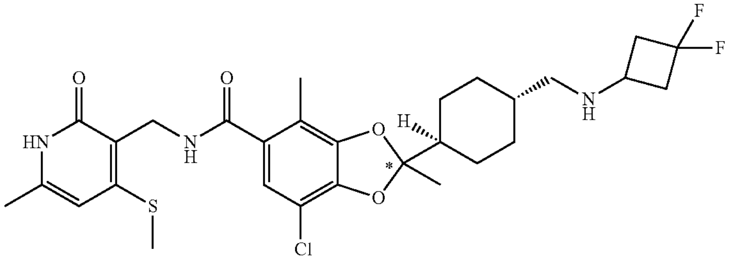

Compound 40, isomer 1 & Compound 40, isomer 2

Step 1: methyl-7-chloro-2-(4-(methoxymethylene) cyclohexyl)-2,4-dimethylbenzo[d][1,3]dioxole-5-carboxylate (40A)

Chloro-(methoxymethyl)-triphenylphosphine (0.91 g, 2.66 mol) was dissolved in tetrahydrofuran (10 mL). Potassium tert-butoxide (0.30 g, 2.66 mmol) was added, and the mixture was reacted at 0° C. for 30 minutes. Methyl 7-chloro-2,4-dimethyl-2-(4-oxocyclohexyl)-1,3-benzodioxole-5-carboxylate (intermediate 2) (0.3 g, 0.89 mmol) was added, and the mixture was reacted at 0° C. for 1 hour and at room temperature for 2 hours. A saturated aqueous ammonium chloride solution (30 mL) was added to the reaction liquid, and the mixture was extracted with ethyl acetate (50 mL). Liquid separation was performed. The aqueous phase was extracted with ethyl acetate (50 mL×3). The organic phases were combined, washed with water (50 mL×2), dried over anhydrous sodium sulfate and concentrated to obtain the title compound methyl-7-chloro-2-(4-(methoxymethylene)cyclohexyl)-2,4-dimethylbenzo[d][1,3]dioxole-5-carboxylate (40A) as a colorless oil (0.25 g, yield: 80%).

LCMS m/z=367.1 $[M+1]^+$.

Step 2: methyl-7-chloro-2-(4-formylcyclohexyl)-2,4-dimethylbenzo[d][1,3]dioxole-5-carboxylate (40B)

Methyl-7-chloro-2-(4-(methoxymethylene)cyclohexyl)-2,4-dimethylbenzo[d][1,3]dioxole-5-carboxylate (40A) (0.25 g, 0.68 mol) was dissolved in a mixed solvent (10 mL) of DCM/HCOOH (v/v=1/1), and the mixture was reacted at room temperature for 1 hour. The reaction liquid was concentrated to obtain the title compound methyl-7-chloro-2-(4-formylcyclohexyl)-2,4-dimethylbenzo[d][1,3]dioxole-5-carboxylate (40B) as a yellow oil (0.23 g, yield: 96%).

LCMS m/z=353.1 $[M+1]^+$.

Step 3: methyl-7-chloro-2-(4-(((3,3-difluorocyclobutyl)amino)methyl)cyclohexyl)-2,4-dimethylbenzo[d][1,3]dioxole-5-carboxylate (40C)

Methyl-7-chloro-2-(4-formylcyclohexyl)-2,4-dimethylbenzo[d][1,3]dioxole-5-carboxylate (40B) (0.40 g, 1.13 mmol) was dissolved in DCM (10 mL). 3,3-difluorocyclobutylamine hydrochloride (0.16 g, 1.13 mmol) and one drop of glacial acetic acid were successively added, and the mixture was stirred at room temperature for 2 hours. Sodium triacetylborohydride (0.72 g, 3.40 mmol) was then added, and the mixture was reacted at room temperature for another 3 hours. Water (30 mL) was added to the reaction liquid, and the mixture was extracted with ethyl acetate (50 mL×2). The combined organic phase was washed with saturated brine (50 mL), dried over anhydrous sodium sulfate and concentrated under reduced pressure to obtain the title compound methyl-7-chloro-2-(4-(((3,3-difluorocyclobutyl)amino)methyl)cyclohexyl)-2,4-dimethylbenzo[d][1,3]dioxole-5-carboxylate (40C) as a yellow solid (0.45 g, yield: 89%).

LCMS m/z=444.1 $[M+1]^+$.

Step 4: 7-chloro-2-(4-(((3,3-difluorocyclobutyl)amino)methyl)cyclohexyl)-2,4-dimethylbenzo[d][1,3]dioxole-5-carboxylic acid (40D)

The compound methyl-7-chloro-2-(4-(((3,3-difluorocyclobutyl)amino)methyl)cyclohexyl)-2,4-dimethylbenzo[d][1,3]dioxole-5-carboxylate (40C) (0.4 g, 0.90 mmol) was dissolved in a mixed solvent (12 mL) of $THF/MeOH/H_2O$ (1/1/1). Sodium hydroxide (0.42 g, 10.42 mmol) was added, and the mixture was reacted at room temperature for 4 hours. The reaction liquid was adjusted to about pH=2 by adding a hydrochloric acid solution (6 mol/L) and extracted with ethyl acetate (50 mL×3). The organic phases were combined, washed with water (50 mL), dried over anhydrous sodium sulfate and concentrated to obtain the title compound 7-chloro-2-(4-(((3,3-difluorocyclobutyl)amino)methyl)cyclohexyl)-2,4-dimethylbenzo[d][1,3]dioxole-5-carboxylic acid (40D) as a pale yellow solid (0.30 g, yield: 77%).

LCMS m/z=430.1 $[M+1]^+$.

Step 5: 7-chloro-2-(4-(((3,3-difluorocyclobutyl)amino)methyl)cyclohexyl)-2,4-dimethyl-N-((6-methyl-4-(methylthio)-2-oxo-1,2-dihydropyridin-3-yl)methyl)benzo[d][1,3]dioxole-5-carboxamide (compound 40, isomer 1 and compound 40, isomer 2)

The compound 7-chloro-2-(4-(((3,3-difluorocyclobutyl)amino)methyl)cyclohexyl)-2,4-dimethylbenzo[d][1,3]dioxole-5-carboxylic acid (40D) (0.4 g, 0.93 mmol), intermediate 2 (0.20 g, 1.10 mmol), HATU (0.52 g, 1.36 mmol) and DIEA (0.36 g, 2.72 mmol) were dissolved in dichloromethane (12 mL), and the mixture was reacted at room temperature for 12 hours. The reaction liquid was diluted by adding water. Liquid separation was performed. The aqueous phase was extracted with ethyl acetate (50 mLx3). The organic phases were combined, washed with water (50 mL), dried over anhydrous sodium sulfate and concentrated. The residue was separated and purified by silica gel column chromatography (dichloromethane:methanol (v/v)=1:0-9:1) to obtain the title compound 7-chloro-2-(4-(((3,3-difluorocyclobutyl)amino)methyl)cyclohexyl)-2,4-dimethyl-N-((6-methyl-4-(methylthio)-2-oxo-1,2-dihydropyridin-3-yl)methyl)benzo[d][1,3]dioxole-5-carboxamide (compound 40) (0.4 g, yield: 72%).

LCMS m/z=596.2 $[M+1]^+$.

Step 6: Resolution of Compound 40:

7-chloro-2-(4-(((3,3-difluorocyclobutyl)amino)methyl)cyclohexyl)-2,4-dimethyl-N-((6-methyl-4-(methylthio)-2-oxo-1,2-dihydropyridin-3-yl)methyl)benzo[d][1,3]dioxole-5-carboxamide (compound 40) (400 mg) was resolved and separated to obtain isomer 1 (retention time: 4.48 s, 167 mg) of compound 40 and isomer 2 (retention time: 8.72 s, 153 mg) of compound 40.

Resolution Conditions:

instrument: MG II preparative SFC (SFC-1); chromatographic column: ChiralPak IG, 250×30 mm I.D., 10 μm; mobile phase A: $CO_2$, mobile phase B: ethanol (0.1% $NH_3 \cdot H_2O$); gradient elution, mobile phase B: 50%; flow rate: 80 mL/min; column temperature: 38° C.; and elution time: 11 min.

Isomer 1 of Compound 40

$^1$H NMR (400 MHz, $CD_3OD$) δ 6.88 (s, 1H), 6.27 (s, 1H), 4.49 (s, 2H), 3.60 (m, 1H), 3.16 (m, 1H), 2.76 (m, 2H), 2.54 (s, 1H), 2.52 (s, 3H), 2.33 (m, 1H), 2.29 (s, 3H), 2.19 (s, 3H), 1.92 (m, 1H), 1.72 (m, 5H), 1.61 (s, 3H), 1.54 (m, 2H), 1.41 (m, 2H), 1.17 (m, 1H).

MS M/Z (ESI): 596.2 $[M+1]^+$.

Isomer 2 of Compound 40

$^1$H NMR (400 MHz, $CD_3OD$) δ 6.88 (s, 1H), 6.27 (s, 1H), 4.49 (s, 2H), 3.60 (m, 1H), 3.13 (m, 1H), 2.99 (m, 1H), 2.75 (m, 2H), 2.52 (s, 3H), 2.35 (m, 1H), 2.29 (s, 3H), 2.19 (s, 3H), 1.90 (m, 5H), 1.60 (s, 3H), 1.25 (m, 2H), 1.17 (t, 2H), 0.98 (m, 2H).

MS M/Z (ESI): 596.2 $[M+1]^+$.

Embodiment 41

7-chloro-2-(4-((cis-3-fluorocyclobutyl)amino)cyclohexyl)-2,4-dimethyl-N-((6-methyl-4-(methylthio)-2-oxo-1,2-dihydropyridin-3-yl)methyl)benzo[d][1,3]dioxole-5-carboxamide (compound 41)

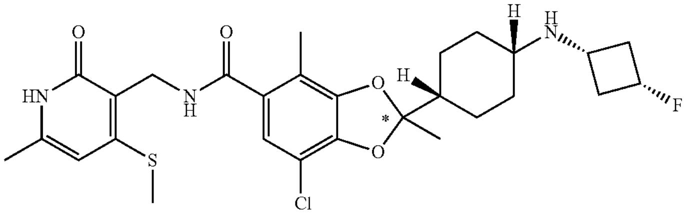

+

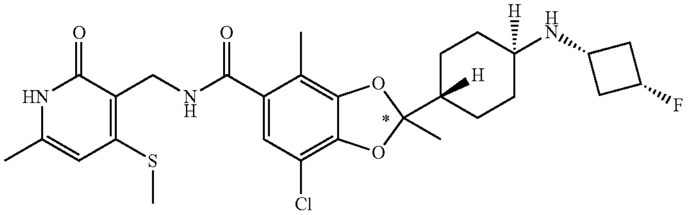

Compound 41, isomer 1 & Compound 41, isomer 2

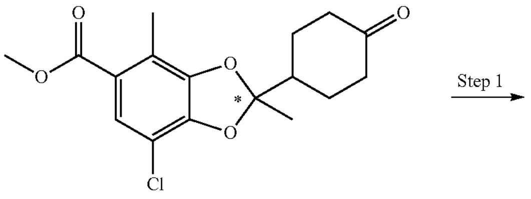

Intermediate 2

-continued

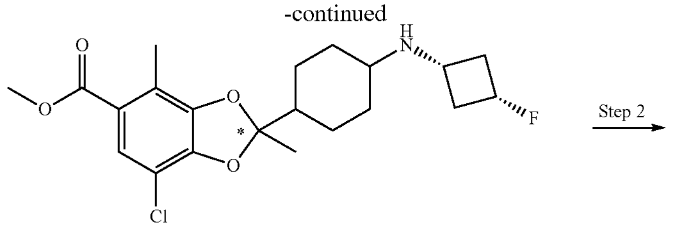

41A

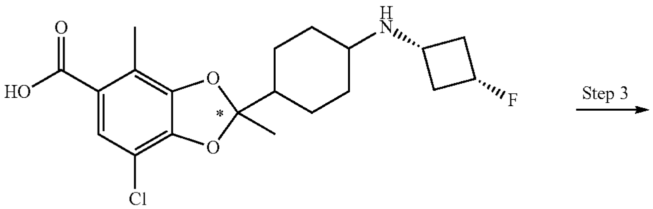

41B

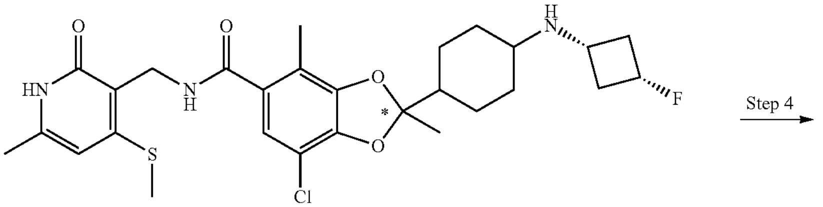

Compound 41

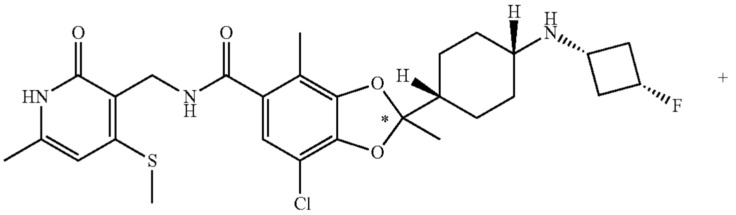

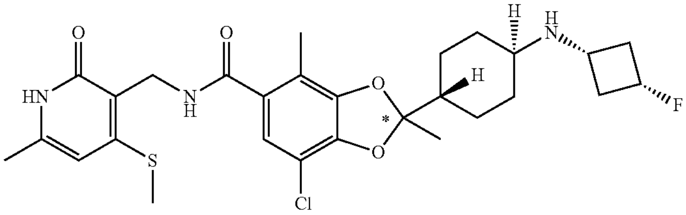

Compound 41, isomer 1 & Compound 41, isomer 2

Step 1: methyl-7-chloro-2-(4-((cis-3-fluorocyclobutyl)amino)cyclohexyl)-2,4-dimethylbenzo[d][1,3]dioxole-5-carboxylate (41A)

With reference to the synthetic method (step 3) of compound 40, methyl 7-chloro-2,4-dimethyl-2-(4-oxocyclohexyl)-1,3-benzodioxole-5-carboxylate (intermediate 2) (0.3 g, 0.89 mmol) and cis 3-fluorocyclobutylamine hydrochloride were used as raw materials to obtain the title compound methyl-7-chloro-2-(4-((cis-3-fluorocyclobutyl)amino)cyclohexyl)-2,4-dimethylbenzo[d][1,3]dioxole-5-carboxylate (41A) as a colorless oil (0.35 g, yield: 96%).

LCMS m/z=412.2 $[M+1]^+$.

Step 2: 7-chloro-2-(4-((cis-3-fluorocyclobutyl)amino)cyclohexyl)-2,4-dimethylbenzo[d][1,3]dioxole-5-carboxylic acid (41B)

With reference to the synthetic method (step 4) of compound 40, methyl-7-chloro-2-(4-((cis-3-fluorocyclobutyl)amino)cyclohexyl)-2,4-dimethylbenzo[d][1,3]dioxole-5-carboxylate (41A) (0.35 g, 0.85 mol) was used as a raw material to obtain the title compound 7-chloro-2-(4-((cis-3-fluorocyclobutyl)amino)cyclohexyl)-2,4-dimethylbenzo[d][1,3]dioxole-5-carboxylic acid (41B) as a yellow oil (0.30 g, yield: 89%).

LCMS m/z=398.2 $[M+1]^+$.

Step 3: 7-chloro-2-(4-((cis-3-fluorocyclobutyl)amino)cyclohexyl)-2,4-dimethyl-N-((6-methyl-4-(methylthio)-2-oxo-1,2-dihydropyridin-3-yl)methyl)benzo[d][1,3]dioxole-5-carboxamide (compound 41)

With reference to the synthetic method (step 5) of compound 40, 7-chloro-2-(4-((cis-3-fluorocyclobutyl)amino)cyclohexyl)-2,4-dimethylbenzo[d][1,3]dioxole-5-carboxylic acid (41B) (0.30 g, 0.75 mmol) was used as a raw material to obtain the title compound 7-chloro-2-(4-((cis-3-fluorocyclobutyl)amino)cyclohexyl)-2,4-dimethyl-N-((6-methyl-4-(methylthio)-2-oxo-1,2-dihydropyridin-3-yl)methyl)benzo[d][1,3]dioxole-5-carboxamide (compound 41) (0.25 g, yield: 59%).

LCMS m/z=564.2 $[M+1]^+$.

Step 4: Resolution of Compound 41

7-chloro-2-(4-((cis-3-fluorocyclobutyl)amino)cyclohexyl)-2,4-dimethyl-N-((6-methyl-4-(methylthio)-2-oxo-1,2-dihydropyridin-3-yl)methyl)benzo[d][1,3]dioxole-5-carboxamide (compound 41) (250 mg) was resolved and separated to obtain isomer 1 (retention time: 12.48 min, 54 mg) of compound 41 and isomer 2 (retention time: 14.72 min, 63 mg) of compound 41.

Resolution conditions:

instrument: waters 2767 (preparative liquid phase chromatographic instrument); chromatographic column: XSelect@ CSH Prep (19 mm×150 mm); mobile phase A: acetonitrile; mobile phase B: water (containing 5 nM ammonium bicarbonate); gradient elution, mobile phase A: 30%-75%; flow rate: 12 mL/min; elution time: 20 min.

Isomer 1 of Compound 41

$^1$H NMR (400 MHz, $CD_3OD$) δ 6.88 (s, 1H), 6.26 (s, 1H), 4.65 (m, 1H), 4.49 (s, 2H), 2.87 (m, 1H), 2.67 (m, 2H), 2.52 (s, 3H), 2.43 (m, 1H), 2.29 (s, 3H), 2.18 (s, 3H), 1.92 (m, 7H), 1.60 (s, 3H), 1.27 (m, 2H), 1.12 (m, 2H).

MS M/Z (ESI): 564.2 $[M+1]^+$.

Isomer 2 of Compound 41

$^1$H NMR (400 MHz, $CD_3OD$) δ 6.88 (s, 1H), 6.26 (s, 1H), 4.65 (m, 1H), 4.49 (s, 2H), 2.81 (m, 2H), 2.68 (m, 2H), 2.52 (s, 3H), 2.29 (s, 3H), 2.20 (s, 3H), 1.92 (m, 3H), 1.80 (m, 2H), 1.59 (m, 10H).

MS M/Z (ESI): 564.2 $[M+1]^+$.

Embodiment 42

7-chloro-2,4-dimethyl-N-((6-methyl-4-(methylthio)-2-oxo-1,2-dihydropyridin-3-yl)methyl)-2-(4-(5-methylhexahydropyrrolo[3,4-c]pyrrol-2(1H)-yl)cyclohexyl)benzo[d][1,3]dioxole-5-carboxamide (compound 42)

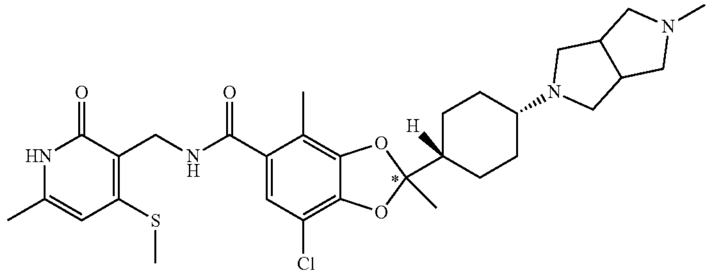

+

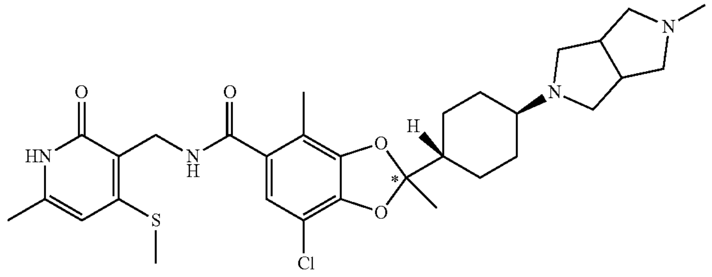

Compound 42

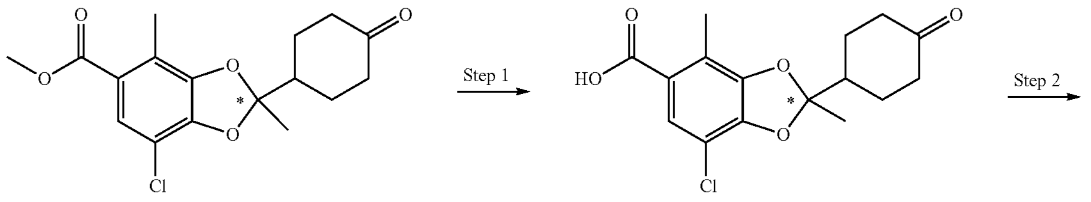

Intermediate 2

42A

-continued

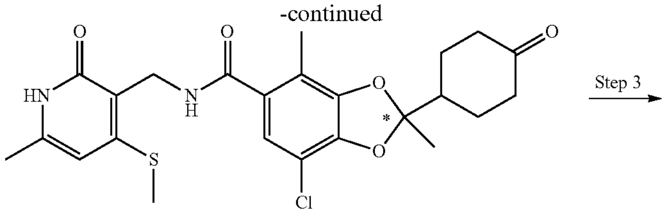

42B

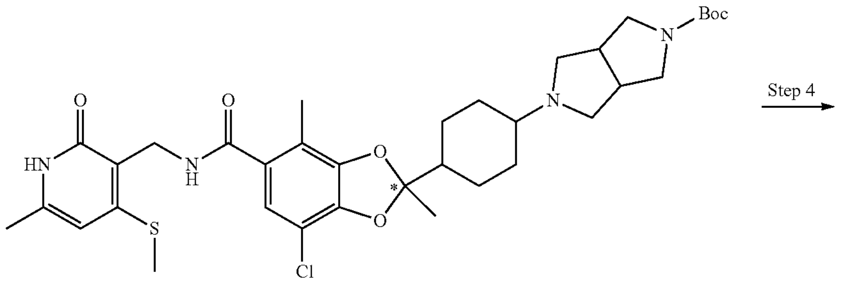

42C

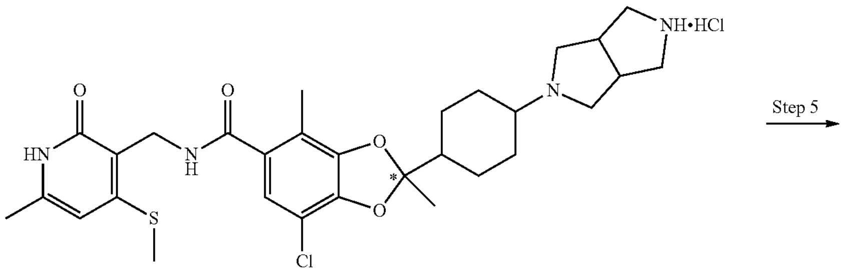

42D

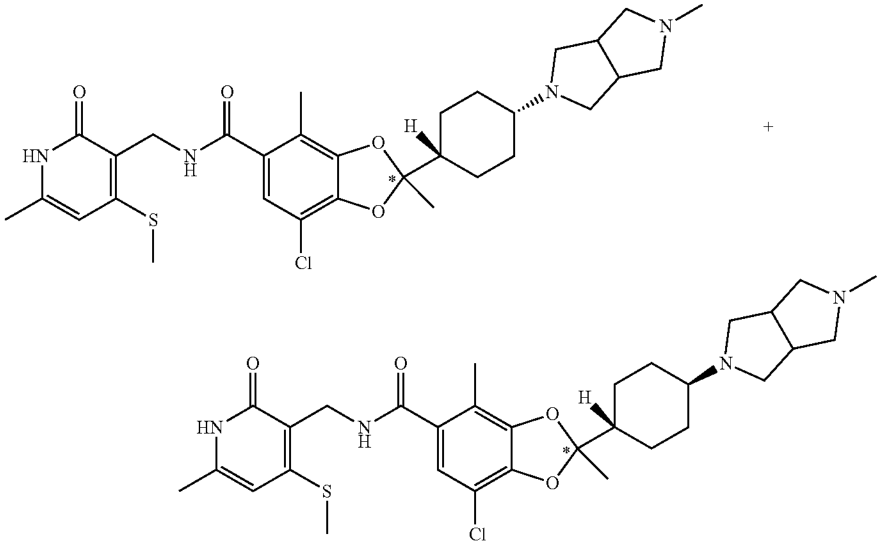

Compound 42

Step 1: 7-chloro-2,4-dimethyl-2-(4-oxocyclohexyl)benzo[d][1,3]dioxole-5-carboxylic acid (42A)

Methyl 7-chloro-2,4-dimethyl-2-(4-oxocyclohexyl)benzo[d][1,3]dioxole-5-carboxylate (intermediate 2) (1.5 g, 4.4 mmol) was dissolved in anhydrous methanol (20 mL). Water (20 mL) and sodium hydroxide (358 mg, 8.8 mmol) were added. The mixture was warmed to 50° C., reacted for 2 hours and cooled to room temperature. The reaction liquid was adjusted to pH=4-5 by dropwise adding to a hydrochloric acid solution (1 M/L) and extracted with ethyl acetate (50 mL×3). The organic phases were combined, washed with saturated brine (50 mL×1), dried over anhydrous sodium sulfate and concentrated to obtain the title compound 7-chloro-2,4-dimethyl-2-(4-oxocyclohexyl)benzo[d][1,3]dioxole-5-carboxylic acid (42A) as a light yellow solid (1.4 g, yield: 98%).

LCMS m/z=325.08 $[M+1]^+$.

Step 2: 7-chloro-2,4-dimethyl-N-((6-methyl-4-(methylthio)-2-oxo-1,2-dihydropyridin-3-yl)methyl)-2-(4-oxocyclohexyl)benzo[d][1,3]dioxole-5-carboxamide (42B)

7-chloro-2,4-dimethyl-2-(4-oxocyclohexyl)benzo[d][1,3]dioxole-5-carboxylic acid (42A) (1.4 g, 4.3 mmol) was dissolved in anhydrous tetrahydrofuran (40 mL). HOBT (988 mg, 6.5 mmol), EDCI (1.65 g, 8.6 mmol), 3-(aminomethyl)-6-methyl-4-(methylthio)pyridine-2(1H)-hydrochloride (1.43 g, 6.5 mmol) and TEA (2.17 g, 21.5 mmol) were successively added, and the mixture was reacted at room temperature for 4 hours. Water (50 mL) was added, and the reaction liquid was extracted with ethyl acetate (50 mL×3). The organic phases were combined, washed with saturated brine (50 mL), dried over anhydrous sodium sulfate and concentrated. The residue was separated and purified by silica gel column chromatography (dichloromethane:methanol (v/v)=0.01:1-0.05:1) to obtain the title compound 7-chloro-2,4-dimethyl-N-((6-methyl-4-(methylthio)-2-oxo-1,2-dihydropyridin-3-yl)methyl)-2-(4-oxocyclohexyl)benzo[d][1,3]dioxole-5-carboxamide (42B) as a yellow solid (1.6 g, yield: 76%).

LCMS m/z=491.13 $[M+1]^+$.

Step 3: tert-butyl 5-(4-(7-chloro-2,4-dimethyl-5-(((6-methyl-4-(methylthio)-2-oxo-1,2-dihydropyridin-3-yl)methyl)carbamoyl)benzo[d][1,3]dioxol-2-yl)cyclohexyl) hexahydropyrrolo[3,4-c]pyrrole-2(1H)-carboxylate (42C)

7-chloro-2,4-dimethyl-N-((6-methyl-4-(methylthio)-2-oxo-1,2-dihydropyridin-3-yl)methyl)-2-(4-oxocyclohexyl)benzo[d][1,3]dioxole-5-carboxamide (42B) (300 mg, 0.62 mmol) was dissolved in anhydrous ethanol (20 mL). Tert-butyl hexahydropyrrolo[3,4-c]pyrrole-2-(1H)-carboxylate (263 mg, 1.24 mmol) and sodium triacetoxyborohydride (657 mg, 3.1 mmol) were successively added. The mixture was reacted at room temperature for 4 hours and then concentrated. Water (50 mL) was added, and the reaction liquid was extracted with dichloromethane (50 mL×3). The organic phases were combined, washed with a saturated aqueous sodium carbonate solution (50 mL), dried over anhydrous sodium sulfate and concentrated. The residue was separated and purified by silica gel column chromatography (dichloromethane:methanol (v/v)=0.01:1-0.05:1) to obtain the title compound tert-butyl 5-(4-(7-chloro-2,4-dimethyl-5-(((6-methyl-4-(methylthio)-2-oxo-1,2-dihydropyridin-3-yl)methyl)carbamoyl)benzo[d][1,3]dioxol-2-yl)cyclohexyl) hexahydropyrrolo[3,4-c]pyrrole-2(1H)-carboxylate (42C) as a yellow solid (320 mg, yield: 75%).

LCMS m/z=687.29 $[M+1]^+$.

Step 4: 7-chloro-2-(4-(hexahydropyrrolo[3,4-c]pyrrol-2(1H)-yl)cyclohexyl)-2,4-dimethyl-N-((6-methyl-4-(methylthio)-2-oxo-1,2-dihydropyridin-3-yl)methyl)benzo[d][1,3]dioxole-5-carboxamide hydrochloride (42D)

Tert-butyl 5-(4-(7-chloro-2,4-dimethyl-5-(((6-methyl-4-(methylthio)-2-oxo-1,2-dihydropyridin-3-yl)methyl)carbamoyl)benzo[d][1,3]dioxol-2-yl)cyclohexyl) hexahydropyrrolo[3,4-c]pyrrole-2(1H)-carboxylate (42C) (320 mg, 0.47 mmol) was dissolved in a solution of hydrogen chloride in dioxane (4 N, 10 mL). The mixture was reacted at room temperature for 1 hour and then concentrated to obtain the title compound 7-chloro-2-(4-(hexahydropyrrolo[3,4-c]pyrrol-2(1H)-yl)cyclohexyl)-2,4-dimethyl-N-((6-methyl-4-(methylthio)-2-oxo-1,2-dihydropyridin-3-yl)methyl)benzo[d][1,3]dioxole-5-carboxamide hydrochloride (42D) as a yellow solid (310 mg, yield: 100%).

LCMS m/z=587.24 $[M+1]^+$.

Step 5: 7-chloro-2,4-dimethyl-N-((6-methyl-4-(methylthio)-2-oxo-1,2-dihydropyridin-3-yl)methyl)-2-(4-(5-methylhexahydropyrrolo[3,4-c]pyrrol-2(1H)-yl)cyclohexyl)benzo[d][1,3]dioxole-5-carboxamide (compound 42)

7-chloro-2-(4-(hexahydropyrrolo[3,4-c]pyrrol-2(1H)-yl)cyclohexyl)-2,4-dimethyl-N-((6-methyl-4-(methylthio)-2-oxo-1,2-dihydropyridin-3-yl)methyl)benzo[d][1,3]dioxole-5-carboxamide hydrochloride (42D) (310 mg, 0.47 mmol) was dissolved in anhydrous ethanol (30 mL). Paraformaldehyde (310 mg) and sodium triacetoxyborohydride (299 mg, 1.41 mmol) were successively added. The mixture was reacted at room temperature for 4 hours and then concentrated. Water (50 mL) was added, and the reaction liquid was extracted with dichloromethane (50 mL×3). The organic phases were combined, washed with a saturated aqueous sodium carbonate solution (50 mL) and dried over anhydrous sodium sulfate. The residue was separated and purified by silica gel column chromatography (dichloromethane:methanol (v/v)=0.01:1-0.1:1) to obtain a crude compound, which was separated by chiral preparative HPLC to obtain isomer 1 (25 mg, 8%) of the title compound 7-chloro-2,4-dimethyl-N-((6-methyl-4-(methylthio)-2-oxo-1,2-dihydropyridin-3-yl)methyl)-2-(4-(5-methylhexahydropyrrolo[3,4-c]pyrrol-2(1H)-yl)cyclohexyl)benzo[d][1,3]dioxole-5-carboxamide (compound 42) and isomer 2 (25 mg, 8%) of compound 42.

Chiral HPLC Separation Conditions for Compound 42:

7-chloro-2,4-dimethyl-N-((6-methyl-4-(methylthio)-2-oxo-1,2-dihydropyridin-3-yl)methyl)-2-(4-(5-methylhexahydropyrrolo[3,4-c]pyrrol-2(1H)-yl)cyclohexyl)benzo[d][1,3]dioxole-5-carboxamide (compound 42) (180 mg) was resolved and separated to obtain two isomers, isomer 1 (retention time: 2.088 s, 25 mg) of compound 42 and isomer 2 (retention time: 4.188 s, 25 mg) of compound 42.

Resolution conditions:

instrument: MG II preparative SFC (SFC-14); column: ChiralPak AD, 250×30 mm I.D.; mobile phase: A: $CO_2$, B: ethanol (0.1% $NH_3 \cdot H_2O$); gradient: B 40%; flow rate: 70 mL/min; back pressure: 100 bar; column temperature: 38° C.; wavelength: 220 nm; cycle: 13 min; sample preparation: compound 1 was dissolved in methanol to achieve the concentration of 15 mg/mL; injection: 1.0 mL/injection.

Isomer 1 of Compound 42

$^1$H NMR (400 MHz, DMSO-d6) δ 11.49 (s, 1H), 8.32-7.78 (m, 1H), 6.84 (s, 1H), 6.07 (s, 1H), 4.27 (d, 2H), 2.88-2.75 (m, 2H), 2.68 (s, 1H), 2.60-2.52 (m, 2H), 2.47-2.45 (m, 1H), 2.44 (s, 3H), 2.19 (d, 3H), 2.15 (d, 7H), 2.01-1.78 (m, 5H), 1.60 (s, 3H), 1.57-1.43 (m, 3H), 1.40-1.30 (m, 2H), 1.27-1.18 (m, 2H), 1.17 (s, 1H).

MS M/Z (ESI): m/z=601.25 $(M+1)^+$.

Isomer 2 of Compound 42

$^1$H NMR (400 MHz, DMSO-d6) δ 11.49 (s, 1H), 8.08-7.84 (m, 1H), 6.85 (s, 1H), 6.07 (s, 1H), 4.27 (d, 2H), 2.76-2.55 (m, 2H), 2.46-2.37 (m, 5H), 2.33-2.09 (m, 13H), 2.06-1.68 (m, 7H), 1.59 (s, 3H), 1.32-0.97 (m, 5H).

MS M/Z (ESI): m/z=601.25 $(M+1)^+$.

Embodiment 43

7-chloro-2,4-dimethyl-N-((6-methyl-4-(methylthio)-2-oxo-1,2-dihydropyridin-3-yl)methyl)-2-(4-(3-(pyrrolidin-1-yl)azetidin-1-yl)cyclohexyl)benzo[d][1,3]dioxole-5-carboxamide (compound 43)

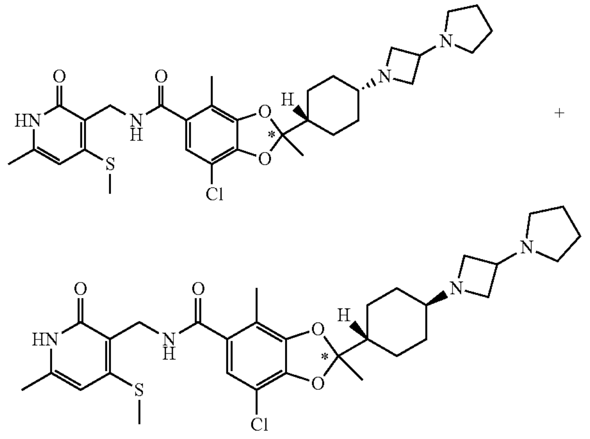

Compound 43

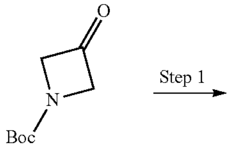

43A

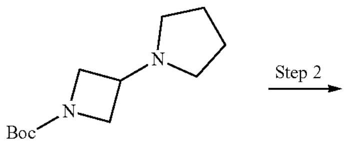

43B

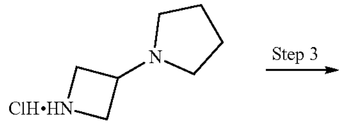

43C

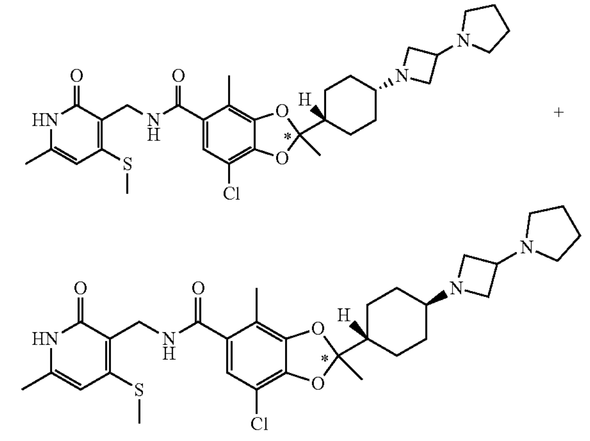

Compound 43

Step 1: tert-butyl 3-(pyrrolidin-1-yl)azetidine-1-carboxylate (43B)

Tert-butyl 3-oxazetidine-1-carboxylate (1.7 g, 10.0 mmol) was dissolved in anhydrous ethanol (20 mL). Pyrrolidine (1.41 g, 20.0 mmol) and sodium cyanoborohydride (1.26 g, 20.0 mmol) were then added. The mixture was reacted at room temperature for 4 hours and concentrated under reduced pressure to remove most of ethanol. Water (30 mL) was added, and the reaction liquid was extracted with ethyl acetate (30 mL×3). The organic phases were combined, washed with a saturated aqueous sodium carbonate solution (50 mL×1), washed with saturated brine (50 mL×1), dried over anhydrous sodium sulfate and concentrated to obtain the title compound tert-butyl 3-(pyrrolidin-1-yl)azetidine-1-carboxylate (43B) as a light yellow liquid crude (2.3 g, yield: 100%).

LCMS m/z=227.17 $[M+1]^+$.

Step 2: 1-(azetidin-3-yl)pyrrolidine hydrochloride (43C)

Tert-butyl 3-(pyrrolidin-1-yl)azetidine-1-carboxylate (43B) (2.3 g, 10 mmol) was dissolved in a solution of hydrogen chloride in dioxane (4 N, 10 mL), and the mixture was reacted at room temperature for 1 hour, concentrated, washed with dichloromethane (50 mL×1) and concentrated to obtain the title compound 1-(azetidin-3-yl)pyrrolidine hydrochloride (43C) as a yellow solid crude (1.7 g, yield: 100%).

LCMS m/z=127.12 $[M+1]^+$.

Step 3:

7-chloro-2,4-dimethyl-N-((6-methyl-4-(methylthio)-2-oxo-1,2-dihydropyridin-3-yl)methyl)-2-(4-(3-(pyrrolidin-1-yl)azetidin-1-yl)cyclohexyl)benzo[d][1,3]dioxole-5-carboxamide (compound 43)

7-chloro-2,4-dimethyl-N-((6-methyl-4-(methylthio)-2-oxo-1,2-dihydropyridin-3-yl)methyl)-2-(4-oxocyclohexyl)benzo[d][1,3]dioxole-5-carboxamide (42B) (300 mg, 0.61 mmol) was dissolved in anhydrous ethanol (20 mL). 1-(azetidin-3-yl)pyrrolidine hydrochloride (43C) (494 mg, 3.05 mmol) and sodium triacetoxyborohydride (258 mg, 1.22 mmol) were successively added. The mixture was reacted at room temperature for 2 hours and then concentrated. Water (50 mL) was added, and the reaction liquid was extracted with dichloromethane (50 mL×3). The organic phases were combined, washed with a saturated aqueous sodium carbonate solution (50 mL), dried over anhydrous sodium sulfate and concentrated to obtain a crude compound, which was separated and purified by a liquid phase preparative column (liquid phase preparative conditions: C18 reverse-phase preparative column, mobile phase: deionized water containing 0.05% ammonia water (A) and acetonitrile (B), gradient elution, mobile phase B=5%-50%, elution time: 15 min, flow rate: 12 mL/min, and column temperature: 30° C.) to obtain isomer 1 (30 mg, 8%, retention time: about 8 min) of the title compound 7-chloro-2,4-dimethyl-N-((6-methyl-4-(methylthio)-2-oxo-1,2-dihydropyridin-3-yl)methyl)-2-(4-(3-(pyrrolidin-1-yl)azetidin-1-yl)cyclohexyl)benzo[d][1,3]dioxole-5-carboxamide (compound 43) and isomer 2 (25 mg, 7%, retention time: about 10 min) of compound 43.

Isomer 1 of Compound 43

$^1H$ NMR (400 MHz, DMSO-d6) δ 11.50 (s, 1H), 7.99 (s, 1H), 6.85 (s, 1H), 6.08 (s, 1H), 4.27 (d, 2H), 3.48-3.40 (m, 2H), 3.10-2.89 (m, 3H), 2.45 (s, 3H), 2.43-2.32 (m, 4H), 2.20-2.12 (m, 6H), 1.90-1.72 (m, 6H), 1.71-1.65 (m, 4H), 1.60 (s, 3H), 1.28-1.19 (m, 4H).

MS M/Z (ESI): m/z=601.25 $(M+1)^+$.

Isomer 2 of Compound 43

$^1H$ NMR (400 MHz, DMSO-$d_6$) δ 11.46 (s, 1H), 8.21-7.85 (m, 1H), 6.85 (s, 1H), 6.07 (s, 1H), 4.27 (d, 2H), 3.27-3.24 (m, 2H), 3.00-2.92 (m, 1H), 2.76-2.69 (m, 2H), 2.44 (s, 3H), 2.37-2.31 (m, 4H), 2.25-2.20 (m, 1H), 2.18-2.12 (m, 6H), 1.87-1.76 (m, 1H), 1.68-1.59 (m, 6H), 1.56 (s, 3H), 1.50-1.40 (m, 4H), 1.33-1.19 (m, 2H).

MS M/Z (ESI): m/z=601.25 $(M+1)^+$.

Embodiment 44

7-chloro-2-(4-((3,3-difluorocyclobutyl)amino)cyclohexyl)-2,4-dimethyl-N-((6-methyl-4-(methylthio)-2-oxo-1,2-dihydropyridin-3-yl)methyl-d2)benzo[d][1,3]dioxole-5-carboxamide (compound 44)

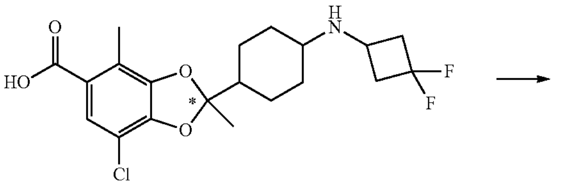

4C

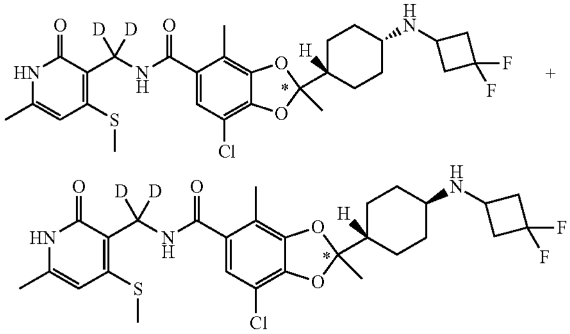

Compound 44

Compound 4C (11.9 g, 28.62 mmol) was dissolved in DMF (286 mL). 3-(aminomethyl-d2)-6-methyl-4-(methylthio)pyridine-2(1H)-one hydrochloride (intermediate 6) (9.56 g, 42.93 mmol), HATU (13.06 g, 34.34 mmol) and DIEA (N,N-diisopropylethylamin, 12.95 g, 100.17 mmol) were successively added, and the mixture was reacted at room temperature overnight. Water (600 mL) was added, and the reaction liquid was extracted with ethyl acetate (500 mL×2), washed with saturated brine, dried over anhydrous sodium sulfate and concentrated under reduced pressure to obtain a crude compound as a yellow solid, which was separated by column chromatography to obtain isomer 1 (4.4 g, dichloromethane:methanol (V/V)=60:1, Rf=0.40) of compound 44 and isomer 2 (4.6 g, dichloromethane:methanol (V/V)=50:1, Rf=0.35) of compound 44.

Isomer 1 of Compound 44

$^1H$ NMR (400 MHz, $CDCl_3$) δ 7.97 (s, 1H), 6.85 (s, 1H), 6.07 (s, 1H), 3.11 (dd, 1H), 2.78-2.65 (m, 3H), 2.45 (s, 3H), 2.37-2.23 (m, 2H), 2.15 (d, 6H), 1.88-1.79 (m, 1H), 1.68 (d, 2H), 1.58 (s, 3H), 1.51 (t, 4H), 1.38 (t, 2H).

LCMS m/z=584.2 $[M+1]^+$.

Isomer 2 of Compound 44

$^1H$ NMR (400 MHz, DMSO-d6) δ 11.50 (s, 1H), 7.97 (s, 1H), 6.85 (s, 1H), 6.07 (s, 1H), 3.18 (d, 1H), 2.77-2.64 (m, 2H), 2.45 (s, 3H), 2.34-2.21 (m, 3H), 2.15 (d, 6H), 1.83 (dd, 5H), 1.59 (s, 3H), 1.21-1.09 (m, 2H), 0.98 (dd, 2H).

LCMS m/z=584.2 $[M+1]^+$.

Embodiment 45

7-chloro-2-(4-((trans-3-hydroxycyclobutyl)amino)cyclohexyl)-2,4-dimethyl-N-((6-methyl-4-(methylthio)-2-oxo-1,2-dihydropyridin-3-yl)methyl)benzo[d][1,3]dioxole-5-carboxamide (compound 45)

Compound 45

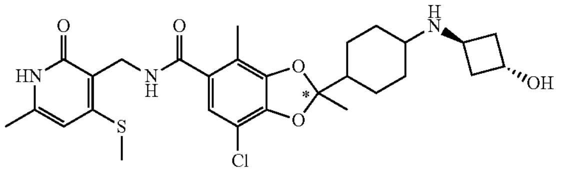

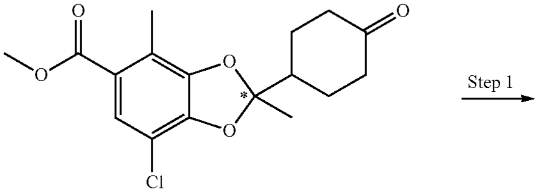

Intermediate 2

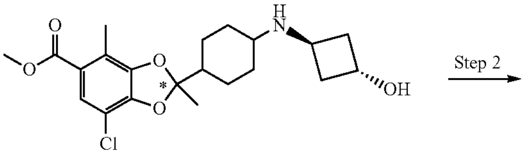

45A

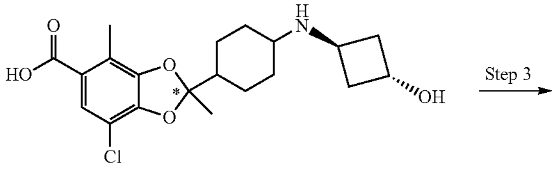

45B

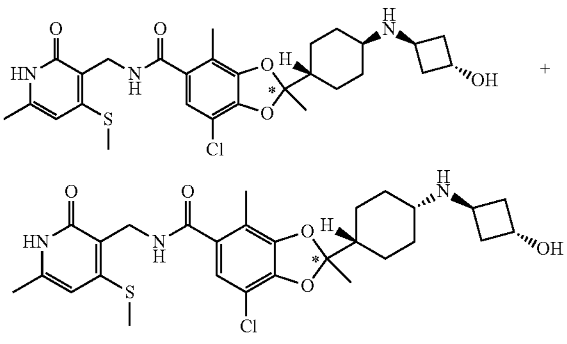

Compound 45, isomer 1 & isomer 2

Step 1: methyl 7-chloro-2-(4-(((1r,3r)-3-hydroxycyclobutyl)amino)cyclohexyl)-2,4-dimethylbenzo[d][1,3]dioxole-5-carboxylate (45A)

Methyl 7-chloro-2,4-dimethyl-2-(4-oxocyclohexyl)benzo[d][1,3]dioxole-5-carboxylate (intermediate 2) (400 mg, 1.18 mmol) and trans-3-aminocyclobutanol hydrochloride (175 mg, 1.42 mmol) were dissolved in 1,2-dichloroethan (10 mL). Acetic acid (71 mg, 1.18 mmol) was added dropwise, and the mixture was reacted at room temperature for 1 hour. Sodium triacetoxyborohydride (500 mg, 2.36 mmol) was then slowly added, and the mixture was reacted at room temperature for 16 hours. The reaction was quenched by slowly adding water (100 mL) to the reaction liquid. Liquid separation was performed. The aqueous phase was extracted with ethyl acetate (100 mL×3). The organic phases were combined, washed with water (100 mL×2), dried over anhydrous sodium sulfate and concentrated. The residue was separated and purified by silica gel column chromatography (petroleum ether:ethyl acetate (v/v)=0:1-1:1) to obtain the title compound methyl 7-chloro-2-(4-(((1r,3r)-3-hydroxycyclobutyl)amino)cyclohexyl)-2,4-dimethylbenzo[d][1,3]dioxole-5-carboxylate (45A) as a white powder solid (390 mg, yield: 80%).

LCMS m/z=410.1 $[M+1]^+$.

Step 2: 7-chloro-2-(4-(((1r,3r)-3-hydroxycyclobutyl)amino)cyclohexyl)-2,4-dimethylbenzo[d][1,3]dioxole-5-carboxylic acid (45B)

Methyl 7-chloro-2-(4-(((1r,3r)-3-hydroxycyclobutyl)amino)cyclohexyl)-2,4-dimethylbenzo[d][1,3]dioxole-5-carboxylate (45A) (390 mg, 0.95 mmol) was dissolved in methanol (15 mL). An aqueous sodium hydroxide solution (2M, 5 mL) was added dropwise, and the mixture was reacted at room temperature for 16 hours. The reaction liquid was adjusted to about pH=3 by slowly dropwise adding dilute hydrochloric acid. Water (50 ml) was added. Liquid separation was performed. The aqueous phase was extracted with ethyl acetate (50 mL×5). The organic phases were combined, washed with water (50 mL), dried over anhydrous sodium sulfate and concentrated to obtain the title compound 7-chloro-2-(4-(((1r,3r)-3-hydroxycyclobutyl)amino)cyclohexyl)-2,4-dimethylbenzo[d][1,3]dioxole-5-carboxylic acid (45B) as a white powder solid (300 mg, yield: 80%).

LCMS m/z=396.1 $[M+1]^+$.

Step 3: 7-chloro-2-(4-(((1r,3r)-3-hydroxycyclobutyl)amino)cyclohexyl)-2,4-dimethyl-N-((6-methyl-4-(methylthio)-2-oxo-1,2-dihydropyridin-3-yl)methyl)benzo[d][1,3]dioxole-5-carboxamide (compound 45)

7-chloro-2-(4-(((1r,3r)-3-hydroxycyclobutyl)amino)cyclohexyl)-2,4-dimethylbenzo[d][1,3]dioxole-5-carboxylic acid (45B) (250 mg, 0.63 mmol), 3-(aminomethyl)-6-methyl-4-(methylthio)pyridine-2(1H)-one hydrochloride (intermediate 5) (167 mg, 0.76 mmol) and HATU (288 mg, 0.76 mmol) were dissolved in DMF (15 mL). DIPEA (320 mg, 3.2 mmol) was added dropwise, and the mixture was reacted at room temperature for 8 hours. Water (50 mL) was added. The aqueous phase was extracted with ethyl acetate (50 mL×5). The organic phases were combined, washed with water (50 mL), dried over anhydrous sodium sulfate and concentrated. The residue was separated and purified by silica gel column chromatography (dichloromethane:methanol (v/v)=0:1-10:1) to obtain the title compound 7-chloro-2-(4-(((1r,3r)-3-hydroxycyclobutyl)amino)cyclohexyl)-2,4-dimethyl-N-((6-methyl-4-(methylthio)-2-oxo-1,2-dihydropyridin-3-yl)methyl)benzo[d][1,3]dioxole-5-carboxamide (compound 45) (220 mg, yield: 62%).

LCMS m/z=562.2 $[M+1]^+$.

Resolution of Compound 45

7-chloro-2-(4-(((1r,3r)-3-hydroxycyclobutyl)amino)cyclohexyl)-2,4-dimethyl-N-((6-methyl-4-(methylthio)-2-oxo-1,2-dihydropyridin-3-yl)methyl)benzo[d][1,3]dioxole-5-carboxamide (compound 45) (220 mg) was resolved and separated to obtain isomer 1 (retention time: 5.082 min, 145 mg) of compound 45 and isomer 2 (retention time: 5.440 min, 45 mg) of compound 45.

Resolution Conditions:

instrument: MG II preparative SFC (SFC-14); column: ChiralCel OD, 250×30 mm I.D., 5 μm; mobile phase: A for $CO_2$ and B for ethanol (0.1% $NH_3{\cdot}H_2O$); gradient: B 40%; flow rate: 70 mL/min; back pressure: 100 bar; column temperature: 38° C.; wavelength: 220 nm; cycle: about 6 min; sample preparation: compound was dissolved in 25 ml of methanol/DCM; injection: 1 mL/injection.

Isomer 1 of Compound 45

$^1$H NMR (400 MHz, DMSO-$d_6$) δ 11.51 (s, 1H), 8.00 (s, 1H), 6.89 (s, 1H), 6.08 (s, 1H), 4.33 (s, 1H), 4.27 (d, 2H), 3.92 (s, 1H), 3.24 (s, 1H), 2.47-2.37 (m, 5H), 2.20-2.11 (m, 8H), 1.98 (t, 1H), 1.89 (d, 2H), 1.67 (s, 3H), 1.61 (s, 3H), 1.55-1.45 (m, 2H).

LCMS m/z=562.2 $[M+1]^+$.

Isomer 2 of Compound 45

$^1$H NMR (400 MHz, DMSO-$d_6$) δ 11.60-11.33 (m, 1H), 8.01 (s, 1H), 6.85 (s, 1H), 6.07 (s, 1H), 4.74 (s, 1H), 4.27 (d, 2H), 4.19 (s, 1H), 3.37 (dd, 1H), 2.44 (s, 3H), 2.24 (d, 1H), 2.16 (s, 3H), 2.13 (s, 3H), 1.89-1.86 (m, 8H), 1.59 (s, 3H), 1.16 (dd, 3H), 0.95 (dd, 2H).

LCMS m/z=562.2 $[M+1]^+$.

Embodiment 46

7-chloro-2-(4-(4-fluorophenyl)cyclohexyl)-2,4-dimethyl-N-((6-methyl-4-(methylthio)-2-oxo-1,2-dihydropyridin-3-yl)methyl)benzo[d][1,3]dioxole-5-carboxamide (compound 46)

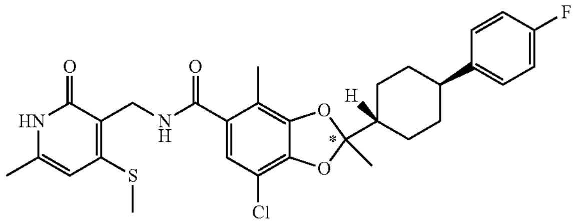

+

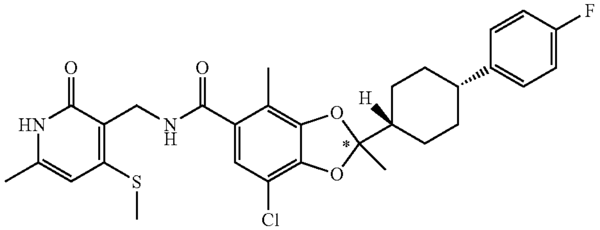

Compound 46, isomer 1 & isomer 2

With reference to the synthetic method of compound 8, 8A and 4-(4,4,5,5-tetramethyl-1,3,2-dioxaborolan-2-yl)fluorobenzene were used as raw materials to obtain compound 46, which was further separated by preparative HPLC to obtain two isomers.

The resolution method was as follows: instrument: MG II preparative SFC (SFC-14); column: ChiralPak AD, 250×30 mm I.D., 5 μm; mobile phase: A for $CO_2$ and B for ethanol; gradient: B 50%; flow rate: 80 mL/min; back pressure: 100 bar; column temperature: 38° C.; wavelength: 220 nm; cycle: about 5 min; sample preparation: compound was dissolved in 120 ml of methanol/DCM; injection: 3.5 ml/injection.

Post-treatment: after separation, the separated product was subjected to rotary evaporation and dried in a water bath at 40° C. to obtain the desired isomer.

LC-MS (ESI): m/z=571.2 $[M+H]^+$.

Compound 46, isomer 1: $^1$H NMR (400 MHz, $CDCl_3$) δ 7.23 (dd, 2H), 7.15 (s, 1H), 6.96 (t, 2H), 6.90 (s, 1H), 6.03 (s, 1H), 4.59 (d, 2H), 2.81 (s, 1H), 2.47 (s, 3H), 2.30 (s, 3H), 2.25 (s, 3H), 2.11-1.93 (m, 4H), 1.71 (d, 6H), 1.62 (s, 3H).

Compound 46, isomer 2: $^1$H NMR (400 MHz, $CDCl_3$) δ 7.13 (d, 2H), 6.96 (t, 2H), 6.87 (s, 1H), 6.53 (s, 1H), 6.37 (s, 1H), 4.61 (d, 2H), 2.54 (s, 3H), 2.50 (d, 1H), 2.44 (s, 3H), 2.24 (s, 3H), 2.03 (d, 2H), 1.94 (t, 3H), 1.65 (s, 3H), 1.49-1.35 (m, 5H).

Embodiment 47

7-chloro-2-(4-(3,3-difluoroazetidine-1-carbonyl) cyclohexyl)-2,4-dimethyl-N-(di-deuterated(6-methyl-4-(methylthio)-2-oxo-1,2-dihydropyridin-3-yl)di-deuterated-methyl)benzo[d][1,3]dioxole-5-carboxamide (compound 47)

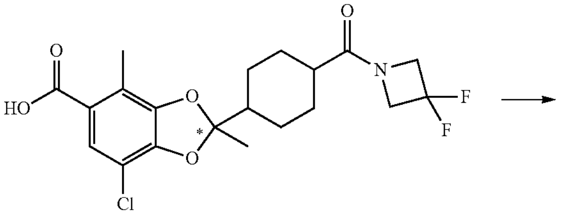

17B

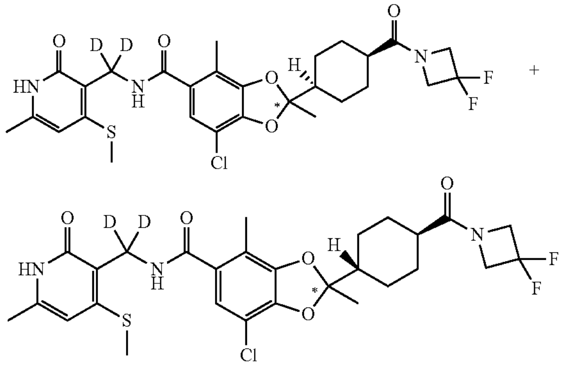

Compound 47

At room temperature, intermediate 6 (540 mg, 2.44 mmol), DCM (15 mL), HATU (930 mg, 2.44 mmol) and N,N-diisopropylethylamin (630 mg, 4.89 mmol) were successively added to 7-chloro-2-(4-(3,3-difluoroazetidine-1-carbonyl)cyclohexyl)-2,4-dimethyl benzo[d][1,3]dioxole-5-carboxylic acid (17B) (740 mg, 1.63 mmol). The mixture was stirred at room temperature for 2 hours, diluted by adding water and extracted with DCM. The organic phase was washed with saturated brine (20 mL), dried over anhydrous sodium sulfate and concentrated under reduced pressure to obtain a crude product, which was separated and purified by preparative HPLC to obtain isomer 1 (200 mg, 20%) of compound 47 and isomer 2 (190 mg, 19%) of compound 47. Preparative HPLC separation methods: 1. Instrument: waters 2767 (preparative liquid phase chromatographic instrument); chromatographic column: SunFire@ Prep C18 (19 mm×250 mm). 2. The sample was dissolved in DMF and filtered with a 0.45 μm filter to prepare a sample solution. 3. Preparative chromatography conditions: a. composition of mobile phases A and B: mobile phase A: acetonitrile; mobile phase B: water (containing 0.1% ammonium acetate); b. gradient elution, mobile phase A: 5% to 50%; c. flow rate: 12 mL/min; d. elution time: 20 min;

retention time for isomer 1 of compound 47: 14.2 min; $^1$H NMR (400 MHz, $CDCl_3$) δ 7.09 (s, 1H), 6.90 (s, 1H), 6.04 (s, 1H), 4.44-4.43 (m, 4H), 2.56-2.51 (m, 1H), 2.48 (s, 3H), 2.31 (s, 3H), 2.26 (s, 3H), 2.00 (s, 1H), 1.97-1.94 (m, 2H), 1.90-1.83 (m, 1H), 1.80-1.70 (m, 4H), 1.59 (s, 3H), 1.58-1.48 (m, 2H).

LC-MS (ESI): m/z=598.2 $[M+H]^+$.

retention time for isomer 2 of compound 47: 14.5 min; $^1$H NMR (400 MHz, $CDCl_3$) δ 6.93 (s, 1H), 6.90 (s, 1H), 6.08 (s, 1H), 4.44 (t, 2H), 4.30 (t, 2H), 2.49 (s, 3H), 2.33 (s, 3H), 2.26 (s, 3H), 2.16-2.10 (m, 1H), 2.02-1.99 (m, 2H), 1.98-1.97 (m, 1H), 1.91-1.79 (m, 3H), 1.61 (s, 3H), 1.60-1.49 (m, 2H), 1.30-1.18 (m, 2H).

LC-MS (ESI): m/z=598.2 $[M+H]^+$.

Embodiment 48

6,7-dichloro-2-(4-(3-methoxyazetidin-1-yl)cyclohexyl)-2,4-dimethyl-N-((6-methyl-4-(methylthio)-2-oxo-1,2-dihydropyridin-3-yl)methyl)benzo[d][1,3] dioxole-5-carboxamide (compound 48)

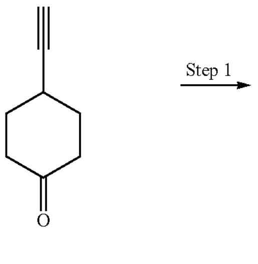

1c

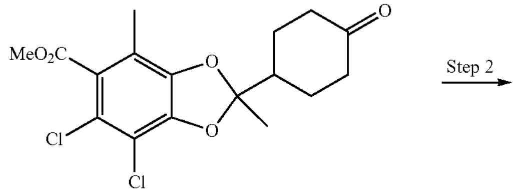

48A

-continued

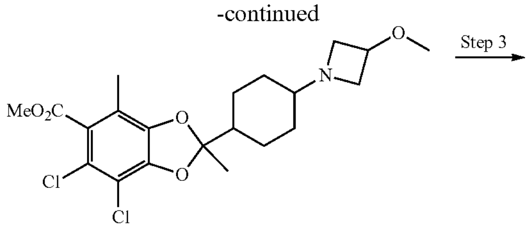

48B

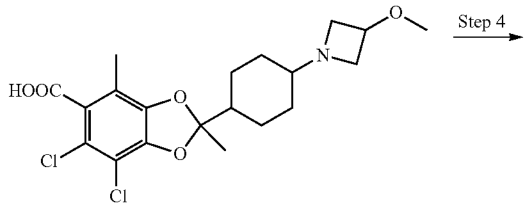

48C

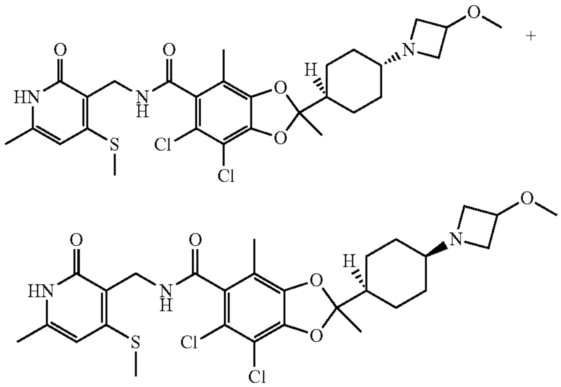

Compound 48

Step 1: methyl-6,7-dichloro-2,4-dimethyl-2-(4-oxo-cyclohexyl)benzo[d][1,3]dioxole-5-carboxylate (48A)

5,6-dichloro-methyl 3,4-dihydroxy-2-methylbenzoate (5.12 g, 20.5 mmol), triruthenium dodecacarbonyl (1.3 g, 2.05 mmol), triphenylphosphine (1.07 g, 4.1 mmol) were successively added to toluene (80 mL). Under nitrogen protection, the reaction was heated to reflux for half an hour. 4-ethynylcyclohexyl-1-one (5 g, 41 mmol) was dissolved in toluene (17 mL) and added to the reaction system, and the mixture was refluxed and stirred for 23 h. After the reaction was completed, the reaction system was cooled to room temperature and concentrated under reduced pressure, and then the residue was separated by column chromatography (PE:EA=5:1) to obtain compound 48A (2.2 g, 29%).

LC-MS (ESI): m/z=373.1 $[M+H]^+$.

Step 2: methyl-6,7-dichloro-2-(4-(3-methoxyazetidin-1-yl)cyclohexyl)-2,4-dimethylbenzo[d][1,3]dioxole-5-carboxylate (48B)

Compound 48A (2.2 g, 5.9 mmol) was dissolved in 25 mL of dichloromethane. 3-methoxy-azetidine (770 mg, 8.85 mmol) and acetic acid (0.1 mL) were added, and the mixture was stirred at room temperature for 15 minutes. Sodium triacetoxyborohydride (2.5 g, 11.8 mmol) was then added in portions, and the mixture was stirred at room temperature for another 2 hours. After LCMS showed that the reaction of the raw materials was completed, the reaction was quenched by adding a saturated aqueous ammonium chloride solution and extracted with DCM. The organic phase was dried and concentrated, and the residue was separated by column chromatography (PE:EA=3:1) to obtain compound 48B (1.95 g, 74%).

LC-MS (ESI): m/z=444.1 $[M+H]^+$.

Step 3: 6,7-dichloro-2-(4-(3-methoxyazetidin-1-yl)cyclohexyl)-2,4-dimethylbenzo[d][1,3]dioxole-5-carboxylic acid (48C)

Compound 48B (1.95 g, 4.4 mmol) was dissolved in 50 mL of methanol. An aqueous NaOH solution (352 mg, 8.8 mmol) was added, and the mixture was heated to 45° C. and reacted for 3 hours. After LCMS showed that the reaction was completed, the reaction liquid was concentrated and adjusted to pH 6 by adding an aqueous hydrochloric acid solution (2N). Solids were precipitated out and filtered by suction, and the filter cake was dried to obtain compound 48C (1.6 g, 84%).

LC-MS (ESI): m/z=430.1 $[M+H]^+$.

Step 4: 6,7-dichloro-2-(4-(3-methoxyazetidin-1-yl)cyclohexyl)-2,4-dimethyl-N-((6-methyl-4-(methylthio)-2-oxo-1,2-dihydropyridin-3-yl)methyl)benzo[d][1,3]dioxole-5-carboxamide (compound 48)

Compound 48C (300 mg, 0.7 mmol) was dissolved in 10 mL of DMF. Intermediate 5 (231 mg, 1.05 mmol), HATU (399 mg, 1.05 mmol) and DIEA (180 mg, 1.4 mmol) were added, and the mixture was reacted at room temperature for 2 hours. After LCMS showed that the reaction was completed, the reaction liquid was extracted with EA and saturated brine. The organic phase was dried and concentrated, and the residue was separated by column chromatography (DCM:MeOH=7:1) to obtain compound 48 (315 mg, 75%), which was further separated by chiral preparative HPLC to obtain isomer 1 (105 mg) of compound 48 and isomer 2 (95 mg) of compound 48.

Chiral preparative separation conditions: preparation instrument: Waters UPCC with PDA Detector, preparative column: Chiralpak AY-3 150×4.6 mm I.D., 3 um, mobile phase system: A: $CO_2$, B: isopropanol (0.05% DEA); retention time: isomer 1:6.205 min, isomer 2:9.635 min.

LC-MS (ESI): m/z=596.2 $[M+H]^+$.

$^1$H NMR (400 MHz, $CD_3OD$): 6.25 (s, 1H), 4.51 (s, 2H), 3.95-4.03 (m, 1H), 3.55-3.58 (m, 2H), 3.25 (s, 3H), 2.80-2.83 (m, 2H), 2.51 (s, 3H), 2.34 (s, 1H), 2.28 (s, 3H), 2.12 (s, 3H), 1.82-1.90 (m, 1H), 1.73-1.76 (m, 2H), 1.49-1.61 (m, 7H), 1.33-1.45 (m, 3H), 0.84-0.90 (m, 1H).

Embodiment 49

7-chloro-2-(4-(4,4-dimethyl-1,4-azasilinan-1-yl) cyclohexyl)-2,4-dimethyl-N-((6-methyl-4-(methylthio)-2-oxo-1,2-dihydropyridin-3-yl)methyl)benzo [d][1,3]dioxole-5-carboxamide (compound 49, isomer 1 and isomer 2)

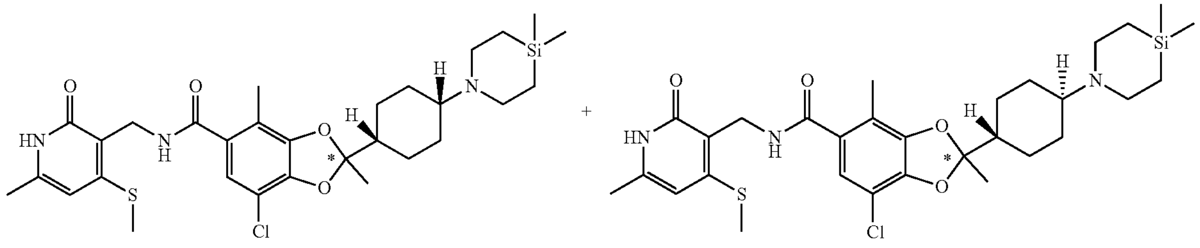

Compound 49

With reference to the synthetic method of compound 34, intermediate 2 and 4,4-dimethyl-[1,4]silapiperidine hydrochloride were used as raw materials to obtain compound 49, which was further separated by preparative HPLC to obtain two isomers, isomer 1 (14 mg, 2.0%) and isomer 2 (8 mg, 1.1%).

Preparative HPLC separation conditions: instrument: waters 2767 (preparative liquid phase chromatographic instrument); chromatographic column: SunFire@ Prep C18 (19 mm×250 mm). The sample was dissolved in DMF and filtered with a 0.45 μm filter to prepare a sample solution. Preparative chromatography conditions: composition of mobile phases A and B: mobile phase A: acetonitrile; mobile phase B: water (containing 5 mM ammonium acetate); gradient elution, mobile phase A: 40%-70%; flow rate: 15 mL/min; elution time: 18 min;

retention time for isomer 1 of compound 49: 10.45 min;

LC-MS (ESI): m/z=604.2 $[M+H]^+$.

$^1$H NMR (400 MHz, $CDCl_3$) δ 6.97-6.83 (m, 1H), 6.22 (s, 1H), 4.61 (d, 2H), 3.64 (dd, 2H), 3.35 (s, 1H), 3.07 (s, 2H), 2.50 (d, 3H), 2.36 (d, 3H), 2.22 (d, 3H), 2.10 (d, 3H), 2.03-1.77 (m, 4H), 1.81-1.58 (m, 5H), 1.46-1.30 (m, 2H), 0.89 (d, 2H), 0.16 (d, 6H).

retention time for isomer 2 of compound 49: 13.87 min;

LC-MS (ESI): m/z=604.2 $[M+H]^+$.

$^1$H NMR (400 MHz, $CDCl_3$) δ 6.89 (s, 1H), 6.16 (s, 1H), 4.58 (d, 2H), 3.62-3.47 (m, 2H), 3.15 (d, 3H), 2.50 (s, 3H), 2.36 (s, 3H), 2.24-2.14 (m, 5H), 2.07 (d, 2H), 1.85 (d, 1H), 1.66-1.46 (m, 5H), 1.35 (dt, 4H), 0.90 (d, 2H), 0.17 (d, 6H).

Embodiment 50

7-chloro-2-(1-(cyclobutylmethyl)piperidin-4-yl)-2,4-dimethyl-N-((6-methyl-4-(methylthio)-2-oxo-1,2-dihydropyridin-3-yl)methyl-d2)benzo[d][1,3]dioxole-5-carboxamide (compound 50)

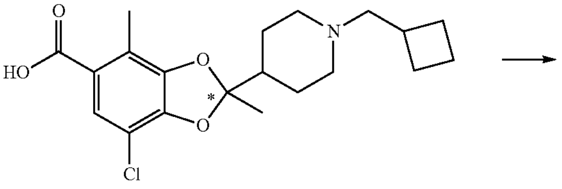

37B

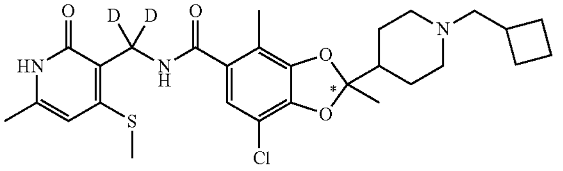

Compound 50

In a 250 mL single-necked flask, 37B (2.8 g, 7.37 mmol) was added and dissolved in DMF (50 mL). DIPEA (2.85 g, 22.1 mmol) and HATU (3.64 g, 9.58 mmol) were added, and the mixture was stirred at room temperature for 0.2 h. 3-(aminomethyl-d2)-6-methyl-4-(methylthio)pyridine-2 (1H)-one hydrochloride (intermediate 6) (3.29 g, 14.74 mmol) was added, and the mixture was stirred at room temperature for 5 h. Water (100 mL) was added to the reaction liquid, and the mixture was extracted with EA (100 mL×4). The combined organic phase was dried over anhydrous sodium sulfate and concentrated, and the residue was separated by column chromatography (DCM:MeOH=10:1) to obtain compound 50 (1.3 g, yield: 32%).

LC-MS (ESI): m/z=548.3 $[M+H]^+$.

$^1$H NMR (400 MHz, DMSO-$d_6$) δ 11.50 (s, 1H), 7.97 (s, 1H), 6.85 (s, 1H), 6.07 (s, 1H), 2.84 (d, 2H), 2.44 (s, 3H), 2.41-2.47 (m, 1H), 2.28-2.30 (m, 2H), 2.17 (s, 3H), 2.14 (s,

3H), 1.95-2.01 (m, 2H), 1.75-1.85 (m, 5H), 1.64-1.69 (m, 2H), 1.57-1.62 (m, 5H), 1.32-1.33 (m, 2H).

Embodiment 51

7-chloro-2,4-dimethyl-N-((6-methyl-4-(methylthio)-2-oxo-1,2-dihydropyridin-3-yl)methyl-d2)-2-(1-(oxetan-3-ylmethyl)piperidin-4-yl)benzo[d][1,3]dioxole-5-carboxamide (compound 51)

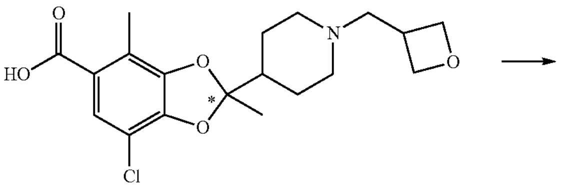

38B

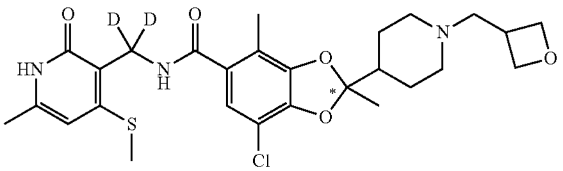

Compound 51

In a 50 mL single-necked flask, 38B (300 mg, 0.79 mmol) was added and dissolved in DMF (8 mL). DIPEA (304 mg, 2.36 mmol) and HATU (450 mg, 1.19 mmol) were added, and the mixture was stirred at room temperature for 0.2 h. 3-(aminomethyl-d2)-6-methyl-4-(methylthio)pyridine-2(1H)-one hydrochloride (intermediate 6) (351 mg, 1.58 mmol) was added, and the mixture was stirred at room temperature for 1 h. Water (10 mL) was added to the reaction liquid, and the mixture was extracted with EA (30 mL×4). The combined organic phase was dried over anhydrous sodium sulfate and concentrated, and the residue was separated by column chromatography (DCM:MeOH=10:1) to obtain compound 51 (60 mg, yield: 14%).

LC-MS (ESI): m/z=550.3 $[M+H]^+$.

$^1$H NMR (400 MHz, DMSO-$d_6$) δ 11.50 (s, 1H), 7.97 (s, 1H), 6.86 (s, 1H), 6.07 (s, 1H), 4.59-4.63 (m, 2H), 4.23-4.24 (m, 2H), 3.16-3.17 (m, 1H), 2.78-2.79 (m, 2H), 2.56-2.57 (m, 1H), 2.44 (s, 3H), 2.17 (s, 3H), 2.14 (s, 3H), 1.70-1.85 (m, 5H), 1.61 (s, 3H), 1.34-1.37 (m, 3H).

Embodiment 52

7-chloro-2-(1-(3,3-difluorocyclobutane-1-carbonyl)piperidin-4-yl)-2,4-dimethyl-N-((6-methyl-4-(methylthio)-2-oxo-1,2-dihydropyridin-3-yl)methyl)benzo[d][1,3]dioxole-5-carboxamide (compound 52)

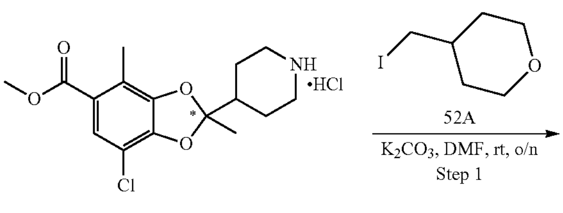

Intermediate 3

-continued

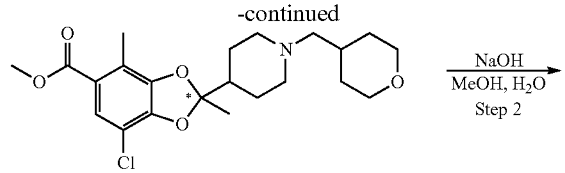

52B

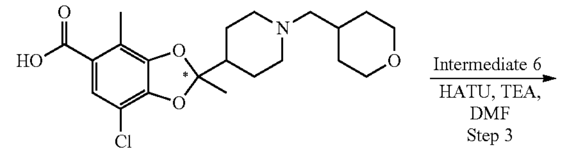

52C

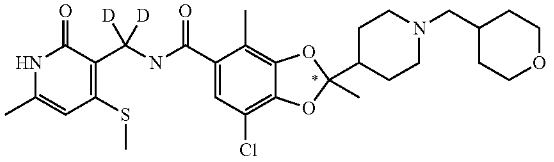

Compound 52

Step 1:

Intermediate 3 (300 mg, 0.83 mmol) was dissolved in DMF (6 mL). Potassium carbonate (343 mg, 2.49 mmol) and 4-(iodomethyl)tetrahydro-2H-pyran (563 mg, 2.49 mmol) were added, and the mixture was stirred at 50° C. overnight. Water (20 mL) was added to the reaction liquid, and the mixture was extracted three times with EA (20 mL). The combined organic phase was dried over anhydrous sodium sulfate, filtered and concentrated, and the residue was separated by column chromatography (PE:EA=1:1) to obtain 52B (260 mg, 74% yield) as a colorless oil.

LC-MS (ESI): m/z=424.2 $[M+H]^+$.

Step 2:

52B (260 mg, 0.61 mmol) was dissolved in methanol (8 mL). An aqueous NaOH solution (123 mg, 3.07 mmol, 2 mL) was added, and the reaction was stirred at 25° C. TLC showed that the reaction of the raw materials was completed. The reaction liquid was adjusted to pH=3-4 by dropwise adding 2N hydrochloric acid and concentrated under reduced pressure to obtain a crude. The crude was soaked with a mixed solvent (DCM:MeOH=10:1, 20 mL) and then filtered, and the filtrate was concentrated to obtain 52C (250 mg, 100%).

LC-MS (ESI): m/z=410.2 $[M+H]^+$.

Step 3:

In a 50 mL single-necked flask, 52C (250 mg, 0.61 mmol) was added and dissolved in DMF (10 mL). DIPEA (393 mg, 3.05 mmol) and HATU (348 mg, 0.92 mmol) were added, and the mixture was stirred at room temperature for 0.5 h. Intermediate 6 (227 mg, 1.22 mmol) was added, and the mixture was stirred at room temperature for 1 h. Water (20 mL) was added to the reaction liquid, and the mixture was extracted with EA (30 mL×3). The combined organic phase was dried over anhydrous sodium sulfate and concentrated, and the residue was separated by column chromatography (DCM:MeOH=10:1) to obtain compound 52 (100 mg, yield: 28%).

LC-MS (ESI): m/z=578.2 $[M+H]^+$.

$^1$H NMR (400 MHz, DMSO-$d_6$) δ 11.51 (s, 1H), 7.98 (s, 1H), 6.87 (s, 1H), 6.08 (s, 1H), 3.81 (d, 2H), 3.24-3.28 (m, 2H), 2.87-2.89 (m, 3H), 2.45 (s, 3H), 2.17 (s, 3H), 2.15 (s,

3H), 2.12-2.14 (m, 1H), 1.91 (s, 3H), 1.57-1.78 (m, 8H), 1.37-1.40 (m, 2H), 1.11-1.13 (m, 2H).

Embodiment 53

7-chloro-2-(4-((trans-3-fluorocyclobutyl)amino)cyclohexyl)-2,4-dimethyl-N-((6-methyl-4-(methylthio)-2-oxo-1,2-dihydropyridin-3-yl)methyl-d2) benzo[d][1,3]dioxole-5-carboxamide (compound 53)

DIEA (N,N-diisopropylethylamin, 13.01 g, 100.67 mmol) were successively added, and the mixture was reacted at room temperature overnight. Water (400 mL) was added, and the reaction liquid was extracted with ethyl acetate (400 mL×2), washed with saturated brine, dried over anhydrous sodium sulfate and concentrated under reduced pressure to obtain a crude compound as a yellow solid, which was separated by column chromatography (dichloromethane: methanol (V/V)=15:1) to obtain isomer 2 (11.4 g, dichloromethane:methanol (V/V)=50:1, Rf=0.35) of compound 53.

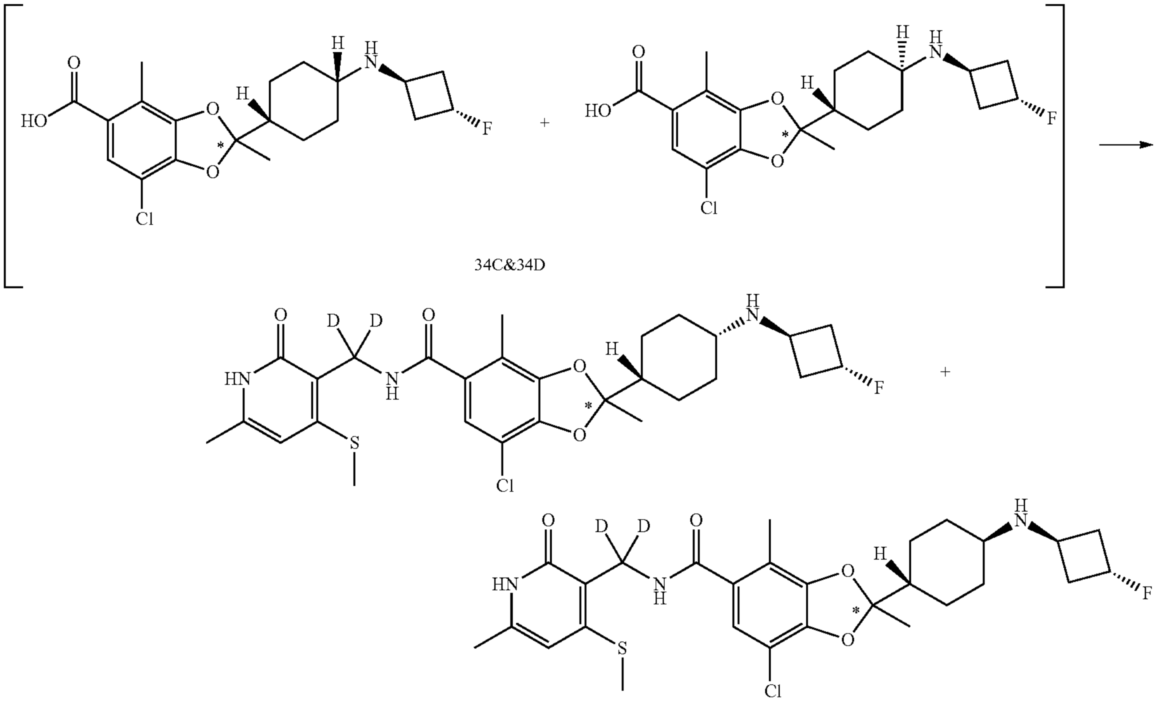

34C&34D

Compound 53

Compound 34C (14.5 g, 36.44 mmol) was dissolved in DMF (364 mL). 3-(aminomethyl-d2)-6-methyl-4-(methylthio)pyridine-2(1H)-one hydrochloride (intermediate 6) (13.58 g, 72.88 mmol), HATU (20.78 g, 54.66 mmol) and DIEA (N,N-diisopropylethylamin, 21.19 g, 163.98 mmol) were successively added, and the mixture was reacted at room temperature overnight. Water (600 mL) was added, and the reaction liquid was extracted with ethyl acetate (500 mL×2), washed with saturated brine, dried over anhydrous sodium sulfate and concentrated under reduced pressure to obtain a crude compound as a yellow solid, which was separated by column chromatography (dichloromethane: methanol (V/V)=15:1) to obtain isomer 1 (11 g, dichloromethane methanol (V/V)=60:1, Rf=0.40) of compound 53.

$^1$H NMR (400 MHz, DMSO-d6) δ 11.50 (s, 1H), 7.97 (s, 1H), 6.85 (s, 1H), 6.07 (s, 1H), 5.23-5.09 (s, 1H), 3.44 (d, 1H), 2.71 (s, 1H), 2.45 (s, 3H), 2.34-2.21 (m, 2H), 2.17 (s, 3H), 2.14 (s, 3H), 2.06 (d, 2H), 1.83 (s, 1H), 1.66 (d, 2H), 1.58 (s, 3H), 1.51 (t, 4H), 1.37 (t, 2H).

LCMS m/z=566.3 [M+1]$^+$.

Compound 34D (8.9 g, 22.37 mmol) was dissolved in DMF (223 mL). 3-(aminomethyl-d2)-6-methyl-4-(methylthio)pyridine-2(1H)-one hydrochloride (intermediate 6) (6.25 g, 33.55 mmol), HATU (12.76 g, 33.55 mmol) and $^1$H NMR (400 MHz, DMSO-d6) δ 11.51 (s, 1H), 7.97 (s, 1H), 6.85 (s, 1H), 6.07 (s, 1H), 5.21-5.06 (s, 1H), 3.51 (d, 1H), 2.44 (s, 3H), 2.27 (s, 3H), 2.17 (s, 3H), 2.13 (s, 3H), 2.06 (d, 2H), 1.82 (dd, 5H), 1.59 (s, 3H), 1.23-1.08 (m, 2H), 0.97 (dd, 2H).

LCMS m/z=566.3 [M+1]$^+$.

Embodiment 54

7-chloro-2,4-dimethyl-N-((6-methyl-4-(methylthio)-2-oxo-1,2-dihydropyridin-3-yl)methyl-d2)-2-(1-(oxetan-2-ylmethyl)piperidin-4-yl)benzo[d][1,3] dioxole-5-carboxamide (compound 54)

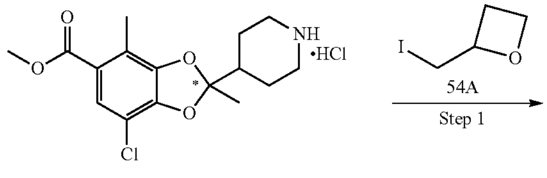

Intermediate 3

-continued

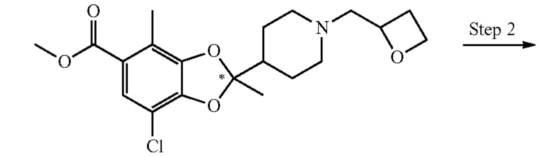

54B

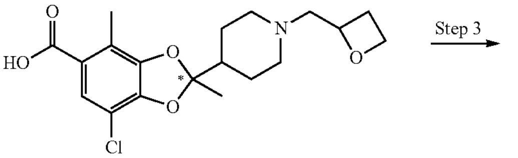

54C

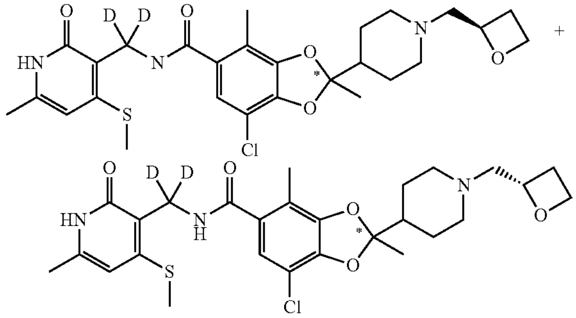

Compound 54

Step 1: methyl 7-chloro-2,4-dimethyl-2-(1-(oxetan-2-ylmethyl)piperidin-4-yl)benzo[d][1,3]dioxole-5-carboxylate (54B)

Intermediate 3 (0.5 g, 1.38 mmol) was dissolved in DMF (15 mL). $K_2CO_3$ (0.57 g, 4.14 mmol) was added, and the mixture was stirred at room temperature for 10 minutes. 2-iodomethyloxetane (0.55 g, 2.76 mmol) was then added. The reaction was warmed to 70° C. and stirred overnight. After the reaction was cooled to room temperature, the mixture was concentrated under reduced pressure to remove the reaction solvent, and the residue was directly used in the next reaction.

LCMS m/z=396.1 $[M+1]^+$.

Step 2: 7-chloro-2,4-dimethyl-2-(1-(oxetan-2-ylmethyl)piperidin-4-yl)benzo[d][1,3]dioxole-5-carboxylic acid (54C)

Compound 54B (0.55 g, 1.38 mmol) was dissolved in methanol/water=1/1 (20 mL). $LiOH \cdot H_2O$ (0.29 g, 6.9 mmol) was added. The mixture was stirred at room temperature overnight and concentrated under reduced pressure to remove most of methanol. 20 mL of water was added to the residue, and the reaction liquid was extracted 3 times with EA. The aqueous phase was then adjusted to pH=5 with 2N dilute hydrochloric acid and extracted 4 times with EA. The organic phases were combined, dried over anhydrous sodium sulfate and filtered, and the filtrate was concentrated under reduced pressure to obtain the title compound (54C) as a pale yellow solid (0.45 g, two-step yield: 85.4%).

LCMS m/z=382.1 $[M+1]^+$.

Step 3: 7-chloro-2,4-dimethyl-N-((6-methyl-4-(methylthio)-2-oxo-1,2-dihydropyridin-3-yl)methyl-d2)-2-(1-(oxetan-2-ylmethyl)piperidin-4-yl)benzo[d][1,3]dioxole-5-carboxamide (compound 54, isomer 1 and isomer 2)

Compound 54C (0.45 g, 1.18 mmol) was placed in a 50 mL single-necked flask. DMF (20 mL) and HATU (0.67 g, 1.77 mmol) were successively added. The mixture was stirred at room temperature for 10 minutes. DIPEA (0.76 g, 5.90 mmol) and intermediate 6(0.53 g, 2.36 mmol) were then successively added. After the addition was completed, the mixture was stirred at room temperature overnight. 40 mL of water was added to the reaction liquid, and the mixture was extracted with 5 times with EA. The combined organic phase was dried over anhydrous sodium sulfate and concentrated under reduced pressure, and the residue was purified by preparative HPLC to obtain the racemate compound 54 (0.5 g, yield: 72.6%).

Preparative HPLC separation methods: instrument: waters 2767 (preparative liquid phase chromatographic instrument); chromatographic column: SunFire@ Prep C18 (19 mm×250 mm). The sample was dissolved in DMF and filtered with a 0.45 μm filter to prepare a sample solution. Preparative chromatography conditions: a. composition of mobile phases A and B: mobile phase A: acetonitrile; mobile phase B: water (containing 0.05% ammonia water); b. gradient elution, mobile phase A: 25%-70%; c. flow rate: 16 mL/min; d. elution time: 20 min; retention time: 14.81 min.

The racemate (0.5 g) was further separated by chiral resolution to obtain two optical isomers:

isomer 1 of compound 54 (retention time: 5.583 min, 180 mg, ee %=99%, wherein the structure of compound a was one of the structures shown in compound 1 and compound 2 above) and isomer 2 of compound 54 (retention time: 5.807 min, 140 mg, ee %=98%, wherein the structure of compound b was one of the structures shown in compound 1 and compound 2 above), which was an enantiomer with isomer 1 of compound 54.

Resolution Conditions:

instrument: MG II preparative SFC (SFC-1); column: ChiralPak AD, 250×30 mm I.D., 10 μm; mobile phase: A: $CO_2$, B: ethanol (0.1% $NH_3H_2O$); gradient: B 30%; flow rate: 60 mL/min; back pressure: 100 bar; column temperature: 38° C.; wavelength: 220 nm; cycle: about 5 min; sample preparation: compound was dissolved in ethanol/dichloromethane; injection: 0.5 mL/injection.

Isomer 1 of Compound 54:

$^1H$ NMR (400 MHz, DMSO-d6) δ 11.49 (s, 1H), 7.97 (s, 1H), 6.85 (s, 1H), 6.07 (s, 1H), 4.87-4.81 (m, 1H), 4.49-4.44 (m, 1H), 4.36-4.31 (m, 1H), 2.88 (d, 2H), 2.62-2.53 (m, 2H), 2.48 (d, 1H), 2.44 (s, 3H), 2.35-2.26 (m, 1H), 2.17 (s, 3H), 2.14 (s, 3H), 1.96-1.90 (m, 2H), 1.86-1.80 (m, 1H), 1.67 (d, 2H), 1.60 (s, 3H), 1.38-1.32 (m, 2H).

LCMS m/z=550.2 $[M+1]^+$.

Isomer 2 of Compound 54:

$^1H$ NMR (400 MHz, DMSO-d6) δ 11.49 (s, 1H), 7.97 (s, 1H), 6.85 (s, 1H), 6.07 (s, 1H) 4.87-4.81 (m, 1H), 4.49-4.44 (m, 1H), 4.36-4.31 (m, 1H), 2.88 (d, 2H), 2.62-2.55 (m, 2H), 2.48 (d, 1H), 2.44 (s, 3H), 2.35-2.26 (m, 1H), 2.17 (s, 3H), 2.14 (s, 3H), 1.96-1.91 (m, 2H), 1.86-1.80 (m, 1H), 1.69-1.64 (m, 2H), 1.60 (s, 3H), 1.40-1.30 (m, 2H).

LCMS m/z=550.2 $[M+1]^+$.

Embodiment 55

7-chloro-N-(dideuterium(6-methyl-4-(methylthio)-2-oxo-1,2-dihydropyridin-3-yl)methyl)-2,4-dimethyl-2-(1-((tetrahydrofuran-2-yl)methyl)piperidin-4-yl)benzo[d][1,3]dioxole-5-carboxamide (compound 55)

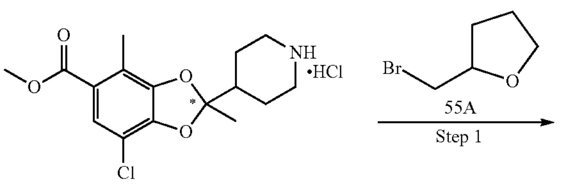

Intermediate 3

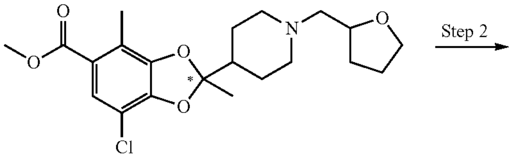

55B

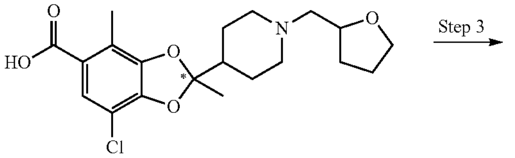

55C

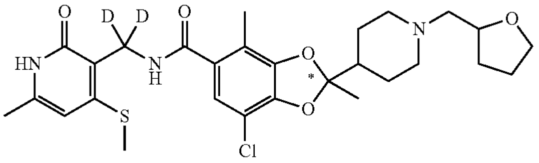

Compound 55

Step 1: methyl 7-chloro-2,4-dimethyl-2-(1-((tetrahydrofuran-2-yl)methyl)piperidin-4-yl)benzo[d][1,3]dioxole-5-carboxylate (55B)

Intermediate 3 (0.7 g, 1.93 mmol) was dissolved in DMF (20 mL). $K_2CO_3$ (0.80 g, 5.79 mmol) was added. The mixture was stirred at room temperature for 10 minutes, and 2-bromomethyl tetrahydrofuran (0.96 g, 5.79 mmol) was then added. The reaction was warmed to 70° C. and stirred overnight. After the reaction was cooled to room temperature, the mixture was concentrated under reduced pressure to remove the reaction solvent, and the residue was directly used in the next reaction.

LCMS m/z=410.2 $[M+1]^+$.

Step 2: 7-chloro-2,4-dimethyl-2-(1-((tetrahydrofuran-2-yl)methyl)piperidin-4-yl)benzo[d][1,3]dioxole-5-carboxylic acid (55C)

Compound 55B (0.79 g, 1.93 mmol) was dissolved in methanol/water=1/1 (20 mL). $LiOH·H_2O$ (0.41 g, 9.65 mmol) was added. The mixture was stirred at room temperature overnight and concentrated under reduced pressure to remove most of methanol. 20 mL of water was added to the residue, and the reaction liquid was extracted 3 times with EA. The aqueous phase was adjusted to pH=5 with 2N dilute hydrochloric acid and extracted 4 times with EA. The organic phases were combined, dried over anhydrous sodium sulfate, filtered and concentrated under reduced pressure to obtain the title compound (55C) as a pale yellow solid (0.6 g, two-step yield: 78.5%).

LCMS m/z=396.1 $[M+1]^+$.

Step 3: 7-chloro-N-(dideuterium(6-methyl-4-(methylthio)-2-oxo-1,2-dihydropyridin-3-yl)methyl)-2,4-dimethyl-2-(1-((tetrahydrofuran-2-yl)methyl)piperidin-4-yl)benzo[d][1,3]dioxole-5-carboxamide (compound 55)

Compound 55C (0.6 g, 1.52 mmol) was placed in a 50 mL single-necked flask. DMF (20 mL) and HATU (0.87 g, 2.28 mmol) were successively added. The mixture was stirred at room temperature for 10 minutes. DIPEA (0.98 g, 7.60 mmol) and intermediate 6 (0.68 g, 3.04 mmol) were then successively added, and the mixture was stirred at room temperature overnight. 40 mL of water was added to the reaction liquid, and the mixture was extracted with 5 times with EA. The organic phases were combined and concentrated under reduced pressure, and the residue was purified by preparative HPLC to obtain the title compound (compound 55) (0.65 g, yield: 75.8%).

Preparative HPLC separation methods: instrument: waters 2767 (preparative liquid phase chromatographic instrument); chromatographic column: SunFire@ Prep C18 (19 mm×250 mm). The sample was dissolved in DMF and filtered with a 0.45 μm filter to prepare a sample solution. Preparative chromatography conditions: a. composition of mobile phases A and B: mobile phase A: acetonitrile; mobile phase B: water (containing 1% TFA); b. gradient elution, mobile phase A: 25%-70%; c. flow rate: 16 mL/min; d. elution time: 20 min; retention time: 14.22 min.

$^1H$ NMR (400 MHz, DMSO-d6) δ 11.53 (s, 1H), 9.37 (s, 1H), 8.00 (s, 1H), 6.90 (s, 1H), 6.09 (s, 1H), 4.24-4.18 (m, 1H), 3.85-3.79 (m, 1H), 3.75-3.69 (m, 1H), 3.59 (s, 2H), 3.21-3.17 (m, 1H), 3.11-3.06 (m, 1H), 3.01-3.92 (m, 2H), 2.46 (s, 3H), 2.27-2.20 (m, 1H), 2.17 (s, 3H), 2.17 (s, 3H), 2.09-2.02 (m, 1H), 1.99-1.92 (m, 2H), 1.91-1.80 (m, 2H), 1.70-1.77 (m, 1H), 1.66 (s, 3H), 1.54-1.46 (m, 1H).

LCMS m/z=564.2 $[M+1]^+$.

Embodiment 56

7-chloro-N-(dideuterium(6-methyl-4-(methylthio)-2-oxo-1,2-dihydropyridin-3-yl)methyl)-2,4-dimethyl-2-(1-((tetrahydrofuran-3-yl)methyl)piperidin-4-yl)benzo[d][1,3]dioxole-5-carboxamide (compound 56)

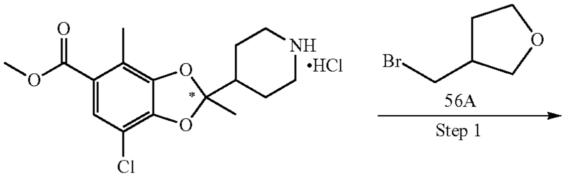

Intermediate 3

-continued

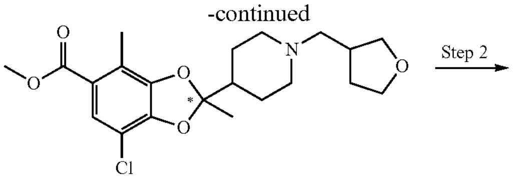

56B

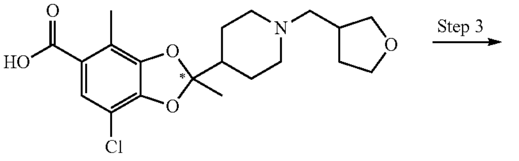

56C

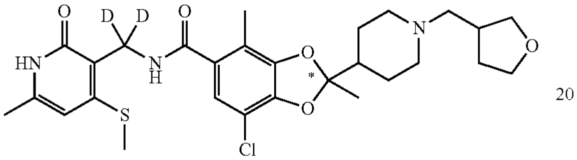

Compound 56

Step 1: methyl 7-chloro-2,4-dimethyl-2-(1-((tetrahydrofuran-3-yl)methyl)piperidin-4-yl)benzo[d][1,3]dioxole-5-carboxylate (56B)

Intermediate 3 (0.7 g, 1.93 mmol) was dissolved in DMF (20 mL). $K_2CO_3$ (0.80 g, 5.79 mmol) was added. The mixture was stirred at room temperature for 10 minutes, and 2-bromomethyl tetrahydrofuran (0.96 g, 5.79 mmol) was then added. The reaction was warmed to 70° C. and stirred overnight. After the reaction was cooled to room temperature, the mixture was concentrated under reduced pressure to remove the reaction solvent, and the residue was directly used in the next reaction.

LCMS m/z=410.2 $[M+1]^+$.

Step 2: 7-chloro-2,4-dimethyl-2-(1-((tetrahydrofuran-3-yl)methyl)piperidin-4-yl)benzo[d][1,3]dioxole-5-carboxylic acid (56C)

Compound 55B (0.79 g, 1.93 mmol) was dissolved in methanol/water=1/1 (20 mL). $LiOH \cdot H_2O$ (0.41 g, 9.65 mmol) was added. The mixture was stirred at room temperature overnight and concentrated under reduced pressure to remove most of methanol. 20 mL of water was added to the residue, and the reaction liquid was extracted 3 times with EA. The aqueous phase was adjusted to pH=5 with 2N dilute hydrochloric acid and extracted 4 times with EA. The organic phases were combined, dried over anhydrous sodium sulfate, filtered and concentrated under reduced pressure to obtain the title compound (56C) as a pale yellow solid (0.5 g, two-step yield: 65.4%).

LCMS m/z=396.1 $[M+1]^+$.

Step 3: 7-chloro-N-(dideuterium(6-methyl-4-(methylthio)-2-oxo-1,2-dihydropyridin-3-yl)methyl)-2,4-dimethyl-2-(1-((tetrahydrofuran-3-yl)methyl)piperidin-4-yl)benzo[d][1,3]dioxole-5-carboxamide (compound 56)

Compound 56C (0.5 g, 1.26 mmol) was placed in a 50 mL single-necked flask. DMF (20 mL) and HATU (0.72 g, 1.89 mmol) were successively added. The mixture was stirred at room temperature for 10 minutes. DIPEA(0.81 g, 6.30 mmol) and intermediate 6 (0.56 g, 2.52 mmol) were then successively added, and the mixture was stirred at room temperature overnight. 40 mL of water was added to the reaction liquid, and the mixture was extracted with 5 times with EA. The organic phases were combined and concentrated under reduced pressure, and the residue was purified by preparative HPLC to obtain the title compound (compound 56) (0.58 g, yield: 67.9%).

Preparative HPLC separation methods: instrument: waters 2767 (preparative liquid phase chromatographic instrument); chromatographic column: SunFire@ Prep C18 (19 mm×250 mm). The sample was dissolved in DMF and filtered with a 0.45 μm filter to prepare a sample solution. Preparative chromatography conditions: a. composition of mobile phases A and B: mobile phase A: acetonitrile; mobile phase B: water (containing 1% TFA); b. gradient elution, mobile phase A: 25%-70%; c. flow rate: 16 mL/min; d. elution time: 20 min; retention time: 14.18 min.

$^1H$ NMR (400 MHz, DMSO-d6) δ 11.61 (s, 1H), 9.13 (s, 1H), 8.00 (s, 1H), 6.91 (s, 1H), 6.09 (s, 1H), 3.84-3.80 (m, 1H), 3.77-3.71 (m, 1H), 3.66-3.60 (m, 1H), 3.60-3.54 (m, 2H), 3.39-3.35 (m, 1H), 3.13-3.09 (m, 2H), 2.97-2.88 (m, 2H), 2.63-2.56 (m, 1H), 2.46 (s, 3H), 2.28-2.22 (m, 1H), 2.17 (s, 3H), 2.17 (s, 3H), 2.10-2.05 (m, 1H), 1.97-1.94 (m, 2H), 1.74-1.68 (m, 1H), 1.66 (s, 3H), 1.63-1.56 (m, 1H).

LCMS m/z=564.2 $[M+1]^+$.

Embodiment 57

7-chloro-2,4-dimethyl-N-((6-methyl-4-(methylthio)-2-oxo-1,2-dihydropyridin-3-yl)methyl-d2)-2-(4-(morpholinomethyl)cyclohexyl)benzo[d][1,3]dioxole-5-carboxamide (compound 57)

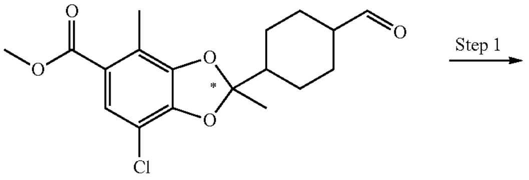

15B

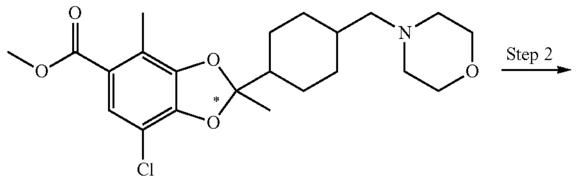

57A

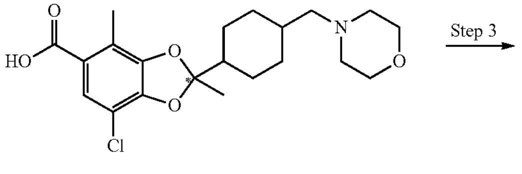

57B

-continued

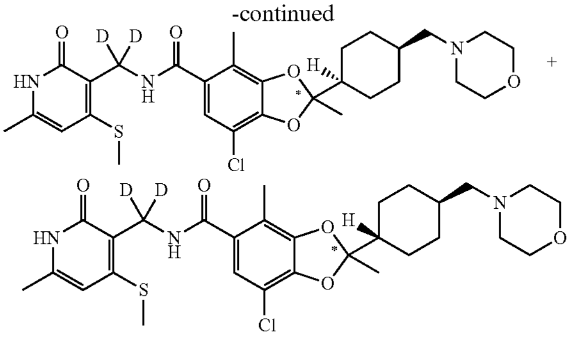

Compound 57, isomer 1 and isomer 2

Step 1: methyl-7-chloro-2,4-dimethyl-2-(4-(morpholinomethyl)cyclohexyl)benzo[d][1,3]dioxole-5-carboxylate (57A)

Methyl-7-chloro-2-(4-formylcyclohexyl)-2,4-dimethyl-benzo[d][1,3]dioxole-5-carboxylate (15B) (1.4 g, 3.98 mmol), morpholine (0.69 g, 7.95 mmol) and acetic acid (0.5 mL) were successively added to dichloromethane (15 mL), and the mixture was reacted at room temperature for 1 h. Sodium triacetoxyborohydride (1.67 g, 7.95 mmol) was added, and the mixture was reacted at room temperature overnight. The reaction was quenched by adding water and extracted with dichloromethane (30 mL×3). The organic phases were combined, washed with a saturated sodium chloride solution, dried over anhydrous sodium sulfate and filtered, and the filtrate was concentrated, and then the residue was separated and purified by silica gel column chromatography (ethyl acetate:petroleum ether (v/v)=0:1-5:1) to obtain the compound methyl-7-chloro-2,4-dimethyl-2-(4-(morpholinomethyl)cyclohexyl)benzo[d][1,3]dioxole-5-carboxylate (57A) (1.4 g).

LC-MS (ESI): m/z=424.2 $[M+H]^+$.

Step 2: 7-chloro-2,4-dimethyl-2-(4-(morpholinomethyl)cyclohexyl)benzo[d][1,3]dioxole-5-carboxylic acid (57B)

MeOH (15 mL) and an aqueous sodium hydroxide solution (4 mol/L, 6 mL) were successively added to methyl-7-chloro-2,4-dimethyl-2-(4-(morpholinomethyl)cyclohexyl)benzo[d][1,3]dioxole-5-carboxylate (57A) (1.4 g, 3.3 mmol). The mixture was warmed to 65° C. and reacted for 4 h. The reaction liquid was cooled to room temperature and adjusted to pH=5-6 with an aqueous hydrochloric acid solution. Water (30 mL) was added, and the reaction liquid was extracted with DCM. The organic phases were combined, washed with a saturated sodium chloride solution, dried over anhydrous sodium sulfate and filtered, and the filtrate was concentrated to obtain the crude compound 7-chloro-2,4-dimethyl-2-(4-(morpholinomethyl)cyclohexyl)benzo[d][1,3]dioxole-5-carboxylic acid (57B) (1.3 g).

LC-MS (ESI): m/z=410.2 $[M+H]^+$.

Step 3: 7-chloro-2,4-dimethyl-N-((6-methyl-4-(methylthio)-2-oxo-1,2-dihydropyridin-3-yl)methyl-d2)-2-(4-(morpholinomethyl)cyclohexyl)benzo[d][1,3]dioxole-5-carboxamide (compound 57, isomer 1 and isomer 2)

At room temperature, 3-(aminomethyl-d2)-6-methyl-4-(methylthio)pyridine-2(1H)-hydrochloride (566 mg, 2.55 mmol), DCM (10 mL), HATU (969 mg, 2.55 mmol) and N,N-diisopropylethylamin (1315 mg, 10.2 mmol) were successively added to 7-chloro-2,4-dimethyl-2-(4-(morpholinomethyl)cyclohexyl)benzo[d][1,3]dioxole-5-carboxylic acid (57B) (700 mg, 1.7 mmol). The mixture was stirred at room temperature for 2 hours, diluted by adding water and extracted with DCM. The organic phase was washed with saturated brine (20 mL), dried over anhydrous sodium sulfate and concentrated under reduced pressure, and then the residue was separated and purified by silica gel column chromatography (methanol:dichloromethane (v/v)=0:1-1:10) to obtain compound 57 (500 mg).

Compound 57 (500 mg) was resolved and separated to obtain two isomers: isomer 1 of compound 57 (retention time: 5.463 min, 150 mg, ee %=99%, wherein the structure of isomer 1 was one of the structures shown in isomer 1 and isomer 2 of compound 57 above) and isomer 2 of compound 57 (retention time: 5.981 min, 270 mg, ee %=99%, wherein the structure of isomer 2 was one of the structures shown in isomer 1 and isomer 2 of compound 57 above), which was a cis-trans isomer with isomer 1.

Resolution conditions: instrument: MG II preparative SFC (SFC-1); column: ChiralPak AD, 250×30 mm I.D., 10 μm.; mobile phase: A: $CO_2$, B: ethanol (0.1% $NH_3 \cdot H_2O$); gradient: B 40%; flow rate: 60 mL/min; back pressure: 100 bar; column temperature: 38° C.; wavelength: 220 nm; cycle: 10 min; sample preparation: compound 1 was dissolved in 15 mL of methanol/DCM; injection: 1 mL/injection.

Isomer 1 of Compound 57:

$^1H$ NMR (400 MHz, DMSO-d6) δ 11.49 (s, 1H), 7.97 (s, 1H), 6.85 (s, 1H), 6.07 (s, 1H), 3.59-3.49 (m, 4H), 2.44 (s, 3H), 2.32-2.28 (m, 4H), 2.20 (d, 2H), 2.17 (s, 3H), 2.13 (s, 3H), 1.92-1.82 (m, 2H), 1.67-1.61 (m, 2H), 1.60 (s, 3H), 1.57-1.53 (m, 2H), 1.41 (t, J=12.3 Hz, 2H), 1.32-1.26 (m, 2H).

LC-MS (ESI): m/z=578.2 $[M+H]^+$.

Isomer 2 of Compound 57:

$^1H$ NMR (400 MHz, DMSO-d6) δ 11.50 (s, 1H), 7.97 (s, 1H), 6.85 (s, 1H), 6.07 (s, 1H), 3.57-3.50 (m, 4H), 2.45 (s, 3H), 2.30-2.26 (m, 4H), 2.17 (s, 3H), 2.14 (s, 3H), 2.05 (d, 2H), 1.87-1.80 (m, 5H), 1.59 (s, 3H), 1.48-1.40 (m, 1H), 1.20-1.10 (m, 2H), 0.89-0.81 (m, 2H).

LC-MS (ESI): m/z=578.2 $[M+H]^+$.

Embodiment 58

7-chloro-2-(1-((2,2-difluorocyclopropyl)methyl)piperidin-4-yl)-2,4-dimethyl-N-((6-methyl-4-(methylthio)-2-oxo-1,2-dihydropyridin-3-yl)methyl-d2)benzo[d][1,3]dioxole-5-carboxamide (compound 58)

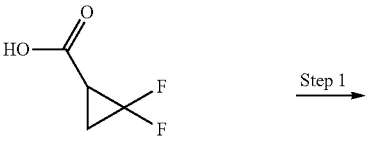

58A

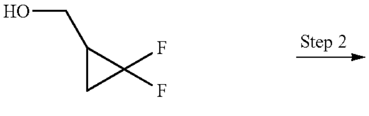

58B

-continued

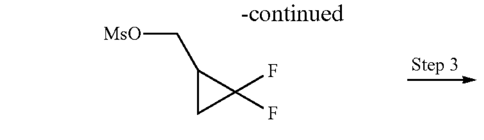

58C

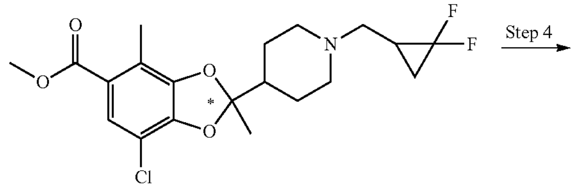

58D

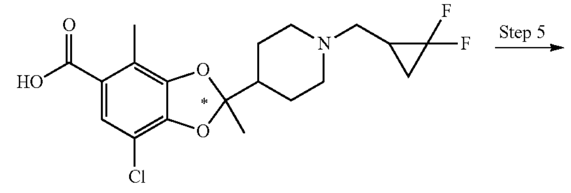

58E

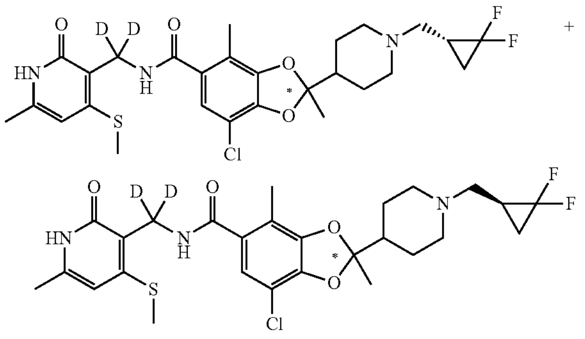

Compound 58

Step 1: (2,2-difluorocyclopropyl)methanol (58B)

2,2-difluorocyclopropanecarboxylic acid (58A) (6 g, 49.15 mmol) was dissolved in anhydrous THE (100 mL) and cooled to 0° C. in an ice bath. $LiAlH_4$ (2.8 g, 73.73 mmol) was added in portions. After the addition was completed, the mixture was slowly returned to room temperature and stirred for 2 hours. The reaction liquid was cooled in an ice bath. The reaction was quenched by dropwise adding water. $Mg_2SO_4$ (25 g) was then added. The mixture was stirred for 10 minutes and then filtered. The filter cake was washed twice with THF. The filtrate was concentrated under reduced pressure to obtain the title compound (58B) as a colorless oil (3.4 g, yield: 64.0%).

Step 2: (2,2-difluorocyclopropyl)methyl methanesulfonate (58C)

(2,2-difluorocyclopropyl)methanol (58B) (3.4 g, 31.46 mmol) was dissolved in DCM (45 mL). $Et_3N$ (9.5 g, 94.38 mmol) and DMAP (385 mg, 3.15 mmol) were successively added. At 0° C., MsCl (4.3 g, 37.75 mol) was added dropwise. After the addition was completed, the mixture was slowly returned to room temperature and stirred overnight. 80 mL of water was added to the reaction liquid, and the mixture was extracted 3 times with DCM. The combined organic phase was washed twice with a saturated aqueous NaCl solution, dried over anhydrous sodium sulfate, filtered and concentrated under reduced pressure to obtain the title compound (58C) as a colorless oil (3.2 g, yield: 54.6%).

Step 3: methyl 7-chloro-2-(1-((2,2-difluorocyclopropyl)methyl)piperidin-4-yl)-2,4-dimethylbenzo[d][1,3]dioxole-5-carboxylate (58D)

Intermediate 3 (3.1 g, 8.60 mmol) was placed in a 50 mL single-necked flask. Acetonitrile (60 mL), DIPEA (4.4 g, 34.38 mmol), KI (1.4 g, 8.60 mmol) and 58C (3.2 g, 17.19 mmol) were successively added. After the addition was completed, the mixture was warmed to 60° C. and stirred for 4 hours. The reaction was cooled to room temperature and then concentrated under reduced pressure to remove most of acetonitrile. 100 mL of water was added to the residue, and the reaction liquid was extracted 3 times with EA. The combined organic phase was dried over anhydrous sodium sulfate, filtered and concentrated under reduced pressure. The residue was then purified by silica gel chromatography (PE/EA=10/1) to obtain the title compound (58D) as a colorless oil (2.9 g, yield: 81.1%).

Step 4: 7-chloro-2-(1-((2,2-difluorocyclopropyl)methyl)piperidin-4-yl)-2,4-dimethylbenzo[d][1,3]dioxole-5-carboxylic acid (58E)

58D (2.9 g, 6.97 mmol) was dissolved in 50 mL of THF/$H_2O$ (v/v=2/1). LiOH·$H_2O$ (1.5 g, 34.85 mmol) was added. After the addition was completed, the mixture was warmed to 60° C. and stirred overnight. The reaction was cooled to room temperature and then concentrated under reduced pressure to remove most of THF. 50 mL of water was added to the residue, and the reaction liquid was adjusted to pH=5 with 2N dilute hydrochloric acid and extracted 3 times with EA. The organic phases were combined, dried over anhydrous sodium sulfate and filtered, and the filtrate was concentrated under reduced pressure to obtain the title compound (58E) as a white solid (2.7 g, yield: 96.4%).

Step 5: 7-chloro-2-(1-((2,2-difluorocyclopropyl)methyl)piperidin-4-yl)-2,4-dimethyl-N-((6-methyl-4-(methylthio)-2-oxo-1,2-dihydropyridin-3-yl)methyl-d2)benzo[d][1,3]dioxole-5-carboxamide (compound 58, isomer 1 and isomer 2)

Compound 58E (2.7 g, 6.72 mmol) was dissolved in DMF (50 mL). HATU (3.8 g, 10.08 mmol) was added, and the mixture was stirred at room temperature for 15 minutes. DIPEA (4.3 g, 33.60 mmol) and intermediate 6 (1.8 g, 8.06 mmol) were then successively added. After the addition was completed, the mixture was stirred at room temperature overnight. 100 mL of water was added to the reaction liquid, and the mixture was extracted 4 times with EA. The organic phases were combined, washed twice with a saturated aqueous NaCl solution, dried over anhydrous sodium sulfate, filtered and concentrated under reduced pressure. The residue was purified by preparative HPLC to obtain the racemate compound 58 (2.3 g, yield: 60.0%).

Preparative HPLC separation methods: instrument: waters 2767 (preparative liquid phase chromatographic instrument); chromatographic column: SunFire@ Prep C18 (19 mm×250 mm). The sample was dissolved in DMF and filtered with a 0.45 μm filter to prepare a sample solution.

Preparative chromatography conditions: a. composition of mobile phases A and B: mobile phase A: acetonitrile; mobile phase B: water (containing 0.05% ammonia water); b. gradient elution, mobile phase A: 25%-70%; c. flow rate: 12 mL/min; d. elution time: 20 min; retention time: 14.07 min.

Compound 58 (2.3 g, 4.03 mmol) obtained by the above preparative HPLC was subjected to chiral separation by a chiral chromatography column, with purification conditions as follows: instrument: MG II preparative SFC (SFC-14); chromatographic column: ChiralPak AD, 250×30 mm I.D., 10 μm. The sample was dissolved in DCM/MeOH. Preparative chromatography conditions: mobile phase system: A: $CO_2$, B: ethanol (0.1% $NH_3 \cdot H_2O$); gradient: B: 20%; flow rate: 60 mL/min. Isomer 1 (retention time: 4.669 min, 0.82 g) of compound 58 and isomer 2 of compound 58 (retention time: 4.807 min, 0.97 g) were obtained.

Isomer 1 of Compound 58:

$^1H$ NMR (400 MHz, $CDCl_3$) δ 11.51 (s, 1H), 7.97 (s, 1H), 6.86 (s, 1H), 6.07 (s, 1H), 2.92 (t, 2H), 2.56-2.53 (m, 1H), 2.45 (s, 3H), 2.31-2.25 (m, 1H), 2.17 (s, 3H), 2.14 (s, 3H), 1.98-1.93 (m, 1H), 1.90 (s, 1H), 1.87-1.76 (m, 2H), 1.74-1.70 (m, 2H), 1.62 (s, 3H), 1.59-1.50 (m, 1H), 1.42-1.33 (m, 2H), 1.15-1.09 (m, 1H).

LCMS m/z=570.2 $[M+1]^+$.

Isomer 2 of Compound 58:

$^1H$ NMR (400 MHz, $CDCl_3$) δ 11.50 (s, 1H), 7.97 (s, 1H), 6.86 (s, 1H), 6.07 (s, 1H), 2.92 (t, 2H), 2.56-2.53 (m, 1H), 2.45 (s, 3H), 2.31-2.25 (m, 1H), 2.17 (s, 3H), 2.14 (s, 3H), 1.98-1.86 (m, 3H), 1.83-1.69 (m, 3H), 1.62 (s, 3H), 1.59-1.50 (m, 1H), 1.44-1.32 (m, 2H), 1.16-1.08 (m, 1H).

LCMS m/z=570.1 $[M+1]^+$.

Embodiment 59

7-chloro-2,4-dimethyl-N-((6-methyl-4-(methylthio)-2-oxo-1,2-dihydropyridin-3-yl)methyl-d2)-2-(4-(oxetan-3-ylamino)cyclohexyl)benzo[d][1,3]dioxole-5-carboxamide (compound 59, isomer 1 and isomer 2)

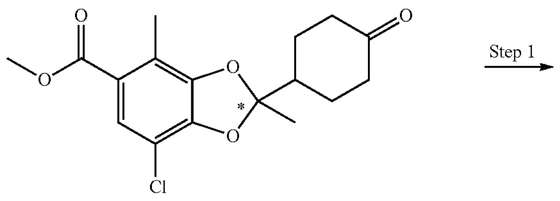

Intermediate 2

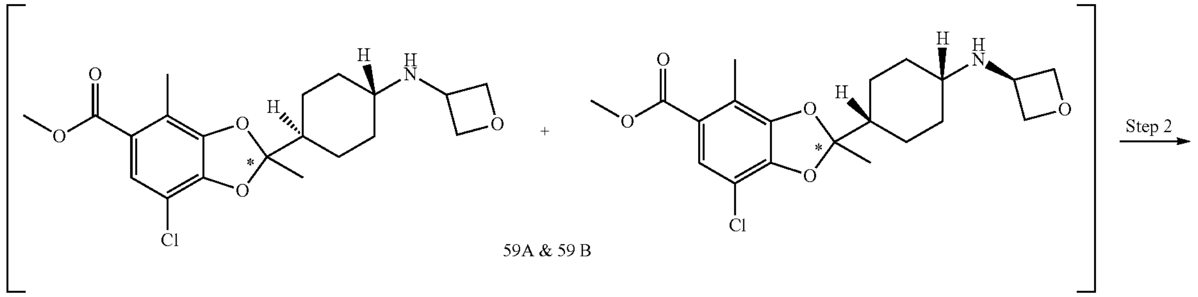

59A & 59 B

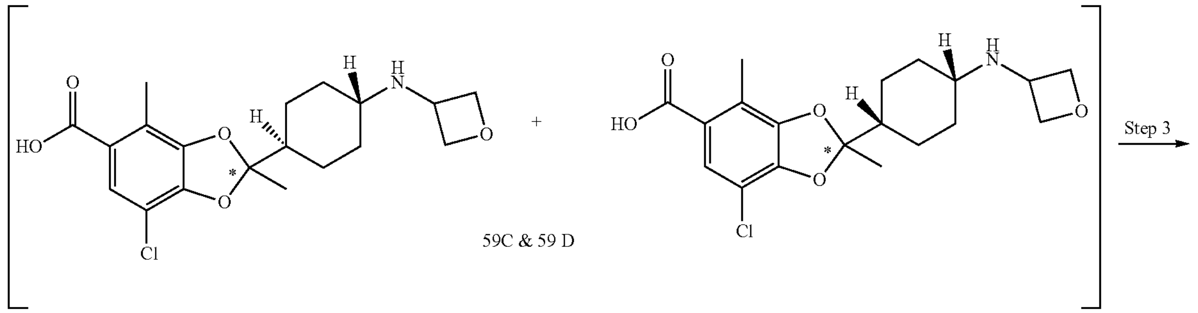

59C & 59 D

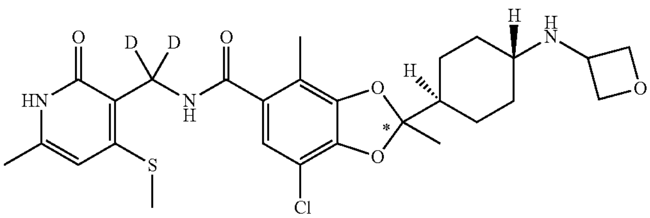

+

-continued

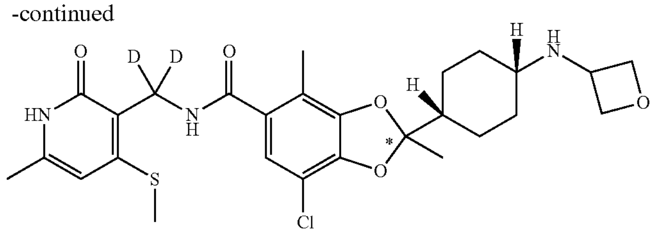

Compound 59, isomer 1 & Compound 59, isomer 2

Step 1: methyl 7-chloro-2,4-dimethyl-2-(4-(oxetan-3-ylamino)cyclohexyl)benzo[d][1,3]dioxole-5-carboxylate (59A & 59B)

Methyl 7-chloro-2,4-dimethyl-2-(4-oxocyclohexyl)-1,3-benzodioxole-5-carboxylate (intermediate 2) (1.8 g, 5.31 mmol) was dissolved in 1,2-dichloroethan (30 mL). Oxetamine (0.39 g, 5.31 mmol), sodium triacetoxyborohydride (2.25 g, 10.62 mmol) and glacial acetic acid (2d) were added. After the addition, the mixture was reacted at room temperature overnight. The reaction was quenched by adding a saturated sodium bicarbonate solution and extracted with dichloromethane (50 mL×2). The organic phase was washed with a saturated aqueous sodium chloride solution (25 mL), dried over anhydrous sodium sulfate, filtered and concentrated to obtain the title compound methyl-7-chloro-2,4-dimethyl-2-((1R,4S)-4-(oxetane-3-ylamino)cyclohexyl) benzo[d][1,3]dioxolene-5-carboxylate (59A&59B), which was separated and purified by silica gel column chromatography (dichloromethane:methanol (v/v)=40:1) to obtain isomer 59A as a white solid (1.20 g, 57.1%) and isomer 59B as a white solid (0.50 g, 23.8%).

LCMS m/z=396.2 $[M+1]^+$.

Step 2: 7-chloro-2,4-dimethyl-2-(4-(oxetan-3-ylamino)cyclohexyl)benzo[d][1,3]dioxole-5-carboxylic acid (59C & 59D)

59A (1.20 g, 3.03 mol) was dissolved in a mixed solvent (methanol:tetrahydrofuran:water (v/v/v)=1:1:1) (12 mL). Sodium hydroxide (1.21 g, 30.30 mmol) was added. After the addition, the mixture was reacted at room temperature overnight and adjusted to about pH=3 by adding dilute acid. Solids were precipitated out and filtered by suction, and the filter cake was collected. The filtrate was extracted with dichloromethane (50 mL×2). The organic phase was washed with a saturated aqueous sodium chloride solution (25 mL×2), dried over anhydrous sodium sulfate, filtered and concentrated, and the resulting product and the filter cake were combined to obtain the title compound 7-chloro-2,4-dimethyl-2-(4-(oxetane-3-ylamino)cyclohexyl)benzo[d][1,3]dioxolene-5-carboxylic acid (isomer 59C) as a white solid (1.1 g, yield: 95%).

LCMS m/z=382.1 $[M+1]^+$.

59B (0.50 g, 1.26 mol) was dissolved in a mixed solvent (methanol:tetrahydrofuran:water (v/v/v)=1:1:1) (9 mL). Sodium hydroxide (0.2 g, 5.04 mmol) was added. After the addition, the mixture was reacted at room temperature overnight and adjusted to about pH=3 by adding dilute acid. Solids were precipitated out and filtered by suction, and the filter cake was collected. The filtrate was extracted with dichloromethane (50 mL×2). The organic phase was washed with a saturated aqueous sodium chloride solution (25 mL×2), dried over anhydrous sodium sulfate, filtered and concentrated, and the resulting product and the filter cake were combined to obtain the title compound 7-chloro-2,4-dimethyl-2-(4-(oxetane-3-ylamino)cyclohexyl)benzo[d][1,3]dioxolene-5-carboxylic acid (isomer 59D) as a white solid (0.4 g, yield: 83%).

LCMS m/z=382.1 $[M+1]^+$.

Step 3: 7-chloro-2,4-dimethyl-N-((6-methyl-4-(methylthio)-2-oxo-1,2-dihydropyridin-3-yl)methyl-d2)-2-(4-(oxetan-3-ylamino)cyclohexyl)benzo[d][1,3]dioxole-5-carboxamide (compound 59, isomer 1 and isomer 2)

59C (1.1 g, 2.88 mmol) was dissolved in DMF (15 mL). N,N-diisopropylethylamin (1.12 g, 8.64 mmol), HATU (1.64 g, 4.32 mmol) and intermediate 6 (0.96 g, 4.32 mmol) were added. After the addition, the mixture was reacted at room temperature overnight. The reaction was quenched by dropwise adding a saturated aqueous ammonium chloride solution. A saturated aqueous sodium chloride solution (30 mL) was added. The reaction liquid was extracted with ethyl acetate (25 mL). The organic phase was washed with a saturated aqueous sodium chloride solution (25 mL×3), dried over anhydrous sodium sulfate, filtered and concentrated. The residue was separated and purified by preparative HPLC to obtain isomer 1 (1.14 g, 69%) of the product compound 59. Preparative HPLC separation conditions: instrument: waters 2767 (preparative liquid phase chromatographic instrument); chromatographic column: SunFire@ Prep C18 (19 mm×250 mm). The sample was dissolved in DMF and filtered with a 0.45 μm filter to prepare a sample solution. Preparative chromatography conditions: composition of mobile phases A and B: mobile phase A: acetonitrile; mobile phase B: water (containing 5 mM ammonium acetate); gradient elution, mobile phase A: 40%-70%; flow rate: 15 mL/min; elution time: 18 min; retention time: 11.97 min.

LC-MS (ESI): m/z=550.2 $[M+H]^+$.

$^1H$ NMR (400 MHz, $CD_3OD$) δ 6.89 (s, 1H), 6.27 (s, 1H), 4.77 (d, 2H), 4.55-4.51 (m, 2H), 4.10-4.06 (m, 1H), 2.85-2.83 (m, 1H), 2.52 (s, 3H), 2.29 (s, 3H), 2.20 (s, 3H), 1.96-1.91 (m, 2H), 1.76-1.64 (m, 4H), 1.61 (s, 3H), 1.57-1.51 (m, 3H).

59D (0.4 g, 1.05 mmol) was dissolved in DMF (10 mL). N,N-diisopropylethylamin (0.41 g, 3.14 mmol), HATU (0.60 g, 1.57 mmol) and intermediate 6 (0.35 g, 1.57 mmol) were added. After the addition, the mixture was reacted at room temperature overnight. The reaction was quenched by dropwise adding a saturated aqueous ammonium chloride solution. A saturated aqueous sodium chloride solution (30 mL) was added. The reaction liquid was extracted with ethyl acetate (25 mL). The organic phase was washed with a saturated aqueous sodium chloride solution (25 mL×3), dried over anhydrous sodium sulfate, filtered and concentrated. The residue was separated and purified by preparative HPLC to obtain isomer 2 (306 mg, 53%) of the product compound 59. Preparative HPLC separation conditions: instrument: waters 2767 (preparative liquid phase chromatographic instrument); chromatographic column: SunFire@ Prep C18 (19 mm×250 mm). The sample was dissolved in DMF and filtered with a 0.45 μm filter to prepare a sample solution. Preparative chromatography conditions: composition of mobile phases A and B: mobile phase A: acetonitrile; mobile phase B: water (containing 5 mM ammonium acetate); gradient elution, mobile phase A: 40%-70%; flow rate: 15 mL/min; elution time: 18 min; retention time: 12.50 min.

LC-MS (ESI): m/z=550.2 $[M+H]^+$.

$^1H$ NMR (400 MHz, $CD_3OD$) δ 6.88 (s, 1H), 6.27 (s, 1H), 4.78 (d, 2H), 4.52-4.48 (m, 2H), 4.16-4.09 (m, 1H), 2.52 (s, 3H), 2.50-2.45 (m, 1H), 2.29 (s, 3H), 2.18 (s, 3H), 1.95-1.83 (m, 6H), 1.60 (s, 3H), 1.32-1.10 (m, 3H).

Embodiment 60

7-chloro-2,4-dimethyl-N-((6-methyl-4-(methylthio)-2-oxo-1,2-dihydropyridin-3-yl)methyl-d2)-2-(4-(tetrahydro-1H-furo[3,4-c]pyrrol-5(3H)-yl)cyclohexyl) benzo[d][1,3]dioxole-5-carboxamide (compound 60)

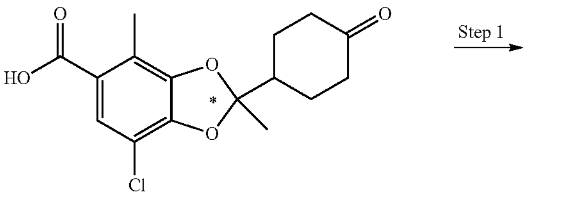

42A

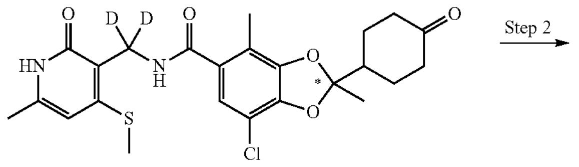

60A

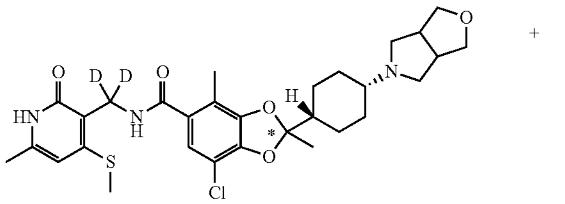

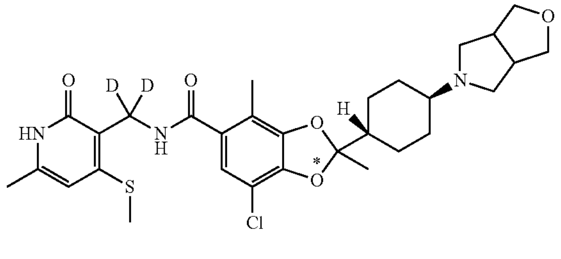

Compound 60, isomer 1 & Compound 60, isomer 2

Step 1: 7-chloro-2,4-dimethyl-N-((6-methyl-4-(methylthio)-2-oxo-1,2-dihydropyridin-3-yl)methyl-d2)-2-(4-oxocyclohexyl)benzo[d][1,3]dioxole-5-carboxamide (60A)

7-chloro-2,4-dimethyl-2-(4-oxocyclohexyl)benzo[d][1,3] dioxole-5-carboxylic acid (42A) (1.9 g, 5.9 mmol) was dissolved in anhydrous tetrahydrofuran (40 mL). HATU (2.5 g, 6.5 mmol), 3-(aminomethyl-d2)-6-methyl-4-(methylthio) pyridine-2(1H)-hydrochloride (intermediate 6) (1.5 g, 6.5 mmol) and DIEA (2.2 g, 17.7 mmol) were successively added, and the mixture was reacted at room temperature for 4 hours. Water (50 mL) was added, and the reaction liquid was extracted with ethyl acetate (50 mL×3). The organic phases were combined, washed with water (30 mL×3) and saturated brine (50 mL×1), dried over anhydrous sodium sulfate and concentrated. The residue was separated and purified by silica gel column chromatography (dichloromethane:methanol (v/v)=0.01:1-0.05:1) to obtain the title compound (60A) as a yellow solid (2.0 g, yield: 69%).

LCMS m/z=493.01 $[M+1]^+$.

Step 2: 7-chloro-2,4-dimethyl-N-((6-methyl-4-(methylthio)-2-oxo-1,2-dihydropyridin-3-yl)methyl-d2)-2-(4-(tetrahydro-1H-furo[3,4-c]pyrrol-5(3H)-yl) cyclohexyl)benzo[d][1,3]dioxole-5-carboxamide (compound 60)

7-chloro-2,4-dimethyl-N-((6-methyl-4-(methylthio)-2-oxo-1,2-dihydropyridin-3-yl)methyl-d2)-2-(4-oxocyclohexyl)benzo[d][1,3]dioxole-5-carboxamide (60A) (1.0 g, 2.0 mmol) was dissolved in anhydrous ethanol (30 mL). Hexahydro-1H-furan[3,4-c]pyrrole hydrochloride (450 mg, 3.0 mmol), triethylamine (303 mg, 3.0 mmol) and acetic acid (330 mg) were added, and the mixture was stirred for 10 minutes. Sodium triacetoxyborohydride (633 mg, 3.0 mmol) was then added, and the mixture was reacted at room temperature for 4 hours and concentrated. Water (50 mL) was then added, and the reaction liquid was extracted with dichloromethane (50 mL×3). The organic phases were combined, washed with a saturated aqueous sodium carbonate solution (50 mL) and dried over anhydrous sodium sulfate. The residue was separated and purified by silica gel column chromatography (dichloromethane:methanol (v/v)=0.01:1-0.1:1) to obtain isomer 1 (117 mg, 10%, dichloromethane: methanol (v/v)=0.1:1, Rf=0.5) of compound 60 and isomer 2 (150 mg, 13%, dichloromethane:methanol (v/v)=0.1:1, Rf=0.2) of compound 60.

Isomer 1 of Compound 60

$^1H$ NMR (400 MHz, DMSO-d6) δ 11.49 (s, 1H), 7.98 (s, 1H), 6.84 (s, 1H), 6.07 (s, 1H), 3.95-3.83 (m, 2H), 3.29 (s, 3H), 3.24-3.13 (m, 2H), 2.67-2.57 (m, 2H), 2.44 (s, 3H), 2.19-2.14 (m, 5H), 2.12 (s, 3H), 2.07 (s, 1H), 1.96-1.79 (m, 3H), 1.60 (s, 3H), 1.59-1.34 (m, 5H).

MS M/Z (ESI): m/z=590.17 (M+1).

Isomer 2 of Compound 60

$^1H$ NMR (400 MHz, DMSO-d6) δ 11.50 (s, 1H), 7.99 (s, 1H), 6.86 (s, 1H), 6.08 (s, 1H), 3.68 (s, 2H), 3.30 (s, 3H), 3.02-2.51 (m, 4H), 2.45 (s, 3H), 2.41-2.23 (m, 1H), 2.15 (d, 6H), 2.10-1.67 (m, 6H), 1.60 (s, 3H), 1.36-0.92 (m, 4H)

MS M/Z (ESI): m/z=590.17 (M+1).

Embodiment 61

7-chloro-2,4-dimethyl-N-((6-methyl-4-(methylthio)-2-oxo-1,2-dihydropyridin-3-yl)methyl)-2-(4-(oxetan-3-ylamino)cyclohexyl)benzo[d][1,3]dioxole-5-carboxamide(compound 61, isomer 1 and isomer 2)

adding water. Some solids were precipitated out and filtered by suction. The filter cake was washed with a small amount of water and collected. The filtrate was extracted with DCM (50 mL×3). The organic phase was washed with a saturated aqueous sodium chloride solution (50 mL), dried over anhydrous sodium sulfate, filtered and concentrated. The

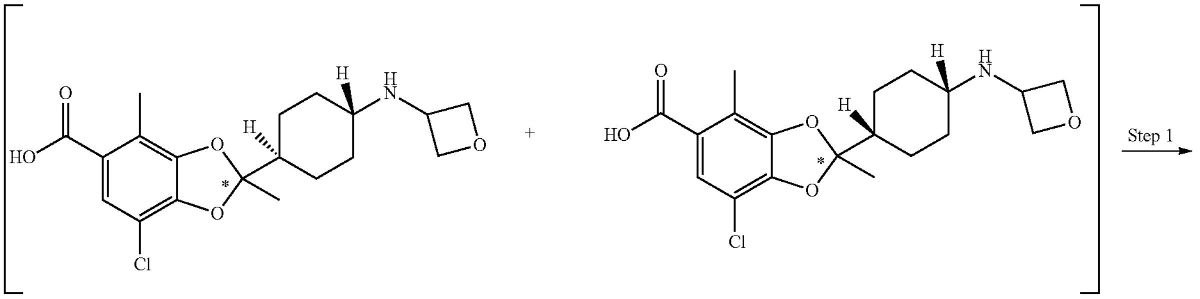

59C & 59 D

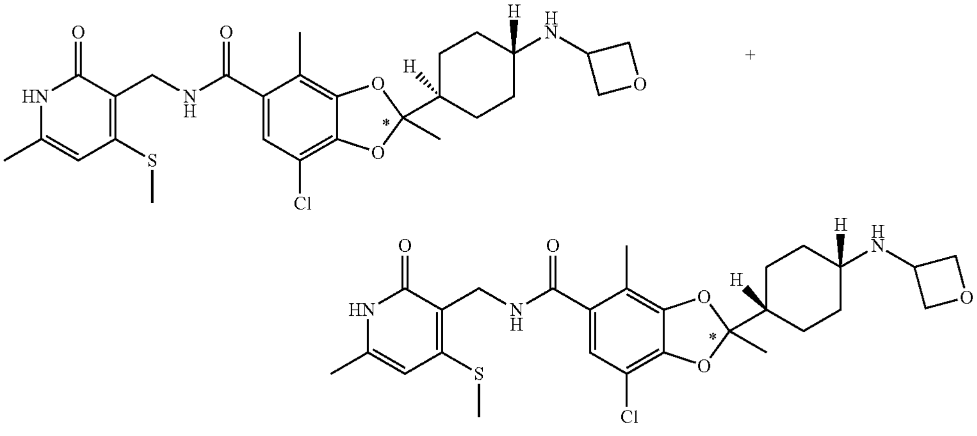

Compound 61, isomer 1 & Compound 61, isomer 2

59C (3 g, 7.86 mmol) was dissolved in DMF (20 mL). N,N-diisopropylethylamin (3.56 g, 27.51 mmol), HOBt (2.12 g, 15.72 mmol), EDCI (3.01 g, 15.72 mmol) and 3-(aminomethyl)-6-methyl-4-(methylsulfanyl)-1,2-dihydropyridine-2-one hydrochloride (intermediate 5) (2.62 g, 11.79 mmol) were added. After the addition, the mixture was reacted at room temperature overnight. The reaction was quenched by adding water. Some solids were precipitated out and filtered by suction. The filter cake was washed with a small amount of water and collected. The filtrate was extracted with DCM (50 mL×4). The organic phase was washed with a saturated aqueous sodium chloride solution (50 mL), dried over anhydrous sodium sulfate, filtered and concentrated. The residue was combined with the filter cake before the extraction, and the resultant was subjected to column chromatography (DCM:MeOH=10:1) to obtain the product compound 61, isomer 1 (1.71 g, 40%).

LC-MS (ESI): m/z=548.2 $[M+H]^+$.

59D (1 g, 2.62 mmol) was dissolved in DMF (15 mL). N,N-diisopropylethylamin (1.19 g, 9.17 mmol), HOBt (0.71 g, 5.24 mmol), EDCI (1 g, 5.24 mmol) and 3-(aminomethyl)-6-methyl-4-(methylsulfanyl)-1,2-dihydropyridine-2-one hydrochloride (intermediate 5) (0.87 g, 3.93 mmol) were added. After the addition, the mixture was reacted at room temperature overnight. The reaction was quenched by residue was combined with the filter cake before the extraction, and the resultant was subjected to column chromatography (DCM:MeOH=10:1) to obtain the product compound 61, isomer 2 (0.56 g, 39%).

LC-MS (ESI): m/z=548.2 $[M+H]^+$.

1H NMR (400 MHz, $CD_3OD$) δ 6.88 (s, 1H), 6.27 (s, 1H), 4.77 (d, 2H), 4.50-4.47 (m, 4H), 4.12-4.09 (m, 1H), 2.52 (s, 3H), 2.48-2.43 (m, 1H), 2.29 (s, 3H), 2.18 (s, 3H), 1.95-1.86 (m, 5H), 1.60 (s, 3H), 1.32-1.22 (m, 2H), 1.18-1.12 (m, 2H).

BIOLOGICAL TEST EXAMPLES

1. SU-DHL-6 Cell Proliferation Test

SU-DHL-6 cells are human B-cell lymphoma cell lines purchased from ATCC and cultured under the following conditions: RPMI-1640+10% FBS+1% double antibody in a 37° C., 5% $CO_2$ incubator. The cells were plated in a 12-well plate, with a cell concentration of $1\times10^5$ cells/mL. After the cells were plated, the compounds at different concentrations were added and cultured in a 37° C., 5% $CO_2$ incubator. The cells were counted every 3-4 days (Countstar automated cell counter), centrifuged to remove the supernatant, re-diluted to $1\times10^5$ cells/mL and plated, and then the compounds at different concentrations were further added. After the mixture was incubated for 14 days and the cells were counted, the test was terminated, and the $IC_{50}$ values were calculated by using the Origen9.2 software.

Test results: the compounds of the present disclosure showed inhibitory activity against EZH2 receptors, and the IC50 values of the example compounds against SU-DHL-6 cells were in the range of 0.1-100 nM. The test results of some examples were shown in Table 1.

TABLE 1

Cell proliferation activity

| Compound | Cell proliferation IC50 (nM) |
|---|---|
| Compound 1, isomer 1 | 13.13 |
| Compound 4, isomer 1 | 10.23 |
| Compound 4, isomer 2 | 9.79 |
| Compound 26 | 63.2 |
| Compound 27 | 93.7 |
| Compound 29 | 77.9 |
| Compound 30 | 22.6 |
| Compound 31 | 68 |
| Compound 34, isomer 1 | 33.0 |
| Compound 34, isomer 2 | 27.1 |
| Compound 36 | 8.96 |
| Compound 37 | 32.1 |
| Compound 38 | 14.1 |
| Compound 39, isomer 1 | 28.2 |
| Compound 39, isomer 2 | 63.2 |
| Compound 41, isomer 1 | 35.3 |
| Compound 41, isomer 2 | 22.0 |
| Compound 43, isomer 1 | 59.3 |
| Compound 44, isomer 1 | 24.0 |
| Compound 47, isomer 1 | 26.3 |
| Compound 49, isomer 2 | 38.9 |
| Compound 59, isomer 1 | 10.0 |
| Compound 59, isomer 2 | 6.35 |
| Compound 60, isomer 1 | 58.6 |
| Compound 60, isomer 2 | 7.12 |

2. Test Method for EZH2 Enzyme Activity

The compounds were dissolved in DMSO, formulated into 10 mM solutions and serially diluted with DMSO to obtain 100-fold the final concentration. 200 nL of the solutions of the compounds was transferred to a 384-well plate (Perkin Elmer, Cat. No. 6007299) by using Echo550. EZH2 (BPS, Cat. No. 51004) was diluted with 1× assay buffer (50 mM Tris-HCl 9.0, 0.01% Tween-20, 1 mM DTT) to 2-fold the final concentration (EZH2:3 nM). A mixed solution of H3K27(21-44) and [3H]-SAM (PerkinElmer, Lot. No. 2146246) (H3K27(21-44): 200 nM, [3H]-SAM: 100 nM) was formulated. The EZH2 diluted solution was taken and added to the 384-well plate at 10 μL/well (10 μL of 1× assay buffer was added in the control group). The plate was sealed and then incubated at room temperature for 15 minutes. 10 μL of the mixed solution of H3K27 (21-44) and [3H]-SAM was added to each well. The plate was sealed and then incubated at room temperature for 60 minutes. 50 μM of SAM (Sigma, Cat. No. A7007) was formulated at low temperature and added to the 384-well plate at 10 μL/well. The sample was taken at 25 μL/well, transferred to a flashplate and incubated at room temperature for at least 1 hour. The flashplate was washed 3 times with a plate washing liquid ($dH_2O$+0.1% Tween-20) and read by using Microbeta. The inhibition rate was calculated in Excel according to: inhibition rate (%)=(maximum $value_{positive\ control}$−detection signal value)/(maximum $value_{positive\ control}$−minimum $value_{negative\ control}$)*100, and IC50 values were fitted by using XL-Fit.

Test results: the compounds of the present disclosure showed inhibitory activity against EZH2 receptors, and the IC50 values of the example compounds against EZH2 enzyme activity were in the range of 0.01-10 nM. The test results of some examples were shown in Table 2.

TABLE 2

EZH2 enzyme activity

| Compound | Enzyme activity IC50 (nM) |
|---|---|
| Compound 1, isomer 1 | 0.67 |
| Compound 1, isomer 2 | 0.60 |
| Compound 2, isomer 1 | 0.92 |
| Compound 2, isomer 2 | 0.72 |
| Compound 3, isomer 1 | 0.65 |
| Compound 3, isomer 2 | 0.51 |
| Compound 4, isomer 1 | 0.46 |
| Compound 4, isomer 2 | 0.56 |
| Compound 5, isomer 1 | 0.58 |
| Compound 6, isomer 1 | 0.52 |
| Compound 6, isomer 2 | 0.64 |
| Compound 7, isomer 1 | 0.52 |
| Compound 8, isomer 1 | 0.51 |
| Compound 8, isomer 2 | 0.90 |
| Compound 9, isomer 1 | 0.81 |
| Compound 9, isomer 2 | 0.48 |
| Compound 10, isomer 1 | 0.56 |
| Compound 11, isomer 1 | 0.73 |
| Compound 11, isomer 2 | 0.88 |
| Compound 12, isomer 1 | 0.74 |
| Compound 13 | 0.43 |
| Compound 14 | 0.48 |
| Compound 18, isomer 2 | 0.78 |
| Compound 21 | 0.61 |
| Compound 24 | 0.58 |
| Compound 26 | 0.52 |
| Compound 27 | 0.52 |
| Compound 28 | 0.49 |
| Compound 29 | 0.44 |
| Compound 30 | 0.66 |
| Compound 31 | 0.52 |
| Compound 32 | 0.58 |
| Compound 33 | 0.57 |
| Compound 34, isomer 1 | 0.57 |
| Compound 34, isomer 2 | 0.57 |
| Compound 35 | 0.59 |
| Compound 36 | 0.55 |
| Compound 37 | 0.44 |
| Compound 38 | 0.70 |
| Compound 39, isomer 1 | 0.42 |
| Compound 39, isomer 2 | 0.58 |
| Compound 40, isomer 1 | 0.61 |
| Compound 40, isomer 2 | 0.51 |
| Compound 41, isomer 1 | 0.52 |
| Compound 41, isomer 2 | 0.44 |
| Compound 42, isomer 1 | 0.34 |
| Compound 42, isomer 2 | 0.23 |
| Compound 43, isomer 1 | 0.49 |
| Compound 43, isomer 2 | 0.42 |
| Compound 44, isomer 1 | 0.48 |
| Compound 44, isomer 2 | 0.51 |
| Compound 45, isomer 1 | 0.28 |
| Compound 45, isomer 2 | 0.35 |
| Compound 47, isomer 1 | 0.34 |
| Compound 47, isomer 2 | 0.92 |

TABLE 2-continued

| EZH2 enzyme activity | |
|---|---|
| Compound | Enzyme activity IC50 (nM) |
| Compound 49, isomer 1 | 0.51 |
| Compound 49, isomer 2 | 0.32 |
| Compound 53, isomer 1 | 0.33 |
| Compound 57, isomer 1 | 0.46 |
| Compound 57, isomer 2 | 0.49 |
| Compound 59, isomer 1 | 0.57 |
| Compound 59, isomer 2 | 0.44 |
| Compound 60, isomer 1 | 0.18 |
| Compound 60, isomer 2 | 0.34 |
| Compound 61, isomer 1 | 0.52 |
| Compound 61, isomer 2 | 0.25 |

3. Pharmacokinetic Experiment in Mice

Experimental objective: a single dose of test compounds was administered to ICR mice intragastrically, and the concentrations of the test compounds in plasma of the mice were measured to evaluate pharmacokinetic characteristics of the test compounds in the mice.

Experimental subject: example compounds.

Experimental animal: male ICR mice, about 20-25 g, 6-8 weeks old, 3 mice/compound, purchased from Chengdu Dossy Experimental Animals Co., Ltd.

Experimental method: on the day of the experiment, three ICR mice were randomly grouped according to their body weight. The animals were fasted with water available for 12 to 14 hours one day before the administration, and were fed 4 hours after the administration. The administration was performed according to table 3.

TABLE 3

| Administration information | | | | | | | | |
|---|---|---|---|---|---|---|---|---|
| | Administration information | | | | | | | |
| Group | Number Male | Test compound | Administration dosage* (mg/kg) | Administration concentration (mg/mL) | Administration volume (mL/kg) | Collected sample | Mode of administration | Vehicle |
| | 3 | Compound | 20 | 2 | 10 | Plasma | PO | 2% DMA + 98% (0.5% MC) |

*Dosage is calculated based on free base.

Biological Sample Collection

Before and after the administration, 0.03 mL of blood was taken from the orbit of the animals under isoflurane anesthesia, and placed in an EDTAK2 centrifuge tube. Centrifugation was carried out at 5000 rpm at 4° C. for 10 min, and the plasma was collected.

Time points for sample collection comprise 0 (before the administration), 15 min, 30 min, 1 h, 2 h, 4 h, 6 h, 8 h and 24 h.

The concentrations of the compounds in EDTA-$K_2$ anticoagulant plasma were determined by the LC-MS/MS method. The linear range of the standard curve of the compounds is 2-2000 ng/mL. After subjected to precipitating proteins with acetonitrile, the samples were analyzed by LC-MS/MS. The standard curve was subjected to a regression calculation using the weighted least square method ($W=1/X^2$), and quantified by calculating the ratio of test compound peak area to internal standard peak area.

Before analysis and detection, all samples were stored at −80° C.

The results were as shown in Table 4.

TABLE 4

| Experimental results | | | | |
|---|---|---|---|---|
| | Pharmacokinetic experiment (20 mg/kg) | | | |
| Compound No. | Plasma drug concentration Cmax (ng/mL) | Curve area AUC (h · ng · mL − 1) | Half-life $T_{1/2}$ (h) | Time to reach peak Tmax |
| Compound 10, isomer 1 | 1238 | 1097 | 1.72 | 0.25 |
| Compound 34, isomer 1 | 598 | 1347 | 3.37 | 0.25 |

Conclusion: the compounds of the present disclosure, especially isomer 1 of compound 10 and isomer 1 of compound 34, have good pharmacokinetics with long half-life and short time to reach the highest concentration.

4. Pharmacokinetic Experiment in Mice

Experimental objective: a single dose of test compounds was administered to ICR mice intravenously or intragastrically, and the concentrations of the test compounds in plasma of the mice were measured to evaluate pharmacokinetic characteristics of the test compounds in the mice.

Experimental subject: known compound I-2 and example compounds.

Experimental animal: male ICR mice, about 20-25 g, 6-8 weeks old, 18 mice/compound, purchased from Chengdu Dossy Experimental Animals Co., Ltd.

Experimental method: on the day of the experiment, eighteen ICR mice were randomly grouped according to their body weight. The animals were fasted with water available for 12 to 14 hours one day before the administration, and were fed 4 hours after the administration. The administration was performed according to table 5.

TABLE 5

| Administration information | | | | | | | |
|---|---|---|---|---|---|---|---|
| | | Administration information | | | | | |
| Group | Number Male | Test compound | Administration dosage (mg/kg) | Administration concentration (mg/mL) | Administration volume (mL/kg) | Collected sample | Mode of administration |
| G1 | 9 | Compound | 5 | 1 | 5 | Plasma | Intravenously |
| G2 | 9 | Compound | 30 | 3 | 10 | Plasma | Intragastrically |

Vehicle for intravenous administration: 5% DMA + 5% Solutol + 90% Saline;

Vehicle for intragastric administration: 0.5% MC;

*Dosage is calculated based on free base.

Biological Sample Collection

Before and after the administration, 0.1 ml of blood was taken from the orbit of the animals under isoflurane anesthesia, and placed in an EDTAK2 centrifuge tube. Centrifugation was carried out at 5000 rpm at 4° C. for 10 min, and the plasma was collected.

Time points for sample collection in G1&G2 groups comprise 0, 5.15 min, 30 min, 1 h, 2 h, 4 h, 6 h, 8 h and 24 h.

Before analysis and detection, all samples were stored at −80° C.

Pretreatment of Samples:

(1) except to the blank sample, 400 μL of internal standard working solution (Verapamil internal standard concentration in precipitant acetonitrile is 10.0 ng/mL) was added to a 1.5 mL centrifuge tube containing 30 μL of standard curve samples and quality control samples;

200 μL of internal standard working solution (Verapamil internal standard concentration in precipitant acetonitrile is 10.0 ng/mL) was added to a 1.5 mL centrifuge tube containing 15 μL of unknown samples;

and 400 μL of acetonitrile was added to the blank sample;

(2) the mixture was mixed evenly for about 1 min in a vortex mixer;

(3) centrifugation was carried out at 10000 rpm at 4C for 10 mi;

(4) 175 μL of the supernatant was transferred to a new 96-well polypropylene plate, and then the plate was sealed and placed in a 10° C. sample tray for injection.

The experimental results can be seen in Table 6.

TABLE 6

| Experimental results | | | | | | |
|---|---|---|---|---|---|---|
| Embodiment No. | Mode of administration | C0 or Cmax (ng/ml) | AUC (h*ng/ml) | $T_{1/2}$ (h) | Tmax (h) | F % |
| Compound I-2 | IV 5 mg/kg | 2138 | 1184 | 6.31 | — | — |
| | PO 30 mg/kg | 262 | 645 | 3.05 | 0.25 | 9.08 |
| Compound 27 | IV 5 mg/kg | 1973 | 839 | 1.42 | — | — |
| | PO 30 mg/kg | 865 | 2653 | 0.934 | 2.00 | 52.7 |
| Compound 44, | IV 5 mg/kg | 2340 | 574 | 0.427 | — | — |
| Isomer 1 | PO 30 mg/kg | 971 | 1527 | 1.27 | | 44.3 |
| Compound 44, | IV 5 mg/kg | 2482 | 713 | 2.33 | — | — |
| Isomer 2 | PO 30 mg/kg | 463 | 917 | 1.81 | 1.00 | 27.4 |
| Compound 50 | IV 5 mg/kg | 1291 | 569 | 1.91 | — | — |
| | PO 30 mg/kg | 563 | 1953 | 2.79 | 1.00 | 57.2 |
| Compound 53, | IV 5 mg/kg | 2365 | 703 | 1.21 | — | — |
| Isomer 1 | PO 30 mg/kg | 1025 | 2020 | 1.10 | 0.500 | 47.9 |
| Compound 53, | IV 5 mg/kg | 2665 | 954 | 1.87 | — | — |
| Isomer 2 | PO 30 mg/kg | 476 | 2201 | 4.51 | 4.00 | 38.4 |

Compound I-2 is Valemetostat (DS-3201).

Conclusion: the compounds of the present disclosure have excellent pharmacokinetics and significantly improved bioavailability.

5. Pharmacokinetic Experiment in Monkeys

Experimental animal: twelve cynomolgus monkeys, 2.4-5.9 kg, male, 3-5.5 years old, purchased from Suzhou Xishan Zhongke Laboratory Animal Co., Ltd, with the production license number of SCXK(SU) 2018-0001.

Experimental Design:

| | | Administration information | | | | | |
|---|---|---|---|---|---|---|---|
| Group | Number Male | Test compound | Administration dosage (mg/kg) | Administration concentration (mg/mL) | Administration volume (mL/kg) | Collected sample | Mode of administration |
| G1 | 3 | HSK33499 | 3 | 3 | 1 | Plasma | Intravenously |
| G2 | 3 | HSK33499 | 15 | 3 | 5 | Plasma | Intragastrically |

Vehicle for intravenous administration: 5% DMSO + 5% Solutol + 90% Saline;

Vehicle for intragastric administration: 0.5% MC

Before and after the administration, 1.0 mL of blood was taken from the front and rear limb veins of the animals, and placed in an EDTAK2 centrifuge tube. Centrifugation was carried out at 5000 rpm at 4° C. for 10 min to collect the plasma. Time points for blood sampling comprise 0, 5 min, 15 min, 30 min, 1 h, 2 h, 4 h, 6 h, 8 h, 10 h, 12 h and 24 h. Before analysis and detection, all plasma samples were stored at −80° C.

The experimental results can be seen in Table 7.

TABLE 7

Experimental results

| Embodiment No. | Mode of administration | C0 or Cmax (ng/ml) | AUC (h*ng/ml) | $T_{1/2}$ (h) | Tmax (h) | F % |
|---|---|---|---|---|---|---|
| Compound 59, isomer 2 | IV 3 mg/kg | 2962 ± 601 | 1573 ± 39 | 2.68 ± 0.14 | — | — |
| | PO 15 mg/kg | 2318 ± 562 | 3310 ± 526 | 5.11 ± 0.32 | 1.00 ± 0.00 | 42.1 ± 6.7 |

Conclusion: the compounds of the present disclosure have excellent pharmacokinetics and significantly improved bioavailability.

6. Cytochrome P450 Isozyme Inhibition Experiment

Experimental objective: the inhibitory effects of test compounds on the activity of human liver microsomal cytochrome P450 isozymes (CYP1A2, CYP2C9, CYP2C19, CYP2D6 and CYP3A4) were determined.

Experimental operation: firstly, the test compounds (10.0 mM) were serially diluted to prepare working solutions (100×the final concentration) at concentrations of 5.00, 1.50, 0.500, 0.150, 0.0500, 0.0150 and 0.00500 mM; the working solutions of each positive inhibitor of P450 isozymes (CYP1A2, CYP2C9, CYP2C19, CYP2D6 and CYP3A4) and its specific substrate mixture (5 in 1) were prepared; the human liver microsomes stored in the refrigerator below −60° C. were thawed on ice; after completely thawed, the human liver microsomes were diluted with potassium phosphate buffer (PB) to prepare working solutions at given concentrations (0.253 mg/mL); 20.0 μL of the substrate mixed solutions was added to a reaction plate (20.0 μL of PB was added to the Blank well), and then 158 μL of human liver microsome working solutions was added to the reaction plate; the reaction plate was placed on ice for use; at this point, 2.00 μL of test compounds (N=1) at each concentration and specific inhibitors (N=2) were added to the corresponding wells; and the corresponding organic solvents were added in the groups without inhibitors (for test compounds or for positive inhibitors) as control samples (for test compounds, the control sample is 1:1 DMSO:MeOH, and for positive inhibitors, the control sample is 1:9 DMSO:MeOH); after pre-incubating in a water bath at 37° C. for 10 min, 20.0 μL of the coenzyme factor (NADPH) solution was added to the reaction plate, which was then incubated in a water bath at 37° C. for another 10 min; the reaction was terminated by adding 400 μL of the pre-cooled acetonitrile solution (containing 200 ng/mL Tolbutamide and Labetalol as internal standards); the reaction plate was shaken on a shaker for 10 min to mix well; centrifugation was then carried out at 4000 rpm at 4° C. for 20 min; 200 μL of the supernatant was added to 100 μL of water for sample dilution; finally, the plate was sealed and shaken for 10 min to mix well, and the LC/MS/MS detection was performed.

The experimental results can be seen in Table 8.

TABLE 8

Experimental results

| Compound | CYP1A2 ($IC_{50}$ (μM)) | CYP2C9 | CYP2C19 | CYP2D6 | CYP3A4-M |
|---|---|---|---|---|---|
| Compound I-2 | >50 | >50 | >50 | >50 | 16.3 |
| Compound 59, isomer 2 | >50 | >50 | >50 | >50 | >50 |

Compound I-2 is Valemetostat (DS-3201)

Conclusion: the compounds of the present disclosure have no inhibitory effects on CYP enzymes.

What is claimed is:

1. A compound of formula (I-4), or a stereoisomer, pharmaceutically acceptable salt, solvate, eutectic or deuterated compound thereof, wherein the compound has a structure of formula (I-4):

(I-4)

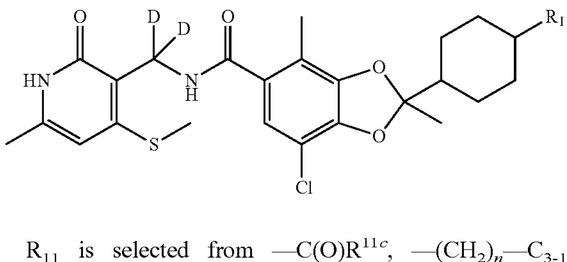

$R_{11}$ is selected from —C(O)$R^{11c}$, —$(CH_2)_n$—$C_{3-12}$ cycloalkyl, —$CH_2$-(3-to 12-membered heterocycloalkyl), or —$(CH_2)_n$—$NR^{11a}R^{11b}$, wherein the $CH_2$ or cycloalkyl is optionally substituted with 1-3 groups selected from: halogen, D, $C_{1-4}$ alkyl, halo $C_{1-4}$ alkyl, $C_{1-4}$ alkoxy, —$C_{1-4}$ alkyl-$C_{1-4}$ alkoxy, =O, CN, or OH;

$R^{11a}$ is H;

$R^{11b}$ is selected from —$(CH_2)_n$—$C_{3-12}$ cycloalkyl, or —$(CH_2)_n$-(3- to 12-membered heterocycloalkyl), wherein the cycloalkyl is optionally substituted with 1-3 $R^a$;

$R^{11c}$ is selected from —$(CH_2)_n$—$C_{3-6}$ cycloalkyl, —$(CH_2)_n$-(3- to 6-membered heterocycloalkyl), $(CH_2)_n$-(6- to 12-membered aryl), or —$(CH_2)_n$-(5- to 12-membered heteroaryl), wherein the heterocycloalkyl, cycloalkyl, aryl or heteroaryl is optionally substituted with 1-3 of halogen, cyano, $C_{1-4}$ alkyl, halo $C_{1-4}$ alkyl, $C_{1-4}$ alkoxy, or halo $C_{1-4}$ alkoxy;

$R^a$ is selected from halogen, D, OH, cyano, $C_{1-4}$ alkyl, halo $C_{1-4}$ alkyl, $C_{1-4}$ alkoxy, or halo $C_{1-4}$ alkoxy, wherein the alkyl or alkoxy is optionally substituted with 1-3 of halogen, D, cyano, hydroxyl, $C_{1-4}$ alkyl or halo $C_{1-4}$ alkyl;

and n is selected from 0, 1, 2, 3, 4 or 5.

2. The compound of formula (I-4), or the stereoisomer, pharmaceutically acceptable salt, solvate, eutectic or deuterated compound thereof according to claim 1, wherein (1) $R_{11}$ is selected from $—NR^{11a}R^{11b}$;

$R^{11a}$ is selected from H;

$R^{11b}$ is selected from $—(CH_2)_n—C_{3-12}$ cycloalkyl, or $—(CH_2)_n$-(3- to 12-membered heterocycloalkyl), wherein the cycloalkyl is optionally substituted with 1-3 $R^a$; or (2) $R_{11}$;

is selected from $—CH_2$-$C_{3-12}$ cycloalkyl, wherein the cycloalkyl is optionally substituted with 1-3 groups selected from: halogen, D, $C_{1-4}$ alkoxy, $C_{1-4}$ alkyl, $—C_{1-4}$ alkyl-$C_{1-4}$ alkoxy, =O, CN, or OH.

3. The compound of formula (I-4), or the stereoisomer, pharmaceutically acceptable salt, solvate, eutectic or deuterated compound thereof according to claim 1, wherein (1) $R_{11}$ is selected from $—NR^{11a}R^{11b}$;

$R^{11a}$ is selected from H;

$R^{11b}$ is selected from $—(CH_2)_n$-3-membered monocyclic cycloalkyl, $—(CH_2)_n$-4-membered monocyclic cycloalkyl, $—(CH_2)_n$-5-membered monocyclic cycloalkyl, or $—(CH_2)_n$-6-membered monocyclic cycloalkyl, wherein the cycloalkyl is optionally substituted with 1-3 $R^a$;

$R^a$ is selected from halogen, D, OH, cyano, $C_{1-4}$ alkyl, $C_{1-2}$ alkoxy, or halo $C_{1-4}$ alkoxy wherein the alkyl or alkoxy is optionally substituted with 1-3 of halogen, D or cyano;

and n is 0 or 1; or (2) $R_{11}$ is selected from $—NR^{11a}R^{11b}$;

$R^{11a}$ is selected from H;

and $R^{11b}$ is selected from 4-membered monocyclic heterocycloalkyl containing 1-3 heteroatoms selected from N, O or S, 5-membered monocyclic heterocycloalkyl containing 1-3 heteroatoms selected from N, O or S, 6-membered monocyclic heterocycloalkyl containing 1-3 heteroatoms selected from N, O or S, a 5-membered bridged ring containing 1-3 heteroatoms selected from N, O or S, a 6-membered bridged ring containing 1-3 heteroatoms selected from N, O or S, a 7-membered bridged ring containing 1-3 heteroatoms selected from N, O or S or a 8-membered bridged ring containing 1-3 heteroatoms selected from N, O or S.

4. A pharmaceutical composition, wherein the pharmaceutical composition comprises the compound, or the stereoisomer, pharmaceutically acceptable salt, solvate, eutectic or deuterated compound thereof according to claim 1, and a pharmaceutically acceptable adjuvant and/or carrier.

5. A method for treating an EZH2-mediated disease, wherein the method comprises administering the compound, or the stereoisomer, pharmaceutically acceptable salt, solvate or eutectic compound thereof according to claim 1.

6. The method according to claim 5, wherein the EZH2-mediated disease is a tumor or an autoimmune disease.

7. The compound of formula (I-4), or the stereoisomer, pharmaceutically acceptable salt, solvate, eutectic or deuterated compound thereof according to claim 1, wherein $R_{11}$ is selected from

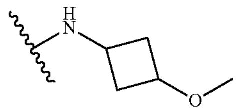 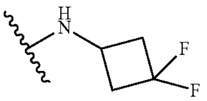

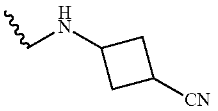 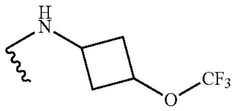

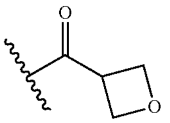 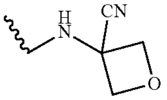 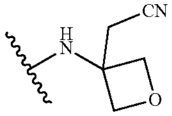

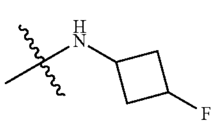 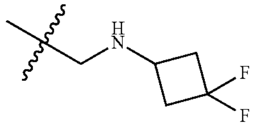

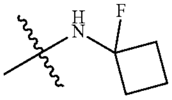 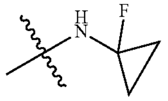

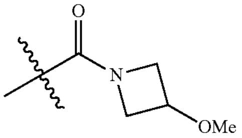 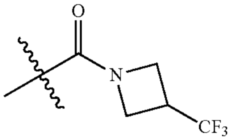

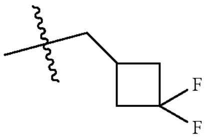 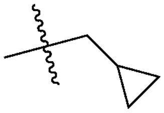

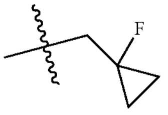 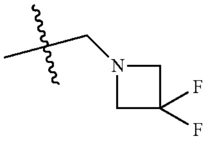

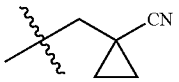 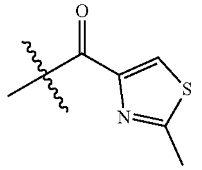

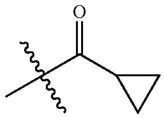 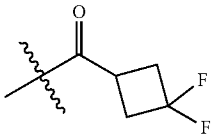

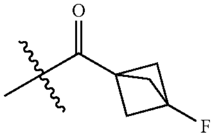 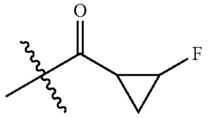

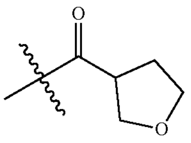 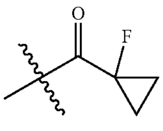

-continued
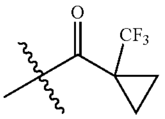
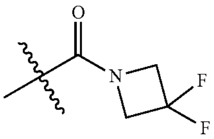
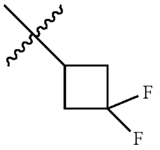
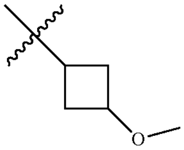
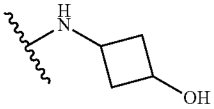
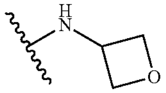
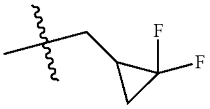
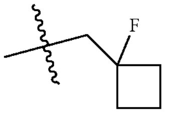
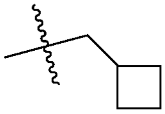
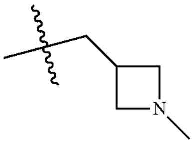
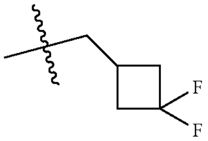
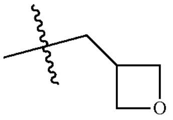
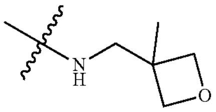
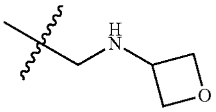
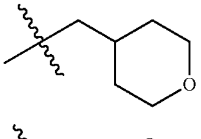
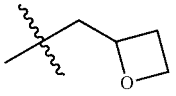
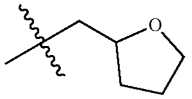
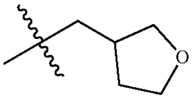
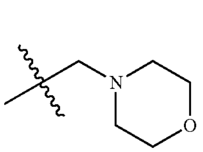
or
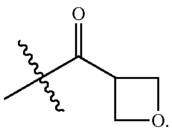
8. The compound, or the stereoisomer, pharmaceutically acceptable salt, solvate, eutectic or deuterated compound thereof according to claim 1, wherein the compound has a structure selected from one of
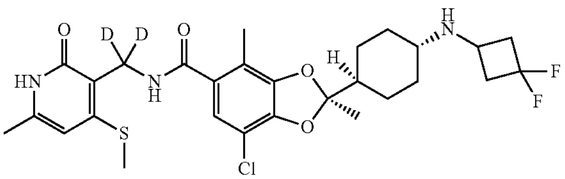
-continued
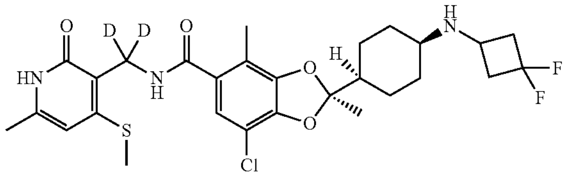
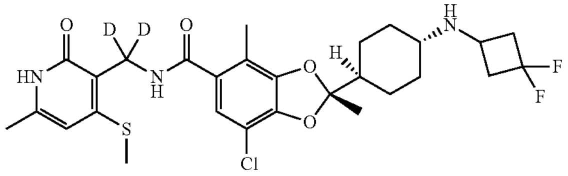
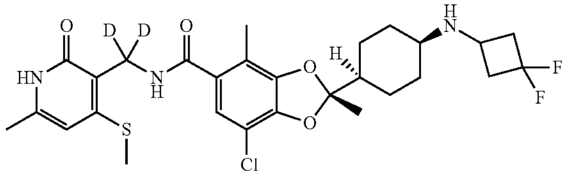
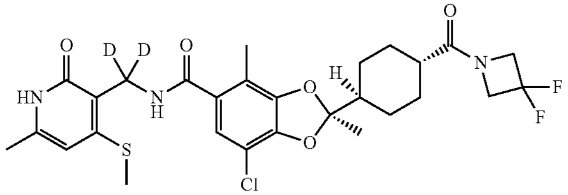
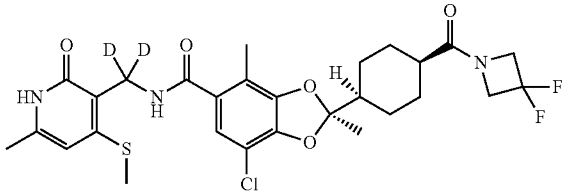
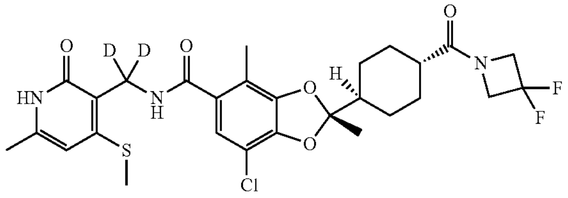
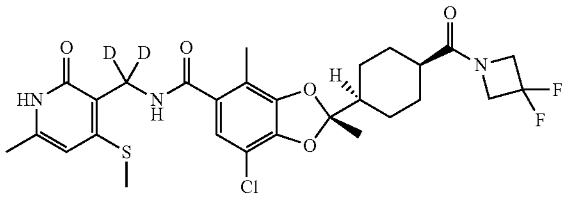
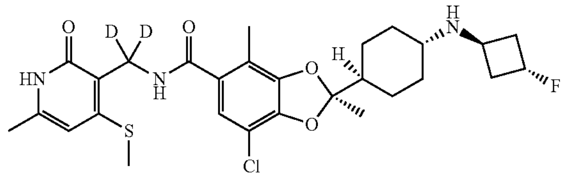
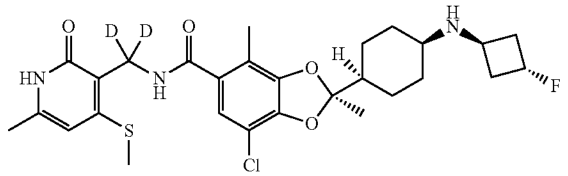

-continued
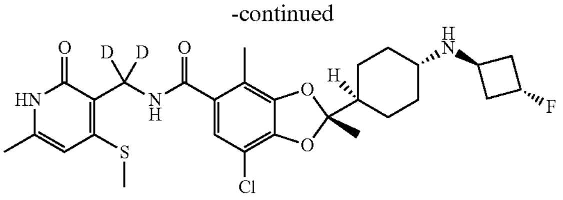
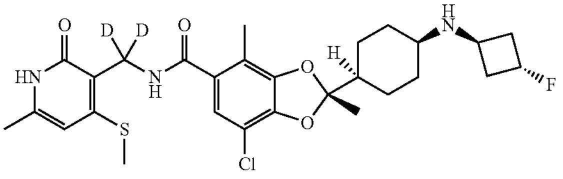
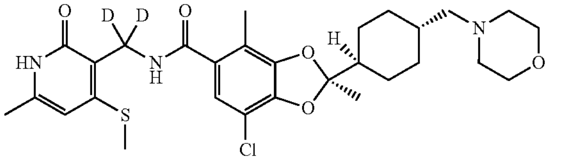
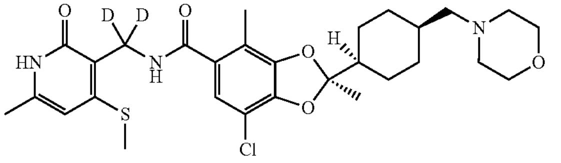
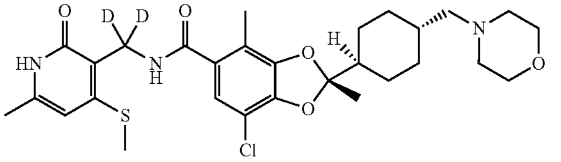
-continued
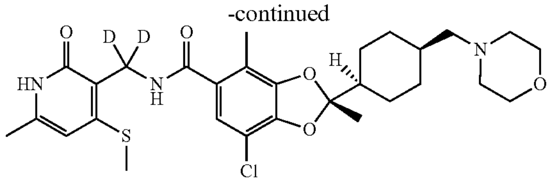
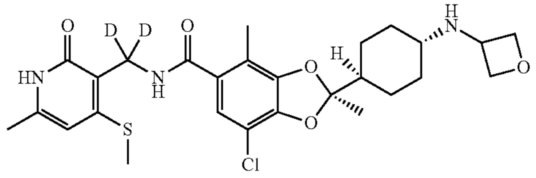
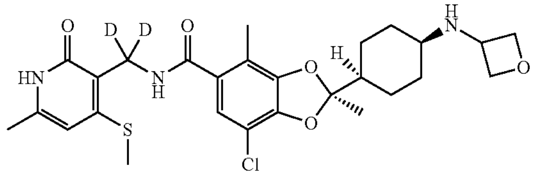
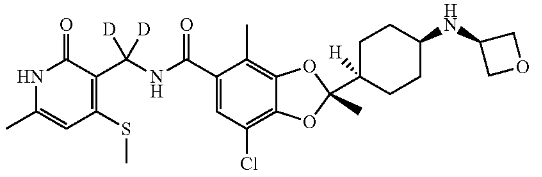 or
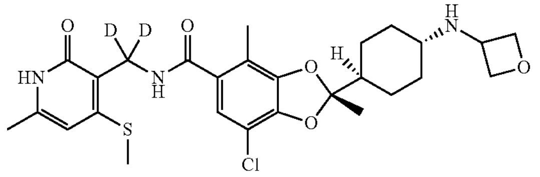 .
* * * * *